US011896648B2

(12) United States Patent
Baca et al.

(10) Patent No.: US 11,896,648 B2
(45) Date of Patent: Feb. 13, 2024

(54) INTERLEUKIN-2 VARIANT PROTEINS FUSED TO HUMAN IGG4 FC AND USES THEREOF

(71) Applicant: Gilead Sciences, Inc., Foster City, CA (US)

(72) Inventors: Manuel Baca, Lexington, MA (US); Sarah A. Gilmore, San Mateo, CA (US); Hassan Javanbakht, San Francisco, CA (US); Prasenjit K. Mukherjee, South San Francisco, CA (US)

(73) Assignee: GILEAD SCIENCES, INC., Foster City, CA (US)

( * ) Notice: Subject to any disclaimer, the term of this patent is extended or adjusted under 35 U.S.C. 154(b) by 34 days.

(21) Appl. No.: 17/506,483

(22) Filed: Oct. 20, 2021

(65) Prior Publication Data

US 2022/0125884 A1 Apr. 28, 2022

Related U.S. Application Data

(60) Provisional application No. 63/181,075, filed on Apr. 28, 2021, provisional application No. 63/104,376, filed on Oct. 22, 2020.

(51) Int. Cl.

| | |
|---|---|
| ***A61K 38/20*** | (2006.01) |
| ***A61P 35/00*** | (2006.01) |
| ***A61K 39/395*** | (2006.01) |
| ***C07K 14/55*** | (2006.01) |
| ***A61K 38/00*** | (2006.01) |
| ***A61P 31/20*** | (2006.01) |

(52) U.S. Cl.

CPC ...... *A61K 38/2013* (2013.01); *A61K 39/3955* (2013.01); *A61P 31/20* (2018.01); *A61P 35/00* (2018.01); *C07K 14/55* (2013.01); *A61K 38/00* (2013.01); *C07K 2319/30* (2013.01)

(58) Field of Classification Search

CPC ........................ A61K 38/2013; C07K 2319/30

See application file for complete search history.

(56) References Cited

U.S. PATENT DOCUMENTS

| | | | |
|---|---|---|---|
| 4,518,584 | A | 5/1985 | Mark et al. |
| 4,752,585 | A | 6/1988 | Koths et al. |
| 5,037,644 | A | 8/1991 | Shaked et al. |
| 5,229,109 | A | 7/1993 | Grimm et al. |
| 5,314,995 | A | 5/1994 | Fell, Jr. et al. |
| 5,349,053 | A | 9/1994 | Landolfi |
| 5,650,150 | A | 7/1997 | Gillies |
| 6,689,353 | B1 | 2/2004 | Wang et al. |
| 7,091,321 | B2 | 8/2006 | Gillies et al. |
| 7,371,371 | B2 | 5/2008 | Epstein et al. |
| 7,514,073 | B2 | 4/2009 | Epstein et al. |
| 7,803,361 | B2 | 9/2010 | Epstein et al. |
| 7,955,590 | B2 | 6/2011 | Gillies et al. |
| 8,043,608 | B2 | 10/2011 | Gillies et al. |
| 9,206,243 | B2 | 12/2015 | León Monzón et al. |
| 9,266,938 | B2 | 2/2016 | Ast et al. |
| 9,428,567 | B2 | 8/2016 | Garcia et al. |
| 9,725,496 | B1 | 8/2017 | Peters et al. |
| 9,844,582 | B2 | 12/2017 | Wittrup et al. |
| 10,183,980 | B2 | 1/2019 | Garcia et al. |
| 10,815,303 | B2 | 10/2020 | Yue et al. |
| 11,117,943 | B2 | 9/2021 | Garcia et al. |
| 11,377,478 | B2 | 7/2022 | Seidel, III et al. |
| 11,492,383 | B2 | 11/2022 | Gillies |
| 11,746,137 | B2 | 9/2023 | Oh et al. |
| 2006/0269515 | A1 | 11/2006 | Denis-Mize et al. |
| 2019/0202881 | A1 | 7/2019 | Greve |
| 2020/0230208 | A1 | 7/2020 | Wang et al. |
| 2020/0246467 | A1 | 8/2020 | Ptacin et al. |
| 2020/0317787 | A1 | 10/2020 | Li et al. |
| 2020/0369740 | A1 | 11/2020 | Jang |
| 2021/0221863 | A1 | 7/2021 | Kang et al. |
| 2021/0238246 | A1 | 8/2021 | Hernández García et al. |
| 2022/0152107 | A1 | 5/2022 | León Monzón et al. |
| 2023/0145766 | A1 | 5/2023 | He et al. |
| 2023/0174604 | A1 | 6/2023 | Fu et al. |
| 2023/0242607 | A1 | 8/2023 | Kwon et al. |

FOREIGN PATENT DOCUMENTS

| | | | |
|---|---|---|---|
| EP | 0673257 | B1 | 10/2002 |
| EP | 2639241 | B1 | 7/2015 |
| EP | 2673294 | B1 | 4/2016 |
| EP | 4215542 | A1 | 7/2023 |
| WO | WO-2005/086798 | A2 | 9/2005 |
| WO | WO-2006/086823 | A1 | 8/2006 |
| WO | WO-2014/023752 | A1 | 2/2014 |
| WO | WO-2018/234862 | A1 | 12/2018 |
| WO | WO-2019/091384 | A1 | 5/2019 |
| WO | WO-2019/125732 | A1 | 6/2019 |

(Continued)

OTHER PUBLICATIONS

Bell, C. J. M. et al. (2015), "Sustained in vivo signaling by long-lived IL-2 induces prolonged increases of regulatory T cells", Journal of Autoimmunity 56, 66-80.

Carmenate, T. et al. (2013), "Human IL-2 Mutein with Higher Antitumor Efficacy Than Wild Type IL-2", J Immunol 2013, 190(12):6230-6238.

Carmenate, T. et al. (2018), "Blocking IL-2 Signal In Vivo with an IL-2 Antagonist Reduces Tumor Growth through the Control of Regulatory T Cells", J Immunol 2018, 200:3475-3484.

Casadesús, A. V. et al. (2020), "A rationally-engineered IL-2 improves the antitumor effect of anti-CD20 therapy", ONCOIMMUNOLOGY, vol. 9, No. 1, 1-12.

(Continued)

*Primary Examiner* — Elly-Gerald Stoica

(57) ABSTRACT

Provided are serum half-life extended-IL-2 variant (IL-2v) heterodimers having reduced binding to the IL2Rα (CD25) subunit. In particular, Fc-IL-2v heterodimers are provided and methods for making and using, e.g. for enhancing an immune response, e.g. in the prevention and treatment of viral infections and cancer.

14 Claims, 39 Drawing Sheets

Specification includes a Sequence Listing.

(56) References Cited

FOREIGN PATENT DOCUMENTS

| | | | |
|---|---|---|---|
| WO | WO-2019/173832 | A2 | 9/2019 |
| WO | WO-2019/173832 | A3 | 10/2019 |
| WO | WO-2019/214757 | A1 | 11/2019 |
| WO | WO-2019/173832 | A4 | 1/2020 |
| WO | WO-2020/057646 | A1 | 3/2020 |
| WO | WO-2020/187340 | A2 | 9/2020 |
| WO | WO-2020/247843 | A2 | 12/2020 |
| WO | WO-2020/252418 | A1 | 12/2020 |
| WO | WO-2020/252421 | A2 | 12/2020 |
| WO | WO-2021/185361 | A1 | 9/2021 |
| WO | WO-2021/185362 | A1 | 9/2021 |
| WO | WO-2022/009123 | A1 | 1/2022 |
| WO | WO-2022/050401 | A2 | 3/2022 |
| WO | WO-2022/059794 | A1 | 3/2022 |
| WO | WO-2022/089601 | A1 | 5/2022 |
| WO | WO-2022/117692 | A2 | 6/2022 |
| WO | WO-2022/221746 | A1 | 10/2022 |

OTHER PUBLICATIONS

Emerson, S. D. et al. (2003), "NMR characterization of interleukin-2 in complexes with the IL-2Rα receptor component, and with low molecular weight compounds that inhibit the IL-2/IL-Rα interaction", Protein Science, 12:811-822.

Heaton, K. M. et al. (1993), "Characterization of Lymphokine-Activated Killing by Human Peripheral Blood Mononuclear Cells Stimulated with Interleukin 2 (IL-2) Analogs Specific for the Intermediate Affinity IL-2 Receptor", Cellular Immunology 147, 167-179.

Heaton, K. M. et al. (1993), "Human Interleukin 2 Analogues That Preferentially Bind the Intermediate-Affinity Interleukin 2 Receptor Lead to Reduced Secondary Cytokine Secretion: Implications for the Use of These Interleukin 2 Analogues in Cancer Immunotherapy", Cancer Research 53, 2597-2602.

Heaton, K. M. et al. (1994), "Induction of Lymphokine-Activated Killing with Reduced Secretion of Interleukin-1β, Tumor Necrosis Factor-α, and Interferon-γ by Interleukin-2 Analogs", Annals of Surgical Oncology, 1(3):198-203.

Heaton, K. M. et al. (1995), "Differential Inhibition of Lymphokiine-Activated Killing, Proliferation, and Cytokine Secretion by Humanized Antibodies Against the Low- and Intermediate-Affinity Interleukin-2 Receptors: A Novel Model for Activation of Human Peripheral Blood Mononuclear Cells by Interleukin 2", Human Immunology 42, 274-280.

Hu, P. et al. (2003), "Generation of low-toxicity interleukin-2 fusion proteins devoid of vasopermeability activity", Blood, vol. 101, No. 12, 4853-4861.

Intl. Search Report-Written Opinion dated Apr. 25, 2022 for Intl. Appl. No. PCT/US2021/055877, 17 pages.

Klein, C. et al. (2017), "Cergutuzumab amunaleukin (CEA-IL2v), a CEA-targeted IL-2 variant-based immunocytokine for combination cancer immunotherapy: Overcoming limitations of aldesleukin and conventional IL-2-based immunocytokines", OncoImmunology, 6:3, e1277306.

Office Action and Search Report dated Jan. 30, 2023 for Taiwanese Appl. No. 110137881, 11 pages.

Rickert, M. et al. (2005), "The Structure of Interleukin-2 Complexed with Its Alpha Receptor", Science 308 (5727), 1477-1480.

Rojas, G. et al. (2014), "Molecular dissection of the interaction of an antitumor interleukin-2-derived mutein on a phage display-based platform", J. Mol. Recognit. 2015, 28: 261-268.

Satyanarayana, M. (2021), "IL-2 treatment can be dangerous. Here's how drug firms are trying to fix it", C&EN Magazine, vol. 99, Issue 12.

Sauvé, K. et al. (1991), "Localization in human interleukin 2 of the binding site to the α chain (p55) of the interleukin 2 receptor", Proc. Natl. Acad. Sci. USA, vol. 88, pp. 4636-4640, Immunology.

Shanafelt, A. B. et al. (2000), "A T-cell-selective interleukin 2 mutein exhibits potent antitumor activity and is well tolerated in vivo", Nature Biotechnology, vol. 18, 1197-1202.

Sim, G. C. et al. (2016), "IL2 Variant Circumvents ICOS+ Regulatory T-cell Expansion and Promotes NK Cell Activation", Cancer Immunol Res 2016, 4:983-994.

Sun, Z. et al. (2019), "A next-generation tumor-targeting IL-2 preferentially promotes tumor-infiltrating CD8+ T-cell response and effective tumor control", Nature Communications 10:3874, 1-12.

Vazquez-Lombardi, R. et al. (2017), "Potent antitumour activity of interleukin-2-Fc fusion proteins requires Fc-mediated depletion of regulatory T-cells", Nat. Commun. 8, 15373, pp. 1-12.

Wang, Z. et al. (1995), "Substitutions at the Glu62 residue of human interleukin-2 differentially affect its binding to the a chain and the βγ complex of the interleukin-2 receptor", Eur. J. Immunol. 25: 1212-1216.

Yamaue, H. et al. (1994), "Enhanced Interleukin-2 Production in Human Tumor-Infiltrating Lymphocytes Engineered by 3'-Truncated Interleukin-2 Gene", Journal of Immunotherapy 16(4):262-274.

Intl. Preliminary Report on Patentability-Written Opinion dated May 4, 2023 for Intl. Appl. No. PCT/US2021/055877.

Notice of Allowance dated Jul. 21, 2023 for Taiwanese Appl. No. 110137881.

First Examination Report dated Sep. 1, 2023 for Australian Appl. No. 2021365129, 6 pages.

SEQUENCE LISTING

```
<160> NUMBER OF SEQ ID NOS: 265

<210> SEQ ID NO 1
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: R, S, G or A
<220> FEATURE:
<221> NAME/KEY: MOD_RES
<222> LOCATION: (36)..(36)
<223> OTHER INFORMATION: T, G or A
<220> FEATURE:
<221> NAME/KEY: MOD_RES
<222> LOCATION: (37)..(37)
<223> OTHER INFORMATION: F, G or A
<220> FEATURE:
<221> NAME/KEY: MOD_RES
<222> LOCATION: (40)..(40)
<223> OTHER INFORMATION: Y, G or A
<220> FEATURE:
<221> NAME/KEY: MOD_RES
<222> LOCATION: (56)..(56)
<223> OTHER INFORMATION: E, G or A
<220> FEATURE:
<221> NAME/KEY: MOD_RES
<222> LOCATION: (57)..(57)
<223> OTHER INFORMATION: E, G or A
<220> FEATURE:
<221> NAME/KEY: MOD_RES
<222> LOCATION: (63)..(63)
<223> OTHER INFORMATION: E, G or A
<220> FEATURE:
<221> NAME/KEY: MOD_RES
<222> LOCATION: (67)..(67)
<223> OTHER INFORMATION: L, G or A
<220> FEATURE:
<221> NAME/KEY: MOD_RES
<222> LOCATION: (69)..(69)
<223> OTHER INFORMATION: Q, G or A
<220> FEATURE:
<221> NAME/KEY: MOD_RES
<222> LOCATION: (102)..(102)
<223> OTHER INFORMATION: Y, G or A

<400> SEQUENCE: 1
```

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Xaa Met Leu Xaa Xaa Lys Phe Xaa Met Pro Lys Lys Ala Thr Glu Leu
        35                  40                  45

Lys His Leu Gln Cys Leu Glu Xaa Xaa Leu Lys Pro Leu Glu Xaa Val
    50                  55                  60

Leu Asn Xaa Ala Xaa Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Xaa Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 2
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (33)..(33)
<223> OTHER INFORMATION: R, S, G or A
<220> FEATURE:
<221> NAME/KEY: MOD_RES
<222> LOCATION: (37)..(37)
<223> OTHER INFORMATION: F, G or A
<220> FEATURE:
<221> NAME/KEY: MOD_RES
<222> LOCATION: (40)..(40)
<223> OTHER INFORMATION: Y, G or A
<220> FEATURE:
<221> NAME/KEY: MOD_RES
<222> LOCATION: (56)..(56)
<223> OTHER INFORMATION: E, G or A
<220> FEATURE:
<221> NAME/KEY: MOD_RES
<222> LOCATION: (57)..(57)
<223> OTHER INFORMATION: E, G or A
<220> FEATURE:
<221> NAME/KEY: MOD_RES
<222> LOCATION: (67)..(67)
<223> OTHER INFORMATION: L, G or A

<400> SEQUENCE: 2

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Xaa Met Leu Thr Xaa Lys Phe Xaa Met Pro Lys Lys Ala Thr Glu Leu
        35                  40                  45

Lys His Leu Gln Cys Leu Glu Xaa Xaa Leu Lys Pro Leu Glu Glu Val
    50                  55                  60

Leu Asn Xaa Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110
```

Leu Asn Arg Trp Ile Thr Phe Ser Gln Ser Ile Ile Ser Thr Leu Thr
115 120 125

<210> SEQ ID NO 3
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (33)..(33)
<223> OTHER INFORMATION: R, S, G or A
<220> FEATURE:
<221> NAME/KEY: MOD_RES
<222> LOCATION: (37)..(37)
<223> OTHER INFORMATION: F, G or A
<220> FEATURE:
<221> NAME/KEY: MOD_RES
<222> LOCATION: (40)..(40)
<223> OTHER INFORMATION: Y, G or A
<220> FEATURE:
<221> NAME/KEY: MOD_RES
<222> LOCATION: (56)..(56)
<223> OTHER INFORMATION: E, G or A
<220> FEATURE:
<221> NAME/KEY: MOD_RES
<222> LOCATION: (57)..(57)
<223> OTHER INFORMATION: E, G or A

<400> SEQUENCE: 3

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Xaa Met Leu Thr Xaa Lys Phe Xaa Met Pro Lys Lys Ala Thr Glu Leu
35 40 45

Lys His Leu Gln Cys Leu Glu Xaa Xaa Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 4
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (33)..(33)
<223> OTHER INFORMATION: R, S, G or A
<220> FEATURE:
<221> NAME/KEY: MOD_RES
<222> LOCATION: (37)..(37)
<223> OTHER INFORMATION: F, G or A
<220> FEATURE:
<221> NAME/KEY: MOD_RES
<222> LOCATION: (40)..(40)
<223> OTHER INFORMATION: Y, G or A
<220> FEATURE:
<221> NAME/KEY: MOD_RES
<222> LOCATION: (57)..(57)
<223> OTHER INFORMATION: E, G or A

<400> SEQUENCE: 4

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Xaa Met Leu Thr Xaa Lys Phe Xaa Met Pro Lys Lys Ala Thr Glu Leu
        35                  40                  45

Lys His Leu Gln Cys Leu Glu Glu Xaa Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 5
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (33)..(33)
<223> OTHER INFORMATION: R, S, G or A
<220> FEATURE:
<221> NAME/KEY: MOD_RES
<222> LOCATION: (37)..(37)
<223> OTHER INFORMATION: F, G or A
<220> FEATURE:
<221> NAME/KEY: MOD_RES
<222> LOCATION: (57)..(57)
<223> OTHER INFORMATION: E, G or A

<400> SEQUENCE: 5

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Xaa Met Leu Thr Xaa Lys Phe Tyr Met Pro Lys Lys Ala Thr Glu Leu
        35                  40                  45

Lys His Leu Gln Cys Leu Glu Glu Xaa Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 6
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (33)..(33)
<223> OTHER INFORMATION: R, S, G or A

<400> SEQUENCE: 6

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Xaa Met Leu Thr Ala Lys Phe Tyr Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 7
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 7

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Tyr Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 8
<211> LENGTH: 128
<212> TYPE: PRT
<213> ORGANISM: Artificial Sequence
<220> FEATURE:

<223> OTHER INFORMATION: Description of Artificial Sequence: Synthetic
polypeptide

<400> SEQUENCE: 8

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Ala Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 9
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 9

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Gly Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 10
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 10

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr 20 25 30

Arg Met Leu Ala Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 11
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 11

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Gly Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 12
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 12

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Ala Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu

```
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 13
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Gly Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 14
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Ala Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
```

115 120 125

<210> SEQ ID NO 15
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 15

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Ala Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 16
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 16

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Ala Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 17
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 17

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Ala Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 18
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 18

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Gly Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 19
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 19

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gly Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 20
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 20

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Gly Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 21
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 21

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Ala Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 22
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 22

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Gly Met Pro Lys Lys Ala Thr Glu Leu
35 40 45

Lys His Leu Gln Cys Leu Glu Ala Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 23
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 23

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Gly Met Pro Lys Lys Ala Thr Glu Leu
35 40 45

Lys His Leu Gln Cys Leu Glu Glu Ala Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 24
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Gly Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 25
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 25

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Tyr Met Pro Lys Lys Ala Thr Glu Leu
        35                  40                  45

Lys His Leu Gln Cys Leu Glu Ala Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 26
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Ala Lys Phe Tyr Met Pro Lys Lys Ala Thr Glu Leu
        35                  40                  45

Lys His Leu Gln Cys Leu Glu Ala Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125

<210> SEQ ID NO 27
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Ala Lys Phe Gly Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125

<210> SEQ ID NO 28
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Gly Met Pro Lys Lys Ala Thr Glu Leu
35 40 45

Lys His Leu Gln Cys Leu Glu Ala Ala Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 29
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 29

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Phe Lys Phe Tyr Met Pro Lys Lys Ala Thr Glu Leu
35 40 45

Lys His Leu Gln Cys Leu Glu Ala Ala Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 30
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 30

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Gly Met Leu Thr Ala Lys Phe Tyr Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 31
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 31

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Ala Lys Phe Ala Met Pro Lys Lys Ala Thr Glu Leu
35 40 45

Lys His Leu Gln Cys Leu Glu Glu Glu Leu Lys Pro Leu Glu Glu Val
50 55 60

Leu Asn Gly Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 32
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 32

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Gly Met Leu Thr Ala Lys Phe Gly Met Pro Lys Lys Ala Thr Glu Leu
35 40 45

Lys His Leu Gln Cys Leu Glu Glu Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 33
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Ala Lys Phe Tyr Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 34
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Ala Lys Phe Gly Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 35
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 35

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Arg Met Leu Thr Ala Lys Phe Gly Met Pro Lys Lys Ala Thr Glu Leu
35 40 45

Lys His Leu Gln Cys Leu Glu Ala Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 36
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 36

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Gly Met Leu Thr Phe Lys Phe Gly Met Pro Lys Lys Ala Thr Glu Leu
35 40 45

Lys His Leu Gln Cys Leu Glu Ala Glu Leu Lys Pro Leu Glu Glu Val
50 55 60

Leu Asn Leu Ala Gln Ser Lys Asn Phe His Leu Arg Pro Arg Asp Leu
65 70 75 80

Ile Ser Asn Ile Asn Val Ile Val Leu Glu Leu Lys Gly Ser Glu Thr
85 90 95

Thr Phe Met Cys Glu Tyr Ala Asp Glu Thr Ala Thr Ile Val Glu Phe
100 105 110

Leu Asn Arg Trp Ile Thr Phe Ser Gln Ser Ile Ile Ser Thr Leu Thr
115 120 125

<210> SEQ ID NO 37
<211> LENGTH: 128
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 37

Ser Thr Lys Lys Thr Gln Leu Gln Leu Glu His Leu Leu Leu Asp Leu
1 5 10 15

Gln Met Ile Leu Asn Gly Ile Asn Asn Tyr Lys Asn Pro Lys Leu Thr
20 25 30

Gly Met Leu Thr Ala Lys Phe Tyr Met Pro Lys Lys Ala Thr Glu Leu

```
        35                  40                  45

Lys His Leu Gln Cys Leu Glu Ala Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 38
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Gly Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 39
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Tyr Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
```

```
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 40
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 40

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Ala Lys Phe Tyr Met Pro Lys Lys Ala Thr Glu Leu
        35                  40                  45

Lys His Leu Gln Cys Leu Glu Glu Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125


<210> SEQ ID NO 41
<211> LENGTH: 128
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 41

Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Ala Lys Phe Tyr Met Pro Lys Lys Ala Thr Glu Leu
        35                  40                  45

Lys His Leu Gln Cys Leu Glu Ala Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 42
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 42

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Gly Met Leu Thr Phe Lys Phe Tyr Met Pro Lys Lys Ala Thr Glu Leu
        35                  40                  45

Lys His Leu Gln Cys Leu Glu Ala Ala Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 43
<211> LENGTH: 128
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 43

```
Ser Thr Lys Lys Thr Gln Leu Gln Leu Glu His Leu Leu Leu Asp Leu
1               5                   10                  15

Gln Met Ile Leu Asn Gly Ile Asn Asn Tyr Lys Asn Pro Lys Leu Thr
            20                  25                  30

Arg Met Leu Thr Phe Lys Phe Tyr Met Pro Lys Lys Ala Thr Glu Leu
        35                  40                  45

Lys His Leu Gln Cys Leu Glu Glu Glu Leu Lys Pro Leu Glu Glu Val
    50                  55                  60

Leu Asn Leu Ala Gln Ser Lys Asn Phe His Leu Arg Pro Arg Asp Leu
65                  70                  75                  80

Ile Ser Asn Ile Asn Val Ile Val Leu Glu Leu Lys Gly Ser Glu Thr
                85                  90                  95

Thr Phe Met Cys Glu Tyr Ala Asp Glu Thr Ala Thr Ile Val Glu Phe
            100                 105                 110

Leu Asn Arg Trp Ile Thr Phe Ser Gln Ser Ile Ile Ser Thr Leu Thr
        115                 120                 125
```

<210> SEQ ID NO 44
<211> LENGTH: 133
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 44

Ala Pro Ala Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110

Thr Ile Val Glu Phe Leu Asn Arg Trp Ile Thr Phe Ser Gln Ser Ile
        115                 120                 125

Ile Ser Thr Leu Thr
    130

<210> SEQ ID NO 45
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 45

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser 210 215 220

Leu Ser Leu Gly
225

<210> SEQ ID NO 46
<211> LENGTH: 229
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 46

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu
180 185 190

Thr Val Asp Lys Ser Arg Trp Gln Glu Gly Asn Val Phe Ser Cys Ser
195 200 205

Val Met His Glu Ala Leu His Asn Arg Phe Thr Gln Lys Ser Leu Ser
210 215 220

Leu Ser Leu Gly Lys
225

<210> SEQ ID NO 47
<211> LENGTH: 228
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 47

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val 35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu
180 185 190

Thr Val Asp Lys Ser Arg Trp Gln Glu Gly Asn Val Phe Ser Cys Ser
195 200 205

Val Met His Glu Ala Leu His Asn Arg Phe Thr Gln Lys Ser Leu Ser
210 215 220

Leu Ser Leu Gly
225

<210> SEQ ID NO 48
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 48

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

```
Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 49
<211> LENGTH: 228
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Tyr Ile Thr Arg Glu Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly
225


<210> SEQ ID NO 50
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 50

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Leu His Glu Ala Leu His Ser His Tyr Thr Gln Lys Ser Leu Ser
210 215 220

Leu Ser Leu Gly Lys
225

<210> SEQ ID NO 51
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 51

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Tyr Ile Thr Arg Glu Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu
180 185 190

Thr Val Asp Lys Ser Arg Trp Gln Glu Gly Asn Val Phe Ser Cys Ser
195 200 205

Val Met His Glu Ala Leu His Asn Arg Phe Thr Gln Lys Ser Leu Ser
210 215 220

Leu Ser Leu Gly Lys
225

<210> SEQ ID NO 52
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 52

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Tyr Ile Thr Arg Glu Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Val Ser Arg Leu
180 185 190

Thr Val Asp Lys Ser Arg Trp Gln Glu Gly Asn Val Phe Ser Cys Ser
195 200 205

Val Met His Glu Ala Leu His Asn Arg Phe Thr Gln Lys Ser Leu Ser
210 215 220

Leu Ser Leu Gly

225

<210> SEQ ID NO 53
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 53

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Tyr Ile Thr Arg Glu Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 54
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 54

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val 50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Leu His Glu Ala Leu His Ser His Tyr Thr Gln Lys Ser Leu Ser
210 215 220

Leu Ser Leu Gly
225

<210> SEQ ID NO 55
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 55

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Ser Cys Ala Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

```
Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Leu His Glu Ala Leu His Ser Arg Phe Thr Gln Lys Ser Leu Ser
    210                 215                 220

Leu Ser Leu Gly Lys
225
```

<210> SEQ ID NO 56
<211> LENGTH: 228
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 56

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Leu His Glu Ala Leu His Ser Arg Phe Thr Gln Lys Ser Leu Ser
    210                 215                 220

Leu Ser Leu Gly
225
```

<210> SEQ ID NO 57
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 57

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230
```

<210> SEQ ID NO 58
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 58

```
Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125
```

```
Arg Glu Pro Gln Val Tyr Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230


<210> SEQ ID NO 59
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 59

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly
225                 230
```

<210> SEQ ID NO 60
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 60

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 61
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 61

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
```

65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly
225 230

<210> SEQ ID NO 62
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 62

Glu Pro Lys Ser Cys Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Tyr Ile Thr Arg Glu Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Ser Cys Ala Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Val
180 185 190

```
Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly Lys
225                 230


<210> SEQ ID NO 63
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly
225                 230


<210> SEQ ID NO 64
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Glu Pro Lys Ser Ser Asp Lys Thr His Thr Cys Pro Pro Cys Pro Ala
1               5                   10                  15
```

Pro Glu Ala Ala Gly Gly Pro Ser Val Phe Leu Phe Pro Pro Lys Pro
20 25 30

Lys Asp Thr Leu Tyr Ile Thr Arg Glu Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn Arg Phe Thr Gln Lys
210 215 220

Ser Leu Ser Leu Ser Pro Gly Lys
225 230

<210> SEQ ID NO 65
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 65

Glu Pro Lys Ser Cys Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Tyr Ile Thr Arg Glu Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

```
Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly
225                 230


<210> SEQ ID NO 66
<211> LENGTH: 232
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 66

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 67
<211> LENGTH: 231
<212> TYPE: PRT
```

<213> ORGANISM: Artificial Sequence
<220> FEATURE:
<223> OTHER INFORMATION: Description of Artificial Sequence: Synthetic polypeptide

<400> SEQUENCE: 67

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn Arg Phe Thr Gln Lys
    210                 215                 220

Ser Leu Ser Leu Ser Pro Gly
225                 230
```

<210> SEQ ID NO 68
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 68

```
Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Tyr Ile Thr Arg Glu Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
```

```
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230


<210> SEQ ID NO 69
<211> LENGTH: 231
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205
```

Ser Cys Ser Val Leu His Glu Ala Leu His Ser His Tyr Thr Gln Lys
    210                 215                 220

Ser Leu Ser Leu Ser Pro Gly
225                 230

<210> SEQ ID NO 70
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 70

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Ser Cys Ala Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Val
            180                 185                 190

Ser Lys Leu Thr Val Asp Lys Ser Arg Trp Gln Gln Gly Asn Val Phe
        195                 200                 205

Ser Cys Ser Val Leu His Glu Ala Leu His Ser Arg Phe Thr Gln Lys
    210                 215                 220

Ser Leu Ser Leu Ser Pro Gly Lys
225                 230

<210> SEQ ID NO 71
<211> LENGTH: 231
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 71

Glu Pro Lys Ser Cys Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Ser Cys Ala Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Val
180 185 190

Ser Lys Leu Thr Val Asp Lys Ser Arg Trp Gln Gln Gly Asn Val Phe
195 200 205

Ser Cys Ser Val Leu His Glu Ala Leu His Ser Arg Phe Thr Gln Lys
210 215 220

Ser Leu Ser Leu Ser Pro Gly
225 230

<210> SEQ ID NO 72
<211> LENGTH: 232
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 72

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Leu His Glu Ala Leu His Ser His Tyr Thr Gln Lys
210 215 220

Ser Leu Ser Leu Ser Pro Gly Lys
225 230

<210> SEQ ID NO 73

<400> SEQUENCE: 73

000

<210> SEQ ID NO 74
<211> LENGTH: 232
<212> TYPE: PRT
<213> ORGANISM: Homo sapiens

<400> SEQUENCE: 74

Glu Pro Lys Ser Cys Asp Lys Thr His Thr Cys Pro Pro Cys Pro Ala
1 5 10 15

Pro Glu Leu Leu Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Pro Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Thr Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Lys
225 230

<210> SEQ ID NO 75
<211> LENGTH: 376

<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (281)..(281)
<223> OTHER INFORMATION: R, S, G or A
<220> FEATURE:
<221> NAME/KEY: MOD_RES
<222> LOCATION: (284)..(284)
<223> OTHER INFORMATION: T, G or A
<220> FEATURE:
<221> NAME/KEY: MOD_RES
<222> LOCATION: (285)..(285)
<223> OTHER INFORMATION: F, G or A
<220> FEATURE:
<221> NAME/KEY: MOD_RES
<222> LOCATION: (288)..(288)
<223> OTHER INFORMATION: Y, G or A
<220> FEATURE:
<221> NAME/KEY: MOD_RES
<222> LOCATION: (304)..(304)
<223> OTHER INFORMATION: E, G or A
<220> FEATURE:
<221> NAME/KEY: MOD_RES
<222> LOCATION: (305)..(305)
<223> OTHER INFORMATION: E, G or A
<220> FEATURE:
<221> NAME/KEY: MOD_RES
<222> LOCATION: (311)..(311)
<223> OTHER INFORMATION: E, G or A
<220> FEATURE:
<221> NAME/KEY: MOD_RES
<222> LOCATION: (315)..(315)
<223> OTHER INFORMATION: L, G or A
<220> FEATURE:
<221> NAME/KEY: MOD_RES
<222> LOCATION: (317)..(317)
<223> OTHER INFORMATION: Q, G or A
<220> FEATURE:
<221> NAME/KEY: MOD_RES
<222> LOCATION: (350)..(350)
<223> OTHER INFORMATION: Y, G or A

<400> SEQUENCE: 75

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
```

165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Xaa Met Leu Xaa Xaa Lys Phe Xaa
275 280 285

Met Pro Lys Lys Ala Thr Glu Leu Lys His Leu Gln Cys Leu Glu Xaa
290 295 300

Xaa Leu Lys Pro Leu Glu Xaa Val Leu Asn Xaa Ala Xaa Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Xaa Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 76
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide
<220> FEATURE:
<221> NAME/KEY: MOD_RES
<222> LOCATION: (281)..(281)
<223> OTHER INFORMATION: R, S, G or A
<220> FEATURE:
<221> NAME/KEY: MOD_RES
<222> LOCATION: (285)..(285)
<223> OTHER INFORMATION: F, G or A
<220> FEATURE:
<221> NAME/KEY: MOD_RES
<222> LOCATION: (288)..(288)
<223> OTHER INFORMATION: Y, G or A
<220> FEATURE:
<221> NAME/KEY: MOD_RES
<222> LOCATION: (304)..(304)
<223> OTHER INFORMATION: E, G or A
<220> FEATURE:
<221> NAME/KEY: MOD_RES
<222> LOCATION: (305)..(305)
<223> OTHER INFORMATION: E, G or A
<220> FEATURE:
<221> NAME/KEY: MOD_RES
<222> LOCATION: (315)..(315)
<223> OTHER INFORMATION: L, G or A

<400> SEQUENCE: 76

Glu Ser Lys Tyr Gly Pro Pro Cys Pro Pro Cys Pro Ala Pro Glu Ala
1 5 10 15

```
Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Xaa Met Leu Thr Xaa Lys Phe Xaa
        275                 280                 285

Met Pro Lys Lys Ala Thr Glu Leu Lys His Leu Gln Cys Leu Glu Xaa
    290                 295                 300

Xaa Leu Lys Pro Leu Glu Glu Val Leu Asn Xaa Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 77
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (281)..(281)
<223> OTHER INFORMATION: R, S, G or A
<220> FEATURE:
<221> NAME/KEY: MOD_RES
<222> LOCATION: (285)..(285)
<223> OTHER INFORMATION: F, G or A
<220> FEATURE:
<221> NAME/KEY: MOD_RES
<222> LOCATION: (288)..(288)
<223> OTHER INFORMATION: Y, G or A
<220> FEATURE:
<221> NAME/KEY: MOD_RES
<222> LOCATION: (304)..(304)
<223> OTHER INFORMATION: E, G or A
<220> FEATURE:
<221> NAME/KEY: MOD_RES
<222> LOCATION: (305)..(305)
<223> OTHER INFORMATION: E, G or A

<400> SEQUENCE: 77

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Xaa Met Leu Thr Xaa Lys Phe Xaa
        275                 280                 285

Met Pro Lys Lys Ala Thr Glu Leu Lys His Leu Gln Cys Leu Glu Xaa
    290                 295                 300

Xaa Leu Lys Pro Leu Glu Glu Val Leu Asn Leu Ala Gln Ser Lys Asn
```

305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 78
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (281)..(281)
<223> OTHER INFORMATION: R, S, G or A
<220> FEATURE:
<221> NAME/KEY: MOD_RES
<222> LOCATION: (285)..(285)
<223> OTHER INFORMATION: F, G or A
<220> FEATURE:
<221> NAME/KEY: MOD_RES
<222> LOCATION: (288)..(288)
<223> OTHER INFORMATION: Y, G or A
<220> FEATURE:
<221> NAME/KEY: MOD_RES
<222> LOCATION: (305)..(305)
<223> OTHER INFORMATION: E, G or A

<400> SEQUENCE: 78

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

```
Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Xaa Met Leu Thr Xaa Lys Phe Xaa
        275                 280                 285

Met Pro Lys Lys Ala Thr Glu Leu Lys His Leu Gln Cys Leu Glu Glu
    290                 295                 300

Xaa Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 79
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (281)..(281)
<223> OTHER INFORMATION: R, S, G or A
<220> FEATURE:
<221> NAME/KEY: MOD_RES
<222> LOCATION: (285)..(285)
<223> OTHER INFORMATION: F, G or A
<220> FEATURE:
<221> NAME/KEY: MOD_RES
<222> LOCATION: (305)..(305)
<223> OTHER INFORMATION: E, G or A

<400> SEQUENCE: 79

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
```

```
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Xaa Met Leu Thr Xaa Lys Phe Tyr
        275                 280                 285

Met Pro Lys Lys Ala Thr Glu Leu Lys His Leu Gln Cys Leu Glu Glu
    290                 295                 300

Xaa Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 80
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (281)..(281)
<223> OTHER INFORMATION: R, S, G or A

<400> SEQUENCE: 80

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80
```

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Xaa Met Leu Thr Ala Lys Phe Tyr
275 280 285

Met Pro Lys Lys Ala Thr Glu Leu Lys His Leu Gln Cys Leu Glu Glu
290 295 300

Ala Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 81
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 81

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val

-continued

```
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 82
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 82

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30
```

-continued

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Ala Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 83
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 83

Glu Ser Lys Tyr Gly Pro Pro Cys Pro Pro Cys Pro Ala Pro Glu Ala
1               5                   10                  15
```

```
Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Gly Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 84
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide -continued

<400> SEQUENCE: 84

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Ala Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 85
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 85

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Gly Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 86
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 86

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Ala Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365
```

```
Gln Ser Ile Ile Ser Thr Leu Thr
    370                 375


<210> SEQ ID NO 87
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Gly
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350
```

```
Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 88
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Ala
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
```

```
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 89
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Ala
    290                 295                 300
```

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 90
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 90

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Phe Lys Phe Tyr
275 280 285

```
Met Pro Lys Lys Ala Thr Glu Leu Lys His Leu Gln Cys Leu Glu Glu
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 91
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 91

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
```

260 265 270

Asn Tyr Lys Asn Pro Lys Leu Thr Arg Met Leu Thr Phe Lys Phe Tyr
275 280 285

Met Pro Lys Lys Ala Thr Glu Leu Lys His Leu Gln Cys Leu Glu Glu
290 295 300

Glu Leu Lys Pro Leu Glu Ala Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 92
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 92

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

```
Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Gly Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 93
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 93

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220
```

```
Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gly Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 94
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
```

```
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Gly Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 95
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 95

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Phe Lys Phe Tyr
275 280 285

Met Pro Lys Lys Ala Thr Glu Leu Lys His Leu Gln Cys Leu Glu Glu
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Ala Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 96
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 96

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Phe Lys Phe Gly
275 280 285

Met Pro Lys Lys Ala Thr Glu Leu Lys His Leu Gln Cys Leu Glu Ala
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 97
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 97

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln 130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Phe Lys Phe Gly
275 280 285

Met Pro Lys Lys Ala Thr Glu Leu Lys His Leu Gln Cys Leu Glu Glu
290 295 300

Ala Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 98
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 98

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

```
Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Phe Lys Phe Gly
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 99
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95
```

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Gly Met Leu Thr Phe Lys Phe Tyr
275 280 285

Met Pro Lys Lys Ala Thr Glu Leu Lys His Leu Gln Cys Leu Glu Ala
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 100
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 100

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser 65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Ala Lys Phe Tyr
275 280 285

Met Pro Lys Lys Ala Thr Glu Leu Lys His Leu Gln Cys Leu Glu Ala
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 101
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 101

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Ala Lys Phe Gly
275 280 285

Met Pro Lys Lys Ala Thr Glu Leu Lys His Leu Gln Cys Leu Glu Glu
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 102
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 102

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

```
Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Gly
        275                 280                 285

Met Pro Lys Lys Ala Thr Glu Leu Lys His Leu Gln Cys Leu Glu Ala
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 103
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 103

```
Glu Ser Lys Tyr Gly Pro Pro Cys Pro Pro Cys Pro Ala Pro Glu Ala
```

-continued

```
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Ala
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 104
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 104

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Ala Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 105
<211> LENGTH: 376
<212> TYPE: PRT

<213> ORGANISM: Artificial Sequence
<220> FEATURE:
<223> OTHER INFORMATION: Description of Artificial Sequence: Synthetic
polypeptide

<400> SEQUENCE: 105

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Ala Lys Phe Ala
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Gly Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

```
<210> SEQ ID NO 106
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Ala Lys Phe Gly
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365
```

Gln Ser Ile Ile Ser Thr Leu Thr
    370                 375

<210> SEQ ID NO 107
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 107

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Ala Lys Phe Tyr
        275                 280                 285

Met Pro Lys Lys Ala Thr Glu Leu Lys His Leu Gln Cys Leu Glu Glu
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp 340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 108
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 108

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Ala Lys Phe Gly
275 280 285

Met Pro Lys Lys Ala Thr Glu Leu Lys His Leu Gln Cys Leu Glu Glu
290 295 300

Ala Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 109
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 109

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Ala Lys Phe Gly
275 280 285

Met Pro Lys Lys Ala Thr Glu Leu Lys His Leu Gln Cys Leu Glu Ala
290 295 300

Glu Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 110
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 110

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Gly Met Leu Thr Phe Lys Phe Gly

```
        275                 280                 285

Met Pro Lys Lys Ala Thr Glu Leu Lys His Leu Gln Cys Leu Glu Ala
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 111
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255
```

```
Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Ala Lys Phe Tyr
        275                 280                 285

Met Pro Lys Lys Ala Thr Glu Leu Lys His Leu Gln Cys Leu Glu Ala
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 112
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 112

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240
```

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Gly Met Leu Thr Phe Lys Phe Gly
275 280 285

Met Pro Lys Lys Ala Thr Glu Leu Lys His Leu Gln Cys Leu Glu Glu
290 295 300

Ala Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 113
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 113

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser

```
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
            245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Phe Lys Phe Tyr
        275                 280                 285

Met Pro Lys Lys Ala Thr Glu Leu Lys His Leu Gln Cys Leu Glu Glu
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
            325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375
```

<210> SEQ ID NO 114
<211> LENGTH: 376
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 114

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
            85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
            165                 170                 175

Pro Pro Val Leu Asp Ser Asp Gly Ser Phe Phe Leu Tyr Ser Arg Leu
            180                 185                 190
```

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Ala Lys Phe Tyr
        275                 280                 285

Met Pro Lys Lys Ala Thr Glu Leu Lys His Leu Gln Cys Leu Glu Glu
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 115
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 115

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Gly Gly Gly Gly Ser Gly Gly Gly Gly Ser Gly Gly
225 230 235 240

Gly Gly Ser Gly Gly Gly Gly Ser Ser Thr Lys Lys Thr Gln Leu Gln
245 250 255

Leu Glu His Leu Leu Leu Asp Leu Gln Met Ile Leu Asn Gly Ile Asn
260 265 270

Asn Tyr Lys Asn Pro Lys Leu Thr Arg Met Leu Thr Ala Lys Phe Tyr
275 280 285

Met Pro Lys Lys Ala Thr Glu Leu Lys His Leu Gln Cys Leu Glu Ala
290 295 300

Ala Leu Lys Pro Leu Glu Glu Val Leu Asn Leu Ala Gln Ser Lys Asn
305 310 315 320

Phe His Leu Arg Pro Arg Asp Leu Ile Ser Asn Ile Asn Val Ile Val
325 330 335

Leu Glu Leu Lys Gly Ser Glu Thr Thr Phe Met Cys Glu Tyr Ala Asp
340 345 350

Glu Thr Ala Thr Ile Val Glu Phe Leu Asn Arg Trp Ile Thr Phe Ser
355 360 365

Gln Ser Ile Ile Ser Thr Leu Thr
370 375

<210> SEQ ID NO 116
<211> LENGTH: 376
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 116

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala

```
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Gly Met Leu Thr Phe Lys Phe Tyr
        275                 280                 285

Met Pro Lys Lys Ala Thr Glu Leu Lys His Leu Gln Cys Leu Glu Ala
    290                 295                 300

Ala Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375


<210> SEQ ID NO 117
<211> LENGTH: 376
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 117

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125
```

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ser Thr Lys Lys Thr Gln Leu Gln
                245                 250                 255

Leu Glu His Leu Leu Leu Asp Leu Gln Met Ile Leu Asn Gly Ile Asn
            260                 265                 270

Asn Tyr Lys Asn Pro Lys Leu Thr Arg Met Leu Thr Phe Lys Phe Tyr
        275                 280                 285

Met Pro Lys Lys Ala Thr Glu Leu Lys His Leu Gln Cys Leu Glu Glu
    290                 295                 300

Glu Leu Lys Pro Leu Glu Glu Val Leu Asn Leu Ala Gln Ser Lys Asn
305                 310                 315                 320

Phe His Leu Arg Pro Arg Asp Leu Ile Ser Asn Ile Asn Val Ile Val
                325                 330                 335

Leu Glu Leu Lys Gly Ser Glu Thr Thr Phe Met Cys Glu Tyr Ala Asp
            340                 345                 350

Glu Thr Ala Thr Ile Val Glu Phe Leu Asn Arg Trp Ile Thr Phe Ser
        355                 360                 365

Gln Ser Ile Ile Ser Thr Leu Thr
    370                 375

<210> SEQ ID NO 118
<211> LENGTH: 381
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

```
Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Trp Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Gly Gly Gly Gly Ser Gly Gly Gly Gly Ser Gly Gly
225                 230                 235                 240

Gly Gly Ser Gly Gly Gly Gly Ser Ala Pro Ala Ser Ser Ser Thr Lys
                245                 250                 255

Lys Thr Gln Leu Gln Leu Glu His Leu Leu Leu Asp Leu Gln Met Ile
            260                 265                 270

Leu Asn Gly Ile Asn Asn Tyr Lys Asn Pro Lys Leu Thr Arg Met Leu
        275                 280                 285

Thr Phe Lys Phe Tyr Met Pro Lys Lys Ala Thr Glu Leu Lys His Leu
    290                 295                 300

Gln Cys Leu Glu Glu Glu Leu Lys Pro Leu Glu Glu Val Leu Asn Leu
305                 310                 315                 320

Ala Gln Ser Lys Asn Phe His Leu Arg Pro Arg Asp Leu Ile Ser Asn
                325                 330                 335

Ile Asn Val Ile Val Leu Glu Leu Lys Gly Ser Glu Thr Thr Phe Met
            340                 345                 350

Cys Glu Tyr Ala Asp Glu Thr Ala Thr Ile Val Glu Phe Leu Asn Arg
        355                 360                 365

Trp Ile Thr Phe Ser Gln Ser Ile Ile Ser Thr Leu Thr
    370                 375                 380
```

<210> SEQ ID NO 119
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (284)..(284)
<223> OTHER INFORMATION: R, S, G or A
<220> FEATURE:
<221> NAME/KEY: MOD_RES
<222> LOCATION: (287)..(287)
<223> OTHER INFORMATION: T, G or A
<220> FEATURE:
<221> NAME/KEY: MOD_RES
<222> LOCATION: (288)..(288)
<223> OTHER INFORMATION: F, G or A
<220> FEATURE:
<221> NAME/KEY: MOD_RES
<222> LOCATION: (291)..(291)
<223> OTHER INFORMATION: Y, G or A
<220> FEATURE:
<221> NAME/KEY: MOD_RES
<222> LOCATION: (307)..(307)

<223> OTHER INFORMATION: E, G or A
<220> FEATURE:
<221> NAME/KEY: MOD_RES
<222> LOCATION: (308)..(308)
<223> OTHER INFORMATION: E, G or A
<220> FEATURE:
<221> NAME/KEY: MOD_RES
<222> LOCATION: (314)..(314)
<223> OTHER INFORMATION: E, G or A
<220> FEATURE:
<221> NAME/KEY: MOD_RES
<222> LOCATION: (318)..(318)
<223> OTHER INFORMATION: L, G or A
<220> FEATURE:
<221> NAME/KEY: MOD_RES
<222> LOCATION: (320)..(320)
<223> OTHER INFORMATION: Q, G or A
<220> FEATURE:
<221> NAME/KEY: MOD_RES
<222> LOCATION: (353)..(353)
<223> OTHER INFORMATION: Y, G or A

<400> SEQUENCE: 119

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Xaa Met Leu Xaa Xaa
        275                 280                 285

Lys Phe Xaa Met Pro Lys Lys Ala Thr Glu Leu Lys His Leu Gln Cys
```

290 295 300

Leu Glu Xaa Xaa Leu Lys Pro Leu Glu Xaa Val Leu Asn Xaa Ala Xaa
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Xaa Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 120
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (284)..(284)
<223> OTHER INFORMATION: R, S, G or A
<220> FEATURE:
<221> NAME/KEY: MOD_RES
<222> LOCATION: (288)..(288)
<223> OTHER INFORMATION: F, G or A
<220> FEATURE:
<221> NAME/KEY: MOD_RES
<222> LOCATION: (291)..(291)
<223> OTHER INFORMATION: Y, G or A
<220> FEATURE:
<221> NAME/KEY: MOD_RES
<222> LOCATION: (307)..(307)
<223> OTHER INFORMATION: E, G or A
<220> FEATURE:
<221> NAME/KEY: MOD_RES
<222> LOCATION: (308)..(308)
<223> OTHER INFORMATION: E, G or A
<220> FEATURE:
<221> NAME/KEY: MOD_RES
<222> LOCATION: (318)..(318)
<223> OTHER INFORMATION: L, G or A

<400> SEQUENCE: 120

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

-continued

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Xaa Met Leu Thr Xaa
275 280 285

Lys Phe Xaa Met Pro Lys Lys Ala Thr Glu Leu Lys His Leu Gln Cys
290 295 300

Leu Glu Xaa Xaa Leu Lys Pro Leu Glu Glu Val Leu Asn Xaa Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 121
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (284)..(284)
<223> OTHER INFORMATION: R, S, G or A
<220> FEATURE:
<221> NAME/KEY: MOD_RES
<222> LOCATION: (288)..(288)
<223> OTHER INFORMATION: F, G or A
<220> FEATURE:
<221> NAME/KEY: MOD_RES
<222> LOCATION: (291)..(291)
<223> OTHER INFORMATION: Y, G or A
<220> FEATURE:
<221> NAME/KEY: MOD_RES
<222> LOCATION: (307)..(307)
<223> OTHER INFORMATION: E, G or A
<220> FEATURE:
<221> NAME/KEY: MOD_RES
<222> LOCATION: (308)..(308)
<223> OTHER INFORMATION: E, G or A

<400> SEQUENCE: 121

Glu Pro Lys Ser Ser Asp Lys Thr His Thr Cys Pro Pro Cys Pro Ala
1 5 10 15

```
Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Xaa Met Leu Thr Xaa
        275                 280                 285

Lys Phe Xaa Met Pro Lys Lys Ala Thr Glu Leu Lys His Leu Gln Cys
    290                 295                 300

Leu Glu Xaa Xaa Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

<210> SEQ ID NO 122
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (284)..(284)
<223> OTHER INFORMATION: R, S, G or A
<220> FEATURE:
<221> NAME/KEY: MOD_RES
<222> LOCATION: (288)..(288)
<223> OTHER INFORMATION: F, G or A
<220> FEATURE:
<221> NAME/KEY: MOD_RES
<222> LOCATION: (291)..(291)
<223> OTHER INFORMATION: Y, G or A
<220> FEATURE:
<221> NAME/KEY: MOD_RES
<222> LOCATION: (308)..(308)
<223> OTHER INFORMATION: E, G or A

<400> SEQUENCE: 122

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Xaa Met Leu Thr Xaa
        275                 280                 285

Lys Phe Xaa Met Pro Lys Lys Ala Thr Glu Leu Lys His Leu Gln Cys
    290                 295                 300

Leu Glu Glu Xaa Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335
```

```
Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 123
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (284)..(284)
<223> OTHER INFORMATION: R, S, G or A
<220> FEATURE:
<221> NAME/KEY: MOD_RES
<222> LOCATION: (288)..(288)
<223> OTHER INFORMATION: F, G or A
<220> FEATURE:
<221> NAME/KEY: MOD_RES
<222> LOCATION: (308)..(308)
<223> OTHER INFORMATION: E, G or A

<400> SEQUENCE: 123

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
```

245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Xaa Met Leu Thr Xaa
275 280 285

Lys Phe Tyr Met Pro Lys Lys Ala Thr Glu Leu Lys His Leu Gln Cys
290 295 300

Leu Glu Glu Xaa Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 124
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MOD_RES
<222> LOCATION: (284)..(284)
<223> OTHER INFORMATION: R, S, G or A

<400> SEQUENCE: 124

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Xaa Met Leu Thr Ala
        275                 280                 285

Lys Phe Tyr Met Pro Lys Lys Ala Thr Glu Leu Lys His Leu Gln Cys
    290                 295                 300

Leu Glu Glu Ala Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375

<210> SEQ ID NO 125
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr

```
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Gly Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 126
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 126

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Ala Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

```
<210> SEQ ID NO 127
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140
```

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Gly Phe
275 280 285

Lys Phe Tyr Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 128
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 128

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro

```
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Ala Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 129
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 129

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95
```

```
Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Gly
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 130
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 130

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80
```

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Ala
275 280 285

Lys Phe Tyr Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 131
<211> LENGTH: 379
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 131

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val 50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Gly Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 132
<211> LENGTH: 379
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 132

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Ala Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 133
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 133

Glu Pro Lys Ser Ser Asp Lys Thr His Thr Cys Pro Pro Cys Pro Ala
1 5 10 15

```
Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Ala Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

<210> SEQ ID NO 134
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide -continued

<400> SEQUENCE: 134

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Tyr Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 135
<211> LENGTH: 379
<212> TYPE: PRT
<213> ORGANISM: Artificial Sequence

```
<220> FEATURE:
<223> OTHER INFORMATION: Description of Artificial Sequence: Synthetic
      polypeptide

<400> SEQUENCE: 135

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Ala Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

<210> SEQ ID NO 136
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 136

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Gly Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365
```

```
Thr Phe Ser Gln Ser Ile Ile Ser Thr Leu Thr
    370                 375


<210> SEQ ID NO 137
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 137

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gly
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350
```

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 138
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 138

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Tyr Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn

```
                325                 330                 335

Val Ile Val Leu Glu Leu Lys Gly Ser Glu Thr Thr Phe Met Cys Glu
            340                 345                 350

Gly Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 139
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 139

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300
```

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Ala Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 140
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 140

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Gly Met Pro Lys Lys Ala Thr Glu Leu Lys His Leu Gln Cys
290 295 300

Leu Glu Ala Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 141
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 141

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn 260 265 270

Gly Ile Asn Asn Tyr Lys Asn Pro Lys Leu Thr Arg Met Leu Thr Phe
275 280 285

Lys Phe Gly Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 142
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 142

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Phe
275 280 285

Lys Phe Gly Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 143
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 143

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Phe
275 280 285

Lys Phe Tyr Met Pro Lys Lys Ala Thr Glu Leu Lys His Leu Gln Cys
290 295 300

Leu Glu Ala Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 144
<211> LENGTH: 379
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 144

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe

```
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Ala
        275                 280                 285

Lys Phe Tyr Met Pro Lys Lys Ala Thr Glu Leu Lys His Leu Gln Cys
    290                 295                 300

Leu Glu Ala Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 145
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 145

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175
```

```
Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Ala
        275                 280                 285

Lys Phe Gly Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 146
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 146

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160
```

```
Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Gly Met Pro Lys Lys Ala Thr Glu Leu Lys His Leu Gln Cys
    290                 295                 300

Leu Glu Ala Ala Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 147
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 147

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
```

130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Phe
275 280 285

Lys Phe Tyr Met Pro Lys Lys Ala Thr Glu Leu Lys His Leu Gln Cys
290 295 300

Leu Glu Ala Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 148
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 148

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Ala
275 280 285

Lys Phe Tyr Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 149
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 149

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Ala
275 280 285

Lys Phe Ala Met Pro Lys Lys Ala Thr Glu Leu Lys His Leu Gln Cys
290 295 300

Leu Glu Glu Glu Leu Lys Pro Leu Glu Glu Val Leu Asn Gly Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 150
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 150

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln 65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Ala
275 280 285

Lys Phe Gly Met Pro Lys Lys Ala Thr Glu Leu Lys His Leu Gln Cys
290 295 300

Leu Glu Glu Glu Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 151
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 151

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Ala
275 280 285

Lys Phe Tyr Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 152
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 152

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Arg Met Leu Thr Ala
275 280 285

Lys Phe Gly Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 153
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 153

Glu Pro Lys Ser Ser Asp Lys Thr His Thr Cys Pro Pro Cys Pro Ala

-continued

```
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Ala
        275                 280                 285

Lys Phe Gly Met Pro Lys Lys Ala Thr Glu Leu Lys His Leu Gln Cys
    290                 295                 300

Leu Glu Ala Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

<210> SEQ ID NO 154
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 154

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Gly Met Leu Thr Phe
        275                 280                 285

Lys Phe Gly Met Pro Lys Lys Ala Thr Glu Leu Lys His Leu Gln Cys
    290                 295                 300

Leu Glu Ala Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375

<210> SEQ ID NO 155
<211> LENGTH: 379
<212> TYPE: PRT

```
<213> ORGANISM: Artificial Sequence
<220> FEATURE:
<223> OTHER INFORMATION: Description of Artificial Sequence: Synthetic
      polypeptide

<400> SEQUENCE: 155

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Gly Met Leu Thr Ala
        275                 280                 285

Lys Phe Tyr Met Pro Lys Lys Ala Thr Glu Leu Lys His Leu Gln Cys
    290                 295                 300

Leu Glu Ala Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375
```

<210> SEQ ID NO 156
<211> LENGTH: 379
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 156

```
Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Gly Met Leu Thr Phe
        275                 280                 285

Lys Phe Gly Met Pro Lys Lys Ala Thr Glu Leu Lys His Leu Gln Cys
    290                 295                 300

Leu Glu Glu Ala Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365
```

Thr Phe Ser Gln Ser Ile Ile Ser Thr Leu Thr
370 375

<210> SEQ ID NO 157
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 157

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Phe
275 280 285

Lys Phe Tyr Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu 340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 158
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 158

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

Gln Leu Gln Leu Glu His Leu Leu Leu Asp Leu Gln Met Ile Leu Asn
260 265 270

Gly Ile Asn Asn Tyr Lys Asn Pro Lys Leu Thr Gly Met Leu Thr Ala
275 280 285

Lys Phe Tyr Met Pro Lys Lys Ala Thr Glu Leu Lys His Leu Gln Cys
290 295 300

Leu Glu Glu Ala Leu Lys Pro Leu Glu Glu Val Leu Asn Leu Ala Gln
305 310 315 320

```
Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 159
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 159

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Ala
        275                 280                 285

Lys Phe Tyr Met Pro Lys Lys Ala Thr Glu Leu Lys His Leu Gln Cys
    290                 295                 300
```

```
Leu Glu Ala Ala Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 160
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 160

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240

Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Gly Met Leu Thr Phe
```

275 280 285

Lys Phe Tyr Met Pro Lys Lys Ala Thr Glu Leu Lys His Leu Gln Cys
290 295 300

Leu Glu Ala Ala Leu Lys Pro Leu Glu Glu Val Leu Asn Leu Ala Gln
305 310 315 320

Ser Lys Asn Phe His Leu Arg Pro Arg Asp Leu Ile Ser Asn Ile Asn
325 330 335

Val Ile Val Leu Glu Leu Lys Gly Ser Glu Thr Thr Phe Met Cys Glu
340 345 350

Tyr Ala Asp Glu Thr Ala Thr Ile Val Glu Phe Leu Asn Arg Trp Ile
355 360 365

Thr Phe Ser Gln Ser Ile Ile Ser Thr Leu Thr
370 375

<210> SEQ ID NO 161
<211> LENGTH: 379
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 161

Glu Pro Lys Ser Ser Asp Lys Thr His Thr Cys Pro Pro Cys Pro Ala
1 5 10 15

Pro Glu Ala Ala Gly Gly Pro Ser Val Phe Leu Phe Pro Pro Lys Pro
20 25 30

Lys Asp Thr Leu Met Ile Ser Arg Thr Pro Glu Val Thr Cys Val Val
35 40 45

Val Asp Val Ser His Glu Asp Pro Glu Val Lys Phe Asn Trp Tyr Val
50 55 60

Asp Gly Val Glu Val His Asn Ala Lys Thr Lys Pro Arg Glu Glu Gln
65 70 75 80

Tyr Asn Ser Thr Tyr Arg Val Val Ser Val Leu Thr Val Leu His Gln
85 90 95

Asp Trp Leu Asn Gly Lys Glu Tyr Lys Cys Lys Val Ser Asn Lys Ala
100 105 110

Leu Pro Ala Ser Ile Glu Lys Thr Ile Ser Lys Ala Lys Gly Gln Pro
115 120 125

Arg Glu Pro Gln Val Tyr Thr Leu Pro Pro Ser Arg Glu Glu Met Thr
130 135 140

Lys Asn Gln Val Ser Leu Trp Cys Leu Val Lys Gly Phe Tyr Pro Ser
145 150 155 160

Asp Ile Ala Val Glu Trp Glu Ser Asn Gly Gln Pro Glu Asn Asn Tyr
165 170 175

Lys Thr Thr Pro Pro Val Leu Asp Ser Asp Gly Ser Phe Phe Leu Tyr
180 185 190

Ser Lys Leu Thr Val Asp Lys Ser Arg Trp Gln Gln Gly Asn Val Phe
195 200 205

Ser Cys Ser Val Met His Glu Ala Leu His Asn His Tyr Thr Gln Lys
210 215 220

Ser Leu Ser Leu Ser Pro Gly Gly Gly Gly Gly Ser Gly Gly Gly Gly
225 230 235 240

Ser Gly Gly Gly Gly Ser Gly Gly Gly Gly Ser Ser Thr Lys Lys Thr
245 250 255

```
Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Ser Gln Ser Ile Ile Ser Thr Leu Thr
    370                 375


<210> SEQ ID NO 162
<211> LENGTH: 379
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 162

Glu Pro Lys Ser Ser Asp Lys Thr His Thr Cys Pro Pro Cys Pro Ala
1               5                   10                  15

Pro Glu Ala Ala Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Ser Ile Glu Lys Thr Ile Ser Lys Ala Lys Gly Gln Pro
        115                 120                 125

Arg Glu Pro Gln Val Tyr Thr Leu Pro Pro Ser Arg Glu Glu Met Thr
    130                 135                 140

Lys Asn Gln Val Ser Leu Trp Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Gly Gly Gly Gly Ser Gly Gly Gly Gly
225                 230                 235                 240
```

```
Ser Gly Gly Gly Gly Ser Gly Gly Gly Gly Ser Ser Thr Lys Lys Thr
                245                 250                 255

Gln Leu Gln Leu Glu His Leu Leu Leu Asp Leu Gln Met Ile Leu Asn
            260                 265                 270

Gly Ile Asn Asn Tyr Lys Asn Pro Lys Leu Thr Arg Met Leu Thr Phe
        275                 280                 285

Lys Phe Tyr Met Pro Lys Lys Ala Thr Glu Leu Lys His Leu Gln Cys
    290                 295                 300

Leu Glu Glu Glu Leu Lys Pro Leu Glu Glu Val Leu Asn Leu Ala Gln
305                 310                 315                 320

Ser Lys Asn Phe His Leu Arg Pro Arg Asp Leu Ile Ser Asn Ile Asn
                325                 330                 335

Val Ile Val Leu Glu Leu Lys Gly Ser Glu Thr Thr Phe Met Cys Glu
            340                 345                 350

Tyr Ala Asp Glu Thr Ala Thr Ile Val Glu Phe Leu Asn Arg Trp Ile
        355                 360                 365

Thr Phe Cys Gln Ser Ile Ile Ser Thr Leu Thr
    370                 375


<210> SEQ ID NO 163
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 163

Ala Pro Thr Ser Ser
1               5


<210> SEQ ID NO 164

<400> SEQUENCE: 164

000


<210> SEQ ID NO 165
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 165

Gly Pro Thr Ile Lys Pro Cys Pro Pro Cys Lys Cys Pro Ala Pro Asn
1               5                   10                  15

Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
```

-continued

```
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Arg Met Leu Thr Phe Lys Phe Tyr Leu Pro Lys
        275                 280                 285

Gln Ala Thr Glu Leu Lys Asp Leu Gln Cys Leu Glu Asp Glu Leu Gly
    290                 295                 300

Pro Leu Arg His Val Leu Asp Leu Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375


<210> SEQ ID NO 166
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 166

Gly Pro Thr Ile Lys Pro Cys Pro Pro Cys Lys Cys Pro Ala Pro Asn
1               5                   10                  15

Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80
```

```
Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Arg Met Leu Thr Ala Lys Phe Ala Leu Pro Lys
        275                 280                 285

Gln Ala Thr Glu Leu Lys Asp Leu Gln Cys Leu Glu Asp Glu Leu Gly
    290                 295                 300

Pro Leu Arg His Val Leu Asp Gly Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375


<210> SEQ ID NO 167
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 167

Gly Pro Thr Ile Lys Pro Cys Pro Pro Cys Lys Cys Pro Ala Pro Asn
1               5                   10                  15

Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60
```

Val Glu Val His Thr Ala Gln Thr Gln Thr His Arg Glu Asp Tyr Asn
65 70 75 80

Ser Thr Leu Arg Val Val Ser Ala Leu Pro Ile Gln His Gln Asp Trp
85 90 95

Met Ser Gly Lys Glu Phe Lys Cys Lys Val Asn Asn Lys Asp Leu Gly
100 105 110

Ala Pro Ile Glu Arg Thr Ile Ser Lys Pro Lys Gly Ser Val Arg Ala
115 120 125

Pro Gln Val Tyr Val Leu Pro Pro Pro Glu Glu Glu Met Thr Lys Lys
130 135 140

Gln Val Thr Leu Trp Cys Met Val Thr Asp Phe Met Pro Glu Asp Ile
145 150 155 160

Tyr Val Glu Trp Thr Asn Asn Gly Lys Thr Glu Leu Asn Tyr Lys Asn
165 170 175

Thr Glu Pro Val Leu Asp Ser Asp Gly Ser Tyr Phe Met Tyr Ser Lys
180 185 190

Leu Arg Val Glu Lys Lys Asn Trp Val Glu Arg Asn Ser Tyr Ser Cys
195 200 205

Ser Val Val His Glu Gly Leu His Asn His His Thr Thr Lys Ser Phe
210 215 220

Ser Arg Thr Pro Gly Gly Gly Gly Gly Ser Gly Gly Gly Gly Ser Gly
225 230 235 240

Gly Gly Gly Ser Gly Gly Gly Gly Ser Gln Gln Gln His Leu Glu Gln
245 250 255

Leu Leu Met Asp Leu Gln Glu Leu Leu Ser Arg Met Glu Asn Tyr Arg
260 265 270

Asn Leu Lys Leu Pro Arg Met Leu Thr Ala Lys Phe Tyr Leu Pro Lys
275 280 285

Gln Ala Thr Glu Leu Lys Asp Leu Gln Cys Leu Glu Asp Glu Leu Gly
290 295 300

Pro Leu Arg His Val Leu Asp Leu Thr Gln Ser Lys Ser Phe Gln Leu
305 310 315 320

Glu Asp Ala Glu Asn Phe Ile Ser Asn Ile Arg Val Thr Val Val Lys
325 330 335

Leu Lys Gly Ser Asp Asn Thr Phe Glu Cys Gln Phe Asp Asp Glu Ser
340 345 350

Ala Thr Val Val Asp Phe Leu Arg Arg Trp Ile Ala Phe Ala Gln Ser
355 360 365

Ile Ile Ser Thr Ser Pro Gln
370 375

<210> SEQ ID NO 168
<211> LENGTH: 375
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 168

Gly Pro Thr Ile Lys Pro Cys Pro Pro Cys Lys Cys Pro Ala Pro Asn
1 5 10 15

Ala Ala Gly Gly Pro Ser Val Phe Ile Phe Pro Pro Lys Ile Lys Asp
20 25 30

Val Leu Met Ile Ser Leu Ser Pro Ile Val Thr Cys Val Val Val Asp

```
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Arg Met Leu Thr Ala Lys Phe Tyr Leu Pro Lys
        275                 280                 285

Gln Ala Thr Glu Leu Lys Asp Leu Gln Cys Leu Glu Asp Ala Leu Gly
    290                 295                 300

Pro Leu Arg His Val Leu Asp Leu Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375


<210> SEQ ID NO 169
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 169

Gly Pro Thr Ile Lys Pro Cys Pro Pro Cys Lys Cys Pro Ala Pro Asn
1               5                   10                  15
```

```
Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Arg Met Leu Thr Ala Lys Phe Gly Leu Pro Lys
        275                 280                 285

Gln Ala Thr Glu Leu Lys Asp Leu Gln Cys Leu Glu Asp Ala Leu Gly
    290                 295                 300

Pro Leu Arg His Val Leu Asp Leu Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375
```

<210> SEQ ID NO 170
<211> LENGTH: 375
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 170

```
Gly Pro Thr Ile Lys Pro Cys Pro Pro Cys Lys Cys Pro Ala Pro Asn
1               5                   10                  15

Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Gly Met Leu Thr Phe Lys Phe Tyr Leu Pro Lys
        275                 280                 285

Gln Ala Thr Glu Leu Lys Asp Leu Gln Cys Leu Glu Asp Ala Leu Gly
    290                 295                 300

Pro Leu Arg His Val Leu Asp Leu Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375
```

<210> SEQ ID NO 171
<211> LENGTH: 375
<212> TYPE: PRT
<213> ORGANISM: Artificial Sequence
<220> FEATURE:

<223> OTHER INFORMATION: Description of Artificial Sequence: Synthetic
      polypeptide

<400> SEQUENCE: 171

Gly Pro Thr Ile Lys Pro Cys Pro Pro Cys Lys Cys Pro Ala Pro Asn
1               5                   10                  15

Ala Ala Gly Gly Pro Ser Val Phe Ile Phe Pro Pro Lys Ile Lys Asp
            20                  25                  30

Val Leu Met Ile Ser Leu Ser Pro Ile Val Thr Cys Val Val Val Asp
        35                  40                  45

Val Ser Glu Asp Asp Pro Asp Val Gln Ile Ser Trp Phe Val Asn Asn
    50                  55                  60

Val Glu Val His Thr Ala Gln Thr Gln Thr His Arg Glu Asp Tyr Asn
65                  70                  75                  80

Ser Thr Leu Arg Val Val Ser Ala Leu Pro Ile Gln His Gln Asp Trp
                85                  90                  95

Met Ser Gly Lys Glu Phe Lys Cys Lys Val Asn Asn Lys Asp Leu Gly
            100                 105                 110

Ala Pro Ile Glu Arg Thr Ile Ser Lys Pro Lys Gly Ser Val Arg Ala
        115                 120                 125

Pro Gln Val Tyr Val Leu Pro Pro Pro Glu Glu Glu Met Thr Lys Lys
    130                 135                 140

Gln Val Thr Leu Trp Cys Met Val Thr Asp Phe Met Pro Glu Asp Ile
145                 150                 155                 160

Tyr Val Glu Trp Thr Asn Asn Gly Lys Thr Glu Leu Asn Tyr Lys Asn
                165                 170                 175

Thr Glu Pro Val Leu Asp Ser Asp Gly Ser Tyr Phe Met Tyr Ser Lys
            180                 185                 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Gly Gly Gly Gly Ser Gly Gly Gly Gly Ser Gly
225                 230                 235                 240

Gly Gly Gly Ser Gly Gly Gly Gly Ser Gln Gln Gln His Leu Glu Gln
                245                 250                 255

Leu Leu Met Asp Leu Gln Glu Leu Leu Ser Arg Met Glu Asn Tyr Arg
            260                 265                 270

Asn Leu Lys Leu Pro Gly Met Leu Thr Ala Lys Phe Tyr Leu Pro Lys
        275                 280                 285

Gln Ala Thr Glu Leu Lys Asp Leu Gln Cys Leu Glu Asp Ala Leu Gly
    290                 295                 300

Pro Leu Arg His Val Leu Asp Leu Thr Gln Ser Lys Ser Phe Gln Leu
305                 310                 315                 320

Glu Asp Ala Glu Asn Phe Ile Ser Asn Ile Arg Val Thr Val Val Lys
                325                 330                 335

Leu Lys Gly Ser Asp Asn Thr Phe Glu Cys Gln Phe Asp Asp Glu Ser
            340                 345                 350

Ala Thr Val Val Asp Phe Leu Arg Arg Trp Ile Ala Phe Ala Gln Ser
        355                 360                 365

Ile Ile Ser Thr Ser Pro Gln
    370                 375

<210> SEQ ID NO 172

<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 172

Gly Pro Thr Ile Lys Pro Cys Pro Pro Cys Lys Cys Pro Ala Pro Asn
1 5 10 15

Ala Ala Gly Gly Pro Ser Val Phe Ile Phe Pro Pro Lys Ile Lys Asp
20 25 30

Val Leu Met Ile Ser Leu Ser Pro Ile Val Thr Cys Val Val Val Asp
35 40 45

Val Ser Glu Asp Asp Pro Asp Val Gln Ile Ser Trp Phe Val Asn Asn
50 55 60

Val Glu Val His Thr Ala Gln Thr Gln Thr His Arg Glu Asp Tyr Asn
65 70 75 80

Ser Thr Leu Arg Val Val Ser Ala Leu Pro Ile Gln His Gln Asp Trp
85 90 95

Met Ser Gly Lys Glu Phe Lys Cys Lys Val Asn Asn Lys Asp Leu Gly
100 105 110

Ala Pro Ile Glu Arg Thr Ile Ser Lys Pro Lys Gly Ser Val Arg Ala
115 120 125

Pro Gln Val Tyr Val Leu Pro Pro Pro Glu Glu Glu Met Thr Lys Lys
130 135 140

Gln Val Thr Leu Trp Cys Met Val Thr Asp Phe Met Pro Glu Asp Ile
145 150 155 160

Tyr Val Glu Trp Thr Asn Asn Gly Lys Thr Glu Leu Asn Tyr Lys Asn
165 170 175

Thr Glu Pro Val Leu Asp Ser Asp Gly Ser Tyr Phe Met Tyr Ser Lys
180 185 190

Leu Arg Val Glu Lys Lys Asn Trp Val Glu Arg Asn Ser Tyr Ser Cys
195 200 205

Ser Val Val His Glu Gly Leu His Asn His His Thr Thr Lys Ser Phe
210 215 220

Ser Arg Thr Pro Gly Lys
225 230

<210> SEQ ID NO 173
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 173

Gly Pro Thr Ile Lys Pro Cys Pro Pro Cys Lys Cys Pro Ala Pro Asn
1 5 10 15

Ala Ala Gly Gly Pro Ser Val Phe Ile Phe Pro Pro Lys Ile Lys Asp
20 25 30

Val Leu Met Ile Ser Leu Ser Pro Ile Val Thr Cys Val Val Val Asp
35 40 45

Val Ser Glu Asp Asp Pro Asp Val Gln Ile Ser Trp Phe Val Asn Asn
50 55 60

Val Glu Val His Thr Ala Gln Thr Gln Thr His Arg Glu Asp Tyr Asn
65 70 75 80

Ser Thr Leu Arg Val Val Ser Ala Leu Pro Ile Gln His Gln Asp Trp
85 90 95

Met Ser Gly Lys Glu Phe Lys Cys Lys Val Asn Asn Lys Asp Leu Gly
100 105 110

Ala Pro Ile Glu Arg Thr Ile Ser Lys Pro Lys Gly Ser Val Arg Ala
115 120 125

Pro Gln Val Tyr Val Leu Pro Pro Pro Glu Glu Glu Met Thr Lys Lys
130 135 140

Gln Val Thr Leu Ser Cys Ala Val Thr Asp Phe Met Pro Glu Asp Ile
145 150 155 160

Tyr Val Glu Trp Thr Asn Asn Gly Lys Thr Glu Leu Asn Tyr Lys Asn
165 170 175

Thr Glu Pro Val Leu Asp Ser Asp Gly Ser Tyr Phe Met Val Ser Lys
180 185 190

Leu Arg Val Glu Lys Lys Asn Trp Val Glu Arg Asn Ser Tyr Ser Cys
195 200 205

Ser Val Val His Glu Gly Leu His Asn His His Thr Thr Lys Ser Phe
210 215 220

Ser Arg Thr Pro Gly Lys
225 230

<210> SEQ ID NO 174
<211> LENGTH: 4
<212> TYPE: PRT
<213> ORGANISM: Artificial Sequence
<220> FEATURE:
<223> OTHER INFORMATION: Description of Artificial Sequence: Synthetic peptide

<400> SEQUENCE: 174

Lys Leu Ile Cys
1

<210> SEQ ID NO 175
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 175
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 176
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 176
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
gccatgctga ccttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 177
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 177
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctgg gcttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 178
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 178
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctgg ccttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 179
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 179
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccggcaagtt ctacatgcct aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 180
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 180
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccgccaagtt ctacatgcct aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 181
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 181
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt cggcatgcct aagaaggcca ccgagctgaa acatctgcag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 182
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 182
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt cgccatgcct aagaaggcca ccgagctgaa acatctgcag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 183
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 183
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcaccttcag 900
tgtctggaag ccgaactgaa gcccctggaa gaggtgctga atctggccca gagcaagaac 960
ttccacctga ggcctaggga cctgatcagc aacatcaacg tgatcgtgct ggaactgaag 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 184
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 184
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgtctggaag aggccctgaa gcctctggaa gaagtgctga atctggccca gagcaagaac 960
ttccacctga ggcctaggga cctgatcagc aacatcaacg tgatcgtgct ggaactgaag 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 185
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 185
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgcctggaag aggaactgaa gcctctggaa gccgtgctga atctggccca gagcaagaac 960
tttcacctga ggcctcggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 186
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 186
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgcctggaag aggaactgaa gcccctggaa gaagtgctga acggcgccca gagcaagaac 960
tttcacctga ggcctcggga cctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 187
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 187
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgcctggaag aggaactgaa gcccctggaa gaagtgctga atctggccgg cagcaagaac 960
ttccacctga ggcctagaga tctgatcagc aacatcaacg tgatcgtgct ggaactgaaa 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 188
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 188
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540

-continued gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caacctttat gtgcgagggc gccgacgaga cagccaccat cgtggaattt 1080
ctgaacagat ggatcacctt cagccagagc atcatcagca ccctgacc 1128

<210> SEQ ID NO 189
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 189
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcacctccag 900
tgcctggaag aggaactgaa gcccctggaa gaagtgctga atctggccca gagcaagaac 960
ttccacctga ggcctaggga cctgatcagc aacatcaacg tgatcgtgct ggaactgaaa 1020
ggcagcgaga caacctttat gtgcgaggcc gccgacgaga cagccaccat cgtggaattt 1080
ctgaacagat ggatcacctt cagccagagc atcatcagca ccctgacc 1128

<210> SEQ ID NO 190
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 190

-continued

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

cggatgctga ccttcaagtt cggcatgccc aagaaggcca ccgagctgaa acatctgcag    900

tgcctggaag ctgagctgaa gcccctggaa gaggtgctga atctggccca gtccaagaac    960

ttccacctga ggcctcggga cctgatctcc aacatcaacg tgatcgtgct ggaactgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 191
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 191

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

cggatgctga ccttcaagtt cggcatgccc aagaaggcca ccgagctgaa acatctgcag    900
```

tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 192
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 192
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccttcaagtt cggcatgccc aagaaggcca ccgagctgaa acatctgcag 900
tgcctggaag aggaactgaa gcccctggaa gaagtgctga atctggccca gtccaagaac 960
ttccacctga ggcctcggga cctgatctcc aacatcaacg tgatcgtgct cgagctgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 193
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 193
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300

```
tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

ggcatgctga ccttcaagtt ctacatgccc aagaaggcca ccgagctgaa acatctgcag    900

tgcctggaag ctgagctgaa gcccctggaa gaggtgctga atctggccca gtccaagaac    960

ttccacctga ggcctcggga cctgatctcc aacatcaacg tgatcgtgct ggaactgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 194
<211> LENGTH: 1128
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 194

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

cggatgctga ccgccaagtt ctacatgccc aagaaggcca ccgagctgaa acatctgcag    900

tgcctggaag ctgagctgaa gcccctggaa gaggtgctga atctggccca gtccaagaac    960

ttccacctga ggcctcggga cctgatctcc aacatcaacg tgatcgtgct ggaactgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 195

<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 195
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccgccaagtt tggcatgcct aagaaggcca ccgagctgaa acatctgcag 900
tgcctggaag aggaactgaa gcccctggaa gaagtgctga atctggccca gtccaagaac 960
ttccacctga ggcctcggga cctgatctcc aacatcaacg tgatcgtgct cgagctgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 196
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 196
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt cggcatgccc aagaaggcca ccgagctgaa gcaccttcag 900
tgtctggaag ccgctctgaa gcccctggaa gaggtgctga atctggccca gagcaagaac 960
ttccacctga ggcctaggga cctgatcagc aacatcaacg tgatcgtgct ggaactgaag 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 197
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 197
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccttcaagtt ctacatgccc aagaaggcca ccgagctgaa gcaccttcag 900
tgtctggaag ccgctctgaa gcccctggaa gaggtgctga atctggccca gagcaagaac 960
ttccacctga ggcctaggga cctgatcagc aacatcaacg tgatcgtgct ggaactgaag 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 198
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 198
gagtctaagt acggccctcc ttgtcctcca tgtcctgctc cagaagctgc tggcggccct 60

-continued

```
tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

ggcatgctga ccgccaagtt ctacatgccc aagaaggcca ccgagctgaa acatctgcag    900

tgcctggaag aggaactgaa gcccctggaa gaagtgctga atctggccca gtccaagaac    960

ttccacctga ggcctcggga cctgatctcc aacatcaacg tgatcgtgct cgagctgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 199
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 199

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggatctg gtggtggtgg atctggcggc    720

ggaggtagcg gtggtggcgg ttcttctacc aagaaaaccc agctgcagtt ggagcatctg    780

ctgctggacc tgcagatgat cctgaacggc atcaacaact acaagaaccc caagctgacc    840

cggatgctga ccgccaagtt tgccatgcct aagaaggcca ccgagctgaa acatctgcag    900

tgcctggaag aggaactgaa gcccctggaa gaagtgctga acggcgccca gtccaagaac    960
```

ttccatctga ggcctcggga cctgatctcc aacatcaacg tgatcgtgct cgagctgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 200
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 200
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccgccaagtt tggcatgcct aagaaggcca ccgagctgaa acatctgcag 900
tgcctggaag aggaactgaa gcccctggaa gaagtgctga atctggccca gtccaagaac 960
ttccacctga ggcctcggga cctgatctcc aacatcaacg tgatcgtgct cgagctgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 201
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 201
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccgccaagtt ctacatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 202
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 202
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtccct tggcggaggc ggaggatctg gtggtggcgg atctggcggc 720
ggaggtagcg gtggcggtgg atcttctacc aagaaaaccc agctgcagtt ggagcatctg 780
ctgctggacc tgcagatgat cctgaatggc atcaacaatt acaagaaccc caagctgacc 840
cggatgctga ccgccaagtt ctacatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 203
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 203

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720

ggtggatcag gcggtggcgg aagctctaca aagaaaaccc agctgcaact ggaacatctg    780

ctgctggacc tgcagatgat cctgaacggc atcaacaact acaagaaccc caagctgacc    840

cggatgctga ccgccaagtt tggcatgcct aagaaggcca ccgagctgaa acatctgcag    900

tgcctggaag aggccctgaa gcctctggaa gaagtgctga atctggccca gtccaagaac    960

ttccacctga ggcctcggga cctgatctcc aacatcaacg tgatcgtgct ggaactgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 204
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 204

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtctct tggcggaggc ggaggaagtg gtggcggagg ttctggtggc    720
```

ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccgccaagtt tggcatgcct aagaaggcca ccgagctgaa acatctgcag 900
tgcctggaag ctgagctgaa gcccctggaa gaggtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 205
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 205
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccttcaagtt cggcatgccc aagaaggcca ccgagctgaa acatctgcag 900
tgcctggaag ctgagctgaa gcccctggaa gaggtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 206
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 206
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccgccaagtt ctacatgccc aagaaggcca ccgagctgaa acatctgcag 900
tgcctggaag ctgagctgaa gcccctggaa gaggtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 207
<211> LENGTH: 1128
<212> TYPE: DNA
<213> ORGANISM: Artificial Sequence
<220> FEATURE:
<223> OTHER INFORMATION: Description of Artificial Sequence: Synthetic
polynucleotide

<400> SEQUENCE: 207
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccttcaagtt cggcatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080

-continued ctgaaccggt ggatcacctt cagccagtcc atcatcagca ccctgacc 1128

<210> SEQ ID NO 208
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 208
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccttcaagtt ctacatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 209
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 209
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
ggcatgctga ccgccaagtt ctacatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 210
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 210
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtccct tggcggaggc ggaggatctg gtggtggcgg atctggcggc 720
ggaggtagcg gtggcggtgg atcttctacc aagaaaaccc agctgcagtt ggagcatctg 780
ctgctggacc tgcagatgat cctgaatggc atcaacaatt acaagaaccc caagctgacc 840
ggcatgctga ccgccaagtt ctacatgccc aagaaggcca ccgagctgaa acatctgcag 900
tgcctggaag aggccctgaa gcctctggaa gaagtgctga atctggccca gtccaagaac 960
ttccacctga ggcctcggga cctgatctcc aacatcaacg tgatcgtgct ggaactgaag 1020
ggctccgaga caaccttcat gtgcgagtac gccgacgaga cagctaccat cgtggaattt 1080
ctgaaccggt ggatcacctt cagccagtcc atcatcagca ccctgacc 1128

<210> SEQ ID NO 211
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 211
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840
cggatgctga ccgccaagtt ctacatgccc aagaaggcca ccgagctgaa gcaccttcag 900
tgtctggaag ccgctctgaa gcccctggaa gaggtgctga atctggccca gagcaagaac 960
ttccacctga ggcctaggga cctgatcagc aacatcaacg tgatcgtgct ggaactgaag 1020
ggcagcgaga caaccttcat gtgcgagtac gccgacgaga cagccaccat cgtggaattt 1080
ctgaacagat ggatcacctt cagccagagc atcatcagca ccctgacc 1128

<210> SEQ ID NO 212
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 212
gagtctaagt acggccctcc ttgtcctcca tgtcctgctc cagaagctgc tggcggccct 60
tccgtgtttc tgttccctcc aaagcctaag gacaccctga tgatctctcg gacccctgaa 120
gtgacctgcg tggtggtgga tgtgtcccaa gaggatcccg aggtgcagtt caattggtac 180
gtggacggcg tggaagtgca caacgccaag accaagccta gagaggaaca gttcaactcc 240
acctacagag tggtgtccgt gctgaccgtg ctgcaccagg attggctgaa cggcaaagag 300
tacaagtgca aggtgtccaa caagggcctg ccttccagca tcgaaaagac catctccaag 360
gccaagggcc agcctaggga accccaggtt tacaccctgc ctccaagcca agaggaaatg 420
accaagaacc aggtgtccct gtggtgcctg gtcaagggct tctacccttc cgatatcgcc 480
gtggaatggg agagcaatgg ccagcctgag aacaactaca agaccacacc tcctgtgctg 540
gactccgacg gctccttctt tctgtactcc cgcctgaccg tggacaagtc cagatggcaa 600
gagggcaacg tgttctcctg ctccgtgatg cacgaggccc tgcacaatca ctacacccag 660
aagtccctgt ctctgtctct tggcggaggc ggaggaagtg gtggcggagg ttctggtggc 720
ggtggatcag gcggtggcgg aagctctaca aagaaaaccc agctgcaact ggaacatctg 780
ctgctggacc tgcagatgat cctgaacggc atcaacaact acaagaaccc caagctgacc 840

```
ggcatgctga ccttcaagtt ctacatgccc aagaaggcca ccgagctgaa gcaccttcag    900

tgtctggaag ccgctctgaa gcccctggaa gaggtgctga atctggccca gagcaagaac    960

ttccacctga ggcctaggga cctgatcagc aacatcaacg tgatcgtgct ggaactgaag   1020

ggcagcgaga caaccttcat gtgcgagtac gccgacgaga cagccaccat cgtggaattt   1080

ctgaacagat ggatcacctt cagccagagc atcatcagca ccctgacc                1128
```

<210> SEQ ID NO 213
<211> LENGTH: 1128
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 213

```
gagtctaagt acggccctcc ttgtcctcca tgtcctgctc cagaagctgc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtggtgcctg gtcaagggct tctacccttc cgatatcgcc    480

gtggaatggg agagcaatgg ccagcctgag aacaactaca agaccacacc tcctgtgctg    540

gactccgacg gctccttctt tctgtactcc cgcctgaccg tggacaagtc cagatggcaa    600

gagggcaacg tgttctcctg ctccgtgatg cacgaggccc tgcacaatca ctacacccag    660

aagtccctgt ctctgtccct tggcggaggc ggaggatctg gtggtggcgg atctggcggc    720

ggaggtagcg gtggcggtgg atcttctacc aagaaaaccc agctgcagtt ggagcatctg    780

ctgctggacc tgcagatgat cctgaatggc atcaacaatt acaagaaccc caagctgacc    840

cggatgctga ccttcaagtt ctacatgccc aagaaggcca ccgagctgaa acatctgcag    900

tgcctggaag aggaactgaa gcccctggaa gaagtgctga atctggccca gtccaagaac    960

ttccacctga ggcctcggga cctgatctcc aacatcaacg tgatcgtgct cgagctgaag   1020

ggctccgaga caaccttcat gtgcgagtac gccgacgaga cagctaccat cgtggaattt   1080

ctgaaccggt ggatcacctt cagccagtcc atcatcagca ccctgacc                1128
```

<210> SEQ ID NO 214
<211> LENGTH: 687
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 214

```
gagtctaagt acggccctcc ttgtcctcca tgtcctgctc cagaagctgc tggcggccct     60

tccgtgtttc tgttccctcc aaagcctaag gacaccctga tgatcagcag aacccctgaa    120

gtgacctgcg tggtggtgga cgtgtcccaa gaggatcctg aggtgcagtt caattggtac    180

gtggacggcg tggaagtgca caacgccaag accaagccta gagaggaaca gttcaacagc    240
```

```
acctatagag tggtgtccgt gctgaccgtg ctgcaccagg attggctgaa cggcaaagag    300

tacaagtgca aggtgtccaa caagggcctg cctagctcca tcgagaaaac catcagcaag    360

gccaagggcc agccaagaga accccaggtg tacacactgc ctccaagcca agaggaaatg    420

accaagaacc aggtgtccct gagctgcgcc gtgaagggct tttacccttc cgatatcgcc    480

gtggaatggg agagcaatgg ccagcctgag aacaactaca agaccacacc tcctgtgctg    540

gacagcgacg gctcattctt cctggtgtcc agactgaccg tggacaagag cagatggcaa    600

gagggcaacg tgttcagctg cagcgtgatg cacgaggccc tgcacaaccg gtttacccag    660

aagtctctga gcctgagcct gggcaaa                                        687


<210> SEQ ID NO 215
<211> LENGTH: 687
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 215

gagtctaagt acggccctcc ttgtcctcca tgtcctgctc cagaagcagc tggcggccct     60

tccgtgtttc tgttccctcc aaagcctaag gacaccctga tgatctctcg gacccctgaa    120

gtgacctgcg tggtggtgga tgtgtcccaa gaggatcccg aggtgcagtt caattggtac    180

gtggacggcg tggaagtgca caacgccaag accaagccta gagaggaaca gttcaactcc    240

acctacagag tggtgtccgt gctgaccgtg ctgcaccagg attggctgaa cggcaaagag    300

tacaagtgca aggtgtccaa caagggcctg ccttccagca tcgaaaagac catctccaag    360

gccaagggcc agcctaggga accccaggtt tacaccctgc ctccaagcca agaggaaatg    420

accaagaacc aggtgtccct gtcctgcgcc gtgaagggct tctacccttc tgatatcgcc    480

gtggaatggg agagcaacgg ccagcctgag aacaactaca agaccacacc tcctgtgctg    540

gactccgacg gctctttctt tctggtgtcc cgcctgaccg tggacaagtc tagatggcaa    600

gagggcaacg tgttctcctg ctccgtgatg cacgaggccc tgcacaacag attcacccag    660

aagtccctgt ctctgtccct gggcaaa                                        687


<210> SEQ ID NO 216
<211> LENGTH: 133
<212> TYPE: PRT
<213> ORGANISM: Homo sapiens

<400> SEQUENCE: 216

Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Lys His Leu Gln Cys Leu Glu Glu Glu Leu Lys
    50                  55                  60

Pro Leu Glu Glu Val Leu Asn Leu Ala Gln Ser Lys Asn Phe His Leu
65                  70                  75                  80

Arg Pro Arg Asp Leu Ile Ser Asn Ile Asn Val Ile Val Leu Glu Leu
                85                  90                  95

Lys Gly Ser Glu Thr Thr Phe Met Cys Glu Tyr Ala Asp Glu Thr Ala
            100                 105                 110
```

Thr Ile Val Glu Phe Leu Asn Arg Trp Ile Thr Phe Cys Gln Ser Ile
115 120 125

Ile Ser Thr Leu Thr
130

<210> SEQ ID NO 217
<211> LENGTH: 134
<212> TYPE: PRT
<213> ORGANISM: Macaca mulatta

<400> SEQUENCE: 217

Ala Pro Thr Ser Ser Ser Thr Lys Lys Thr Gln Leu Gln Leu Glu His
1 5 10 15

Leu Leu Leu Asp Leu Gln Met Ile Leu Asn Gly Ile Asn Asn Tyr Lys
20 25 30

Asn Pro Lys Leu Thr Arg Met Leu Thr Phe Lys Phe Tyr Met Pro Lys
35 40 45

Lys Ala Thr Glu Leu Lys His Leu Gln Cys Leu Glu Glu Glu Leu Lys
50 55 60

Pro Leu Glu Glu Val Leu Asn Leu Ala Gln Ser Lys Asn Phe His Leu
65 70 75 80

Arg Asp Thr Lys Asp Leu Ile Ser Asn Ile Asn Val Ile Val Leu Glu
85 90 95

Leu Lys Gly Ser Glu Thr Thr Leu Met Cys Glu Tyr Ala Asp Glu Thr
100 105 110

Ala Thr Ile Val Glu Phe Leu Asn Arg Trp Ile Thr Phe Cys Gln Ser
115 120 125

Ile Ile Ser Thr Leu Thr
130

<210> SEQ ID NO 218
<211> LENGTH: 17
<212> TYPE: PRT
<213> ORGANISM: Artificial Sequence
<220> FEATURE:
<223> OTHER INFORMATION: Description of Artificial Sequence: Synthetic peptide

<400> SEQUENCE: 218

Lys Trp Val Thr Phe Ile Ser Leu Leu Phe Leu Phe Ser Ser Ala Tyr
1 5 10 15

Ser

<210> SEQ ID NO 219
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 219

Met Tyr Arg Met Gln Leu Leu Ser Cys Ile Ala Leu Ser Leu Ala Leu
1 5 10 15

Val Thr Asn Ser
20

<210> SEQ ID NO 220
<211> LENGTH: 21
<212> TYPE: PRT

<213> ORGANISM: Artificial Sequence
<220> FEATURE:
<223> OTHER INFORMATION: Description of Artificial Sequence: Synthetic
peptide

<400> SEQUENCE: 220

Met Pro Ala Ile Ala Val Leu Ala Ala Ala Ala Ala Ala Trp Cys Phe
1 5 10 15

Leu Gln Val Glu Ser
20

<210> SEQ ID NO 221
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 221

Met Arg Ala Pro Gly Cys Gly Arg Leu Val Leu Pro Leu Leu Leu Leu
1 5 10 15

Ala Ala Ala Ala Leu Ala
20

<210> SEQ ID NO 222
<211> LENGTH: 22
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 222

Met Asp Met Arg Val Pro Ala Gln Leu Leu Gly Leu Leu Leu Leu Trp
1 5 10 15

Leu Ser Gly Ala Arg Cys
20

<210> SEQ ID NO 223
<211> LENGTH: 18
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 223

Met Trp Leu Gln Ser Leu Leu Leu Leu Gly Thr Val Ala Cys Ser Ile
1 5 10 15

Ser Val

<210> SEQ ID NO 224
<211> LENGTH: 23
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 224

Met Asp Ala Met Lys Arg Gly Leu Cys Cys Val Leu Leu Leu Cys Gly
1 5 10 15

Ala Val Phe Val Ser Ala Arg
20

<210> SEQ ID NO 225
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 225

Met His Arg Arg Arg Ser Arg Ser Cys Arg Glu Asp Gln Lys Pro Val
1 5 10 15

<210> SEQ ID NO 226
<211> LENGTH: 31
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 226

Met Arg Lys Ala Ala Val Ser His Trp Gln Gln Gln Ser Tyr Leu Asp
1 5 10 15

Ser Gly Ile His Ser Gly Ala Thr Thr Thr Ala Pro Ser Leu Ser
20 25 30

<210> SEQ ID NO 227
<211> LENGTH: 23
<212> TYPE: PRT
<213> ORGANISM: Artificial Sequence
<220> FEATURE:
<223> OTHER INFORMATION: Description of Artificial Sequence: Synthetic peptide

<400> SEQUENCE: 227

Met Lys Ala Ser Ala Ala Leu Leu Cys Leu Leu Leu Thr Ala Ala Ala
1 5 10 15

Phe Ser Pro Gln Gly Leu Ala
20

<210> SEQ ID NO 228
<211> LENGTH: 76
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 228

Met Gln Ile Phe Val Lys Thr Leu Thr Gly Lys Thr Ile Thr Leu Glu
1 5 10 15

Val Glu Pro Ser Asp Thr Ile Glu Asn Val Lys Ala Lys Ile Gln Asp
20 25 30

Lys Glu Gly Ile Pro Pro Asp Gln Gln Arg Leu Ile Phe Ala Gly Lys
35 40 45

Gln Leu Glu Asp Gly Arg Thr Leu Ser Asp Tyr Asn Ile Gln Lys Glu
50 55 60

Ser Thr Leu His Leu Val Leu Arg Leu Arg Gly Gly
65 70 75

<210> SEQ ID NO 229
<211> LENGTH: 17
<212> TYPE: PRT

<213> ORGANISM: Artificial Sequence
<220> FEATURE:
<223> OTHER INFORMATION: Description of Artificial Sequence: Synthetic peptide

<400> SEQUENCE: 229

Met Leu Leu Ser Val Pro Leu Leu Leu Gly Leu Leu Gly Leu Ala Val
1 5 10 15

Ala

<210> SEQ ID NO 230
<211> LENGTH: 16
<212> TYPE: PRT
<213> ORGANISM: Artificial Sequence
<220> FEATURE:
<223> OTHER INFORMATION: Description of Artificial Sequence: Synthetic peptide

<400> SEQUENCE: 230

Met Lys Cys Leu Leu Tyr Leu Ala Phe Leu Phe Ile Gly Val Asn Cys
1 5 10 15

<210> SEQ ID NO 231
<211> LENGTH: 21
<212> TYPE: PRT
<213> ORGANISM: Artificial Sequence
<220> FEATURE:
<223> OTHER INFORMATION: Description of Artificial Sequence: Synthetic peptide

<400> SEQUENCE: 231

Met Asn Gln Thr Ala Ile Leu Ile Cys Cys Leu Ile Phe Leu Thr Leu
1 5 10 15

Ser Gly Ile Gln Gly
20

<210> SEQ ID NO 232
<211> LENGTH: 5
<212> TYPE: PRT
<213> ORGANISM: Artificial Sequence
<220> FEATURE:
<223> OTHER INFORMATION: Description of Artificial Sequence: Synthetic peptide

<400> SEQUENCE: 232

Glu Pro Lys Ser Cys
1 5

<210> SEQ ID NO 233
<211> LENGTH: 227
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 233

Asp Lys Thr His Thr Cys Pro Pro Cys Pro Ala Pro Glu Leu Leu Gly
1 5 10 15

Gly Pro Ser Val Phe Leu Phe Pro Pro Lys Pro Lys Asp Thr Leu Met
20 25 30

Ile Ser Arg Thr Pro Glu Val Thr Cys Val Val Val Asp Val Ser His
35 40 45

Glu Asp Pro Glu Val Lys Phe Asn Trp Tyr Val Asp Gly Val Glu Val
50 55 60

```
His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Tyr Thr Leu Pro Pro Ser Arg Glu Glu Met Thr Lys Asn Gln Val Ser
    130                 135                 140

Leu Thr Cys Leu Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Tyr Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
    210                 215                 220

Pro Gly Lys
225


<210> SEQ ID NO 234
<211> LENGTH: 149
<212> TYPE: PRT
<213> ORGANISM: Mus musculus

<400> SEQUENCE: 234

Ala Pro Thr Ser Ser Ser Thr Ser Ser Ser Thr Ala Glu Ala Gln Gln
1               5                   10                  15

Gln Gln Gln Gln Gln Gln Gln Gln Gln Gln His Leu Glu Gln Leu Leu
            20                  25                  30

Met Asp Leu Gln Glu Leu Leu Ser Arg Met Glu Asn Tyr Arg Asn Leu
        35                  40                  45

Lys Leu Pro Arg Met Leu Thr Phe Lys Phe Tyr Leu Pro Lys Gln Ala
    50                  55                  60

Thr Glu Leu Lys Asp Leu Gln Cys Leu Glu Asp Glu Leu Gly Pro Leu
65                  70                  75                  80

Arg His Val Leu Asp Leu Thr Gln Ser Lys Ser Phe Gln Leu Glu Asp
                85                  90                  95

Ala Glu Asn Phe Ile Ser Asn Ile Arg Val Thr Val Val Lys Leu Lys
            100                 105                 110

Gly Ser Asp Asn Thr Phe Glu Cys Gln Phe Asp Asp Glu Ser Ala Thr
        115                 120                 125

Val Val Asp Phe Leu Arg Arg Trp Ile Ala Phe Cys Gln Ser Ile Ile
    130                 135                 140

Ser Thr Ser Pro Gln
145


<210> SEQ ID NO 235
<211> LENGTH: 23
<212> TYPE: PRT
<213> ORGANISM: Mus musculus

<400> SEQUENCE: 235
```

Ala Pro Thr Ser Ser Ser Thr Ser Ser Ser Thr Ala Glu Ala Gln Gln
1 5 10 15

Gln Gln Gln Gln Gln Gln Gln
20

<210> SEQ ID NO 236
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 236

Glu Ser Lys Tyr Gly Pro Pro Cys Pro Pro Cys Pro
1 5 10

<210> SEQ ID NO 237
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 237

Glu Pro Lys Ser Cys Asp Lys Thr His Thr Cys Pro Pro Cys Pro
1 5 10 15

<210> SEQ ID NO 238
<211> LENGTH: 20
<212> TYPE: PRT
<213> ORGANISM: Artificial Sequence
<220> FEATURE:
<223> OTHER INFORMATION: Description of Artificial Sequence: Synthetic peptide

<400> SEQUENCE: 238

Glu Pro Lys Ser Cys Asp Lys Thr His Thr Cys Pro Pro Cys Pro Ala
1 5 10 15

Pro Glu Leu Leu
20

<210> SEQ ID NO 239
<211> LENGTH: 212
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 239

Gly Gly Pro Ser Val Phe Leu Phe Pro Pro Lys Pro Lys Asp Thr Leu
1 5 10 15

Met Ile Ser Arg Thr Pro Glu Val Thr Cys Val Val Val Asp Val Ser
20 25 30

His Glu Asp Pro Glu Val Lys Phe Asn Trp Tyr Val Asp Gly Val Glu
35 40 45

Val His Asn Ala Lys Thr Lys Pro Arg Glu Glu Gln Tyr Asn Ser Thr
50 55 60

Tyr Arg Val Val Ser Val Leu Thr Val Leu His Gln Asp Trp Leu Asn
65 70 75 80

Gly Lys Glu Tyr Lys Cys Lys Val Ser Asn Lys Ala Leu Pro Ala Pro

```
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210


<210> SEQ ID NO 240
<211> LENGTH: 212
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 240

Gly Gly Pro Ser Val Phe Leu Phe Pro Pro Lys Pro Lys Asp Thr Leu
1               5                   10                  15

Tyr Ile Thr Arg Glu Pro Glu Val Thr Cys Val Val Val Asp Val Ser
            20                  25                  30

His Glu Asp Pro Glu Val Lys Phe Asn Trp Tyr Val Asp Gly Val Glu
        35                  40                  45

Val His Asn Ala Lys Thr Lys Pro Arg Glu Glu Gln Tyr Asn Ser Thr
    50                  55                  60

Tyr Arg Val Val Ser Val Leu Thr Val Leu His Gln Asp Trp Leu Asn
65                  70                  75                  80

Gly Lys Glu Tyr Lys Cys Lys Val Ser Asn Lys Ala Leu Pro Ala Pro
                85                  90                  95

Ile Glu Lys Thr Ile Ser Lys Ala Lys Gly Gln Pro Arg Glu Pro Gln
            100                 105                 110

Val Tyr Thr Leu Pro Pro Ser Arg Glu Glu Met Thr Lys Asn Gln Val
        115                 120                 125

Ser Leu Thr Cys Leu Val Lys Gly Phe Tyr Pro Ser Asp Ile Ala Val
    130                 135                 140

Glu Trp Glu Ser Asn Gly Gln Pro Glu Asn Asn Tyr Lys Thr Thr Pro
145                 150                 155                 160

Pro Val Leu Asp Ser Asp Gly Ser Phe Phe Leu Tyr Ser Lys Leu Thr
                165                 170                 175

Val Asp Lys Ser Arg Trp Gln Gln Gly Asn Val Phe Ser Cys Ser Val
            180                 185                 190

Met His Glu Ala Leu His Asn His Tyr Thr Gln Lys Ser Leu Ser Leu
        195                 200                 205

Ser Pro Gly Lys
    210
```

<210> SEQ ID NO 241
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 241

```
Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225
```

<210> SEQ ID NO 242
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 242

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60
```

```
Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 243
<211> LENGTH: 229
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 243

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Tyr Ile Thr Arg Glu Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190
```

```
Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225


<210> SEQ ID NO 244
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(20)
<223> OTHER INFORMATION: This sequence may encompass 3-5 "Gly Gly Gly
      Ser" repeating units

<400> SEQUENCE: 244

Gly Gly Gly Ser Gly Gly Gly Ser Gly Gly Gly Ser Gly Gly Gly Ser
1               5                   10                  15

Gly Gly Gly Ser
            20


<210> SEQ ID NO 245
<211> LENGTH: 25
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: SITE
<222> LOCATION: (1)..(25)
<223> OTHER INFORMATION: This sequence may encompass 3-5 "Gly Gly Gly
      Gly Ser" repeating units

<400> SEQUENCE: 245

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25


<210> SEQ ID NO 246
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 246

Gly Gly Gly Gly Ser Gly Gly Gly Gly Ser Gly Gly Gly Gly Ser Gly
1               5                   10                  15

Gly Gly Gly Ser
            20


<210> SEQ ID NO 247
<211> LENGTH: 8
<212> TYPE: PRT
<213> ORGANISM: Homo sapiens

<400> SEQUENCE: 247
```

Lys Pro Ser Ser Pro Pro Glu Glu
1 5

<210> SEQ ID NO 248
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 248

Arg Arg Cys Pro Leu Tyr Ile Ser Tyr Asp Pro Val Cys Arg Arg
1 5 10 15

<210> SEQ ID NO 249
<211> LENGTH: 19
<212> TYPE: PRT
<213> ORGANISM: Artificial Sequence
<220> FEATURE:
<223> OTHER INFORMATION: Description of Artificial Sequence: Synthetic peptide

<400> SEQUENCE: 249

Arg Arg Arg Arg Cys Pro Leu Tyr Ile Ser Tyr Asp Pro Val Cys Arg
1 5 10 15

Arg Arg Arg

<210> SEQ ID NO 250
<211> LENGTH: 230
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 250

Gly Pro Thr Ile Lys Pro Cys Pro Pro Cys Lys Cys Pro Ala Pro Asn
1 5 10 15

Ala Ala Gly Gly Pro Ser Val Phe Ile Phe Pro Pro Lys Ile Lys Asp
20 25 30

Val Leu Met Ile Ser Leu Ser Pro Ile Val Thr Cys Val Val Val Asp
35 40 45

Val Ser Glu Asp Asp Pro Asp Val Gln Ile Ser Trp Phe Val Asn Asn
50 55 60

Val Glu Val His Thr Ala Gln Thr Gln Thr His Arg Glu Asp Tyr Asn
65 70 75 80

Ser Thr Leu Arg Val Val Ser Ala Leu Pro Ile Gln His Gln Asp Trp
85 90 95

Met Ser Gly Lys Glu Phe Lys Cys Lys Val Asn Asn Lys Asp Leu Gly
100 105 110

Ala Pro Ile Glu Arg Thr Ile Ser Lys Pro Lys Gly Ser Val Arg Ala
115 120 125

Pro Gln Val Tyr Val Leu Pro Pro Pro Glu Glu Glu Met Thr Lys Lys
130 135 140

Gln Val Thr Leu Ser Cys Ala Val Thr Asp Phe Met Pro Glu Asp Ile
145 150 155 160

Tyr Val Glu Trp Thr Asn Asn Gly Lys Thr Glu Leu Asn Tyr Lys Asn
165 170 175

Thr Glu Pro Val Leu Asp Ser Asp Gly Ser Tyr Phe Met Val Ser Lys
180 185 190

Leu Arg Val Glu Lys Lys Asn Trp Val Glu Arg Asn Ser Tyr Ser Cys
        195                 200                 205

Ser Val Val His Glu Gly Leu His Asn His His Thr Thr Lys Ser Phe
    210                 215                 220

Ser Arg Thr Pro Gly Lys
225                 230

<210> SEQ ID NO 251
<211> LENGTH: 99
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 251

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly

<210> SEQ ID NO 252
<211> LENGTH: 203
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 252

Lys Lys Val Val Tyr Gly Lys Lys Gly Asp Thr Val Glu Leu Thr Cys
1               5                   10                  15

Thr Ala Ser Gln Lys Lys Asn Ile Gln Phe His Trp Lys Asn Ser Asn
            20                  25                  30

Gln Ile Lys Ile Leu Gly Asn Gln Gly Ser Phe Leu Thr Lys Gly Pro
        35                  40                  45

Ser Lys Leu Asn Asp Arg Val Asp Ser Arg Arg Ser Leu Trp Asp Gln
    50                  55                  60

Gly Asn Phe Pro Leu Ile Ile Lys Asn Leu Lys Pro Glu Asp Ser Asp
65                  70                  75                  80

Thr Tyr Ile Cys Glu Val Glu Asp Gln Lys Glu Glu Val Gln Leu Val
                85                  90                  95

Val Val Gly Gly Gly Gly Ser Gly Lys Lys Val Val Tyr Gly Lys Lys
            100                 105                 110

Gly Asp Thr Val Glu Leu Thr Cys Thr Ala Ser Gln Lys Lys Asn Ile
        115                 120                 125

Gln Phe His Trp Lys Asn Ser Asn Gln Ile Lys Ile Leu Gly Asn Gln
    130                 135                 140

Gly Ser Phe Leu Thr Lys Gly Pro Ser Lys Leu Asn Asp Arg Val Asp
145 150 155 160

Ser Arg Arg Ser Leu Trp Asp Gln Gly Asn Phe Pro Leu Ile Ile Lys
165 170 175

Asn Leu Lys Pro Glu Asp Ser Asp Thr Tyr Ile Cys Glu Val Glu Asp
180 185 190

Gln Lys Glu Glu Val Gln Leu Val Val Val Gly
195 200

<210> SEQ ID NO 253
<211> LENGTH: 99
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 253

Lys Lys Val Val Leu Gly Lys Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

Ser Lys Leu Asn Asp Arg Ala Asp Ser Arg Arg Ser Leu Trp Asp Gln
50 55 60

Gly Asn Phe Pro Leu Ile Ile Lys Asn Leu Lys Ile Glu Asp Ser Asp
65 70 75 80

Thr Tyr Ile Cys Glu Val Glu Asp Gln Lys Glu Glu Val Gln Leu Leu
85 90 95

Val Phe Gly

<210> SEQ ID NO 254
<211> LENGTH: 203
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 254

Lys Lys Val Val Leu Gly Lys Lys Gly Asp Thr Val Glu Leu Thr Cys
1 5 10 15

Thr Ala Ser Gln Lys Lys Ser Ile Gln Phe His Trp Lys Asn Ser Asn
20 25 30

Gln Ile Lys Ile Leu Gly Asn Gln Gly Ser Phe Leu Thr Lys Gly Pro
35 40 45

Ser Lys Leu Asn Asp Arg Ala Asp Ser Arg Arg Ser Leu Trp Asp Gln
50 55 60

Gly Asn Phe Pro Leu Ile Ile Lys Asn Leu Lys Ile Glu Asp Ser Asp
65 70 75 80

Thr Tyr Ile Cys Glu Val Glu Asp Gln Lys Glu Glu Val Gln Leu Leu
85 90 95

Val Phe Gly Gly Gly Gly Ser Gly Lys Lys Val Val Leu Gly Lys Lys
100 105 110

Gly Asp Thr Val Glu Leu Thr Cys Thr Ala Ser Gln Lys Lys Ser Ile
115 120 125

Gln Phe His Trp Lys Asn Ser Asn Gln Ile Lys Ile Leu Gly Asn Gln

```
    130                 135                 140

Gly Ser Phe Leu Thr Lys Gly Pro Ser Lys Leu Asn Asp Arg Ala Asp
145                 150                 155                 160

Ser Arg Arg Ser Leu Trp Asp Gln Gly Asn Phe Pro Leu Ile Ile Lys
                165                 170                 175

Asn Leu Lys Ile Glu Asp Ser Asp Thr Tyr Ile Cys Glu Val Glu Asp
            180                 185                 190

Gln Lys Glu Glu Val Gln Leu Leu Val Phe Gly
        195                 200


<210> SEQ ID NO 255
<211> LENGTH: 456
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 255

Ala Val Asn Gly Thr Ser Gln Phe Thr Cys Phe Tyr Asn Ser Arg Ala
1               5                   10                  15

Asn Ile Ser Cys Val Trp Ser Gln Asp Gly Ala Leu Gln Asp Thr Ser
            20                  25                  30

Cys Gln Val His Ala Trp Pro Asp Arg Arg Arg Trp Asn Gln Thr Cys
        35                  40                  45

Glu Leu Leu Pro Val Ser Gln Ala Ser Trp Ala Cys Asn Leu Ile Leu
    50                  55                  60

Gly Ala Pro Asp Ser Gln Lys Leu Thr Thr Val Asp Ile Val Thr Leu
65                  70                  75                  80

Arg Val Leu Cys Arg Glu Gly Val Arg Trp Arg Val Met Ala Ile Gln
                85                  90                  95

Asp Phe Lys Pro Phe Glu Asn Leu Arg Leu Met Ala Pro Ile Ser Leu
            100                 105                 110

Gln Val Val His Val Glu Thr His Arg Cys Asn Ile Ser Trp Glu Ile
        115                 120                 125

Ser Gln Ala Ser His Tyr Phe Glu Arg His Leu Glu Phe Glu Ala Arg
    130                 135                 140

Thr Leu Ser Pro Gly His Thr Trp Glu Glu Ala Pro Leu Leu Thr Leu
145                 150                 155                 160

Lys Gln Lys Gln Glu Trp Ile Cys Leu Glu Thr Leu Thr Pro Asp Thr
                165                 170                 175

Gln Tyr Glu Phe Gln Val Arg Val Lys Pro Leu Gln Gly Glu Phe Thr
            180                 185                 190

Thr Trp Ser Pro Trp Ser Gln Pro Leu Ala Phe Arg Thr Lys Pro Ala
        195                 200                 205

Ala Leu Gly Lys Asp Thr Gly Ala Gln Asp Lys Thr His Thr Cys Pro
    210                 215                 220

Pro Cys Pro Ala Pro Glu Leu Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser His Glu Asp Pro Glu Val Lys Phe
            260                 265                 270

Asn Trp Tyr Val Asp Gly Val Glu Val His Asn Ala Lys Thr Lys Pro
        275                 280                 285
```

Arg Glu Glu Gln Tyr Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Ala Leu Pro Ala Pro Ile Glu Lys Thr Ile Ser Lys Ala
                325                 330                 335

Lys Gly Gln Pro Arg Glu Pro Gln Val Tyr Thr Leu Pro Pro Ser Arg
            340                 345                 350

Asp Glu Leu Thr Lys Asn Gln Val Ser Leu Ser Cys Ala Val Lys Gly
        355                 360                 365

Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Val Ser Lys Leu Thr Val Asp Lys Ser Arg Trp Gln Gln
                405                 410                 415

Gly Asn Val Phe Ser Cys Ser Val Met His Glu Ala Leu His Asn Arg
            420                 425                 430

Phe Thr Gln Lys Ser Leu Ser Leu Ser Pro Gly Lys Gly Ser Gly Ser
        435                 440                 445

Asp Tyr Lys Asp Asp Asp Asp Lys
    450                 455

<210> SEQ ID NO 256
<211> LENGTH: 497
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 256

Leu Asn Thr Thr Ile Leu Thr Pro Asn Gly Asn Glu Asp Thr Thr Ala
1               5                   10                  15

Asp Phe Phe Leu Thr Thr Met Pro Thr Asp Ser Leu Ser Val Ser Thr
            20                  25                  30

Leu Pro Leu Pro Glu Val Gln Cys Phe Val Phe Asn Val Glu Tyr Met
        35                  40                  45

Asn Cys Thr Trp Asn Ser Ser Ser Glu Pro Gln Pro Thr Asn Leu Thr
    50                  55                  60

Leu His Tyr Trp Tyr Lys Asn Ser Asp Asn Asp Lys Val Gln Lys Cys
65                  70                  75                  80

Ser His Tyr Leu Phe Ser Glu Glu Ile Thr Ser Gly Cys Gln Leu Gln
                85                  90                  95

Lys Lys Glu Ile His Leu Tyr Gln Thr Phe Val Val Gln Leu Gln Asp
            100                 105                 110

Pro Arg Glu Pro Arg Arg Gln Ala Thr Gln Met Leu Lys Leu Gln Asn
        115                 120                 125

Leu Val Ile Pro Trp Ala Pro Glu Asn Leu Thr Leu His Lys Leu Ser
    130                 135                 140

Glu Ser Gln Leu Glu Leu Asn Trp Asn Asn Arg Phe Leu Asn His Cys
145                 150                 155                 160

Leu Glu His Leu Val Gln Tyr Arg Thr Asp Trp Asp His Ser Trp Thr
                165                 170                 175

Glu Gln Ser Val Asp Tyr Arg His Lys Phe Ser Leu Pro Ser Val Asp
            180                 185                 190

Gly Gln Lys Arg Tyr Thr Phe Arg Val Arg Ser Arg Phe Asn Pro Leu
        195                 200                 205

Cys Gly Ser Ala Gln His Trp Ser Glu Trp Ser His Pro Ile His Trp
    210                 215                 220

Gly Ser Asn Thr Ser Lys Glu Asn Pro Phe Leu Phe Ala Leu Glu Ala
225                 230                 235                 240

Gly Ala Gln Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Trp Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys Gly Ser Gly Ser Gly Leu Asn Asp Ile Phe
465                 470                 475                 480

Glu Ala Gln Lys Ile Glu Trp His Glu His His His His His His His
                485                 490                 495

His

<210> SEQ ID NO 257
<211> LENGTH: 8
<212> TYPE: PRT
<213> ORGANISM: Artificial Sequence
<220> FEATURE:
<223> OTHER INFORMATION: Description of Artificial Sequence: Synthetic peptide

<400> SEQUENCE: 257

Asp Tyr Lys Asp Asp Asp Asp Lys
1               5

<210> SEQ ID NO 258
<211> LENGTH: 8
<212> TYPE: PRT
<213> ORGANISM: Artificial Sequence
<220> FEATURE:
<223> OTHER INFORMATION: Description of Artificial Sequence: Synthetic
8xHis tag

<400> SEQUENCE: 258

His His His His His His His His
1 5

<210> SEQ ID NO 259
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 259

Gly Leu Asn Asp Ile Phe Glu Ala Gln Lys Ile Glu Trp His Glu
1 5 10 15

<210> SEQ ID NO 260
<211> LENGTH: 229
<212> TYPE: PRT
<213> ORGANISM: Artificial Sequence
<220> FEATURE:
<223> OTHER INFORMATION: Description of Artificial Sequence: Synthetic
polypeptide

<400> SEQUENCE: 260

Glu Ser Lys Tyr Gly Pro Pro Cys Pro Pro Cys Pro Ala Pro Glu Ala
1 5 10 15

Ala Gly Gly Pro Ser Val Phe Leu Phe Pro Pro Lys Pro Lys Asp Thr
20 25 30

Leu Met Ile Ser Arg Thr Pro Glu Val Thr Cys Val Val Val Asp Val
35 40 45

Ser Gln Glu Asp Pro Glu Val Gln Phe Asn Trp Tyr Val Asp Gly Val
50 55 60

Glu Val His Asn Ala Lys Thr Lys Pro Arg Glu Glu Gln Phe Asn Ser
65 70 75 80

Thr Tyr Arg Val Val Ser Val Leu Thr Val Leu His Gln Asp Trp Leu
85 90 95

Asn Gly Lys Glu Tyr Lys Cys Lys Val Ser Asn Lys Gly Leu Pro Ser
100 105 110

Ser Ile Glu Lys Thr Ile Ser Lys Ala Lys Gly Gln Pro Arg Glu Pro
115 120 125

Gln Val Tyr Thr Leu Pro Pro Ser Gln Glu Glu Met Thr Lys Asn Gln
130 135 140

Val Ser Leu Trp Cys Leu Val Lys Gly Phe Tyr Pro Ser Asp Ile Ala
145 150 155 160

Val Glu Trp Glu Ser Asn Gly Gln Pro Glu Asn Asn Tyr Lys Thr Thr
165 170 175

Pro Pro Val Leu Asp Ser Asp Gly Ser Phe Phe Leu Tyr Ser Arg Leu
180 185 190

Thr Val Asp Lys Ser Arg Trp Gln Glu Gly Asn Val Phe Ser Cys Ser
195 200 205

Val Met His Glu Ala Leu His Asn His Tyr Thr Gln Lys Ser Leu Ser
210 215 220

Leu Ser Leu Gly Lys
225

<210> SEQ ID NO 261
<211> LENGTH: 229
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 261

```
Glu Ser Lys Tyr Gly Pro Pro Cys Pro Pro Cys Pro Ala Pro Glu Ala
1               5                   10                  15

Ala Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Ser Cys Ala Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Val Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn Arg Phe Thr Gln Lys Ser Leu Ser
    210                 215                 220

Leu Ser Leu Gly Lys
225
```

<210> SEQ ID NO 262
<211> LENGTH: 134
<212> TYPE: PRT
<213> ORGANISM: Macaca fascicularis

<400> SEQUENCE: 262

```
Ala Pro Thr Ser Ser Ser Thr Lys Lys Thr Gln Leu Gln Leu Glu His
1               5                   10                  15

Leu Leu Leu Asp Leu Gln Met Ile Leu Asn Gly Ile Asn Asn Tyr Lys
            20                  25                  30

Asn Pro Lys Leu Thr Arg Met Leu Thr Phe Lys Phe Tyr Met Pro Lys
        35                  40                  45

Lys Ala Thr Glu Leu Arg His Leu Gln Cys Leu Glu Glu Glu Leu Lys
    50                  55                  60

Pro Leu Glu Glu Val Leu Asn Leu Ala Gln Ser Lys Ser Phe His Leu
65                  70                  75                  80
```

-continued

```
Arg Asp Thr Lys Asp Leu Ile Ser Asn Ile Asn Val Ile Val Leu Glu
                85                  90                  95

Leu Lys Gly Ser Glu Thr Thr Leu Met Cys Glu Tyr Ala Asp Glu Thr
            100                 105                 110

Ala Thr Ile Val Glu Phe Leu Asn Arg Trp Ile Thr Phe Cys Gln Ser
        115                 120                 125

Ile Ile Ser Thr Leu Thr
    130


<210> SEQ ID NO 263
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 263

Lys Leu Leu Glu Ile Ala Pro Asn Cys
1               5


<210> SEQ ID NO 264
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 264

Gly Gly Gly Gly Ser
1               5


<210> SEQ ID NO 265
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 265

Gly Gly Gly Ser
1
```

INTERLEUKIN-2 VARIANT PROTEINS FUSED TO HUMAN IGG4 FC AND USES THEREOF

CROSS-REFERENCE TO RELATED APPLICATIONS

This application claims the benefit under 35 U.S.C. § 119(e) of U.S. Provisional Application No. 63/104,376, filed on Oct. 22, 2020 and U.S. Provisional Application No. 63/181,075, filed on Apr. 28, 2021, which are hereby incorporated herein by reference in their entireties for all purposes.

SEQUENCE LISTING

The instant application contains a Sequence Listing which has been submitted electronically in ASCII format and is hereby incorporated by reference in its entirety. Said ASCII copy, created on Sep. 20, 2021, is named 1348-WO-PCT-_SL.txt and is 569,532 bytes in size.

BACKGROUND

Interleukin-2 (IL-2, NCBI Gene ID: 3558) is an immunomodulatory cytokine that plays an important role in the generation, differentiation, survival and homeostasis of immune cells. IL-2 has therapeutic potential for treatment of cancer and chronic viral diseases through its immunostimulatory effects on $CD4^+$ and $CD8^+$ T cells as well as NK cells, however, this is compromised by its ability to preferentially stimulate and expand regulatory T (Treg) cells which suppress the immune system. In addition to this preferential activity on immunosuppressive Treg cells, IL-2 has a very short half-life in humans necessitating frequent dosing and can also induce life-threatening toxicities. The short half-life complicates the ability to administer a dose of IL-2 sufficient to elicit a desired immunostimulatory with reduced or minimal immunosuppressive effects but also avoiding toxicity, and presents significant challenges for the treatment of patients. See, e.g., Schwartz, et al., "Managing toxicities of high-dose interleukin-2," in Oncology (Williston Park) (2002) November; 16(11 Suppl 13):11-20.

SUMMARY

In one aspect, provided are interleukin-2 variants (IL-2v). In various embodiments, the IL-2v is truncated at the N-terminus by at least 5 amino acids relative to wild-type IL-2; and binds to the interleukin-2 receptor alpha subunit (IL-2RA; CD25) with reduced binding affinity in comparison to wild-type IL-2 (wt IL-2). In some embodiments, the IL-2v binds to IL-2RA with an equilibrium dissociation constant (KD) of at least 60 μM (e.g., 60 μM or higher). In some embodiments, the IL-2v binds to a complex of interleukin 2 receptor subunit beta (IL-2RB; CD122) and interleukin 2 receptor subunit gamma (IL-2RG; CD132) with a KD of less than 150 nM, e.g., less than 1.5 nM, e.g., less than 120 pM, e.g., less than 100 pM, e.g., less than 80 pM, e.g., less than 75 pM, e.g., less than 70 pM. In some embodiments, the IL-2v promotes equivalent or greater proliferation of CD8+ T cells relative to wild-type (wt) IL-2, or an IL 2v of any one of SEQ ID NOs: 43 and 44. In some embodiments, the concentration at which the IL-2v elicits 50% of maximal (EC50) signal transducer and activator of transcription 5 (STAT5) activation or signaling of regulatory T (Treg) cells is at least 1000-fold, e.g., at least 1500-fold, e.g., at least 1700-fold, e.g., at least 2000-fold, e.g., at least 2500-fold higher, relative to the EC50 for STAT5 activation or signaling of wt IL-2, or an IL-2v of any one of SEQ ID NOs: 43 and 44. In some embodiments, the concentration at which the IL-2v elicits EC50 of IL-2Rαβγ-mediated STAT5 activation or signaling (e.g., measured as STAT5 activation of CTLL2 cells) is at least 2500-fold, e.g., at least 5000-fold, e.g., at least 7500-fold, e.g., at least 10,000-fold, e.g., at least 15,000-fold, e.g., at least 20,000-fold higher, relative to the EC50 for STAT5 activation or signaling of wt IL-2, or an IL-2v of any one of SEQ ID NOs: 43 and 44. In some embodiments, the concentration at which the IL-2v elicits 50% of maximal (EC50) proliferation of natural killer (NK) cells is at least 10-fold, e.g., at least 12-fold, e.g., at least 15-fold, e.g., at least 16-fold, e.g., at least 18-fold, e.g., at least 20-fold higher, e.g., as measured using KHYG-1 cells, relative to the EC50 for proliferation of wt IL-2, or an IL-2v of any one of SEQ ID NOs: 43 and 44. In some embodiments, the IL-2v comprises a serine at position 125 (C125) and at least two, or at least three, substitutions at amino acid positions selected from the group consisting of R38, F42, Y45, E61 and E62, wherein the position numbers are with respect to an IL-2v of SEQ ID NO:44. In some embodiments, the IL-2v comprises a serine at position 125 (C125) and at least two, or at least three, substitutions at amino acid positions selected from the group consisting of R38, F42, Y45 and E62, wherein the position numbers are with respect to an IL-2v of SEQ ID NO:44. In some embodiments, the IL-2v comprises a serine at position 125 (C125) and at least two, or at least three, substitutions at amino acid positions selected from the group consisting of R38, F42 and E62, wherein the position numbers are with respect to an IL-2v of SEQ ID NO:44. In some embodiments, the IL-2v does not comprise amino acid substitutions at one or more positions selected from the group consisting of Y45, E61, E68 and L72. In some embodiments, the IL-2v does not comprise an amino acid substitution at one or more, or all, of positions selected from the group consisting of D20, Y45, E61, E68, V69, L72, A73, L80, R81, L85, L86, I87, I92 and Q126. In some embodiments, the IL-2v does not comprise an amino acid substitution at one or more, or all, of positions selected from the group consisting of H16, D20, E61, N88 and V91. In some embodiments, the IL-2v is PEGylated.

In one aspect, provided are fusion protein. In some embodiments, the fusion proteins comprise a serum half-life extending polypeptide operably linked to an interleukin-2 variant (IL-2v), wherein the IL-2v is truncated at the N-terminus by at least 5 amino acids relative to wild-type IL-2; and binds to the interleukin-2 receptor alpha subunit (IL-2RA; CD25) with reduced binding affinity in comparison to wild-type IL-2 (wt IL-2). In some embodiments, the serum half-life extending polypeptide is selected from the group consisting of: an immunoglobulin fragment crystallizable region (Fc region), a serum albumin, an albumin binding protein or peptide, an IgG, an XTEN polypeptide, a proline/alanine/serine-rich (PAS) polypeptide, an elastin-like polypeptide. In some embodiments, the serum half-life extending polypeptide is an immunoglobulin fragment crystallizable region (Fc region). In some embodiments, the fusion protein binds to IL-2RA with an equilibrium dissociation constant (KD) of at least 60 μM (e.g., 60 μM or higher). In some embodiments, the IL-2v binds to a complex of interleukin 2 receptor subunit beta (IL-2RB; CD122) and interleukin 2 receptor subunit gamma (IL-2RG; CD132) with a KD of less than 150 nM, e.g., less than 1.5 nM, e.g., less than 120 pM, e.g., less than 100 pM, e.g., less than 80 pM, e.g., less than 75 pM, e.g., less than 70 pM. In some embodiments, the fusion protein promotes equivalent or greater proliferation of CD8+ T cells relative to an IL-2v of any one of SEQ ID NOs: 43 and 44, a fusion protein comprising Fc operably linked to wt IL-2, or a fusion protein of any one of SEQ ID NOs. 117, 118, 161 and 162. In some embodiments, the concentration at which the IL-2v fusion protein elicits 50% of maximal (EC50) signal transducer and activator of transcription 5 (STAT5) activation or signaling of regulatory T (Treg) cells is at least 1000-fold, e.g., at least 1500-fold, e.g., at least 1700-fold, e.g., at least 2000-fold, e.g., at least 2500-fold higher, relative to the EC50 for STAT5 for activation or signaling of wt IL-2, or an IL-2v of any one of SEQ ID NOs: 43 and 44, a fusion protein comprising Fc operably linked to wt IL-2, or a fusion protein of any one of SEQ ID NOs. 117, 118, 161 or 162. In some embodiments, the concentration at which the IL-2v fusion protein elicits EC50 of IL-2Rαβγ-mediated STAT5 activation or signaling (e.g., measured as STAT5 activation of CTLL2 cells) is at least 2500-fold, e.g., at least 5000-fold, e.g., at least 7500-fold, e.g., at least 10,000-fold, e.g., at least 15,000-fold, e.g., at least 20,000-fold higher, relative to the EC50 for STAT5 activation or signaling of wt IL-2, or an IL-2v of any one of SEQ ID NOs: 43 and 44, a fusion protein comprising Fc operably linked to wt IL 2, or a fusion protein of any one of SEQ ID NOs. 117, 118, 161 or 162. In some embodiments, the concentration at which the IL-2v fusion protein elicits 50% of maximal (EC50) proliferation of natural killer (NK) cells is at least 10-fold, e.g., at least 12-fold, e.g., at least 15-fold, e.g., at least 16-fold, e.g., at least 18-fold, e.g., at least 20-fold higher, e.g., as measured using KHYG-1 cells, relative to the EC50 for proliferation of wt IL-2, or an IL-2v of any one of SEQ ID NOs: 43 and 44, a fusion protein comprising Fc operably linked to wt IL 2, or a fusion protein of any one of SEQ ID NOs. 117, 118, 161 or 162. In some embodiments, the IL-2v comprises a serine at position 125 (C125) and at least two, or at least three, substitutions at amino acid positions selected from the group consisting of R38, F42, Y45, E61 and E62, wherein the position numbers are with respect to an IL-2v of SEQ ID NO:44. In some embodiments, the IL-2v comprises a serine at position 125 (C125) and at least two, or at least three, substitutions at amino acid positions selected from the group consisting of R38, F42, Y45 and E62, wherein the position numbers are with respect to an IL-2v of SEQ ID NO:44. In some embodiments, the IL-2v comprises a serine at position 125 (C125) and at least two, or at least three, substitutions at amino acid positions selected from the group consisting of R38, F42 and E62, wherein the position numbers are with respect to an IL-2v of SEQ ID NO:44. In some embodiments, the IL-2v does not comprise amino acid substitutions at one or more positions selected from the group consisting of Y45, E61, E68 and L72. In some embodiments, the IL-2v does not comprise the amino acid sequence APTSS (SEQ ID NO: 163). In some embodiments, the IL-2v is from a human wild-type IL-2. In some embodiments, the IL-2v comprises an amino acid sequence selected from the group consisting of SEQ ID NOs: 1-42 or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 1-42. In some embodiments, the Fc region is from a human IgG1, IgG2, IgG3 or IgG4. In some embodiments, the Fc region is from a human IgG1 or IgG4. In some embodiments, the Fc region comprises a human IgG1 isotype and comprises one or more amino acid substitutions in the Fc region at a residue position selected from the group consisting of: N297A, N297G, N297Q, N297G, D265A, L234A, L235A, C226S, C229S, P238S, E233P, L234V, P238A, A327Q, A327G, P329A, P329G, K322A, L234F, L235E, P331S, T394D, A330L, M252Y, S254T, T256E, M428L, N434S, T366W, T366S, L368A, F405L, Y407V, K409R, H435R, Y436F, and any combination thereof, wherein the numbering of the residues is according to EU numbering. In some embodiments, the Fc region comprises a human IgG1 isotype and comprises one or more amino acid substitutions in the Fc region at a residue position selected from the group consisting of: L234A, L234V, L234F, L235A, L235E, D265A, P329G, P331S, and any combination thereof, wherein the numbering of the residues is according to EU numbering. In some embodiments, the Fc region comprises a human IgG4 isotype and comprises one or more amino acid substitutions in the Fc region at a residue position selected from the group consisting of: E233P, F234V, F234A, L235A, G237A, E318A, S228P, L235E, T394D, M252Y, S254T, T256E, N297A, N297G, N297Q, T366W, T366S, L368A, F405L, Y407V, K409R, M428L, N434S, H435R, Y436F, and any combination thereof, wherein the numbering of the residues is according to EU numbering. In some embodiments, the Fc region comprises a human IgG4 isotype and comprises one or more amino acid substitutions in the Fc region at a residue position selected from the group consisting of: F234V, F234A, L235A, L235E, S228P, and any combination thereof, wherein the numbering of the residues is according to EU numbering. In some embodiments, the Fc region comprises the following amino acids at the indicated positions (EU index numbering): Tyrosine at position 252, threonine at position 254 and glutamic acid at position 256 (YTE); or Leucine at position 428 and serine at position 434 (LS). In some embodiments, the Fc region comprises the following amino acids at the indicated positions (EU index numbering): an arginine at position 435 and a phenylalanine at position 436. In some embodiments, the terminal Fc amino acid residue (e.g., K447) is removed or eliminated. In some embodiments, the Fc region comprises an amino acid sequence selected from the group consisting of SEQ ID NOs: 45-72, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 45-72. In some embodiments, the Fc region comprises an amino acid sequence selected from the group consisting of SEQ ID NOs: 45, 47, 49, 52, 54, 56, 57, 59, 61, 63, 65, 67, 69 and 71, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 45, 47, 49, 52, 54, 56, 57, 59, 61, 63, 65, 67, 69 and 71. In some embodiments, the fusion protein comprises in sequential order from N-terminus to C-terminus, the Fc region and the IL-2v. In some embodiments, the fusion protein comprises a flexible linker between the Fc region and the IL-2v. In some embodiments, the linker has a length of from 4 to 50 amino acids, e.g., from 5 amino acids to 25 amino acids, e.g., from 15 amino acids to 25 amino acids. In some embodiments, the linker comprises from 1 to 10 units, e.g., 1 to 5 units, e.g., 3 to 5 units, of a poly-glycine serine linker selected from GGGS (SEQ ID NO: 265), GGGGS (SEQ ID NO: 264) and combinations thereof. In some embodiments, the fusion protein comprises an amino acid sequence selected from the group consisting of SEQ ID NOs: 75-116 and 119-160, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 75-116 and 119-160. In some embodiments, the fusion protein comprises an amino acid sequence selected from the group consisting of SEQ ID NOs: 166-171, or comprising an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 166-171. In some embodiments, the fusion protein does not specifically bind any antigen other than an Fc receptor or a complex of interleukin 2 receptor subunit beta (IL-2RB; CD122) and interleukin 2 receptor subunit gamma (IL-2RG; CD132). In some embodiments, the fusion protein comprises an N terminal signal peptide or leader sequence. In some embodiments, the IL-2v in the fusion protein is not PEGylated.

Further provided is a homodimer comprising two Fc-IL-2v fusion proteins, as described above and herein.

In another aspect, provided is a heterodimer comprising: (i) a first Fc-IL-2v fusion protein, as described above and herein, comprising a first Fc domain, and (ii) a second Fc-IL-2v fusion protein, as described above and herein, comprising a second Fc domain. In another aspect, provided is a heterodimer comprising: (i) an (i.e., one) Fc-IL-2v fusion protein, as described above and herein, comprising a first Fc domain, and (ii) a second Fc domain, e.g., that is empty or without a targeting moiety or an antigen binding domain. In some embodiments, the first Fc domain and the second Fc domain comprise the following amino acid substitutions (EU numbering), respectively: T366W and T366S/L368A/Y407V; T366S/L368A/Y407V and T366W; T366W/S354C and T366S/L368A/Y407V/Y349C; T366S/L368A/Y407V/Y349C and T366W/S354C; S364H/F405A and Y349T/T394F; Y349T/T394F and S364H/F405A; T350V/L351Y/F405A/Y407V and T350V/T366L/K392L/T394W; T350V/T366L/K392L/T394W and T350V/L351Y/F405A/Y407V; K360D/D399M/Y407A and E345R/Q347R/T366V/K409V; E345R/Q347R/T366V/K409V and K360D/D399M/Y407A; K409D/K392D and D399K/E356K; D399K/E356K and K409D/K392D; K360E/K409W and Q347R/D399V/F405T; Q347R/D399V/F405T and K360E/K409W; K360E/K409W/Y349C and Q347R/D399V/F405T/S354C; Q347R/D399V/F405T/S354C and K360E/K409W/Y349C; K370E/K409W and E357N/D399V/F405T; or E357N/D399V/F405T and K370E/K409W. In some embodiments, one or both of the first Fc domain and the second Fc domain comprise the following amino acids at the indicated positions (EU index numbering): Tyrosine at position 252, threonine at position 254 and glutamic acid at position 256 (YTE); or Leucine at position 428 and serine at position 434 (LS). In some embodiments, one or both of the first Fc domain and the second Fc domain comprise the following amino acids at the indicated positions (EU index numbering): an arginine at position 435 and a phenylalanine at position 436. In some embodiments, one or both of the first Fc domain and the second Fc domain comprise a human IgG4 isotype and comprises one or more amino acid substitutions in the Fc region at a residue position selected from the group consisting of: F234V, F234A, L235A, L235E, S228P, and any combination thereof, wherein the numbering of the residues is according to EU numbering. In some embodiments, one or both of the first Fc domain and the second Fc domain comprise a human IgG1 isotype and comprises one or more amino acid substitutions in the Fc region at a residue position selected from the group consisting of: L234A, L234V, L234F, L235A, L235E, P331S, and any combination thereof, wherein the numbering of the residues is according to EU numbering. In some embodiments, the terminal Fc amino acid residue (e.g., K447) is removed or eliminated from one or both of the first Fc domain and the second Fc domain. In some embodiments, the first Fc domain and the second Fc domain comprise amino acid sequences set forth, respectively, below, or comprise amino acid sequences that are at least 80%, at least 85%, at least 90%, at least 91%, at least 92%, at least 93%, at least 94%, at least 95%, at least 96%, at least 97%, at least 98%, or at least 99% identical to the amino acid sequences set forth, respectively, below: SEQ ID NOs.: 45 and 46; SEQ ID NOs.: 47 and 48; SEQ ID NOs.: 49 and 46; SEQ ID NOs.: 45 and 51; SEQ ID NOs.: 49 and 51; SEQ ID NOs.: 52 and 48; SEQ ID NOs.: 47 and 53; SEQ ID NOs.: 52 and 53; SEQ ID NOs.: 54 and 46; SEQ ID NOs.: 45 and 55; SEQ ID NOs.: 54 and 55; SEQ ID NOs.: 56 and 48; SEQ ID NOs.: 47 and 50; SEQ ID NOs.: 56 and 50; SEQ ID NOs.: 57 and 58; SEQ ID NOs.: 59 and 60; SEQ ID NOs.: 61 and 58; SEQ ID NOs.: 57 and 62; SEQ ID NOs.: 63 and 64; SEQ ID NOs.: 65 and 60; SEQ ID NOs.: 59 and 66; SEQ ID NOs.: 67 and 68; SEQ ID NOs.: 69 and 58; SEQ ID NOs.: 57 and 70; SEQ ID NOs.: 69 and 70; SEQ ID NOs.: 71 and 60; SEQ ID NOs.: 59 and 72; or SEQ ID NOs.: 71 and 72. In some embodiments, the heterodimer comprises a human IgG4 Fc-IL-2v fusion protein comprising an amino acid sequence selected from the group consisting of SEQ ID NOs: 75-116, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 75-116; and a second Fc region comprising an amino acid sequence selected from the group consisting of SEQ ID NOs: 46, 51 and 55, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 46, 51 and 55. In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 75 and SEQ ID NO: 46; SEQ ID NO: 76 and SEQ ID NO: 46; SEQ ID NO: 77 and SEQ ID NO: 46; SEQ ID NO: 78 and SEQ ID NO: 46; SEQ ID NO: 79 and SEQ ID NO: 46; SEQ ID NO: 80 and SEQ ID NO: 46; SEQ ID NO: 81 and SEQ ID NO: 46; SEQ ID NO: 82 and SEQ ID NO: 46; SEQ ID NO: 83 and SEQ ID NO: 46; SEQ ID NO: 84 and SEQ ID NO: 46; SEQ ID NO: 85 and SEQ ID NO: 46; SEQ ID NO: 86 and SEQ ID NO: 46; SEQ ID NO: 87 and SEQ ID NO: 46; SEQ ID NO: 88 and SEQ ID NO: 46; SEQ ID NO: 89 and SEQ ID NO: 46; SEQ ID NO: 90 and SEQ ID NO: 46; SEQ ID NO: 91 and SEQ ID NO: 46; SEQ ID NO: 92 and SEQ ID NO: 46; SEQ ID NO: 93 and SEQ ID NO: 46; SEQ ID NO: 94 and SEQ ID NO: 46; SEQ ID NO: 95 and SEQ ID NO: 46; SEQ ID NO: 96 and SEQ ID NO: 46; SEQ ID NO: 97 and SEQ ID NO: 46; SEQ ID NO: 98 and SEQ ID NO: 46; SEQ ID NO: 99 and SEQ ID NO: 46; SEQ ID NO: 100 and SEQ ID NO: 46; SEQ ID NO: 101 and SEQ ID NO: 46; SEQ ID NO: 102 and SEQ ID NO: 46; SEQ ID NO: 103 and SEQ ID NO: 46; SEQ ID NO: 104 and SEQ ID NO: 46; SEQ ID NO: 105 and SEQ ID NO: 46; SEQ ID NO: 106 and SEQ ID NO: 46; SEQ ID NO: 107 and SEQ ID NO: 46; SEQ ID NO: 108 and SEQ ID NO: 46; SEQ ID NO: 109 and SEQ ID NO: 46; SEQ ID NO: 110 and SEQ ID NO: 46; SEQ ID NO: 111 and SEQ ID NO: 46; SEQ ID NO: 112 and SEQ ID NO: 46; SEQ ID NO: 113 and SEQ ID NO: 46; SEQ ID NO: 114 and SEQ ID NO: 46; SEQ ID NO: 115 and SEQ ID NO: 46; or SEQ ID NO: 116 and SEQ ID NO: 46. In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 80 and SEQ ID NO: 46; SEQ ID NO: 107 and SEQ ID NO: 46; or SEQ ID NO: 114 and SEQ ID NO: 46. In some embodiments, the heterodimer comprises a human IgG4 Fc-IL-2v fusion protein comprising (i) a first amino acid sequence of SEQ ID NO: 114 or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO:114; and (ii) a second Fc region comprising an amino acid sequence of SEQ ID NO: 46, or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 46. In some embodiments, the heterodimer comprises a human IgG1 Fc-IL-2v fusion protein comprising an amino acid sequence selected from the group consisting of SEQ ID NOs: 119-160, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 119-160; and a second Fc region comprising an amino acid sequence selected from the group consisting of SEQ ID NOs: 58, 62 and 70, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 58, 62 and 70. In some embodiments, the heterodimer comprises a human IgG1 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 119 and SEQ ID NO: 58; SEQ ID NO: 120 and SEQ ID NO: 58; SEQ ID NO: 121 and SEQ ID NO: 58; SEQ ID NO: 122 and SEQ ID NO: 58; SEQ ID NO: 123 and SEQ ID NO: 58; SEQ ID NO: 124 and SEQ ID NO: 58; SEQ ID NO: 125 and SEQ ID NO: 58; SEQ ID NO: 126 and SEQ ID NO: 58; SEQ ID NO: 127 and SEQ ID NO: 58; SEQ ID NO: 128 and SEQ ID NO: 58; SEQ ID NO: 129 and SEQ ID NO: 58; SEQ ID NO: 130 and SEQ ID NO: 58; SEQ ID NO: 131 and SEQ ID NO: 58; SEQ ID NO: 132 and SEQ ID NO: 58; SEQ ID NO: 133 and SEQ ID NO: 58; SEQ ID NO: 134 and SEQ ID NO: 58; SEQ ID NO: 135 and SEQ ID NO: 58; SEQ ID NO: 136 and SEQ ID NO: 58; SEQ ID NO: 137 and SEQ ID NO: 58; SEQ ID NO: 138 and SEQ ID NO: 58; SEQ ID NO: 139 and SEQ ID NO: 58; SEQ ID NO: 140 and SEQ ID NO: 58; SEQ ID NO: 141 and SEQ ID NO: 58; SEQ ID NO: 142 and SEQ ID NO: 58; SEQ ID NO: 143 and SEQ ID NO: 58; SEQ ID NO: 144 and SEQ ID NO: 58; SEQ ID NO: 145 and SEQ ID NO: 58; SEQ ID NO: 146 and SEQ ID NO: 58; SEQ ID NO: 147 and SEQ ID NO: 58; SEQ ID NO: 148 and SEQ ID NO: 58; SEQ ID NO: 149 and SEQ ID NO: 58; SEQ ID NO: 150 and SEQ ID NO: 58; SEQ ID NO: 151 and SEQ ID NO: 58; SEQ ID NO: 152 and SEQ ID NO: 58; SEQ ID NO: 153 and SEQ ID NO: 58; SEQ ID NO: 154 and SEQ ID NO: 58; SEQ ID NO: 155 and SEQ ID NO: 58; SEQ ID NO: 156 and SEQ ID NO: 58; SEQ ID NO: 157 and SEQ ID NO: 58; SEQ ID NO: 158 and SEQ ID NO: 58; SEQ ID NO: 159 and SEQ ID NO: 58; or SEQ ID NO: 160 and SEQ ID NO: 58. In some embodiments, the heterodimer comprises a human IgG1 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 124 and SEQ ID NO: 58; SEQ ID NO: 151 and SEQ ID NO: 58; or SEQ ID NO: 158 and SEQ ID NO: 58. In some embodiments of the heterodimer, the polypeptide comprising the first Fc domain comprises a first N terminal signal peptide or leader sequence and the polypeptide comprising the second Fc domain comprises a second N terminal signal peptide or leader sequence. In some embodiments, the first N terminal signal peptide or leader sequence and the second first N terminal signal peptide or leader sequence are the same. In some embodiments, the first N terminal signal peptide or leader sequence and the second first N terminal signal peptide or leader sequence are different. In some embodiments, the heterodimer does not specifically bind any antigen other than an Fc receptor or a complex of interleukin 2 receptor subunit beta (IL-2RB; CD122) and interleukin 2 receptor subunit gamma (IL-2RG; CD132). In some embodiments, the second Fc domain is not fused to an antigen binding domain. In some embodiments, neither the first Fc domain nor the second Fc domain is fused to an antigen binding domain. In some embodiments, the heterodimer comprises a serum half-life in a human of at least 6, 9, 12, 15, 18, 21, 24 hours, e.g., at least 1, 2, 3, 4, 5, 6, 7, 8, 9, 10, 11, 12, 13, 14 days, or longer. In some embodiments, the second Fc domain is fused to an antigen binding domain. In some embodiments, the antigen binding domain binds to CD8. In some embodiments, the antigen binding domain binds to an immune checkpoint protein. In some embodiments, the immune checkpoint protein is selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160 (NK1, NK28, BY55), MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); sialic acid binding Ig like lectin 7 (SIGLEC7); sialic acid binding Ig like lectin 9 (SIGLEC9); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); CD160; killer cell lectin like receptor B1 (KLRB1, CD161); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the immune checkpoint protein is selected from the group consisting of: CD274 (CD274, PDL1, PD-L1) and programmed cell death 1 (PDCD1, PD1, PD-1). In some embodiments, the antigen binding domain binds to a target selected from the group consisting of: asialoglycoprotein receptor 1 (ASGR1), asialoglycoprotein receptor 2 (ASGR2), ATP binding cassette (ABC) family transporter (e.g., ATP binding cassette subfamily B member 1 (ABCB1; P-GP), ATP binding cassette subfamily B member 4 (ABCB4; MDR3), ATP binding cassette subfamily C member 1 (ABCC1; MRP1), ATP binding cassette subfamily C member 2 (ABCC2; MRP2), ATP binding cassette subfamily C member 3 (ABCC3; MRP3), ATP binding cassette subfamily C member 4 (ABCC4; MRP4), ATP binding cassette subfamily G member 2 (Junior blood group; ABCG2; BCRP), and ATP binding cassette subfamily B member 11 (ABCB11; a.k.a., Bile Salt Export Pump (BSEP)); a solute carrier (SLC) family transporter (e.g., solute carrier family 10 member 1 (SLC10A1; a.k.a., Sodium-taurocholate Co-transporting Polypeptide (NTCP)); solute carrier family 16 member 1 (SLC16A1; MCT1), solute carrier family 22 member 1 (SLC22A1; OCT1), solute carrier family 22 member 3 (SLC22A3; OCT3), solute carrier family 22 member 7 (SLC22A7; OAT2), solute carrier family 27 member 5 (SLC27A5; FATP5), solute carrier organic anion transporter family member 1B1 (SLCO1B1; OATP1B1), solute carrier organic anion transporter family member 1B3 (SLCO1B3; OATP1B3), and solute carrier organic anion transporter family member 2B1 (SLCO2B1; OATP2B1)), transferrin receptor 2 (TFR2, TFRC2) and an HBV epitope (e.g., HBV core 18-27; env181-193; env 335-343; pol 575-583) presented in major histocompatibility complex (MHC) molecule (pMHC). In some embodiments, the antigen binding domain binds to a target selected from the group consisting of human immunodeficiency virus (HIV) gp120, HIV gp41, human CD4, and human interleukin 7 receptor (IL7R; CD127). In some embodiments, the antigen binding domain binds to a target selected from the group consisting of herpes simple virus (HSV) glycoprotein B (gB), glycoprotein C (gC), glycoprotein D (gD) and glycoprotein E (gE). In some embodiments, the antigen binding domain binds to a target or tumor associated antigen (TAA) selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1 (SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (KIT); C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1);

delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen. In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP), alpha fetoprotein (AFP), A-kinase anchoring protein 4 (AKAP4), ATPase family AAA domain containing 2 (ATAD2), kinetochore scaffold 1 (KNL1; a.k.a., CASC5), centrosomal protein 55 (CEP55), cancer/testis antigen 1A (CTAG1A; a.k.a., ESO1; CT6.1; LAGE-2; LAGE2A; NY-ESO-1), cancer/testis antigen 1B (CTAG1B; a.k.a., CT6.1, CTAG, CTAG1, ESO1, LAGE-2, LAGE2B, NY-ESO-1), cancer/testis antigen 2 (CTAG2; a.k.a., CAMEL, CT2, CT6.2, CT6.2a, CT6.2b, ESO2, LAGE-1, LAGE2B), CCCTC-binding factor like (CTCFL), catenin alpha 2 (CTNNA2), cancer/testis antigen 83 (CT83), cyclin A1 (CCNA1), DEAD-box helicase 43 (DDX43), developmental pluripotency associated 2 (DPPA2), fetal and adult testis expressed 1 (FATE1), FMR1 neighbor (FMR1NB), HORMA domain containing 1 (HORMAD1), insulin like growth factor 2 mRNA binding protein 3 (IGF2BP3), leucine zipper protein 4 (LUZP4), lymphocyte antigen 6 family member K (LY6K), maelstrom spermatogenic transposon silencer (MAEL), MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2), kinesin family member 20B (KIF20B; a.k.a., MPHOSPH1), NUF2 component of NDC80 kinetochore complex (NUF2), nuclear RNA export factor 2 (NXF2), PAS domain containing repressor 1 (PASD1), PDZ binding kinase (PBK), piwi like RNA-mediated gene silencing 2 (PIWIL-2), preferentially expressed antigen in melanoma (PRAME), sperm associated antigen 9 (SPAG9), sperm protein associated with the nucleus, X-linked, family member A1 (SPANXA1), SPANX family member A2 (SPANXA2), SPANX family member C (SPANXC), SPANX family member D (SPANXD), SSX family member 1 (SSX1), SSX family member 2 (SSX2), synaptonemal complex protein 3 (SYCP3), testis expressed 14, intercellular bridge forming factor (TEX14), transcription factor Dp family member 3 (TFDP3), serine protease 50 (PRSS50, a.k.a., TSP50), TTK protein kinase (TTK) and zinc finger protein 165 (ZNF165).

In a further aspect, provided is a conjugate comprising: an IL-2v described above and herein, an Fc-IL-2v fusion protein as described above and herein, a homodimer as described above and herein, or a heterodimer as described above and herein; attached to a therapeutic agent. In some embodiments, the therapeutic agent is covalently linked, e.g., to the IL-2v, the Fc-IL-2v fusion protein, the homodimer or the heterodimer. In some embodiments, the therapeutic agent is a small organic compound. In some embodiments, the therapeutic agent is selected from GS-4224 and GS-4416. In some embodiments, the therapeutic agent is an agonist or activator of a pattern recognition receptor (PRR), e.g., a Toll-like receptor (TLR), a RIG-I-like receptor (RLRs), a NOD-like receptors (NLR), an AIM2-like receptors (ALR), a C-type lectin receptors (CLR), a DNA receptor or an RNA receptor. In some embodiments, the therapeutic agent is an agonist or activator of a toll-like receptor (TLR), DExD/H-box helicase 58 (DDX58; a.k.a., RIG-I) or a stimulator of interferon genes (STING) receptor. In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of vesatolimod (GS-9620), DS-0509, LHC-165, TMX-101 (imiquimod), RO7020531 and JNJ-4964, and/or wherein the TLR8 agonist is selected from the group consisting of selgantolimod (GS-9688) and NKTR-262 (dual TLR7/TLR8 agonist).

In a further aspect, provided is a polynucleotide encoding an IL-2v described above and herein, an Fc-IL-2v fusion protein as described above and herein, or a homodimer as described above and herein. In some embodiments, the polynucleotide comprises a nucleic acid sequence selected from the group consisting of SEQ ID NOs: 175-212, or a nucleic acid sequence that is at least 80%, at least 85%, at least 90%, at least 91%, at least 92%, at least 93%, at least 94%, at least 95%, at least 96%, at least 97%, at least 98%, or at least 99% identical to a nucleic acid sequence selected from the group consisting of SEQ ID NOs: 175-212. Further provided is a polynucleotide or multiple polynucleotides encoding the Fc-IL-2v fusion protein and the second Fc region of a heterodimer described above and herein. In some embodiments, the polynucleotide or polynucleotides encoding the Fc-IL-2v fusion protein comprises a nucleic acid selected from the group consisting of SEQ ID NOs: 175-212, or a nucleic acid sequence that is at least 80%, at least 85%, at least 90%, at least 91%, at least 92%, at least 93%, at least 94%, at least 95%, at least 96%, at least 97%, at least 98%, or at least 99% identical to a nucleic acid sequence selected from the group consisting of SEQ ID NOs: 175-212. In some embodiments, the polynucleotide or polynucleotides encoding the second Fc region comprises a nucleic acid selected from the group consisting of SEQ ID NOs: 214-215, or a nucleic acid sequence that is at least 80%, at least 85%, at least 90%, at least 91%, at least 92%, at least 93%, at least 94%, at least 95%, at least 96%, at least 97%, at least 98%, or at least 99% identical to a nucleic acid sequence selected from the group consisting of SEQ ID NOs: 214-215. In some embodiments, the polynucleotide or polynucleotides are selected from the group consisting of DNA, cDNA, RNA or mRNA. Further provided is an expression cassette or multiple expression cassettes comprising one or more regulatory sequences operably linked to the polynucleotide or polynucleotides described above and herein.

In a further aspect, provided is a vector comprising the polynucleotide or polynucleotides, or an expression cassette, as described above and herein. In some embodiments, the vector is a plasmid vector or a viral vector. In some embodiments, the viral vector comprises an oncolytic viral vector. In some embodiments, the viral vector comprises a DNA virus or an RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Retroviridae (e.g., Lentivirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus) and Enteroviridae (e.g., Echovirus). Further provided is a lipoplex, e.g., lipid nanoparticle (LNP), comprising the polynucleotide or polynucleotides, an expression cassette, or a vector, described above and herein.

In a further aspect, provided is a cell or population of cells comprising the polynucleotide or polynucleotides, an expression cassette or a vector, as described above and herein, wherein the cell or population of cells expresses an IL-2v, an Fc-IL-2v fusion protein, a homodimer, or a heterodimer, as described above and herein. In some embodiments, the cell or population of cells is a eukaryotic cell. In some embodiments, the cell or population of cells comprises a mammalian cell, an insect cell, a plant cell or a yeast cell. In some embodiments, the mammalian cell is a Chinese Hamster Ovary (CHO) cell. In some embodiments, the mammalian cell is a human cell. In some embodiments, the cell is a human embryonic kidney cell.

In a further aspect, provided are methods of producing an Fc-IL-2 fusion protein heterodimer. In some embodiments, the methods comprise: (a) culturing a cell or population of cells, as described above and herein, transformed with at least a polynucleotide or polynucleotides encoding an Fc-IL-2v fusion protein, as described herein, or the expression cassette or multiple expression cassette, as described herein, in a cell culture under conditions sufficient to express the Fc-IL-2 fusion protein heterodimer molecules; and (b) isolating or purifying the Fc-IL-2 fusion protein heterodimer molecules from the cell culture. In some embodiments, the Fc-IL-2 fusion polypeptide and the Fc polypeptide are expressed and assembled in the same cell. In some embodiments, the isolating or purifying step comprises Protein A chromatography. In some embodiments, the isolating or purifying step further comprises in-stream pH neutralization or immediate pH neutralization of Protein A chromatography eluate. In some embodiments, the isolating or purifying step further comprises anion exchange chromatography. In some embodiments, at least 90%, 91%, 92%, 93%, 94%, 95%, 96%, 97%, 98%, 99%, or more, of the Fc-IL-2 fusion protein heterodimer molecules are isolated or purified (e.g., in monodispersed form). In some embodiments, at least 95%, 96%, 97%, 98%, 99%, or more, of the Fc-IL-2 fusion protein heterodimer molecules are isolated or purified (e.g., in monodispersed form). In some embodiments, at least 98%, 99%, or more, of the Fc-IL-2 fusion protein heterodimer molecules are isolated or purified (e.g., in monodispersed form). In some embodiments, the cell or population of cells are cultured in a culture volume of at least 2 L, e.g., at least 5 L, 10 L, 50 L, 100 L, 150 L, 200 L, 250 L, or more. In some embodiments, the methods further comprise formulating the Fc-IL-2 fusion protein heterodimer molecules into a sterile pharmaceutical composition suitable for administration to a human subject.

In a further aspect, provided is a pharmaceutical composition comprising an IL-2v, an Fc-IL-2v fusion protein, a homodimer, a heterodimer, a conjugate, the polynucleotide or polynucleotides, an expression cassette, a vector, or the lipoplex (e.g., LNP), as described herein, and a pharmaceutically acceptable carrier. In some embodiments, the composition comprises an aqueous formulation. In some embodiments, the pharmaceutical composition comprises the IL-2v, the Fc-IL-2v fusion protein, the homodimer, the heterodimer and/or the conjugate at a concentration in the range of 0.05 mg/ml to 50 mg/ml, e.g., from 0.05 mg/ml to 20 mg/ml, e.g., from 0.1 mg/ml to 40 mg/ml, e.g., from 1.0 mg/ml to 30 mg/ml, e.g., from 0.05 mg/ml to 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml or 50 mg/ml. In some embodiments, the composition is lyophilized. In some embodiments, the pharmaceutical composition further comprises one or more additional therapeutic agents. In some embodiments, the composition is lyophilized. In some embodiments, the pharmaceutical composition further comprises a second therapeutic agent. In some embodiments, the composition is lyophilized. In some embodiments, the pharmaceutical composition further comprises second and third therapeutic agents.

In a further aspect, provided are methods for eliciting an immune response to human hepatitis B virus (HBV) in a subject in need thereof. Further provided are methods of treating or preventing human hepatitis B virus (HBV) in a subject in need thereof. In some embodiments, the anti-HBV methods comprise administering to the subject a therapeutically effective amount of an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein. In some embodiments, the subject is infected with HBV, is suspected of being infected with HBV, or is at risk of being infected with HBV. In some embodiments, the subject is asymptomatic. In some embodiments, the subject is chronically infected with HBV. In some embodiments, the subject is exhibiting or experiencing one or more symptoms selected from hepatic failure, hepatic cancer, hepatic fibrosis and hepatic cirrhosis. In some embodiments, the subject is acutely infected with HBV. In some embodiments, the subject is exhibiting or experiencing one or more symptoms selected from jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. In some embodiments, the subject is co-infected with hepatitis D virus (HDV). In some embodiments, the subject is not receiving antiviral therapy or antiviral therapy is discontinued prior to administration of the IL-2v, the Fc-IL-2v fusion protein, the homodimer, the heterodimer, the conjugate, the polynucleotide or polynucleotides, the expression cassette, the vector, or the lipoplex (e.g., LNP) or the pharmaceutical composition. In some embodiments, antiviral therapy is discontinued after one or more administrations of the IL-2v, the Fc-IL-2v fusion protein, the homodimer, the heterodimer, the conjugate, the polynucleotide, the vector, the lipoplex (e.g., LNP) and/or the pharmaceutical composition. In some embodiments, the methods further comprise co-administering to the subject one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir alafenamide (TAF or VEMLIDY®), ledipasvir+sofosbuvir (HARVONI®) and a PEGylated interferon (e.g., PEG-IFN-$\alpha$2a and/or PEG-IFN-$\alpha$2b). In some embodiments, the methods further comprise co-administering to the subject one or more therapeutic agents selected from the group consisting of HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors, HBsAg secretion or assembly inhibitors, HBV viral entry inhibitors, and CAR-T and T cell bispecific (redirected T cells) for specific killing of HBV-infected cells.

In a further aspect, provided are methods of activating a latent viral reservoir in a subject infected with human immunodeficiency virus (HIV). Further provided are methods of treating or preventing human immunodeficiency virus (HIV) in a subject in need thereof. In some embodiments, the anti-HIV methods comprise administering to the subject a therapeutically effective amount of an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein. In some embodiments, the methods further comprise administering to the subject an additional therapeutic agent. In some embodiments, the methods further comprise administering to the subject one or more anti-HIV broadly neutralizing antibodies. In some embodiments, the one or more anti-HIV broadly neutralizing antibodies bind to an epitope or region of gp120 selected from the group consisting of: (i) third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. In some embodiments, the one or more anti-HIV broadly neutralizing antibodies bind to an epitope or region of gp120 in the third variable loop (V3) and/or high mannose patch comprising a N332 oligomannose glycan and competes with or comprises VH and VL regions from an antibody selected from the group consisting of GS-9722, PGT-121, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. In some embodiments, the one or more anti-HIV broadly neutralizing antibodies bind to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CHO1, CH59, PGDM1400, CAP256, CAP256-VRC26.08, CAP256-VRC26.09, CAP256-VRC26.25, PCT64-24E and VRC38.01. In some embodiments, the one or more anti-HIV broadly neutralizing antibodies bind to an epitope or region of gp120 in the CD4 binding site (CD4bs) and competes with or comprises VH and VL regions from an antibody selected from the group consisting of 3BNC117, GS-9723, 3BNC60, b12, F105, VRC01, VRC07, VRC07-523, VRC03, VRC06, VRC06b01 VRC08, VRC0801, NIH45-46, VRC-PG04, PGV04; CH103, 44-VRC13.01, 1NC9, 12A12, N6, N49-P7, NC-Cow1, IOMA, CH235 and CH235.12, N49P6, N49P7, N49P11, N49P9 and N60P25. In some embodiments, the one or more anti-HIV broadly neutralizing antibodies bind to an epitope or region of gp120 in the gp120/gp41 interface and competes with or comprises VH and VL regions from an antibody selected from the group consisting of PGT-151, CAP248-2B, 35022, 8ANC195, ACS202, VRC34 and VRC34.01. In some embodiments, the one or more anti-HIV broadly neutralizing antibodies bind to an epitope or region of the gp120 silent face and competes with or comprises VH and VL regions from an antibody selected from VRC-PG05 and SF12. In some embodiments, the one or more anti-HIV broadly neutralizing antibodies bind to an epitope or region of gp41 in the membrane proximal region (MPER). In some embodiments, the one or more anti-HIV broadly neutralizing antibodies bind to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01. In some embodiments, the one or more anti-HIV broadly neutralizing antibodies bind to an epitope or region of the gp41 fusion peptide and competes with or comprises VH and VL regions from an antibody selected from the group consisting of VRC34 and ACS202. In some embodiments, the subject is not receiving antiretroviral therapy (ART) or ART is discontinued prior to administration of the IL-2v, the Fc-IL-2v fusion protein, the homodimer, the heterodimer, the conjugate, the polynucleotide or polynucleotides, the expression cassette, the vector, the lipoplex (e.g., LNP) or the pharmaceutical composition. In some embodiments, ART is discontinued after one or more administrations of the IL-2v, the Fc-IL-2v fusion protein, the homodimer, the heterodimer, the conjugate, the polynucleotide or polynucleotides, the expression cassette, the vector, the lipoplex (e.g., LNP) or the pharmaceutical composition. In some embodiments, the methods further comprise administering one or more antiretroviral therapy (ART) agents to the subject. In some embodiments, the subject is chronically infected with HIV.

In a further aspect, provided are methods of enhancing, improving, and/or increasing the response to a vaccine therapy in a subject in need thereof. In some embodiments, the vaccine enhancing methods comprise co-administering to the subject (1) an effective amount of an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein; and (2) an effective amount of a vaccine. In some embodiments, the vaccine is selected from the group consisting of an antiviral vaccine, an antibacterial vaccine and an anticancer vaccine. In some embodiments, the vaccine comprises an antiviral vaccine against a virus selected from the group consisting of hepatitis A virus (HAV), hepatitis B virus (HBV), human immunodeficiency virus (HIV), cytomegalovirus (CMV), a herpes simplex virus (HSV), Epstein-Barr virus (EBV), human orthopneumovirus or human respiratory syncytial virus (RSV), human papillomavirus (HPV), varicella-zoster virus, measles virus, mumps virus, poliovirus vaccine, influenza virus, paramyxovirus, rotavirus, Zika virus, Dengue virus, Ebola virus and coronavirus (e.g., betacoronavirus, e.g., severe acute respiratory syndrome-related coronavirus, e.g., SARS-CoV2). In some embodiments, the vaccine comprises an antibacterial vaccine against a bacterium selected from the group consisting of *Mycobacterium tuberculosis*, pertussis, tetanus, diphtheria, meningococcus, pneumococcus, *Haemophilus* influenza, cholera, typhoid, and anthrax. In some embodiments, the methods comprise a prime-boost regimen comprising administering a priming composition at a first time point and administering one or more boosting compositions at one or more subsequent time points. In some embodiments, the priming composition comprises an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein. In some embodiments, the one or more boosting compositions comprise an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein. In some embodiments, the priming composition and the boosting composition are the same. In some embodiments, the priming composition and the boosting composition are different.

In a further aspect, provided are methods of preventing, reducing and/or inhibiting the recurrence, growth, proliferation, migration and/or metastasis of a cancer cell or population of cancer cells in a subject in need thereof. In some embodiments, the anti-cancer methods comprise administering to the subject a therapeutically effective amount of an IL-2v, an Fc-IL-2v fusion protein, a homodimer, a heterodimer, a conjugate, the polynucleotide or polynucleotides, an expression cassette, a vector, the lipoplex (e.g., LNP), or a pharmaceutical composition, as described herein. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more anti-neoplastic or chemotherapeutic agents. In some embodiments, the one or more anti-neoplastic or chemotherapeutic agents are selected from the group consisting of a nucleoside analog (e.g., 5-fluorouracil, gemcitabine, cytarabine, cladribine, pentostatin, fludarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), and mixtures thereof. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with a FOLFOX regimen, a FOLFIRI regimen, a FOLFOXIRI regimen or a FOLFIRINOX regimen. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with an immunotherapy comprising one or more antibodies or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins directed against one or more targets or tumor associated antigens (TAAs) selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1 (SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (KIT); C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1); delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen. In some embodiments, the one or more antibodies or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins binds to an epitope of a target or tumor associated antigen (TAA) presented in a major histocompatibility complex (MHC) molecule. In some embodiments, the NK cell-activating receptor is selected from the group consisting of CD16, NKp30, NKp44, NKp46, NKp80 and NKG2D. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more cellular therapies selected from the group consisting of: natural killer (NK) cells, NK-T cells, T cells, cytokine-induced killer (CIK) cells, macrophage (MAC) cells, tumor infiltrating lymphocytes (TILs) and dendritic cells (DCs). In some embodiments, the one or more cellular therapies comprise a T cell therapy selected from the group consisting of: alpha/beta TCR T cells, gamma/delta TCR T cells, regulatory T (Treg) cells and TRuC™ T cells. In some embodiments, the one or more cellular therapies comprise a NK cell therapy, e.g., comprising NK-92 cells. In some embodiments, the one or more cellular therapies comprise cells that are autologous, syngeneic or allogeneic to the subject. In some embodiments, the one or more cellular therapies comprise cells comprising chimeric antigen receptors (CARs). In some embodiments, the cells in the cellular therapy bind to a target or tumor associated antigen (TAA) selected from the group consisting of selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1 (SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (KIT); C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1); delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen. In some embodiments, the cells in the cellular therapy bind to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP), alpha fetoprotein (AFP), A-kinase anchoring protein 4 (AKAP4), ATPase family AAA domain containing 2 (ATAD2), kinetochore scaffold 1 (KNL1; a.k.a., CASC5), centrosomal protein 55 (CEP55), cancer/testis antigen 1A (CTAG1A; a.k.a., ESO1; CT6.1; LAGE-2; LAGE2A; NY-ESO-1), cancer/testis antigen 1B (CTAG1B; a.k.a., CT6.1, CTAG, CTAG1, ESO1, LAGE-2, LAGE2B, NY-ESO-1), cancer/testis antigen 2 (CTAG2; a.k.a., CAMEL, CT2, CT6.2, CT6.2a, CT6.2b, ESO2, LAGE-1, LAGE2B), CCCTC-binding factor like (CTCFL), catenin alpha 2 (CTNNA2), cancer/testis antigen 83 (CT83), cyclin A1 (CCNA1), DEAD-box helicase 43 (DDX43), developmental pluripotency associated 2 (DPPA2), fetal and adult testis expressed 1 (FATE1), FMR1 neighbor (FMR1NB), HORMA domain containing 1 (HORMAD1), insulin like growth factor 2 mRNA binding protein 3 (IGF2BP3), leucine zipper protein 4 (LUZP4), lymphocyte antigen 6 family member K (LY6K), maelstrom spermatogenic transposon silencer (MAEL), MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2), kinesin family member 20B (KIF20B; a.k.a., MPHOSPH1), NUF2 component of NDC80 kinetochore complex (NUF2), nuclear RNA export factor 2 (NXF2), PAS domain containing repressor 1 (PASD1), PDZ binding kinase (PBK), piwi like RNA-mediated gene silencing 2 (PIWIL-2), preferentially expressed antigen in melanoma (PRAME), sperm associated antigen 9 (SPAG9), sperm protein associated with the nucleus, X-linked, family member A1 (SPANXA1), SPANX family member A2 (SPANXA2), SPANX family member C (SPANXC), SPANX family member D (SPANXD), SSX family member 1 (SSX1), SSX family member 2 (SSX2), synaptonemal complex protein 3 (SYCP3), testis expressed 14, intercellular bridge forming factor (TEX14), transcription factor Dp family member 3 (TFDP3), serine protease 50 (PRSS50, a.k.a., TSP50), TTK protein kinase (TTK) and zinc finger protein 165 (ZNF165). In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with a targeted E3 ligase ligand conjugate. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more additional therapeutic agents comprising an inhibitor or antagonist of: protein tyrosine phosphatase, non-receptor type 11 (PTPN11 or SHP2), myeloid cell leukemia sequence 1 (MCL1) apoptosis regulator, 5'-nucleotidase ecto (NT5E or CD73), ectonucleoside triphosphate diphosphohydrolase 1 (ENTPD1 or CD39), transforming growth factor beta 1 (TGFB1 or TGFβ), heme oxygenase 1 (HMOX1, HO-1 or HO1), heme oxygenase 2 (HMOX2, HO-2 or HO2), vascular endothelial growth factor A (VEGFA or VEGF), erb-b2 receptor tyrosine kinase 2 (ERBB2, HER2, HER2/neu or CD340), epidermal growth factor receptor (EGFR, ERBB, ERBB1 or HER1), ALK receptor tyrosine kinase (ALK, CD246), poly(ADP-ribose) polymerase 1 (PARP1), poly(ADP-ribose) polymerase 2 (PARP2), TCDD inducible poly(ADP-ribose) polymerase (TIPARP, PARP7), cyclin dependent kinase 4 (CDK4), cyclin dependent kinase 6 (CDK6), TNF receptor superfamily member 14 (TNFRSF14, HVEM, CD270), C-C motif chemokine receptor 2 (CCR2, CD192), C-C motif chemokine receptor 5 (CCR5, CD195), C-C motif chemokine receptor 8 (CCR8, CDw198), C-X-C motif chemokine receptor 2 (CXCR2, CD182), C-X-C motif chemokine receptor 3 (CXCR3, CD182, CD183), C-X-C motif chemokine receptor 4 (CXCR4, CD184), arginase (ARG1, ARG2), carbonic anhydrase (CA1, CA2, CA3, CA4, CA5A, CA5B, CA6, CA7, CA8, CA9, CA10, CA11, CA12, CA13, CA14), prostaglandin-endoperoxide synthase 1 (PTGS1, COX-1), prostaglandin-endoperoxide synthase 2 (PTGS2, COX-2), secreted phospholipase A2, prostaglandin E synthase (PTGES, PGES), arachidonate 5-lipoxygenase (ALOX5, 5-LOX), soluble epoxide hydrolase 2 (EPHX2), indoleamine 2,3-dioxygenase 1 (IDO1), indoleamine 2,3-dioxygenase 2 (IDO2), hypoxia inducible factor 1 subunit alpha (HIF1A), angiopoietin 1 (ANGPT1), endothelial TEK tyrosine kinase (TIE-2, TEK), Janus kinase 1 (JAK1), catenin beta 1 (CTNNB1), histone deacetylase 9 (HDAC9), 5'-3' exoribonuclease 1 (XRN1), and/or WRN RecQ like helicase (WRN). In some embodiments, the inhibitor comprises an antibody or an antigen-binding fragment thereof, or antibody-drug conjugate thereof, CD3-targeting multi-specific molecule, NK cell-activating receptor-targeting multi-specific molecule, non-immunoglobulin antigen binding molecule or antibody mimetic protein. In some embodiments, the inhibitor comprises an inhibitory nucleic acid. In some embodiments, the inhibitor comprises a small organic molecule. In some embodiments, the inhibitor of 5'-nucleotidase ecto (NT5E or CD73) is selected from the group consisting of MEDI9447 (oleclumab), CPI-006, BMS-986179, IPH5301, TJ4309 (TJD5), NZV-930, AB-680, PSB-12379, PSB-12441, PSB-12425, CB-708 and PBF-1662. In some embodiments, the inhibitor of CCR2 and/or CCR5 is selected from the group consisting of BMS-813160, PF-04136309 and CCX-872. In some embodiments, the inhibitor of MCL1 is selected from the group consisting of GS-9716, tapotoclax (AMG-176), AMG-397, S-64315, AZD-5991, 483-LM, A 1210477, UMI-77, JKY-5-037, PRT-1419 and APG-3526. In some embodiments, the inhibitor of PTPN11 or SHP2 is selected from the group consisting of TNO155 (SHP-099), RMC-4550, JAB-3068 and RMC-4630. In some embodiments, the inhibitor of Janus kinase 1 (JAK1) is selected from the group consisting of filgotinib, tofacitinib, baricitinib and ABT-494. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with an oncolytic viral vector. In some embodiments, the oncolytic viral vector comprises a DNA virus or a RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus). In some embodiments, the subject has cancer. In some embodiments, the subject is in cancer remission. In some embodiments, the subject has a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldenström's macroglobulinemia (WM)) and/or a myeloma (e.g., multiple myeloma (MM)). In some embodiments, the subject has a solid tumor. In some embodiments, the tumor is a malignant tumor. In some embodiments, the tumor is a metastatic tumor. In some embodiments, the subject has a cancer selected from the group consisting of an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), and a lymphoma. In some embodiments, the subject has a solid tumor in or arising from a tissue or organ selected from the group consisting of: bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma); lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors); esophagus (e.g., Barrett's esophagus, dysplasia and adenocarcinoma); gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus; pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma); gall bladder (e.g. carcinoma of the gallbladder and extrahepatic bile ducts, intrahepatic cholangiocarcinoma); neuro-endocrine (e.g., adrenal cortical carcinoma, carcinoid tumors, phaeochromocytoma, pituitary adenomas); thyroid (e.g., anaplastic (undifferentiated) carcinoma, medullary carcinoma, oncocytic tumors, papillary carcinoma, adenocarcinoma); liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor); kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma); breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma, peritoneum (e.g., mesothelioma; primary peritoneal cancer); female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, Müllerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina; male sex organ tissues, including prostate, testis (e.g., germ cell tumors, spermatocytic seminoma), penis; bladder (e.g., squamous cell carcinoma, urothelial carcinoma, bladder urothelial carcinoma); brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors; eye (e.g., retinoma, retinoblastoma, ocular melanoma, posterior uveal melanoma, iris hamartoma); head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal); thymus (e.g., thymoma); heart (e.g., cardiac myxoma); lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma); lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis); central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma); neuroendocrine tissues (e.g., paraganglionic system including adrenal medulla (pheochromocytomas) and extra-adrenal paraganglia ((extra-adrenal) paragangliomas); skin (e.g., clear cell hidradenoma, cutaneous benign fibrous histiocytomas, cylindroma, hidradenoma, melanoma (including cutaneous melanoma, mucosal melanoma), pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma. In some embodiments, the subject has a hematological cancer selected from the group consisting of melanoma, leukemia, acute myeloid leukemia (AML), chronic lymphocytic leukemia (CLL); lymphoma; B-cell Non-Hodgkin Lymphoma; and multiple myeloma (MM); or a solid tumor cancer selected from the group consisting of melanoma; head and neck; ovarian; mesothelioma; endometrial; prostate; sarcoma; neuroblastoma; liver, lung; breast; esophageal, gastric and pancreatic. In some embodiments, the subject has a cancer selected from the group consisting of a lung cancer, a colorectal cancer, a breast cancer, a prostate cancer, a cervical cancer and a head and neck cancer. In some embodiments, the subject is naïve to or has not received chemotherapy. In some embodiments, the subject has received a lymphodepleting chemotherapy regimen. In some embodiments, the subject has bone marrow cells, or is not depleted of bone marrow cells.

With respect to the antiviral, anticancer and vaccine enhancement combination therapy methods, in some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more additional therapeutic agents. In some embodiments, the one or more additional therapeutic agents comprise one or more agonists or activators of one or more toll-like receptors (TLRs). In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620 (vesatolimod), R848 (Resiquimod), DS-0509, LHC-165, TMX-101 (imiquimod), RO7020531 and JNJ-4964, and/or wherein the TLR8 agonist is selected from the group consisting of selgantolimod (GS-9688), R848 (Resiquimod) and NKTR-262 (dual TLR7/TLR8 agonist). In some embodiments, the cytokine or chemokine therapy comprises co-administering one or more immunostimulatory cytokines or chemokines that promote or increase the proliferation or activation of α/β T cells, γ/δ T cells, NK-T cells, NK cells, and/or dendritic cells. In some embodiments, the one or more immunostimulatory cytokines or chemokines are selected from the group consisting of: IL-10, IL-12, IL-18, gamma chain-dependent cytokines (e.g., IL-4, IL-7, IL-9, IL-15 and IL-21), fms related tyrosine kinase 3 (FLT3) ligand (FLT3L; FLT3LG; NCBI Gene ID: 2323), interferon (IFN)-α, IFN-β, a PEGylated interferon (e.g., PEG-IFN-α2a and/or PEG-IFN-α2b), IFN-γ, CXCL9/Mig (monokine induced by interferon-γ), CXCL10/IP10 (interferon-γ-inducible 10 kDa protein) and CXCL11/I-TAC (interferon-inducible T cell α-chemoattractant), CXCL4/PF4 (platelet factor 4), monocyte chemoattractant protein 2 (MCP-2), macrophage inflammatory protein 1 alpha (MIP-1α), macrophage inflammatory protein 1 beta (MIP-1β) and regulated on activation normal T expressed and secreted protein (RANTES). In some embodiments, the one or more additional therapeutic agents comprise one or more interleukin receptor agonists of an interleukin receptor selected from IL-10, IL-12, IL-18 and gamma chain-dependent cytokines (e.g., IL-4, IL-7, IL-9, IL-15 and IL-21). In some embodiments, the one or more additional therapeutic agents comprise one or more cytokines selected from the group consisting of IL-10, IL-12, IL-18, gamma chain-dependent cytokines (e.g., IL-4, IL-7, IL-9, IL-15 and IL-21), IFN-α, IFN-β, a PEGylated interferon (e.g., PEG-IFN-α2a and/or PEG-IFN-α2b), IFN-γ, and variants thereof. In some embodiments, the one or more additional therapeutic agents comprise one or more innate immune activators. In some embodiments, the one or more innate immune activators comprises an agonist of a receptor selected from the group consisting of fms related tyrosine kinase 3 (FLT3, a.k.a., CD135, FLK-2, FLK2, STK1), stimulator of interferon genes (STING) receptor, DExD/H-box helicase 58 (DDX58; a.k.a., RIG-I), NLR family pyrin domain containing 3 (NLRP3) and nucleotide binding oligomerization domain containing 2 (NOD2). In some embodiments, the one or more innate immune activators comprise one or both of GS-3583 and GS-9992. In some embodiments, the one or more additional therapeutic agents comprise an immunotherapy, an immunostimulatory therapy, a cytokine therapy, a chemokine therapy, a cellular therapy, a gene therapy, and combinations thereof. In some embodiments, the immunotherapy comprises co-administering one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160 (NK1, NK28, BY55), MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); sialic acid binding Ig like lectin 7 (SIGLEC7); sialic acid binding Ig like lectin 9 (SIGLEC9); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); CD160; killer cell lectin like receptor B1 (KLRB1, CD161); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the immunotherapy comprises co-administering one or more blockers or inhibitors of one or more T-cell inhibitory immune checkpoint proteins or receptors. In some embodiments, the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the immunotherapy comprises co-administering one or more agonists or activators of one or more T-cell stimulatory immune checkpoint proteins or receptors. In some embodiments, the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the immunotherapy comprises co-administering one or more blockers or inhibitors of one or more NK-cell inhibitory immune checkpoint proteins or receptors. In some embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); CD160; killer cell lectin like receptor B1 (KLRB1, CD161); killer cell lectin like receptor C1 (KLRC1, NKG2A, CD159A); killer cell lectin like receptor D1 (KLRD1, CD94), killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the immunotherapy comprises co-administering one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the one or more immune checkpoint inhibitors comprises a proteinaceous (e.g., antibody) inhibitor of PD-L1 (CD274), PD-1 (PDCD1) or CTLA4. In some embodiments, the one or more immune checkpoint proteins or receptors are selected from the group consisting of: CD274 (CD274, PDL1, PD-L1) and programmed cell death 1 (PDCD1, PD1, PD-1). In some embodiments, the proteinaceous (e.g., antibody) inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN-2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous (e.g., antibody) inhibitor of programmed cell death 1 (PDCD1; NCBI Gene ID: 5133; CD279, PD-1, PD1) is selected from the group consisting of zimberelimab (AB122, GLS-010, WBP-3055), pembrolizumab (KEYTRUDA®, MK-3475, SCH900475), nivolumab (OPDIVO®, BMS-936558, MDX-1106), cemiplimab (LIBTAYO®; cemiplimab-rwlc, REGN-2810), pidilizumab (CT-011), AMG-404, MEDI0680 (AMP-514), spartalizumab (PDR001), tislelizumab (BGB-A317), toripalimab (JS-001), genolimzumab (CBT-501, APL-501, GB 226), SHR-1201, camrelizumab (SHR-1210), sintilimab (TYVYT®; IBI-308), dostarlimab (TSR-042, WBP-285), lambrolizumab (MK-3475); sasanlimab (PF-06801591), cetrelimab (JNJ-63723283), serplulimab (HLX-10), retifanlimab (MGA-012), balstilimab (AGEN2034), prolgolimab (BCD 100), budigalimab (ABBV-181), vopratelimab (JTX-4014), AK-103 (HX-008), AK-105, CS 1003, BI-754091, LZM-009, Sym-021, BAT-1306, PD1-PIK, tebotelimab (MGD013; PD-1/LAG-3), RO-7247669 (PD-1/LAG-3), FS-118 (LAG-3/PD-L1), RO-7121661 (PD 1/TIM-3), RG7769 (PD-1/TIM-3), PF-06936308 (PD 1/CTLA4), MGD-019 (PD-1/CTLA4), KN-046 (PD 1/CTLA4), XmAb-20717 (PD 1/CTLA4), AK-104 (CTLA4/PD-1) and MEDI-5752 (CTLA4/PD-1). In some embodiments, the proteinaceous (e.g., antibody) inhibitor of CD274 molecule (NCBI Gene ID: Gene ID: 29126; B7-H, B7H1, PD-L1) is selected from the group consisting of atezolizumab (TECENTRIQ®), avelumab (BAVENCIO®; MSB0010718C), envafolimab (ASC22), durvalumab (IMFINZI®; MEDI-4736), BMS-936559 (MDX1105), cosibelimab (CK-301), lodapolimab (LY 3300054), garivulimab (BGB A333), envafolimab (KN035), opucolimab (HLX 20), manelimab (BCD 135), CX-072, CBT-502 (TQB2450), MSB-2311, SHR-1316, sugemalimab (CS-1001; WBP3155), A167 (KL-A167, HBM 9167), STI-A1015 (IMC-001), FAZ-053, BMS-936559 (MDX1105), INCB086550, GEN-1046 (PD-L1/4-1BB), FPT-155 (CTLA4/PD-L1/CD28), M7824 (PD-L1/TGFβ-EC domain), CA-170 (PD-L1/VISTA), CDX-527 (CD27/PD-L1), LY-3415244 (TIM-3/PDL1), INBRX-105 (4-1BB/PDL1) and GNS-1480 (PD-L1/EGFR). In some embodiments, the one or more immune checkpoint inhibitors comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002. In some embodiments, the immunotherapy comprises co-administering one or more agents that selectively deplete regulatory T (Treg) cells. In some embodiments, the one or more agents that selectively deplete effector regulatory T (Treg) cells comprise an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL-2RA (CD25), and combinations thereof. In some embodiments, the immunotherapy comprises co-administering one or more agents that selectively deplete suppressive myeloid cells. In some embodiments, the suppressive myeloid cells are selected from tumor-associated macrophages (TAM) and myeloid derived suppressor cells (MDSC). In some embodiments, the one or more agents that selectively deplete suppressive myeloid cells comprise an antibody or antigen-binding fragment thereof that selectively binds to a cell surface receptor selected from the group consisting of colony stimulating factor 1 receptor (CSF1R), C-C motif chemokine receptor 2 (CCR2), C-C motif chemokine ligand 2 (CCL2), triggering receptor expressed on myeloid cells 2 (TREM2), complement C5a receptor 1 (C5AR1), and mixtures thereof. In some embodiments, the one or more agents that selectively deplete suppressive myeloid cells comprise an agent that inhibits nuclear receptor subfamily 1 group H member 3 (NR1H3; LXRA) or nuclear receptor subfamily 1 group H member 2 (NR1H2; LXRB). In some embodiments, the one or more additional therapeutic agents comprise an inhibitor or antagonist of: mitogen-activated protein kinase kinase kinase kinase 1 (MAP4K1) (also called Hematopoietic Progenitor Kinase 1 (HPK1)), phosphatidylinositol-4,5-bisphosphate 3-kinase, including catalytic subunit alpha (PIK3CA), catalytic subunit beta (PIK3CB), catalytic subunit gamma (PIK3CG) and catalytic subunit delta (PIK3CD), diacylglycerol kinase alpha (DGKA, DAGK, DAGK1 or DGK-alpha), T cell immunoreceptor with Ig and ITIM domains (TIGIT), X-linked inhibitor of apoptosis (XIAP, BIRC4, IAP-3), baculoviral IAP repeat containing 2 (BIRC2, cIAP1), baculoviral IAP repeat containing 3 (BIRC3, cIAP2), baculoviral IAP repeat containing 5 (BIRC5, survivin), or cytokine inducible SH2 containing protein (CISH). In some embodiments, the one or more additional therapeutic agents comprise an activator or agonist of: a toll-like receptor (TLR); a stimulator of interferon genes (STING) receptor, inducible T cell costimulator (ICOS, CD278); and/or a TNF receptor superfamily (TNFRSF) member. In some embodiments, the TNF receptor superfamily (TNFRSF) member is selected from the group consisting of: TNFRSF1A, TNFRSF1B, TNFRSF4 (OX40), TNFRSF5 (CD40), TNFRSF6 (FAS), TNFRSF7 (CD27), TNFRSF8 (CD30), TNFRSF9 (4-1BB, CD137), TNFRSF10A (CD261, DR4, TRAILR1), TNFRSF10B (CD262, DR5, TRAILR2), TNFRSF10C (CD263, TRAILR3), TNFRSF10D (CD264, TRAILR4), TNFRSF11A (CD265, RANK), TNFRSF11B, TNFRSF12A (CD266), TNFRSF13B (CD267), TNFRSF13C (CD268), TNFRSF16 (NGFR, CD271), TNFRSF17 (BCMA, CD269), TNFRSF18 (GITR, CD357), TNFRSF19, TNFRSF21 (CD358, DR6), and TNFRSF25 (DR3). In some embodiments, the TNFRSF4 (OX40 or CD134) activator or agonist comprises INCAGN1949, tavolimab (MEDI0562), pogalizumab (MOXR0916/RG7888), MEDI6469, BMS 986178, PF-04518600, GSK3174998, IBI101, ATOR-1015, ABBV-368 or SL-279252; the TNFRSF9 (4-1BB or CD137) activator or agonist comprises urelumab, BMS-663513, utomilumab (PF-05082566), CTX-471, MP-0310, ADG-106, ATOR-1017, AGEN2373 or QL1806; and/or the TNFRSF18 (GITR or CD357) activator or agonist comprises GWN323, MEDI1873, MK-1248, MK-4166, TRX518, INCAGN1876, BMS-986156, BMS-986256, AMG-228, ASP1951 (PTZ 522), FPA-154 or OMP-336B11. In some embodiments, the methods comprise co-administering a molecule that concurrently binds to TNF receptor superfamily member 4 (TNFRSF4, OX40 or CD134) and TNF receptor superfamily member 18 (TNFRSF18, GITR or CD357). In some embodiments, the methods comprise co-administering a molecule selected from the group consisting of AGEN1884 (zalifrelimab), AGEN1181, AGEN 2034 (balstilimab), AGEN1307, AGEN1327, AGEN1777, AGEN2373, AGEN1223 and GS-1423.

With respect to the antiviral, anticancer and vaccine enhancement methods, in some embodiments, in some embodiments, the IL-2v, the Fc-IL-2v fusion protein, the homodimer, the heterodimer, the conjugate, the polynucleotide, the vector, the lipoplex (e.g., LNP) and/or the pharmaceutical composition are administered systemically or locally, e.g., via a route selected from intravenous, subcutaneous, intramuscular, intradermal, intratumoral and mucosal (e.g. buccal, intranasal, intrarectal, intravaginal). In various embodiments, the IL-2v, the Fc-IL-2v fusion protein, the homodimer, the heterodimer, the conjugate, the polynucleotide, the vector, the lipoplex (e.g., LNP) and/or the pharmaceutical composition and the one or more additional therapeutic agents are administered by the same or by different routes of administration. In various embodiments, the IL-2v, the Fc-IL-2v fusion protein, the homodimer, the heterodimer, the conjugate, the polynucleotide, the vector, the lipoplex (e.g., LNP) and/or the pharmaceutical composition and the one or more additional therapeutic agents are co-administered according to the same schedule (e.g., co-administered at the same time intervals), or according to different schedules (e.g., co-administered at different time intervals). In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is administered at a dose in the range of 0.5 μg/kg to 1000 μg/kg, e.g., in the range of from 1 μg/kg to 500 μg/kg, e.g., in the range of from 10 μg/kg to 300 μg/kg, e.g., in the range of from 30 μg/kg to 600 μg/kg, e.g., at least 0.5 μg/kg per dose and up to 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 1.5 μg/kg, 2 μg/kg, 2.5 μg/kg, 3 μg/kg, 3.5 μg/kg, 4 μg/kg, 4.5 μg/kg, 5 μg/kg, 6 μg/kg, 7 μg/kg, 8 μg/kg, 9 μg/kg, 10 μg/kg, 15 μg/kg, 20 μg/kg, 25 μg/kg, 30 μg/kg, 40 μg/kg, 50 μg/kg, 60 μg/kg, 70 μg/kg, 80 μg/kg, 90 μg/kg, 100 μg/kg, 110 μg/kg, 120 μg/kg, 130 μg/kg, 140 μg/kg, 150 μg/kg, 200 μg/kg, 250 μg/kg, 300 μg/kg, 400 μg/kg, 500 μg/kg, 600 μg/kg, 700 μg/kg, 800 μg/kg, 900 μg/kg, 1000 μg/kg per dose. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is administered at a dose in the range of 0.02 mg to 100 mg, e.g., 0.04 mg to 80 mg, e.g., at least 0.02 mg per dose and up to 0.03 mg, 0.04 mg, 0.05 mg, 0.1 mg, 0.5 mg, 1 mg, 2 mg, 3 mg, 4 mg, 5 mg, 10 mg, 12 mg, 15 mg, 20 mg, 40 mg, 50 mg, 60 mg, 70 mg, 80 mg or 100 mg per dose. In various embodiments, the methods comprise multiple administrations of the IL-2v, the Fc-IL-2v fusion protein, the homodimer, the heterodimer, the conjugate, the polynucleotide, the vector, the lipoplex (e.g., LNP) and/or the pharmaceutical composition, optionally with one or more additional therapeutic agents, at predetermined intervals. In various embodiments, the methods comprise multiple administrations of the IL-2v, the Fc-IL-2v fusion protein, the homodimer, the heterodimer, the conjugate, the polynucleotide, the vector, the lipoplex (e.g., LNP) and/or the pharmaceutical composition, optionally with one or more additional therapeutic agents, over a time period of at least 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer. In some embodiments, the methods comprise administering the IL-2v, the Fc-IL-2v fusion protein, the homodimer, the heterodimer, the conjugate, the polynucleotide, the vector, the lipoplex (e.g., LNP) and/or the pharmaceutical composition, optionally with one or more additional therapeutic agents, one or more times at predetermined intervals spaced at least 1 week and up to at least 2 weeks, 3 weeks, 1 month, 2 months, 3 months, 4 months, 5 months or 6 months apart. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is administered once weekly (i.e., QW), once bi-weekly (i.e. once every other week, or once every two weeks or Q2W), once thrice-weekly (i.e. once every three weeks or Q3W), once monthly (i.e., QM) or once bi-monthly dosing (i.e. once every other month, or once every two months or Q2M), once every three months (Q3M), once every four months (Q4M), once every five months (Q5M), once every six months (Q6M), or less often. In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is administered two or more times subcutaneously at an interval or at intervals between once bi-weekly (i.e. once every other week, or once every two weeks or Q2W) to once thrice-weekly (i.e. once every three weeks or Q3W). In some embodiments, the IL-2v, the Fc-IL-2v fusion protein, the homodimer, the heterodimer or the conjugate have a serum half-life in a human of at least 6, 9, 12, 15, 18, 21, 24 hours, e.g., at least 1, 2, 3, 4, 5, 6, 7, 8, 9, 10, 11, 12, 13, 14 days, or longer. In some embodiments, the subject or the mammal is a human.

In another aspect, provided is a kit. In various embodiments, the kit comprises one or more unitary doses of the IL-2v, the Fc-IL-2v fusion protein, the homodimer, the heterodimer, the conjugate, the polynucleotide, the vector, the lipoplex (e.g., LNP) and/or the pharmaceutical composition, described above and herein. In some embodiments, the one or more unitary doses are in a single container, or are in two or more separate containers. In some embodiments, the kit comprises one or more containers selected from the group consisting of vials, ampules and pre-loaded syringes. In some embodiments, the kit comprises one or more containers comprising the fusion protein and/or the homodimer in an aqueous solution. In some embodiments, the aqueous solution comprises the IL-2v, the Fc-IL-2v fusion protein, the homodimer, the heterodimer, the conjugate, the polynucleotide, the vector, the lipoplex (e.g., LNP) and/or the pharmaceutical composition at a concentration in the range of 0.05 mg/ml to 50 mg/ml, e.g., from 0.05 mg/ml to 20 mg/ml, e.g., from 0.1 mg/ml to 40 mg/ml, e.g., from 1.0 mg/ml to 30 mg/ml, e.g., from 0.05 mg/ml to 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml or 50 mg/ml. In various embodiments, the one or more unitary doses are the same or are different. In some embodiments, each unitary dose is in the range of 0.5 μg/kg to 1000 μg/kg, e.g., in the range of from 1 μg/kg to 500 μg/kg, e.g., in the range of from 10 μg/kg to 300 μg/kg, e.g., in the range of from 30 μg/kg to 600 μg/kg, e.g., at least 0.5 μg/kg per dose and up to 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 1.5 μg/kg, 2 μg/kg, 2.5 μg/kg, 3 μg/kg, 3.5 μg/kg, 4 μg/kg, 4.5 μg/kg, 5 μg/kg, 6 μg/kg, 7 μg/kg, 8 μg/kg, 9 μg/kg, 10 μg/kg, 15 μg/kg, 20 μg/kg, 25 μg/kg, 30 μg/kg, 40 μg/kg, 50 μg/kg, 60 μg/kg, 70 μg/kg, 80 μg/kg, 90 μg/kg, 100 μg/kg, 110 μg/kg, 120 μg/kg, 130 μg/kg, 140 μg/kg, 150 μg/kg, 200 μg/kg, 250 μg/kg, 300 μg/kg, 400 μg/kg, 500 μg/kg, 600 μg/kg, 700 μg/kg, 800 μg/kg, 900 μg/kg, 1000 μg/kg per dose. In some embodiments, each unitary dose is in the range of 0.02 mg to 100 mg, e.g., 0.04 mg to 80 mg, e.g., at least 0.02 mg per dose and up to 0.03 mg, 0.04 mg, 0.05 mg, 0.1 mg, 0.5 mg, 1 mg, 2 mg, 3 mg, 4 mg, 5 mg, 10 mg, 12 mg, 15 mg, 20 mg, 40 mg, 50 mg, 60 mg, 70 mg, 80 mg or 100 mg per dose. In some embodiments, the kit further comprises one or more unitary doses of one or more additional therapeutic agents. In some embodiments, the kit comprises one or more unitary doses of one or more antiviral agents, e.g., against HBV, HIV, HSV or coronavirus. In some embodiments, the kit comprises one or more agonists or activators of one or more toll-like receptors (TLRs). In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of GS 9620 (vesatolimod), R848 (Resiquimod), DS-0509, LHC-165, TMX-101 (imiquimod), RO7020531 and JNJ-4964, and/or wherein the TLR8 agonist is selected from the group consisting of selgantolimod (GS-9688), R848 (Resiquimod) and NKTR-262 (dual TLR7/TLR8 agonist). In some embodiments, the kit comprises one or more immunostimulatory cytokines or chemokines that promote or increase the proliferation or activation of α/β T cells, γ/δ T cells, NK-T cells, NK cells, and/or dendritic cells. In some embodiments, the one or more immunostimulatory cytokines or chemokines are selected from the group consisting of: IL-10, IL-12, IL-18, gamma chain-dependent cytokines (e.g., IL-4, IL-7, IL-9, IL-15 and IL-21), fms related tyrosine kinase 3 (FLT3) ligand (FLT3L; FLT3LG; NCBI Gene ID: 2323), interferon (IFN)-α, IFN-β, a PEGylated interferon (e.g., PEG-IFN-α2a and/or PEG-IFN-α2b), IFN-γ, CXCL9/Mig (monokine induced by interferon-γ), CXCL10/IP10 (interferon-γ-inducible 10 kDa protein) and CXCL11/I-TAC (interferon-inducible T cell α-chemoattractant), CXCL4/PF4 (platelet factor 4), monocyte chemoattractant protein 2 (MCP-2), macrophage inflammatory protein 1 alpha (MIP-1α), macrophage inflammatory protein 1 beta (MIP-10) and regulated on activation normal T expressed and secreted protein (RANTES). In some embodiments, the kit comprises one or more interleukin receptor agonists of an interleukin receptor selected from IL-10, IL-12, IL-18 and gamma chain-dependent cytokines (e.g., IL-4, IL-7, IL-9, IL-15 and IL-21). In some embodiments, the kit comprises one or more cytokines selected from the group consisting of IL-10, IL-12, IL-18, gamma chain-dependent cytokines (e.g., IL-4, IL-7, IL-9, IL-15 and IL-21), IFN-α, IFN-β, a PEGylated interferon (e.g., PEG-IFN-α2a and/or PEG-IFN-α2b), IFN-γ, and variants thereof. In some embodiments, the kit comprises one or more innate immune activators. In some embodiments, the kit comprises an agonist of a receptor selected from the group consisting of fms related tyrosine kinase 3 (FLT3, a.k.a., CD135, FLK-2, FLK2, STK1), stimulator of interferon genes (STING) receptor, DExD/H-box helicase 58 (DDX58; a.k.a., RIG-I), NLR family pyrin domain containing 3 (NLRP3) and nucleotide binding oligomerization domain containing 2 (NOD2). In some embodiments, the kit comprises one or both of GS-3583 and GS-9992. In some embodiments, the kit comprises one or more antagonists or inhibitors of an inhibitory immune checkpoint protein or receptor and/or one or more activators or agonists of a stimulatory immune checkpoint protein or receptor. In some embodiments, the one or more immune checkpoint proteins or receptors are selected from the group consisting of: CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160 (NK1, NK28, BY55), MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); sialic acid binding Ig like lectin 7 (SIGLEC7); sialic acid binding Ig like lectin 9 (SIGLEC9); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); CD160; killer cell lectin like receptor B1 (KLRB1, CD161); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the kit comprises one or more blockers or inhibitors of one or more T-cell inhibitory immune checkpoint proteins or receptors. In some embodiments, the T-cell inhibitory immune checkpoint proteins or receptors are selected from the group consisting of CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In some embodiments, the kit comprises one or more agonists or activators of one or more T-cell stimulatory immune checkpoint proteins or receptors. In some embodiments, the T-cell stimulatory immune checkpoint proteins or receptors are selected from the group consisting of CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); Poliovirus receptor (PVR) cell adhesion molecule (PVR, CD155). In some embodiments, the kit comprises one or more blockers or inhibitors of one or more NK-cell inhibitory immune checkpoint proteins or receptors. In some embodiments, the NK-cell inhibitory immune checkpoint proteins or receptors are selected from the group consisting of killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); CD160; killer cell lectin like receptor B1 (KLRB1, CD161); killer cell lectin like receptor C1 (KLRC1, NKG2A, CD159A); killer cell lectin like receptor D1 (KLRD1, CD94); killer cell lectin like receptor G1 (KLRG1; CLEC15A, MAFA, 2F1); sialic acid binding Ig like lectin 7 (SIGLEC7); and sialic acid binding Ig like lectin 9 (SIGLEC9). In some embodiments, the kit comprises one or more agonists or activators of one or more NK-cell stimulatory immune checkpoint proteins or receptors. In some embodiments, the NK-cell stimulatory immune checkpoint proteins or receptors are selected from CD16, CD226 (DNAM-1); killer cell lectin like receptor K1 (KLRK1, NKG2D, CD314); and SLAM family member 7 (SLAMF7). In some embodiments, the kit comprises a proteinaceous (e.g., antibody) inhibitor of PD-L1 (CD274), PD-1 (PDCD1) or CTLA4. In some embodiments, the kit comprises a proteinaceous (e.g., antibody) inhibitor of PD-L1 (CD274) or PD-1 (PDCD1). In some embodiments, the proteinaceous (e.g., antibody) inhibitor of CTLA4 is selected from the group consisting of ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN2041, JHL-1155, KN-044, CG-0161, ATOR-1144, PBI-5D3H5, FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4) and AK-104 (CTLA4/PD-1). In some embodiments, the proteinaceous (e.g., antibody) inhibitor of programmed cell death 1 (PDCD1; NCBI Gene ID: 5133; CD279, PD-1, PD1) is selected from the group consisting of zimberelimab (AB122, GLS-010, WBP-3055), pembrolizumab (KEYTRUDA®, MK-3475, SCH900475), nivolumab (OPDIVO®, BMS-936558, MDX-1106), cemiplimab (LIBTAYO®; cemiplimab-rwlc, REGN-2810), pidilizumab (CT-011), AMG-404, MEDI0680 (AMP-514), spartalizumab (PDR001), tislelizumab (BGB-A317), toripalimab (JS-001), genolimzumab (CBT-501, APL-501, GB 226), SHR-1201, camrelizumab (SHR-1210), sintilimab (TYVYT®; IBI-308), dostarlimab (TSR-042, WBP-285), lambrolizumab (MK-3475); sasanlimab (PF-06801591), cetrelimab (JNJ-63723283), serplulimab (HLX-10), retifanlimab (MGA-012), balstilimab (AGEN2034), prolgolimab (BCD 100), budigalimab (ABBV-181), vopratelimab (JTX-4014), AK-103 (HX-008), AK-105, CS 1003, BI-754091, LZM-009, Sym-021, BAT-1306, PD1-PIK, tebotelimab (MGD013; PD-1/LAG-3), RO-7247669 (PD-1/LAG-3), FS-118 (LAG-3/PD-L1), RO-7121661 (PD 1/TIM-3), RG7769 (PD-1/TIM-3), PF-06936308 (PD 1/CTLA4), MGD-019 (PD-1/CTLA4), KN-046 (PD 1/CTLA4), XmAb-20717 (PD 1/CTLA4), AK-104 (CTLA4/PD-1) and MEDI-5752 (CTLA4/PD-1). In some embodiments, the proteinaceous (e.g., antibody) inhibitor of CD274 molecule (NCBI Gene ID: Gene ID: 29126; B7-H, B7H1, PD-L1) is selected from the group consisting of atezolizumab (TECENTRIQ®), avelumab (BAVENCIO®; MSB0010718C), envafolimab (ASC22), durvalumab (IMFINZI®; MEDI-4736), BMS-936559 (MDX1105), cosibelimab (CK-301), lodapolimab (LY 3300054), garivulimab (BGB A333), envafolimab (KN035), opucolimab (HLX 20), manelimab (BCD 135), CX-072, CBT-502 (TQB2450), MSB-2311, SHR-1316, sugemalimab (CS-1001; WBP3155), A167 (KL-A167, HBM 9167), STI-A1015 (IMC-001), FAZ-053, BMS-936559 (MDX1105), INCB086550, GEN-1046 (PD-L1/4-1BB), FPT-155 (CTLA4/PD-L1/CD28), M7824 (PD-L1/TGFβ-EC domain), CA-170 (PD-L1/VISTA), CDX-527 (CD27/PD-L1), LY-3415244 (TIM-3/PDL1), INBRX-105 (4-1BB/PDL1) and GNS-1480 (PD-L1/EGFR). In some embodiments, the kit comprises a small molecule inhibitor of CD274 (PDL1, PD-L1), programmed cell death 1 (PDCD1, PD1, PD-1) or CTLA4. In some embodiments, the small molecule inhibitor of CD274 or PDCD1 is selected from the group consisting of GS-4224, GS-4416, INCB086550 and MAX10181. In some embodiments, the small molecule inhibitor of CTLA4 comprises BPI-002. In some embodiments, the kit comprises one or more agents that selectively deplete regulatory T (Treg) cells. In some embodiments, the one or more agents that selectively deplete effector regulatory T (Treg) cells comprise an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL-2RA (CD25), and combinations thereof. In some embodiments, the kit comprises one or more additional therapeutic agents comprising an inhibitor or antagonist of: mitogen-activated protein kinase kinase kinase kinase 1 (MAP4K1) (also called Hematopoietic Progenitor Kinase 1 (HPK1)), phosphatidylinositol-4,5-bisphosphate 3-kinase, including catalytic subunit alpha (PIK3CA), catalytic subunit beta (PIK3CB), catalytic subunit gamma (PIK3CG) and catalytic subunit delta (PIK3CD), diacylglycerol kinase alpha (DGKA, DAGK, DAGK1 or DGK-alpha), T cell immunoreceptor with Ig and ITIM domains (TIGIT), X-linked inhibitor of apoptosis (XIAP, BIRC4, IAP-3), baculoviral IAP repeat containing 2 (BIRC2, cIAP1), baculoviral IAP repeat containing 3 (BIRC3, cIAP2), baculoviral IAP repeat containing 5 (BIRC5, survivin), or cytokine inducible SH2 containing protein (CISH). In some embodiments, the kit comprises one or more additional therapeutic agents comprising an activator or agonist of: a toll-like receptor (TLR); a stimulator of interferon genes (STING) receptor; inducible T cell costimulator (ICOS, CD278); and/or a TNF receptor superfamily (TNFRSF) member. In some embodiments, the TNF receptor superfamily (TNFRSF) member is selected from the group consisting of: TNFRSF1A, TNFRSF1B, TNFRSF4 (OX40), TNFRSF5 (CD40), TNFRSF6 (FAS), TNFRSF7 (CD27), TNFRSF8 (CD30), TNFRSF9 (4-1BB, CD137), TNFRSF10A (CD261, DR4, TRAILR1), TNFRSF10B (CD262, DR5, TRAILR2), TNFRSF10C (CD263, TRAILR3), TNFRSF10D (CD264, TRAILR4), TNFRSF11A (CD265, RANK), TNFRSF11B, TNFRSF12A (CD266), TNFRSF13B (CD267), TNFRSF13C (CD268), TNFRSF16 (NGFR, CD271), TNFRSF17 (BCMA, CD269), TNFRSF18 (GITR, CD357), TNFRSF19, TNFRSF21 (CD358, DR6), and TNFRSF25 (DR3). In some embodiments, the kit comprises: aTNFRSF4 (OX40 or CD134) activator or agonist selected from INCAGN1949, tavolimab (MEDI0562), pogalizumab (MOXR0916/RG7888), MEDI6469, BMS 986178, PF-04518600, GSK3174998, IBI101, ATOR-1015, ABBV-368 or SL-279252; a TNFRSF9 (4-1BB or CD137) activator or agonist selected from urelumab, BMS-663513, utomilumab (PF-05082566), CTX-471, MP-0310, ADG-106, ATOR-1017, AGEN2373 or QL1806; and/or a TNFRSF18 (GITR or CD357) activator or agonist selected from GWN323, MEDI1873, MK-1248, MK-4166, TRX518, INCAGN1876, BMS-986156, BMS-986256, AMG-228, ASP1951 (PTZ 522), FPA-154 or OMP-336B11. In some embodiments, the kit comprises a molecule that concurrently binds to TNF receptor superfamily member 4 (TNFRSF4, OX40 or CD134) and TNF receptor superfamily member 18 (TNFRSF18, GITR or CD357). In some embodiments, the kit comprises a molecule selected from the group consisting of AGEN1884 (zalifrelimab), AGEN1181, AGEN 2034 (balstilimab), AGEN1307, AGEN2373, AGEN1223 and GS-1423.

With respect to kits comprising therapeutic agents for anti-HBV combination therapies, in some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir alafenamide (TAF or VEMLIDY®), ledipasvir+sofosbuvir (HARVONI®) and a PEGylated interferon (e.g., PEG-IFN-$\alpha$2a and/or PEG-IFN-$\alpha$2b). In some embodiments, the kit further comprises one or more unitary doses of one or more therapeutic agents selected from the group consisting of HBV antigen inhibitors (e.g., HBV core antigen (HBcAg) inhibitors, HBV surface antigen (HBsAg) inhibitors, HBx inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), covalently closed circular DNA (cccDNA) inhibitors, HBsAg secretion or assembly inhibitors, HBV viral entry inhibitors, and CAR-T and T cell bispecific (redirected T cells) for specific killing of HBV-infected cells.

With respect to kits comprising therapeutic agents for anti-HBV combination therapies, in some embodiments, the kit comprises one or more unitary doses of one or more antiretroviral agents. In some embodiments, the kit comprises one or more anti-HIV broadly neutralizing antibodies. In some embodiments, the one or more anti-HIV broadly neutralizing antibodies bind to an epitope or region of gp120 selected from the group consisting of: (i) third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. In some embodiments, the one or more anti-HIV broadly neutralizing antibodies bind to an epitope or region of gp120 in the third variable loop (V3) and/or high mannose patch comprising a N332 oligomannose glycan and competes with or comprises VH and VL regions from an antibody selected from the group consisting of GS-9722, PGT-121, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. In some embodiments, the one or more anti-HIV broadly neutralizing antibodies bind to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CHO1, CH59, PGDM1400, CAP256, CAP256-VRC26.08, CAP256-VRC26.09, CAP256-VRC26.25, PCT64-24E and VRC38.01. In some embodiments, the one or more anti-HIV broadly neutralizing antibodies bind to an epitope or region of gp120 in the CD4 binding site (CD4bs) and competes with or comprises VH and VL regions from an antibody selected from the group consisting of 3BNC117, GS-9723, 3BNC60, b12, F105, VRC01, VRC07, VRC07-523, VRC03, VRC06, VRC06b01 VRC08, VRC0801, NIH45-46, VRC-PG04, PGV04; CH103, 44-VRC13.01, 1NC9, 12A12, N6, N49-P7, NC-Cow1, IOMA, CH235 and CH235.12, N49P6, N49P7, N49P11, N49P9 and N60P25. In some embodiments, the one or more anti-HIV broadly neutralizing antibodies bind to an epitope or region of gp120 in the gp120/gp41 interface and competes with or comprises VH and VL regions from an antibody selected from the group consisting of PGT-151, CAP248-2B, 35022, 8ANC195, ACS202, VRC34 and VRC34.01. In some embodiments, the one or more anti-HIV broadly neutralizing antibodies bind to an epitope or region of the gp120 silent face and competes with or comprises VH and VL regions from an antibody selected from VRC-PG05 and SF12. In some embodiments, the one or more anti-HIV broadly neutralizing antibodies bind to an epitope or region of gp41 in the membrane proximal region (MPER). In some embodiments, the one or more anti-HIV broadly neutralizing antibodies bind to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01. In some embodiments, the one or more anti-HIV broadly neutralizing antibodies bind to an epitope or region of the gp41 fusion peptide and competes with or comprises VH and VL regions from an antibody selected from the group consisting of VRC34 and ACS202.

With respect to kits comprising therapeutic agents for vaccine enhancement combination therapies, in some embodiments, the kit comprises one or more unitary doses of a vaccine. In some embodiments, the vaccine is selected from the group consisting of an antiviral vaccine, an antibacterial vaccine and an anticancer vaccine. In some embodiments, the vaccine comprises an antiviral vaccine against a virus selected from the group consisting of hepatitis A virus (HAV), hepatitis B virus (HBV), human immunodeficiency virus (HIV), cytomegalovirus (CMV), a herpes simplex virus (HSV), Epstein-Barr virus (EBV), human orthopneumovirus or human respiratory syncytial virus (RSV), human papillomavirus (HPV), varicella-zoster virus, measles virus, mumps virus, poliovirus vaccine, influenza virus, paramyxovirus, rotavirus, Zika virus, Dengue virus, Ebola virus and coronavirus (e.g., betacoronavirus, e.g., severe acute respiratory syndrome-related coronavirus, e.g., SARS-CoV2). In some embodiments, the vaccine comprises an antibacterial vaccine against a bacterium selected from the group consisting of *Mycobacterium tuberculosis*, pertussis, tetanus, diphtheria, meningococcus, pneumococcus, *Haemophilus* influenza, cholera, typhoid, and anthrax.

With respect to kits comprising therapeutic agents for anticancer combination therapies, in some embodiments, the kit comprises one or more unitary doses of one or more anti-neoplastic or chemotherapeutic agents. In some embodiments, the kit comprises one or more unitary doses of one or more anti-neoplastic or chemotherapeutic agents are selected from the group consisting of a nucleoside analog (e.g., 5-fluorouracil, gemcitabine, cytarabine, cladribine, pentostatin, fludarabine), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), and mixtures thereof. In some embodiments, the kit comprises one or more unitary doses of one or more antibodies or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins directed against one or more targets or tumor associated antigens (TAAs) selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1 (SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (KIT); C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1); delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen. In some embodiments, the kit comprises one or more antibodies or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins binds to an epitope of a target or tumor associated antigen (TAA) presented in a major histocompatibility complex (MHC) molecule. In some embodiments, the NK cell-activating receptor is selected from the group consisting of CD16, NKp30, NKp44, NKp46, NKp80 and NKG2D. In some embodiments, the kit comprises one or more populations of immune cells selected from the group consisting of: natural killer (NK) cells, NK-T cells, T cells, cytokine-induced killer (CIK) cells, macrophage (MAC) cells, tumor infiltrating lymphocytes (TILs) and dendritic cells (DCs). In some embodiments, the kit comprises a population of T cells selected from the group consisting of: alpha/beta TCR T cells, gamma/delta TCR T cells, regulatory T (Treg) cells and TRuC™ T cells. In some embodiments, the one or more cellular therapies comprise a NK cell therapy comprising NK-92 cells. In some embodiments, the cells are allogeneic to an intended recipient. In some embodiments, the one or more populations of immune cells comprise one or more chimeric antigen receptors (CARs). In some embodiments, the one or more CARs bind to a target or tumor associated antigen (TAA) selected from the group consisting of selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1 (SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (KIT); C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1); delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen. In some embodiments, the one or more CARs bind to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP), alpha fetoprotein (AFP), A-kinase anchoring protein 4 (AKAP4), ATPase family AAA domain containing 2 (ATAD2), kinetochore scaffold 1 (KNL1; a.k.a., CASC5), centrosomal protein 55 (CEP55), cancer/testis antigen 1A (CTAG1A; a.k.a., ESO1; CT6.1; LAGE-2; LAGE2A; NY-ESO-1), cancer/testis antigen 1B (CTAG1B; a.k.a., CT6.1, CTAG, CTAG1, ESO1, LAGE-2, LAGE2B, NY-ESO-1), cancer/testis antigen 2 (CTAG2; a.k.a., CAMEL, CT2, CT6.2, CT6.2a, CT6.2b, ESO2, LAGE-1, LAGE2B), CCCTC-binding factor like (CTCFL), catenin alpha 2 (CTNNA2), cancer/testis antigen 83 (CT83), cyclin A1 (CCNA1), DEAD-box helicase 43 (DDX43), developmental pluripotency associated 2 (DPPA2), fetal and adult testis expressed 1 (FATE1), FMR1 neighbor (FMR1NB), HORMA domain containing 1 (HORMAD1), insulin like growth factor 2 mRNA binding protein 3 (IGF2BP3), leucine zipper protein 4 (LUZP4), lymphocyte antigen 6 family member K (LY6K), maelstrom spermatogenic transposon silencer (MAEL), MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member D1 (MAGED1); MAGE family member D2 (MAGED2), kinesin family member 20B (KIF20B; a.k.a., MPHOSPH1), NUF2 component of NDC80 kinetochore complex (NUF2), nuclear RNA export factor 2 (NXF2), PAS domain containing repressor 1 (PASD1), PDZ binding kinase (PBK), piwi like RNA-mediated gene silencing 2 (PIWIL-2), preferentially expressed antigen in melanoma (PRAME), sperm associated antigen 9 (SPAG9), sperm protein associated with the nucleus, X-linked, family member A1 (SPANXA1), SPANX family member A2 (SPANXA2), SPANX family member C (SPANXC), SPANX family member D (SPANXD), SSX family member 1 (SSX1), SSX family member 2 (SSX2), synaptonemal complex protein 3 (SYCP3), testis expressed 14, intercellular bridge forming factor (TEX14), transcription factor Dp family member 3 (TFDP3), serine protease 50 (PRSS50, a.k.a., TSP50), TTK protein kinase (TTK) and zinc finger protein 165 (ZNF165). In some embodiments, the kit comprises one or more unitary doses of a targeted E3 ligase ligand conjugate. In some embodiments, the kit comprises one or more unitary doses of an inhibitor or antagonist of: protein tyrosine phosphatase, non-receptor type 11 (PTPN11 or SHP2), myeloid cell leukemia sequence 1 (MCL1) apoptosis regulator, 5'-nucleotidase ecto (NT5E or CD73), ectonucleoside triphosphate diphosphohydrolase 1 (ENTPD1 or CD39), transforming growth factor beta 1 (TGFB1 or TGFβ), heme oxygenase 1 (HMOX1, HO-1 or HO1), heme oxygenase 2 (HMOX2, HO-2 or HO2), vascular endothelial growth factor A (VEGFA or VEGF), erb-b2 receptor tyrosine kinase 2 (ERBB2, HER2, HER2/neu or CD340), epidermal growth factor receptor (EGFR, ERBB, ERBB1 or HER1), ALK receptor tyrosine kinase (ALK, CD246), poly(ADP-ribose) polymerase 1 (PARP1), poly(ADP-ribose) polymerase 2 (PARP2), TCDD inducible poly(ADP-ribose) polymerase (TIPARP, PARP7), cyclin dependent kinase 4 (CDK4), cyclin dependent kinase 6 (CDK6), TNF receptor superfamily member 14 (TNFRSF14, HVEM, CD270), C-C motif chemokine receptor 2 (CCR2, CD192), C-C motif chemokine receptor 5 (CCR5, CD195), C-C motif chemokine receptor 8 (CCR8, CDw198), C-X-C motif chemokine receptor 2 (CXCR2, CD182), C-X-C motif chemokine receptor 3 (CXCR3, CD182, CD183), C-X-C motif chemokine receptor 4 (CXCR4, CD184), cytokine inducible SH2 containing protein (CISH), arginase (ARG1, ARG2), carbonic anhydrase (CA1, CA2, CA3, CA4, CA5A, CA5B, CA6, CA7, CA8, CA9, CA10, CA11, CA12, CA13, CA14), prostaglandin-endoperoxide synthase 1 (PTGS1, COX-1), prostaglandin-endoperoxide synthase 2 (PTGS2, COX-2), secreted phospholipase A2, prostaglandin E synthase (PTGES, PGES), arachidonate 5-lipoxygenase (ALOX5, 5-LOX), soluble epoxide hydrolase 2 (EPHX2), indoleamine 2,3-dioxygenase 1 (IDO1), indoleamine 2,3-dioxygenase 2 (IDO2), hypoxia inducible factor 1 subunit alpha (HIF1A), angiopoietin 1 (ANGPT1), Endothelial TEK tyrosine kinase (TIE-2, TEK), Janus kinase 1 (JAK1), catenin beta 1 (CTNNB1), histone deacetylase 9 (HDAC9), 5'-3' exoribonuclease 1 (XRN1), and/or WRN RecQ like helicase (WRN). In some embodiments, the inhibitor of 5'-nucleotidase ecto (NT5E or CD73) is selected from the group consisting of MEDI9447 (oleclumab), CPI-006, BMS-986179, IPH5301, TJ4309 (TJD5), NZV-930, AB-680, PSB-12379, PSB-12441, PSB-12425, CB-708 and PBF-1662. In some embodiments, the inhibitor of CCR2 and/or CCR5 is selected from the group consisting of BMS-813160, PF-04136309 and CCX-872. In some embodiments, the inhibitor of MCL1 is selected from the group consisting of GS-9716, tapotoclax (AMG-176), AMG-397, S-64315, AZD-5991, 483-LM, A 1210477, UMI-77, JKY-5-037 and PRT-1419. In some embodiments, the inhibitor of PTPN11 or SHP2 is selected from the group consisting of TNO155 (SHP-099), RMC-4550, JAB-3068 and RMC-4630. In some embodiments, the inhibitor of Janus kinase 1 (JAK1) is selected from the group consisting of filgotinib, tofacitinib, baricitinib and ABT-494.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, the exemplary methods and materials are described below. All publications, patent applications, patents, and other references mentioned herein are incorporated by reference in their entirety. In case of conflict, the present application, including definitions, will control. The materials, methods, and examples are illustrative only and not intended to be limiting.

Other features and advantages of the invention will be apparent from the following detailed description and from the claims.

DETAILED DESCRIPTION

1. Introduction

Figure 1A:
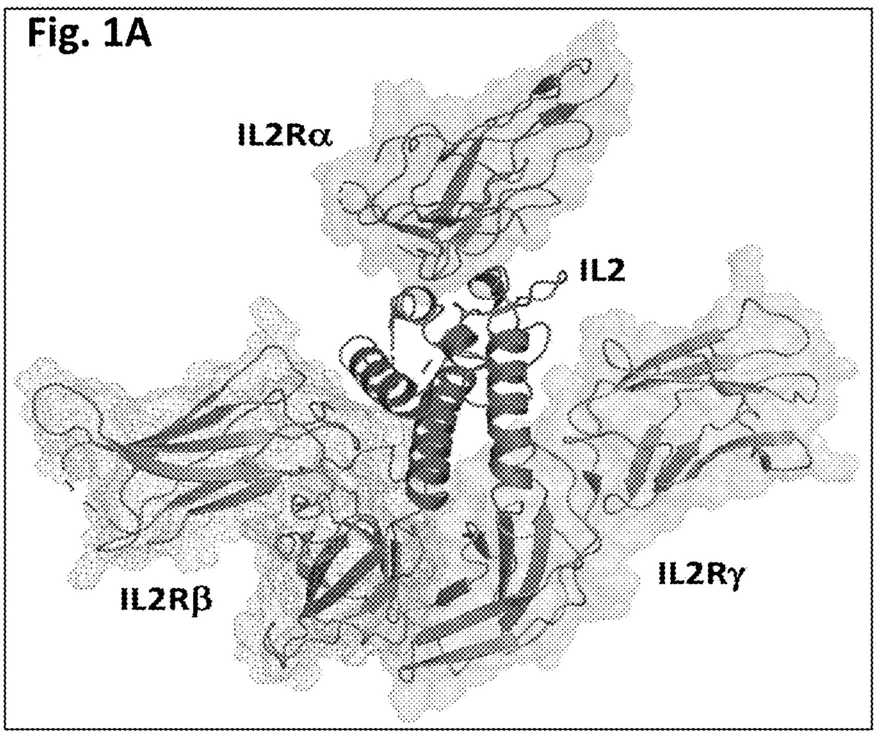
FIGS. 1A-1L illustrate graphics showing the (FIG. 1A) IL-2 receptor quaternary complex, (FIG. 1B) IL-2 Interface with key residues selected for mutation and (FIGS. 1C-IL) interaction of these key residues with surrounding residues from IL-2Rα and IL-2.
Figure 1B:
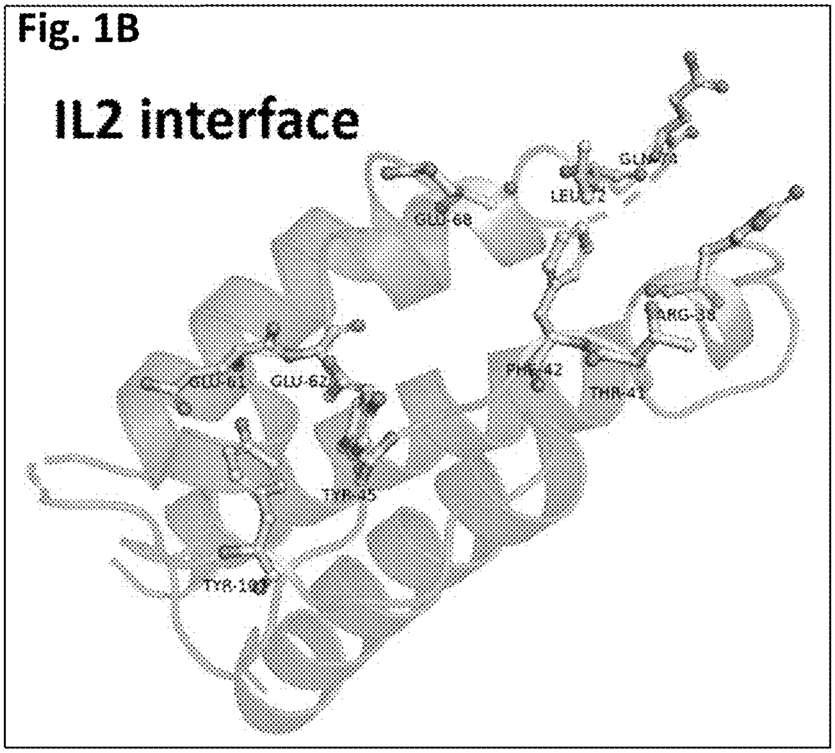
Figure 1C:
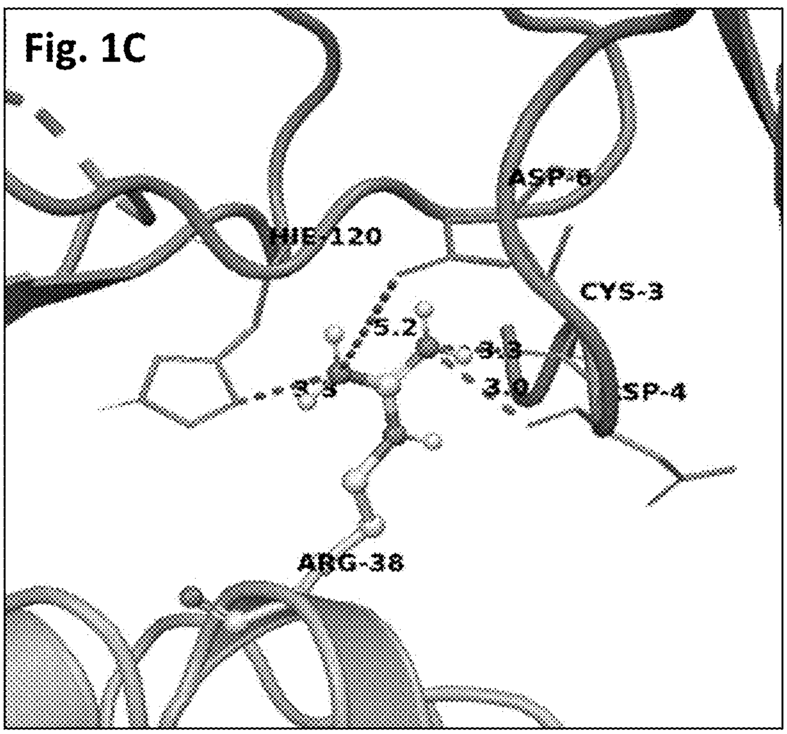
Figure 1D:
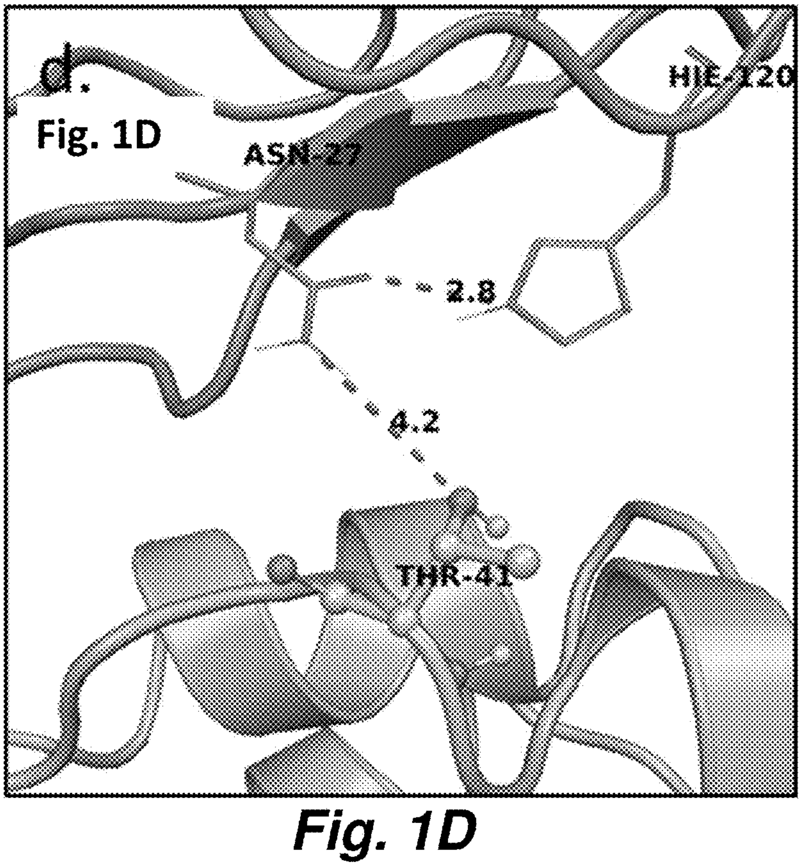
Figure 1E:
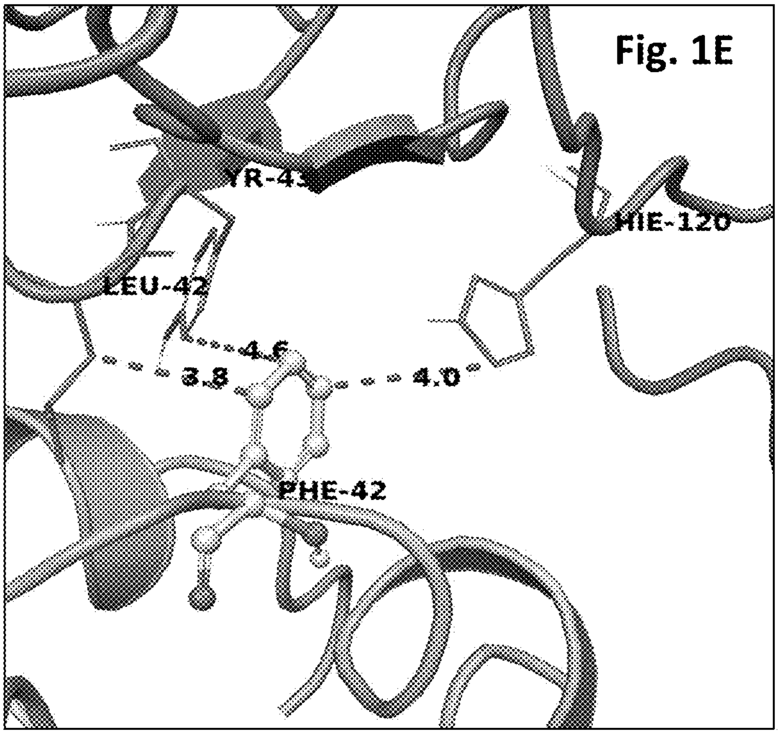
Figure 1F:
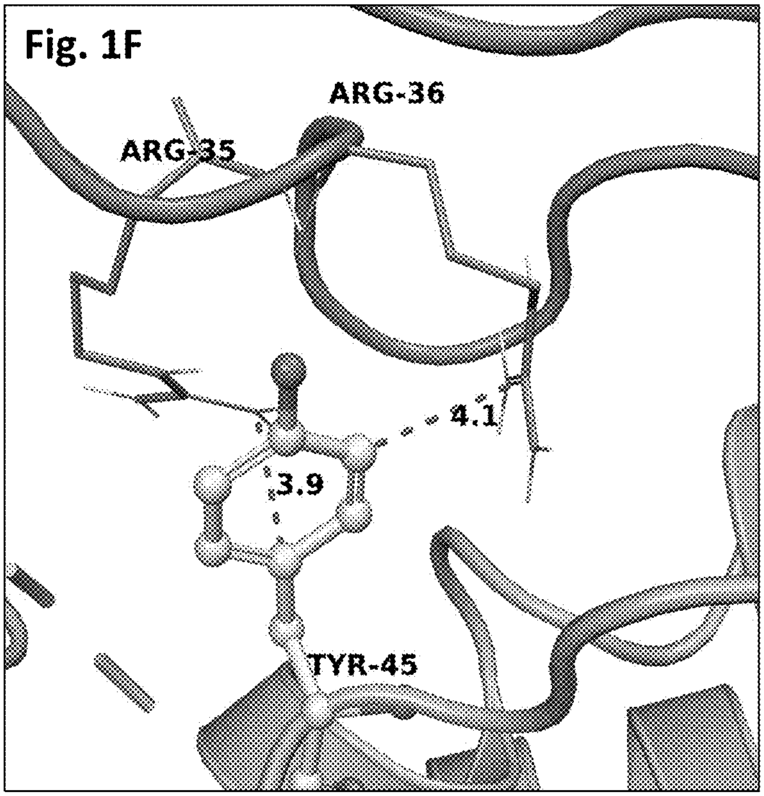
Figure 1G:
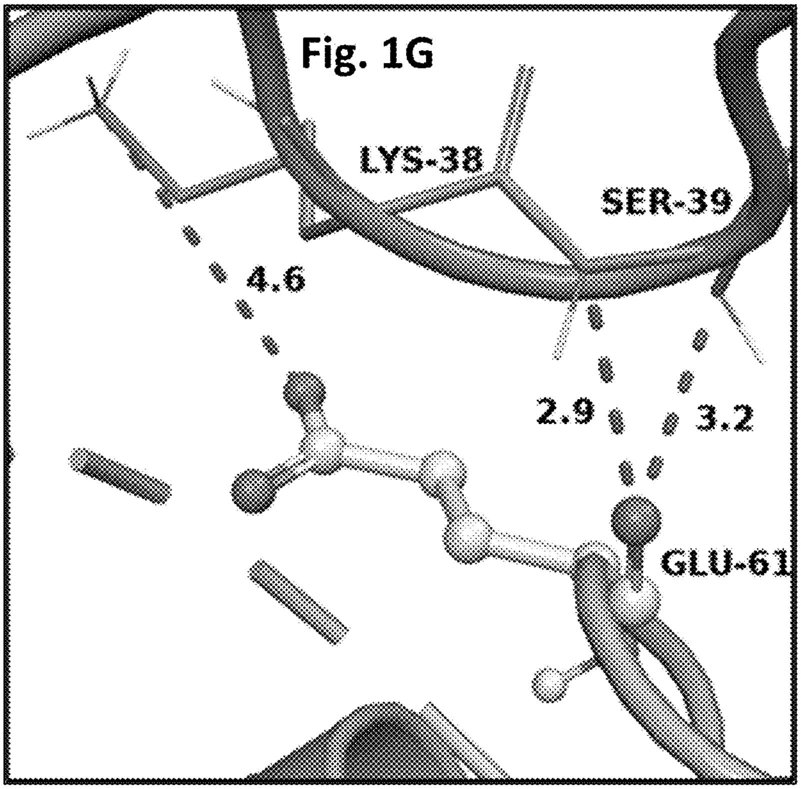
Figure 1H:
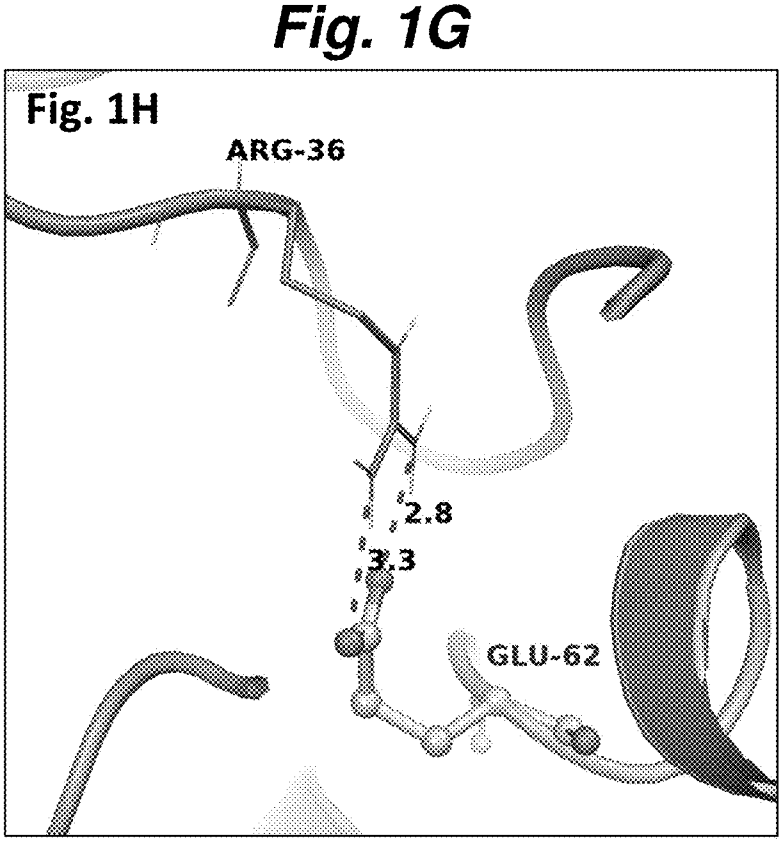
Figure 1I:
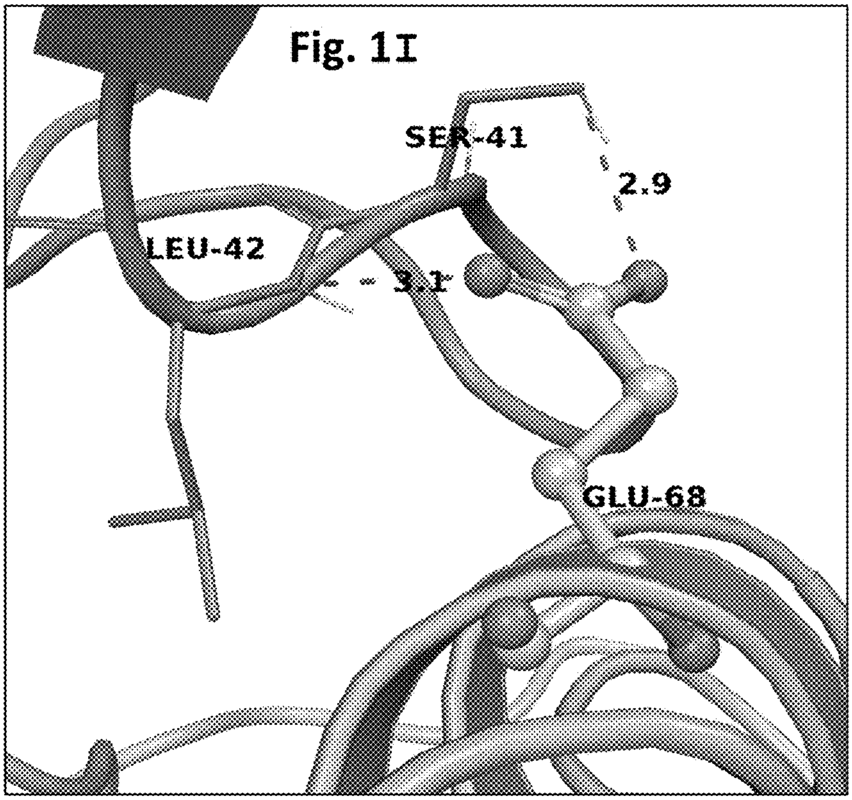
Figure 1J:
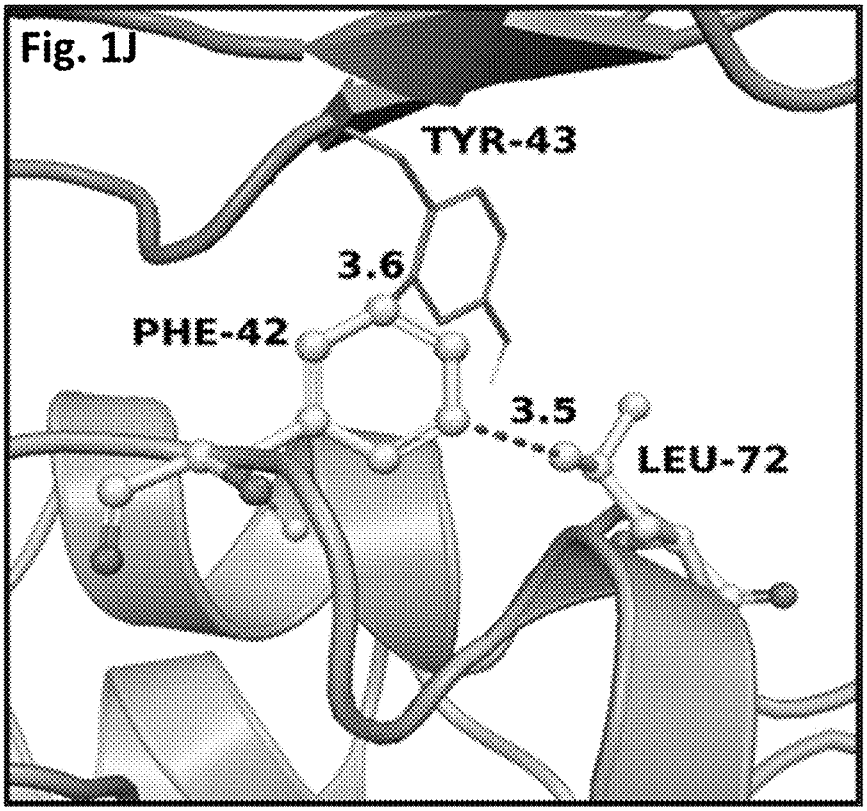
Figure 1K:
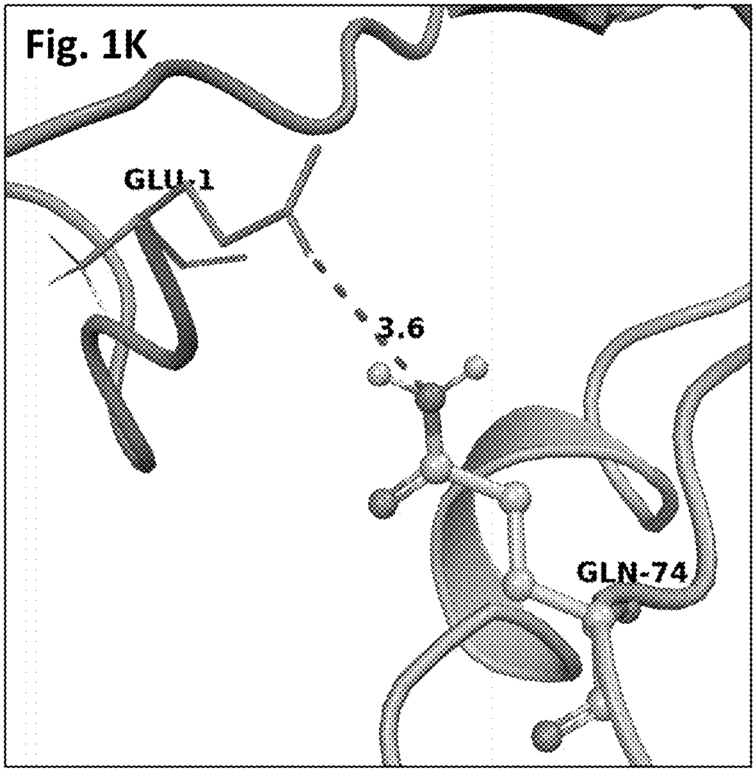
Figure 1L:
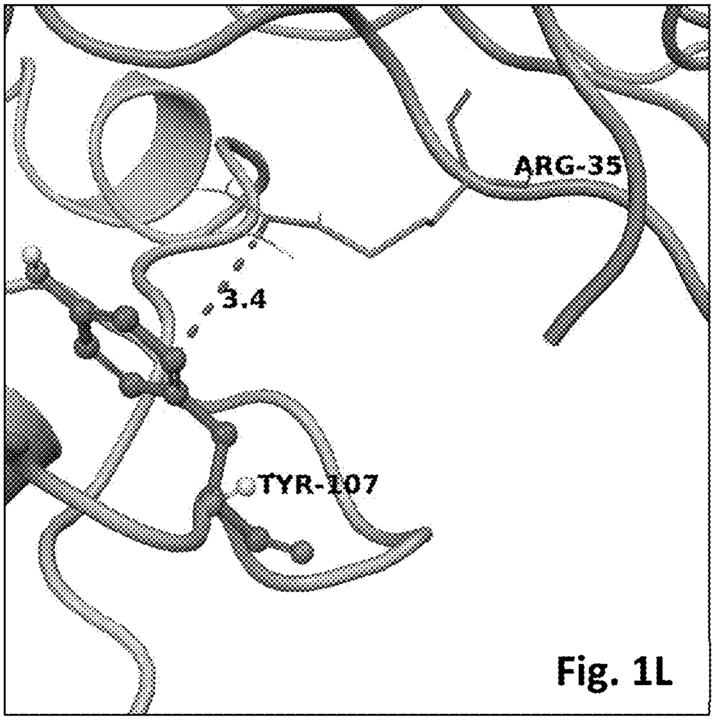

Provided are fusion proteins comprising a serum half-life extending polypeptide operably linked to a variant or mutant or non-naturally occurring IL-2 (IL-2v). In various embodiments, the IL-2v of the fusion protein is truncated at the N-terminus by at least 5 amino acids relative to wild-type IL-2 (i.e., does not comprise amino acid residues corresponding to amino acid residues 1-5 of mature wild-type IL-2 (wt IL-2)); and binds to the interleukin-2 receptor alpha subunit (IL-2RA; CD25) with reduced binding affinity in comparison to wt IL-2. The IL-2 variant fusion proteins described herein have several structural features that enhance its safety and therapeutic efficacy while significantly reducing the frequency of dosing. In addition, these features contribute to improved manufacturability through high level production of a soluble product using expression and purification platforms that are typically employed for monoclonocal antibody manufacturing. For example, Fc-IL-2v fusion proteins described herein were engineered to have negligible affinity for the IL-2Rα highly expressed on Treg cells by the introduction of point mutations in IL-2 at the IL-2/IL-2Rα interface. In addition, use of a heterodimeric Fc enabled fusion of a single copy of the IL-2v to dimeric Fc. This fusion design mimics the monovalent nature of native IL-2 and avoids the potential for avidity-driven binding to IL-2 receptors. One feature that enhances manufacturability is the introduction of mutations to one subunit of the Fc heterodimer to disrupt protein A binding and avoid co-purification of the corresponding homodimer contaminant with the desired heterodimer product. The use of an IgG4-derived Fc, which naturally lacks the ability to activate complement and has decreased Fc gamma receptor (FcγR) binding relative to IgG1, combined with additional mutations to further minimize FcγR binding eliminated the potential for antibody-dependent cell-mediated cytotoxicity (ADCC), antibody-dependent cellular phagocytosis (ADCP) or complement-dependent cytotoxicity (CDC). These Fc modifications are combined with additional changes in the IL-2v proteins to further enhance manufacturability, namely, substitution of an unpaired cysteine residue with serine to prevent unwanted aggregation or modification that might otherwise occur at this unpaired cysteine residue. Unpaired cysteines within the Fc domain can also be substituted, e.g., with a serine (e.g., the position corresponding to position 136 of any one of SEQ ID NOs: 45-56 or 141-143). Furthermore, deletion of the first five residues of the mature native IL-2 sequence eliminated a potential O-glycosylation site on threonine (T3) to improve manufacturing control. Deletion of the first five residues of mature native IL-2 does not require substitution of T3 to a residue that cannot be O-glycosylated (e.g., T3A) to reduce the potential for sequence-dependent immunogenicity. The herein described serum half-life extended IL-2v molecules described herein provide a safer, more efficacious, less frequently dosed IL-2-based therapeutic that can be applied to treating a wider variety of diseases than is currently the case.

Among other things, the present disclosure identifies the source of a problem of determining a minimal combination of amino acid substitutions in wild-type (wt) IL-2 that can abrogate binding to IL-2Rα to a sufficient degree so as to minimize preferential stimulation of immunosuppressive Treg cells over effector CD4+ and CD8+ T cells as well as NK cells. Various literature reports describing studies of IL-2 substitutions fail to provide a comprehensive analysis of the contribution of individual amino acid side chains to IL-2α binding, either due to the limited set of IL-2 residues evaluated in any single study or due to the drastic nature of substitutions reported in such studies, for instance, where replacing an amino acid with a charged side chain to an amino acid with a side chain carrying the opposite charge. The present disclosure, among other things, provides particularly useful and effective constructs including a variant IL-2 moiety. The present disclosure provides IL-2v constructs combining a minimal number of substitutions that could elicit the desired biology (i.e., minimize preferential stimulation of immunosuppressive Treg cells over effector immune cells, while also restricting substitutions to either of alanine or glycine). For example, the present disclosure provides a heterodimeric Fc-IL-2v fusion protein comprising amino acid substitutions of R38G, F42A, and E62A in IL-2. In some embodiments, a provided heterodimeric Fc-IL-2v fusion protein can further comprise: (i) an amino acid substitution of C125S; and/or (ii) deletion of first five residues of mature native IL-2 sequence. Without wishing to be bound by any particular theory, the present disclosure notes that such a C125S substitution may be particularly useful and/or effective to reduce aggregation. Analogously, without wishing to be bound by any particular theory, the present disclosure notes that deletion of first five residues removes a potential O-glycosylation site on a threonine (T3), which may, in some embodiments, be useful and/or effective to improve manufacturing control as well as reduce the risk of sequence-dependent immunogenicity.

In some embodiments, a heterodimeric Fc-IL-2v fusion protein described herein comprising R38G, F42A, and E62A is characterized by one, two, three, four, five, or more (e.g., all) of: (i) extremely weak or essentially undetectable binding to IL-2Rα, while retaining binding to IL-2Rβγ compared to an Fc-IL-2 fusion protein with a native IL-2Rα binding interface (See Example 8); (ii) lower potency in STAT5 activation of CTLL-2 cells expressing IL-2Rαβγ compared to an Fc-IL-2 fusion protein with a native IL-2Rα binding interface or to Fc-IL-2v heterodimers with R38G and E62A or F42A and E62A substitutions (see Example 9); (iii) lower potency of STAT5 activation in human Treg cells relative to activation by an Fc-IL-2 fusion protein with a native IL-2Rα binding interface (See Example 10); (iv) comparable potency of STAT5 activation in human CD8+ T cells relative to activation by an Fc-IL-2 fusion protein with a native IL-2Rα binding interface (See Example 10); (v) similar proliferation of human CD8+ T cells and NK cells as an Fc-IL-2 fusion protein with a native IL-2Rα binding interface (See, Example 12); (vi) lower potency of STAT5 activation in non-human primate Treg cells relative to activation by an Fc-IL-2 fusion protein with a native IL-2Rα binding interface (See, Example 13); (vii) comparable potency of STAT5 activation in non-human primate CD8+ T cells relative to activation by an Fc-IL-2 fusion protein with a native IL-2Rα binding interface (See, Example 13); (viii) Increased in vivo drug exposure in non-human primates relative to equivalent doses of Fc-IL-2v heterodimer with F42A and E62A substitutions (See Examples 17 and 18); or (ix) lower in vivo expansion of Treg cells relative to an Fc-IL-2v heterodimer with F42A and E62A (Example 19).

IL-2 variants have been the subject of significant research for more than two decades, with much effort focused on developing variants with reduced affinity (relative to wild type IL-2, for example as set forth in SEQ ID NO: 216) for IL-2Rα as part of the trimeric IL 2Rαβγ. Positions of particular focus have included R38, F42, K43, Y45, E61, and E62, which were determined in studies of analogs that utilized binding assays for IL-2Rα (see, for example, Ju, et al. (1990) in *The Biology and Clinical Applications of Interleukin*-2, ed. Rees, R. C. (Oxford Univ. Press, Oxford), pp. 7-14). Various reports describe substitutions at one or more of these positions, and assess their impact on IL-2Rα binding, however, these studies often made use of drastic substitutions to native side chains, for instance, replacing a native amino acid with a charged side chain to an amino acid with a side chain carrying the opposite charge or, for instance, replacing a native amino acid with an uncharged side chain to an amino acid with a charged side chain (see, Sauve et al., *Proc. Natl. Acad. Sci. U.S.A.,* 88:4636, 1991, Heaton, et al, *Cancer Res.* 53(11):2597-602, 1993, Wang, et al. *Eur J Immunol.* 25(5):1212-6, 1995, Vazquez-Lombardi, et al., *Nat Commun.* 12; 8:15373, 2017). Such drastic changes may appear favorable with respect to binding disruption, but could increase the risk of introducing sequence-dependent immunogenicity. IL-2 variant molecules can be immunogenic in the clinic (see, Satyanarayana, C&EN Magazine, "IL-2 treatment can be dangerous. Here's how drug firms are trying to fix it," Apr. 4, 2021, 99(12) (cen.acs.org/pharmaceuticals/biologics/safer-IL2-cancer-immunotherapy-autoimmunity/99/i12)). Thus, it is advantageous to reduce the risk of immunogenicity by incorporating fewer amino acid substitutions in the IL-2 molecule. In addition, no one study systemically compared the effect of a large panel of single point substitutions and/or combinations thereof, making it challenging to design a minimally substituted IL-2 variant that achieved the dual goals of limiting preferential stimulation of immunosuppressive Treg cells over effector CD4+ and CD8+ T cells and NK cells, while simultaneously limiting the total number and nature of substitutions so as to reduce the possibility of said variant being immunogenic in humans.

Among other things, the present disclosure surprisingly demonstrates that multiple substitutions of IL-2 of G at position 38, A at position F42, and A at position E62 are particularly useful and/or effective. Indeed, results of prior studies that assessed multiple substitutions in IL-2 variants have indicated that at least four substitutions are necessary with different positions and/or substitutions than G at position 38, A at position F42, or A at position E62. Indeed, studies of multiple substitutions of IL-2 variants indicate that substitution of at least 4 substitutions is required to significantly reduce Treg expansion and IL-2Rα binding relative to wt IL-2 while maintaining CD8+ T cell and NK cell proliferation similar to wt IL-2.

For example, an assessment of an IL-2 variant made a combination of substitutions, including A at positions 38, 42, 45, and 62 (Carmenate et al., *J Immunol.* 190 (12) 6230-6238, 2013), and determined its ability to stimulate CD8+ T cells and NK cell proliferation, decrease Treg expansion, and reduce IL-2Rα binding. The results showed that an IL-2 variant including R38A, F42A, Y45A, and E62A stimulated CD8+ T cells and NK cell proliferation similar to wt IL-2, while significantly reducing Treg expansion and IL 2Rα binding relative to wtIL-2. Thus, at least four substitutions including a substitution of A at position 45 were apparently required to stimulate CD8+ T cells and NK cell proliferation, while significantly reducing Treg expansion and IL-2Rα binding. In contrast, the present disclosure provides IL-2 variants that include G at position 38, A at position 42, and A at position E62 and do not include a substitution of A at position 45.

In another example, an IL-2 variant described above including A at positions 38, 42, 45, and 62 in combination (Carmenate, et al., 2013, supra) was further assessed to determine the contribution of each substitution to impairment of IL-2Rα binding (Rojas, et al., *J Mol Recognit.* 28(4):261-8, 2015). The results of binding assays showed that single IL-2 substitutions of R38A and Y45A still bound IL-2Rα (34% and 4% of wt IL-2, respectively), while single IL-2 substitutions of F42A and E62A resulted in negligible IL-2Rα binding (<1% of wtIL-2 for each). The results of proliferation assays showed that single IL-2 substitutions of R38A and Y45A still caused proliferation in IL-2Rα expressing CTLL-2 cells (48.2% and 7.1% of wt, respectively), while single IL-2 substitutions of F42A and E62A resulted in negligible proliferation in CTLL-2 cells (2.0% and 1.3%, respectively), and the combination of all four IL-2 substitutions (R38A, F42A, Y45A, and E62A) resulted in non-detectable CTLL-2 cell proliferation. These results indicate that: (i) at least four mutations are required to reduce IL-2Rα binding sufficiently for non-detectable proliferation of IL-2Rα-expressing CTLL-2 cells; and (ii) among these four mutations, R38A is the least helpful with the most residual binding to IL-2Rα and highest proliferation in CTLL-2 cells. Unlike the Carmenate et al. work, the present disclosure demonstrated that R38G was a more effective single mutation to reduce IL-2Rα binding than R38A, and thus an IL-2 variant with only three substitutions comprising R38G combined with F42A and E62A was sufficient to attenuate STAT5 activation of CTLL-2 cells by over 30,000-fold relative to the equivalent molecule with a native IL-2Rα binding interface, and elicit the desired biology on primary human immune cells by minimizing preferential stimulation of immunosuppressive Treg cells over effector T and NK cells.

Additionally, work by Roche (see, for example, WO2012/107417), has described the development of IL-2 variants in the context of heterodimer IgG fusion molecules with antigen binding domains specific for antigens including, for example, tumor antigens. This work indicates, among other things: (i) substitution of position L72 in IL-2 to G is necessary for the desired abolishment of IL-2Rα binding and reduction of human Treg activation in the context of substitutions F42A and Y45A; (ii) desirable IgG IL-2 fusions have a T3A substitution in IL-2 to eliminate the O-glycosylation site; and (iii) desirable IgG IL-2 fusions have a C125A substitution to avoid inter-molecular disulfide bridges. The present disclosure demonstrates that IL-2 variants that contain substitutions at positions R38G, F42A, and E62A reduce STAT5 activation of CTLL-2 cells by over 30,000-fold while IL-2 variants with substitutions at F42A, Y45A, and L72G reduce STAT5 activation of CTLL-2 cells by only 3,800-fold relative to the equivalent molecule with a native IL-2Rα binding interface. In addition, as shown in Example 10, IL-2 variants containing the native IL-2Rα binding interface, or either of R38G/F42A/E62A or F42A/Y45A/L72G triple substitutions had comparable activities to each other in activating CD8+ T cells. However, while both of these triple substitution variants had significantly reduced activity on Treg cells, the R38G/F42A/E62A-containing variant was superior in exhibiting a more modest difference between activity on Treg versus effector CD8 cells (EC50 values of 3.0 nM and 10.7 nM respectively) as compared to the F42A/Y45A/L72G-containing variant (EC50 values of 1.2 and 9.8 nM respectively). Furthermore, this present disclosure demonstrates that deletion the first five N-terminal amino acids of IL-2 can be used as a preferred strategy to eliminate the O-glycosylation site, as this avoids any mutagenesis of native IL-2 sequence for this purpose which could otherwise increase the risk of potential immunogenicity in humans.

Furthermore, recent work reported by Cugene (see, for example, WO2020/252418), has described development of IL-2 variants in the context of bivalent IL-2 homodimer Fc fusions and indicates, among other things: (i) at position R38, none of A, F, or G substitutions dramatically improved specificity for IL-2Rβγ as compared with IL-2Rαβγ, comparably fused; (ii) among the tested substitutions, R38A was more helpful (EC50 of 3.23) than either of the others (EC50 of 2.0 and 0.42 for R38G and R38F, respectively) at improving such specificity; (iii) at position E62, all substitutions of F, H, L, and A did improve specificity for IL-2Rβγ as compared with IL-2Rαβγ, comparably fused; (iv) among the tested substitutions, E62F was more helpful (EC50 of 151) than any of the others (EC50 of 2.57, 2.38, and 60.5 for E26H, E62L, and E62A, respectively) at improving such specificity; and (iii) desirable IL-2-Fc fusions do not have an S residue at position 125. In fact, the reference IL-2 used in Cugene's work apparently naturally included an S125 residue; Cugene recommends substituting away from S (specifically, using an S125I substitution), whereas the present disclosure substitutes to S (specifically, using a C125S substitution). In contrast to this recent work by Cugene, the present disclosure provides IL-2 Fc fusion protein variants that include G at position 38, A at position 42, A at position 62, and S at position 125.

Whether taken individually or together, it is clear that, the teachings available prior to the present disclosure would have led one skilled in the art to develop IL-2 variants different from those described herein, particularly in the context of Fc fusions.

2. Variant Interleukin-2 (IL-2v) Proteins a. Variant IL-2 (IL-2v) with Reduced Binding Affinity to IL-2 Receptor Alpha Subunit (IL-2RA)

With respect to functional attributes, generally, the variant IL-2 (IL-2v) domain, e.g., of the herein described fusion proteins, binds to the alpha subunit of IL-2 receptor (IL-2RA) with reduced affinity, e.g., with a KD of at least 60 μM. The alpha subunit of IL-2 receptor can be human, non-human primate or mouse. Human IL-2RA (a.k.a., CD25; IDDM10, IL-2R, IMD41, TCGFR, p55) is assigned NCBI Gene ID: 3559. Mouse il2ra (a.k.a., CD25; Il2r, Ly-43) is assigned NCBI Gene ID: 16184. Rhesus monkey IL-2RA is assigned NCBI Gene ID: 574300. *Macaca fascicularis* (cynomolgus or crab-eating macaque) IL-2RA is assigned NCBI Gene ID: 102123605. In some embodiments, the IL-2v binds to IL-2RA with an equilibrium dissociation constant ($K_D$) of at least 60 μM (e.g., 60 μM or higher). Further, in some embodiments, the variant IL-2 (IL-2v) domain, e.g., of the herein described fusion proteins, binds to a complex of interleukin 2 receptor subunit beta (IL-2RB; CD122) and interleukin 2 receptor subunit gamma (IL-2RG; CD132) with a $K_D$ of less than 150 nM, e.g., less than 1.5 nM, e.g., less than 120 pM, e.g., less than 100 pM, e.g., less than 80 pM, e.g., less than 75 pM, e.g., less than 70 pM, e.g., as determined in a cell line having an artificial Fc-fused IL2Rβ/IL2Rγ heterodimer, described herein. in some embodiments, the variant IL-2 (IL-2v) domain, e.g., of the herein described fusion proteins, binds to a complex of interleukin 2 receptor subunit beta (IL-2RB; CD122) and interleukin 2 receptor subunit gamma (IL-2RG; CD132) with a $K_D$ within 10-fold, e.g., within 9-fold, 8-fold, 7-fold, 6-fold, 5-fold, 4-fold, 3-fold, 2-fold, or less, of the $K_D$ of wild-type IL-2 under equivalent conditions. The complex of interleukin 2 receptor subunit beta (IL-2RB; CD122) and interleukin 2 receptor subunit gamma (IL-2RG; CD132) can be human, non-human primate or mouse. Human IL-2RB (a.k.a., CD122, IL15RB, IMD63, P70-75) is assigned NCBI Gene ID: 3560 and human IL-2RG (a.k.a., P64; CIDX; IMD4; CD132; SCIDX; IL-2RG; SCIDX1) is assigned NCBI Gene ID: 3561. Mouse il2rb (a.k.a., p70; CD122; IL15Rbeta; Il-2Rbeta; IL-15Rbeta; Il-2/15Rbeta) is assigned NCBI Gene ID: 16185 and mouse il2rg (a.k.a., gc; p64; [g]c; CD132; gamma(c)) is assigned NCBI Gene ID: 16186. Rhesus monkey IL-2RB is assigned NCBI Gene ID: 696331 and rhesus monkey IL-2RG is assigned NCBI Gene ID: 641338. Cynomolgus monkey IL-2RB is assigned NCBI Gene ID: 102138714 and rhesus monkey IL-2RG is assigned NCBI Gene ID: 102144912. Binding affinity can be determined according to any method in the art. One method for determining binding affinity is surface plasmon resonance (SPR).

In various embodiments, the variant IL-2 (IL-2v) domain, e.g., of the herein described fusion proteins, promotes or induces equivalent or greater proliferation of CD8+ T cells relative to wt IL-2, an IL-2v of any one of SEQ ID NOs: 43 and 44. Additionally, in some embodiments, the concentration at which the IL-2v, e.g., of the herein described fusion proteins, elicits 50% of maximal ($EC_{50}$) signal transducer and activator of transcription 5 (STAT5) activation or signaling of regulatory T (Treg) cells is at least 1000-fold, e.g., at least 1500-fold, e.g., at least 1700-fold, e.g., at least 2000-fold, e.g., at least 2500-fold higher, relative to the $EC_{50}$ for STAT5 activation or signaling of wt IL-2, or an IL-2v of any one of SEQ ID NOs: 43 and 44. See, e.g., Gilmour, et al., *Proc Natl Acad Sci USA* (1995) 92(23):10772-6; Gaffen, *Cytokine* (2001) 14(2):63-77; Varker, et al., *Clin Cancer Res* (2006) 12(19):5850-8. "Regulatory T cells" (Tregs; Treg cells), also known as "suppressor T cells," are a subpopulation of T cells that are immunosuppressive and generally suppress or downregulate induction and proliferation of effector T cells. Tregs express the surface biomarkers CD4 and CD25 (IL-2 receptor α-chain) and intracellular DNA binding biomarker FOXP3. Human Foxp3+CD4+ T cells have been divided into three subfractions based upon the expression level of Foxp3 and the cell surface molecules CD25 and CD45RA. The Foxp3hiCD45RA−CD25hi and Foxp3loCD45RA+CD25lo phenotypes correspond to suppressive Treg cells, whereas the Foxp3loCD45RA−CD25lo fraction marks activated T effector (Teff) cells without suppressive activity. In addition, Treg cells from cancer patients, as compared to those in healthy subjects, are usually characterized by a distinct expression profile of chemokine receptors, such as CCR4, CXCR4, and CCR5, which facilitates their migration into tumors in response to the corresponding chemokine ligands derived from tumor microenvironment. See, e.g., Liu, et al., *FEBS J.* (2016) 283(14):2731-48 and Miyara, et al., *Immunity* (2009) 30, 899-911.

In some embodiments, the concentration at which the IL-2v, e.g., of the herein described fusion proteins, elicits 50% of maximal ($EC_{50}$) of IL-2Rαβγ-mediated STAT5 activation or signaling (e.g., measured as STAT5 activation of CTLL2 cells) is at least 2500-fold, e.g., at least 5000-fold, e.g., at least 7500-fold, e.g., at least 10,000-fold, e.g., at least 15,000-fold, e.g., at least 20,000-fold higher, relative to the $EC_{50}$ for STAT5 activation or signaling of wt IL-2, or an IL-2v of any one of SEQ ID NOs: 43 and 44. See, e.g., Gilmour, et al., *Proc Natl Acad Sci USA* (1995) 92(23): 10772-6; Gaffen, *Cytokine* (2001) 14(2):63-77; Ortega, et al., *J Immunol.* (1984) 133(4):1970-5; Gillis, et al., *J Immunol.* (1978) 120(6):2027-32.

In some embodiments, the concentration at which the IL-2v, e.g., of the herein described fusion proteins, elicits 50% of maximal ($EC_{50}$) proliferation of natural killer (NK) cells is at least 10-fold, e.g., at least 12-fold, e.g., at least 15-fold, e.g., at least 16-fold, e.g., at least 18-fold, e.g., at least 20-fold higher, e.g., as measured using KHYG-1 cells, relative to the $EC_{50}$ for proliferation of wt IL-2, or an IL-2v of any one of SEQ ID NOs: 43 and 44. See, e.g., Suck, et al., *Exp Hematol* (2005) October; 33(10):1160-71; Yagita, et al., *Leukemia* (2000) 14(5):922-30; Cell line KHYG-1 has DSMZ no.: ACC 725; ExPASy Cellosaurus KHYG-1 (CVCL_2976); CellBank Australia CODE: JCRB0156.

A "polypeptide variant," as the term is used herein, is a polypeptide that typically differs from a polypeptide specifically disclosed herein in one or more substitutions, deletions, additions and/or insertions. Such variants may be naturally occurring or may be synthetically generated, for example, by modifying one or more of the above polypeptide sequences described herein and evaluating one or more biological activities of the polypeptide as described herein and/or using any of a number of techniques well known in the art.

The term "variant" may also refer to any naturally occurring or engineered molecule comprising one or more nucleotide or amino acid mutations. In one embodiment, the multi-specific antigen binding molecule is a bispecific antigen binding molecule. In one embodiment, the multi-specific antigen binding molecule is a bispecific antibody. For example, somatic variants may encompass all related naturally occurring antibodies that are part of or derived from the same B-cell lineage. Engineered variants may encompass all single mutations or combinatorial mutations made to an antibody.

With respect to structural attributes, generally, the IL-2v domain, e.g., of the herein described fusion proteins, do not comprise the first five amino acid residues corresponding to amino acid positions 1-5 of wt IL-2 (e.g., do not comprise the amino acid sequence APTSS (SEQ ID NO: 163)). As used herein, numbering of a given amino acid polymer or nucleic acid polymer "corresponds to", is "corresponding to" or is "relative to" the numbering of a selected or reference amino acid polymer or nucleic acid polymer when the position of any given polymer component (e.g., amino acid, nucleotide, also referred to generically as a "residue") is designated by reference to the same or to an equivalent position (e.g., based on an optimal alignment or a consensus sequence) in the selected amino acid or nucleic acid polymer, rather than by the actual numerical position of the component in the given polymer. Stated another way, in the IL-2v domain, e.g., of the herein described IL-2v and IL-2v fusion proteins, the first five amino acids corresponding to a wild-type or native mature IL-2 are truncated. For fusion proteins based on human IL-2, the numbering of IL-2 positions is with reference to mature human IL-2 (NCBI Gene ID: 3558), shown below, or with reference to SEQ ID NO:44 (IL-2v having a serine at position 125 (C125S):

```
                                        (SEQ ID NO: 216)
APTSSSTKKTQLQLEHLLLDLQMILNGINNYKNPKLTRMLTFKFYMPK

KATELKHLQCLEEELKPLEEVLNLAQSKNFHLRPRDLISNINVIVLEL

KGSETTFMCEYADETATIVEFLNRWITFCQSIISTLT.
```

In various embodiments, the IL-2v domain is from (e.g., based on or derived from) a human wild-type IL-2 or a wild-type IL-2 of a non-human primate. For fusion proteins based on rhesus monkey IL-2, the numbering of IL-2 positions is with reference to mature rhesus monkey IL-2 (NCBI Gene ID: 708017), shown below:

```
                                        (SEQ ID NO: 217)
APTSSSTKKTQLQLEHLLLDLQMILNGINNYKNPKLTRMLTFKFYMPK

KATELKHLQCLEEELKPLEEVLNLAQSKNFHLRDTKDLISNINVIVLE

LKGSETTLMCEYADETATIVEFLNRWITFCQSIISTLT.
```

For fusion proteins based on cynomolgus monkey IL-2, the numbering of IL-2 positions is with reference to mature cynomolgus monkey IL-2 (NCBI Gene ID: 102129830), shown below:

(SEQ ID NO: 262)
APTSSSTKKTQLQLEHLLLDLQMILNGINNYKNPKLTRMLTFKFYMPK

KATELRHLQCLEEELKPLEEVLNLAQSKSFHLRDTKDLISNINVIVLE

LKGSETTLMCEYADETATIVEFLNRWITFCQSIISTLT.

In some embodiments, the IL-2v comprises a serine at position 125 (C125) and at least two, or at least three, substitutions (e.g., to glycine or alanine) at amino acid positions selected from the group consisting of R38, F42, Y45, E61, E62 and L72. In some embodiments, the IL-2v comprises a serine at position 125 (C125) and at least two, or at least three, no more than three, no more than two, substitutions (e.g., to glycine or alanine) at amino acid positions selected from the group consisting of R38, F42, Y45, E61 and E62. In some embodiments, the IL-2v comprises a serine at position 125 (C125) and at least two, or at least three, no more than three, no more than two, substitutions (e.g., to glycine or alanine) at amino acid positions selected from the group consisting of R38, F42, Y45 and E62. In some embodiments, the IL-2v comprises a serine at position 125 (C125) and at least two, or at least three, no more than three, no more than two, substitutions (e.g., to glycine or alanine) at amino acid positions selected from the group consisting of R38, F42 and E62. In some embodiments, the IL-2v comprises a serine at position 125 (C125) and at least two, or at least three, no more than three, no more than two, substitutions at amino acid positions selected from the group consisting of R38G, F42A, Y45G, E61A, E62A and L72G. In some embodiments, the IL-2v comprises a serine at position 125 (C125) and at least two, or at least three, no more than three, no more than two, substitutions at amino acid positions selected from the group consisting of R38G, F42A, Y45G, E61A and E62A. In some embodiments, the IL-2v comprises a serine at position 125 (C125) and at least two, or at least three, no more than three, no more than two, substitutions at amino acid positions selected from the group consisting of R38G, F42A, Y45G and E62A. In some embodiments, the IL-2v comprises a serine at position 125 (C125) and at least two, or at least three, no more than three, no more than two, substitutions at amino acid positions selected from the group consisting of R38G, F42A and E62A. The foregoing position numbers are with respect to an IL-2v of SEQ ID NO:44. In some embodiments, the IL-2v does not comprise an amino acid substitution at one or more, or all, of positions selected from the group consisting of D20, Y45, E61, E68, V69, L72, A73, L80, R81, L85, L86, I87, I92 and Q126. In some embodiments, the IL-2v does not comprise an amino acid substitution at one or more, or all, of positions selected from the group consisting of H16, D20, E61, N88 and V91.

In some embodiments, the IL-2v comprises an amino acid sequence selected from the group consisting of SEQ ID NOs: 1-42 or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 1-42. Illustrative IL-2v sequences based on wild-type human IL-2, including SEQ ID Nos:1-44, are provided in Table A.

TABLE A variant IL-2 with reduced binding to interleukin-2 receptor subunit alpha (IL-2RA; CD25)

| PROTEIN NO: SEQ ID NO: | Features | Polypeptide Sequence |
|---|---|---|
| 1 | Δ1-5_R38$X_1$_ T41$X_2$_F42$X_3$_ Y45$X_4$_E61$X_5$_ E62$X_6$_E68$X_7$_ L72$X_8$_Q74$X_9$_ Y107$X_{10}$_C125S<br>$X_1$ is R, S, G or A<br>$X_2$ is T, G or A<br>$X_3$ is F, G or A<br>$X_4$ is Y, G or A<br>$X_5$ is E, G or A<br>$X_6$ is E, G or A<br>$X_7$ is E, G or A<br>$X_8$ is L, G or A<br>$X_9$ is Q, G or A<br>$X_{10}$ is Y, G or A | STKKTQLQLEHLLLDLQMILNGINNYKNPKLT$X_1$ML$X_2X_3$KF$X_4$MPKKATELKHLQCLE$X_5X_6$LKP LE$X_7$VLN$X_8$A$X_9$SKNFHLRPRDLISNINVIVLELKGSETTFMCE$X_{10}$ADETATIVEFLNRWITFS QSIISTLT |
| 2 | Δ1-5_R38$X_1$_ F42$X_3$_Y45$X_4$_ E61$X_5$_E62$X_6$_ L72$X_8$_C125S<br>$X_1$ is R, S, G or A<br>$X_3$ is F, G or A<br>$X_4$ is Y, G or A<br>$X_5$ is E, G or A<br>$X_6$ is E, G or A<br>$X_8$ is L, G or A | STKKTQLQLEHLLLDLQMILNGINNYKNPKLT$X_1$MLT$X_3$KF$X_4$MPKKATELKHLQCLE$X_5X_6$LKP LEEVLN$X_8$AQSKNFHLRPRDLISNINVIVLELKGSETTFMCEYADETATIVEFLNRWITFSQSI ISTLT |
| 3 | Δ1-5_ R38$X_1$_F42$X_3$_ Y45$X_4$_E61$X_5$_ E62$X_6$_C125S<br>$X_1$ is R, S, G | STKKTQLQLEHLLLDLQMILNGINNYKNPKLT$X_1$MLT$X_3$KF$X_4$MPKKATELKHLQCLE$X_5X_6$LKP LEEVLNLAQSKNFHLRPRDLISNINVIVLELKGSETTFMCEYADETATIVEFLNRWITFSQSII SILT |

TABLE A-continued variant IL-2 with reduced binding to interleukin-2 receptor subunit alpha (IL-2RA; CD25)

| PROTEIN NO:<br>SEQ ID NO: | Features | Polypeptide Sequence |
|---|---|---|
| | or A<br>$X_3$ is F, G or A<br>$X_4$ is Y, G or A<br>$X_5$ is E, G or A<br>$X_6$ is E, G or A | |
| 4 | Δ1-5_R38$X_1$_F42$X_3$_Y45$X_4$_E62$X_6$_C125S<br>$X_1$ is R, S, G or A<br>$X_3$ is F, G or A<br>$X_4$ is Y, G or A<br>$X_6$ is E, G or A | STKKTQLQLEHLLLDLQMILNGINNYKNPKLT$X_1$MLT$X_3$KF$X_4$MPKKATELKHLQCLEE$X_6$LKPL<br>EEVLNLAQSKNFHLRPRDLISNINVIVLELKGSETTFMCEYADETATIVEFLNRWITFSQSIIS<br>TLT |
| 5 | Δ1-5_R38$X_1$_F42$X_2$_E62$X_5$_C125S<br>$X_1$ is R, S, G or A<br>$X_3$ is F, G or A<br>$X_6$ is E, G or A | STKKTQLQLEHLLLDLQMILNGINNYKNPKLT$X_1$MLT$X_3$KFYMPKKATELKHLQCLEE$X_6$LKPLE<br>EVLNLAQSKNFHLRPRDLISNINVIVLELKGSETTFMCEYADETATIVEFLNRWITFSQSIIST<br>LT |
| 6 | Δ1-5_R38$X_1$_F42A_E62A_C125S<br>$X_1$ is R, S, G or A | STKKTQLQLEHLLLDLQMILNGINNYKNPKLT$X_1$MLTAKFYMPKKATELKHLQCLEEALKPLEE<br>VLNLAQSKNFHLRPRDLISNINVIVLELKGSETTFMCEYADETATIVEFLNRWITFSQSIISTL<br>T |
| 7 | Δ1-5_R38G_C125S | STKKTQLQLEHLLLDLQMILNGINNYKNPKLTGMLTFKFYMPKKATELKHLQCLEEELKPLEEV<br>LNLAQSKNFHLRPRDLISNINVIVLELKGSETTFMCEYADETATIVEFLNRWITFSQSIISTLT |
| 8 | Δ1-5_R38A_C125S | STKKTQLQLEHLLLDLQMILNGINNYKNPKLTAMLTFKFYMPKKATELKHLQCLEEELKPLEEV<br>LNLAQSKNFHLRPRDLISNINVIVLELKGSETTFMCEYADETATIVEFLNRWITFSQSIISTLT |
| 9 | Δ1-5_T41G_C125S | STKKTQLQLEHLLLDLQMILNGINNYKNPKLTRMLGFKFYMPKKATELKHLQCLEEELKPLEEV<br>LNLAQSKNFHLRPRDLISNINVIVLELKGSETTFMCEYADETATIVEFLNRWITFSQSIISTLT |
| 10 | Δ1-5_T41A_C125S | STKKTQLQLEHLLLDLQMILNGINNYKNPKLTRMLAFKFYMPKKATELKHLQCLEEELKPLEEV<br>LNLAQSKNFHLRPRDLISNINVIVLELKGSETTFMCEYADETATIVEFLNRWITFSQSIISTLT |
| 11 | Δ1-5_F42G_C125S | STKKTQLQLEHLLLDLQMILNGINNYKNPKLTRMLTGKFYMPKKATELKHLQCLEEELKPLEEV<br>LNLAQSKNFHLRPRDLISNINVIVLELKGSETTFMCEYADETATIVEFLNRWITFSQSIISTLT |
| 12 | Δ1-5_F42A_C125S | STKKTQLQLEHLLLDLQMILNGINNYKNPKLTRMLTAKFYMPKKATELKHLQCLEEELKPLEEV<br>LNLAQSKNFHLRPRDLISNINVIVLELKGSETTFMCEYADETATIVEFLNRWITFSQSIISTLT |
| 13 | Δ1-5_Y45G_C125S | STKKTQLQLEHLLLDLQMILNGINNYKNPKLTRMLTFKFGMPKKATELKHLQCLEEELKPLEEV<br>LNLAQSKNFHLRPRDLISNINVIVLELKGSETTFMCEYADETATIVEFLNRWITFSQSIISTLT |
| 14 | Δ1-5_Y45A_C125S | STKKTQLQLEHLLLDLQMILNGINNYKNPKLTRMLTFKFAMPKKATELKHLQCLEEELKPLEEV<br>LNLAQSKNFHLRPRDLISNINVIVLELKGSETTFMCEYADETATIVEFLNRWITFSQSIISTLT |
| 15 | Δ1-5_E61A_C125S | STKKTQLQLEHLLLDLQMILNGINNYKNPKLTRMLTFKFYMPKKATELKHLQCLEAELKPLEEV<br>LNLAQSKNFHLRPRDLISNINVIVLELKGSETTFMCEYADETATIVEFLNRWITFSQSIISTLT |
| 16 | Δ1-5_E62A_C125S | STKKTQLQLEHLLLDLQMILNGINNYKNPKLTRMLTFKFYMPKKATELKHLQCLEEALKPLEEV<br>LNLAQSKNFHLRPRDLISNINVIVLELKGSETTFMCEYADETATIVEFLNRWITFSQSIISTLT |
| 17 | Δ1-5_E68A_C125S | STKKTQLQLEHLLLDLQMILNGINNYKNPKLTRMLTFKFYMPKKATELKHLQCLEEELKPLEAV<br>LNLAQSKNFHLRPRDLISNINVIVLELKGSETTFMCEYADETATIVEFLNRWITFSQSIISTLT |
| 18 | Δ1-5_L72G_C125S | STKKTQLQLEHLLLDLQMILNGINNYKNPKLTRMLTFKFYMPKKATELKHLQCLEEELKPLEEV<br>LNGAQSKNFHLRPRDLISNINVIVLELKGSETTFMCEYADETATIVEFLNRWITFSQSIISTLT |
| 19 | Δ1-5_Q74G_C125S | STKKTQLQLEHLLLDLQMILNGINNYKNPKLTRMLTFKFYMPKKATELKHLQCLEEELKPLEEV<br>LNLAGSKNFHLRPRDLISNINVIVLELKGSETTFMCEYADETATIVEFLNRWITFSQSIISTLT |
| 20 | Δ1-5_Y107G_C125S | STKKTQLQLEHLLLDLQMILNGINNYKNPKLTRMLTFKFYMPKKATELKHLQCLEEELKPLEEV<br>LNLAQSKNFHLRPRDLISNINVIVLELKGSETTFMCEGADETATIVEFLNRWITFSQSIISTLT |
| 21 | Δ1-5_Y107A_C125S | STKKTQLQLEHLLLDLQMILNGINNYKNPKLTRMLTFKFYMPKKATELKHLQCLEEELKPLEEV<br>LNLAQSKNFHLRPRDLISNINVIVLELKGSETTFMCEAADETATIVEFLNRWITFSQSIISTLT |

TABLE A-continued variant IL-2 with reduced binding to interleukin-2 receptor subunit alpha (IL-2RA; CD25)

| PROTEIN NO: SEQ ID NO: | Features | Polypeptide Sequence |
|---|---|---|
| 22 | Δ1-5<br>Y45G_E61A_C125S | STKKTQLQLEHLLLDLQMILNGINNYKNPKLTRMLTFKFGMPKKATELKHLQCLEAELKPLEEV<br>LNLAQSKNFHLRPRDLISNINVIVLELKGSETTFMCEYADETATIVEFLNRWITFSQSIISTLT |
| 23 | Δ1-5_<br>Y45G_E62A_C125S | STKKTQLQLEHLLLDLQMILNGINNYKNPKLTRMLTFKFGMPKKATELKHLQCLEEALKPLEEV<br>LNLAQSKNFHLRPRDLISNINVIVLELKGSETTFMCEYADETATIVEFLNRWITFSQSIISTLT |
| 24 | Δ1-5_<br>R38G_Y45G_C125S | STKKTQLQLEHLLLDLQMILNGINNYKNPKLTGMLTFKFGMPKKATELKHLQCLEEELKPLEEV<br>LNLAQSKNFHLRPRDLISNINVIVLELKGSETTFMCEYADETATIVEFLNRWITFSQSIISTLT |
| 25 | Δ1-5_<br>R38G_E61A_C125S | STKKTQLQLEHLLLDLQMILNGINNYKNPKLTGMLTFKFYMPKKATELKHLQCLEAELKPLEEV<br>LNLAQSKNFHLRPRDLISNINVIVLELKGSETTFMCEYADETATIVEFLNRWITFSQSIISTLT |
| 26 | Δ1-5_<br>F42A_E61A_C125S | STKKTQLQLEHLLLDLQMILNGINNYKNPKLTRMLTAKFYMPKKATELKHLQCLEAELKPLEEV<br>LNLAQSKNFHLRPRDLISNINVIVLELKGSETTFMCEYADETATIVEFLNRWITFSQSIISTLT |
| 27 | Δ1-5_<br>F42A_Y45G_C125S | STKKTQLQLEHLLLDLQMILNGINNYKNPKLTRMLTAKFGMPKKATELKHLQCLEEELKPLEEV<br>LNLAQSKNFHLRPRDLISNINVIVLELKGSETTFMCEYADETATIVEFLNRWITFSQSIISTLT |
| 28 | Δ1-5_Y45G_<br>E61A_E62A_C125S | STKKTQLQLEHLLLDLQMILNGINNYKNPKLTRMLTFKFGMPKKATELKHLQCLEAALKPLEEV<br>LNLAQSKNFHLRPRDLISNINVIVLELKGSETTFMCEYADETATIVEFLNRWITFSQSIISTLT |
| 29 | Δ1-5_E61A_<br>E62A_C125S | STKKTQLQLEHLLLDLQMILNGINNYKNPKLTRMLTFKFYMPKKATELKHLQCLEAALKPLEEV<br>LNLAQSKNFHLRPRDLISNINVIVLELKGSETTFMCEYADETATIVEFLNRWITFSQSIISTLT |
| 30 | Δ1-5_R38G_<br>F42A_C125S | STKKTQLQLEHLLLDLQMILNGINNYKNPKLTGMLTAKFYMPKKATELKHLQCLEEELKPLEEV<br>LNLAQSKNFHLRPRDLISNINVIVLELKGSETTFMCEYADETATIVEFLNRWITFSQSIISTLT |
| 31 | Δ1-5_F42A_Y45A_<br>L72G_C125S | STKKTQLQLEHLLLDLQMILNGINNYKNPKLTRMLTAKFAMPKKATELKHLQCLEEELKPLEEV<br>LNGAQSKNFHLRPRDLISNINVIVLELKGSETTFMCEYADETATIVEFLNRWITFSQSIISTLT |
| 32 | Δ1-5_R38G_F42A_<br>Y45G_C125S | STKKTQLQLEHLLLDLQMILNGINNYKNPKLTGMLTAKFGMPKKATELKHLQCLEEELKPLEEV<br>LNLAQSKNFHLRPRDLISNINVIVLELKGSETTFMCEYADETATIVEFLNRWITFSQSIISTLT |
| 33 | Δ1-5_F42A_<br>E62A_C125S | STKKTQLQLEHLLLDLQMILNGINNYKNPKLTRMLTAKFYMPKKATELKHLQCLEEALKPLEEV<br>LNLAQSKNFHLRPRDLISNINVIVLELKGSETTFMCEYADETATIVEFLNRWITFSQSIISTLT |
| 34 | Δ1-5_F42A_Y45G_<br>E62A_C125S | STKKTQLQLEHLLLDLQMILNGINNYKNPKLTRMLTAKFGMPKKATELKHLQCLEEALKPLEEV<br>LNLAQSKNFHLRPRDLISNINVIVLELKGSETTFMCEYADETATIVEFLNRWITFSQSIISTLT |
| 35 | Δ1-5_F42A_Y45G_<br>E61A_C125S | STKKTQLQLEHLLLDLQMILNGINNYKNPKLTRMLTAKFGMPKKATELKHLQCLEAELKPLEEV<br>LNLAQSKNFHLRPRDLISNINVIVLELKGSETTFMCEYADETATIVEFLNRWITFSQSIISTLT |
| 36 | Δ1-5_R38G_Y45G_<br>E61A_C125S | STKKTQLQLEHLLLDLQMILNGINNYKNPKLTGMLTFKFGMPKKATELKHLQCLEAELKPLEEV<br>LNLAQSKNFHLRPRDLISNINVIVLELKGSETTFMCEYADETATIVEFLNRWITFSQSIISTLT |
| 37 | Δ1-5_R38G_F42A_<br>E61A_C125S | STKKTQLQLEHLLLDLQMILNGINNYKNPKLTGMLTAKFYMPKKATELKHLQCLEAELKPLEEV<br>LNLAQSKNFHLRPRDLISNINVIVLELKGSETTFMCEYADETATIVEFLNRWITFSQSIISTLT |
| 38 | Δ1-5_R38G_Y45G_<br>E62A_C125S | STKKTQLQLEHLLLDLQMILNGINNYKNPKLTGMLTFKFGMPKKATELKHLQCLEEALKPLEEV<br>LNLAQSKNFHLRPRDLISNINVIVLELKGSETTFMCEYADETATIVEFLNRWITFSQSIISTLT |
| 39 | Δ1-5_R38G_<br>E62A_C125S | STKKTQLQLEHLLLDLQMILNGINNYKNPKLTGMLTFKFYMPKKATELKHLQCLEEALKPLEEV<br>LNLAQSKNFHLRPRDLISNINVIVLELKGSETTFMCEYADETATIVEFLNRWITFSQSIISTLT |
| 40 | Δ1-5_R38G_F42A_<br>E62A_C125S | STKKTQLQLEHLLLDLQMILNGINNYKNPKLTGMLTAKFYMPKKATELKHLQCLEEALKPLEEV<br>LNLAQSKNFHLRPRDLISNINVIVLELKGSETTFMCEYADETATIVEFLNRWITFSQSIISTLT |
| 41 | Δ1-5_F42A_E61A_<br>E62A_C125S | STKKTQLQLEHLLLDLQMILNGINNYKNPKLTRMLTAKFYMPKKATELKHLQCLEAALKPLEEV<br>LNLAQSKNFHLRPRDLISNINVIVLELKGSETTFMCEYADETATIVEFLNRWITFSQSIISTLT |
| 42 | Δ1-5_R38G_E61A_<br>E62A_C125S | STKKTQLQLEHLLLDLQMILNGINNYKNPKLTGMLTFKFYMPKKATELKHLQCLEAALKPLEEV<br>LNLAQSKNFHLRPRDLISNINVIVLELKGSETTFMCEYADETATIVEFLNRWITFSQSIISTLT |
| 43 | Δ1-5_C125S | STKKTQLQLEHLLLDLQMILNGINNYKNPKLTRMLTFKFYMPKKATELKHLQCLEEELKPLEEV<br>LNLAQSKNFHLRPRDLISNINVIVLELKGSETTFMCEYADETATIVEFLNRWITFSQSIISTLT |
| 44 | T3A_C125S | APASSSTKKTQLQLEHLLLDLQMILNGINNYKNPKLTRMLTFKFYMPKKATELKHLQCLEEELK<br>PLEEVLNLAQSKNFHLRPRDLISNINVIVLELKGSETTFMCEYADETATIVEFLNRWITFSQSI<br>ISTLT |

Modifications may be made in the structure of the IL-2v, and IL-2v fusion polynucleotides and polypeptides, described herein and still obtain a functional molecule that encodes a variant or derivative polypeptide with desirable characteristics. When it is desired to alter the amino acid sequence of a polypeptide to create an equivalent, or even an improved, variant or portion of a polypeptide described herein, one skilled in the art will typically change one or more of the codons of the encoding DNA sequence.

For example, certain amino acids may be substituted for other amino acids in a protein structure without appreciable loss of its ability to bind other polypeptides (e.g., antigens) or cells. Since it is the binding capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated that various changes may be made in the polypeptide sequences of the disclosed antibodies and antigen-binding fragments thereof, or corresponding DNA sequences that encode said polypeptides without appreciable loss of their biological utility or activity.

In many instances, a polypeptide variant will contain one or more conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged.

As used herein, "identity" means the percentage of identical nucleotide or amino acid residues at corresponding positions in two or more sequences when the sequences are aligned to maximize sequence matching, i.e., taking into account gaps and insertions. Sequences are generally aligned for maximum correspondence over a designated region, e.g., a region at least 20, 25, 30, 35, 40, 45, 50, 55, 60, 65 or more amino acids or nucleotides in length, and can be up to the full length of the reference polypeptide or polynucleotide sequence. For sequence comparison, typically one sequence acts as a reference sequence, to which test sequences are compared. When using a sequence comparison algorithm, test and reference sequences are input into a computer program, subsequence coordinates are designated, if necessary, and sequence algorithm program parameters are designated. Otherwise, standard parameters can be used. The sequence comparison algorithm then calculates the percent sequence identity for the test sequence (s) relative to the reference sequence, based on the designated program parameters.

When comparing polynucleotide and polypeptide sequences, two sequences are said to be "identical" if the sequence of nucleotides or amino acids in the two sequences is the same when aligned for maximum correspondence, as described below. Comparisons between two sequences are typically performed by comparing the sequences over a comparison window to identify and compare local regions of sequence similarity. A "comparison window" as used herein, refers to a segment of at least 20 contiguous positions, usually 30 to 75 contiguous positions, 40 to 50 contiguous positions, or over the full length of a sequence, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, WI), using default parameters. This program embodies several alignment schemes described in the following references: Dayhoff, M. O. (1978) A model of evolutionary change in proteins—Matrices for detecting distant relationships. In Dayhoff, M. O. (ed.) Atlas of Protein Sequence and Structure, National Biomedical Research Foundation, Washington DC Vol. 5, Suppl. 3, pp. 345-358; Hein J. (1990) Unified Approach to Alignment and Phylogenes pp. 626-645 Methods in Enzymology vol. 183, Academic Press, Inc., San Diego, CA; Higgins, D. G. and Sharp, P. M. (1989) CABIOS 5: 151-153; Myers, E. W. and Muller W. (1988) CABIOS 4:11-17; Robinson, E. D. (1971) Comb. Theor 77: 105; Santou, N. Nes, M. (1987) Mol. Biol. Evol. 4:406-425; Sneath, P. H. A. and Sokal, R. R. (1973) Numerical Taxonomy—the Principles and Practice of Numerical Taxonomy, Freeman Press, San Francisco, CA; Wilbur, W. J. and Lipman, D. J. (1983) Proc. Natl. Acad., Sci. USA 80:726-730.

Alternatively, optimal alignment of sequences for comparison may be conducted by the local identity algorithm of Smith and Waterman (1981) Add. APL. Math 2:482, by the identity alignment algorithm of Needleman and Wunsch (1970) J. Mol. Biol. 48:443, by the search for similarity methods of Pearson and Lipman (1988) Proc. Natl. Acad. Sci. USA 85: 2444, by computerized implementations of these algorithms (GAP, BESTFIT, BLAST, FASTA, and TFASTA in the Wisconsin Genetics Software Package, Genetics Computer Group (GCG), 575 Science Dr., Madison, WI), or by inspection.

One example of algorithms that are suitable for determining percent sequence identity and sequence similarity are the BLAST and BLAST 2.0 algorithms, which are described in Altschul et al. (1977) Nucl. Acids Res. 25:3389-3402 and Altschul et al. (1990) J. Mol. Biol. 215:403-410, respectively. BLAST and BLAST 2.0 can be used, for example with the parameters described herein, to determine percent sequence identity for the polynucleotides and polypeptides described herein. Software for performing BLAST analyses is publicly available through the National Center for Biotechnology Information (blast.ncbi.nlm.nih.gov/Blast.cgi).

In one illustrative example, cumulative scores can be calculated using, for nucleotide sequences, the parameters M (reward score for a pair of matching residues; always >0) and N (penalty score for mismatching residues; always <0). Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLASTN program (for nucleotide sequences) uses as defaults a word length (W) of 11, and expectation (E) of 10, and the BLOSUM62 scoring matrix (see Henikoff and Henikoff (1989) Proc. Natl. Acad. Sci. USA 89: 10915) alignments, (B) of 50, expectation (E) of 10, M=5, N=-4 and a comparison of both strands.

For amino acid sequences, a scoring matrix can be used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment.

In one approach, the "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residues occur in both sequences to yield the number of matched positions, dividing the number of matched positions by the total number of positions in the reference sequence (i.e., the window size) and multiplying the results by 100 to yield the percentage of sequence identity.

In some embodiments, the IL-2v, serum half-life extended IL-2v, e.g., Fc-IL-2v fusion proteins, and homodimers and heterodimers thereof, do not comprise a signal peptide. In some embodiments, the IL-2v, serum half-life extended IL-2v, e.g., Fc-IL-2v fusion proteins, and homodimers and heterodimers thereof comprise an N-terminal signal peptide. The signal peptide can be an endogenous signal peptide (e.g., from a native or wild-type IL-2 protein), or from a heterologous polypeptide. In various embodiments, the signal peptide or leader sequence is from a source protein selected from a serum protein, an immunoglobulin, a cytokine, a chemokine, a chaperone protein, an invariant protein, and a protein that directs proteins to the lysosomal compartment. In various embodiments, the signal peptide or leader sequence is from a source protein selected from colony stimulating factor 2 (CSF2, GM-CSF), tissue type plasminogen activator (PLAT, t-PA), C-C motif chemokine ligand 7 (CCL7, MCP-3), C-X-C motif chemokine ligand 10 (CXCL10, IP-10), CD74 (p33; DHLAG; HLADG; immunoglobulin Kappa; Ia-GAMMA, invariant chain), serum albumin (ALB), SPARC (osteonectin), cwcv and kazal like domains proteoglycan 1 (SPOCK1); SPARC (osteonectin), cwcv and kazal like domains proteoglycan 2 (SPOCK2); polyubiquitin B/C (UBB/UBC), calreticulin (CALR) and vesicular stomatitis virus G protein (VSV-G). In various embodiments, the signal peptide or leader sequence is from a source protein selected from colony stimulating factor 2 (CSF2, GM-CSF), immunoglobulin Kappa; Ia-GAMMA, invariant chain), and serum albumin (ALB). In some embodiments, the signal peptide is from a serum albumin signal peptide (e.g., comprising the amino acid sequence KWVTFISLLFLFSSAYS (SEQ ID NO: 218). In various embodiments, the signal peptide or leader sequence is selected from an amino acid sequence of any one of SEQ ID NOs: 218-231, or a sequence that is at least 95%, 96%, 97%, 98%, or 99% identical to any one of SEQ ID NOs: 218-231. Illustrative signal sequences that can be used in the present IL-2v, serum half-life extended IL-2v, e.g., Fc-IL-2v fusion proteins, and homodimers and heterodimers thereof are provided in Table B.

TABLE B illustrative signal sequences

| SEQ ID NO: | source protein name | SEQUENCE |
|---|---|---|
| 218 | albumin | KWVTFISLLFLFSSAYS |
| 219 | IL-2 | MYRMQLLSCIALSLALVTNS |
| 220 | SPOCK1 | MPAIAVLAAAAAAWCFLQVES |

TABLE B-continued illustrative signal sequences

| SEQ ID NO: | source protein name | SEQUENCE |
|---|---|---|
| 221 | SPOCK2 | MRAPGCGRLVLPLLLLAAAALA |
| 222 | Ig Kappa | MDMRVPAQLLGLLLLWLSGARC |
| 223 | CSF2, GM-CSF | MWLQSLLLLGTVACSISV |
| 224 | PLAT, t-PA | MDAMKRGLCCVLLLCGAVFVSAR |
| 225 | CD74 | MHRRRSRSCREDQKPV |
| 226 | β-catenin | MRKAAVSHWQQQSYLDSGIHSGATTTAPSLS |
| 227 | CCL7, MCP-3 | MKASAALLCLLLTAAAFSPQGLA |
| 228 | ubiquitin | MQIFVKTLTGKTITLEVEPSDTIENVKAKI QDKEGIPPDQQRLIFAGKQLEDGRTLS DYNIQKESTLHLVLRLRGG |
| 229 | calreticulin | MLLSVPLLLGLLGLAVA |
| 230 | VSV-G | MKCLLYLAFLFIGVNC |
| 231 | CXCL10, IP-10 | MNQTAILICCLIFLTLSGIQG |

The signal peptide can be designed to be cleaved off, e.g., after secretion from the cell, to form a mature fusion protein. A modified human serum albumin signal peptide to secrete proteins in cells that can find use in expressing the present fusion proteins is described, e.g., in Attallah, et al., *Protein Expr Purif.* (2017) 132:27-33. Additional signal peptide sequences for use in expressing the herein described fusion proteins are described, e.g., in Kober, et al., *Biotechnol Bioeng.* (2013) 110(4):1164-73.

In certain embodiments, the IL-2v domain comprises or is derived from a mouse or murine IL-2 sequence. *Mus musculus* IL-2 is identified as NCBI Gene ID 16183. For fusion proteins based on mouse IL-2, the numbering of IL-2 positions is with reference to mature mouse IL-2, shown below:

(SEQ ID NO: 234)

APTSSSTSSSTAEAQQQQQQQQQQQQHLEQLLMDLQELLSRMENYRNL

KLPRMLTFKFYLPKQATELKDLQCLEDELGPLRHVLDLTQSKSFQLED

AENFISNIRVTVVKLKGSDNTFECQFDDESATVVDFLRRWIAFCQSII

STSPQ.

Illustrative IL-2v domains based on or derived from a wild-type mouse IL-2 having reduced binding to a mouse IL-2RA (a.k.a., il2ra, CD25; Il2r, Ly-43; NCBI Gene ID: 16184) are provided in Table D. Generally, the IL-2v domain of the herein described fusion proteins do not comprise the first 23 amino acid residues of the mature wild type mouse IL-2 sequence (e.g., do not comprise the amino acid sequence APTSSSTSSSTAEAQQQQQQQQQ (SEQ ID NO: 235)). In some embodiments, the mouse IL-2v comprises an alanine at position 140 (C140) and at least one, two, or at least three, substitutions at amino acid positions selected from the group consisting of R52, F56, Y59, E76, L86, wherein the position numbers are with respect to the sequence of mature mouse IL-2 represented by SEQ ID NO:

234. In some embodiments, the mouse IL-2v comprises an alanine at position 140 (C140) and at least one, two, or at least three, substitutions to alanine or glycine at amino acid positions selected from the group consisting of R52, F56, Y59, E76, L86, wherein the position numbers are with respect to the sequence of mature mouse IL-2 represented by SEQ ID NO: 234. In some embodiments, the mouse IL-2v comprises an amino acid sequence corresponding to residues 250-375 of an amino acid sequence selected from the group consisting of SEQ ID NOs: 166-171, or comprising an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence corresponding to residues 250-375 of an amino acid sequence selected from the group consisting of SEQ ID NOs: 166-171.

As appropriate or desired, the IL-2v polypeptides described herein can be PEGylated or not PEGylated.

b. Serum Half-Life Extending Polypeptide

The herein described fusion proteins comprise a variant IL-2 that binds to IL-2RA with reduced binding affinity, and a serum half-life extending polypeptide. In some embodiments, the fusion protein comprises in sequential order from N-terminus to C-terminus, the serum half-life extending polypeptide (e.g., the Fc region) and the IL-2v. In some embodiments, the fusion protein comprises in sequential order from N-terminus to C-terminus, the IL-2v and the serum half-life extending polypeptide (e.g., the Fc region). Polypeptides that can used to extend the serum half-life of another polypeptide, e.g., via linking or fusion, are known in the art and can be used in the present fusion proteins. Illustrative serum half-life extending polypeptides that can be linked or fused with the herein described IL-2v include without limitation an immunoglobulin fragment crystallizable region (Fc region), one or more serum albumin moieties, an albumin binding protein or peptide, an IgG, an XTEN polypeptide, a proline/alanine/serine-rich (PAS) polypeptide, an elastin-like polypeptide. IL-2v linked or fused to one or more serum albumin moieties, an albumin binding protein or peptide, an IgG, an XTEN polypeptide, a proline/alanine/serine-rich (PAS) polypeptide, an elastin-like polypeptide need not dimerize (e.g., need not form homodimers or heterodimers). The one or more serum albumin moieties, an albumin binding protein or peptide, an IgG, an XTEN polypeptide, a proline/alanine/serine-rich (PAS) polypeptide, an elastin-like polypeptide can be linked or fused to either or both of the N-terminus or the C-terminus of the IL-2v. Illustrative XTEN protein polymers that can be used in the present IL-2v fusion proteins are described, e.g., in Schellenberger, et al., *Nat Biotechnol.* 2009 December; 27(12):1186-90; Podust, et al., *Journal of Controlled Release* 240 (2016) 52-66; WO2010091122, WO2011123813, WO2013130683, WO2016077505 and WO2017197048. Illustrative proline/alanine/serine-rich (PAS) polypeptides that can be used in the present IL-2v fusion proteins are described, e.g., in Schlapschy, et al., *Protein Eng Des Sel.* (2013) 26(8):489-501 and Breibeck, et al., *Biopolymers.* (2018) January; 109(1). doi: 10.1002/bip.23069, WO2016122806 and WO2016130451. The foregoing references are which are hereby incorporated herein by reference in their entirety for all purposes.

In some embodiments, the serum half-life extending polypeptide is an immunoglobulin fragment crystallizable region (Fc region). Generally, the Fc domain is comprised of or derived from the same species as the IL-2v domain (e.g., human, dog, cat, mouse or monkey). In some embodiments, the Fc region is from a human IgG1, IgG2, IgG3 or IgG4. In some embodiments, the Fc region is from a human IgG1 or IgG4.

In some embodiments, the Fc modifications can promote one or more of increased serum half-life or decreased antibody effector function of the molecule. In other embodiments, certain of these modifications, decrease antibody effector function and increase half-life of the antibody. In some embodiments, the Fc-IL-2v fusion proteins described herein comprise two or more, three or more, four or more, five or more, six or more, six or fewer, five or fewer, four or fewer, three or fewer, two or fewer, or one modified Fc amino acid residue(s). Exemplary amino acid substitutions are described below.

In some embodiments, the Fc domain of the fusion protein does not comprise a hinge region; it is truncated or deleted, in whole or in part. The structural hinge region of human IgG1, IgG2 and IgG4 antibodies is a peptide linker of 19 to 23 amino acids containing two to four cysteine residues, is genetically encoded on the hinge exon together with the 5'-end of the CH2 exon, and allows for disulfide bridges between first and second Fc domains (Roux, et al., *J. Immunol.* (1998) 161:4083). The structural hinge region is comprised of amino acid residue positions 216-238 (EU numbering) or 226-251 (Kabat numbering) (identified on imgt.org). In some embodiments, the Fc region comprises or is derived from a human IgG4 isotype and does not comprise the amino acid sequence ESKYGPPCPPCP (SEQ ID NO: 236). In some embodiments, the Fc region comprises or is derived from a human IgG1 isotype and does not comprise the amino acid sequence EPKSCDKTHTCPPCP (SEQ ID NO: 237) or EPKSCDKTHTCPPCPAPELL (SEQ ID NO: 238).

Fc Mutations that Increase Serum Half-Life

In some embodiments, the Fc region comprises amino acid modifications that promote an increased serum half-life of the fusion protein. Mutations that increase the half-life of an antibody have been described. In one embodiment, the constant region of a Fc-IL-2v fusion proteins described herein comprise a methionine to tyrosine substitution at position 252 (EU numbering), a serine to threonine substitution at position 254 (EU numbering), and a threonine to glutamic acid substitution at position 256 (EU numbering). See, e.g., U.S. Pat. No. 7,658,921. This type of mutant, designated as a "YTE mutant" exhibits a four-fold increased half-life relative to wild-type versions of the same antibody (Dall'Acqua, et al., J Biol Chem, 281: 23514-24 (2006); Robbie, et al., Antimicrob Agents Chemotherap., 57(12): 6147-6153 (2013)). In certain embodiments, the Fc-IL-2v fusion proteins described herein comprise an IgG constant domain comprising one, two, three or more amino acid substitutions of amino acid residues at positions 251-257, 285-290, 308-314, 385-389, and 428-436 (EU numbering). Alternatively, M428L and N434S ("LS") substitutions can increase the pharmacokinetic half-life of the fusion protein. In other embodiments, the Fc-IL-2v fusion proteins described herein comprise a M428L and N434S substitution (EU numbering). In other embodiments, the Fc-IL-2v fusion proteins described herein comprise T250Q and M428L (EU numbering) mutations. In other embodiments, the Fc-IL-2v fusion proteins described herein comprise H433K and N434F (EU numbering) mutations.

Fc Mutations that Reduce or Eliminate Effector Activity

In some embodiments, the Fc-IL-2v fusion proteins described herein can have an Fc domain with amino acid substitutions that reduce or eliminate Fc effector function (including, e.g., antibody-dependent cellular cytotoxicity (ADCC), antibody-dependent cellular phagocytosis (ADCP), and complement-dependent cytotoxicity (CDC)).

In some embodiments, the Fc region is altered by replacing at least one amino acid residue with a different amino acid residue to reduce or eliminate effector function(s) of the antibody. For example, one or more amino acids selected from amino acid residues 234, 235, 236, 237, 297, 318, 320 and 322 (EU numbering) can be replaced with a different amino acid residue such that the fusion protein has decreased affinity for an effector ligand. The effector ligand to which affinity is altered can be, for example, an Fc receptor (e.g., at residue positions 234, 235, 236, 237, 297 (EU numbering)) or the C1 component of complement (e.g., at residue positions 297, 318, 320, 322 (EU numbering)). U.S. Pat. Nos. 5,624,821 and 5,648,260, both by Winter et al.

Fc modifications reducing or eliminating effector function include substitutions, insertions, and deletions, e.g., at one or more positions including 234, 235, 236, 237, 267, 269, 325, and 328, e.g., 234G, 235G, 236R, 237K, 267R, 269R, 325L, and 328R (EU numbering). Further, an Fc variant may comprise 236R/328R. Other modifications for reducing FcγR and complement interactions include substitutions at positions 297A, 234A, 235A, 318A, 228P, 236E, 268Q, 309L, 329G, 330S, 331S, 220S, 226S, 229S, 238S, 233P, and 234V (EU numbering). These and other modifications are reviewed in Strohl (2009) *Current Opinion in Biotechnology* 20:685-691; see also, Schlothauer, et al., *Protein Eng Des Sel.* (2016) 29(10):457-466. Effector functions (both ADCC and complement activation) can be reduced, while maintaining neonatal FcR binding (maintaining half-life), by mutating IgG residues at one or more of positions 233-236 and 327-331, such as E233P, L234V, L235A, optionally G236A, A327G, A330S and P331S in IgG1; E233P, F234V, L235A, optionally G236A, in IgG4; and A330S and P331S in IgG2 (EU numbering). See Armour et al. (1999) Eur. J. Immunol. 29:2613; WO 99/58572. Other mutations that reduce effector function include L234A and L235A in IgG1 (Alegre et al. (1994) Transplantation 57:1537); V234A and G237A in IgG2 (Cole et al. (1997) J. Immunol. 159:3613; see also U.S. Pat. No. 5,834,597); and S228P and L235E for IgG4 (Reddy et al. (2000) J. Immunol. 164:1925). Another combination of mutations for reducing effector function in a human IgG1 include L234F, L235E and P331S. Oganesyan et al. (2008) Acta Crystallogr. D. Biol. Crystallogr. 64:700. See generally Labrijn et gal. (2008) Curr. Op. Immunol. 20:479. Additional mutations found to decrease effector function in the context of an Fc (IgG1) fusion protein (abatacept) include C226S, C229S and P238S (EU numbering). Davis et al. (2007) J. Immunol. 34:2204.

ADCC activity may be reduced by modifying the Fc region. In certain embodiments, sites that affect binding to Fc receptors may be removed, e.g., sites other than salvage receptor binding sites. In other embodiments, an Fc region may be modified to remove an ADCC site. Exemplary ADCC sites have been described with respect to ADCC sites in IgG1 (Sarmay, et al, (1992) Molec. Immunol. 29 (5): 633-9). In one embodiment, the G236R and L328R variant of human IgG1 effectively eliminates FcγR binding (Horton, et al. (2011) J. Immunol. 186:4223 and Chu, et al. (2008) Mol. Immunol. 45:3926). In other embodiments, the Fc having reduced binding to FcγRs comprises the amino acid substitutions L234A, L235E and G237A. Gross, et al. (2001) Immunity 15:289. Modifications in the IgG Fc region to decrease binding to FcγRI to decrease ADCC (e.g., 234A; 235E; 236A; G237A) identified in WO 88/007089 can be used in the present fusion proteins. See also Duncan & Winter (1988) Nature 332:563; Chappel et al. (1991) Proc. Nat'l Acad. Sci. (USA) 88:9036; and Sondermann et al. (2000) Nature 406:267 (discussing the effects of these mutations on FcγRIII binding).

CDC activity may also be reduced by modifying the Fc region. Mutations at IgG1 positions D270, K322, P329 and P331, specifically alanine mutations D270A, K322A, P329A and P331A, significantly reduce the ability of the corresponding antibody to bind C1q and activate complement (Idusogie et al. (2000) J. Immunol. 164:4178; WO 99/51642. Modification of position 331 of IgG1 (e.g. P331S) has been shown to reduce complement binding (Tao et al. (1993) J. Exp. Med. 178:661; Xu Y, et al. J Biol Chem. 1994. 269:3469-74; and Canfield & Morrison (1991) J. Exp. Med. 173:1483). In another example, one or more amino acid residues within amino acid positions 231 to 239 are altered to thereby reduce the ability of the antibody to fix complement (WO 94/29351). Modifications in the IgG Fc region identified in WO 88/007089 that reduce or eliminate binding to complement component C1q, and therefore reduce or eliminate CDC (e.g., E318A or V/K320A and K322A/Q) can be used in the present fusion proteins.

In some embodiments, the Fc with reduced complement fixation has the amino acid substitutions A330S and P331S. Gross et al. (2001) Immunity 15:289.

Other Fc variants having reduced ADCC and/or CDC are disclosed at Glaesner et al. (2010) Diabetes Metab. Res. Rev. 26:287 (F234A and L235A to decrease ADCC and ADCP in an IgG4); Hutchins et al. (1995) Proc. Nat'l Acad. Sci. (USA) 92:11980 (F234A, G237A and E318A in an IgG4); An et al. (2009) MAbs 1:572 and U.S. Pat. App. Pub. 2007/0148167 (H268Q, V309L, A330S and P331S in an IgG2); McEarchern et al. (2007) Blood 109:1185 (C226S, C229S, E233P, L234V, L235A in an IgG1); Vafa et al. (2014) Methods 65:114 (V234A, G237A, P238S, H268A, V309L, A330S, P331S in an IgG2) (EU numbering).

In certain embodiments, the fusion protein has an Fc having essentially no effector function, e.g., the Fc has reduced or eliminated binding to FcγRs and reduced or eliminated complement fixation, e.g., is effectorless. An exemplary IgG1 Fc that is effectorless comprises the following five mutations: L234A, L235E, G237A, A330S and P331S (EU numbering) (Gross et al. (2001) Immunity 15:289). These five substitutions may be combined with N297A to eliminate glycosylation as well.

Mutations that Facilitate Heterodimerization

In some embodiments, first and second Fc domains have mutations to facilitate heterodimerization. Mutations in Fc domain pairs that facilitate or promote heterodimerization are reviewed in Ha, et al., Front. Immunol. (2016) 7:394. In some embodiments, the first Fc domain and the second Fc domain comprise the following amino acid substitutions (EU numbering), respectively (or vice versa): T366W and T366S/L368A/Y407V; T366W/S354C and T366S/L368A/Y407V/Y349C; S364H/F405A and Y349T/T394F; T350V/L351Y/F405A/Y407V and T350V/T366L/K392L/T394W; K360D/D399M/Y407A and E345R/Q347R/T366V/K409V; K409D/K392D and D399K/E356K; K360E/K409W and Q347R/D399V/F405T; K360E/K409W/Y349C and Q347R/D399V/F405T/S354C; F405L and K409R; or K370E/K409W and E357N/D399V/F405T.

In some embodiments, Fc region heterodimerization of the two different heavy chain-containing species can be facilitated by so-called 'knobs-into-holes' mutations (Atwell et al. 1997. JMB 270:26-35). The 'hole' mutations (T366S, L368A and Y407V) are incorporated into one Fc-containing chain, the T366W 'knob' mutation is incorporated into the other chain. In addition, a C220S mutation can be incorporated into an IgG1 hinge region of a scFv-containing arm to eliminate a free cysteine that otherwise forms a disulfide bond with a corresponding cysteine in the light chain in a wild-type IgG1. Co-transfection of such constructs leads to preferential formation of a heterodimeric Fc, with low levels of homodimer contaminants. Additionally, incorporating a S354C mutation can be incorporated into the Fc containing the 'knob' mutations and a Y349C mutation into the Fc containing the 'hole' mutations can optionally be used to generate a covalent bond between the two halves of the heterodimeric Fc if additional thermodynamic stability is desired (Merchant et al. 1998. Nat. Biotechnol. 16: 677-81).

To facilitate purification of the heterodimeric molecule away from contaminating homodimeric products, the H435R or H435R+Y436F mutations to reduce or eliminate protein A binding can be introduced into one but not both of the Fc-containing chains (Jendeberg, L. et al. 1997 J. Immunol. Methods 201:25-34). This reduces or eliminates protein A binding of the homodimer contaminant containing these mutations, and greatly simplifies purification of the desired heterodimer away from remaining homodimer contaminant via additional chromatography steps (e.g. ion exchange, e.g., anion exchange). In embodiments incorporating H435R (or H435R+Y436F) mutations in the first or second Fc region of a heavy chain, if the VH region in the same heavy chain is from a VH3 family variable region, this VH region can also include amino acid substitutions, as described herein, to reduce or eliminate Protein A binding of the entire heavy chain.

IgG1 Isotype Fc

In one embodiment, the Fc region comprises or is derived from a human IgG1. In some embodiments, the antibody has a chimeric heavy chain constant region (e.g., having the CH1, hinge, CH2 regions of IgG4 and CH3 region of IgG1).

IgG1 antibodies exist in various allotypes and isoallotypes. In particular embodiments, the Fc-IL-2v fusion proteins described herein include an IgG1 heavy chain having an allotype of G1m1; nG1m2; G1m3; G1m17,1; G1m17,1,2; G1m3,1; or G1m17. Each of these allotypes or isoallotypes is characterized by the following amino acid residues at the indicated positions within the IgG1 heavy chain constant region (Fc) (EU numbering):

G1m1: D356, L358;
nG1m1: E356, M358;
G1m3: R214, E356, M358, A431;
G1m17,1: K214, D356, L358, A431;
G1m17,1,2: K214, D356, L358, G431;
G1m3,1: R214, D356, L358, A431; and
G1m17: K214, E356, M358, A431.

In a specific embodiment, the IL-2v domain, or truncated fragment thereof, is directly linked to, or linked via an intervening amino acid sequence (e.g., a G-S linker), to a wild type IgG1m3 sequence, or fragment thereof, provided below.

(SEQ ID NO: 74)
```
EPKSCDKTHTCPPCPAPELLGGPSVFLFPPKPKDTLMISRTPEVTCVV

VDVSHEDPEVKFNWYVDGVEVHNAKTKPREEQYNSTYRVVSVLTVLHQ

DWLNGKEYKCKVSNKALPAPIEKTISKAKGQPREPQVYTLPPSREEMT

KNQVSLTCLVKGFYPSDIAVEWESNGQPENNYKTTPPVLDSDGSFFLY

SKLTVDKSRWQQGNVFSCSVMHEALHNHYTQKSLSLSPGK.
```

For example, in various embodiments, the IgG1m3 fragment has the first five residues (EPKSC; SEQ ID NO: 232) removed, having the following sequence:

(SEQ ID NO: 233)
```
DKTHTCPPCPAPELLGGPSVFLFPPKPKDTLMISRTPEVTCVVVDVSH

EDPEVKFNWYVDGVEVHNAKTKPREEQYNSTYRVVSVLTVLHQDWLNG

KEYKCKVSNKALPAPIEKTISKAKGQPREPQVYTLPPSREEMTKNQVS

LTCLVKGFYPSDIAVEWESNGQPENNYKTTPPVLDSDGSFFLYSKLTV

DKSRWQQGNVFSCSVMHEALHNHYTQKSLSLSPGK.
```

In certain embodiments, the Fc-IL-2v fusion protein has an IgG1 isotype. In some embodiments, the Fc-IL-2v fusion protein contains a human IgG1 constant region. In some embodiments, the human IgG1 Fc region contains one or more modifications. For example, in some embodiments, the Fc region contains one or more amino acid substitutions (e.g., relative to a wild-type Fc region of the same isotype). In some embodiments, the one or more amino acid substitutions are selected from N297A, N297Q (Bolt S et al. (1993) Eur J Immunol 23:403-411), D265A, L234A, L235A (McEarchem et al., (2007) Blood, 109:1185-1192), C226S, C229S (McEarchem et al., (2007) Blood. 109:1185-1192), P238S (Davis et al., (2007) J Rheumatol, 34:2204-2210), E233P, L234V (McEarchern et al., (2007) Blood, 109:1185-1192), P238A, A327Q, A327G, P329A (Shields R L. et al., (2001) J Biol Chem. 276(9):6591-604), P329G (Schlothauer, et al., *Protein Eng Des Sel*. (2016) 29(10):457-466); K322A, L234F, L235E (Hezareh, et al., (2001) J Virol 75, 12161-12168; Oganesyan et al., (2008). Acta Crystallographica 64, 700-704), P331S (Oganesyan et al., (2008) Acta Crystallographica 64, 700-704), T394D (Wilkinson et al. (2013) MAbs 5(3): 406-417), A330L, M252Y, S254T, and/or T256E, where the amino acid position is according to the EU numbering convention. In certain embodiments, the Fc region further includes an amino acid deletion at a position corresponding to glycine 236 according to the EU numbering convention.

In some embodiments, the Fc-IL-2v fusion protein has an IgG1 isotype with a heavy chain constant region that contains a C220S amino acid substitution according to the EU numbering convention.

In some embodiments, the Fc region comprises a human IgG1 isotype and comprises one or more amino acid substitutions in the Fc region at a residue position selected from the group consisting of: N297A, N297G, N297Q, N297G, D265A, L234A, L235A, C226S, C229S, P238S, E233P, L234V, P238A, A327Q, A327G, P329A, P329G, K322A, L234F, L235E, P331S, T394D, A330L, M252Y, S254T, T256E, M428L, N434S, T366W, T366S, L368A, Y407V, H435R, Y436F, and any combination thereof, wherein the numbering of the residues is according to EU numbering. In some embodiments, the Fc region comprises a human IgG1 isotype and comprises one or more amino acid substitutions in the Fc region at a residue position selected from the group consisting of: L234A, L234V, L234F, L235A, L235E, P329G, A330L, P331S, and any combination thereof, wherein the numbering of the residues is according to EU numbering.

IgG4 Isotype Fc

For uses where effector function is to be avoided altogether, e.g. when antigen binding alone is sufficient to generate the desired therapeutic benefit, and effector function only leads to (or increases the risk of) undesired side effects, IgG4 antibodies may be used, or antibodies or fragments lacking the Fc region or a substantial portion thereof can be devised, or the Fc may be mutated to eliminate glycosylation altogether (e.g. N297A). Alternatively, a hybrid construct of human IgG2 (CH1 domain and hinge region) and human IgG4 (CH2 and CH3 domains) has been generated that is devoid of effector function, lacking the ability to bind the FcγRs (like IgG2) and unable to activate complement (like IgG4). (see, Rother et al. (2007) Nat. Biotechnol. 25:1256; Mueller et al. (1997) Mol. Immunol. 34:441; and Labrijn et al. (2008) Curr. Op. Immunol. 20:479, discussing Fc modifications to reduce effector function generally).

In certain embodiments, the Fc-IL-2v fusion protein has an IgG4 isotype. In some embodiments, the Fc-IL-2v fusion protein contains a human IgG4 constant region. In some embodiments, the human IgG4 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from E233P, F234V, F234A, L235A, G237A, E318A, S228P, L235E, T394D, M252Y, S254T, T256E, N297A, N297G, N297Q, T366W, T366S, L368A, Y407V, M428L, N434S, H435R, Y436F, and any combination thereof, where the amino acid position is according to the EU numbering convention. See, e.g., Hutchins et al. (1995) *Proc Natl Acad Sci USA,* 92:11980-11984; Reddy et al., (2000) *J Immunol,* 164:1925-1933; Angal et al., (1993) *Mol Immunol.* 30(1):105-8; U.S. Pat. No. 8,614,299 B2; Vafa O. et al., (2014) *Methods* 65:114-126; and Jacobsen et. al., *J. Biol. Chem.* (2017) 292(5):1865-1875. In some embodiments, the Fc region comprises a human IgG4 isotype and comprises one or more amino acid substitutions in the Fc region at a residue position selected from the group consisting of: F234V, F234A, L235A, L235E, S228P, and any combination thereof, wherein the numbering of the residues is according to EU numbering.

In some embodiments, an IgG4 variant of the present disclosure may be combined with an S228P mutation according to the EU numbering convention (Angal et al., (1993) Mol Immunol, 30:105-108) and/or with one or more mutations described in Peters et al., (2012) J Biol Chem. 13; 287(29):24525-33) to enhance antibody stabilization.

IgG2 Isotype Fc

In certain embodiments, the Fc-IL-2v fusion protein has an IgG2 isotype. In some embodiments, the Fc-IL-2v fusion protein contains a human IgG2 constant region. In some embodiments, the human IgG2 constant region includes an Fc region. In some embodiments, the Fc region contains one or more modifications. For example, in some embodiments, the Fc region contains one or more amino acid substitutions (e.g., relative to a wild-type Fc region of the same isotype). In some embodiments, the one or more amino acid substitutions are selected from P238S, V234A, G237A, H268A, H268Q, H268E, V309L, N297A, N297G, N297Q, V309L, A330S, P331 S, C232S, C233S, M252Y, S254T, and/or T256E, where the amino acid position is according to the EU numbering convention (Vafa, et al., (2014) Methods 65:114-126).

In certain embodiments, the Fc-IL-2v fusion proteins described herein comprise the L234F, L235E, D265A mutations, which are collectively referred to as "FEA." The FEA mutations decrease or abrogate effector function. In certain embodiments, the Fc-IL-2v fusion proteins described herein comprise the L234F, L235E, D265A, and F405L mutations, which are collectively referred to as "FEAL." In certain embodiments, the Fc-IL-2v fusion proteins described herein comprise the L234F, L235E, D265A, and a mutation selected from the group consisting of F405L, F405A, F405D, F405E, F405H, F405I, F405K, F405M, F405N, F405Q, F405S, F405T, F405V, F405W, and F405Y. In certain embodiments, the Fc-IL-2v fusion proteins described herein comprise the L234F, L235E, D265A, and K409R mutations, which are collectively referred to as "FEAR." In certain embodiments, FEAL and FEAR are comprised in a fusion protein described herein. In certain embodiments, the Fc-IL-2v fusion proteins described herein additionally comprise the M428L and N434S mutations, which are collectively referred to as LS. In certain embodiments, the Fc-IL-2v fusion proteins described herein comprise the L234F, L235E, D265A, F405L, M428L, and N434S mutations, which are collectively referred to as "FEALLS." In certain embodiments, the Fc-IL-2v fusion proteins described herein comprise the L234F, L235E, D265A, M428L, and N434S mutations along with one further mutation selected from the group consisting of F405L, F405A, F405D, F405E, F405H, F405I, F405K, F405M, F405N, F405Q, F405S, F405T, F405V, F405W, and F405Y. In certain embodiments, the Fc-IL-2v fusion proteins described herein comprise the L234F, L235E, D265A, K409R, M428L, and N434S mutations which are collectively referred to as "FEARLS." In certain embodiments, FEALLS and FEARLS are comprised in a fusion protein described herein. By reducing or abrogating effector function on the Fc domains of the Fc-IL-2v fusion protein, cells bound by the molecule are not killed by innate effector cells e.g., NK cells, macrophages.

In certain embodiments, the one or more modifications are selected from the following Fc amino acid substitutions (EU numbering) or combinations thereof: L234F; L235E; G236A; S239D; F243L; D265E; D265A; S267E; H268F; R292P; N297Q; N297G, N297A; S298A; S324T; I332E; S239D; A330L; L234F; L235E; P331S; F243L; Y300L; V305I; P396L; S298A; E333A; K334A; E345R; L235V; F243L; R292P; Y300L; P396L; M428L; E430G; N434S; G236A, S267E, H268F, S324T, and I332E; G236A, S239D, and I332E; S239D, A330L, I332E; L234F, L235E, and P331S; F243L, R292P, Y300L, V305I, and P396L; G236A, H268F, S324T, and I332E; S239D, H268F, S324T, and I332E; S298A, E333A, and K334A; L235V, F243L, R292P, Y300L, and P396L; S239D, I332E; S239D, S298A, and I332E; G236A, S239D, I332E, M428L, and N434S; G236A, S239D, A330L, I332E, M428L, and N434S; S239D, I332E, G236A and A330L; M428L and N4343S; M428L, N434S; G236A, S239D, A330L, and I332E; and G236A and I332E. In certain embodiments, the one or more modifications is selected from the group consisting of: D265A, L234F, L235E, N297A, N297G, N297Q, and P331S. In certain embodiments, the one or more modifications are selected from N297A and D265A. In certain embodiments, the one or more modifications are selected from L234F and L235E. In certain embodiments, the one or more modifications are selected from L234F, L234E, and D265A. In certain embodiments, the one or more modifications are selected from L234F, L234E, and N297Q. In certain embodiments, the one or more modifications are selected from L234F, L235E, and P331S. In certain embodiments, the one or more modifications are selected from D265A and N297Q. In certain embodiments, the one or more modifications are selected from L234F, L235E, D265A, N297A, N297G, N297Q, and P331S.

Mutations that reduce Fc-receptor binding and find use in the herein described fusion proteins include, for example, N297A; N297G; N297Q; D265A; L234F/L235E; L234F/L235E/N297Q; L234F/L235E/P331S; D265A/N297Q; and L234F/L235E/D265A/N297Q/P331S (all EU numbering). In certain embodiments the Fc-IL-2v fusion proteins described herein described herein comprise L234F and L235E mutations. In certain embodiments the Fc-IL-2v fusion proteins described herein described herein comprise L234F, L235E, and D265A mutations. In certain embodiments the Fc-IL-2v fusion proteins described herein described herein comprise L234F, L235E, and N297Q mutations. In certain embodiments the Fc-IL-2v fusion proteins described herein described herein comprise an N297A or N297Q mutation. In certain embodiments the Fc-IL-2v fusion proteins described herein described herein comprise an N297A, N297G or N297Q mutation as well as L234F, L235E, and D265A mutations. In certain embodiments, one, two, three, four, or more amino acid substitutions are introduced into a Fc region to alter the effector function of the antigen binding molecule. For example, these substitutions are located at positions selected from the group consisting of amino acid residues 234, 235, 236, 237, 265, 297, 318, 320, and 322, (according to EU numbering). These positions can be replaced with a different amino acid residue such that the antigen binding molecule has an altered (e.g., reduced) affinity for an effector ligand (e.g., an Fc receptor or the C1 component of complement), but retains the antigen binding ability of the parent antibody. In certain embodiments, the Fc-IL-2v fusion proteins described herein described herein comprise E233P, L234V, L235A, and/or G236A mutations (EU numbering). In some embodiments, the Fc-IL-2v fusion proteins described herein comprise A327G, A330S, and/or P331S mutations (EU numbering). In some embodiments, the Fc-IL-2v fusion proteins described herein comprise K322A mutations (EU numbering). In some embodiments the Fc-IL-2v fusion proteins described herein comprise E318A, K320A, and K322A (EU numbering) mutations. In certain embodiments, the Fc-IL-2v fusion proteins described herein comprise a L235E (EU numbering) mutation.

In some embodiments, the Fc portion of the fusion protein comprises an amino acid sequence having at least 80%, at least 85%, at least 90%, at least 91%, at least 92%, at least 93%, at least 94%, at least 95%, at least 96%, at least 97%, at least 98%, at least 99%, or 100%, identical to an amino acid sequence of (SEQ ID NO: 239)
GGPSVFLFPPKPKDTLMISRTPEVTCVVVDVSHEDPEVKFNWYVDGVE
VHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSV
MHEALHNHYTQKSLSLSPGK;

(SEQ ID NO: 240)
GGPSVFLFPPKPKDTLYITREPEVTCVVVDVSHEDPEVKFNWYVDGVE
VHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAV
EWESNGQPENNYKTTPPVLDSDGSFFLYSKLTVDKSRWQQGNVFSCSV
MHEALHNHYTQKSLSLSPGK;

(SEQ ID NO: 241)
ESKYGPPCPPCPAPEFEGGPSVFLFPPKPKDTLMISRTPEVTCVVVDV

-continued

SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRL
TVDKSRWQEGNVFSCSVMHEALHNHYTQKSLSLSLGK;

(SEQ ID NO: 46)
ESKYGPPCPPCPAPEAAGGPSVFLFPPKPKDTLMISRTPEVTCVVVDV
SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLSCAVKGFYPSDIAVEWESNGQPENNYKTTPPVLDSDGSFFLVSRL
TVDKSRWQEGNVFSCSVMHEALHNRFTQKSLSLSLGK;

(SEQ ID NO: 242)
ESKYGPPCPPCPAPEAAGGPSVFLFPPKPKDTLMISRTPEVTCVVVDV
SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRL
TVDKSRWQEGNVFSCSVMHEALHNHYTQKSLSLSLGK; or (SEQ ID NO: 243)
ESKYGPPCPPCPAPEFEGGPSVFLFPPKPKDTLYITREPEVTCVVVDV
SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLTCLVKGFYPSDIAVEWESNGQPENNYKTTPPVLDSDGSFFLYSRL
TVDKSRWQEGNVFSCSVMHEALHNHYTQKSLSLSLGK.

In some embodiments, the terminal Fc amino acid residue (e.g., K447) is removed or eliminated. In some embodiments, the Fc region comprises an amino acid sequence selected from the group consisting of SEQ ID NOs: 45-72, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 45-72. In some embodiments, the Fc region comprises an amino acid sequence selected from the group consisting of SEQ ID NOs: 45, 47, 49, 52, 54, 56, 57, 59, 61, 63, 65, 67, 69 and 71, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 45, 47, 49, 52, 54, 56, 57, 59, 61, 63, 65, 67, 69 and 71. In some embodiments, the Fc region comprises an amino acid sequence selected from the group consisting of SEQ ID NOs: 46, 48, 50, 51, 53, 55, 58, 60 and 62, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 46, 48, 50, 51, 53, 55, 58, 60 and 62.

c. Linker

In various embodiments, the IL-2v domain, or truncated fragment thereof, is directly linked or contiguously linked or abutted to the serum half-life extending polypeptide (e.g., Fc domain). In some embodiments, the IL-2v domain, or truncated fragment thereof, is operably linked to the serum half-life extending polypeptide (e.g., Fc domain) via a linker. e.g., the linker is positioned between the serum half-life extending polypeptide (e.g., Fc domain) and the IL-2v. As appropriate, the linker can be a flexible linker. For example, the linker can be an amino acid sequence comprising 1 to 10 repeats or units, e.g., 1 to 5 repeats or units, e.g., 3 to 5 repeats or units, e.g., 3 or 4 or 5 repeats of a GGGS motif (SEQ ID NO: 265), e.g., 3 or 4 or 5 repeats of a GGGGS motif (SEQ ID NO: 264), or mixtures thereof ("G-S linker") (Desplancq et al. 1994, *Protein Engineering* 7:1027-1033). In some embodiments, the linker has a length of from 4 to 50 amino acids, e.g., from 5 amino acids to 25 amino acids, e.g., from 12 amino acids to 15, 16, 20 or 25 amino acids. In some embodiments, the linker comprises 4 repeats of a GGGGS motif (SEQ ID NO: 246).

In certain embodiments the IL-2v domain, or truncated fragment thereof, is directly linked to, or linked via an intervening amino acid sequence (e.g., a G-S linker), to a human IgG1 (e.g., mutant IgG1m3 sequence), IgG2, IgG3 or IgG4 with 1 to 10 (e.g., 1, 2, 3, 4, 5, 6, 7, 8, 9, 10) amino acid substitutions.

d. Illustrative Fc-IL-2v Fusion Proteins

Further provided are Fc-IL-2v fusion proteins, comprising an IL-2v domain, as described above and herein, and an Fc domain, as described above and herein.

Functionally, in various embodiments, the Fc-IL-2v fusion protein binds to IL-2RA with an equilibrium dissociation constant ($K_D$) of at least 60 μM (e.g., 60 μM or higher), e.g., at least 70 μM, 80 μM, 90 μM, 100 μM, or higher (indicative of a weaker binding affinity or $K_D$). In some embodiments, the Fc-IL-2v fusion protein binds to a complex of interleukin 2 receptor subunit beta (IL-2RB; CD122) and interleukin 2 receptor subunit gamma (IL-2RG; CD132) with a $K_D$ of less than 150 nM, e.g., less than 1.5 nM, e.g., less than 120 pM, e.g., less than 100 pM, e.g., less than 80 pM, e.g., less than 75 pM, e.g., less than 70 pM. In some embodiments, the Fc-IL-2v fusion protein promotes equivalent or greater proliferation of CD8+ T cells relative to an IL-2v of any one of SEQ ID NOs: 43 and 44, a fusion protein comprising Fc operably linked to wt IL-2, or a fusion protein of any one of SEQ ID NOs. 117, 118, 161 and 162. In some embodiments, the concentration at which the IL-2v fusion protein elicits 50% of maximal ($EC_{50}$) signal transducer and activator of transcription 5 (STAT5) activation or signaling of regulatory T (Treg) cells is at least 1000-fold, e.g., at least 1500-fold, e.g., at least 1700-fold, e.g., at least 2000-fold, e.g., at least 2500-fold higher, relative to the EC50 for STAT5 activation or signaling of wt IL-2, or an IL-2v of any one of SEQ ID NOs: 43 and 44, a fusion protein comprising Fc operably linked to wt IL-2, or a fusion protein of any one of SEQ ID NOs. 117, 118, 161 or 162. In some embodiments, the concentration at which the IL-2v fusion protein elicits EC50 of IL-2Rαβγ-mediated STAT5 activation or signaling (e.g., measured as STAT5 activation of CTLL2 cells) is at least 2500-fold, e.g., at least 5000-fold, e.g., at least 7500-fold, e.g., at least 10,000-fold, e.g., at least 15,000-fold, e.g., at least 20,000-fold higher, relative to the $EC_{50}$ for STAT5 activation or signaling of wt IL-2, or an IL-2v of any one of SEQ ID NOs: 43 and 44, a fusion protein comprising Fc operably linked to wt IL-2, or a fusion protein of any one of SEQ ID NOs. 117, 118, 161 or 162. In some embodiments, the concentration at which the IL-2v fusion protein elicits 50% of maximal ($EC_{50}$) proliferation of natural killer (NK) cells is at least 10-fold, e.g., at least 12-fold, e.g., at least 15-fold, e.g., at least 16-fold, e.g., at least 18-fold, e.g., at least 20-fold higher, e.g., as measured using KHYG-1 cells, relative to the $EC_{50}$ for proliferation of wt IL-2, or an IL-2v of any one of SEQ ID NOs: 43 and 44, a fusion protein comprising Fc operably linked to wt IL-2, or a fusion protein of any one of SEQ ID NOs. 117, 118, 161 or 162.

Structurally, in various embodiments, the Fc-IL-2v fusion protein comprises an amino acid sequence selected from the group consisting of SEQ ID NOs: 75-116 and 119-160, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 75-116 and 119-160. Illustrative Fc-IL-2v fusion proteins based on or derived from human wild-type Fc and human wild-type IL-2 are provided in Table C.

In various embodiments, the Fc-IL-2v fusion protein is based on or derived from mouse wild-type Fc and mouse wild-type IL-2, comprises an amino acid sequence selected from the group consisting of SEQ ID NOs: 166-171, or comprising an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 166-171. Illustrative Fc-IL-2v fusion proteins based on or derived from mouse wild-type Fc and mouse wild-type IL-2 are provided in Table D. In various embodiments, the mouse Fc-IL-2v fusion proteins are in the form of a heterodimer, e.g., with an Fc domain comprising an amino acid sequence of SEQ ID NO: 250, or comprising an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of SEQ ID NOs: 250.

```
                                        (SEQ ID NO: 250)
GPTIKPCPPCKCPAPNAAGGPSVFIFPPKIKDVLMISLSPIVICVVVD

VSEDDPDVQISWFVNNVEVHTAQTQTHREDYNSTLRVVSALPIQHQDW

MSGKEFKCKVNNKDLGAPIERTISKPKGSVRAPQVYVLPPPEEEMTKK

QVTLSCAVTDFMPEDIYVEWTNNGKTELNYKNTEPVLDSDGSYFMVSK

LRVEKKNWVERNSYSCSVVHEGLHNHHTTKSFSRTPGK
```

Generally, the Fc-IL-2v fusion proteins described herein, are not fused to a second cytokine. For example, the Fc-IL-2v fusion proteins described herein are not fused to a second interleukin, including a second IL-2, or an interferon.

In some embodiments, the Fc-IL-2v fusion proteins are not glycosylated. In some embodiments, the IL-2v in the Fc-IL-2v fusion proteins is not glycosylated. In some embodiments, the Fc region or Fc domain of the Fc-IL-2v fusion proteins is glycosylated, e.g., has a single N-linked glycan at position N297 in one or both of the Fc regions or Fc domains (EU numbering) of the herein described Fc-IL-2v heterodimers.

TABLE C

Illustrative human Fc-IL-2v fusion proteins

| PROTEIN NO: SEQ ID NO: | Features | Polypeptide Sequence (Fc domain is underlined) |
|---|---|---|
| | IgG4 variants | |
| 75 | hIgG4<br>S228P/F234A/L235A<br>T366W<br>hIL-2v_Δ1-5_R38X$_1$_<br>T41X$_2$_F42X$_3$_<br>Y45X$_4$_E61X$_5$_<br>E62X$_6$_E68X$_7$_<br>L72X$_8$_Q74X$_9$_<br>Y107X$_{10}$_C125S<br>X$_1$ is R, S, G or A<br>X$_2$ is T, G or A<br>X$_3$ is F, G or A<br>X$_4$ is Y, G or A<br>X$_5$ is E, G or A<br>X$_6$ is E, G or A<br>X$_7$ is E, G or A<br>X$_8$ is L, G or A<br>X$_9$ is Q, G or A<br>X$_{10}$ is Y, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLX$_2$X$_3$KFX$_4$MPKKATELKHLQCLEX$_5$X$_6$LKPLEX$_7$VLNX$_8$<br>AX$_9$SKNFHLRPRDLISNINVIVLELKGSETTFMCEX$_{10}$ADETATIVEFLNRWITFSQSIISTLT |
| 76 | hIgG4<br>S228P/F234A/L235A<br>T366W<br>hIL-2v_Δ1-5_R38X$_1$_<br>F42X$_2$_Y45X$_3$_E61X$_4$_<br>E62X$_5$_L72X$_6$_C125S<br>X$_1$ is R, S, G or A<br>X$_2$ is F, G or A<br>X$_3$ is Y, G or A<br>X$_4$ is E, G or A<br>X$_5$ is E, G or A<br>X$_6$ is L, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLTX$_2$KFX$_3$MPKKATELKHLQCLEX$_4$X$_5$LKPLEEVLNX$_6$A<br>QSKNFHLRPRDLISNINVIVLELKGSETTFMCEYADETATIVEFLNRWITFSQSIISTLT |
| 77 | hIgG4<br>S228P/F234A/L235A<br>T366W<br>hIL-2v_Δ1-5_R38X$_1$_<br>F42X$_2$_Y45X$_3$_E61X$_4$_<br>E62X$_5$_C125S<br>X$_1$ is R, S, G or A<br>X$_2$ is F, G or A<br>X$_3$ is Y, G or A<br>X$_4$ is E, G or A<br>X$_6$ is E, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLTX$_2$KFX$_3$MPKKATELKHLQCLEX$_4$X$_5$LKPLEEVLNLA<br>QSKNFHLRPRDLISNINVIVLELKGSETTFMCEYADETATIVEFLNRWITFSQSIISTLT |
| 78 | hIgG4<br>S228P/F234A/L235A<br>T366W<br>hIL-2v_Δ1-5_<br>R38X$_1$_F42X$_2$_<br>Y45X$_3$_E62X$_5$_C125S<br>X$_1$ is R, S, G or A<br>X$_2$ is F, G or A<br>X$_3$ is Y, G or A<br>X$_5$ is E, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLTX$_2$KFX$_3$MPKKATELKHLQCLEEX$_5$LKPLEEVLNLAQ<br>SKNFHLRPRDLISNINVIVLELKGSETTFMCEYADETATIVEFLNRWITFSQSIISTLT |
| 79 | hIgG4<br>S228P/F234A/L235A<br>T366W<br>hIL-2v_Δ1-5_<br>R38X$_1$_F42X$_2$_<br>E62X$_5$_C125S<br>X$_1$ is R, S, G or A<br>X$_2$ is F, G or A<br>X$_5$ is E, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLTX$_2$KFYMPKKATELKHLQCLEEX$_5$LKPLEEVLNLAQS<br>KNFHLRPRDLISNINVIVLELKGSETTFMCEYADETATIVEFLNRWITFSQSIISTLT |
| 80 | hIgG4<br>S228P/F234A/L235A<br>T366W<br>hIL-2v_Δ1-5_R38X$_1$_<br>F42A_E62A_C125S<br>X$_1$ is R, S, G or A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTX$_1$MLTAKFYMPKKATELKHLQCLEEALKPLEEVLNLAQSK<br>NFHLRPRDLISNINVIVLELKGSETTFMCEYADETATIVEFLNRWITFSQSIISILT |

TABLE C-continued

Illustrative human Fc-IL-2v fusion proteins

| PROTEIN NO: SEQ ID NO: | Features | Polypeptide Sequence (Fc domain is underlined) |
|---|---|---|
| 81 | hIgG4<br>S228P/F234A/L235A<br>I366W<br>hIL-2v_Δ1-5_<br>R38G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFYMPKKATELKHLQCLEEELKPLEEVLNLAQSKN<br>FHLRPRDLISNINVIVLELKGSETTFMCEYADETATIVEFLNRWITFSQSIISTLT |
| 82 | hIgG4<br>S228P/F234A/L235A<br>T366W<br>hIL-2v_Δ1-5_<br>R38A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTAMLTFKFYMPKKATELKHLQCLEEELKPLEEVLNLAQSKN<br>FHLRPRDLISNINVIVLELKGSETTFMCEYADETATIVEFLNRWITFSQSIISTLT |
| 83 | hIgG4<br>S228P/F234A/L235A<br>T366W<br>hIL-2v_Δ1-5_<br>T41G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLGFKFYMPKKATELKHLQCLEEELKPLEEVLNLAQSKN<br>FHLRPRDLISNINVIVLELKGSETTFMCEYADETATIVEFLNRWITFSQSIISTLT |
| 84 | hIgG4<br>S228P/F234A/L235A<br>T366W<br>hIL-2v_Δ1-5_<br>T41A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLAFKFYMPKKATELKHLQCLEEELKPLEEVLNLAQSKN<br>FHLRPRDLISNINVIVLELKGSETTFMCEYADETATIVEFLNRWITFSQSIISTLT |
| 85 | hIgG4<br>S228P/F234A/L235A<br>T366W<br>hIL-2v_Δ1-5_<br>F42G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTGKFYMPKKATELKHLQCLEEELKPLEEVLNLAQSKN<br>FHLRPRDLISNINVIVLELKGSETTFMCEYADETATIVEFLNRWITFSQSIISTLT |
| 86 | hIgG4<br>S228P/F234A/L235A<br>T366W<br>hIL-2v_Δ1-5_<br>F42A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFYMPKKATELKHLQCLEEELKPLEEVLNLAQSKN<br>FHLRPRDLISNINVIVLELKGSETTFMCEYADETATIVEFLNRWITFSQSIISTLT |
| 87 | hIgG4<br>S228P/F234A/L235A<br>T366W<br>hIL-2v_Δ1-5_<br>Y45G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFGMPKKATELKHLQCLEEELKPLEEVLNLAQSKN<br>FHLRPRDLISNINVIVLELKGSETTFMCEYADETATIVEFLNRWITFSQSIISTLT |
| 88 | hIgG4<br>S228P/F234A/L235A<br>T366W<br>hIL-2v_Δ1-5_<br>Y45A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFAMPKKATELKHLQCLEEELKPLEEVLNLAQSKN<br>FHLRPRDLISNINVIVLELKGSETTFMCEYADETATIVEFLNRWITFSQSIISTLT |
| 89 | hIgG4<br>S228P/F234A/L235A<br>T366W<br>hIL-2v_Δ1-5_<br>E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEAELKPLEEVLNLAQSKN<br>FHLRPRDLISNINVIVLELKGSETTFMCEYADETATIVEFLNRWITFSQSIISTLT |
| 90 | hIgG4<br>S228P/F234A/L235A<br>T366W<br>hIL-2v_Δ1-5_<br>E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEALKPLEEVLNLAQSKN<br>FHLRPRDLISNINVIVLELKGSETTFMCEYADETATIVEFLNRWITFSQSIISTLT |
| 91 | hIgG4<br>S228P/F234A/L235A<br>T366W<br>hIL-2v_Δ1-5_ | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ |

TABLE C-continued

Illustrative human Fc-IL-2v fusion proteins

| PROTEIN NO: SEQ ID NO: | Features | Polypeptide Sequence (Fc domain is underlined) |
|---|---|---|
| | E68A_C125S | LEHLLLDLQMILNGINNYKNPKLTRMLTFKFYMPKKATELKHLQCLEEELKPLEAVLNLAQSKN<br>FHLRPRDLISNINVIVLELKGSETTFMCEYADETATIVEFLNRWITFSQSIISTLT |
| 92 | hIgG4<br>S228P/F234A/L235A<br>T366W<br>hIL-2v_Δ1-5_<br>L72G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEELKPLEEVLNGAQSKN<br>FHLRPRDLISNINVIVLELKGSETTFMCEYADETATIVEFLNRWITFSQSIISTLT |
| 93 | hIgG4<br>S228P/F234A/L235A<br>T366W<br>hIL-2v_Δ1-5_<br>Q74G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEELKPLEEVLNLAGSKN<br>FHLRPRDLISNINVIVLELKGSETTFMCEYADETATIVEFLNRWITFSQSIISTLT |
| 94 | hIgG4<br>S228P/F234A/L235A<br>T366W<br>hIL-2v_Δ1-5_<br>Y107G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEELKPLEEVLNLAQSKN<br>FHLRPRDLISNINVIVLELKGSETTFMCEGADETATIVEFLNRWITFSQSIISTLT |
| 95 | hIgG4<br>S228P/F234A/L235A<br>T366W<br>hIL-2v_Δ1-5_<br>Y107A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEELKPLEEVLNLAQSKN<br>FHLRPRDLISNINVIVLELKGSETTFMCEAADETATIVEFLNRWITFSQSIISTLT |
| 96 | hIgG4<br>S228P/F234A/L235A<br>T366W<br>hIL-2v_Δ1-5_<br>Y45G_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFGMPKKATELKHLQCLEAELKPLEEVLNLAQSKN<br>FHLRPRDLISNINVIVLELKGSETTFMCEYADETATIVEFLNRWITFSQSIISTLT |
| 97 | hIgG4<br>S228P/F234A/L235A<br>T366W<br>hIL-2v_Δ1-5_<br>Y45G_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFGMPKKATELKHLQCLEEALKPLEEVLNLAQSKN<br>FHLRPRDLISNINVIVLELKGSETTFMCEYADETATIVEFLNRWITFSQSIISTLT |
| 98 | hIgG4<br>S228P/F234A/L235A<br>T366W<br>hIL-2v_Δ1-5_<br>R38G_Y45G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFGMPKKATELKHLQCLEEELKPLEEVLNLAQSKN<br>FHLRPRDLISNINVIVLELKGSETTFMCEYADETATIVEFLNRWITFSQSIISTLT |
| 99 | hIgG4<br>S228P/F234A/L235A<br>T366W<br>hIL-2v_Δ1-5_<br>R38G_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFYMPKKATELKHLQCLEAELKPLEEVLNLAQSKN<br>FHLRPRDLISNINVIVLELKGSETTFMCEYADETATIVEFLNRWITFSQSIISTLT |
| 100 | hIgG4<br>S228P/F234A/L235A<br>T366W<br>hIL-2v_Δ1-5_<br>F42A_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFYMPKKATELKHLQCLEAELKPLEEVLNLAQSKN<br>FHLRPRDLISNINVIVLELKGSETTFMCEYADETATIVEFLNRWITFSQSIISTLT |
| 101 | hIgG4<br>S228P/F234A/L235A<br>T366W<br>hIL-2v_Δ1-5_<br>F42A_Y45G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFGMPKKATELKHLQCLEEELKPLEEVLNLAQSKN<br>FHLRPRDLISNINVIVLELKGSETTFMCEYADETATIVEFLNRWITFSQSIISTLT |
| 102 | hIgG4<br>S228P/F234A/L235A | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP |

TABLE C-continued

Illustrative human Fc-IL-2v fusion proteins

| PROTEIN NO:<br>SEQ ID NO: | Features | Polypeptide Sequence (Fc domain is underlined) |
|---|---|---|
| | T366W<br>hIL-2v_Δ1-5_Y45G_<br>E61A_E62A_C125S | QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFGMPKKATELKHLQCLEAALKPLEEVLNLAQSKN<br>FHLRPRDLISNINVIVLELKGSETTFMCEYADETATIVEFLNRWITFSQSIISTLT |
| 103 | hIgG4<br>S228P/F234A/L235A<br>T366W<br>hIL-2v_Δ1-5_<br>E61A_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEAALKPLEEVLNLAQSKN<br>FHLRPRDLISNINVIVLELKGSETTFMCEYADETATIVEFLNRWITFSQSIISTLT |
| 104 | hIgG4<br>S228P/F234A/L235A<br>T366W<br>hIL-2v_Δ1-5_<br>R38G_F42A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTAKFYMPKKATELKHLQCLEEELKPLEEVLNLAQSKN<br>FHLRPRDLISNINVIVLELKGSETTFMCEYADETATIVEFLNRWITFSQSIISTLT |
| 105 | hIgG4<br>S228P/F234A/L235A<br>T366W<br>hIL-2v_Δ1-5_F42A_<br>Y45A_L72G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFAMPKKATELKHLQCLEEELKPLEEVLNGAQSKN<br>FHLRPRDLISNINVIVLELKGSETTFMCEYADETATIVEFLNRWITFSQSIISTLT |
| 106 | hIgG4<br>S228P/F234A/L235A<br>T366W<br>hIL-2v_Δ1-5_R38G_<br>F42A_Y45G_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTAKFGMPKKATELKHLQCLEEELKPLEEVLNLAQSKN<br>FHLRPRDLISNINVIVLELKGSETTFMCEYADETATIVEFLNRWITFSQSIISTLT |
| 107 | hIgG4<br>S228P/F234A/L235A<br>T366W<br>hIL-2v_Δ1-5_<br>F42A_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFYMPKKATELKHLQCLEEALKPLEEVLNLAQSKN<br>FHLRPRDLISNINVIVLELKGSETTFMCEYADETATIVEFLNRWITFSQSIISTLT |
| 108 | hIgG4<br>S228P/F234A/L235A<br>T366W<br>hIL-2v_Δ1-5_F42A_<br>Y45G_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFGMPKKATELKHLQCLEEALKPLEEVLNLAQSKN<br>FHLRPRDLISNINVIVLELKGSETTFMCEYADETATIVEFLNRWITFSQSIISTLT |
| 109 | hIgG4<br>S228P/F234A/L235A<br>T366W<br>hIL-2v_Δ1-5_F42A_<br>Y45G_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFGMPKKATELKHLQCLEAELKPLEEVLNLAQSKN<br>FHLRPRDLISNINVIVLELKGSETTFMCEYADETATIVEFLNRWITFSQSIISTLT |
| 110 | hIgG4<br>S228P/F234A/L235A<br>T366W<br>hIL-2v_Δ1-5_R38G_<br>Y45G_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFGMPKKATELKHLQCLEAELKPLEEVLNLAQSKN<br>FHLRPRDLISNINVIVLELKGSETTFMCEYADETATIVEFLNRWITFSQSIISTLT |
| 111 | hIgG4<br>S228P/F234A/L235A<br>T366W<br>hIL-2v_Δ1-5_R38G_<br>F42A_E61A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTAKFYMPKKATELKHLQCLEAELKPLEEVLNLAQSKN<br>FHLRPRDLISNINVIVLELKGSETTFMCEYADETATIVEFLNRWITFSQSIISTLT |
| 112 | hIgG4<br>S228P/F234A/L235A<br>T366W<br>hIL-2v_Δ1-5_R38G_<br>Y45G_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFGMPKKATELKHLQCLEEALKPLEEVLNLAQSKN<br>FHLRPRDLISNINVIVLELKGSETTFMCEYADETATIVEFLNRWITFSQSIISTLT |

TABLE C-continued

Illustrative human Fc-IL-2v fusion proteins

| PROTEIN NO:<br>SEQ ID NO: | Features | Polypeptide Sequence (Fc domain is underlined) |
|---|---|---|
| 113 | hIgG4<br>S228P/F234A/L235A<br>T366W<br>hIL-2v_Δ1-5_<br>R38G_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFYMPKKATELKHLQCLEEALKPLEEVLNLAQSKN<br>FHLRPRDLISNINVIVLELKGSETTFMCEYADETATIVEFLNRWITFSQSIISTLT |
| 114 | hIgG4<br>S228P/F234A/L235A<br>T366W<br>hIL-2v_Δ1-5_R38G_<br>F42A_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTAKFYMPKKATELKHLQCLEEALKPLEEVLNLAQSKN<br>FHLRPRDLISNINVIVLELKGSETTFMCEYADETATIVEFLNRWITFSQSIISTLT |
| 115 | hIgG4<br>S228P/F234A/L235A<br>T366W<br>hIL-2v_Δ1-5_F42A_<br>E61A_E62A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTAKFYMPKKATELKHLQCLEAALKPLEEVLNLAQSKN<br>FHLRPRDLISNINVIVLELKGSETTFMCEYADETATIVEFLNRWITFSQSIISTLT |
| 116 | hIgG4<br>S228P/F234A/L235A<br>T366W<br>hIL-2v_Δ1-5_R38G_<br>E61A_E62A_C125S<br>hIgG4 | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTGMLTFKFYMPKKATELKHLQCLEAALKPLEEVLNLAQSKN<br>FHLRPRDLISNINVIVLELKGSETTFMCEYADETATIVEFLNRWITFSQSIISTLT |
| 117 | hIgG4<br>S228P/F234A/L235A<br>T366W<br>hIL-2v_Δ1-5_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSSTKKTQLQ<br>LEHLLLDLQMILNGINNYKNPKLTRMLTFKFYMPKKATELKHLQCLEEELKPLEEVLNLAQSKN<br>FHLRPRDLISNINVIVLELKGSETTFMCEYADETATIVEFLNRWITFSQSIISTLT |
| 118 | hIgG4<br>S228P/F234A/L235A<br>T366W<br>hIL-2v_T3A_C125S | ESKYGPPCPPCPAPEAAGGPSVFLFPPKPKDTLMISRTPEVTCVVVDVSQEDPEVQFNWYVDGV<br>EVHNAKTKPREEQFNSTYRVVSVLTVLHQDWLNGKEYKCKVSNKGLPSSIEKTISKAKGQPREP<br>QVYTLPPSQEEMTKNQVSLWCLVKGFYPSDIAVEWESNGQPENNYKTTPPVLDSDGSFFLYSRL<br>TVDKSRWQEGNVFSCSVMHEALHNHYTQKSLSLSLGGGGGSGGGGSGGGGSGGGGSAPASSSTK<br>KTQLQLEHLLLDLQMILNGINNYKNPKLTRMLTFKFYMPKKATELKHLQCLEEELKPLEEVLNL<br>AQSKNFHLRPRDLISNINVIVLELKGSETTFMCEYADETATIVEFLNRWITFSQSIISTLT |
| | | IgG1 variants |
| 119 | hIgG1<br>L234A/L235A/P331S/<br>T366W<br>hIL-2v_Δ1-5_R38$X_1$_<br>T41$X_2$_F42$X_3$_<br>Y45$X_4$_E61$X_5$_<br>E62$X_6$_E68$X_7$_<br>L72$X_8$_Q74$X_9$_<br>Y107$X_{10}$_C125S<br>$X_1$ is R, S, G or A<br>$X_2$ is T, G or A<br>$X_3$ is F, G or A<br>$X_4$ is Y, G or A<br>$X_5$ is E, G or A<br>$X_6$ is E, G or A<br>$X_7$ is E, G or A<br>$X_8$ is L, G or A<br>$X_9$ is Q, G or A<br>$X_{10}$ is Y, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLT$X_1$ML$X_2X_3$KF$X_4$MPKKATELKHLQCLE$X_5X_6$LKPLE$X_7$V<br>LN$X_8$A$X_9$SKNFHLRPRDLISNINVIVLELKGSETTFMCEX10ADETATIVEFLNRWITFSQSIIS<br>TLT |
| 120 | hIgG1<br>L234A/L235A/P331S/<br>T366W<br>hIL-2v_Δ1-5_<br>R38$X_1$_F42$X_2$_<br>Y45$X_3$_E61$X_4$_E62$X_5$_<br>L72$X_6$_C125S<br>$X_1$ is R, S, G or A<br>$X_2$ is F, G or A<br>$X_3$ is Y, G or A<br>$X_4$ is E, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLT$X_1$MLT$X_2$KF$X_3$MPKKATELKHLQCLE$X_4X_5$LKPLEEVL<br>N$X_6$AQSKNFHLRPRDLISNINVIVLELKGSETTFMCEYADETATIVEFLNRWITFSQSIISTLT |

TABLE C-continued

| Illustrative human Fc-IL-2v fusion proteins | | |
|---|---|---|
| PROTEIN NO:<br>SEQ ID NO: | Features | Polypeptide Sequence (Fc domain is underlined) |
| | $X_5$ is E, G or A<br>$X_6$ is L, G or A | |
| 121 | hIgG1<br>L234A/L235A/P331S/<br>T366W<br>hIL-2v_Δ1-5_<br>R38$X_1$_F42$X_2$_<br>Y45$X_3$_E61$X_4$_E62$X_5$_<br>C125S<br>$X_1$ is R, S, G or A<br>$X_2$ is F, G or A<br>$X_3$ is Y, G or A<br>$X_4$ is E, G or A<br>$X_5$ is E, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLT$X_1$MLT$X_2$KF$X_3$MPKKATELKHLQCLE$X_4X_5$LKPLEEVL<br>NLAQSKNFHLRPRDLISNINVIVLELKGSETTFMCEYADETATIVEFLNRWITFSQSIISTLT |
| 122 | hIgG1<br>L234A/L235A/P331S/<br>T366W<br>hIL-2v_Δ1-5_<br>R38$X_1$_F42$X_2$_<br>Y45$X_3$_E62$X_5$_C125S<br>$X_1$ is R, S, G or A<br>$X_2$ is F, G or A<br>$X_3$ is Y, G or A<br>$X_5$ is E, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLI$X_1$MLI$X_2$KF$X_3$MPKKATELKHLQCLEE$X_5$LKPLEEVLN<br>LAQSKNFHLRPRDLISNINVIVLELKGSETTFMCEYADETATIVEFLNRWITFSQSIISTLT |
| 123 | hIgG1<br>L234A/L235A/P331S/<br>T366W<br>hIL-2v_Δ1-5 R38X1<br>F42$X_2$_E62$X_5$_C125S<br>$X_1$ is R, S, G or A<br>$X_2$ is F, G or A<br>$X_5$ is E, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLI$X_1$MLI$X_2$KFYMPKKATELKHLQCLEE$X_5$LKPLEEVLNL<br>AQSKNFHLRPRDLISNINVIVLELKGSETTFMCEYADETATIVEFLNRWITFSQSIISTLT |
| 124 | hIgG1<br>L234A/L235A/P331S/<br>T366W<br>hIL-2v_Δ1-5_R38$X_1$_<br>F42A_E62A_C125S<br>$X_1$ is R, S, G or A | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLT$X_1$MLTAKFYMPKKATELKHLQCLEEALKPLEEVLNLA<br>QSKNFHLRPRDLISNINVIVLELKGSETTFMCEYADETATIVEFLNRWITFSQSIISTLT |
| 125 | hIgG1<br>L234A/L235A/P331S/<br>T366W<br>hIL-2v_Δ1-5_<br>R38G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFYMPKKATELKHLQCLEEELKPLEEVLNLAQ<br>SKNFHLRPRDLISNINVIVLELKGSETTFMCEYADETATIVEFLNRWITFSQSIISTLT |
| 126 | hIgG1<br>L234A/L235A/P331S/<br>T366W<br>hIL-2v_Δ1-5_<br>R38A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTAMLTFKFYMPKKATELKHLQCLEEELKPLEEVLNLAQ<br>SKNFHLRPRDLISNINVIVLELKGSETTFMCEYADETATIVEFLNRWITFSQSIISTLT |
| 127 | hIgG1<br>L234A/L235A/P331S/<br>T366W<br>hIL-2v_Δ1-5_<br>T41G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLGFKFYMPKKATELKHLQCLEEELKPLEEVLNLAQ<br>SKNFHLRPRDLISNINVIVLELKGSETTFMCEYADETATIVEFLNRWITFSQSIISTLT |
| 128 | hIgG1<br>L234A/L235A/P331S/<br>T366W<br>hIL-2v_Δ1-5_<br>T41A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLAFKFYMPKKATELKHLQCLEEELKPLEEVLNLAQ<br>SKNFHLRPRDLISNINVIVLELKGSETTFMCEYADETATIVEFLNRWITFSQSIISTLT |
| 129 | hIgG1<br>L234A/L235A/P331S/<br>T366W<br>hIL-2v_Δ1-5_ | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGFFLY<br>SKLTVDKSRWQQGNVFSCSVMHEALHNHYTQKSLSLSPGGGGGSGGGGSGGGGSGGGGSSTKKT |

TABLE C-continued

Illustrative human Fc-IL-2v fusion proteins

| PROTEIN NO: SEQ ID NO: | Features | Polypeptide Sequence (Fc domain is underlined) |
|---|---|---|
| | F42G_C125S | QLQLEHLLLDLQMILNGINNYKNPKLTRMLTGKFYMPKKATELKHLQCLEEELKPLEEVLNLAQ<br>SKNFHLRPRDLISNINVIVLELKGSETTFMCEYADETATIVEFLNRWITFSQSIISTLT |
| 130 | hIgG1<br>L234A/L235A/P331S/<br>T366W<br>hIL-2v_Δ1-5_<br>F42A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFYMPKKATELKHLQCLEEELKPLEEVLNLAQ<br>SKNFHLRPRDLISNINVIVLELKGSETTFMCEYADETATIVEFLNRWITFSQSIISTLT |
| 131 | hIgG1<br>L234A/L235A/P331S/<br>T366W<br>hIL-2v_Δ1-5_<br>Y45G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFGMPKKATELKHLQCLEEELKPLEEVLNLAQ<br>SKNFHLRPRDLISNINVIVLELKGSETTFMCEYADETATIVEFLNRWITFSQSIISTLT |
| 132 | hIgG1<br>L234A/L235A/P331S/<br>T366W<br>hIL-2v_Δ1-5_<br>Y45A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFAMPKKATELKHLQCLEEELKPLEEVLNLAQ<br>SKNFHLRPRDLISNINVIVLELKGSETTFMCEYADETATIVEFLNRWITFSQSIISTLT |
| 133 | hIgG1<br>L234A/L235A/P331S/<br>T366W<br>hIL-2v_Δ1-5_<br>E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEAELKPLEEVLNLAQ<br>SKNFHLRPRDLISNINVIVLELKGSETTFMCEYADETATIVEFLNRWITFSQSIISTLT |
| 134 | hIgG1<br>L234A/L235A/P331S/<br>T366W<br>hIL-2v_Δ1-5_<br>E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEALKPLEEVLNLAQ<br>SKNFHLRPRDLISNINVIVLELKGSETTFMCEYADETATIVEFLNRWITFSQSIISTLT |
| 135 | hIgG1<br>L234A/L235A/P331S/<br>T366W<br>hIL-2v_Δ1-5_<br>E68A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEELKPLEAVLNLAQ<br>SKNFHLRPRDLISNINVIVLELKGSETTFMCEYADETATIVEFLNRWITFSQSIISTLT |
| 136 | hIgG1<br>L234A/L235A/P331S/<br>T366W<br>hIL-2v_Δ1-5_<br>L72G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEELKPLEEVLNGAQ<br>SKNFHLRPRDLISNINVIVLELKGSETTFMCEYADETATIVEFLNRWITFSQSIISTLT |
| 137 | hIgG1<br>L234A/L235A/P331S/<br>T366W<br>hIL-2v_Δ1-5_<br>Q74G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEELKPLEEVLNLAG<br>SKNFHLRPRDLISNINVIVLELKGSETTFMCEYADETATIVEFLNRWITFSQSIISTLT |
| 138 | hIgG1<br>L234A/L235A/P331S/<br>T366W<br>hIL-2v_Δ1-5_<br>Y107G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEELKPLEEVLNLAQ<br>SKNFHLRPRDLISNINVIVLELKGSETTFMCEGADETATIVEFLNRWITFSQSIISTLT |
| 139 | hIgG1<br>L234A/L235A/P331S/<br>T366W<br>hIL-2v_Δ1-5_<br>Y107A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEEELKPLEEVLNLAQ<br>SKNFHLRPRDLISNINVIVLELKGSETTFMCEAADETATIVEFLNRWITFSQSIISTLT |
| 140 | hIgG1<br>L234A/L235A/P331S/ | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP |

TABLE C-continued

Illustrative human Fc-IL-2v fusion proteins

| PROTEIN NO: SEQ ID NO: | Features | Polypeptide Sequence (Fc domain is underlined) |
|---|---|---|
| | T366W<br>hIL-2v_Δ1-5_<br>Y45G_E61A_C125S | REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFGMPKKATELKHLQCLEAELKPLEEVLNLAQ<br>SKNFHLRPRDLISNINVIVLELKGSETTFMCEYADETATIVEFLNRWITFSQSIISTLT |
| 141 | hIgG1<br>L234A/L235A/P331S/<br>T366W<br>hIL-2v_Δ1-5_<br>Y45G_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFGMPKKATELKHLQCLEEALKPLEEVLNLAQ<br>SKNFHLRPRDLISNINVIVLELKGSETTFMCEYADETATIVEFLNRWITFSQSIISTLT |
| 142 | hIgG1<br>L234A/L235A/P331S/<br>T366W<br>hIL-2v_Δ1-5_<br>R38G_Y45G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFGMPKKATELKHLQCLEEELKPLEEVLNLAQ<br>SKNFHLRPRDLISNINVIVLELKGSETTFMCEYADETATIVEFLNRWITFSQSIISTLT |
| 143 | hIgG1<br>L234A/L235A/P331S/<br>T366W<br>hIL-2v_Δ1-5_<br>R38G_E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFYMPKKATELKHLQCLEAELKPLEEVLNLAQ<br>SKNFHLRPRDLISNINVIVLELKGSETTFMCEYADETATIVEFLNRWITFSQSIISTLT |
| 144 | hIgG1<br>L234A/L235A/P331S/<br>T366W<br>hIL-2v_Δ1-5_<br>F42A_E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFYMPKKATELKHLQCLEAELKPLEEVLNLAQ<br>SKNFHLRPRDLISNINVIVLELKGSETTFMCEYADETATIVEFLNRWITFSQSIISTLT |
| 145 | hIgG1<br>L234A/L235A/P331S/<br>T366W<br>hIL-2v_Δ1-5_<br>F42A_Y45G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFGMPKKATELKHLQCLEEELKPLEEVLNLAQ<br>SKNFHLRPRDLISNINVIVLELKGSETTFMCEYADETATIVEFLNRWITFSQSIISTLT |
| 146 | hIgG1<br>L234A/L235A/P331S/<br>T366W<br>hIL-2v_Δ1-5_Y45G_<br>E61A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFGMPKKATELKHLQCLEAALKPLEEVLNLAQ<br>SKNFHLRPRDLISNINVIVLELKGSETTFMCEYADETATIVEFLNRWITFSQSIISTLT |
| 147 | hIgG1<br>L234A/L235A/P331S/<br>T366W<br>hIL-2v_Δ1-5_<br>E61A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTFKFYMPKKATELKHLQCLEAALKPLEEVLNLAQ<br>SKNFHLRPRDLISNINVIVLELKGSETTFMCEYADETATIVEFLNRWITFSQSIISTLT |
| 148 | hIgG1<br>L234A/L235A/P331S/<br>T366W<br>hIL-2v_Δ1-5_<br>R38G_F42A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTAKFYMPKKATELKHLQCLEEELKPLEEVLNLAQ<br>SKNFHLRPRDLISNINVIVLELKGSETTFMCEYADETATIVEFLNRWITFSQSIISTLT |
| 149 | hIgG1<br>L234A/L235A/P331S/<br>T366W<br>hIL-2v_Δ1-5_F42A_<br>Y45A_L72G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFAMPKKATELKHLQCLEEELKPLEEVLNGAQ<br>SKNFHLRPRDLISNINVIVLELKGSETTFMCEYADETATIVEFLNRWITFSQSIISTLT |
| 150 | hIgG1<br>L234A/L235A/P331S/<br>T366W<br>hIL-2v_Δ1-5_R38G_<br>F42A_Y45G_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTAKFGMPKKATELKHLQCLEEELKPLEEVLNLAQ<br>SKNFHLRPRDLISNINVIVLELKGSETTFMCEYADETATIVEFLNRWITFSQSIISTLT |

TABLE C-continued

Illustrative human Fc-IL-2v fusion proteins

| PROTEIN NO: SEQ ID NO: | Features | Polypeptide Sequence (Fc domain is underlined) |
|---|---|---|
| 151 | hIgG1<br>L234A/L235A/P331S/<br>T366W<br>hIL-2v_Δ1-5_<br>F42A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLTVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFYMPKKATELKHLQCLEEALKPLEEVLNLAQ<br>SKNFHLRPRDLISNINVIVLELKGSETTFMCEYADETATIVEFLNRWITFSQSIISTLT |
| 152 | hIgG1<br>L234A/L235A/P331S/<br>T366W<br>hIL-2v_Δ1-5_F42A_<br>Y45G_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFGMPKKATELKHLQCLEEALKPLEEVLNLAQ<br>SKNFHLRPRDLISNINVIVLELKGSETTFMCEYADETATIVEFLNRWITFSQSIISTLT |
| 153 | hIgG1<br>L234A/L235A/P331S/<br>T366W<br>hIL-2v_Δ1-5_F42A_<br>Y45G_E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFGMPKKATELKHLQCLEAELKPLEEVLNLAQ<br>SKNFHLRPRDLISNINVIVLELKGSETTFMCEYADETATIVEFLNRWITFSQSIISTLT |
| 154 | hIgG1<br>L234A/L235A/P331S/<br>T366W<br>hIL-2v_Δ1-5_R38G_<br>Y45G_E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFGMPKKATELKHLQCLEAELKPLEEVLNLAQ<br>SKNFHLRPRDLISNINVIVLELKGSETTFMCEYADETATIVEFLNRWITFSQSIISTLT |
| 155 | hIgG1<br>L234A/L235A/P331S/<br>T366W<br>hIL-2v_Δ1-5_R38G_<br>F42A_E61A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTAKFYMPKKATELKHLQCLEAELKPLEEVLNLAQ<br>SKNFHLRPRDLISNINVIVLELKGSETTFMCEYADETATIVEFLNRWITFSQSIISTLT |
| 156 | hIgG1<br>L234A/L235A/P331S/<br>T366W<br>hIL-2v_Δ1-5_R38G_<br>Y45G_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFGMPKKATELKHLQCLEEALKPLEEVLNLAQ<br>SKNFHLRPRDLISNINVIVLELKGSETTFMCEYADETATIVEFLNRWITFSQSIISTLT |
| 157 | hIgG1<br>L234A/L235A/P331S/<br>T366W<br>hIL-2v_Δ1-5_R38G_<br>E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFYMPKKATELKHLQCLEEALKPLEEVLNLAQ<br>SKNFHLRPRDLISNINVIVLELKGSETTFMCEYADETATIVEFLNRWITFSQSIISTLT |
| 158 | hIgG1<br>L234A/L235A/P331S/<br>T366W<br>hIL-2v_Δ1-5_R38G_<br>F42A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTAKFYMPKKATELKHLQCLEEALKPLEEVLNLAQ<br>SKNFHLRPRDLISNINVIVLELKGSETTFMCEYADETATIVEFLNRWITFSQSIISTLT |
| 159 | hIgG1<br>L234A/L235A/P331S/<br>T366W<br>hIL-2v_Δ1-5_F42A_<br>E61A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTRMLTAKFYMPKKATELKHLQCLEAALKPLEEVLNLAQ<br>SKNFHLRPRDLISNINVIVLELKGSETTFMCEYADETATIVEFLNRWITFSQSIISTLT |
| 160 | hIgG1<br>L234A/L235A/P331S/<br>T366W<br>hIL-2v_Δ1-5_R38G_<br>E61A_E62A_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLTGMLTFKFYMPKKATELKHLQCLEAALKPLEEVLNLAQ<br>SKNFHLRPRDLISNINVIVLELKGSETTFMCEYADETATIVEFLNRWITFSQSIISTLT |
| 161 | hIgG1<br>L234A/L235A/P331S/<br>T366W<br>hIL-2v_Δ1-5_C125S | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT |

TABLE C-continued

| Illustrative human Fc-IL-2v fusion proteins | | |
|---|---|---|
| PROTEIN NO: SEQ ID NO: | Features | Polypeptide Sequence (Fc domain is underlined) |
| | | QLQLEHLLLDLQMILNGINNYKNPKLTRMLTFKFYMPKKATELKHLQCLEEELKPLEEVLNLAQ<br>SKNFHLRPRDLISNINVIVLELKGSETTFMCEYADETATIVEFLNRWITFSQSIISTLT |
| 162 | hIgG1<br>L234A/L235A/P331S/<br>T366W<br>Δ1-5_wt hIL-2 | EPKSSDKTHTCPPCPAPEAAGGPSVFLFPPKPKDTLMISRTPEVTCVVVDVSHEDPEVKFNWYV<br>DGVEVHNAKTKPREEQYNSTYRVVSVLIVLHQDWLNGKEYKCKVSNKALPASIEKTISKAKGQP<br>REPQVYTLPPSREEMTKNQVSLWCLVKGFYPSDIAVEWESNGQPENNYKTTPPVLDSDGSFFLY<br>SKLTVDKSRWQQGNVFSCSVMHEALHNHYTQKSLSLSPGGGGGSGGGGSGGGGSGGGGSSTKKT<br>QLQLEHLLLDLQMILNGINNYKNPKLIRMLIFKFYMPKKATELKHLQCLEEELKPLEEVLNLAQ<br>SKNFHLRPRDLISNINVIVLELKGSETTFMCEYADETATIVEFLNRWITFCQSIISTLT |

TABLE D

| Illustrative mouse Fc-IL-2v fusion proteins | | |
|---|---|---|
| PROTEIN NO: SEQ ID NO: | Features | Polypeptide Sequence(Fc domain is underlined) |
| 165 | mIgG2a<br>L234_L235A_P329G<br>IL-2v_C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPRMLTFKFYLPKQATELKDLQCLEDELGPLRHVLDLTQS<br>KSFQLEDAENFISNIRVTVVKLKGSDNTFECQFDDESATVVDFLRRWIAFAQSIISTSPQ |
| 166 | mIgG2a<br>L234A_L235A_P329G<br>IL-2v_F56A_Y59A_L86G<br>C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPRMLTAKFALPKQATELKDLQCLEDELGPLRHVLDGTQS<br>KSFQLEDAENFISNIRVTVVKLKGSDNTFECQFDDESATVVDFLRRWIAFAQSIISTSPQ |
| 167 | mIgG2a<br>L234A_L235A_P329G<br>IL-2v_F56A_C140AG | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPRMLTAKFYLPKQATELKDLQCLEDELGPLRHVLDLTQS<br>KSFQLEDAENFISNIRVTVVKLKGSDNTFECQFDDESATVVDFLRRWIAFAQSIISTSPQ |
| 168 | mIgG2a<br>L234A_L235A_P329G<br>IL-<br>2v_F56A_E76A_C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPRMLTAKFYLPKQATELKDLQCLEDALGPLRHVLDLTQS<br>KSFQLEDAENFISNIRVTVVKLKGSDNTFECQFDDESATVVDFLRRWIAFAQSIISTSPQ |
| 169 | mIgG2a<br>L234A_L235A_P329G<br>2v_F56A_Y59G_E76A_C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPRMLTAKFGLPKQATELKDLQCLEDALGPLRHVLDLTQS<br>KSFQLEDAENFISNIRVTVVKLKGSDNTFECQFDDESATVVDFLRRWIAFAQSIISTSPQ |
| 170 | mIgG2a<br>L234A_L235A_P329G<br>IL-<br>2v_R52G_E76A_C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPGMLTFKFYLPKQATELKDLQCLEDALGPLRHVLDLTQS<br>KSFQLEDAENFISNIRVTVVKLKGSDNTFECQFDDESATVVDFLRRWIAFAQSIISTSPQ |
| 171 | mIgG2a<br>L234A_L235A_P329G<br>IL-<br>2v-R52G_F56A_E76A_C140A | GPTIKPCPPCKCPAPNAAGGPSVFIFPPKIKDVLMISLSPIVTCVVVDVSEDDPDVQISWFVN<br>NVEVHTAQTQTHREDYNSTLRVVSALPIQHQDWMSGKEFKCKVNNKDLGAPIERTISKPKGSV<br>RAPQVYVLPPPEEEMTKKQVTLWCMVTDFMPEDIYVEWTNNGKTELNYKNTEPVLDSDGSYFM<br>YSKLRVEKKNWVERNSYSCSVVHEGLHNHHTTKSFSRTPGGGGGSGGGGSGGGGSGGGGSQQQ<br>HLEQLLMDLQELLSRMENYRNLKLPGMLTAKFYLPKQATELKDLQCLEDALGPLRHVLDLTQS<br>KSFQLEDAENFISNIRVTVVKLKGSDNTFECQFDDESATVVDFLRRWIAFAQSIISTSPQ |

e. Conjugates

Any of the IL-2v, IL-2v fusion proteins, or homodimers or heterodimers thereof, disclosed herein may be conjugated. IL-2v, IL-2v fusion proteins, or homodimers or heterodimers thereof, can be bound or attached to various molecules (e.g., labels) including without limitation macromolecular substances such as polymers (e.g., polyethylene glycol (PEG), polyethylenimine (PEI) modified with PEG (PEI-PEG), polyglutamic acid (PGA) (N-(2-Hydroxypropyl) methacrylamide (HPMA) copolymers), hyaluronic acid, radioactive materials (e.g. $^{90}Y$, $^{131}I$, $^{125}I$, $^{35}S$, $^{3}H$, $^{121}In$, $^{99}Tc$), fluorescent substances (e.g., fluorescein and rhodamine), fluorescent proteins, luminescent substances (e.g., luminol), Qdots, haptens, enzymes (e.g., glucose oxidase), metal chelates, biotin, avidin, drugs (including antiviral and anticancer drugs, described herein).

The above-described conjugated IL-2v, IL-2v fusion proteins, or homodimers or heterodimers thereof, can be prepared according to known methods, e.g., performing chemical modifications on the IL-2v, IL-2v fusion proteins, or homodimers or heterodimers thereof, described herein. In certain embodiments, the labelling moiety or therapeutic moiety is conjugated to the Fc portion of the fusion protein. Methods for modifying antibody Fc regions are well known in the art (e.g., U.S. Pat. Nos. 5,057,313 and 5,156,840).

In some embodiments, the IL-2v, IL-2v fusion proteins, or homodimers or heterodimers thereof, is conjugated to a drug or therapeutic agent. In various embodiments, the drug is a small organic compound or an inhibitory nucleic acid, e.g., a short-inhibitory RNA (siRNA), a microRNA (miRNA). In some embodiments, the drug or therapeutic agent is an anti-neoplastic agent or a chemotherapeutic agent, as known in the art and described herein. In some embodiments, the drug or therapeutic agent is a bacterial toxin, e.g., diphtheria toxin.

In some embodiments, the therapeutic agent is a small molecule immune checkpoint inhibitor, e.g., GS-4224 or GS-4416. In some embodiments, the therapeutic agent is an agonist or activator of a pattern recognition receptor (PRR), e.g., a Toll-like receptor (TLR), a RIG-I-like receptor (RLRs), a NOD-like receptors (NLR), an AIM2-like receptors (ALR), a C-type lectin receptors (CLR), a DNA receptor or an RNA receptor. In some embodiments, the therapeutic agent is an agonist or activator of a toll-like receptor (TLR), DExD/H-box helicase 58 (DDX58; a.k.a., RIG-I) or a stimulator of interferon genes (STING) receptor. In some embodiments, the TLR agonist or activator is selected from the group consisting of a TLR2 agonist, a TLR3 agonist, a TLR4 agonist, a TLR5 agonist, a TLR7 agonist, a TLR8 agonist and a TLR9 agonist. In some embodiments, the TLR7 agonist is selected from the group consisting of vesatolimod (GS-9620), DS-0509, LHC-165, TMX-101 (imiquimod), RO7020531 and JNJ-4964, and/or the TLR8 agonist is selected from the group consisting of selgantolimod (GS-9688) and/or a dual TLR7/TLR8 agonist, such as NKTR-262, telratolimod, BDB-001 and CV8102.

In some embodiments, the drug or therapeutic agent is selected from the group consisting of monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, and a duocarmycin (A, B1, B2, C1, C2, D, SA, CC-1065).

f. Homodimers

Further provided are homodimers. In some embodiments, the homodimer comprises two Fc-IL-2v fusion proteins, as described above and herein.

g. Heterodimers

Further provided are heterodimers. In various formats and configurations, the heterodimer can comprise (i) one IL-2v domain, (ii) two IL-2v domains, (iii) one IL-2v domain and an antigen binding domain, (iv) one IL-2v domain and two antigen binding domains (which bind to the same or different target antigens), or (v) two IL-2v domains and two antigen binding domains (which bind to the same or different target antigens). The heterodimers generally comprise a half-life extending moiety (e.g., an Fc domain, one or more serum albumin moieties, an albumin binding protein or peptide, an IgG, an XTEN polypeptide, a proline/alanine/serine-rich (PAS) polypeptide, an elastin-like polypeptide). In some embodiments, the heterodimers are monovalent for the IL-2v, e.g., have one IL-2v domain.

Otherwise Untargeted (IL-2βγ-Receptor Complex Targeted) Heterodimers

In some embodiments, the heterodimer comprises two IL-2v domains. Such heterodimers comprise: (i) a first Fc-IL-2v fusion protein as described herein comprising a first Fc domain, and (ii) a second Fc-IL-2v fusion protein as described herein comprising a second Fc domain. In such untargeted embodiments, the first Fc domain and the second Fc domain do not comprise or are not fused to an antigen binding domain. In such untargeted embodiments, the first Fc domain and the second Fc domain are heterodimerized.

In some embodiments, the heterodimer comprises one IL-2v domain. Such heterodimers comprise: (i) an (i.e., one) Fc-IL-2v fusion protein as described herein comprising a first Fc domain, and (ii) a second Fc domain. In such untargeted embodiments, the second Fc domain does not comprise or is not fused to an antigen binding domain. In such untargeted embodiments, the second Fc domain is "empty," but heterodimerized (e.g., using Fc substitutions) to the Fc-IL-2v fusion protein, e.g., to promote stability of the molecule and to reduce or prevent homodimerization or the assembly of a molecule having two IL-2v domains. In some embodiments, neither the first Fc domain nor the second Fc domain is fused to an antigen binding domain. Such embodiments of the heterodimer bind to a complex of interleukin 2 receptor subunit beta (IL-2RB; CD122) and interleukin 2 receptor subunit gamma (IL-2RG; CD132) with a greater affinity and/or specificity relative to any other antigen or target molecule. In some embodiments of a heterodimer having one IL-2v domain and no antigen binding domain, the heterodimer does not specifically bind to an antigen or target molecule other than the interleukin 2 receptor subunit beta (IL-2RB; CD122) or the complex of IL-2RB with the interleukin 2 receptor subunit gamma (IL-2RG; CD132). Specific binding of a heterodimer means an affinity of at least $10^7$, $10^8$, $10^9$, or $10^{10}$ $M^{-1}$. Specific binding is detectably higher in magnitude and distinguishable from non-specific binding occurring to at least one unrelated target. Specific binding can be the result of formation of bonds between particular functional groups or particular spatial fit (e.g., lock and key type) whereas nonspecific binding is usually the result of van der Waals forces.

Heterodimer Platform—First and Second Fc Domains

Generally, the heterodimers have a first Fc domain and a second Fc domain (or a first Fc region and a second Fc region), wherein the first Fc domain and the second Fc domain are different. In order to facilitate heterodimerization, in some embodiments, the first Fc domain and the second Fc domain comprise amino acid the following amino acid substitutions (EU numbering), respectively: T366W and T366S/L368A/Y407V; T366S/L368A/Y407V and T366W; T366W/S354C and T366S/L368A/Y407V/Y349C; T366S/L368A/Y407V/Y349C and T366W/S354C; S364H/F405A and Y349T/T394F; Y349T/T394F and S364H/F405A; T350V/L351Y/F405A/Y407V and T350V/T366U/K392I/T394W; T350V/T366L/K392I/T394W and T350V/

L351Y/F405A/Y407V; K360D/D399M/Y407A and E345R/Q347R/T366V/K409V; E345R/Q347R/T366V/K409V and K360D/D399M/Y407A; K409D/K392D and D399K/E356K; D399K/E356K and K409D/K392D; K360E/K409W and Q347R/D399V/F405T; Q347R/D399V/F405T and K360E/K409W; K360E/K409W/Y349C and Q347R/D399V/F405T/S354C; Q347R/D399V/F405T/S354C and K360E/K409W/Y349C; K370E/K409W and E357N/D399V/F405T; or E357N/D399V/F405T and K370E/K409W.

To promote extended serum half-life of the heterodimer, in some embodiments, one or both of the first Fc domain and the second Fc domain comprise the following amino acids at the indicated positions (EU index numbering): Tyrosine at position 252, threonine at position 254 and glutamic acid at position 256 (YTE); or Leucine at position 428 and serine at position 434 (LS).

To facilitate protein A purification of the heterodimer, in some embodiments, either the first Fc domain or the second Fc domain comprise the following amino acids at the indicated positions (EU index numbering): an arginine at position 435 and a phenylalanine at position 436. In some embodiments, either the first Fc domain or the second Fc domain an arginine at position 435 and a phenylalanine at position 436 and the T366S/L368A/Y407V amino acid substitutions.

In some embodiments, the effector functions of one or both Fc domains of the heterodimer are reduced or eliminated. In some embodiments, one or both of the first Fc domain and the second Fc domain comprise a human IgG4 isotype and comprises one or more amino acid substitutions in the Fc domain or Fc region at a residue position selected from the group consisting of: F234V, F234A, L235A, L235E, S228P, and any combination thereof, wherein the numbering of the residues is according to EU numbering. In some embodiments, one or both of the first Fc domain and the second Fc domain comprise a human IgG1 isotype and comprises one or more amino acid substitutions in the Fc region at a residue position selected from the group consisting of: L234A, L234V, L234F, L235A, L235E, P331S, and any combination thereof, wherein the numbering of the residues is according to EU numbering.

In some embodiments, the terminal Fc amino acid residue (e.g., K447) is removed or eliminated from one or both of the first Fc domain and the second Fc domain. In some embodiments, the first Fc domain and the second Fc domain comprise amino acid sequences set forth, respectively, below, or comprise amino acid sequences that are at least 80%, at least 85%, at least 90%, at least 91%, at least 92%, at least 93%, at least 94%, at least 95%, at least 96%, at least 97%, at least 98%, or at least 99% identical to the amino acid sequences set forth, respectively, below: SEQ ID NOs.: 45 and 46; SEQ ID NOs.: 47 and 48; SEQ ID NOs.: 49 and 46; SEQ ID NOs.: 45 and 51; SEQ ID NOs.: 49 and 51; SEQ ID NOs.: 52 and 48; SEQ ID NOs.: 47 and 53; SEQ ID NOs.: 52 and 53; SEQ ID NOs.: 54 and 46; SEQ ID NOs.: 45 and 55; SEQ ID NOs.: 54 and 55; SEQ ID NOs.: 56 and 48; SEQ ID NOs.: 47 and 50; SEQ ID NOs.: 56 and 50; SEQ ID NOs.: 57 and 58; SEQ ID NOs.: 59 and 60; SEQ ID NOs.: 61 and 58; SEQ ID NOs.: 57 and 62; SEQ ID NOs.: 63 and 64; SEQ ID NOs.: 65 and 60; SEQ ID NOs.: 59 and 66; SEQ ID NOs.: 67 and 68; SEQ ID NOs.: 69 and 58; SEQ ID NOs.: 57 and 70; SEQ ID NOs.: 69 and 70; SEQ ID NOs.: 71 and 60; SEQ ID NOs.: 59 and 72; or SEQ ID NOs.: 71 and 72.

In some embodiments, the heterodimer comprises a human IgG4 Fc-IL-2v fusion protein comprising an amino acid sequence selected from the group consisting of SEQ ID NOs: 75-116, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 75-116; and a second Fc region comprising an amino acid sequence selected from the group consisting of SEQ ID NOs: 46, 51 and 55, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 46, 51 and 55. In some embodiments, the second Fc region comprises an amino acid sequence of SEQ ID NO: 46, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of SEQ ID NO: 46. In some embodiments, the human IgG4 Fc-IL-2v fusion protein comprises an amino acid sequence selected from the group consisting of SEQ ID NOs: 80, 107 and 114, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 80, 107 and 114. In some embodiments, the human IgG4 Fc-IL-2v fusion protein comprises an amino acid sequence selected from the group consisting of SEQ ID NOs: 80, 107 and 114, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 80, 107 and 114; and the second Fc region comprises an amino acid sequence of SEQ ID NO: 46, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of SEQ ID NO: 46.

In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 75 and SEQ ID NO: 46; SEQ ID NO: 76 and SEQ ID NO: 46; SEQ ID NO: 77 and SEQ ID NO: 46; SEQ ID NO: 78 and SEQ ID NO: 46; SEQ ID NO: 79 and SEQ ID NO: 46; SEQ ID NO: 80 and SEQ ID NO: 46; SEQ ID NO: 81 and SEQ ID NO: 46; SEQ ID NO: 82 and SEQ ID NO: 46; SEQ ID NO: 83 and SEQ ID NO: 46; SEQ ID NO: 84 and SEQ ID NO: 46; SEQ ID NO: 85 and SEQ ID NO: 46; SEQ ID NO: 86 and SEQ ID NO: 46; SEQ ID NO: 87 and SEQ ID NO: 46; SEQ ID NO: 88 and SEQ ID NO: 46; SEQ ID NO: 89 and SEQ ID NO: 46; SEQ ID NO: 90 and SEQ ID NO: 46; SEQ ID NO: 91 and SEQ ID NO: 46; SEQ ID NO: 92 and SEQ ID NO: 46; SEQ ID NO: 93 and SEQ ID NO: 46; SEQ ID NO: 94 and SEQ ID NO: 46; SEQ ID NO: 95 and SEQ ID NO: 46; SEQ ID NO: 96 and SEQ ID NO: 46; SEQ ID NO: 97 and SEQ ID NO: 46; SEQ ID NO: 98 and SEQ ID NO: 46; SEQ ID NO: 99 and SEQ ID NO: 46; SEQ ID NO: 100 and SEQ ID NO: 46; SEQ ID NO: 101 and SEQ ID NO: 46; SEQ ID NO: 102 and SEQ ID NO: 46; SEQ ID NO: 103 and SEQ ID NO: 46; SEQ ID NO: 104 and SEQ ID NO: 46; SEQ ID NO: 105 and SEQ ID NO: 46; SEQ ID NO: 106 and SEQ ID NO: 46; SEQ ID NO: 107 and SEQ ID NO: 46; SEQ ID NO: 108 and SEQ ID NO:46; SEQ ID NO: 109 and SEQ ID NO:46; SEQ ID NO: 110 and SEQ ID NO: 46; SEQ ID NO: 111 and SEQ ID NO: 46; SEQ ID NO: 112 and SEQ ID NO: 46; SEQ ID NO: 113 and SEQ ID NO: 46; SEQ ID NO: 114 and SEQ ID NO: 46; SEQ ID NO: 115 and SEQ ID NO: 46; or SEQ ID NO: 116 and SEQ ID NO: 46. In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 80 and SEQ ID NO: 46; SEQ ID NO: 107 and SEQ ID NO: 46; or SEQ ID NO: 114 and SEQ ID NO: 46.

In some embodiments, the heterodimer comprises or consists of a human IgG4 Fc-IL-2v fusion protein comprising (i) a first amino acid sequence of SEQ ID NO: 114, or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 114; and (ii) a second Fc region comprising an amino acid sequence of SEQ ID NO: 46, or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 46. In some embodiments, the heterodimer comprises or consists of a human IgG4 Fc-IL-2v fusion protein comprising (i) a first amino acid sequence of SEQ ID NO: 114, or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 114, comprising amino acid substitutions of R38G, F42A, and E62A in IL-2 domain (i.e., the amino acid at position 281 of SEQ ID NO: 114 is G; the amino acid at position 285 of SEQ ID NO: 114 is A; and the amino acid at position 305 is A) and not comprising residues corresponding to amino acid positions 1-5 of wild-type human IL-2 (e.g., not comprising APTSS (SEQ ID NO: 163)); and (ii) a second Fc region comprising an amino acid sequence of SEQ ID NO: 46, or an amino acid sequence that is at least 80%, at least 85%, at least 90%, at least 91%, at least 92%, at least 93%, at least 94%, at least 95%, at least 96%, at least 97%, at least 98%, or at least 99% identical to SEQ ID NO: 46. In some embodiments, the heterodimer comprises or consists of a human IgG4 Fc-IL-2v fusion protein comprising (i) a first amino acid sequence of SEQ ID NO: 114, or an amino acid sequence that is at least 95%, at least 96%, at least 97%, at least 98%, or at least 99% identical to SEQ ID NO: 114, comprising amino acid substitutions of R38G, F42A, and E62A in IL-2 domain (i.e., the amino acid at position 281 of SEQ ID NO: 114 is G; the amino acid at position 285 of SEQ ID NO: 114 is A; and the amino acid at position 305 is A) and not comprising residues corresponding to amino acid positions 1-5 of wild-type human IL-2 (e.g., not comprising APTSS (SEQ ID NO: 163)); and (ii) a second Fc region comprising an amino acid sequence of SEQ ID NO: 46, or an amino acid sequence that is at least 95%, at least 96%, at least 97%, at least 98%, or at least 99% identical to SEQ ID NO: 46. In some embodiments, the heterodimer comprises or consists of a human IgG4 Fc-IL-2v fusion protein comprising (i) a first amino acid sequence of SEQ ID NO: 114; and (ii) a second Fc region comprising an amino acid sequence of SEQ ID NO: 46. In some embodiments, the heterodimer does not specifically bind any antigen other than an Fc receptor or a complex of interleukin 2 receptor subunit beta (IL-2RB; CD122) and interleukin 2 receptor subunit gamma (IL-2RG; CD132). In some embodiments, the heterodimer does not comprise an immunoglobulin antigen binding domain (i.e., does not comprise immunoglobulin heavy or light chain variable regions, i.e., no VH or VL). In some embodiments, the IL-2 domain does not comprise amino acid substitutions relative to wild-type human IL-2 other than or in addition to R38G, F42A, E62A and C125S.

In some embodiments, the heterodimer comprises a human IgG1 Fc-IL-2v fusion protein comprising an amino acid sequence selected from the group consisting of SEQ ID NOs: 119-160, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 119-160; and a second Fc region comprising an amino acid sequence selected from the group consisting of SEQ ID NOs: 58, 62 and 70, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 58, 62 and 70. In some embodiments, the second Fc region comprises an amino acid sequence of SEQ ID NO: 58, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of SEQ ID NO: 58. In some embodiments, the human IgG1 Fc-IL-2v fusion protein comprises an amino acid sequence selected from the group consisting of SEQ ID NOs: 124, 151 and 158, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 124, 151 and 158. In some embodiments, the human IgG1 Fc-IL-2v fusion protein comprises an amino acid sequence selected from the group consisting of SEQ ID NOs: 124, 151 and 158, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence selected from the group consisting of SEQ ID NOs: 124, 151 and 158, and the second Fc region comprises an amino acid sequence of SEQ ID NO: 58, or an amino acid sequence that is at least 80%, at least 85%, at least 90%, at least 91%, at least 92%, at least 93%, at least 94%, at least 95%, at least 96%, at least 97%, at least 98%, or at least 99% identical to an amino acid sequence of SEQ ID NO: 58.

In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 119 and SEQ ID NO: 58; SEQ ID NO: 120 and SEQ ID NO: 58; SEQ ID NO: 121 and SEQ ID NO: 58; SEQ ID NO: 122 and SEQ ID NO: 58; SEQ ID NO: 123 and SEQ ID NO: 58; SEQ ID NO: 124 and SEQ ID NO: 58; SEQ ID NO: 125 and SEQ ID NO: 58; SEQ ID NO: 126 and SEQ ID NO: 58; SEQ ID NO: 127 and SEQ ID NO: 58; SEQ ID NO: 128 and SEQ ID NO: 58; SEQ ID NO: 129 and SEQ ID NO: 58; SEQ ID NO: 130 and SEQ ID NO: 58; SEQ ID NO: 131 and SEQ ID NO: 58; SEQ ID NO: 132 and SEQ ID NO: 58; SEQ ID NO: 133 and SEQ ID NO: 58; SEQ ID NO: 134 and SEQ ID NO: 58; SEQ ID NO: 135 and SEQ ID NO: 58; SEQ ID NO: 136 and SEQ ID NO: 58; SEQ ID NO: 137 and SEQ ID NO: 58; SEQ ID NO: 138 and SEQ ID NO: 58; SEQ ID NO: 139 and SEQ ID NO: 58; SEQ ID NO: 140 and SEQ ID NO: 58; SEQ ID NO: 141 and SEQ ID NO: 58; SEQ ID NO: 142 and SEQ ID NO: 58; SEQ ID NO: 143 and SEQ ID NO: 58; SEQ ID NO: 144 and SEQ ID NO: 58; SEQ ID NO: 145 and SEQ ID NO: 58; SEQ ID NO: 146 and SEQ ID NO: 58; SEQ ID NO: 147 and SEQ ID NO: 58; SEQ ID NO: 148 and SEQ ID NO: 58; SEQ ID NO: 149 and SEQ ID NO: 58; SEQ ID NO: 150 and SEQ ID NO: 58; SEQ ID NO: 151 and SEQ ID NO: 58; SEQ ID NO: 152 and SEQ ID NO: 58; SEQ ID NO: 153 and SEQ ID NO: 58; SEQ ID NO: 154 and SEQ ID NO: 58; SEQ ID NO: 155 and SEQ ID NO: 58; SEQ ID NO: 156 and SEQ ID NO: 58; SEQ ID NO: 157 and SEQ ID NO: 58; SEQ ID NO: 158 and SEQ ID NO: 58; SEQ ID NO: 159 and SEQ ID NO: 58; or SEQ ID NO: 160 and SEQ ID NO: 58. In some embodiments, the heterodimer comprises a human IgG4 Fc-IL-2v fusion protein comprising (i) a first amino acid sequence as set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a first amino acid sequence set forth below; and (ii) a second Fc region comprising a second amino acid sequence set forth below, or an amino acid sequence that is at least 80%, at least 85%, at least 90%, at least 91%, at least 92%, at least 93%, at least 94%, at least 95%, at least 96%, at least 97%, at least 98%, or at least 99% identical to a second amino acid sequence set forth below, respectively: SEQ ID NO: 124 and SEQ ID NO: 58; SEQ ID NO: 151 and SEQ ID NO: 58; or SEQ ID NO: 158 and SEQ ID NO: 58.

Polypeptide sequences of illustrative first and second Fc domain pairs are provided in Table E.

TABLE E

Fc regions - Heterodimeric pairs

| Fc aa subst | SEQ ID NO: | First Fc region | Fc aa subst | SEQ ID NO: | Second Fc region |
|---|---|---|---|---|---|
| IgG4 variants | | | | | |
| S228P, F234A, L235A, + T366W | 45 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLG | S228P, F234A, L235A, T366S, L368A, Y407V, H435R, Y436F | 46 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSLGK |
| S228P, F234A, L235A, T366S, L368A, Y407V, H435R, Y436F | 47 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSLG | S228P, F234A, L235A, T366W | 48 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLGK |
| S228P, F234A, L235A, T366W, M252Y, S254T, T256E | 49 | ESKYGPPCPPCPAPEAAGGPSVFLFPPKPKDTLYITREPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLG | S228P, F234A, L235A, T366S, L368A, Y407V, H435R, Y436F | 46 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSLGK |
| S228P, F234A, L235A, T366W | 45 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWES | S228P, F234A, L235A, M252Y, S254T, | 51 | ESKYGPPCPPCPAPEAAGGPSVFLFPPKPKDTLYITREPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVL |

TABLE E-continued

| Fc regions - Heterodimeric pairs | | | | | |
|---|---|---|---|---|---|
| Fc aa subst | SEQ ID NO: | First Fc region | Fc aa subst | SEQ ID NO: | Second Fc region |
| | | NGQPENNYKTTPPVLDSDGSFFLYSRLTVDKSR WQEGNVFSCSVMHEALHNHYTQKSLSLSLG | T256E, T366S, L368A, Y407V, H435R, Y436F | | DSDGSFFLVSRLTVDKSRWQEGNVFSCSVMHEALHN RFTQKSLSLSLGK |
| S228P, F234A, L235A, M252Y, S254T, T256E, T366W | 49 | ESKYGPPCPPCPAPEAAGGPSVFLFPPKPKDTL YITREPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLWCLVKGFYPSDIAVEWES NGQPENNYKTTPPVLDSDGSFFLYSRLTVDKSR WQEGNVFSCSVMHEALHNHYTQKSLSLSLG | S228P, F234A, L235A, M252Y, S254T, T256E T366S, L368A, Y407V, H435R, Y436F | 51 | ESKYGPPCPPCPAPEAAGGPSVFLFPPKPKDTLYIT REPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLSCAVKGFYPSDIAVEWESNGQPENNYKTTPPVL DSDGSFFLVSRLTVDKSRWQEGNVFSCSVMHEALHN RFTQKSLSLSLGK |
| S228P, F234A, L235A, M252Y, S254T, T256E, T366S, L368A, Y407V, H435R, Y436F, | 52 | ESKYGPPCPPCPAPEAAGGPSVFLFPPKPKDTL YITREPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLSCAVKGFYPSDIAVEWES NGQPENNYKTTPPVLDSDGSFFLVSRLTVDKSR WQEGNVFSCSVMHEALHNRFTQKSLSLSLG | S228P, F234A, L235A, T366W | 48 | ESKYGPPCPPCPAPEAAGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLWCLVKGFYPSDIAVEWESNGQPENNYKTTPPVL DSDGSFFLYSRLTVDKSRWQEGNVFSCSVMHEALHN HYTQKSLSLSLGK |
| S228P, F234A, L235A, T366S, L368A, Y407V, H435R, Y436F | 47 | ESKYGPPCPPCPAPEAAGGPSVFLFPPKPKDTL MISRTPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLSCAVKGFYPSDIAVEWES NGQPENNYKTTPPVLDSDGSFFLVSRLTVDKSR WQEGNVFSCSVMHEALHNRFTQKSLSLSLG | S228P, F234A, L235A, M252Y, S254T, T256E, T366W | 53 | ESKYGPPCPPCPAPEAAGGPSVFLFPPKPKDTLYIT REPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLWCLVKGFYPSDIAVEWESNGQPENNYKTTPPVL DSDGSFFLYSRLTVDKSRWQEGNVFSCSVMHEALHN HYTQKSLSLSLGK |
| S228P, F234A, L235A, M252Y, S254T, T256E, T366S, L368A, Y407V, H435R, Y436F | 52 | ESKYGPPCPPCPAPEAAGGPSVFLFPPKPKDTL YITREPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLSCAVKGFYPSDIAVEWES NGQPENNYKTTPPVLDSDGSFFLVSRLTVDKSR WQEGNVFSCSVMHEALHNRFTQKSLSLSLG | S228P, F234A, L235A, M252Y, S254T, T256E, T366W | 53 | ESKYGPPCPPCPAPEAAGGPSVFLFPPKPKDTLYIT REPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLWCLVKGFYPSDIAVEWESNGQPENNYKTTPPVL DSDGSFFLYSRLTVDKSRWQEGNVFSCSVMHEALHN HYTQKSLSLSLGK |
| S228P, F234A, L235A, T366W, M428L, N434S | 54 | ESKYGPPCPPCPAPEAAGGPSVFLFPPKPKDTL MISRTPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLWCLVKGFYPSDIAVEWES NGQPENNYKTTPPVLDSDGSFFLYSRLTVDKSR WQEGNVFSCSVLHEALHSHYTQKSLSLSLG | S228P, F234A, L235A, T366S, L368A, Y407V, H435R, Y436F, | 46 | ESKYGPPCPPCPAPEAAGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLSCAVKGFYPSDIAVEWESNGQPENNYKTTPPVL DSDGSFFLVSRLTVDKSRWQEGNVFSCSVMHEALHN RFTQKSLSLSLGK |
| S228P, F234A, L235A, T366W | 45 | ESKYGPPCPPCPAPEAAGGPSVFLFPPKPKDTL MISRTPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT LPPSQEEMTKNQVSLWCLVKGFYPSDIAVEWES NGQPENNYKTTPPVLDSDGSFFLYSRLTVDKSR WQEGNVFSCSVMHEALHNHYTQKSLSLSLG | S228P, F234A, L235A, T366S, L368A, Y407V, M428L, N434S | 55 | ESKYGPPCPPCPAPEAAGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ VSLSCAVKGFYPSDIAVEWESNGQPENNYKTTPPVL DSDGSFFLVSRLTVDKSRWQEGNVFSCSVLHEALHS RFTQKSLSLSLGK |
| S228P, F234A, L235A, T366W, | 54 | ESKYGPPCPPCPAPEAAGGPSVFLFPPKPKDTL MISRTPEVTCVVVDVSQEDPEVQFNWYVDGVEV HNAKTKPREEQFNSTYRVVSVLTVLHQDWLNGK EYKCKVSNKGLPSSIEKTISKAKGQPREPQVYT | S228P, F234A, L235A, T366S, | 55 | ESKYGPPCPPCPAPEAAGGPSVFLFPPKPKDTLMIS RTPEVTCVVVDVSQEDPEVQFNWYVDGVEVHNAKTK PREEQFNSTYRVVSVLTVLHQDWLNGKEYKCKVSNK GLPSSIEKTISKAKGQPREPQVYTLPPSQEEMTKNQ |

TABLE E-continued

| Fc aa subst | SEQ ID NO: | First Fc region | Fc aa subst | SEQ ID NO: | Second Fc region |
|---|---|---|---|---|---|
| Fc regions - Heterodimeric pairs | | | | | |
| M428L, N434S | | LPPSQEEMTKNQVSLWCLVKGFYPSDIAVEWESNGQPENNYKTTPPVLDSDGSFFLYSRLTVDKSRWQEGNVFSCSVLHEALHSHYTQKSLSLSLG | L368A, Y407V, M428L, N434S | | VSLSCAVKGFYPSDIAVEWESNGQPENNYKTTPPVLDSDGSFFLVSRLTVDKSRWQEGNVFSCSVLHEALHSRFTQKSLSLSLGK |
| S228P, F234A, L235A, T366S, L368A, Y407V, M428L, N434S, H435R, Y436F, | 56 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVLHEALHSRFTQKSLSLSLG | S228P, F234A, L235A, T366W | 48 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVMHEALHNHYTQKSLSLSLGK |
| S228P, F234A, L235A, T366S, L368A, Y407V, H435R, Y436F | 47 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVMHEALHNRFTQKSLSLSLG | S228P, F234A, L235A, T366W, M428L, N434S | 50 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVLHEALHSHYTQKSLSLSLGK |
| S228P, F234A, L235A, T366S, L368A, Y407V, M428L, N434S, H435R, Y436F | 56 | ESKYGPPCPPCPAPEAAGGPSVFLFPPKPKDTLMISRTPEVICVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLSCAVKGFYPSDIAVEWESNGQPENNYKTTPPVLDSDGSFFLVSRLTVDKSRWQEGNVFSCSVLHEALHSRFTQKSLSLSLG | S228P, F234A, L235A, T366W, M428L, N434S | 50 | ESKYGPPCPPCPAPEAAGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLWCLVKGFYPSDIAVEWESNGQPENNYKTTPPVLDSDGSFFLYSRLTVDKSRWQEGNVFSCSVLHEALHSHYTQKSLSLSLGK |
| IgG1 variants | | | | | |
| L234A, L235A, P331S, T366W | 57 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG | L234A, L235A, P331S, T366S, L368A, Y407V, H435R, Y436F | 58 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPGK |
| L234A, L235A, P331S, T366S, L368A, Y407V, H435R, Y436F | 59 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPG | L234A, L235A, P331S, T366W | 60 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| L234A, L235A, P331S, M252Y, S254T, T256E, T366W | 61 | EPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG | L234A, L235A, P331S, T366S, L368A, Y407V, H435R, Y436F | 58 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPGK |
| L234A, L235A, P331S, T366W | 57 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG | L234A, L235A, P331S, M252Y S254T, T256E, T366S, L368A, Y407V, | 62 | EPKSCDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPGK |

TABLE E-continued

| Fc regions - Heterodimeric pairs | | | | | |
|---|---|---|---|---|---|
| Fc aa subst | SEQ ID NO: | First Fc region | Fc aa subst | SEQ ID NO: | Second Fc region |
| | | | H435R, Y436F | | |
| L234A, L235A, P331S, M252Y S254T, T256E, T366W | 63 | EPKSCDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPG | L234A, L235A, P331S, M252Y, S254T, T256E, T366S, L368A, Y407V, H435R, Y436F | 64 | EPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNRFTQKSLSLSPGK |
| L234A, L235A, P331S, M252Y, S254T, T256E, T366S, L368A, Y407V | 65 | EPKSCDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPG | L234A, L235A, P331S, T366W | 60 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| L234A, L235A, P331S, T366S, L368A, Y407V, H435R, Y436F | 59 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPG | L234A, L235A, P331S, M252Y, S254T, T256E, T366W, | 66 | EPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| L234A, L235A, P331S, M252Y S254T, T256E, T366S, L368A, Y407V, H435R, Y436F | 67 | EPKSSDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNRFTQKSLSLSPG | L234A, L235A, P331S, M252Y, S254T, T256E, T366W | 68 | EPKSCDKTHTCPPCPAPEAAGGPSVFLFPPKPKDTLYITREPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNHYTQKSLSLSPGK |
| L234A, L235A, P331S, T366W, M428L, N434S | 69 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVLHEALHSHYTQKSLSLSPG | L234A, L235A, P331S, T366S, L368A, Y407V, H435R, Y436F, | 58 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPGK |
| L234A, L235A, P331S, T366W | 57 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPG | L234A, L235A, P331S, T366S, L368A, Y407V, M428L, N434S, H435R Y436F | 70 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVLHEALHSRFTQKSLSLSPGK |
| L234A, L235A, P331S, T366W, M428L, N434S | 69 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVLHEALHSHYTQKSLSLSPG | L234A, L235A, P331S, T366S, L368A, Y407V, M428L, N434S, | 70 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVLHEALHSRFTQKSLSLSPGK |

TABLE E-continued

Fc regions - Heterodimeric pairs

| Fc aa subst | SEQ ID NO: | First Fc region | Fc aa subst | SEQ ID NO: | Second Fc region |
|---|---|---|---|---|---|
| | | | H435R, Y436F | | |
| L234A, L235A, P331S, T366S, L368A, Y407V, M428L, N434S, H435R, Y436F | 71 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVLHEALHSRFTQKSLSLSPG | L234A, L235A, P331S, T366W | 60 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVMHEALHNHYTQKSLSLSPGK |
| L234A, L235A, P331S, T366S, L368A, Y407V, H435R, Y436F | 59 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVMHEALHNRFTQKSLSLSPG | L234A, L235A, P331S, T366W, M428L, N434S | 72 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVLHEALHSHYTQKSLSLSPGK |
| L234A, L235A, P331S, T366S, L368A, Y407V, M428L, N434S, H435R, Y436F | 71 | EPKSCDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLSCAVKGFYPSDIAVEWESNGQPENNYKTTPPVLDSDGSFFLVSKLTVDKSRWQQGNVFSCSVLHEALHSRFTQKSLSLSPG | L234A, L235A, P331S, T366W, M428L, N434S | 72 | EPKSSDKTHTCPPCPAPEAAGGPSVFLFPPKPKDTLMISRTPEVTCVVVDVSHEDPEVKFNWYVDGVEVHNAKTKPREEQYNSTYRVVSVLTVLHQDWLNGKEYKCKVSNKALPASIEKTISKAKGQPREPQVYTLPPSREEMTKNQVSLWCLVKGFYPSDIAVEWESNGQPENNYKTTPPVLDSDGSFFLYSKLTVDKSRWQQGNVFSCSVLHEALHSHYTQKSLSLSPGK |

As appropriate, one or both of the polypeptide comprising the first Fc domain and/or the polypeptide comprising the second Fc domain can comprise an N-terminal signal peptide or leader sequence. In embodiments, where both the first Fc domain and/or the polypeptide comprising the second Fc domain can comprise an N-terminal signal peptide or leader sequence, the first N-terminal signal peptide or leader sequence and the second first N-terminal signal peptide or leader sequence can be the same or different.

Targeted Heterodimers

Further provided are targeted heterodimers. In some embodiments, the targeted heterodimers comprise a single Fc-IL-2v fusion protein dimerized with a fusion protein comprising second Fc domain fused to an antigen binding domain. In some embodiments, the targeted heterodimers comprise a first fusion protein comprising an antigen binding domain fused to a Fc-IL-2v fusion protein comprising a first Fc domain dimerized with a second fusion protein comprising a second antigen binding domain fused to a second Fc domain. In some embodiments, the targeted heterodimers comprise a first fusion protein comprising a first antigen binding domain fused to a first Fc-IL-2v fusion protein dimerized with a second fusion protein comprising a second antigen binding domain fused to a second Fc-IL-2v fusion protein. Targeted heterodimer embodiments comprising first and second antigen binding domains can be bi-specific, binding first and second target molecules, wherein the target molecules are the same or different.

As appropriate, the first and/or the second Fc domain can be fused to an antigen binding domain directly or via a linker and/or hinge region. In some embodiments, the fusion protein comprising the second Fc domain fused to an antigen binding domain comprises in sequential order from N-terminus to C-terminus, the antigen binding domain and the Fc region. In some embodiments, the fusion protein comprising the second Fc domain fused to an antigen binding domain comprises in sequential order from N-terminus to C-terminus, the Fc region and the antigen binding domain. Such targeted heterodimers usually comprise a single antigen binding domain. In heterodimers comprising a second antigen binding domain, the second antigen binding domain can be fused to the N-terminal end of the Fc-IL-2v fusion protein. Heterodimers having one or two (first and second) antigen binding domains allows for directing the IL-2v to the vicinity of an antigen or target of interest. The targeted IL-2v heterodimers are useful in several therapeutic area contexts, including anticancer and antiviral (e.g., hepatitis B virus (HBV; NCBI:txid10407); human immunodeficiency virus (HIV; e.g., HIV-1; NCBI:txid11676); a Herpesviridae (NCBI:txid10292), including a herpes simplex virus (HSV) including HSV-1 (NCBI:txid102980) and HSV-2 (NCBI:txid10310); a cytomegalovirus (CMV; NCBI:txid10358); Varicella-zoster virus (VZV; NCBI:txid10335); Epstein-Barr virus (EBV; NCBI:txid10376)); severe acute respiratory syndrome (SARS)-related coronaviruses (NCBI:txid694009), including SARS-CoV2 (NCBI:txid2697049)).

In some embodiments, the targeting moiety or domain comprises an antibody fragment. "Antibody fragments" comprise a portion of an intact antibody, for example, the antigen-binding or variable region of the intact antibody. Examples of antibody fragments include single-chain antibody molecules (e.g., scFv); sc(Fv)2, Fab, F(ab)2, Fab', F(ab')2, Facb, and Fv fragments; diabodies; linear antibodies (e.g., Zapata et al., Protein Eng. 8(10): 1057-1062 (1995)); and multispecific antibodies formed from antibody fragments. "Single-chain Fv" or "scFv" or "sFv" antibody fragments comprise the heavy chain variable region (VH) and light chain variable region (VL) domains of antibody, wherein these domains are present in a single polypeptide chain. The VH and VL are generally linked by a peptide linker. In other examples, the linker can be a single amino acid. In some examples, the linker can be a chemical bond. The VHs and VLs can be arranged in any order. Examples of arrangements include: [VH] linker [VL]; or [VL] linker [VH]. see e.g., Huston et al., Proc. Natl. Acad. Sci. U.S.A., 85:5879-5883 (1988); and Plückthun, "The Pharmacology of Monoclonal Antibodies" Vol. 113, Ed Resenburg and Moore, Springer Verlag, New York, pp. 269-315, (1994). In some embodiments, the antibody fragment comprises a Fab or a single-chain variable fragment (scFv).

In some embodiments, the targeting moiety or antigen binding domain comprises a non-immunoglobulin or antibody mimetic protein. Examples of non-immunoglobulin or antibody mimetic protein targeting moieties or domains include without limitation adnectins, affibody molecules, affilins, affimers, affitins, alphabodies, anticalins, peptide aptamers, armadillo repeat proteins (ARMs), atrimers, avimers, designed ankyrin repeat proteins (DARPins®), fynomers, knottins, Kunitz domain peptides, monobodies, and nanoCLAMPs. Non-immunoglobulin or antibody mimetic protein targeting moieties or domains of use in the herein described IL-2v fusion protein heterodimers are described, e.g., in Zhang, et al., Methods Mol Biol. 2017; 1575:3-13; Ta, et al., Future Med Chem. 2017 August; 9(12):1301-1304; Yu, et al., Annu Rev Anal Chem (Palo Alto Calif.). 2017 Jun. 12; 10(1):293-320; Baloch, et al., Crit Rev Biotechnol. 2016; 36(2):268-75; and Bruce, et al., Chembiochem. 2016 Oct. 17; 17(20):1892-1899. In some embodiments, the targeting moiety or antigen binding domain is a peptide, e.g., a cyclic or cyclized peptide. In some embodiments, the targeting moiety or antigen binding domain is from the extracellular domain of a cell surface receptor.

In some embodiments, the targeting moiety or antigen binding domain has T-cell receptor (TCR)-like binding properties, and binds to an epitope of a target (e.g., a tumor-associated antigen (TAA) or an intracellularly expressed viral protein) presented in a major histocompatibility complex (MHC) molecule.

Therapeutic Areas Benefitting from Immune Stimulation

In some embodiments, the first and/or second antigen binding domain binds to CD8a molecule (CD8A; (NCBI Gene ID: 925; CD8, Leu2, p32) and competes with or comprises VH and VL regions from an antibody selected from the group IAB22M2C, OKT8.

Immune Checkpoint Proteins

Antigen targets useful in several therapeutic area contexts, including the prevention and treatment of cancer and viral infections, include immune checkpoint proteins. Accordingly, in some embodiments, the first and/or second antigen binding domain binds to an immune checkpoint protein. Examples of immune checkpoint proteins or receptors include without limitation CD27 (NCBI Gene ID: 939); CD70 (NCBI Gene ID: 970); CD40 (NCBI Gene ID: 958); CD40LG (NCBI Gene ID: 959); CD47 (NCBI Gene ID: 961); CD48 (SLAMF2; NCBI Gene ID: 962); transmembrane and immunoglobulin domain containing 2 (TMIGD2, CD28H; NCBI Gene ID: 126259); CD84 (LY9B, SLAMF5; NCBI Gene ID: 8832); CD96 (NCBI Gene ID: 10225); CD160 (a.k.a., NK1, NK28, BY55; NCBI Gene ID: 11126); MS4A1 (CD20; NCBI Gene ID: 931); CD244 (SLAMF4; NCBI Gene ID: 51744); CD276 (B7H3; NCBI Gene ID: 80381); V-set domain containing T cell activation inhibitor 1 (VTCN1, B7H4; NCBI Gene ID: 79679); V-set immunoregulatory receptor (VSIR, B7H5, VISTA; NCBI Gene ID: 64115); immunoglobulin superfamily member 11 (IGSF11, VSIG3; NCBI Gene ID: 152404); natural killer cell cytotoxicity receptor 3 ligand 1 (NCR3LG1, B7H6; NCBI Gene ID: 374383); HERV-H LTR-associating 2 (HHLA2, B7H7; NCBI Gene ID: 11148); inducible T cell co-stimulator (ICOS, CD278; NCBI Gene ID: 29851); inducible T cell co-stimulator ligand (ICOSLG, B7H2; NCBI Gene ID: 23308); TNF receptor superfamily member 4 (TNFRSF4, OX40; NCBI Gene ID: 7293); TNF superfamily member 4 (TNFSF4, OX40L; NCBI Gene ID: 7292); TNFRSF8 (CD30; NCBI Gene ID: 943); TNFSF8 (CD30L; NCBI Gene ID: 944); TNFRSF10A (CD261, DR4, TRAILR1; NCBI Gene ID: 8797); TNFRSF9 (CD137; NCBI Gene ID: 3604); TNFSF9 (CD137L; NCBI Gene ID: 8744); TNFRSF10B (CD262, DR5, TRAILR2; NCBI Gene ID: 8795); TNFRSF10 (TRAIL; NCBI Gene ID: 8743); TNFRSF14 (HVEM, CD270; NCBI Gene ID: 8764); TNFSF14 (HVEML; NCBI Gene ID: 8740); CD272 (B and T lymphocyte associated (BTLA); NCBI Gene ID: 151888); TNFRSF17 (BCMA, CD269; NCBI Gene ID: 608); TNFSF13B (BAFF; NCBI Gene ID: 10673); TNFRSF18 (GITR; NCBI Gene ID: 8784); TNFSF18 (GITRL; NCBI Gene ID: 8995); MHC class I polypeptide-related sequence A (MICA; NCBI Gene ID: 100507436); MHC class I polypeptide-related sequence B (MICB; NCBI Gene ID: 4277); CD274 (CD274, PDL1, PD-L1; NCBI Gene ID: 29126); programmed cell death 1 (PDCD1, PD1, PD-1; NCBI Gene ID: 5133); cytotoxic T-lymphocyte associated protein 4 (CTLA4, CD152; NCBI Gene ID: 1493); CD80 (B7-1; NCBI Gene ID: 941); CD28 (NCBI Gene ID: 940); nectin cell adhesion molecule 2 (NECTIN2, CD112; NCBI Gene ID: 5819); CD226 (DNAM-1; NCBI Gene ID: 10666); Poliovirus receptor (PVR) cell adhesion molecule (PVR, CD155; NCBI Gene ID: 5817); PVR related immunoglobulin domain containing (PVRIG, CD112R; NCBI Gene ID: 79037); T cell immunoreceptor with Ig and ITIM domains (TIGIT; NCBI Gene ID: 201633); T cell immunoglobulin and mucin domain containing 4 (TIMD4; TIM4; NCBI Gene ID: 91937); hepatitis A virus cellular receptor 2 (HAVCR2, TIMD3, TIM3; TIM-3; NCBI Gene ID: 84868); galectin 9 (LGALS9; NCBI Gene ID: 3965); lymphocyte activating 3 (LAG3, LAG-3; CD223; NCBI Gene ID: 3902); signaling lymphocytic activation molecule family member 1 (SLAMF1, SLAM, CD150; NCBI Gene ID: 6504); lymphocyte antigen 9 (LY9, CD229, sialic acid binding Ig like lectin 7 (SIGLEC7; p75; QA79; AIRM1; CD328; CDw328; D-siglec; SIGLEC-7; SIGLECP2; SIGLEC19P; p75/AIRM1; NCBI Gene ID: 27036); sialic acid binding Ig like lectin 9 (SIGLEC9; CD329; CDw329; FOAP-9; siglec-9; OBBP-LIKE; NCBI Gene ID: 27180); SLAMF3; NCBI Gene ID: 4063); SLAM family member 6 (SLAMF6, CD352; NCBI Gene ID: 114836); SLAM family member 7 (SLAMF7, CD319; NCBI Gene ID: 57823); UL16 binding protein 1 (ULBP1; NCBI Gene ID: 80329); UL16 binding protein 2 (ULBP2; NCBI Gene ID: 80328); UL16 binding protein 3 (ULBP3; NCBI Gene ID: 79465); retinoic acid early transcript 1E (RAET1E; ULBP4; NCBI Gene ID: 135250); retinoic acid early transcript 1G (RAET1G; ULBP5; NCBI Gene ID: 353091); retinoic acid early transcript 1L (RAET1L; ULBP6; NCBI Gene ID: 154064); killer cell lectin like receptor C1 (KLRC1, NKG2A, CD159A; NCBI Gene ID: 3821); killer cell lectin like receptor K1 (KLRK1, NKG2D, CD314; NCBI Gene ID: 22914); killer cell lectin like receptor C2 (KLRC2, CD159c, NKG2C; NCBI Gene ID: 3822); killer cell lectin like receptor C3 (KLRC3, NKG2E; NCBI Gene ID: 3823); killer cell lectin like receptor C4 (KLRC4, NKG2F; NCBI Gene ID: 8302); killer cell lectin like receptor D1 (KLRD1; NCBI Gene ID: 3824); killer cell lectin like receptor G1 (KLRG1; 2F1; MAFA; MAFA-L; CLEC15A; MAFA-2F1; MAFA-LIKE; NCBI Gene ID: 10219); killer cell immunoglobulin like receptor, two Ig domains and long cytoplasmic tail 1 (KIR2DL1; NCBI Gene ID: 3802); killer cell immunoglobulin like receptor, two Ig domains and long cytoplasmic tail 2 (KIR2DL2; NCBI Gene ID: 3803); killer cell immunoglobulin like receptor, two Ig domains and long cytoplasmic tail 3 (KIR2DL3; NCBI Gene ID: 3804); and killer cell immunoglobulin like receptor, three Ig domains and long cytoplasmic tail 1 (KIR3DL1, KIR, CD158E1; NCBI Gene ID: 3811) (e.g., Lirilumab (IPH2102/BMS-986015), IPH-4102).

Co-Inhibitory Checkpoint Proteins

In some embodiments, the first and/or second antigen binding domain binds to CTLA4 and competes with or comprises VH and VL regions from an antibody selected from the group ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN2041, JHL-1155, KN-044, CG-0161, ATOR-1144, PBI-5D3H5, BPI-002, HBM-4003, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

In some embodiments, the first and/or second antigen binding domain binds to programmed cell death 1 (PDCD1; NCBI Gene ID: 5133; CD279, PD-1, PD1) and competes with or comprises VH and VL regions from an antibody selected from zimberelimab (AB122, GLS-010, WBP-3055), pembrolizumab (KEYTRUDA®, MK-3475, SCH900475), nivolumab (OPDIVO®, BMS-936558, MDX-1106), cemiplimab (LIBTAYO®; cemiplimab-rwlc, REGN-2810), pidilizumab (CT-011), AMG-404, MEDI0680 (AMP-514), spartalizumab (PDR001), tislelizumab (BGB-A317), toripalimab (JS-001), genolimzumab (CBT-501, APL-501, GB 226), SHR-1201, camrelizumab (SHR-1210), sintilimab (TYVYT®; IBI-308), dostarlimab (TSR-042, WBP-285), lambrolizumab (MK-3475); sasanlimab (PF-06801591), cetrelimab (JNJ-63723283), serplulimab (HLX-10), retifanlimab (MGA-012), balstilimab (AGEN2034), prolgolimab (BCD 100), budigalimab (ABBV-181), vopratelimab (JTX-4014), AK-103 (HX-008), AK-105, CS-1003, BI-754091, LZM-009, Sym-021, BAT-1306, PD1-PIK, tebotelimab (MGD013; PD-1/LAG-3), RO-7247669 (PD-1/LAG-3), FS-118 (LAG-3/PD-L1), RO-7121661 (PD-1/TIM-3), RG7769 (PD-1/TIM-3), PF-06936308 (PD-1/CTLA4), MGD-019 (PD-1/CTLA4), KN-046 (PD-1/CTLA4), XmAb-20717 (PD-1/CTLA4), AK-104 (CTLA4/PD-1) and MEDI-5752 (CTLA4/PD-1). In some embodiments, the first and/or second antigen binding domain comprises the extracellular domain of the human programmed cell death 1 ligand 2 (PD-L2) and binds to PD1 (e.g., AMP-224).

In some embodiments, the first and/or second antigen binding domain binds to CD274 molecule (NCBI Gene ID: Gene ID: 29126; B7-H, B7H1, PD-L1) and competes with or comprises VH and VL regions from an antibody selected from atezolizumab (TECENTRIQ®), avelumab (BAVENCIO®; MSB0010718C), envafolimab (ASC22), durvalumab (IMFINZI®; MEDI-4736), BMS-936559 (MDX1105), cosibelimab (CK-301), lodapolimab (LY 3300054), garivulimab (BGB A333), envafolimab (KN035), opucolimab (HLX 20), manelimab (BCD 135), CX-072, CBT-502 (TQB2450), MSB-2311, SHR-1316, sugemalimab (CS-1001; WBP3155), A167 (KL-A167, HBM 9167), STI-A1015 (IMC-001), FAZ-053, BMS-936559 (MDX1105), INCB086550, GEN-1046 (PD-L1/4-1BB), FPT-155 (CTLA4/PD-L1/CD28), M7824 (PD-L1/TGFβ-EC domain), CA-170 (PD-L1/VISTA), CDX-527 (CD27/PD-L1), LY-3415244 (TIM-3/PDL1), INBRX-105 (4-1BB/PDL1) and GNS-1480 (PD-L1/EGFR).

In some embodiments, the first and/or second antigen binding domain binds to hepatitis A virus cellular receptor 2 (HAVCR2, TIMD3, TIM3; TIM-3) and competes with or comprises VH and VL regions from an antibody selected from the group cobolimab (TSR-022), LY-3321367, sabatolimab (MBG-453; Novartis Pharmaceuticals), INCAGN-2390, BMS-986258, BGB-A425, SHR-1702, Sym-023, RO-7121661 (a.k.a., RG-7769; PD-1/TIM-3) and LY-3415244 (TIM-3/PDL1).

In some embodiments, the first and/or second antigen binding domain binds to lymphocyte activating 3 (LAG3, LAG-3; CD223) and competes with or comprises VH and VL regions from an antibody selected from the group relatlimab (ONO-4482), LAG-525, MK-4280, REGN-3767, INCAGN2385, TSR-033, MGD-013 (PD-1/LAG-3), FS-118 (LAG-3/PD-L1) and BMS-986016 (Bristol-Myers Squibb).

In some embodiments, the first and/or second antigen binding domain binds to killer cell immunoglobulin like receptor, three Ig domains and long cytoplasmic tail 1 (KIR3DL1; KIR) and competes with or comprises VH and VL regions from an antibody selected from the group lirilumab (IPH-2102) and IPH-4102.

In some embodiments, the first and/or second antigen binding domain binds to killer cell lectin like receptor C1 (KLRC1, NKG2A, CD159A) and competes with or comprises VH and VL regions from the antibody monalizumab.

In some embodiments, the first and/or second antigen binding domain binds to PVR related immunoglobulin domain containing (PVRIG, CD112R and competes with or comprises VH and VL regions from the antibody COM-701.

In some embodiments, the first and/or second antigen binding domain binds to T cell immunoreceptor with Ig and ITIM domains (TIGIT) and competes with or comprises VH and VL regions from an antibody selected from the group etigilimab, BMS-986207, tiragolumab (a.k.a., MTIG-7192A; RG-6058; RO 7092284), vibostolimab (MK-7684), ociperlimab (BGB-A1217), domvanalimab (AB154), AGEN1307, AGEN1327, AGEN1777, COM-902, IBI-939, SGN-TGT, MG1131 and EOS884448 (EOS-448).

In some embodiments, the first and/or second antigen binding domain binds to V-set immunoregulatory receptor (VSIR, B7H5, VISTA) and competes with or comprises VH and VL regions from an antibody selected from the group CI-8993 (onvatilimab), HMBD-002 and CA-170 (PD-L1/VISTA).

Co-Stimulatory Checkpoint Proteins

In some embodiments, the first and/or second antigen binding domains comprises an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFRSF11A (CD265, RANK, NCBI Gene ID: 8792), TNFRSF11B (NCBI Gene ID: 4982), TNFRSF12A (CD266, NCBI Gene ID: 51330), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

In some embodiments, the first and/or second antigen binding domain binds to TNFRSF4 (OX40) and competes with or comprises VH and VL regions from an antibody selected from the group MEDI6469, MEDI6383, MEDI0562 (tavolixizumab), MOXR0916, PF-04518600, RG-7888, GSK-3174998, INCAGN1949, BMS-986178, GBR-8383, ABBV-368, BGB-A445, and those described in WO2016179517, WO2017096179, WO2017096182, WO2017096281, and WO2018089628.

In some embodiments, the first and/or second antigen binding domain binds to TNF receptor superfamily member 10b (TNFRSF10B, DR5, TRAILR2) and competes with or comprises VH and VL regions from an antibody selected from the group DS-8273, CTB-006, INBRX-109, GEN-1029;

In some embodiments, the first and/or second antigen binding domain binds to TNFRSF5 (CD40) and competes with or comprises VH and VL regions from an antibody selected from the group mitazalimab, RG7876, SEA-CD40, APX-005M and ABBV-428, ABBV-927, JNJ-64457107.

In some embodiments, the first and/or second antigen binding domain binds to TNFRSF7 (CD27) and competes with or comprises VH and VL regions from the antibody varlilumab (CDX-1127).

In some embodiments, the first and/or second antigen binding domain binds to TNFRSF9 (4-1BB, CD137) and competes with or comprises VH and VL regions from an antibody selected from the group urelumab, utomilumab (PF-05082566), ATOR-1017, AGEN2373, ADG-106 and QL1806.

In some embodiments, the first and/or second antigen binding domain binds to TNFRSF17 (BCMA) and competes with or comprises VH and VL regions from the antibody GSK-2857916.

In some embodiments, the first and/or second antigen binding domain binds to TNFRSF18 (GITR) and competes with or comprises VH and VL regions from an antibody selected from the group MEDI1873, FPA-154, INCAGN-1876, TRX-518, BMS-986156, MK-1248, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO2017096179 and WO2018089628.

In some embodiments, the first and/or second antigen binding domain binds to CD70 and competes with or comprises VH and VL regions from the antibody AMG-172.

In some embodiments, the first and/or second antigen binding domain binds to inducible T cell co-stimulator (ICOS, CD278) and competes with or comprises VH and VL regions from an antibody selected from the group JTX-2011 and GSK3359609.

Antiviral—HBV

In some embodiments, the first and/or second antigen binding domain binds to an antigen or target useful for the prevention or treatment of a Hepatitis B Virus (HBV) infection. Such antigens or targets include those specifically or preferentially or predominantly expressed on liver tissue and epitopes of HBV antigens presented in a major histocompatibility protein (an HBV pMHC target). Accordingly, in some embodiments, the first and/or second antigen binding domain binds to a target selected from the group consisting of: asialoglycoprotein receptor 1 (ASGR1; NCBI Gene ID: 432; ASGPR, ASGPR1, CLEC4H1, HL-1), asialoglycoprotein receptor 2 (ASGR2; NCBI Gene ID: 433; ASGP-R2, ASGPR2, CLEC4H2, HBXBP, HL-2) an ATP binding cassette (ABC) family transporter (e.g., ATP binding cassette subfamily B member 1 (ABCB1; NCBI Gene ID: 5243; ABC20, CD243, CLCS, GP170, MDR1, P-GP, PGY1), ATP binding cassette subfamily B member 4 (ABCB4; NCBI Gene ID: 5244; ABC21, GBD1, ICP3, MDR2, MDR2/3, MDR3, PFIC-3, PGY3), ATP binding cassette subfamily C member 1 (ABCC1; NCBI Gene ID: 4363; ABC29, ABCC, GS-X, MRP, MRP1), ATP binding cassette subfamily C member 2 (ABCC2; NCBI Gene ID: 1244; ABC30, CMOAT, DJS, MRP2, cMRP), ATP binding cassette subfamily C member 3 (ABCC3; NCBI Gene ID: 8714; ABC31, EST90757, MLP2, MOAT-D, MRP3, cMOAT2), ATP binding cassette subfamily C member 4 (ABCC4; NCBI Gene ID: 10257; MOAT-B, MOATB, MRP4), ATP binding cassette subfamily G member 2 (Junior blood group)(ABCG2; NCBI Gene ID: 9429; ABC15, ABCP, BCRP, BCRP1, BMDP, CD338, CDw338, EST157481, GOUT1, MRX, MXR, MXR-1, MXR1, UAQTL1), and ATP binding cassette subfamily B member 11 (ABCB11; NCBI Gene ID: 8647; ABC16, BRIC2, BSEP, PFIC-2, PFIC2, PGY4, SPGP)); a solute carrier (SLC) family transporter (e.g., solute carrier family 10 member 1 (SLC10A1; NCBI Gene ID: 6554; a.k.a., Sodium-taurocholate Co-transporting Polypeptide (NTCP)); solute carrier family 16 member 1 (SLC16A1; NCBI Gene ID: 6566; HHF7, MCT, MCT1, MCT1D), solute carrier family 22 member 1 (SLC22A1; NCBI Gene ID: 6580; HOCT1, OCT1, oct1_cds), solute carrier family 22 member 3 (SLC22A3; NCBI Gene ID: 6581; EMT, EMTH, OCT3), solute carrier family 22 member 7 (SLC22A7; NCBI Gene ID: 10864; NLT, OAT2, hOAT11), solute carrier family 27 member 5 (SLC27A5; NCBI Gene ID: 10998; ACSB, ACSVL6, BACS, BAL, FACVL3, FATP-5, FATP5, VLACSR, VLCS-H2, VLCSH2), solute carrier organic anion transporter family member 1B1 (SLCO1B1; NCBI Gene ID: 10599; HBLRR, LST-1, LST1, OATP-C, OATP1B1, OATP2, OATPC, SLC21A6), solute carrier organic anion transporter family member 1B3 (SLCO1B3; NCBI Gene ID: 28234; HBLRR, LST-2, LST-3TM13, LST3, OATP-8, OATP1B3, OATP8, SLC21A8), and solute carrier organic anion transporter family member 2B1 (SLCO2B1; NCBI Gene ID: 11309; OATP-B, OATP2B1, OATPB, SLC21A9)), transferrin receptor 2 (TFR2; NCBI Gene ID: 7036; HFE3, TFRC2), and an HBV epitope (e.g., HBV core18-27; env183-191; env 335-343; pol 575-583) presented in major histocompatibility complex (MHC) molecule (pMHC). Illustrative antigen binding domains for targeting a liver tissue antigen or an HBV antigen that can find use in the herein described heterodimers are described, e.g., in U.S. Pat. No. 9,771,427 (ASGR1); Schulze, et al., *J*

*Virol* (2010) 84: 1989-2000 (Myrcludex B peptide); WO2017102906 (cyclic NTCP-targeting peptides), He, et al., *J Virol.* (2016) Sep. 12; 90(19):8866-74 (anti-NTCP antibody); Li, et al. *eLife* (2017) 6:e26738 (anti-HBV preS1 antibody), WO2016055534 (HBV pre-S1 peptides); WO2009136874 and U.S. Pat. No. 8,603,810 (TCR-like antibody against HBV epitope core18-27), WO2011062562 and U.S. Pat. No. 9,334,317 (TCR-like antibody against HBV epitope env183-191), Sastry, et al., *J Virol.* 2011 March; 85(5):1935-42 (HBV env 183-191; WO2018056897A1 (Hepatitis B Virus (HBV) antigen specific binding molecules), WO2017059878 (describing anti-HBV antibody VIR-3434; Humabs Biomed; Vir Biotechnology) and GC-1102 (lenvervimab; Green Cross Pharma).

In some embodiments, the first and/or second antigen binding domain binds to an HBV antigen (e.g., HBsAg) and competes with or comprises VH and VL regions from an antibody selected from lenvervimab, libivirumab, exbivirumab, VIR-3434, HBV-ISS (a.k.a., HBsAg-1018, HBsAg-ISS, V-270), and combinations thereof.

Antiviral—HIV

In some embodiments, the first and/or second antigen binding domain binds to an antigen or target useful for the prevention or treatment of a Human Immunodeficiency Virus (HIV) infection, including HIV-1 and HIV-2. In some embodiments, the first and/or second antigen binding domain binds to a target selected from the group consisting of human immunodeficiency virus (HIV) gp120, HIV gp41, human CD4, and human interleukin 7 receptor (IL7R; CD127).

Antigen binding domains that bind to HIV gp120 are known in the art and can be fused to the second Fc domain in the herein described heterodimers. In some embodiments, the first and/or second antigen binding domain binds to an epitope or region of gp120 selected from the group consisting of: (i) third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. The foregoing epitopes or regions of gp120 bound by broadly neutralizing antibodies are described, e.g., in McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37, which are hereby incorporated herein by reference in their entirety for all purposes.

In some embodiments, the first and/or second antigen binding domain binds to an epitope or region of gp120 in the third variable loop (V3) and/or high mannose patch comprising a N332 oligomannose glycan and competes with or comprises VH and VL regions from an antibody selected from the group consisting of GS-9722 (elipovimab), PGT-121, PGT-121.66, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, GS-2872, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03. Additional broadly neutralizing antibodies that bind to gp120 in the third variable loop (V3) and/or high mannose patch comprising a N332 oligomannose glycan and which can be used in the first and/or second antigen binding domain of the herein described targeted heterodimers are described, e.g., in WO 2012/030904; WO 2014/063059; WO 2016/149698; WO 2017/106346; WO 2018/075564, WO 2018/125813; WO 2018/237148, WO 2019/226829, WO 2020/023827, WO2020/056145 and Kerwin, et al., *J Pharm Sci.* 2020 January; 109(1):233-246, which are hereby incorporated herein by reference in their entireties for all purposes.

In some embodiments, the first and/or second antigen binding domain binds to an epitope or region of gp120 in the second variable loop (V2) and/or Env trimer apex and competes with or comprises VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01. Additional broadly neutralizing antibodies that bind to gp120 in the second variable loop (V2) and/or Env trimer apex and which can be used in the first and/or second antigen binding domain of the herein described targeted heterodimers are described, e.g., in WO 2010/107939; WO 2012/030904; WO 2018/075564 and WO 2018/125813, which are hereby incorporated herein by reference in their entireties for all purposes.

In some embodiments, the first and/or second antigen binding domain binds to an epitope or region of gp120 in the CD4 binding site (CD4bs) and competes with or comprises VH and VL regions from an antibody selected from the group consisting of b12, F105, VRC01, VRC07, VRC07-523, VRC03, VRC06, VRC06b01 VRC08, VRC0801, NIH45-46, GS-5423, 3BNC117, 3BNC60, VRC-PG04, PGV04; CH103, 44-VRC13.01, 1NC9, 12A12, N6, N49-P7, NC-Cow1, IOMA, CH235 and CH235.12, N49P6, N49P7, N49P11, N49P9 and N60P25. Additional broadly neutralizing antibodies that bind to gp120 in the CD4 binding site (CD4bs) and which can be used in the first and/or second antigen binding domain of the herein described targeted heterodimers are described, e.g., in WO 2011/038290; WO 2012/158948; WO 2013/016468; WO 2013/192589; WO 2013/086533; WO 2015/128846; WO 2016/149698; WO 2016/149695; WO 2018/075564; WO 2018/125813; WO 2018/237357, WO 2020/010107, WO 2020/086446 and U.S. Pat. Nos. 9,493,549 and 9,879,068, which are hereby incorporated herein by reference in their entireties for all purposes.

In some embodiments, the first and/or second antigen binding domain binds to an epitope or region of gp120 in the CD4 binding site (CD4bs) and comprises an EC domain of CD4 (e.g., domain 1 (D1), D1-D2, D1-D3, or D1-D4). In some embodiments, the EC domain of CD4 comprises a sequence comprising or that is at least 80%, at least 85%, at least 90%, at least 91%, at least 92%, at least 93%, at least 94%, at least 95%, at least 96%, at least 97%, at least 98%, or at least 99% identical to a sequence selected from the group consisting of:

(i)

(SEQ ID NO: 251)

KKVVYGKKGDTVELTCTASQKKNIQFHWKNSNQIKILGNQGSFLTKGPSK

LNDRVDSRRSLWDQGNFPLIIKNLKPEDSDTYICEVEDQKEEVQLVVVG (See, e.g., Chen, et al., *J Virol.* 2014 Jan;88(2):1125-39);

(ii)

(SEQ ID NO: 252)

KKVVYGKKGDTVELTCTASQKKNIQFHWKNSNQIKILGNQGSFLTKGPSK

LNDRVDSRRSLWDQGNFPLIIKNLKPEDSDTYICEVEDQKEEVQLVVVGG

-continued

GGSGKKVVYGKKGDTVELTCTASQKKNIQFHWKNSNQIKILGNQGSFLTK

GPSKLNDRVDSRRSLWDQGNFPLIIKNLKPEDSDTYICEVEDQKEEVQLV

VVG;

(iii)

(SEQ ID NO: 253)

KKVVLGKKGDTVELTCTASQKKSIQFHWKNSNQIKILGNQGSFLTKGPSK

LNDRADSRRSLWDQGNFPLIIKNLKIEDSDTYICEVEDQKEEVQLLVFG;

or (iv)

(SEQ ID NO: 254)

KKVVLGKKGDTVELTCTASQKKSIQFHWKNSNQIKILGNQGSFLTKGPSK

LNDRADSRRSLWDQGNFPLIIKNLKIEDSDTYICEVEDQKEEVQLLVFGG

GGSGKKVVLGKKGDTVELTCTASQKKSIQFHWKNSNQIKILGNQGSFLTK

GPSKLNDRADSRRSLWDQGNFPLIIKNLKIEDSDTYICEVEDQKEEVQLL

VFG.

In some embodiments, the first and/or second antigen binding domain binds to an epitope or region of gp120 in the gp120/gp41 interface and competes with or comprises VH and VL regions from an antibody selected from the group consisting of PGT-151, CAP248-2B, 35022, 8ANC195, ACS202, VRC34 and VRC34.01. Additional broadly neutralizing antibodies that bind to gp120 in the gp120/gp41 interface and which can be used in the first and/or second antigen binding domain of the herein described targeted heterodimers are described, e.g., in WO 2011/038290; WO 2012/030904 and WO2017/079479, which are hereby incorporated herein by reference in their entireties for all purposes.

In some embodiments, the first and/or second antigen binding domain binds to an epitope or region of the gp120 silent face and competes with or comprises VH and VL regions from an antibody selected from VRC-PG05 and SF12. See, e.g., Schoofs, et al., *Immunity*. (2019) 50(6): 1513-1529.

In some embodiments, the first and/or second antigen binding domain binds to an epitope or region of gp41 in the membrane proximal region (MPER). Additional broadly neutralizing antibodies that bind to gp41 in the MPER and which can be used in the first and/or second antigen binding domain of the herein described targeted heterodimers are described, e.g., in WO 2011/034582; WO 2011/038290; WO 2011/046623 and WO 2013/070776, which are hereby incorporated herein by reference in their entireties for all purposes.

In some embodiments, the first and/or second antigen binding domain binds to an epitope or region of gp41 in the membrane proximal region (MPER) and competes with or comprises VH and VL regions from an antibody selected from the group consisting of 10E8, 10E8v4, 10E8-5R-100cF, 4E10, DH511.11P, 2F5, 7b2, and LN01.

In some embodiments, the first and/or second antigen binding domain binds to an epitope or region of the gp41 fusion peptide and competes with or comprises VH and VL regions from an antibody selected from the group consisting of VRC34 and ACS202.

In some embodiments, the first and/or second antigen binding domain binds to an epitope or region of CD4, and competes with or comprises VH and VL regions from an antibody selected from the group consisting of HuMax-CD4, UB-421, RPA-T4, SK3, MEM241, ibalizumab and OKT-4.

Antiviral—HSV

In some embodiments, the first and/or second antigen binding domain binds to an antigen or target useful for the prevention or treatment of a Herpes Simplex Virus (HIV) infection, including HSV-1 and HSV-2. In some embodiments, the first and/or second antigen binding domain binds to an HSV protein, e.g., HSV glycoprotein B (gB), glycoprotein C (gC), glycoprotein D (gD), glycoprotein E (gE), and combinations thereof. In some embodiments, the first and/or second antigen binding domain binds to an epitope or region of HSV glycoprotein B (gB), and competes with or comprises VH and VL regions from HDIT101, or mAb 2c, described in Krawczyk, et al., *J Virol*. 2011 February; 85(4):1793-803 and Krawczyk, et al., *Proc Natl Acad Sci USA*. 2013 Apr. 23; 110(17):6760-5; and U.S. Pat. Nos. 8,889,137 and 9,657,088. Additional antibodies against HSV gB that can be used in the present targeted heterodimers are described in WO2019044926. In some embodiments, the first and/or second antigen binding domain binds to an epitope or region of HSV glycoprotein D (gD), and competes with or comprises VH and VL regions from the antibody UB-621, described in Lee, et al., *Acta Crystallogr D Biol Crystallogr*. 2013 October; 69(Pt 10):1935-45 and U.S. Pat. Nos. 8,431,118 and 8,252,906. Additional antibodies against HSV gD that can be used in the present targeted heterodimers are described in WO2012139106, WO2016120410 and CN105925537A. Additional HSV-targeted antibodies that can be used in the present targeted heterodimers are described, e.g., in WO2015197763, WO2016120410, WO2018019897, WO2020041910 (antibody 14F5F6) and WO2020041911 (antibody 11B2C7).

Antiviral—Coronavirus

In some embodiments, the first and/or second antigen binding domain binds to an antigen or target useful for the prevention or treatment of a coronavirus (e.g., betacoronavirus, e.g., severe acute respiratory syndrome-related coronavirus, e.g., SARS-CoV2) infection. In some embodiments, the first and/or second antigen binding domain binds to a target antigen on a coronavirus, e.g., spike protein Si, spike protein S2. In some embodiments, the first and/or second antigen binding domain binds to an epitope or region of SARS-CoV2 spike protein S1, and competes with or comprises VH and VL regions from an antibody selected from VIR-7831 (GSK4182136); VIR-7832 (GlaxoSmithKline/Vir Biotechnology); AZD7442 (AZD8895+AZD1061) (AstraZeneca; Vanderbilt University; Chinese Academy of Sciences); (47D11 (Universiteit Utrecht; Abbvie; Harbour BioMed); JS-016 (Lilly; Beijing Institute for Microbiology; Shanghai Junshi Biosciences); REGN10933, REGN10934, REGN10987 and/or REGN10989, e.g., REGN10933 and/or REGN10987 (REGN10933 and REGN10987 also known as REGN-COV2 or REGEN-COV™ (casirivimab and imdevimab)) (Regeneron; Hansen, et al., *Science* (2020) 369(6506):1010-1014); bamlanivimab (LY-CoV555; Eli Lilly/Abcellera); JS016 (etesevimab; LY-CoV016) (Junshi Biosciences; Chinese Academy of Sciences; Eli Lilly; Amgen); bamlanivimab (LY-CoV555) and etesevimab (LY-CoV016); BRII-196 and/or BRII-198 (Brii Bio; Tsinghua University; Third People's Hospital of Shenzhen); BD-368-2 (Peking University); S-309 (Humabs); STI-4920 and/or STI-1499 (Sorrento Therapeutics); 40591-MM43 and/or 40592-MM57 (Sino Biological); TY027 (Tychan); BAT2019 and/or BAT2020 (Bio-Thera Solutions); C19-AR (Kleo Pharmaceuticals); CT-P59 (Celltrion); ACE-MAB; CMAB-020; CR3022 (a.k.a., ab273073; abcam); IgY-110 (IGY Immune Technologies & Life Sciences); and B38 and H4 (described in Wu, et al., *Science* (2020) 368(6496):1274-1278).

Anticancer

In some embodiments, the first and/or second antigen binding domain binds to an antigen or target useful for the prevention or treatment of a cancer. In some embodiments the first and/or second antigen binding domain binds to a target or tumor associated antigen (TAA) selected from the group consisting of: CD19 (NCBI Gene ID: 930; B4; CVID3); membrane spanning 4-domains A1 (MS4A1; NCBI Gene ID: 931; B1; S7; Bp35; CD20; CVID5; MS4A2; LEU-16); CD22 (NCBI Gene ID: 933; SIGLEC2; SIGLEC-2); CD27 (NCBI Gene ID: 939; T14; S152; Tp55; TNFRSF7; S152. LPFS2); TNFRSF8 (NCBI Gene ID: 943; CD30; Ki-1; DIS166E); CD33 (NCBI Gene ID: 945; p67; SIGLEC3; SIGLEC-3); CD37 (NCBI Gene ID: 951; GP52-40; TSPAN26); CD38 (NCBI Gene ID: 952; ADPRC1; ADPRC 1); CD40 (NCBI Gene ID: 958; p50; Bp50; CDW40; TNFRSF5), CD44 (NCBI Gene ID: 960; IN; LHR; MC56; MDU2; MDU3; MIC4; Pgp1; CDW44; CSPG8; HCELL; HUTCH-I; ECMR-III); CD47 (NCBI Gene ID: 961; IAP, MER6, OA3); CD48 (NCBI Gene ID: 962; BCM1; BLAST; hCD48; mCD48; BLAST1; SLAMF2; MEM-102); CD52 (NCBI Gene ID; 1043; HE5; CDW52; EDDM5); CD70 (NCBI Gene ID: 970; CD27L; LPFS3; CD27-L; CD27LG; TNFSF7; TNLG8A); 5'-nucleotidase ecto (NT5E; NCBI Gene ID: 4907; NT; eN; NT5; NTE; eNT; CD73; E5NT; CALJA), ectonucleoside triphosphate diphosphohydrolase 1 (ENTPD1; NCBI Gene ID: 953; CD39; SPG64; ATPDase; NTPDase-1), CD74 (NCBI Gene ID: 972; II; p33; DHLAG; HLADG; Ia-GAMMA); CD79b molecule (CD79B; NCBI Gene ID: 974; B29; IGB; AGM6); CD80 (NCBI Gene ID: 941; B7; BB1; B7-1; B7.1; LAB7; CD28LG; CD28LG1); CD86 (NCBI Gene ID: 942; B70; B7-2; B7.2; LAB72; CD28LG2), interleukin 3 receptor subunit alpha (IL3RA; NCBI Gene ID: 3563; IL3R; CD123; IL3RX; IL3RY; IL3RAY; hIL-3Ra), prominin 1 (PROM1; NCBI Gene ID: 8842; RP41; AC133; CD133; MCDR2; STGD4; CORD12; PROML1; MSTP061); TNF receptor superfamily member 9 (TNFRSF9; NCBI Gene ID: 3604; 4-1BB, CD137, CDw137, ILA); syndecan 1 (SDC1; NCBI Gene ID: 6382; SDC; CD138; SYND1; syndecan); CD200 molecule (CD200; NCBI Gene ID: 4345; MOX1, MOX2, MRC, OX-2); alpha fetoprotein (AFP; NCBI Gene ID: 174; AFPD, FETA, HPAFP), BAG cochaperone 6 (BAG6; NCBI Gene ID: 7917; BAG-6, BAT3, D6S52E, G3); MET proto-oncogene, receptor tyrosine kinase (MET; NCBI Gene ID: 4233; HGFR; AUTS9; RCCP2; c-Met; DFNB97); KIT proto-oncogene, receptor tyrosine kinase (KIT; NCBI Gene ID: 3815; PBT; SCFR; C-Kit; CD117; MASTC); C-type lectin domain family 12 member A (CLEC12A; NCBI Gene ID: 160364; CLL1; MICL; CD371; CLL-1; DCAL-2); C-type lectin domain containing 9A (CLEC9A; NCBI Gene ID: 283420; CD370; DNGR1; DNGR-1; UNQ9341); cadherin 3 (CDH3; NCBI Gene ID: 1001; CDHP; HJMD; p-cadherin; PCAD); carbonic anhydrase 6 (CA6; NCBI Gene ID: 765; CA-VI; GUSTIN); carbonic anhydrase 9 (CA9; NCBI Gene ID: 768; MN; CAIX); carcinoembryonic antigen related cell adhesion molecule 3 (CEACAM3; NCBI Gene ID; 1084; CEA; CGM1; W264; W282; CD66D); carcinoembryonic antigen related cell adhesion molecule 5 (CEACAM5; NCBI Gene ID: 1048; CEA; CD66e); carcinoembryonic antigen related cell adhesion molecule 6 (CEACAM6; NCBI Gene ID: 4680; NCA; CEAL; CD66c); chorionic somatomammotropin hormone 1 (CSH1; NCBI Gene ID: 1442; PL; CSA; CS-1; CSMT; GHB3; hCS-1; hCS-A); coagulation factor III, tissue factor (F3; NCBI Gene ID: 2152; TF; TFA; CD142); collectin subfamily member 10 (COLEC10; NCBI Gene ID: 10584; 3MC3; CLL1; CL-34); delta like canonical Notch ligand 3 (DLL3; NCBI Gene ID: 10683; SCDO1); ectonucleotide pyrophosphatase/phosphodiesterase 3 (ENPP3; NCBI Gene ID: 5169; B10; NPP3; PDNP3; CD203c; PD-IBETA); ephrin A1 (EFNA1; NCBI Gene ID: 1942; B61; EFL1; ECKLG; EPLG1; LERK1; LERK-1; TNFAIP4); epidermal growth factor receptor (EGFR; NCBI GeneID: 1956; ERBB; HER1; mENA; ERBB1; PIG61; NISBD2); EGFR variant III (EGFRvIII); EPH receptor A2 (EPHA2; NCBI Gene ID: 1969; ECK; CTPA; ARCC2; CTPP1; CTRCT6); epithelial cell adhesion molecule (EPCAM; NCBI Gene ID: 4072; ESA; KSA; M4S1; MK-1; DIAR5; EGP-2; EGP40; KS1/4; MIC18; TROP1; EGP314; HNPCC8; TACSTD1); erb-b2 receptor tyrosine kinase 2 (ERBB2; NCBI Gene ID: 2064; NEU; NGL; HER2; TKR1; CD340; HER-2; MLN 19; HER-2/neu); fibroblast activation protein alpha (FAP; NCBI Gene ID: 2191; DPPIV, FAPA, FAPalpha, SIMP); fibroblast growth factor receptor 2 (FGFR2; NCBI Gene ID: 2263; BEK; JWS; BBDS; CEK3; CFD1; ECT1; KGFR; TK14; TK25; BFR-1; CD332; K-SAM); fibroblast growth factor receptor 3 (FGFR3; NCBI Gene ID: 2261; ACH, CD333, CEK2, HSFGFR3EX, JTK4); folate hydrolase 1 (FOLH1; NCBI Gene ID: 2346; PSM; FGCP; FOLH; GCP2; PSMA; mGCP; GCPII; NAALAD1; NAALAdase, carboxypeptidase II); folate receptor 1 (FOLR1; NCBI Gene ID: 2348; FBP; FOLR, FRα); GD2 ganglioside; glycoprotein NMB (GPNMB; NCBI Gene ID: 10457; NMB; HGFIN; PLCA3; osteoactivin); guanylate cyclase 2C (GUCY2C; NCBI Gene ID: 2984; GC-C; STAR; DIAR6; GUC2C; MECIL; MUCIL); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E; NCBI Gene ID: 3133; QA1; HLA-6.2); major histocompatibility complex, class I, F (HLA-F; NCBI Gene ID: 3134; HLAF; CDA12; HLA-5.4; HLA-CDA12); major histocompatibility complex, class I, G (HLA-G, MHC-G; NCBI Gene ID: 3135; MHC-G); MHC class I polypeptide-related sequence A (MICA; NCBI Gene ID: 100507436; MIC-A, PERB11.1); MHC class I polypeptide-related sequence B (MICB; NCBI Gene ID: 4277; PERB11.2); integrin subunit beta 7 (ITGB7; NCBI Gene ID: 3695); leukocyte immunoglobulin like receptor B1 (LILRB1; NCBI Gene ID: 10859; ILT2; LIR1; MIR7; PIRB; CD85J; ILT-2; LIR-1; MIR-7; PIR-B); leukocyte immunoglobulin like receptor B2 (LILRB2; NCBI Gene ID: 10288; ILT4; LIR2; CD85D; ILT-4; LIR-2; MIR10; MIR-10); LY6/PLAUR domain containing 3 (LYPD3; NCBI Gene ID: 27076; C4.4A); glypican 3 (GPC3; NCBI Gene ID: 2719; SGB; DGSX; MXR7; SDYS; SGBS; OCI-5; SGBS1; GTR2-2); KRAS proto-oncogene, GTPase (KRAS; NCBI Gene ID: 3845; NS; NS3; CFC2; RALD; K-Ras; KRAS1; KRAS2; RASK2; KI-RAS; C-K-RAS; K-RAS2A; K-RAS2B; K-RAS4A; K-RAS4B; c-Ki-ras2); MAGE family member A1 (MAGEA1; NCBI Gene ID: 4100; CT1.1; MAGE1); MAGE family member A3 (MAGEA3; NCBI Gene ID: 4102; HIP8; HYPD; CT1.3; MAGE3; MAGEA6); MAGE family member A4 (MAGEA4; NCBI Gene ID: 4103; CT1.4; MAGE4; MAGE4A; MAGE4B; MAGE-41; MAGE-X2); MAGE family member A11 (MAGEA11; NCBI Gene ID: 4110; CT1.11; MAGE11; MAGE-11; MAGEA-11); MAGE family member C1 (MAGEC1; NCBI Gene ID: 9947; CT7; CT7.1); MAGE family member C2 (MAGEC2; NCBI Gene ID: 51438; CT10, HCA587, MAGEE1); MAGE family member C3 (MAGEC3; NCBI Gene ID: 139081; CT7.2, HCA2, MAGE-C3, MAGEC4); MAGE family member D1 (MAGED1; NCBI Gene ID: 9500; NRAGE; DLXIN-1); MAGE family member D2 (MAGED2; NCBI Gene ID: 10916; 11B6; BCG1; BCG-1; HCA10; BARTS5; MAGE-D2); mesothelin (MSLN; NCBI Gene ID: 10232; MPF, SMRP); mucin 1 (MUC1; NCBI Gene ID: 4582; ADMCKD, ADMCKD1, CA 15-3, CD227, EMA, H23AG, KL-6, MAM6, MCD, MCKD, MCKD1, MUC-1, MUC-1/SEC, MUC-1/X, MUC1/ZD, PEM, PEMT, PUM) and splice variants thereof (e.g., including MUC1/A, C, D, X, Y, Z and REP); mucin 16 (MUC16; NCBI Gene ID: 94025; CA125); natural killer cell cytotoxicity receptor 3 ligand 1 (NCR3LG1; NCBI Gene ID: 374383; B7-H6, B7H6, DKFZp686024166); necdin, MAGE family member (NDN; NCBI Gene ID: 4692; PWCR; HsT16328); nectin cell adhesion molecule 2 (NECTIN2; NCBI Gene ID: 5819; CD112, HVEB, PRR2, PVRL2, PVRR2); nectin cell adhesion molecule 4 (NECTIN4; NCBI Gene ID: 81607; EDSS1, LNIR, PRR4, PVRL4, nectin-4); SLIT and NTRK like family member 6 (SLITRK6; NCBI Gene ID: 84189; DFNMYP); promyelocytic leukemia (PML; NCBI Gene ID: 5371; MYL, PP8675, RNF71, TRIM19); protein tyrosine kinase 7 (inactive) (PTK7; NCBI Gene ID: 5754; CCK-4, CCK4); Poliovirus receptor (PVR) cell adhesion molecule (PVR; NCBI Gene ID: 5817; CD155, HVED, NECL5, Necl-5, PVS, TAGE4); SLAM family member 6 (SLAMF6; NCBI Gene ID: 114836; CD352, KALI, KALIb, Ly108, NTB-A, NTBA, SF2000); SLAM family member 7 (SLAMF7; NCBI Gene ID: 57823; 19A, CD319, CRACC, CS1); sialic acid binding Ig like lectin 7 (SIGLEC7; NCBI Gene ID: 27036; AIRM1, CD328, CDw328, D-siglec, QA79, SIGLEC-7, SIGLEC19P, SIGLECP2, p75, p75/AIRM1); sialic acid binding Ig like lectin 9 (SIGLEC9; NCBI Gene ID: 27180; CD329; CDw329; FOAP-9; siglec-9; OBBP-LIKE); sialic acid binding Ig like lectin 10 (SIGLEC10; (NCBI Gene ID: 89790; SLG2; PRO940; SIGLEC-10); signal regulatory protein alpha (SIRPA; NCBI Gene ID: 140885; BIT; MFR; P84; SIRP; MYD-1; SHPS1; CD172A; PTPNS1) solute carrier family 34 (sodium phosphate), member 2 (SLC34A2; NCBI Gene ID: 10568; NPTIIb; NAPI-3B; NAPI-IIb); solute carrier family 39 member 6 (SLC39A6; NCBI Gene ID: 25800; LIV-1, ZIP6); STEAP family member 1 (STEAP1; NCBI Gene ID: 26872; PRSS24, STEAP); suppression of tumorigenicity 2 (ST2; NCBI Gene ID: 6761); TNF receptor superfamily member 4 (TNFRSF4; NCBI Gene ID: 7293; OX40; ACT35; CD134; IMD16; TXGP1L); TNF superfamily member 9 (TNFSF9; NCBI Gene ID: 8744; 4-1BB-L, CD137L, TNLG5A); TNF receptor superfamily member 10a (TNFRSF10A; NCBI Gene ID: 8797; APO2, CD261, DR4, TRAILR-1, TRAILR1); TNF receptor superfamily member 10b (TNFRSF10B; NCBI Gene ID: 8795; CD262, DR5, KILLER, KILLER/DR5, TRAIL-R2, TRAILR2, TRICK2, TRICK2A, TRICK2B, TRICKB, ZTNFR9); TNF receptor superfamily member 13B (TNFRSF13B; NCBI Gene ID: 10673; BAFF, BLYS, CD257, DTL, TALL-1, TALL1, THANK, TNFSF20, TNLG7A, ZTNF4); TNF receptor superfamily member 17 (TNFRSF17; NCBI Gene ID: 608; BCM, BCMA, CD269, TNFRSF13A); TNF receptor superfamily member 18 (TNFRSF18; NCBI Gene ID: 8784; AITR, CD357, GITR, GITR-D); transferrin (TF; NCBI Gene ID: 7018; HEL-S-71p, PRO1557, PRO2086, TFQTL1); transforming growth factor beta 1 (TGFB1; NCBI Gene ID: 7040; CED, DPD1, IBDIMDE, LAP, TGFB, TGFbeta) and isoforms thereof; triggering receptor expressed on myeloid cells 1 (TREM1; NCBI Gene ID: 54210; CD354, TREM-1); triggering receptor expressed on myeloid cells 2 (TREM2; NCBI Gene ID: 54209; PLOSL2, TREM-2, Trem2a, Trem2b, Trem2c); trophoblast glycoprotein (TPBG; NCBI Gene ID: 7162; 5T4, 5T4AG, M6P1, WAIF1); trophinin (TRO; NCBI Gene ID: 7216; MAGE-d3, MAGED3); tumor associated calcium signal transducer 2 (TACSTD2; NCBI Gene ID: 4070; EGP-1, EGP1, GA733-1, GA7331, GP50, M1S1, TROP2); Fucosyl GM1; sialyl Lewis adhesion molecule (sLe); and Lewis Y antigen.

In some embodiments, the first and/or second antigen binding domain binds to an epitope of a target or tumor associated antigen (TAA) presented in a major histocompatibility complex (MHC) molecule. In some embodiments, the TAA is human papillomavirus (HPV) E6 or HPV E7. In some embodiments, the TAA is a neoantigen or a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen IA (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member CI (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2;

11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL-2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPSIL1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC include GSK01 (NY-ESO-1), and those described, e.g., in Stewart-Jones, et al., *Proc Natl Acad Sci USA*. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC include IMC-F106C (PRAME) and those described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

In some embodiments, the first and/or second antigen binding domain binds CCR8 (NCBI Gene ID: 1237; CC-CKR-8, CCR-8, CDw198, CKRL1, CMKBR8, CMKBRL2, CY6, GPRCY6, TER1) and competes with or comprises VH and VL regions from an antibody selected from JTX-1811, I-309, SB-649701, HG-1013, RAP-310.

In some embodiments, the first and/or second antigen binding domain binds triggering receptor expressed on myeloid cells 1 (TREM1) (NCBI Gene ID: 54210; CD354, TREM-1) and competes with or comprises VH and VL regions PY159.

In some embodiments, the first and/or second antigen binding domain binds triggering receptor expressed on myeloid cells 2 (TREM2) (NCBI Gene ID: 54209; PLOSL2, TREM-2, Trem2a, Trem2b, Trem2c) and competes with or comprises VH and VL regions PY314.

In some embodiments, the first and/or second antigen binding domain binds tumor associated calcium signal transducer 2 (TACSTD2) (NCBI Gene ID: 4070; EGP-1, EGP1, GA733-1, GA7331, GP50, M1S1, TROP2) and competes with or comprises VH and VL regions of sacituzumab.

In some embodiments, the first and/or second antigen binding domain binds T cell immunoreceptor with Ig and ITIM domains (TIGIT) (NCBI Gene ID: 201633; VSIG9, VSTM3, WUCAM) and competes with or comprises VH and VL regions from an antibody selected from etigilimab, BMS-986207, tiragolumab (a.k.a., MTIG-7192A; RG-6058; RO 7092284), vibostolimab (MK-7684), AGEN1307, AGEN1327, AGEN1777, COM-902, IBI-939, AB154, SGN-TGT, MG1131, BGB-A1217 and EOS884448 (EOS-448).

In some embodiments, the first and/or second antigen binding domain binds to membrane spanning 4-domains A1 (MS4A1; CD20; B1; S7; Bp35; CD20; CVID5; MS4A2; LEU-16; NCBI Gene ID: 931) and competes with or comprises VH and VL regions from an antibody selected from rituximab (Rituxan/Biogen Idec), ofatumumab (Arzerra/Genmab), tositumomab (V10XA53/Bexxar), ibritumomab (V10XX02/Biogen Idec), veltuzumab, IMMU-106 (Immunomedics), ocrelizumab (Ocrevus/Biogen Idec; Genentech), obinutuzumab (Gazyva/Roche Glycart Biotech), ocaratuzumab, LY2469298 (Applied Molecular Evolution), ublituximab, LFB-R603 (LFB Biotech.; rEVO Biologics), IGN-002, and PF-05280586.

In some embodiments, the first and/or second antigen binding domain binds to CD19; NCBI Gene ID: NCBI Gene ID: 930; B4; CVID3) and competes with or comprises VH and VL regions from an antibody selected from tafasitamab (MOR208, formerly Xmab®5574), inebilizumab (MEDI-551) and SAR3419.

In some embodiments, the first and/or second antigen binding domain binds to CD22 (NCBI Gene ID: 933; SIGLEC2; SIGLEC-2) and competes with or comprises VH and VL regions from an antibody selected from inotuzumab, bectumomab, and epratuzumab.

In some embodiments, the first and/or second antigen binding domain binds to TNF receptor superfamily member 8 (TNFRSF8, a.k.a., CD30; NCBI Gene ID: 943) and competes with or comprises VH and VL regions from an antibody selected from brentuximab.

In some embodiments, the first and/or second antigen binding domain binds to CD33 (NCBI Gene ID: 945; p67; SIGLEC3; SIGLEC-3) and competes with or comprises VH and VL regions from an antibody selected from gemtuzumab and IMGN-779.

In some embodiments, the first and/or second antigen binding domain binds to CD37 (NCBI Gene ID: 951; GP52-40; TSPAN26) and competes with or comprises VH and VL regions from an antibody selected from otlertuzumab (TRU-016).

In some embodiments, the first and/or second antigen binding domain binds to CD38 (a.k.a., ADP ribosyl cyclase-1 (ADPRC1); NCBI Gene ID: 952) and competes with or comprises VH and VL regions from an antibody selected from daratumumab (DARZALEX®), isatuximab, MOR-202 and TAK-079.

In some embodiments, the first and/or second antigen binding domain binds to ectonucleoside triphosphate diphosphohydrolase 1 (ENTPD1 or CD39; NCBI Gene ID: 593) and competes with or comprises VH and VL regions from an antibody selected from TTX-030.

In some embodiments, the first and/or second antigen binding domain binds 5'-nucleotidase ecto (NCBI Gene ID: 4907; NT5E; NT; eN; NT5; NTE; eNT; CD73; E5NT; CALJA) and competes with or comprises VH and VL regions from an antibody selected from GS-1423, MEDI-9447 (oleclumab), CPX-006, IPH-53, BMS-986179, NZV-930, CPI-006; and antibodies described in WO2019173692.

In some embodiments, the first and/or second antigen binding domain binds to CD40 (a.k.a., TNFRSF5; NCBI Gene ID: 958) and competes with or comprises VH and VL regions from an antibody selected from lucatumumab, RG7876, SEA-CD40, APX-005M and ABBV-428, or comprises an extracellular domain of CD40 ligand (CD40LG; a.k.a., TNFSF5, CD40L, CD154; NCBI Gene ID: 959), e.g., MEDI5083.

In some embodiments, the first and/or second antigen binding domain binds to CD47 (NCBI Gene ID: 961; IAP, MER6, OA3) and competes with or comprises VH and VL regions from an antibody selected from magrolimab, IBI-188, lemzoparlimab (TJC-4), SHR-1603, HLX-24, LQ-001, IMC-002, ZL-1201, IMM-01, B6H12, GenSci-059, TAY-018, PT-240, 1F8-GMCSF, SY-102, KD-015, STI-6643 and GenSci-059. In some embodiments, the first and/or second antigen binding domain binds to CD47 and comprises an extracellular domain from SIRPA, e.g., ALX148, TTI-621, TTI-622, SG-404 and SIRPα-Fc fusion proteins described in WO2013109752, WO2014094122 and WO2016022971.

In some embodiments, the first and/or second antigen binding domain binds to signal regulatory protein alpha (SIRPA; NCBI Gene ID: 140885; BIT; MFR; P84; SIRP; MYD-1; SHPS1; CD172A; PTPNS1) and competes with or comprises VH and VL regions from an antibody selected from FSI-189 (GS-0189), ES-004, BI765063, ADU1805, CC-95251, and antibodies described in WO/2019023347 (e.g., 1H9, 3C2).

In some embodiments, the first and/or second antigen binding domain binds to CD52 (NCBI Gene ID: 1043) and competes with or comprises VH and VL regions from an antibody selected from alemtuzumab.

In some embodiments, the first and/or second antigen binding domain binds to NCAM1 (a.k.a., CD56; NCBI Gene ID: 4684) and competes with or comprises VH and VL regions from an antibody selected from lorvotuzumab.

In some embodiments, the first and/or second antigen binding domain binds to CEA cell adhesion molecule 5 (CEACAM5, a.k.a., CD66e; NCBI Gene ID: 1048) and competes with or comprises VH and VL regions from an antibody selected from labetuzumab and cergutuzumab.

In some embodiments, the first and/or second antigen binding domain binds to CD70 (a.k.a., TNFSF7, CD27L; NCBI Gene ID: 970) and competes with or comprises VH and VL regions from an antibody selected from SGN-75.

In some embodiments, the first and/or second antigen binding domain binds to CD74 (p33; DHLAG; HLADG; immunoglobulin Kappa; Ia-GAMMA, invariant chain) and competes with or comprises VH and VL regions from an antibody selected from milatuzumab.

In some embodiments, the first and/or second antigen binding domain binds to TNF receptor superfamily member 9 (TNFRSF9, a.k.a., 4-1BB, CD137, CDw137; NCBI Gene ID: 3604) and competes with or comprises VH and VL regions from an antibody selected from urelumab, utomilumab (PF-05082566), AGEN2373, ADG-106, BT-7480, QL1806.

In some embodiments, the first and/or second antigen binding domain binds to syndecan 1 (SDC1, a.k.a., CD138, SYND1; NCBI Gene ID: 6382) and competes with or comprises VH and VL regions from an antibody selected from BT062.

In some embodiments, the first and/or second antigen binding domain binds to cytotoxic T-lymphocyte associated protein 4 (CTLA4, a.k.a., CD152; NCBI Gene ID: 1493) and competes with or comprises VH and VL regions from an antibody selected from ipilimumab, tremelimumab, BMS-986218, AGEN1181, AGEN1884 (zalifrelimab), BMS-986249, MK-1308, REGN-4659, ADU-1604, CS-1002, BCD-145, APL-509, JS-007, BA-3071, ONC-392, AGEN2041, JHL-1155, KN-044, CG-0161, ATOR-1144, PBI-5D3H5, BPI-002.

In some embodiments, the first and/or second antigen binding domain binds to insulin like growth factor 1 receptor (IGF1R, a.k.a., CD221; NCBI Gene ID: 3480) and competes with or comprises VH and VL regions from an antibody selected from AVE1642, IMC-A12, MK-0646, R150, CP-751871.

In some embodiments, the first and/or second antigen binding domain binds to TNF superfamily member 11 (TNFSF11, a.k.a., CD254, osteoclast differentiation factor (ODF), RANKL; NCBI Gene ID: 8600) and competes with or comprises VH and VL regions from an antibody selected from denosumab.

In some embodiments, the first and/or second antigen binding domain binds to TNF receptor superfamily member 10a (TNFRSF10A; a.k.a., DR4; APO2; CD261; TRAILR1) and competes with or comprises VH and VL regions from an antibody selected from mapatumumab (HGS-ETR1) and ABBV-621.

In some embodiments, the first and/or second antigen binding domain binds to TNF receptor superfamily member 10b (TNFRSF10B, a.k.a., CD262, DR5, TRAILR2; NCBI Gene ID: 8795) and competes with or comprises VH and VL regions from an antibody selected from HGS-ETR2 and CS-1008.

In some embodiments, the first and/or second antigen binding domain binds to epithelial cell adhesion molecule (EPCAM; a.k.a., TROP1, TACSTD1; NCBI Gene ID: 4072) and competes with or comprises VH and VL regions from an antibody selected from edrecolomab, catumaxomab, adecatumumab, VB4-845, 17-1A and IGN101.

In some embodiments, the first and/or second antigen binding domain competes with or comprises VH and VL regions from an antibody that disrupts binding of VEGFA to its cognate receptors fms related receptor tyrosine kinase 1

(FLT1, a.k.a., VEGFR1; NCBI Gene ID: 2321) and/or kinase insert domain receptor (KDR, a.k.a., VEGFR2; NCBI Gene ID: 3791), such as bevacizumab and biosimilars thereof (targeting VEGFA), ramucirumab (CYRAMZA™) (targeting VEGFR2), IM-2C6 and CDP791.

In some embodiments, the first and/or second antigen binding domain binds to SLAMF7 (a.k.a., CD319; NCBI Gene ID: 57823) and competes with or comprises VH and VL regions from an antibody selected from HuLuc63.

In some embodiments, the first and/or second antigen binding domain binds to epidermal growth factor receptor (EGFR; a.k.a., ERBB, ERBB1, HER1; NCBI Gene ID: 1956) and competes with or comprises VH and VL regions from an antibody selected from cetuximab, panitumumab, nimotuzumab, seribantumab, CDX-3379, HLX-02 and 806.

In some embodiments, the first and/or second antigen binding domain binds to erb-b2 receptor tyrosine kinase 2 (ERBB2; a.k.a., HER2, HER-2/neu, CD340; NCBI Gene ID: 2064) and competes with or comprises VH and VL regions from an antibody selected from trastuzumab, margetuximab, pertuzumab, MEDI4276, BAT-8001, RG6264 and ZW25.

In some embodiments, the first and/or second antigen binding domain binds to erb-b2 receptor tyrosine kinase 3 (ERBB3, a.k.a., HER3; NCBI Gene ID: 2065) and competes with or comprises VH and VL regions from an antibody selected from MM-121.

In some embodiments, the first and/or second antigen binding domain binds to carbonic anhydrase 9 (CA9, CAIX; NCBI Gene ID: 768) and competes with or comprises VH and VL regions from an antibody selected from TX-250 and cG250.

In some embodiments, the first and/or second antigen binding domain binds to EPHA3 (a.k.a., HEK, HEK4; NCBI Gene ID: 2042) and competes with or comprises VH and VL regions from an antibody selected from fibatuzumab (KB-004) and IIIA4.

In some embodiments, the first and/or second antigen binding domain binds to fibroblast activation protein alpha (FAP; NCBI Gene ID: 2191) and competes with or comprises VH and VL regions from an antibody selected from sibrotuzumab and F19.

In some embodiments, the first and/or second antigen binding domain binds to folate hydrolase 1 (FOLH1, a.k.a., GCPII, GCP2, PSMA; NCBI Gene ID: 2346) and competes with or comprises VH and VL regions from an antibody selected from ATL-101, ADC and J591.

In some embodiments, the first and/or second antigen binding domain binds to folate receptor alpha (a.k.a., FRalpha, FOLR1; NCBI Gene ID: 2348) and competes with or comprises VH and VL regions from an antibody selected from farletuzumab.

In some embodiments, the first and/or second antigen binding domain binds to trophoblast glycoprotein (TPBG; NCBI Gene ID: 7162; 5T4, 5T4AG, M6P1, WAIF1) and competes with or comprises VH and VL regions from an antibody selected from anatumomab.

In some embodiments, the first and/or second antigen binding domain binds to ganglioside G2 (GD2) and/or ganglioside GD3 (αNeuSAc(2-8)αNeuSAc(2-3)βDGaip(1-4)bDGIcp(1-1)Cer) and competes with or comprises VH and VL regions from an antibody selected from 3F8, ch14.18 and KW-2871.

In some embodiments, the first and/or second antigen binding domain binds to Lewis Y antigen and competes with or comprises VH and VL regions from an antibody selected from hu3S193 and IgN311.

In some embodiments, the first and/or second antigen binding domain binds to glycoprotein A33 (GPA33; NCBI Gene ID: 10223) and competes with or comprises VH and VL regions from an antibody selected from huA33.

In some embodiments, the first and/or second antigen binding domain binds to glycoprotein NMB (GPNMB; NCBI Gene ID: 10457; NMB; HGFIN; PLCA3; osteoactivin) and competes with or comprises VH and VL regions from an antibody selected from glembatumumab.

In some embodiments, the first and/or second antigen binding domain binds to integrin α5β3 and competes with or comprises VH and VL regions from an antibody selected from etaracizumab.

In some embodiments, the first and/or second antigen binding domain binds to integrin α5β1 and competes with or comprises VH and VL regions from an antibody selected from volociximab.

In some embodiments, the first and/or second antigen binding domain binds to cell surface associated mucin 1 (MUC1, a.k.a., CD227; NCBI Gene ID: 4582) and competes with or comprises VH and VL regions from an antibody selected from pentumomab, oregovomab and cantuzumab.

In some embodiments, the first and/or second antigen binding domain binds to MET proto-oncogene, receptor tyrosine kinase MET (a.k.a., c-Met, hepatocyte growth factor receptor (HGFR), c-Met; NCBI Gene ID: 4233) and competes with or comprises VH and VL regions from an antibody selected from ABBV-399; AMG 102, METMAB and SCH900105.

In some embodiments, the first and/or second antigen binding domain binds to TAG-72 (CA 72-4) and competes with or comprises VH and VL regions from an antibody selected from minretumomab (CC49).

In some embodiments, the first and/or second antigen binding domain binds to tenascin C (TNC; NCBI Gene ID: 3371) and competes with or comprises VH and VL regions from an antibody selected from 81C6.

In some embodiments, the first and/or second antigen binding domain binds to hepatitis A virus cellular receptor 2 (HAVCR2, a.k.a., CD366, TIM3, Tim-3; NCBI Gene ID: 84868) and competes with or comprises VH and VL regions from an antibody selected from cobolimab (TSR-022), LY-3321367, sabatolimab (MBG-453), INCAGN-2390, BGB-A425, BMS-986258, BGB-A425, SHR-1702 and Sym-023.

In some embodiments, the first and/or second antigen binding domain binds to leukocyte immunoglobulin like receptor B2 (e.g., LILRB2, a.k.a., CD85D, ILT-4, ILT4, LIR-2, LIR2, MIR-10, MIR10 (NCBI Gene ID: 10288) and competes with or comprises VH and VL regions from an antibody selected from MK-4830, JTX-8064 and IO-108.

In some embodiments, the first and/or second antigen binding domain binds to leukocyte immunoglobulin like receptor B1 (e.g., LILRB1, a.k.a., CD85J, ILT-2, ILT2, LIR-1, LIR1, MIR-7, MIR7, PIR-B, PIRB (NCBI Gene ID: 10859) and competes with or comprises VH and VL regions from an antibody selected from BND-22, 12D12, 30A10, 11D9.A4, c138 dimer, NGM-707, IMC138, HuB1-176-N297A.

In some embodiments, the first and/or second antigen binding domain competes with or comprises VH and VL regions from an antibody selected from abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, sacituzumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab and 3F8.

In various embodiments, the herein described IL-2v, serum half-life extended IL-2v, e.g., Fc-IL-2v fusion proteins, and homodimers and heterodimers thereof, can be provided in isolated form. This means that such an agent is typically at least 50% w/w pure of interfering proteins and other contaminants arising from its production or purification but does not exclude the possibility that the agent is combined or co-administered with an excess of pharmaceutical acceptable carrier(s) or other vehicle intended to facilitate its use. Sometimes an IL-2v, serum half-life extended IL-2v, e.g., Fc-IL-2v fusion proteins, and homodimers and heterodimers thereof, is at least 60, 70, 80, 90, 95 or 99% w/w pure of interfering proteins and contaminants from production or purification. Often an IL-2v, serum half-life extended IL-2v, e.g., Fc-IL-2v fusion proteins, and homodimers and heterodimers thereof, is the predominant macromolecular species remaining after its purification.

3. Polynucleotides Encoding Fc-IL-2v Fusion Proteins

Provided are polynucleotides encoding the herein described IL-2v, serum half-life extended IL-2v, e.g., Fc-IL-2v fusion proteins, and homodimers and heterodimers thereof, vectors comprising such polynucleotides, and host cells (e.g., human cells, mammalian cells, yeast cells, plant cells, insect cells, bacterial cells, e.g., *E. coli*) comprising such polynucleotides or expression vectors. Provided herein are polynucleotides comprising nucleotide sequence(s) encoding any of the IL-2v or Fc-IL-2v fusion proteins provided herein, and homodimers and heterodimers thereof, as well as expression cassettes and vector(s) comprising such polynucleotide sequences, e.g., expression vectors for their efficient expression in host cells, e.g., mammalian cells. In various embodiments, the polynucleotide is a DNA, a cDNA, or an mRNA.

The terms "polynucleotide" and "nucleic acid molecule" interchangeably refer to a polymeric form of nucleotides and includes both sense and anti-sense strands of RNA, cDNA, genomic DNA, and synthetic forms and mixed polymers of the above. As used herein, the term nucleic acid molecule may be interchangeable with the term polynucleotide. In some embodiments, a nucleotide refers to a ribonucleotide, deoxynucleotide or a modified form of either type of nucleotide, and combinations thereof. The terms also include without limitation, single- and double-stranded forms of DNA. In addition, a polynucleotide, e.g., a cDNA or mRNA, may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analogue, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.). The above term is also intended to include any topological conformation, including single-stranded, double-stranded, partially duplexed, triplex, hairpinned, circular and padlocked conformations. A reference to a nucleic acid sequence encompasses its complement unless otherwise specified. Thus, a reference to a nucleic acid molecule having a particular sequence should be understood to encompass its complementary strand, with its complementary sequence. The term also includes codon-biased polynucleotides for improved expression in a desired host cell.

A "substitution," as used herein, denotes the replacement of one or more amino acids or nucleotides by different amino acids or nucleotides, respectively.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. "Isolated nucleic acid encoding an Fc-IL-2v fusion protein" refers to a first nucleic acid molecule encoding such Fc-IL-2v fusion protein and optionally, a second nucleic acid molecule encoding an Fc region (e.g., without an antigen binding domain), including such nucleic acid molecule(s) in a single vector or separate vectors, and such nucleic acid molecule(s) present at one or more locations in a host cell.

A "polynucleotide variant," as the term is used herein, is a polynucleotide that typically differs from a polynucleotide specifically disclosed herein in one or more substitutions, deletions, additions and/or insertions. Such variants may be naturally occurring or may be synthetically generated, for example, by modifying one or more of the polynucleotide sequences described herein and evaluating one or more biological activities of the encoded polypeptide as described herein and/or using any of a number of techniques well known in the art.

In some embodiments, the nucleic acid molecule is codon-biased to enhance expression in a desired host cell, e.g., in human cells, mammalian cells, yeast cells, plant cells, insect cells, or bacterial cells, e.g., *E. coli* cells. Accordingly, provided are polynucleotides encoding a Fc-IL-2v fusion protein wherein the polynucleotides are codon-biased, comprise replacement heterologous signal sequences, and/or have mRNA instability elements eliminated. Methods to generate codon-biased nucleic acids can be carried out by adapting the methods described in, e.g., U.S. Pat. Nos. 5,965,726; 6,174,666; 6,291,664; 6,414,132; and 6,794,498. Preferred codon usage for expression of the Fc-IL-2v fusion proteins in desired host cells is provided, e.g., at kazusa.or.jp/codon/; and genscript.com/tools/codon-frequency-table.

In some embodiments, the polynucleotide encoding a Fc-IL-2v fusion protein, as described herein, has at least 80%, at least 85%, at least 90%, at least 91%, at least 92%, at least 93%, at least 94%, at least 95%, at least 96%, at least 97%, at least 98%, at least 99% identical, or 100% identical, to an nucleic acid sequence selected from the group consisting of SEQ ID NOs: 175-213, as provided in Table F. In some embodiments, the polynucleotide encoding a second Fc, e.g., that heterodimerizes with a Fc-IL-2v fusion protein, as described herein, has at least 80%, at least 85%, at least 90%, at least 91%, at least 92%, at least 93%, at least 94%, at least 95%, at least 96%, at least 97%, at least 98%, at least 99% identical, or 100% identical, to an nucleic acid sequence selected from the group consisting of SEQ ID NOs: 214-215, as provided in Table F.

As appropriate, in certain embodiments, the 3'-end of the polynucleotide encoding the Fc-IL-2v fusion protein comprises one or multiple tandem stop codons, e.g., two or more tandem TAG ("amber"), TAA ("ochre") or TGA ("opal" or "umber") stop codons. The multiple tandem stop codons can be the same or different.

In some embodiments, the polynucleotide or polynucleotides encoding an IL-2v or Fc-IL-2v fusion protein, homodimer or heterodimer thereof, are formulated or encapsulated in a lipoplex, such as a lipid nanoparticle (LNP). As used herein, a "lipoplex" refers to cationic liposomes that are nonviral (synthetic) lipid carriers of DNA. As used herein, the term "lipid nanoparticle" or "LNP" refers to one or more spherical nanoparticles with an average diameter of between 10 to 1000 nanometers, and which comprise a solid lipid core matrix that can solubilize lipophilic molecules. In certain embodiments, the lipid core is stabilized by surfactants (e.g., emulsifiers), and can comprise one or more of triglycerides (e.g., tristearin), diglycerides (e.g., glycerol bahenate), monoglycerides (e.g., glycerol monostearate), fatty acids (e.g., stearic acid), steroids (e.g., cholesterol), and waxes (e.g., cetyl palmitate), including combinations thereof. Lipid nanoparticles are described, for example, in Petrilli et al., Curr Pharm Biotechnol. 15:847-55, 2014; and U.S. Pat. Nos. 6,217,912; 6,881,421; 7,402,573; 7,404,969; 7,550,441; 7,727,969; 8,003,621; 8,691,750; 8,871,509; 9,017,726; 9,173,853; 9,220,779; 9,227,917; and 9,278,130, each of which is incorporated by reference in its entirety.

TABLE F

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| | | IgG4 variants |
| 175 | hIgG4<br>S228P/F234A/L235A<br>T366W<br>hIL-2v_Δ1-5_R38G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 176 | hIgG4<br>S228P/F234A/L235A<br>T366W<br>hIL-2v_Δ1-5_R38A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGCCATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 177 | hIgG4<br>S228P/F234A/L235A | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| | T366W<br>hIL-2v_Δ1-5_T41G_C125S | CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGGGCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 178 | hIgG4<br>S228P/F234A/L235A<br>T366W<br>hIL-2v_Δ1-5_T41A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGGCCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 179 | hIgG4<br>S228P/F234A/L235A<br>T366W<br>hIL-2v_Δ1-5_F42G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGGCAAGTTCTACATGCCTAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 180 | hIgG4<br>S228P/F234A/L235A<br>T366W<br>hIL-2v_Δ1-5_F42A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTCTACATGCCTAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| 181 | hIgG4<br>S228P/F234A/L235A<br>T366W<br>hIL-2v_Δ1-5_Y45G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCGGCATGCCTAAGAAGGCCACCGAGCTGAAACATCT<br>GCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 182 | hIgG4<br>S228P/F234A/L235A<br>T366W<br>hIL-2v_Δ1-5_Y45A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCGCCATGCCTAAGAAGGCCACCGAGCTGAAACATCT<br>GCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 183 | hIgG4<br>S228P/F234A/L235A<br>T366W<br>hIL-2v_Δ1-5_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>TCAGTGTCTGGAAGCCGAACTGAAGCCCCTGGAAGAGGTGCTGAATCTGGCCCAGAGCAAGAAC<br>TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 184 | hIgG4<br>S228P/F234A/L235A<br>T366W<br>hIL-2v_Δ1-5_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGTCTGGAAGAGGCCCTGAAGCCTCTGGAAGAAGTGCTGAATCTGGCCCAGAGCAAGAAC |

TABLE F-continued

| MOLECULE NO: SEQ ID NO: | Features | Polynucleotide Sequence (Fc domain is underlined) |
|---|---|---|
| | | TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 185 | hIgG4<br>S228P/F234A/L235A<br>T366W<br>hIL-2v_Δ1-5_E68A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGCCTGGAAGAGGAACTGAAGCCTCTGGAAGCCGTGCTGAATCTGGCCCAGAGCAAGAAC<br>TTTCACCTGAGGCCTCGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 186 | hIgG4<br>S228P/F234A/L235A<br>T366W<br>hIL-2v_Δ1-5_L72G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAACGGCGCCCAGAGCAAGAAC<br>TTTCACCTGAGGCCTCGGGACCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 187 | hIgG4<br>S228P/F234A/L235A<br>T366W<br>hIL-2v_Δ1-5_Q74G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCGGCAGCAAGAAC<br>TTCCACCTGAGGCCTAGAGATCTGATCAGCAACATCAACGTGATCGTGCTGGAACTGAAAGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 188 | hIgG4<br>S228P/F234A/L235A<br>T366W<br>hIL-2v_Δ1-5_Y107G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
| --- | --- | --- |
| | | CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTTATGTGCGAGGGCGCCGACGAGACAGCCACCATCGTGGAATTTCTGAACAG<br>ATGGATCACCTTCAGCCAGAGCATCATCAGCACCCTGACC |
| 189 | hIgG4<br>S228P/F234A/L235A<br>T366W<br>hIL-2v_Δ1-5_Y107A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>CCAGTGCCTGGAAGAGGAACTGAAGCCCCTGGAAGAAGTGCTGAATCTGGCCCAGAGCAAGAAC<br>TTCCACCTGAGGCCTAGGGACCTGATCAGCAACATCAACGTGATCGTGCTGGAACTGAAAGGCA<br>GCGAGACAACCTTTATGTGCGAGGCCGCCGACGAGACAGCCACCATCGTGGAATTTCTGAACAG<br>ATGGATCACCTTCAGCCAGAGCATCATCAGCACCCTGACC |
| 190 | hIgG4<br>S228P/F234A/L235A<br>T366W<br>hIL-2v_Δ1-5_Y45G_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCGGCATGCCCAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 191 | hIgG4<br>S228P/F234A/L235A<br>T366W<br>hIL-2v_Δ1-5_Y45G_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCGGCATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 192 | hIgG4<br>S228P/F234A/L235A<br>T366W<br>hIL-2v_Δ1-5_R38G_Y45G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
| --- | --- | --- |
| | | ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCGGCATGCCCAAGAAGGCCACCGAGCTGAAACATCT<br>GCAGTGCCTGGAAGAGGAACTGAAGCCCCTGGAAGAAGTGCTGAATCTGGCCCAGTCCAAGAAC<br>TTCCACCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 193 | hIgG4<br>S228P/F234A/L235A<br>T366W<br>hIL-2v_Δ1-5_R38G_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCTACATGCCCAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 194 | hIgG4<br>S228P/F234A/L235A<br>T366W<br>hIL-2v_Δ1-5_F42A_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTCTACATGCCCAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 195 | hIgG4<br>S228P/F234A/L235A<br>T366W<br>hIL-2v A1-5_F42A_Y45G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTTGGCATGCCTAAGAAGGCCACCGAGCTGAAACATCT<br>GCAGTGCCTGGAAGAGGAACTGAAGCCCCTGGAAGAAGTGCTGAATCTGGCCCAGTCCAAGAAC<br>TTCCACCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 196 | hIgG4<br>S228P/F234A/L235A<br>T366W<br>hIL-2v_Δ1-<br>5_Y45G_E61A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| | | CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCGGCATGCCCAAGAAGGCCACCGAGCTGAAGCACCT<br>TCAGTGTCTGGAAGCCGctCTGAAGCCCCTGGAAGAGGTGCTGAATCTGGCCCAGAGCAAGAAC<br>TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 197 | hIgG4<br>S228P/F234A/L235A<br>T366W<br>hIL-2v_Δ1-5_E61A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCTTCAAGTTCTACATGCCCAAGAAGGCCACCGAGCTGAAGCACCT<br>TCAGTGTCTGGAAGCCGctCTGAAGCCCCTGGAAGAGGTGCTGAATCTGGCCCAGAGCAAGAAC<br>TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 198 | hIgG4<br>S228P/F234A/L235A<br>T366W<br>hIL-2v_Δ1-5_R38G_F42A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>AGCTGACCGGCATGCTGACCGCCAAGTTCTACATGCCCAAGAAGGCCACCGAGCTGAAACATCT<br>CTGGAACATCTGCTGCTGGACCTGCAGATGATCCTGAACGGCATCAACAACTACAAGAACCCCA<br>GCAGTGCCTGGAAGAGGAACTGAAGCCCCTGGAAGAAGTGCTGAATCTGGCCCAGTCCAAGAAC<br>TTCCACCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 199 | hIgG4<br>S228P/F234A/L235A<br>T366W<br>hIL-2v_Δ1-<br>5_F42A_Y45A_L72G_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGATCTGGTGG<br>TGGTGGATCTGGCGGCGGAGGTAGCGGTGGTGGCGGTTCTTCTACCAAGAAAACCCAGCTGCAG<br>TTGGAGCATCTGCTGCTGGACCTGCAGATGATCCTGAACGGCATCAACAACTACAAGAACCCCA<br>AGCTGACCCGGATGCTGACCGCCAAGTTTGCCATGCCTAAGAAGGCCACCGAGCTGAAACATCT<br>GCAGTGCCTGGAAGAGGAACTGAAGCCCCTGGAAGAAGTGCTGAACGGCGCCCAGTCCAAGAAC<br>TTCCATCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 200 | hIgG4<br>S228P/F234A/L235A<br>T366W | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG |

TABLE F-continued

| Illustrative polynucleotide sequences encoding hIgG4 S228P/F234A/L235A-IL-2v fusion proteins | | |
|---|---|---|
| MOLECULE NO: SEQ ID NO: | Features | Polynucleotide Sequence (Fc domain is underlined) |
| | hIL-2v_Δ1-5_R38G_F42A_Y45G_C125S | GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCGCCAAGTTTGGCATGCCTAAGAAGGCCACCGAGCTGAAACATCT<br>GCAGTGCCTGGAAGAGGAACTGAAGCCCCTGGAAGAAGTGCTGAATCTGGCCCAGTCCAAGAAC<br>TTCCACCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 201 | hIgG4<br>S228P/F234A/L235A<br>T366W<br>hIL-2v_Δ1-5_F42A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTCTACATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 202 | hIgG4<br>S228P/F234A/L235A<br>T366W<br>hIL-2v_Δ1-5_F42A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCCCTTGGCGGAGGCGGAGGATCTGGTGG<br>TGGCGGATCTGGCGGCGGAGGTAGCGGTGGCGGTGGATCTTCTACCAAGAAAACCCAGCTGCAG<br>TTGGAGCATCTGCTGCTGGACCTGCAGATGATCCTGAATGGCATCAACAATTACAAGAACCCCA<br>AGCTGACCCGGATGCTGACCGCCAAGTTCTACATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 203 | hIgG4<br>S228P/F234A/L235A<br>T366W<br>hIL-2v_Δ1-5_F42A_Y45G_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTTGGCATGCCTAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| 204 | hIgG4<br>S228P/F234A/L235A<br>T366W<br>hIL-2v_Δ1-<br>5_F42A_Y45G_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCCGGATGCTGACCGCCAAGTTTGGCATGCCTAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 205 | hIgG4<br>S228P/F234A/L235A<br>T366W<br>hIL-2v_Δ1-<br>5_R38G_Y45G_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCGGCATGCCCAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 206 | hIgG4<br>S228P/F234A/L235A<br>T366W<br>hIL-2v_Δ1-<br>5_R38G_F42A_E61A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCGCCAAGTTCTACATGCCCAAGAAGGCCACCGAGCTGAAACATCT<br>GCAGTGCCTGGAAGCTGAGCTGAAGCCCCTGGAAGAGGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 207 | hIgG4<br>S228P/F234A/L235A<br>T366W<br>hIL-2v_Δ1-<br>5_R38G_Y45G_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCGGCATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| | | CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 208 | hIgG4<br>S228P/F234A/L235A<br>T366W<br>hIL-2v_Δ1-5_R38G_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCTACATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 209 | hIgG4<br>S228P/F234A/L235A<br>T366W<br>hIL-2v_Δ1-<br>5_R38G_F42A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCGCCAAGTTCTACATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 210 | hIgG4<br>S228P/F234A/L235A<br>T366W<br>hIL-2v_Δ1-<br>5_R38G_F42A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCCCTTGGCGGAGGCGGAGGATCTGGTGG<br>TGGCGGATCTGGCGGCGGAGGTAGCGGTGGCGGTGGATCTTCTACCAAGAAAACCCAGCTGCAG<br>TTGGAGCATCTGCTGCTGGACCTGCAGATGATCCTGAATGGCATCAACAATTACAAGAACCCCA<br>AGCTGACCGGCATGCTGACCGCCAAGTTCTACATGCCCAAGAAGGCCACCGAGCTGAAACATCT<br>GCAGTGCCTGGAAGAGGCCCTGAAGCCTCTGGAAGAAGTGCTGAATCTGGCCCAGTCCAAGAAC<br>TTCCACCTGAGGCCTCGGGACCTGATCTCCAACATCAACGTGATCGTGCTGGAACTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |
| 211 | hIgG4<br>S228P/F234A/L235A<br>T366W<br>hIL-2v_Δ1-<br>5_F42A_E61A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA |

TABLE F-continued

Illustrative polynucleotide sequences encoding hIgG4 S228P/F234A/L235A-IL-2v fusion proteins

| MOLECULE NO: SEQ ID NO: | Features | Polynucleotide Sequence (Fc domain is underlined) |
|---|---|---|
| | | AGCTGACCCGGATGCTGACCGCCAAGTTCTACATGCCCAAGAAGGCCACCGAGCTGAAGCACCT<br>TCAGTGTCTGGAAGCCGctCTGAAGCCCCTGGAAGAGGTGCTGAATCTGGCCCAGAGCAAGAAC<br>TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 212 | hIgG4<br>S228P/F234A/L235A<br>T366W<br>hIL-2v_Δ1-<br>5_R38G_E61A_E62A_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCTCTTGGCGGAGGCGGAGGAAGTGGTGG<br>CGGAGGTTCTGGTGGCGGTGGATCAGGCGGTGGCGGAAGCTCTACAAAGAAAACCCAGCTGCAA<br>CTGGAACATCTGCTGCTGGACCTGCAGATGATCCTGAACGGCATCAACAACTACAAGAACCCCA<br>AGCTGACCGGCATGCTGACCTTCAAGTTCTACATGCCCAAGAAGGCCACCGAGCTGAAGCACCT<br>TCAGTGTCTGGAAGCCGctCTGAAGCCCCTGGAAGAGGTGCTGAATCTGGCCCAGAGCAAGAAC<br>TTCCACCTGAGGCCTAGGGACCTGATCAGCAACATCAACGTGATCGTGCTGGAACTGAAGGGCA<br>GCGAGACAACCTTCATGTGCGAGTACGCCGACGAGACAGCCACCATCGTGGAATTTCTGAACAG<br>ATGGATCACCTTCAGCCAGAGCATCATCAGCACCCTGACC |
| 213 | hIgG4<br>S228P/F234A/L235A<br>T366W<br>hIL-2v_Δ1-5_C125S | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT<br>CCGTGCTGACCGTGCTGCACCAGGATTGGCTGAACGGCAAAGAGTACAAGTGCAAGGTGTCCAA<br>CAAGGGCCTGCCTTCCAGCATCGAAAAGACCATCTCCAAGGCCAAGGGCCAGCCTAGGGAACCC<br>CAGGTTTACACCCTGCCTCCAAGCCAAGAGGAAATGACCAAGAACCAGGTGTCCCTGTGGTGCC<br>TGGTCAAGGGCTTCTACCCTTCCGATATCGCCGTGGAATGGGAGAGCAATGGCCAGCCTGAGAA<br>CAACTACAAGACCACACCTCCTGTGCTGGACTCCGACGGCTCCTTCTTTCTGTACTCCCGCCTG<br>ACCGTGGACAAGTCCAGATGGCAAGAGGGCAACGTGTTCTCCTGCTCCGTGATGCACGAGGCCC<br>TGCACAATCACTACACCCAGAAGTCCCTGTCTCTGTCCCTTGGCGGAGGCGGAGGATCTGGTGG<br>TGGCGGATCTGGCGGCGGAGGTAGCGGTGGCGGTGGATCTTCTACCAAGAAAACCCAGCTGCAG<br>TTGGAGCATCTGCTGCTGGACCTGCAGATGATCCTGAATGGCATCAACAATTACAAGAACCCCA<br>AGCTGACCCGGATGCTGACCTTCAAGTTCTACATGCCCAAGAAGGCCACCGAGCTGAAACATCT<br>GCAGTGCCTGGAAGAGGAACTGAAGCCCCTGGAAGAAGTGCTGAATCTGGCCCAGTCCAAGAAC<br>TTCCACCTGAGGCCTCGGGACCTGATCTCCAACATCAACGTGATCGTGCTCGAGCTGAAGGGCT<br>CCGAGACAACCTTCATGTGCGAGTACGCCGACGAGACAGCTACCATCGTGGAATTTCTGAACCG<br>GTGGATCACCTTCAGCCAGTCCATCATCAGCACCCTGACC |

TABLE G

Illustrative polynucleotide sequences encoding second Fc

| MOLECULE NO: SEQ ID NO: | Features | Polynucleotide Sequence |
|---|---|---|
| | | IgG4 variants |
| 214 | hIgG4<br>S228P/<br>F234A/<br>L235A<br>T366S/<br>L368A/<br>Y407V<br>H435R/<br>Y436F | GAGTCTAAGTACGGCCCTCCTTGTCCTCCATGTCCTGCTCCAGAAGCTGCTGGCGGCCCTTCCG<br>TGTTTCTGTTCCCTCCAAAGCCTAAGGACACCCTGATGATCAGCAGAACCCCTGAAGTGACCTG<br>CGTGGTGGTGGACGTGTCCCAAGAGGATCCTGAGGTGCAGTTCAATTGGTACGTGGACGGCGTG<br>GAAGTGCACAACGCCAAGACCAAGCCTAGAGAGGAACAGTTCAACAGCACCTATAGAGTGGTGT<br>CCGTGCTGACCGTGCTGCACCAGGATTGGCTGAACGGCAAAGAGTACAAGTGCAAGGTGTCCAA<br>CAAGGGCCTGCCTAGCTCCATCGAGAAAACCATCAGCAAGGCCAAGGGCCAGCCAAGAGAACCC<br>CAGGTGTACACACTGCCTCCAAGCCAAGAGGAAATGACCAAGAACCAGGTGTCCCTGAGCTGCG<br>CCGTGAAGGGCTTTTACCCTTCCGATATCGCCGTGGAATGGGAGAGCAATGGCCAGCCTGAGAA<br>CAACTACAAGACCACACCTCCTGTGCTGGACAGCGACGGCTCATTCTTCCTGGTGTCCAGACTG<br>ACCGTGGACAAGAGCAGATGGCAAGAGGGCAACGTGTTCAGCTGCAGCGTGATGCACGAGGCCC<br>TGCACAACCGGTTTACCCAGAAGTCTCTGAGCCTGAGCCTGGGCAAA |
| 215 | hIgG4<br>S228P/<br>F234A/<br>L235A | GAGTCTAAGTACGGCCCTCCTTGTCCTCCATGTCCTGCTCCAGAAGCAGCTGGCGGCCCTTCCG<br>TGTTTCTGTTCCCTCCAAAGCCTAAGGACACCCTGATGATCTCTCGGACCCCTGAAGTGACCTG<br>CGTGGTGGTGGATGTGTCCCAAGAGGATCCCGAGGTGCAGTTCAATTGGTACGTGGACGGCGTG<br>GAAGTGCACAACGCCAAGACCAAGCCTAGAGAGGAACAGTTCAACTCCACCTACAGAGTGGTGT |

TABLE G-continued

Illustrative polynucleotide sequences encoding second Fc

| MOLECULE NO: SEQ ID NO: | Features | Polynucleotide Sequence |
|---|---|---|
| | T366S/ L368A/ Y407V H435R/ Y436F | CCGTGCTGACCGTGCTGCACCAGGATTGGCTGAACGGCAAAGAGTACAAGTGCAAGGTGTCCAA CAAGGGCCTGCCTTCCAGCATCGAAAAGACCATCTCCAAGGCCAAGGGCCAGCCTAGGGAACCC CAGGTTTACACCCTGCCTCCAAGCCAAGAGGAAATGACCAAGAACCAGGTGTCCCTGTCCTGCG CCGTGAAGGGCTTCTACCCTTCTGATATCGCCGTGGAATGGGAGAGCAACGGCCAGCCTGAGAA CAACTACAAGACCACACCTCCTGTGCTGGACTCCGACGGCTCTTTCTTTCTGGTGTCCCGCCTG ACCGTGGACAAGTCTAGATGGCAAGAGGGCAACGTGTTCTCCTGCTCCGTGATGCACGAGGCCC TGCACAACAGATTCACCCAGAAGTCCCTGTCTCTGTCCCTGGGCAAA |

4. Vectors and Host Cells

Further provided are vectors comprising one or more polynucleotides encoding one or more of an IL-2v, serum half-life extended IL-2v, e.g., Fc-IL-2v fusion proteins, and homodimers and heterodimers thereof, as described herein. A vector can be of any type, for example, a recombinant vector such as an expression vector. Vectors include without limitation, plasmids, cosmids, bacterial artificial chromosomes (BAC) and yeast artificial chromosomes (YAC) and vectors derived from bacteriophages or plant or animal (including human) viruses. Vectors can comprise an origin of replication recognized by the proposed host cell and in the case of expression vectors, promoter and other regulatory regions recognized by the host cell. In additional embodiments, a vector comprises a polynucleotide encoding an antibody of the disclosure operably linked to a promoter and optionally additional regulatory elements. Certain vectors are capable of autonomous replication in a host into which they are introduced (e.g., vectors having a bacterial origin of replication can replicate in bacteria). Other vectors can be integrated into the genome of a host upon introduction into the host, and thereby are replicated along with the host genome. Vectors include without limitation, those suitable for recombinant production of the antibodies disclosed herein.

The choice of the vector is dependent on the recombinant procedures followed and the host used. Introduction of vectors into host cells can be effected by inter alia calcium phosphate transfection, virus infection, DEAE-dextran-mediated transfection, lipofectamine transfection or electroporation. Vectors may be autonomously replicating or may replicate together with the chromosome into which they have been integrated. In certain embodiments, the vectors contain one or more selection markers. The choice of the markers may depend on the host cells of choice. These include without limitation, kanamycin, neomycin, puromycin, hygromycin, zeocin, thymidine kinase gene from Herpes simplex virus (HSV-TK), and dihydrofolate reductase gene from mouse (dhfr). Vectors comprising one or more nucleic acid molecules encoding the IL-2v, Fc-IL-2v fusion proteins, and homodimers and heterodimers thereof, described herein, operably linked to one or more nucleic acid molecules encoding proteins or peptides that can be used to isolate the IL-2v, Fc-IL-2v fusion proteins, and homodimers and heterodimers thereof, are also covered by the disclosure. These proteins or peptides include without limitation, glutathione-S-transferase, maltose binding protein, metal-binding polyhistidine, green fluorescent protein, luciferase and beta-galactosidase.

In other embodiments, the vector that is used is pcDNA™ 3.1+ (ThermoFisher, MA).

In some embodiments, the viral vector comprises an oncolytic viral vector. As appropriate, the oncolytic viral vector can be a DNA virus or a RNA virus. In some embodiments, the viral vector is from a viral family selected from the group consisting of: Adenoviridae (e.g., Adenovirus), Arenaviridae (e.g., lymphocytic choriomeningitis mammarenavirus, Cali mammarenavirus (a.k.a., Pichinde mammarenavirus), Poxviridae (e.g., Vaccinia virus), Herpesviridae (e.g., Herpesvirus, e.g., HSV-1), Parvoviridae (e.g., Parvovirus H1), Reoviridae (e.g., Reovirus), Picornaviridae (e.g., Coxsackievirus, Seneca Valley Virus, Poliovirus), Paramyxoviridae (e.g., Measles virus, Newcastle disease virus (NDV)), Rhabdoviridae (e.g., Vesicular stomatitis virus (VSV)), Togaviridae (e.g., Alphavirus, Sindbis virus), Enteroviridae (e.g., Echovirus). The use of oncolytic viruses in cancer therapy is described e.g., Fukuhara, et al., *Cancer Sci*. (2016) 107(10):1373-1379; Kaufman, et al., *Nat Rev Drug Discov*. (2015) 14(9):642-62; Hamid, et al., *Cancer Immunol Immunother*. (2017) 66(10):1249-1264; Taguchi, et al., *Int J Urol*. (2017) 24(5):342-351; and Buijs, et al., *Hum Vaccin Immunother*. (2015) 11(7):1573-84. Illustrative oncolytic viruses that can be combined or co-administered include without limitation pelareorep, CG-0070, MV-NIS therapy, HSV-1716, DS-1647, VCN-01, ONCOS-102, TBI-1401, tasadenoturev (DNX-2401), vocimagene amiretrorepvec, RP-1, CVA21, Celyvir, LOAd-703, OBP-301, IMLYGIC®.

The disclosure also provides host cells comprising a nucleic acid or a vector described herein. Any of a variety of host cells can be used. In one embodiment, a host cell is a prokaryotic cell, for example, *E. coli*. In another embodiment, a host cell is a eukaryotic cell, for example, a yeast cell, a plant cell, an insect cell, a mammalian cell, such as a Chinese Hamster Ovary (CHO)-based or CHO-origin cell line (e.g., CHO-S, CHO DG44, ExpiCHO™, CHOZN® ZFN-modified GS−/− CHO cell line, CHO-K1, CHO-K1a), COS cells, BHK cells, NSO cells or Bowes melanoma cells. Examples of human host cells are, inter alia, HeLa, 911, AT1080, A549 and HEK293 (e.g., HEK293E, HEK293T, Expi293™). In addition, the Fc-IL-2v fusion proteins can be expressed in a yeast cell such as *Pichia* (see, e.g., Powers et al., *J Immunol Methods*. 251:123-35 (2001)), *Hanseula*, or *Saccharomyces*.

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Some vectors are suitable for delivering the nucleic acid molecule or polynucleotide of the present application. Certain vectors are capable of directing the expression of nucleic acids to which they are operatively linked. Such vectors are referred to herein as expression vectors.

The term "operably linked" refers to two or more polypeptide or polynucleotide sequences that are physically linked (e.g., directly or via a linker) and are in a functional relationship with each other such that the linked sequences each can perform their intended functions. For example, in the context of polynucleotide sequence elements, a promoter is operably linked to a coding sequence if the promoter is able to initiate or regulate the transcription or expression of a coding sequence, in which case, the coding sequence should be understood as being "under the control of" the promoter. In a further example, in the context of a fusion polypeptide, a polypeptide operably linked to a signal peptide implies that the signal peptide can direct secretion of the protein or target it for incorporation into a cell membrane.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

As appropriate, the host cells can be stably or transiently transfected with a polynucleotide encoding a IL-2v, Fc-IL-2v fusion proteins, and homodimers and heterodimers thereof, as described herein.

5. Methods of Producing Fc-IL-2v Fusion Proteins

An IL-2v, serum half-life extended IL-2v, e.g., Fc-IL-2v fusion proteins, and homodimers and heterodimers thereof, described herein can be produced by any method known in the art for the synthesis of fusion proteins, for example, by chemical synthesis or by recombinant expression techniques.

Methods of recombinant expression of fusion proteins are known and can be applied to the recombinant production and isolation/purification of an IL-2v, serum half-life extended IL-2v, e.g., Fc-IL-2v fusion proteins, and homodimers and heterodimers thereof. Methods of recombinantly expressing proteins, including fusion proteins, are described, for example, in Green and Sambrook, "Molecular Cloning: A Laboratory Manual," $4^{th}$ Edition, 2012, Cold Spring Harbor Laboratory Press; Current Protocols in Protein Science, Wiley, 1995-2109 (currentprotocols.onlinelibrary.wiley.com/journal/19343663/); and Current Protocols in Molecular Biology, Wiley, 1987-2019 (currentprotocols.onlinelibrary.wiley.com/journal/19343647/). In addition, other publications relating to producing recombinantly expressed fusion proteins include, e.g., Argelia Lorence (Editor), "Recombinant Gene Expression" (Methods in Molecular Biology) 2012, Humana Press; James L Hartley (Editor), "Protein Expression in Mammalian Cells: Methods and Protocols" (Methods in Molecular Biology) 2012, Humana Press; Roslyn M. Bill (Editor), "Recombinant Protein Production in Yeast: Methods and Protocols" (Methods in Molecular Biology) 2012, Humana Press; and MacDonald, Kolotilin and Menassa (Editors) "Recombinant Proteins from Plants: Methods and Protocols" (Methods in Molecular Biology), $2^{nd}$ Edition, 2016, Humana Press.

In various embodiments, an IL-2v, serum half-life extended IL-2v, e.g., Fc-IL-2v fusion proteins, and homodimers and heterodimers thereof, described herein, may be produced in bacterial or eukaryotic cells. An IL-2v, serum half-life extended IL-2v, e.g., Fc-IL-2v fusion proteins, and homodimers and heterodimers thereof, can also be produced in eukaryotic cells such as transformed cell lines (e.g., CHO, CHO-S, CHO DG44, ExpiCHO™, CHOZN®, CHO-K1, CHO-K1a, 293E, 293T, COS, NIH3T3). In addition, the Fc-IL-2v fusion proteins described herein can be expressed in a yeast cell such as *Pichia* (see, e.g., Powers et al., J Immunol Methods. 251:123-35 (2001)), *Hanseula*, or *Saccharomyces*. In one embodiment, an IL-2v, serum half-life extended IL-2v, e.g., Fc-IL-2v fusion proteins, and homodimers and heterodimers thereof, described herein, are produced in a CHO cell line, e.g., a CHO-S, CHO DG44, ExpiCHO™, CHOZN®, CHO-K1, CHO-K1a cell line, or a HEK293 (e.g., HEK293E, HEK293T, Expi293™) cell line. To produce the recombinant proteins of interest, one or more polynucleotides encoding an IL-2v, serum half-life extended IL-2v, e.g., Fc-IL-2v fusion proteins, and homodimers and heterodimers thereof, is constructed, introduced into an expression vector, and then expressed in one or more suitable host cells. In some embodiments, three or four polynucleotides encoding a Fc-IL-2v fusion protein, a Fab heavy chain and a Fab light chain encoding first and/or second antigen binding domains are co-expressed in a single host cell. Standard molecular biology techniques are used to prepare the recombinant expression vector, transfect the host cells, select for transformants, culture the host cells, and recover an IL-2v, serum half-life extended IL-2v, e.g., Fc-IL-2v fusion proteins, and homodimers and heterodimers thereof, as appropriate.

If an IL-2v, serum half-life extended IL-2v, e.g., Fc-IL-2v fusion proteins, and homodimers and heterodimers thereof, are to be expressed in bacterial cells (e.g., *E. coli*), the expression vector should have characteristics that permit amplification of the vector in the bacterial cells. Additionally, when *E. coli* such as JM109, DH5α, HB101, or XL1-Blue is used as a host, the vector must have a promoter, for example, a lacZ promoter (Ward et al., 341:544-546 (1989), araB promoter (Better et al., Science, 240:1041-1043 (1988)), or T7 promoter that can allow efficient expression in *E. coli*. Examples of such vectors include, for example, M13-series vectors, pUC-series vectors, pBR322, pBluescript, pCR-Script, pGEX-5X-1 (Pharmacia), "QIAexpress system" (QIAGEN), pEGFP, and pET (when this expression vector is used, the host is preferably BL21 expressing T7 RNA polymerase). The expression vector may contain a signal sequence for secretion of the Fc-IL-2v fusion proteins. For production into the periplasm of *E. coli*, the pelB signal sequence (Lei et al., J. Bacteriol., 169: 4379 (1987)) may be used as the signal sequence for secretion of the Fc-IL-2v fusion proteins. For bacterial expression, calcium chloride methods or electroporation methods may be used to introduce the expression vector into the bacterial cell.

If an IL-2v, serum half-life extended IL-2v, e.g., Fc-IL-2v fusion proteins, and homodimers and heterodimers thereof, are to be expressed in mammalian cells (e.g., such as CHO-S, CHO DG44, ExpiCHO™, CHOZN®, CHO-K1, CHO-K1a, 293E, 293T, Expi293™, COS, NIH3T3 cells), the expression vector includes a promoter to promote expression in these cells, for example, an SV40 promoter (Mulligan et al., Nature, 277:108 (1979)), MMLV-LTR promoter, EF1α promoter (Mizushima et al., Nucleic Acids Res., 18:5322 (1990)), or CMV promoter. In addition to the nucleic acid sequence encoding the immunoglobulin or domain thereof, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin, or methotrexate, on a host cell into which the vector has been introduced. Examples of vectors with selectable markers include pMAM, pDR2, pBK-RSV, pBK-CMV, pOPRSV, and pOP13.

In one embodiment, an IL-2v, serum half-life extended IL-2v, e.g., Fc-IL-2v fusion proteins, and homodimers and heterodimers thereof, are produced in mammalian cells. Exemplary mammalian host cells for expressing recombinant proteins include Chinese Hamster Ovary (e.g., CHO, CHO-S, CHO DG44, ExpiCHO™, CHOZN®, CHO-K1, CHO-K1a) (including dhfr-CHO cells, described in Urlaub and Chasin (1980) Proc. Natl. Acad. Sci. USA 77: 4216-4220, used with a DHFR selectable marker, e.g., as described in Kaufman and Sharp (1982) Mol. Biol. 159:601 621), human embryonic kidney 293 cells (e.g., 293, 293E, 293T, Expi293™), COS cells, NIH3T3 cells, lymphocytic cell lines, e.g., NS0 myeloma cells and SP2 cells, and a cell from a transgenic animal, e.g., a transgenic mammal. For example, in some embodiments, the cell is a mammary epithelial cell.

In an exemplary system for expression of an IL-2v, serum half-life extended IL-2v, e.g., Fc-IL-2v fusion proteins, and homodimers and heterodimers thereof, recombinant expression vectors encoding the recombinant proteins are introduced into dhfr-CHO cells by calcium phosphate-mediated transfection. In a specific embodiment, the dhfr− CHO cells are cells of the DG44 cell line, such as DG44i (see, e.g., Derouaz et al., Biochem Biophys Res Commun., 340(4): 1069-77 (2006)). Within the recombinant expression vectors, the polynucleotide encoding the Fc-IL-2v fusion protein, and optionally a second polynucleotide encoding a second Fc fusion protein for forming a heterodimer, are operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vectors also carry a DHFR gene, which allows for selection of CHO cells that have been transfected with the vector using methotrexate selection/amplification. The selected transformant host cells are cultured to allow for expression and secretion of an IL-2v, serum half-life extended IL-2v, e.g., Fc-IL-2v fusion proteins, and homodimers and heterodimers thereof, and the recombinant proteins are recovered from the culture medium.

An IL-2v, serum half-life extended IL-2v, e.g., Fc-IL-2v fusion proteins, and homodimers and heterodimers thereof, can also be produced by a transgenic animal. For example, U.S. Pat. No. 5,849,992 describes a method of expressing an antibody in the mammary gland of a transgenic mammal. A transgene is constructed that includes a milk-specific promoter and one or more polynucleotides encoding the IL-2v protein of interest and a signal sequence for secretion. The milk produced by females of such transgenic mammals includes, secreted-therein, the IL-2v protein of interest. The Fc-IL-2v fusion protein can be purified from the milk, or for some applications, used directly. Animals are also provided comprising one or more of the IL-2v-encoding nucleic acids described herein.

In various embodiments, the IL-2v, Fc-IL-2v fusion proteins, homodimers and/or heterodimer described herein, and/or the polynucleotides encoding such polypeptides, are provided in provided in isolated form. This means that such the polypeptide or polynucleotide is at least 50% w/w pure of interfering proteins, cellular and other contaminants arising from its production or purification but does not exclude the possibility that the agent is combined with an excess of pharmaceutical acceptable carrier(s) or other vehicle intended to facilitate its use. The term "isolated," when applied to a polypeptide or polynucleotide, as described herein, denotes that the polypeptide or polynucleotide is essentially free of cellular components with which it is associated in the natural state. It can be, for example, in a homogeneous state and may be in either a dry or aqueous solution. Purity and homogeneity can be determined using known methods, e.g., analytical chemistry techniques such as polyacrylamide gel electrophoresis, column chromatography, thin layer chromatography, or high-performance liquid chromatography (HPLC) analysis. A protein that is the predominant species present in a preparation is substantially purified. An "isolated" or "purified" polypeptide or polynucleotide is substantially free of other cellular material, or culture medium when produced by recombinant techniques, or chemical precursors or other chemicals when chemically synthesized. In various embodiments, purified polypeptides and/or polynucleotides are at least 60%, 70%, 75%, 80%, 85%, 90%, 91%, 92%, 93%, 94%, 95%, 96%, 97%, 98%, 99%, or 100% (w/w), separated from, purified of, or free of interfering proteins and contaminants from production or purification. Often an agent is the predominant macromolecular species remaining after its purification.

An IL-2v, serum half-life extended IL-2v, e.g., Fc-IL-2v fusion proteins, and homodimers and heterodimers thereof, can be isolated from inside or outside (such as medium) of the host cell and purified as substantially pure and homogenous, non-aggregated IL-2v, serum half-life extended IL-2v, e.g., Fc-IL-2v fusion proteins, and homodimers and heterodimers thereof. Methods for isolation and purification commonly used for protein purification, including antibody purification, may be used for the isolation and purification of herein described IL-2v, serum half-life extended IL-2v, e.g., Fc-IL-2v fusion proteins, and homodimers and heterodimers thereof, and are not limited to any particular method. Applicable protein purification techniques are described, e.g., in Labrou, Chronopoulou and Ataya (Editors), "Handbook on Protein Purification: Industry Challenges and Technological Developments, 2018, Nova Science Pub Inc; Gottschalk (Editor), "Process Scale Purification of Antibodies," 2nd Edition, 2017, Wiley; Staby, Rathore and Ahuja (Editors), "Preparative Chromatography for Separation of Proteins, 2017, Wiley; and Labrou (Editor), "Protein Downstream Processing: Design, Development and Application of High and Low-Resolution Methods, 2014, Human Press. An IL-2v, serum half-life extended IL-2v, e.g., Fc-IL-2v fusion proteins, and homodimers and heterodimers thereof, may be isolated and purified by appropriately selecting and combining, for example, column chromatography, filtration, ultrafiltration, salting out, solvent precipitation, solvent extraction, distillation, immunoprecipitation, SDS-polyacrylamide gel electrophoresis, isoelectric focusing, dialysis, and recrystallization. Chromatography includes, for example, affinity chromatography, ion exchange chromatography, hydrophobic chromatography, gel filtration, reverse-phase chromatography, and adsorption chromatography (Strategies for Protein Purification and Characterization: A Laboratory Course Manual. Ed Daniel R. Marshak et al., Cold Spring Harbor Laboratory Press, 1996). Chromatography can be carried out using liquid phase chromatography such as HPLC and FPLC. Columns used for affinity chromatography include protein A column and protein G column. Examples of columns using protein A column include Hyper D, POROS, and Sepharose FF (GE Healthcare Biosciences). In some embodiments, the Fc-IL-2v fusion proteins, and heterodimers thereof, are further purified using anion exchange chromatography, e.g., to separate the heterodimer aggregates from the monodispersed peak. A strong anion exchange matrix or resin can have quaternary ammonium ions (designated Q). An intermediate-strength resin can contain a mixture of tertiary and quaternary amines. A weak anion exchange matrix is diethylaminoethyl (DEAE). Examples of columns for applying anion exchange chromatography include Q-HP, HQ 50, XQ, PI 50, D 50 anion-exchange columns. The present disclosure also includes IL-2v, serum half-life extended IL-2v, e.g., Fc-IL-2v fusion proteins, and homodimers and heterodimers thereof, that are highly purified using these purification methods.

6. Pharmaceutical Compositions

Provided are pharmaceutical compositions comprising a IL-2v, serum half-life extended IL-2v, e.g., Fc-IL-2v fusion proteins, and homodimers and heterodimers thereof, as described herein, or one or more polynucleotides encoding such proteins, as described herein, and a pharmaceutically acceptable diluent, carrier or excipient. In certain embodiments, the pharmaceutical composition comprises a therapeutically effective amount of an IL-2v, serum half-life extended IL-2v, e.g., Fc-IL-2v fusion proteins, and homodimers and heterodimers thereof, or one or more polynucleotides encoding such proteins.

Various pharmaceutically acceptable diluents, carriers, and excipients, and techniques for the preparation and use of pharmaceutical compositions will be known to those of skill in the art in light of the present disclosure. Illustrative pharmaceutical compositions and pharmaceutically acceptable diluents, carriers, and excipients are also described in, e.g., Loyd V. Allen Jr (Editor), "Remington: The Science and Practice of Pharmacy," 22nd Edition, 2012, Pharmaceutical Press; Brunton, Knollman and Hilal-Dandan, "Goodman and Gilman's The Pharmacological Basis of Therapeutics," 13th Edition, 2017, McGraw-Hill Education/Medical; McNally and Hastedt (Editors), "Protein Formulation and Delivery, 2nd Edition, 2007, CRC Press; Banga, "Therapeutic Peptides and Proteins: Formulation, Processing, and Delivery Systems," 3rd Edition, 2015, CRC Press; Lars Hovgaard, Frokjaer and van de Weert (Editors), "Pharmaceutical Formulation Development of Peptides and Proteins," 2nd Edition, 2012, CRC Press; Carpenter and Manning (Editors), "Rational Design of Stable Protein Formulations: Theory and Practice," 2002, Springer (Pharmaceutical Biotechnology (Book 13)); Meyer (Editor), "Therapeutic Protein Drug Products: Practical Approaches to Formulation in the Laboratory, Manufacturing, and the Clinic, 2012, Woodhead Publishing; and Shire, "Monoclonal Antibodies: Meeting the Challenges in Manufacturing, Formulation, Delivery and Stability of Final Drug Product, 2015, Woodhead Publishing.

In some embodiments, each carrier, diluent or excipient is "acceptable" in the sense of being compatible with the other ingredients of the pharmaceutical composition and not injurious to the subject. Often, the pharmaceutically acceptable carrier is an aqueous pH-buffered solution. Some examples of materials which can serve as pharmaceutically-acceptable carriers, diluents or excipients include: water, buffers, e.g., phosphate-buffered saline; sugars, such as lactose, trehalose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water, isotonic saline; Ringer's solution; ethyl alcohol; phosphate buffer solutions; 2-Amino-2-(hydroxymethyl)propane-1,3-diol (tris(hydroxymethyl)aminomethane; Tris) buffers, amino acids (e.g., charged amino acids, including without limitation, aspartate, asparagine, glutamate, glutamine, histidine, lysine, arginine); and other non-toxic compatible substances employed in pharmaceutical formulations. Wetting agents, emulsifiers and lubricants, such as sodium lauryl sulfate, a polysorbate (e.g., polysorbate 20, polysorbate 40, polysorbate 60, polysorbate 80) and magnesium stearate, as well as coloring agents, release agents, coating agents, sweetening, flavoring and perfuming agents, preservatives and antioxidants can also be present in the compositions. In one embodiment, the pharmaceutical composition comprises a physiologically acceptable buffer, pH 5.5 to 8.5, e.g., pH 6.5 to 7.5, sucrose, and polysorbate 80. In one embodiment, the pharmaceutical composition comprises histidine, sucrose, and polysorbate 80. In one embodiment, the pharmaceutical composition comprises sodium phosphate, sucrose, and polysorbate 80. In one embodiment, the pharmaceutical composition comprises a Tris buffer, sucrose, and polysorbate 80.

The formulation of and delivery methods of pharmaceutical compositions will generally be adapted according to the site and the disease to be treated. As appropriate, the pharmaceutical compositions can be administered systemically or locally. Exemplary formulations include without limitation, those suitable for parenteral administration, e.g., subcutaneous, intradermal, intramuscular, intratumoral, intravenous, intra-arterial, intraperitoneal, intravesical, intracranial, intrathecal, intracavitary, intraventricular, or mucosal (e.g., buccal, intranasal, intrarectal, intravaginal, opthalmic), topical, or inhalation administration, including formulations encapsulated in micelles, liposomes or drug-release capsules (active agents incorporated within a biocompatible coating designed for slow-release); ingestible formulations; formulations for topical use, such as creams, ointments and gels; and other formulations such as inhalants, aerosols and sprays. In some embodiments, the pharmaceutical compositions are formulated for parenteral, e.g., intravenous, subcutaneous, or intramuscular). In some embodiments, the pharmaceutical compositions are formulated for intratumoral administration.

In certain embodiments, pharmaceutical compositions are sterile. In certain embodiments, the pharmaceutical composition has a pH in the range of 4.5 to 8.5, 4.5 to 6.5, 5.5 to 7.4, 6.4 to 7.0, 6.5 to 8.5, 6.5 to 7.5, 7.2 to 7.8, or a pH of 5.0, 5.5, 6.0, 6.5, 7.0, 7.5, 8.0 or 8.5. In one embodiment, the pharmaceutical composition has an osmolarity in the range of 240-400 mOsmol/L, e.g., 240-260 or 250-330 mOsmol/L. In certain embodiments, the pharmaceutical composition is isotonic or near isotonic.

In some embodiments, the pharmaceutical compositions are liquids or solids. In some embodiments, the pharmaceutical compositions are a frozen liquid or freeze-dried (i.e., lyophilized). In some embodiments, the pharmaceutical composition comprises an aqueous solution, e.g., suitable for intravenous, subcutaneous or intramuscular administration, e.g., at a concentration in the range of 0.05 mg/ml to 50 mg/ml, e.g., from 0.05 mg/ml to 20 mg/ml, e.g., from 5.0 mg/ml to 10.0 mg/ml, e.g., from 0.1 mg/ml to 40 mg/ml, e.g., from 1.0 mg/ml to 30 mg/ml, e.g., from 0.05 mg/ml to 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 5.5 mg/ml, 6.0 mg/ml, 6.5 mg/ml, 7.0 mg/ml, 7.5 mg/ml, 8.0 mg/ml, 8.5 mg/ml, 9.0 mg/ml, 9.5 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml or 50 mg/ml. In some embodiments, the pharmaceutical composition is lyophilized. In certain embodiments, the pharmaceutical composition has a viscosity less than 50 cP, less than 30 cP, less than 20 cP, less than 10 cP and as low as 1 cP.

In some embodiments, the pharmaceutical composition further comprises one or more additional therapeutic agents, e.g., a second therapeutic agent, or second and third therapeutic agents.

7. Therapeutic Uses; Dosing and Scheduling

An IL-2v, serum half-life extended IL-2v, e.g., Fc-IL-2v fusion proteins, and homodimers and heterodimers thereof, find use in preventing and/or treating, and/or enhancing or improving the prevention and/or treatment of various disease conditions that benefit from immune stimulation, particularly, the expansion of CD8+ T cells. Illustrative conditions include microbial infections, including viral, bacterial or fungal infections and cancers. Illustrative viral infections that can be prevented or treated with the herein described IL-2v, serum half-life extended IL-2v, e.g., Fc-IL-2v fusion proteins, and homodimers and heterodimers thereof, include without limitation hepatitis B virus (HBV) (NCBI:txid10407), human immunodeficiency virus (HIV) (e.g., HIV-1 (NCBI:txid11676); HIV-2 (NCBI:txid11709)), herpes simplex virus (HSV) (NCBI:txid10294) and coronavirus (e.g., SARS-related corona virus (NCBI:txid694009), e.g., SARS-CoV2 (NCBI:txid2697049)). In various embodiments, the "subject," "patient" or the "individual" is a human or a non-human mammal, including a laboratory animal, e.g., a non-human primate (e.g., a chimpanzee, a macaque), woodchuck, Peking duck, mouse, rat, rabbit or guinea pig, or a domesticated mammal, e.g., dog, cat, horse, cow, sheep, goat, pig.

"Treatment" or "treat" or "treating" as used herein refers to an approach for obtaining beneficial or desired results. For purposes of the present disclosure, beneficial or desired results include, but are not limited to, alleviation of a symptom and/or diminishment of the extent of a symptom, delaying of progression and/or preventing a worsening of a symptom associated with a disease or condition. "Treatment" or "treating" can include one or more of the following: a) inhibiting the disease or condition (e.g., decreasing one or more symptoms resulting from the disease or condition, and/or diminishing the extent of the disease or condition); b) slowing or arresting the development of one or more symptoms associated with the disease or condition (e.g., stabilizing the disease or condition, delaying the worsening or progression of the disease or condition); and c) relieving the disease or condition, e.g., causing the regression of clinical symptoms, ameliorating the disease state, delaying the progression of the disease, increasing the quality of life, and/or prolonging survival.

"Delaying" as used herein refers to development of a disease or condition means to defer, hinder, slow, retard, stabilize and/or postpone development of the disease or condition. This delay can be of varying lengths of time, depending on the history of the disease and/or individual being treated. As is evident to one skilled in the art, a sufficient or significant delay can, in effect, encompass prevention, in that the individual does not develop the disease or condition.

"Prevent" or "prevention" or "preventing" as used herein refers to a regimen that protects against the onset of the disease or disorder such that the clinical symptoms of the disease do not develop. Thus, "prevention" relates to administration of a therapy (e.g., administration of a therapeutic substance) to a subject before signs of the disease are detectable in the subject (e.g., administration of a therapeutic substance to a subject in the absence of detectable infectious agent (e.g., virus) in the subject). The subject may be an individual at risk of developing the disease or disorder, such as an individual who has one or more risk factors known to be associated with development or onset of the disease or disorder. Thus, in certain embodiments, the term "preventing viral (e.g., HBV, HIV, HSV, coronavirus) infection" refers to administering to a subject who does not have a detectable viral infection an anti-viral therapeutic substance. It is understood that the subject for anti-viral preventative therapy may be an individual at risk of contracting the virus. It is also understood that prevention does not require a 100% success rate. In some instances, prevention may be understood as a reduction of the risk of infection, but not a complete elimination the occurrence of an infection.

"Therapeutically effective amount" or "effective amount" as used herein refers to an amount that is effective to elicit the desired biological or medical response, including the amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, such that when administered to a subject for treating a disease, is sufficient to effect such treatment for the disease. The effective amount will vary depending on the administered IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, as well as the disease, and its severity and the age, weight, etc., of the subject to be treated. The effective amount can include a range of amounts. An effective amount may be in one or more doses, i.e., a single dose or multiple doses may be required to achieve the desired treatment endpoint. An effective amount may be considered in the context of administering one or more therapeutic agents, and a single agent may be considered to be given in an effective amount if, in conjunction with one or more other agents, a desirable or beneficial result may be or is achieved. Suitable doses of any co-administered compounds may optionally be lowered due to the combined action (e.g., additive or synergistic effects) of the compounds. With respect to antiviral therapy or prevention, the term "effective amount" refers to the amount of a therapy that achieves a desired prophylactic or therapeutic effect.

For in vivo treatment, the subject may be administered or provided a pharmaceutical composition comprising an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. When used for in vivo therapy, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are typically administered or provided to the patient in therapeutically effective amounts (i.e., amounts that eliminate or reduce the patient's viral burden and/or viral reservoir). The IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered or provided to a mammalian subject, e.g., a human, in accord with known methods, such as, but not limited to, intravenous administration, e.g., as a bolus or by continuous infusion over a period of time, e.g., by subcutaneous, intradermal, intramuscular, intracerebrospinal, intrasynovial, intrathecal, oral, intratumoral, intra-arterial, intraperitoneal, intravesical, intracranial, intrathecal, intracavitary, intraventricular, or mucosal (e.g., buccal, intranasal, intrarectal, intravaginal, ophthalmic), topical, or inhalation routes. The IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be administered parenterally, when possible, at the target cell site, e.g., subcutaneously, intravenously or intratumorally. In one embodiment, administration of the an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, to the subject is via an intravenous route. In another embodiment, administration of the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, to the subject is via a subcutaneous route. In additional embodiments, pharmaceutical compositions of the disclosure are administered to a subject systemically, parenterally, or locally. When administered in combination with additional therapeutic agents, the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and the additional agent can be administered formulated together or separately, concurrently or sequentially, via the same or different routes of administration.

As demonstrated herein, in various embodiments, the IL-2v, serum half-life extended IL-2v, e.g., Fc-IL-2v fusion proteins, and homodimers and heterodimers thereof, have a serum half-life in a human of at least 6, 9, 12, 15, 18, 21, 24 hours, e.g., at least 1, 2, 3, 4, 5, 6, 7, 8, 9, 10, 11, 12, 13, 14 days, or longer. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered, optionally with one or more additional therapeutic agents, in a therapeutically effective dosage amount in the range of e.g., 0.02 mg to 100 mg, e.g., 0.04 mg to 80 mg, e.g., at least 0.02 mg per dose and up to 0.03 mg, 0.04 mg, 0.05 mg, 0.1 mg, 0.5 mg, 1 mg, 2 mg, 3 mg, 4 mg, 5 mg, 10 mg, 12 mg, 15 mg, 20 mg, 40 mg, 50 mg, 60 mg, 70 mg, 80 mg or 100 mg per dose In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered, optionally with one or more additional therapeutic agents, in a therapeutically effective dosage amount in the range of e.g., from 0.5 μg/kg to 1000 μg/kg, e.g., in the range of from 1 μg/kg to 500 μg/kg, e.g., in the range of from 10 μg/kg to 300 μg/kg, e.g., in the range of from 30 μg/kg to 600 μg/kg, e.g., at least 0.5 μg/kg per dose and up to 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 1.5 μg/kg, 2 μg/kg, 2.5 μg/kg, 3 μg/kg, 3.5 μg/kg, 4 μg/kg, 4.5 μg/kg, 5 μg/kg, 6 μg/kg, 7 μg/kg, 8 μg/kg, 9 μg/kg, 10 μg/kg, 15 μg/kg, 20 μg/kg, 25 μg/kg, 30 μg/kg, 40 μg/kg, 50 μg/kg, 60 μg/kg, 70 μg/kg, 80 μg/kg, 90 μg/kg, 100 μg/kg, 110 μg/kg, 120 μg/kg, 130 μg/kg, 140 μg/kg, 150 μg/kg, 200 μg/kg, 250 μg/kg, 300 μg/kg, 400 μg/kg, 500 μg/kg, 600 μg/kg, 700 μg/kg, 800 μg/kg, 900 μg/kg, 1000 μg/kg per dose.

With respect to scheduling, in various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, administering over a time period of at least 2 weeks, 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer. In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered one or more times at predetermined intervals spaced at least 1 week and up to at least 2 weeks, 3 weeks, 1 month, 2 months, 3 months, 4 months, 5 months or 6 months apart. In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered once weekly (i.e., QW), once bi-weekly (i.e. once every other week, or once every two weeks or Q2W), once thrice-weekly (i.e. once every three weeks or Q3W), once monthly (i.e., QM) or once bi-monthly dosing (i.e. once every other month, or once every two months or Q2M), once every three months (Q3M), once every four months (Q4M), once every five months (Q5M), once every six months (Q6M), or less often. In some embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered two or more times subcutaneously at an interval or at intervals between once bi-weekly (i.e. once every other week, or once every two weeks or Q2W) to once thrice-weekly (i.e. once every three weeks or Q3W).

In certain embodiments, the IL-2v, serum half-life extended IL-2v, e.g., Fc-IL-2v fusion proteins, and homodimers and heterodimers thereof, described herein, is combined or co-administered with one or more additional therapeutic agents in a therapeutically effective dosage amount.

Combination Therapies, Generally

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one, two, three, four or more additional therapeutic agents. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with two additional therapeutic agents. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with three additional therapeutic agents. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with four additional therapeutic agents. The one, two, three, four or more additional therapeutic agents can be different therapeutic agents selected from the same class of therapeutic agents, and/or they can be selected from different classes of therapeutic agents.

"Co-administration" as used herein refers to administration of unit dosages of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, before or after administration of unit dosages of one or more additional therapeutic agents. For example, administration of the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, can be within seconds, minutes, or hours of the administration of one or more additional therapeutic agents. For example, in some embodiments, a unit dose of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered first, followed within seconds or minutes by administration of a unit dose of one or more additional therapeutic agents. Alternatively, in other embodiments, a unit dose of one or more additional therapeutic agents is administered first, followed by administration of a unit dose of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, following within seconds or minutes. In some embodiments, a unit dose of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is administered first, followed, after a period of hours (e.g., 1-12 hours), by administration of a unit dose of one or more additional therapeutic agents. In other embodiments, a unit dose of one or more additional therapeutic agents is administered first, followed, after a period of hours (e.g., 1-12 hours), by administration of a unit dose of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

Co-administration of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, with one or more additional therapeutic agents generally refers to simultaneous or sequential administration of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and one or more additional therapeutic agents, such that therapeutically effective amounts of each agent are present in the body of the patient.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more additional therapeutic agents as described herein, the components of the composition are administered as a simultaneous or sequential regimen. When administered sequentially, the combination may be administered in two or more administrations. As appropriate, the an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and the additional therapeutic agent can be co-administered according to the same or different schedules (e.g., co-administered at the same or different time intervals).

8. Methods of Prevention and Treatment—HBV

Further provided are methods for eliciting and/or enhancing an immune response to human hepatitis B virus (HBV) in a subject in need thereof. Also provided are methods of treating or preventing human hepatitis B virus (HBV) in a subject in need thereof. Also provided are methods of inhibiting HBV replication in an infected individual. Further provided are methods for reducing the viral load associated with HBV infection. In various embodiments, the methods comprise administering to the subject an effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

In another aspect, provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in eliciting and/or enhancing an immune response to human hepatitis B virus (HBV) in a subject in need thereof. Further provided are provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in inhibiting HBV replication in an infected individual and/or for reducing the viral load associated with HBV infection.

In various embodiments, the subject is infected with HBV, is suspected of being infected with HBV, or is at risk of being infected with HBV. "At risk individual" as used herein refers to an individual who is at risk of developing a condition to be treated. An individual "at risk" may or may not have detectable disease or condition, and may or may not have displayed detectable disease prior to the treatment of methods described herein. "At risk" denotes that an individual has one or more so-called risk factors, which are measurable parameters that correlate with development of a disease or condition and are known in the art. An individual having one or more of these risk factors has a higher probability of developing the disease or condition than an individual without these risk factor(s). In various embodiments, the subject is chronically infected with HBV, e.g., infected with HBV for longer than 6 months. Typically, the individual is suffering from a chronic hepatitis B infection, although it is within the scope of the present disclosure to treat people who are acutely infected with HBV. Accordingly, in some embodiments, the subject is acutely infected with HBV. In some embodiments, the subject is co-infected with hepatitis D virus (HDV).

In various embodiments, the subject may be asymptomatic. In some embodiments, the subject is experiencing or exhibiting symptoms associated with HBV infection. Symptoms of HBV can include, e.g., jaundice, visible webs of swollen blood vessels in the skin, dark-colored (e.g., orange or brown) urine, light-colored feces, fever, persistent fatigue, malaise, abdominal pain, abdominal fluid, loss of appetite, nausea, and vomiting. Chronic infection with HBV can lead to one or more symptoms including, e.g., hepatic failure, hepatic cancer, hepatic fibrosis and hepatic cirrhosis. One or more administrations of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, can prevent, delay, alleviate, mitigate, inhibit, reverse or eliminate one or more symptoms associated with or caused by HBV infection.

As appropriate, a subject can be treated with multiple administrations over a time period of at least 2 weeks to 3 weeks, 1 month, 2 months, 3 months, 4 months, 5 months, 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or longer, or until sAg is no longer detectable in the serum or plasma of the subject.

In some embodiments, after one or more administrations of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally with one or more additional therapeutic agents, described herein, the subject does not exhibit symptoms of HBV in the absence of antiviral treatment for at least 6 months, at least 1 year, at least 2 years, at least 3 years, or more. In some embodiments, after one or more administrations of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally with one or more additional therapeutic agents, described herein, sAg is no longer detectable in the serum or plasma of the subject, in the absence of antiviral treatment for at least 6 months, e.g., at least 1 year, at least 2 years, at least 3 years, or more.

a. HBV Combination Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional anti-HIV therapeutic agents.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional therapeutic agents selected from HBV combination drugs, HBV vaccines, HBV DNA polymerase inhibitors, immunomodulators, toll-like receptor (TLR) modulators, interferon alpha receptor ligands, hyaluronidase inhibitors, HBV antigen inhibitors (e.g., HBV core antigen (HBcAg) inhibitors, HBV surface antigen (HBsAg) inhibitors, HBx interacting protein inhibitors, HBV E antigen inhibitors), anti-HBV antigen antibodies, inhibitory nucleic acids targeting HBV (e.g., antisense oligonucleotide, short interfering RNA (siRNA), DNA-directed RNA interference (ddRNAi)), B and T lymphocyte attenuator inhibitors, HBsAg secretion or assembly inhibitors, HBV viral entry inhibitors, immune checkpoint inhibitor, cytotoxic T-lymphocyte-associated protein 4 (CTLA4) inhibitors, cyclophilin inhibitors, endonuclease modulators, ribonucleotide reductase inhibitors, covalently closed circular DNA (cccDNA) inhibitors, farnesoid X receptor (FXR) agonists, STING agonists, anti-HBV antibodies, CCR2 chemokine antagonists, thymosin agonists, cytokines, nucleoprotein modulators, retinoic acid-inducible gene 1 stimulators, NOD2 stimulators, phosphatidylinositol 3-kinase (PI3K) inhibitors, indoleamine-2, 3-dioxygenase (IDO) pathway inhibitors, PAPD5 or PAPD7 inhibitors, ZCCHC14 inhibitors, inducers of tertiary lymphoid aggregates, MEKKK-1 protein kinase (HPK1 checkpoint) inhibitors, nucleic acid polymers (e.g. NAPs and STOPS), PD-1 inhibitors, PD-L1 inhibitors, recombinant thymosin alpha-1, superinfection therapeutics, synthetic antiviral peptoids, Bruton's tyrosine kinase (BTK) inhibitors, lysine demethylase KDM inhibitors, HBV replication inhibitors, arginase inhibitors, gene therapy and cell therapy, gene editors, cellular therapy, TCR-T cell therapy, and other HBV drugs.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be combined or co-administered with one or more of a chemotherapeutic agent, an immunomodulator, an immunotherapeutic agent, a therapeutic antibody, a therapeutic vaccine, a bispecific antibody and "antibody-like" therapeutic protein (such as DARPins®, anti-pMHC TCR-like antibodies, DARTs®, Duobodies®, Bites®, XmAbs®, TandAbs®, Fab derivatives), an antibody-drug conjugate (ADC), gene modifiers or gene editors targeting HBV (e.g., CRISPR-Cas (e.g., Cas9, Cas12, Cascade, Cas13), zinc finger nucleases, homing endonucleases, homing meganucleases (e.g., ARCUS), synthetic nucleases, TALENs), cell therapies (e.g., T-cells, NK cells, macrophages having a chimeric antigen receptor (CAR)), and TCR-T (an engineered T cell receptor) or any combination thereof.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional therapeutic agents, e.g., as 3-dioxygenase (IDO) inhibitors, apolipoprotein A1 modulator, arginase inhibitors, B- and T-lymphocyte attenuator inhibitors, Bruton's tyrosine kinase (BTK) inhibitors, CCR2 chemokine antagonist, CD137 inhibitors, CD160 inhibitors, CD305 inhibitors, CD4 agonist and modulator, compounds targeting hepatitis B core antigen (HBcAg) (a.k.a., core protein allosteric modulators), covalently closed circular DNA (cccDNA) inhibitors, cyclophilin inhibitors, cytotoxic T-lymphocyte-associated protein 4 (CTLA4) inhibitors, DNA polymerase inhibitor, endonuclease modulators, epigenetic modifiers, farnesoid X receptor (FXR) agonists, HBV DNA polymerase inhibitors, HBV replication inhibitors, HBV RNAse inhibitors, HBV viral entry inhibitors, HBx inhibitors, Hepatitis B large envelope protein modulator, Hepatitis B large envelope protein stimulator, Hepatitis B structural protein modulator, hepatitis B surface antigen (HBsAg) inhibitors, hepatitis B surface antigen (HBsAg) secretion or assembly inhibitors, hepatitis B virus E antigen inhibitors, hepatitis B virus replication inhibitors, Hepatitis virus structural protein inhibitor, HIV-1 reverse transcriptase inhibitor, Hyaluronidase inhibitor, inhibitor of apoptosis proteins family proteins (IAPs) inhibitors, IL-15 agonist, IL-7 agonist, immunomodulators, indoleamine-2 inhibitors, inhibitors of ribonucleotide reductase, ipi4 inhibitors, lysine demethylase inhibitors, histone demethylase inhibitors, KDM1 inhibitors, KDM5 inhibitors, killer cell lectin-like receptor subfamily G member 1 inhibitors, lymphocyte-activation gene 3 inhibitors, lymphotoxin beta receptor activators, modulators of Ax1, modulators of B7-H3, modulators of B7-H4, modulators of CD160, modulators of CD161, modulators of CD27, modulators of CD47, modulators of CD70, modulators of GITR, modulators of HEVEM, modulators of ICOS, modulators of Mer, modulators of NKG2A, modulators of NKG2D, modulators of OX40, modulators of SIRPalpha, modulators of TIGIT, modulators of Tim-4, modulators of Tyro, Na+-taurocholate cotransporting polypeptide (NTCP) inhibitors, natural killer cell receptor 2B4 inhibitors, NOD2 gene stimulator, Nucleoprotein inhibitor, nucleoprotein modulators, OX-40 receptor agonist, PD-1 inhibitors, PD-L1 inhibitors, peptidylprolyl isomerase inhibitor, phosphatidylinositol-3 kinase (PI3K) inhibitors, Retinoic acid-inducible gene 1 stimulator, Reverse transcriptase inhibitor, Ribonuclease inhibitor, RNA DNA polymerase inhibitor, SLC10A1 gene inhibitor, SMAC mimetics, Src tyrosine kinase inhibitor, stimulator of interferon gene (STING) agonists, stimulators of NOD1, T cell surface glycoprotein CD28 inhibitor, T-cell surface glycoprotein CD8 modulator, Thymosin agonist, Thymosin alpha 1 ligand, Tim-3 inhibitors, TLR-3 agonists, TLR-7 agonists, TLR-8 agonists, TLR-9 agonists, viral ribonucleotide reductase inhibitors, and combinations thereof.

HBV Inhibiting Antiviral Drugs

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more antiviral agents. In some embodiments, the one or more antiviral agents are selected from the group consisting of lamivudine (LAM), adefovir dipivoxil (ADV), entecavir (ETV), telbivudine (LdT), tenofovir disoproxil fumarate (TDF), tenofovir disoproxil fumarate and emtricitabine (TRUVADA®), tenofovir alafenamide (TAF or VEMLIDY®), sofosbuvir (SOVALDI®) and ledipasvir and sofosbuvir (HARVONI®).

Examples of other drugs for the treatment of HBV that can be combined or co-administered include alpha-hydroxytropolones, amdoxovir, antroquinonol, β-hydroxycytosine nucleosides, ARB-199, CCC-0975, ccc-R08, CKD-388, DF-006, elvucitabine, ezetimibe, cyclosporin A, gentiopicrin (gentiopicroside), HH-003, hepalatide, ISR-51, JNJ-56136379, M-1428, nitazoxanide, birinapant, NJK14047, NOV-205 (molixan, BAM-205), oligotide, mivotilate, feron, GST-HG-131, levamisole, Ka Shu Ning, alloferon, WS-007, Y-101 (Ti Fen Tai), rSIFN-co, PEG-IIFNm, KW-3, BP-Inter-014, oleanolic acid, HepB-nRNA, cTP-5 (rTP-5), HSK-II-2, HEISCO-106-1, HEISCO-106, Hepbarna, IBPB-0061A, Hepuyinfen, DasKloster 0014-01, ISA-204, Jiangantai (Ganxikang), MIV-210, OB-AI-004, PF-06, picroside, DasKloster-0039, hepulantai, IMB-2613, NCO-48 Fumarate, XTYW-001, SFA-001, TCM-800B, TQA-3810, VRON-0200, ZYF-0057, reduced glutathione, RO-6864018, ENOB-HB-01, RG-7834, QL-007sofosbuvir, ledipasvir, UB-551, PA-1010, HPN-BV1, STSG-0002, and ZH-2N, and the compounds disclosed in US20150210682, (Roche), US 2016/0122344 (Roche), WO2015173164, WO2016023877, US2015252057A (Roche), WO16128335A1 (Roche), WO16120186A1 (Roche), US2016237090A (Roche), WO16107833A1 (Roche), WO16107832A1 (Roche), US2016176899A (Roche), WO16102438A1 (Roche), WO16012470A1 (Roche), US2016220586A (Roche), and US2015031687A (Roche).

Examples of combination drugs for the treatment of HBV that can be combined or co-administered include tenofovir disoproxil fumarate and emtricitabine (TRUVADA®), ledipasvir and sofosbuvir (HARVONI®); ABX-203 (NASVAC), lamivudine and PEG-IFNα; adefovir and PEG-IFNα; and INO-1800 (INO-9112 and RG7944).

HBV DNA Polymerase Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more polymerase inhibitors. Examples of HBV DNA polymerase inhibitors that can be combined or co-administered include adefovir (HEPSERA®), emtricitabine (EMTRIVA®), tenofovir disoproxil fumarate (VIREAD®), tenofovir alafenamide, tenofovir, tenofovir disoproxil, tenofovir alafenamide fumarate, tenofovir alafenamide hemifumarate, tenofovir dipivoxil, tenofovir dipivoxil fumarate, tenofovir octadecyloxyethyl ester, CMX-157, tenofovir exalidex, besifovir, entecavir (BARACLUDE®), entecavir maleate, telbivudine (TYZEKA®), filocilovir, pradefovir, clevudine, ribavirin, lamivudine (EPIVIR-HBV®), phosphazide, famciclovir, fusolin, metacavir, SNC-019754, FMCA, AGX-1009, AR-II-04-26, HIP-1302, tenofovirdisoproxil aspartate, tenofovir disoproxil orotate, AiB-001 and HS-10234.

Hyaluronidase Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more hyaluronidase inhibitors. Examples of hyaluronidase inhibitors that can be combined or co-administered include astodrimer.

Hepatitis B Surface Antigen (HBsAg) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more HBsAg inhibitors. Examples of HBsAg inhibitors that can be combined or co-administered include AK-074, HBF-0259, GP-605, PBHBV-001, PBHBV-2-15, PBHBV-2-1, REP-9AC, REP-9C, REP-9, REP-2139, REP-2139-Ca, REP-2055, REP-2163, REP-2165, REP-2053, REP-2031 and REP-006, and REP-9AC'. Examples of HBsAg secretion inhibitors that can be combined or co-administered include BM601, GST-HG-131, AB-452 and ALG-010093.

Cyclophilin Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more cyclophilin inhibitors. Examples of cyclophilin inhibitors that can be combined or co-administered include CPI-431-32, EDP-494, OCB-030, SCY-635, NVP-015, NVP-018, NVP-019, STG-175, and the compounds disclosed in U.S. Pat. No. 8,513,184 (Gilead Sciences), US20140030221 (Gilead Sciences), US20130344030 (Gilead Sciences), and US20130344029 (Gilead Sciences).

HBV Viral Entry Inhibitors

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more HBV viral entry inhibitors. Examples of HBV viral entry inhibitors that can be combined or co-administered include bulevirtide (Hepcludex; Myrcludex B).

Hepatitis B Large Envelope Protein Inhibitors

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more Hepatitis B large envelope protein inhibitors. Examples of Hepatitis B large envelope protein inhibitors that can be combined or co-administered include without limitation ALG-125097, ALG-125755, EDP-721, KW-027, GP-605, GST-HG-121, ALG-010093, and ALG-01013.

Inhibitory Nucleic Acids

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more inhibitory nucleic acids (e.g., antisense oligonucleotide, short interfering RNA (siRNA), DNA-directed RNA interference (ddRNAi)) specifically targeting an HBV polynucleotide. In some embodiments, the HBV polynucleotide encodes an HBV protein (i.e., is in a coding region within the HBV genome).

Antisense Oligonucleotide Targeting Viral mRNA

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more antisense oligonucleotides. Examples of antisense oligonucleotide targeting viral mRNA that can be combined or co-administered include ISIS-HBVRx, IONIS-HBVRx, IONIS-HBV-LRx, IONIS-GSK6-LRx, GSK-3389404, GSK-3228836, BNC-1701 and RG-6004.

Short Interfering RNAs (siRNA)

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more siRNAs specifically targeting an HBV polynucleotide. Examples of siRNA specifically targeting an HBV polynucleotide that can be combine or co-administered include TKM-HBV (TKM-HepB), ALN-HBV, SR-008, HepB-nRNA, ARC-520, ARC-521, ARB-1740, ARB-1467, AB-729, RG-6084 (PD-L1), RG-6217, ALN-HBV-02, JNJ-3989 (ARO-HBV), STP-155G, STSG-0002, ALG-010133, ALG-020755, ALG-ASO, LUNAR-HBV, VIR-2218 siRNA and DCR-HBVS (DCR-S219).

DNA-Directed RNA Interference (ddRNAi)

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more ddRNAi specifically targeting an HBV polynucleotide. Examples of ddRNAi specifically targeting an HBV polynucleotide that can be combined or co-administered include BB-HB-331.

Endonuclease Modulators

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more endonuclease modulators. Examples of endonuclease modulators that can be combined or co-administered include PGN-514.

Ribonucleotide Reductase Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more ribonucleotide reductase inhibitors. Examples of inhibitors of ribonucleotide reductase that can be combined or co-administered include Trimidox.

Non-Nucleoside Reverse Transcriptase Inhibitors (NNRTIs)

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more NNRTIs. Examples of NNRTIs that can be combined or co-administered include the compounds disclosed in WO2018118826 (Merck), WO2018080903 (Merck), WO2018119013 (Merck), WO2017100108 (Idenix), WO2017027434 (Merck), WO2017007701 (Merck), WO2008005555 (Gilead).

HBV Replication Inhibitors

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more HBV replication inhibitors. Examples of HBV replication inhibitors that can be combined or co-administered include ALG-000111, ALG-000286, ASN-008, KW-034, GP-31502, isothiafludine, IQP-HBV, RM-5038, and Xingantie.

HIV-1 Reverse Transcriptase Inhibitors

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more HIV-1 reverse transcriptase inhibitors. Examples of HIV-1 reverse transcriptase inhibitors that can be combined or co-administered include without limitation 2,5,6-substituted pyrimidone derivative (HBV), KL-210122.

Non Canonical RNA Polymerase PAPD5 and PAPD7 Inhibitors

In various embodiments, IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more non-canonical RNA polymerase PAPD5 and PAPD7 inhibitors. Examples of non-canonical RNA polymerase PAPD5 and PAPD7 inhibitors include without limitation PAPD5 and PAPD7 targeting locked nucleic acid antisense oligonucleotides (HBV infection).

Covalently Closed Circular DNA (cccDNA) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more cccDNA inhibitors. Examples of cccDNA inhibitors that can be combined or co-administered include BSBI-25, ccc-R08, and CHR-101.

Farnesoid X Receptor (FXR) Agonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more FXR agonists. Examples of FXR agonists that can be combined or co-administered include EYP-001, cilofexor (GS-9674), EDP-305, MET-409, Tropifexor, AKN-083, RDX-023, BWD-100, LMB-763, INV-3, NTX-023-1, EP-024297 and GS-8670.

Caspase-9 Stimulators

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more caspase-9 stimulators. Examples of caspase-9 stimulators that can be combined or co-administered include without limitation ENOB-HB-01.

Bispecific T-Cell Receptor (TCR) Molecule

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more bispecific TCR molecules. Examples of bispecific TCR molecules that can be combined or co-administered include without limitation IMC-I109V.

Ffar2 and Ffar3 Agonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more Ffar2 and Ffar3 agonists. Examples of Ffar2 and Ffar3 agonists that can be combined or co-administered include without limitation SFA-001.

Anti-HBV Antibodies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more antibodies that specifically binds to an HBV antigen, including an HBV peptide presented in a major histocompatibility molecule (MHC) molecule (pMHC). Examples of HBV antibodies targeting the surface antigens of the hepatitis B virus that can be combined or co-administered include lenvervimab (GC-1102), XTL-17, XTL-19, KN-003, IV Hepabulin SN, and fully human monoclonal antibody therapy (hepatitis B virus infection, Humabs BioMed). Antibodies targeting HBV X protein (HBx) that can be combined or co-administered are described, e.g., in Kornyeyev, et al., *J Virol.* 2019 Jul. 30; 93(16). pii: e00248-19 and WO 2019/195181.

Examples of HBV antibodies, including monoclonal antibodies and polyclonal antibodies, that can be combined or co-administered include Zutectra, Shang Sheng Gan Di, Uman Big (Hepatitis B Hyperimmune), Omri-Hep-B, Nabi-HB, Hepatect CP, HepaGam B, igantibe, Niuliva, CT-P24, EI-001, hepatitis B immunoglobulin (intravenous, pH4, HBV infection, Shanghai RAAS Blood Products), and Fovepta (BT-088).

Examples of fully human monoclonal HBV antibodies that can be combined or co-administered include HBC-34.

Antibodies against HBV viral peptide/major histocompatibility complex (MHC) class I (pMHC) complexes that can be combined or co-administered are described, e.g., in Sastry, et al., *J Virol.* 2011 March; 85(5):1935-42 and in WO2011062562.

CCR2 Chemokine Antagonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more CCR2 chemokine antagonists. Examples of CCR2 chemokine antagonists that can be combined or co-administered include propagermanium.

Thymosin Agonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more thymosin agonists, e.g., a recombinant thymosin alpha-1. Examples of thymosin agonists that can be combined or co-administered include Thymalfasin, and recombinant thymosin alpha 1 (GeneScience). Examples of recombinant thymosin alpha-1 include NL-004 and PEGylated thymosin alpha-1.

Nucleoprotein Modulators

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more nucleoprotein modulators. Nucleoprotein modulators may be either HBV core or capsid protein inhibitors. Examples of nucleoprotein modulators that can be combined or co-administered include GS-4882, AB-423, AT-130, EDP-514, GLS4, NVR-1221, NVR-3778, AL-3778, BAY 41-4109, morphothiadine mesilate, ARB-168786, ARB-880, ARB-1820, JNJ-379, JNJ-632, RG-7907, GST-HG-141, HEC-72702, KL-060332, AB-506, ABI-H0731, ABI-H3733, JNJ-440, ABI-H2158, CB-HBV-001 and DVR-23.

Examples of capsid inhibitors that can be combined or co-administered include ALG-000184, ABI-H0731, JNJ-3989, NVR 3-778, and compounds disclosed in US20140275167 (Novira Therapeutics), US20130251673 (Novira Therapeutics), US20140343032 (Roche), WO2014037480 (Roche), US20130267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), WO2017198744 (Roche), US 20170334882 (Novira), US 20170334898 (Roche), WO2017202798 (Roche), WO2017214395 (Enanta), WO2018001944 (Roche), WO2018001952 (Roche), WO2018005881 (Novira), WO2018005883 (Novira), WO2018011100 (Roche), WO2018011160 (Roche), WO2018011162 (Roche), WO2018011163 (Roche), WO2018036941 (Roche), WO2018043747 (Kyoto Univ), US20180065929 (Janssen), WO2016168619 (Indiana University), WO2016195982 (The Penn State Foundation), WO2017001655 (Janssen), WO2017048950 (Assembly Biosciences), WO2017048954 (Assembly Biosciences), WO2017048962 (Assembly Biosciences), US20170121328 (Novira), US20170121329 (Novira), H-05, HBV capsid inhibitors (Arbutus Biopharma, Chinese Academy of Sciences/Shanghai University of Traditional Chinese Medicine).

Examples of transcript inhibitors that can be combined or co-administered include compounds disclosed in WO2017013046 (Roche), WO2017016960 (Roche), WO2017017042 (Roche), WO2017017043 (Roche), WO2017061466 (Toyoma chemicals), WO2016177655 (Roche), WO2016161268 (Enanta). WO2017001853 (Redex Pharma), WO2017211791 (Roche), WO2017216685 (Novartis), WO2017216686 (Novartis), WO2018019297 (Ginkgo Pharma), WO2018022282 (Newave Pharma), US20180030053 (Novartis), WO2018045911 (Zhejiang Pharma).

Lysine Demethylase (KDM) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with an inhibitor of a lysine demethylase (KDM). Examples of KDM5 inhibitors that can be combined or co-adminstered include the compounds disclosed in WO2016057924 (Genentech/Constellation Pharmaceuticals), US20140275092 (Genentech/Constellation Pharmaceuticals), US20140371195 (Epitherapeutics), US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), and WO2014164708 (Quanticel).

Examples of KDM1 inhibitors that can be combined or co-administered include the compounds disclosed in U.S. Pat. No. 9,186,337B2 (Oryzon Genomics), GSK-2879552, RG-6016, and ORY-2001.

Arginase Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with an arginase inhibitor. Examples of Arginase inhibitors include CB-1158, C-201, and resminostat.

Bi- and Tri-Specific Natural Killer (NK)-Cell Engagers

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAMF6 and SLAMF7), killer cell immunoglobulin-like receptors (KIR) (KIR-2DS and KIR-3DS), DNAM-1 and CD137 (4-1BB). As appropriate, the anti-CD16 binding bi-specific molecules may or may not have an Fc. Illustrative bi-specific NK-cell engagers that can be co-administered target CD16 and one or more HBV-associated antigens as described herein. BiKEs and TriKEs are described, e.g., in Felices, et al., Methods Mol Biol. (2016) 1441:333-346; Fang, et al., Semin Immunol. (2017) 31:37-54.

CAR-T Cell Therapy

CAR-T cell therapy includes a population of immune effector cells engineered to express a chimeric antigen receptor (CAR), wherein the CAR includes an HBV antigen-binding domain. In certain embodiments, the antigen-binding domain is a domain disclosed herein. In certain embodiments, the antigen-binding domain is other than a domain disclosed herein. In certain embodiments, the antigen is HBsAg (i.e. HbsAg-CART). The immune effector cell is a T-cell or an NK cell. In certain embodiments, the T-cell is a CD4+ T-cell, a CD8+ T-cell, a NK cell or a combination thereof. Cells can be autologous or allogeneic. An example of a CART directed to HBV is described in Kruse, et al., *Cytotherapy*. (2018) 20(5):697-705.

TCR-T Cell Therapy

TCR-T cell therapy includes T cells expressing HBV-specific T cell receptors. TCR-T cells are engineered to target HBV derived peptides presented on the surface of virus-infected cells. An example of a TCR directed to HBV is described in Wisskirchen, et al., *J Clin Invest*. (2019) 129(7):2932-2945.

TCR-T cell therapy includes T-Cells expressing HBV surface antigen (HBsAg)-specific TCR, such as IMC-I109V.

TCR-T cell therapy includes TCR-T therapy directed to treatment of HBV, such as LTCR-H2-1.

Anti-HBV Gene Therapy and Cell Therapy

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with an HBV-directed or HBV-targeted gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection.

Long Acting Treatments

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with a long acting treatment. Long acting entecavir (subcutaneous depot), long acting tenofovir (TFD and TAF) implants (devices) or subcutaneous depot. An example of long acting entecavir is described in Henry, et al., *Eur J Pharm Sci*. (2019) 136:104958.

Gene Editors

The genome editing system can be selected from the group consisting of: a CRISPR/Cas9 system, a zinc finger nuclease system, a TALEN system, a homing endonucleases system, and a meganuclease system (e.g., an ARCUS system); e.g., cccDNA elimination via targeted cleavage, and altering one or more of the hepatitis B virus (HBV) viral genes. Altering (e.g., knocking out and/or knocking down) the PreC, C, X, PreSI, PreS2, S, P or SP gene refers to (1) reducing or eliminating PreC, C, X, PreSI, PreS2, S, P or SP gene expression, (2) interfering with Precore, Core, X protein, Long surface protein, middle surface protein, S protein (also known as HBs antigen and HBsAg), polymerase protein, and/or Hepatitis B spliced protein function (HBe, HBc, HBx, PreS1, PreS2, S, Pol, and/or HBSP or (3) reducing or eliminating the intracellular, serum, intrahepatic and/or intraparenchymal levels of HBe, HBc, HBx, LHBs, MHBs, SHBs, Pol, and/or HBSP proteins. Knockdown of one or more of the PreC, C, X, PreSI, PreS2, S, P and/or SP gene(s) is performed by targeting the gene(s) within HBV cccDNA and/or integrated HBV DNA. Additional examples genome editing systems include, but are not limited to those disclosed in US2019284543 (Gilead Sciences), and US2019338263 (Gilead Sciences).

Examples of gene therapy, such as liver targeted anti-HBV gene therapy (using ARCUS technology), or using CRISPR/Cas9 gene editing technology, or EBT-106 (LNP-delivered CRISPR/CasX nuclease.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with an HBV DNA polymerase inhibitor, one or two additional therapeutic agents selected from the group consisting of immunomodulators, TLR modulators, HBsAg inhibitors, HBsAg secretion or assembly inhibitors, HBV therapeutic vaccines, HBV antibodies including HBV antibodies targeting the surface antigens of the hepatitis B virus and bispecific antibodies and "antibody-like" therapeutic proteins (such as DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2, and one or two additional therapeutic agents selected from the group consisting of HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein modulators).

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with at least a second additional therapeutic agent selected from the group consisting of: HBV DNA polymerase inhibitors, immunomodulator, TLR modulators, HBsAg inhibitors, HBV therapeutic vaccines, HBV antibodies including HBV antibodies targeting the surface antigens of the hepatitis B virus and bispecific antibodies and "antibody-like" therapeutic proteins (such as DARPins®, anti-pMHC TCR-like antibodies, DARTs®, DUOBODIES®, BITES®, XmAbs®, TandAbs®, Fab derivatives, or TCR-like antibodies), cyclophilin inhibitors, stimulators of retinoic acid-inducible gene 1, stimulators of RIG-I like receptors, PD-1 inhibitors, PD-L1 inhibitors, Arginase inhibitors, PI3K inhibitors, IDO inhibitors, and stimulators of NOD2.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with at least a second additional therapeutic agent selected from the group consisting of: HBV DNA polymerase inhibitors, HBV viral entry inhibitors, NTCP inhibitors, HBx inhibitors, cccDNA inhibitors, HBV antibodies targeting the surface antigens of the hepatitis B virus, siRNA, miRNA gene therapy agents, sshRNAs, KDM5 inhibitors, and nucleoprotein modulators (HBV core or capsid protein inhibitors).

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with compounds such as those disclosed in U.S. Publication No. 2010/0143301 (Gilead Sciences), U.S. Publication No. 2011/0098248 (Gilead Sciences), U.S. Publication No. 2009/0047249 (Gilead Sciences), U.S. Pat. No. 8,722,054 (Gilead Sciences), U.S. Publication No. 2014/0045849 (Janssen), U.S. Publication No. 2014/0073642 (Janssen), WO2014/056953 (Janssen), WO2014/076221 (Janssen), WO2014/128189 (Janssen), U.S. Publication No. 2014/0350031 (Janssen), WO2014/023813 (Janssen), U.S. Publication No. 2008/0234251 (Array Biopharma), U.S. Publication No. 2008/0306050 (Array Biopharma), U.S. Publication No. 2010/0029585 (Ventirx Pharma), U.S. Publication No. 2011/0092485 (Ventirx Pharma), US2011/0118235 (Ventirx Pharma), U.S. Publication No. 2012/0082658 (Ventirx Pharma), U.S. Publication No. 2012/0219615 (Ventirx Pharma), U.S. Publication No. 2014/0066432 (Ventirx Pharma), U.S. Publication No. 2014/0088085 (Ventirx Pharma), U.S. Publication No. 2014/0275167 (Novira Therapeutics), U.S. Publication No. 2013/0251673 (Novira Therapeutics), U.S. Pat. No. 8,513,184 (Gilead Sciences), U.S. Publication No. 2014/0030221 (Gilead Sciences), U.S. Publication No. 2013/0344030 (Gilead Sciences), U.S. Publication No. 2013/0344029 (Gilead Sciences), US20140275167 (Novira Therapeutics), US20130251673 (Novira Therapeutics), U.S. Publication No. 2014/0343032 (Roche), WO2014037480 (Roche), U.S. Publication No. 2013/0267517 (Roche), WO2014131847 (Janssen), WO2014033176 (Janssen), WO2014033170 (Janssen), WO2014033167 (Janssen), WO2015/059212 (Janssen), WO2015118057 (Janssen), WO2015011281 (Janssen), WO2014184365 (Janssen), WO2014184350 (Janssen), WO2014161888 (Janssen), WO2013096744 (Novira), US20150225355 (Novira), US20140178337 (Novira), US20150315159 (Novira), US20150197533 (Novira), US20150274652 (Novira), US20150259324, (Novira), US20150132258 (Novira), U.S. Pat. No. 9,181,288 (Novira), WO2014184350 (Janssen), WO2013144129 (Roche), US20100015178 (Incyte), US2016137652 (Flexus Biosciences, Inc.), WO2014073738 (Flexus Biosciences, Inc.), WO2015188085 (Flexus Biosciences, Inc.), U.S. Publication No. 2014/0330015 (Ono Pharmaceutical), U.S. Publication No. 2013/0079327 (Ono Pharmaceutical), U.S. Publication No. 2013/0217880 (Ono pharmaceutical), WO2016057924 (Genentech/Constellation Pharmaceuticals), US20140275092 (Genentech/Constellation Pharmaceuticals), US20140371195 (Epitherapeutics) and US20140371214 (Epitherapeutics), US20160102096 (Epitherapeutics), US20140194469 (Quanticel), US20140171432, US20140213591 (Quanticel), US20160039808 (Quanticel), US20140275084 (Quanticel), WO2014164708 (Quanticel), U.S. Pat. No. 9,186,337B2 (Oryzon Genomics), and other drugs for treating HBV, and combinations thereof.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with 5-30 mg tenofovir alafenamide fumarate, tenofovir alafenamide hemifumarate, or tenofovir alafenamide. In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with 5-10; 5-15; 5-20; 5-25; 25-30; 20-30; 15-30; or 10-30 mg tenofovir alafenamide fumarate, tenofovir alafenamide hemifumarate, or tenofovir alafenamide. In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with 10 mg tenofovir alafenamide fumarate, tenofovir alafenamide hemifumarate, or tenofovir alafenamide. In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with 25 mg tenofovir alafenamide fumarate, tenofovir alafenamide hemifumarate, or tenofovir alafenamide. An agent as disclosed herein may be combined with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, in any dosage amount of the compound (e.g., from 50 mg to 500 mg of compound) the same as if each combination of dosages were specifically and individually listed.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with 100-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 100-150; 100-200, 100-250; 100-300; 100-350; 150-200; 150-250; 150-300; 150-350; 150-400; 200-250; 200-300; 200-350; 200-400; 250-350; 250-400; 350-400 or 300-400 mg tenofovir disoproxil fumarate, tenofovir disoproxil hemifumarate, or tenofovir disoproxil. In certain embodiments, an agent disclosed herein, or a pharmaceutically acceptable salt thereof, is combined with 300 mg tenofovir disoproxil fumarate, tenofovir disoproxil hemifumarate, or tenofovir disoproxil. In certain embodiments, an agent disclosed herein, or a pharmaceutically acceptable salt thereof, is combined with 250 mg tenofovir disoproxil fumarate, tenofovir disoproxil hemifumarate, or tenofovir disoproxil. In certain embodiments, an agent herein, or a pharmaceutically acceptable salt thereof, is combined with 150 mg tenofovir disoproxil fumarate, tenofovir disoproxil hemifumarate, or tenofovir disoproxil. An agent as disclosed herein may be combined with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, in any dosage amount of the compound (e.g., from 50 mg to 500 mg of compound) the same as if each combination of dosages were specifically and individually listed.

9. Methods of Prevention and Treatment—HIV

Further provided are methods for treating or preventing an HIV infection (including HIV-1 and HIV-2) or a related disease or disorder in a subject in need thereof (e.g., a human subject), comprising providing to a subject in need thereof an effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. As appropriate, the polynucleotide may be present in a vector, e.g., a viral vector.

In another aspect, provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in treating or preventing an HIV infection (including HIV-1 and HIV-2) or a related disease or disorder.

In some embodiments, the related disease or disorder is caused by infection with HIV. In some embodiments, it is acquired immune deficiency syndrome (AIDS). In certain embodiments, the subject is a virologically suppressed HIV-infected mammal, while in other embodiments, the subject is a treatment-naïve HIV-infected mammal. In certain embodiments, a treatment-naïve subject has a viral load between $10^3$ and $10^5$ copies/ml (blood, serum or plasma), and in certain embodiments, a virologically suppressed subject has a viral load <50 copies/ml (blood, serum, or plasma). In another embodiment, the subject is a mammal, e.g., a human. In certain embodiments, the subject has been diagnosed with an HIV infection, e.g., HIV-1 or HIV-2, infection or a related disease or disorder, e.g., AIDS, or is considered at risk for developing an HIV, e.g., HIV-1 or HIV-2, infection or a related disease or disorder, e.g., AIDS. Subjects at risk for HIV-related diseases or disorders include patients who have come into contact with an infected person or who have been exposed to HIV in some other way. Administration of a prophylactic agent can occur prior to the manifestation of symptoms characteristic of HIV-related disease or disorder, such that a disease or disorder is prevented or, alternatively, delayed in its progression.

Also provided are methods for preventing or inhibiting an increase in HIV virus titer, virus replication, virus proliferation or an amount of an HIV viral DNA, HIV proviral DNA, or HIV viral protein in a subject (e.g., a human subject). In one embodiment, the method comprises providing to the subject in need thereof an amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, effective to prevent an increase in HIV titer, virus replication, or an amount of an HIV protein of one or more HIV strains or isolates in the subject. In certain embodiments, the method further comprises measuring an amount of HIV viral or proviral DNA or protein at one or more time points, e.g., before and after the subject is provided with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. Methods and biomarkers for determining an amount of HIV viral or proviral DNA or protein in a subject are known and available in the art, and described for example, in Siliciano, J. D. et al., *Curr Opin. HIV AIDS,* 5(6):491-7 (2010), and Rouzioux, C. et al., *Curr Opin HIV AIDS,* 8(3):170-5 (2013).

In certain aspect, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be used in, for example, methods of inhibiting certain viruses such as HIV isolates described herein, prophylactic inhibiting or preventing infections of certain viruses such as HIV isolates described herein, detection of certain viruses such as HIV isolates described herein in a sample, inhibiting certain viruses such as HIV isolates described herein, or diagnosis of certain viruses such as HIV isolates described herein.

Further provided are methods for treating an HIV infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. In some embodiments, the present disclosure provides a method for preventing an HIV infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

In some embodiments, after one or more administrations of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, the subject does not exhibit symptoms of HIV or AIDS in the absence of anti-retroviral treatment (ART) for at least 6 months, at least 1 year, at least 2 years, at least 3 years, at least 4 years, at least 5 years or longer. In some embodiments, after one or more administrations of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, the subject has an HIV viral load copies/ml blood of less than 500, e.g., less than 400, less than 300, less than 200, less than 100, less than 50, in the absence of anti-retroviral treatment (ART) for at least 6 months, at least 1 year, at least 2 years, at least 3 years, or more.

a. HIV Combination Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional anti-HIV therapeutic agents.

Illustrative anti-HIV therapeutic agents that can be combined or co-administered include without limitation, HIV protease inhibitors, HIV non-nucleoside or non-nucleotide inhibitors of reverse transcriptase, HIV nucleoside or nucleotide inhibitors of reverse transcriptase, HIV integrase inhibitors, HIV non-catalytic site (or allosteric) integrase inhibitors, HIV entry inhibitors, HIV maturation inhibitors, HIV capsid inhibitors, nucleocapsid protein 7 (NCp7) inhibitors, HIV Tat or Rev inhibitors, inhibitors of Tat-TAR-P-TEFb, immunomodulators (e.g., immunostimulators), immunotherapeutic agents, antibody-drug conjugates, gene modifiers, gene editors (such as CRISPR/Cas9, zinc finger nucleases, homing nucleases, synthetic nucleases, TALENs), cell therapies (such as chimeric antigen receptor T-cell, CAR-T, and engineered T-cell receptors, TCR-T, autologous T-cell therapies, engineered B cells, NK cells), latency reversing agents, compounds that target the HIV capsid, immune-based therapies, phosphatidylinositol 3-kinase (PI3K) inhibitors, HIV antibodies, bispecific antibodies and "antibody-like" therapeutic proteins, HIV p17 matrix protein inhibitors, IL-13 antagonists, peptidyl-prolyl cis-trans isomerase A modulators, protein disulfide isomerase inhibitors, complement C5a receptor antagonists, DNA methyltransferase inhibitor, Fatty acid synthase inhibitor, HIV vif gene modulators, Vif dimerization antagonists, HIV-1 viral infectivity factor inhibitors, HIV-1 Nef modulators, TNF alpha ligand inhibitors, HIV Nef inhibitors, Hck tyrosine kinase modulators, mixed lineage kinase-3 (MLK-3) inhibitors, HIV-1 splicing inhibitors, integrin antagonists, nucleoprotein inhibitors, splicing factor modulators, COMM domain containing protein 1 modulators, HIV ribonuclease H inhibitors, IFN antagonists, retrocyclin modulators, CD3 antagonists, CDK-4 inhibitors, CDK-6 inhibitors, CDK-9 inhibitors, Cytochrome P450 3 inhibitors, CXCR4 modulators, dendritic ICAM-3 grabbing nonintegrin 1 inhibitors, HIV GAG protein inhibitors, HIV POL protein inhibitors, Complement Factor H modulators, ubiquitin ligase inhibitors, deoxycytidine kinase inhibitors, cyclin dependent kinase inhibitors, HPK1 (MAP4K1) inhibitors, proprotein convertase PC9 stimulators, ATP dependent RNA helicase DDX3X inhibitors, reverse transcriptase priming complex inhibitors, G6PD and NADH-oxidase inhibitors, mTOR complex 1 inhibitors, mTOR complex 2 inhibitors, P-Glycoprotein modulators, RNA polymerase modulators, TAT protein inhibitors, Prolylendopeptidase inhibitors, Phospholipase A2 inhibitors, pharmacokinetic enhancers, HIV gene therapy, HIV vaccines, anti-HIV peptides and combinations thereof.

In various embodiments, the one or more anti-HIV agents are selected from the group consisting of combination drugs for HIV, other drugs for treating HIV, HIV protease inhibitors, HIV reverse transcriptase inhibitors, HIV integrase inhibitors, HIV non-catalytic site (or allosteric) integrase inhibitors, HIV entry (fusion) inhibitors, HIV maturation inhibitors, latency reversing agents, HIV capsid inhibitors, HIV Tat or Rev inhibitors, immunomodulators, (e.g., immunostimulators), immunotherapeutic agents, immune-based therapies, PI3K inhibitors, HIV antibodies, and bispecific antibodies, and "antibody-like" therapeutic proteins, and combinations thereof.

In some embodiments, the additional therapeutic agent or agents are chosen from HIV protease inhibitors, HIV non-nucleoside or non-nucleotide inhibitors of reverse transcriptase, HIV nucleoside or nucleotide inhibitors of reverse transcriptase, HIV integrase inhibitors, HIV capsid inhibitors, gp41 inhibitors, CXCR4 inhibitors, gp120 inhibitors, CCR5 inhibitors, Nef inhibitors, latency reversing agents, HIV bNAbs, agonists of TLR7, TLR8, and TLR9, HIV vaccines, cytokines, immune checkpoint inhibitors, FLT3 ligands, T cell and NK cell recruiting bispecific antibodies, chimeric T cell receptors targeting HIV antigens, pharmacokinetic enhancers, and other drugs for treating HIV, and combinations thereof.

In some embodiments, the additional therapeutic agent or agents are chosen from dolutegravir, cabotegravir, islatravir, darunavir, bictegravir, elsulfavirine, rilpivirine, and lenacapavir, and combinations thereof.

In some embodiments, the additional therapeutic agent or agents are chosen from dolutegravir, cabotegravir, islatravir, darunavir, bictegravir, elsulfavirine, rilpivirine, and lenacapavir.

HIV Combination Drugs

Example anti-HIV therapeutic agents that can be combined include without limitation ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); darunavir, tenofovir alafenamide hemifumarate, emtricitabine, and cobicistat; efavirenz, lamivudine, and tenofovir disoproxil fumarate; lamivudine and tenofovir disoproxil fumarate; tenofovir and lamivudine; tenofovir alafenamide and emtricitabine; tenofovir alafenamide hemifumarate and emtricitabine; tenofovir alafenamide hemifumarate, emtricitabine, and rilpivirine; tenofovir alafenamide hemifumarate, emtricitabine, cobicistat, and elvitegravir; tenofovir analog; COMBIVIR® (zidovudine and lamivudine; AZT+3TC); EPZICOM® (LIVEXA®; abacavir sulfate and lamivudine; ABC+3TC); KALETRA® (ALUVIA®; lopinavir and ritonavir); TRIUMEQ® (dolutegravir, abacavir, and lamivudine); BIKTARVY (bictegravir+emtricitabine+tenofovir alafenamide), DOVATO® (dolutegravir+lamivudine), TRIZIVIR® (abacavir sulfate, zidovudine, and lamivudine; ABC+AZT+3TC); atazanavir and cobicistat; atazanavir sulfate and cobicistat; atazanavir sulfate and ritonavir; darunavir and cobicistat; dolutegravir and rilpivirine; dolutegravir and rilpivirine hydrochloride; dolutegravir, abacavir sulfate, and lamivudine; lamivudine, nevirapine, and zidovudine; raltegravir and lamivudine; doravirine, lamivudine, and tenofovir disoproxil fumarate; doravirine, lamivudine, and tenofovir disoproxil; dolutegravir+lamivudine, lamivudine+abacavir+zidovudine, lamivudine+abacavir, lamivudine+tenofovir disoproxil fumarate, lamivudine+zidovudine+nevirapine, lopinavir+ritonavir, lopinavir+ritonavir+abacavir+lamivudine, lopinavir+ritonavir+zidovudine+lamivudine, tenofovir+lamivudine, and tenofovir disoproxil fumarate+emtricitabine+rilpivirine hydrochloride, lopinavir, ritonavir, zidovudine, lopinavir+ritonavir+abacavir+lamivudine, and lamivudine; cabotegravir+rilpivirine; 3BNC117+albuvirtide, elpida (elsulfavirine; VM-1500; VM-1500A), lenacapavir+islatravir (oral, injectable), and dual-target HIV-1 reverse transcriptase/nucleocapsid protein 7 inhibitors.

Other HIV Drugs

Examples of other drugs for treating HIV that can be combined or co-administered with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, include aspernigrin C, acemannan, alisporivir, BanLec, deferiprone, Gamimune, metenkefalin, naltrexone, Prolastin, REP 9, RPI-MN, VSSP, H1viral, SB-728-T, 1,5-dicaffeoylquinic acid, rHIV7-shl-TAR-CCR5RZ, AAV-eCD4-Ig gene therapy, MazF gene therapy, BlockAide, bevirimat derivatives, ABX-464, AG-1105, APH-0812, bryostatin analogs, BIT-225, BRII-732, BRII-778, CYT-107, CS-TATI-1, fluoro-beta-D-arabinose nucleic acid (FANA)-modified antisense oligonucleotides, FX-101, griffithsin, HGTV-43, HPH-116, HS-10234, hydroxychloroquine, IMB-10035, IMO-3100, IND-02, JL-18008, LADAVRU, MK-1376, MK-2048, MK-4250, MK-8507, MK-8558, islatravir (MK-8591) (islatravir), NOV-205, OB-002H, ODE-Bn-TFV, PA-1050040 (PA-040), PC-707, PGN-007, QF-036, S-648414, SCY-635, SB-9200, SCB-719, TR-452, TEV-90110, TEV-90112, TEV-90111, TEV-90113, RN-18, DIACC-1010, Fasnall, Immuglo, 2-CLIPS peptide, HRF-4467, thrombospondin analogs, TBL-1004HI, VG-1177, xl-081, AVI-CO-004, rfhSP-D, [18F]-MC-225, URMC-099-C, RES-529, Verdinexor, IMC-M113V, IML-106, antiviral fc conjugate (AVC), VIR-576, nipamovir, Covimro, and ABBV-1882.

HIV Protease Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV protease inhibitor. Examples of HIV protease inhibitors that can be combined with an agent of this disclosure include amprenavir, atazanavir, brecanavir, darunavir, fosamprenavir, fosamprenavir calcium, indinavir, indinavir sulfate, lopinavir, nelfinavir, nelfinavir mesylate, ritonavir, saquinavir, saquinavir mesylate, tipranavir, ASC-09+ritonavir, AEBL-2, DG-17, GS-1156, TMB-657 (PPL-100), T-169, BL-008, MK-8122, TMB-607, GRL-02031, and TMC-310911. Additional examples of protease inhibitors that can be combined or co-administered are disclosed in U.S. Pat. Nos. 10,294,234, US2020030327 and US2019210978.

HIV Ribonuclease H Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV ribonuclease H inhibitor. Examples of HIV ribonuclease H inhibitors that can be combined include NSC-727447.

HIV Nef Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV Nef inhibitor. Examples of HIV Nef inhibitors that can be combined with include FP-1.

HIV Reverse Transcriptase Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a non-nucleoside or non-nucleotide inhibitor. Examples of HIV non-nucleoside or non-nucleotide inhibitors of reverse transcriptase include dapivirine, delavirdine, delavirdine mesylate, doravirine, efavirenz, etravirine, lentinan, nevirapine, rilpivirine, ACC-007, ACC-008, AIC-292, F-18, KM-023, PC-1005, M1-TFV, M2-TFV, VM-1500A-LAI, PF-3450074, elsulfavirine (sustained release oral, HIV infection), doravirine+islatravir (fixed dose combination/oral tablet formulation, HIV-1 infection), elsulfavirine (long-acting injectable nanosuspension, HIV infection), and elsulfavirine (VM-1500).

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with long acting anti-HIV regimen. Examples of drugs that are being developed as long acting anti-HIV regimens that can be co-administered include without limitation cabotegravir LA, rilpivirine LA, cabotegravir LA+rilpivirine LA, elvitegravir (extended release), lenacapavir long acting, raltegravir long acting, darunavir long acting, any integrase LA, VM-1500A-LAI, VM-3500, maraviroc (LAI), T-1144, ODE-Bn-TFV, CP-112, S-648414, tenofovir implant, tenofovir long acting, tenofovir prodrug long acting, islatravir (MK-8591) subdermal implant, long-acting dolutegravir, long acting raltegravir+lamivudine, transdermal devices that can deliver HIV drugs, such as transdermal tenofovir (WO2020092990).

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV nucleoside or nucleotide inhibitor. Examples of HIV nucleoside or nucleotide inhibitors of reverse transcriptase that can be combined with an agent of this disclosure include adefovir, adefovir dipivoxil, azvudine, emtricitabine, tenofovir, tenofovir alafenamide, tenofovir alafenamide fumarate, tenofovir alafenamide hemifumarate, tenofovir disoproxil, tenofovir disoproxil fumarate, tenofovir octadecyloxyethyl ester (AGX-1009), tenofovir disoproxil hemifumarate, VIDEX® and VIDEX EC® (didanosine, ddl), abacavir, abacavir sulfate, alovudine, apricitabine, censavudine, didanosine, elvucitabine, festinavir, fosalvudine tidoxil, CMX-157, dapivirine, doravirine, etravirine, OCR-5753, tenofovir disoproxil orotate, fozivudine tidoxil, lamivudine, phosphazid, stavudine, zalcitabine, zidovudine, rovafovir etalafenamide (GS-9131), GS-9148, MK-8504, islatravir (MK-8591), MK-8583, VM-2500 and KP-1461.

HIV Integrase Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV integrase inhibitor. Examples of HIV integrase inhibitors include elvitegravir, elvitegravir (extended-release microcapsules), curcumin, derivatives of curcumin, chicoric acid, derivatives of chicoric acid, 3,5-dicaffeoylquinic acid, derivatives of 3,5-dicaffeoylquinic acid, aurintricarboxylic acid, derivatives of aurintricarboxylic acid, caffeic acid phenethyl ester, derivatives of caffeic acid phenethyl ester, tyrphostin, derivatives of tyrphostin, quercetin, derivatives of quercetin, raltegravir, PEGylated raltegravir, dolutegravir, JTK-351, bictegravir, AVX-15567, cabotegravir (long-acting injectable), diketo quinolin-4-1 derivatives, integrase-LEDGF inhibitor, ledgins, M-522, M-532, MK-0536, NSC-310217, NSC-371056, NSC-48240, NSC-642710, NSC-699171, NSC-699172, NSC-699173, NSC-699174, stilbenedisulfonic acid, T-169, STP-0404, VM-3500, XVIR-110, ACC-017 and cabotegravir.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a HIV non-catalytic site, or allosteric, integrase inhibitor (NCINI). Examples of HIV non-catalytic site, or allosteric, integrase inhibitors (NCINI) include CX-05045, CX-05168, and CX-14442. Additional examples of HIV capsid inhibitors that can be combined or co-administered include without limitation those described in U.S. Patent Nos. US2014221356 and US2016016973.

HIV Viral Infectivity Factor Inhibitor

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV viral infectivity factor inhibitor. Examples of HIV viral infectivity factor inhibitors that can be combined with an agent of this disclosure include 2-amino-N-(2-methoxyphenyl)-6-((4-nitrophenyl)thio)benzamide derivatives and Irino-L.

HIV Entry Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV entry inhibitor. Examples of HIV entry (fusion) inhibitors include AAR-501, LBT-5001, cenicriviroc, CCR5 inhibitors, gp41 inhibitors, CD4 attachment inhibitors, gp120 inhibitors, gp160 inhibitors, CXCR4 inhibitors and D-peptide HIV entry inhibitors (e.g., cholesterol-PIE12-trimer (CPT31)).

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a CCR5 inhibitor. Examples of CCR5 inhibitors include aplaviroc, vicriviroc, maraviroc, maraviroc (long-acting injectable nanoemulsion), cenicriviroc, leronlimab (PRO-140), adaptavir (RAP-101), nifeviroc (TD-0232), anti-GP120/CD4 or CCR5 bispecific antibodies, B-07, MB-66, polypeptide C25P, TD-0680, thioraviroc and vMIP (Haimipu).

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a CXCR4 inhibitor. Examples of CXCR4 inhibitors include plerixafor, ALT-1188, N15 peptide, and vMIP (Haimipu).

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a gp41 inhibitor. Examples of gp41 inhibitors include albuvirtide, enfuvirtide, griffithsin (gp41/gp120/gp160 inhibitor), BMS-986197, enfuvirtide biobetter, enfuvirtide biosimilar, HIV-1 fusion inhibitors (P26-Bapc), ITV-1, ITV-2, ITV-3, ITV-4, CPT-31, Cl3hmAb, lipuvirtide, PIE-12 trimer and sifuvirtide.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a CD4 attachment inhibitor. Examples of CD4 attachment inhibitors include ibalizumab and CADA analogs.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a gp120 inhibitor. Examples of gp120 inhibitors include anti-HIV microbicide, Radha-108 (receptol) 3B3-PE38, BMS-818251, BanLec, bentonite-based nanomedicine, fostemsavir tromethamine, IQP-0831, VVX-004, and BMS-663068.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a gp160 inhibitor. Examples of gp160 inhibitors that can be combined include fangchinoline.

HIV Maturation Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV maturation inhibitor. Examples of HIV maturation inhibitors include BMS-955176, GSK-3640254 and GSK-2838232.

Latency Reversing Agents

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV latency reversing agent. Examples of latency reversing agents that can be combined with the one or more multi-specific antigen binding molecules, described herein, include IL-15 receptor agonists (e.g., ALT-803; interleukin-15/Fc fusion protein (e.g., XmAb24306); recombinant interleukin-15 (e.g., AM0015, NIZ-985); pegylated IL-15 (e.g., NKTR-255)); toll-like receptor (TLR) agonists (including TLR7 agonists, e.g., vesatolimod (GS-9620); TLR8 agonists, e.g., selgantolimod (GS-9688), TLR9 agonists, e.g., lefitolimod (MGN-1703)), histone deacetylase (HDAC) inhibitors, proteasome inhibitors such as velcade, protein kinase C (PKC) activators, Smyd2 inhibitors, BET-bromodomain 4 (BRD4) inhibitors (such as ZL-0580, apabetalone), ionomycin, IAP antagonists (inhibitor of apoptosis proteins, such as APG-1387, LBW-242), SMAC mimetics (including ciapavir, BI-891065, TL32711, LCL161, GDC-0917, HGS1029, AT-406, APG-1387, LCL-161 (NVP-LCL161)), Debio-1143), PMA, SAHA (suberanilohydroxamic acid, or suberoyl, anilide, and hydroxamic acid), NIZ-985, IL-15 modulating antibodies, (including IL-15, IL-15 fusion proteins and IL-15 receptor agonists, e.g., ALT-803), JQ1, disulfiram, amphotericin B, and ubiquitin inhibitors such as largazole analogs, APH-0812, and GSK-343. Examples of HDAC inhibitors include romidepsin, vorinostat, and panobinostat. Examples of PKC activators include indolactam, prostratin, ingenol B, and DAG-lactones. Additional examples of TLR7 agonists that can be combined or co-administered include without limitation described in U.S. Patent Publ. No. US2010143301. Additional examples of TLR8 agonists that can be combined or co-administered include without limitation described in U.S. Patent Publ. No. US2017071944.

HIV Capsid Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a capsid inhibitor. Examples of capsid inhibitors that can be combined with an agent of this disclosure include capsid polymerization inhibitors or capsid disrupting compounds, HIV nucleocapsid p7 (NCp7) inhibitors such as azodicarbonamide, HIV p24 capsid protein inhibitors, GS-6207 (lenacapavir), GS-CA1, AVI-621, AVI-101, AVI-201, AVI-301, and AVI-CAN1-15 series, PF-3450074, HIV-1 capsid inhibitors (HIV-1 infection, Shandong University), and compounds described in Intl. Patent Publ. No. WO 2019/087016. Additional examples of capsid inhibitors that can be combined or co-administered include without limitation those described in U.S. Patent Publ. Nos. US2018051005 and US2016108030.

Cytochrome P450 3 Inhibitors

In certain embodiments, the one or more multi-specific antigen binding molecules described herein are combined or co-administered with a cytochrome P450 3 inhibitor. Examples of Cytochrome P450 3 inhibitors that can be combined or co-administered include without limitation those described in U.S. Pat. No. 7,939,553.

RNA Polymerase Modulators

In certain embodiments, the one or more multi-specific antigen binding molecules described herein are combined or co-administered with a RNA polymerase modulator (e.g., inhibitor). Examples of RNA polymerase modulators (e.g., inhibitors) include without limitation those described in U.S. Pat. Nos. 10,065,958 and 8,008,264.

Pharmacokinetic Enhancers

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a pharmacokinetic enhancer. Examples of pharmacokinetic enhancers include cobicistat and ritonavir.

HIV—Additional Therapeutic Agents

Examples of additional therapeutic agents useful in treating and preventing HIV include the compounds disclosed in WO 2004/096286 (Gilead Sciences); WO 2006/015261 (Gilead Sciences); WO 2006/110157 (Gilead Sciences); WO 2012/003497 (Gilead Sciences); WO 2012/003498 (Gilead Sciences); WO 2012/145728 (Gilead Sciences); WO 2013/006738 (Gilead Sciences); WO 2013/159064 (Gilead Sciences); WO 2014/100323 (Gilead Sciences), US 2013/0165489 (University of Pennsylvania), US 2014/0221378 (Japan Tobacco), US 2014/0221380 (Japan Tobacco); WO 2009/062285 (Boehringer Ingelheim); WO 2010/130034 (Boehringer Ingelheim); WO 2013/006792 (Pharma Resources), US 20140221356 (Gilead Sciences), US 20100143301 (Gilead Sciences) and WO 2013/091096 (Boehringer Ingelheim).

HIV Combination Therapy

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one, two, three, four or more combination therapeutic agents selected from ATRIPLA® (efavirenz, tenofovir disoproxil fumarate, and emtricitabine); COMPLERA® (EVIPLERA®; rilpivirine, tenofovir disoproxil fumarate, and emtricitabine); STRIBILD® (elvitegravir, cobicistat, tenofovir disoproxil fumarate, and emtricitabine); TRUVADA® (tenofovir disoproxil fumarate and emtricitabine; TDF+FTC); DESCOVY® (tenofovir alafenamide and emtricitabine); ODEFSEY® (tenofovir alafenamide, emtricitabine, and rilpivirine); GENVOYA® (tenofovir alafenamide, emtricitabine, cobicistat, and elvitegravir); BIKTARVY (bictegravir+emtricitabine+tenofovir alafenamide), adefovir; adefovir dipivoxil; cobicistat; emtricitabine; tenofovir; tenofovir disoproxil; tenofovir disoproxil fumarate; tenofovir alafenamide; tenofovir alafenamide hemifumarate; TRIUMEQ® (dolutegravir, abacavir, and lamivudine); dolutegravir, abacavir sulfate, and lamivudine; raltegravir;

raltegravir and lamivudine; maraviroc; enfuvirtide; ALUVIA® (KALETRA®; lopinavir and ritonavir); COMBIVIR® (zidovudine and lamivudine; AZT+3TC); EPZICOM® (LIVEXA®; abacavir sulfate and lamivudine; ABC+3TC); TRIZIVIR® (abacavir sulfate, zidovudine, and lamivudine; ABC+AZT+3TC); rilpivirine; rilpivirine hydrochloride; atazanavir sulfate and cobicistat; atazanavir and cobicistat; darunavir and cobicistat; atazanavir; atazanavir sulfate; dolutegravir; elvitegravir; ritonavir; atazanavir sulfate and ritonavir; darunavir; lamivudine; prolastin; fosamprenavir, fosamprenavir calcium efavirenz; etravirine; nelfinavir; nelfinavir mesylate; interferon; didanosine; stavudine; indinavir; indinavir sulfate; tenofovir and lamivudine; zidovudine; nevirapine; saquinavir; saquinavir mesylate; zalcitabine; tipranavir; amprenavir, delavirdine; delavirdine mesylate; Radha-108 (receptol); lamivudine and tenofovir disoproxil fumarate; efavirenz, lamivudine, and tenofovir disoproxil fumarate; phosphazid; lamivudine, nevirapine, and zidovudine; abacavir; and abacavir sulfate.

It will be appreciated by one of skill in the art that the additional therapeutic agents listed above may be included in more than one of the classes listed above. The particular classes are not intended to limit the functionality of those compounds listed in those classes.

In a specific embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV nucleoside or nucleotide inhibitor of reverse transcriptase and an HIV non-nucleoside inhibitor of reverse transcriptase. In another specific embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV nucleoside or nucleotide inhibitor of reverse transcriptase, and an HIV protease inhibiting compound. In an additional embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an HIV nucleoside or nucleotide inhibitor of reverse transcriptase, an HIV non-nucleoside inhibitor of reverse transcriptase, and a pharmacokinetic enhancer. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with at least one HIV nucleoside inhibitor of reverse transcriptase, an integrase inhibitor, and a pharmacokinetic enhancer. In another embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is are combined with two HIV nucleoside or nucleotide inhibitors of reverse transcriptase.

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with abacavir sulfate, tenofovir, tenofovir disoproxil, tenofovir disoproxil fumarate, tenofovir disoproxil hemifumarate, tenofovir alafenamide, or tenofovir alafenamide hemifumarate.

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with tenofovir, tenofovir disoproxil, tenofovir disoproxil fumarate, tenofovir alafenamide, or tenofovir alafenamide hemifumarate.

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a first additional therapeutic agent selected from the group consisting of abacavir sulfate, tenofovir, tenofovir disoproxil, tenofovir disoproxil fumarate, tenofovir alafenamide, and tenofovir alafenamide hemifumarate, and a second additional therapeutic agent selected from the group consisting of emtricitabine and lamivudine.

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a first additional therapeutic agent selected from the group consisting of tenofovir, tenofovir disoproxil, tenofovir disoproxil fumarate, tenofovir alafenamide, and tenofovir alafenamide hemifumarate, and a second additional therapeutic agent, wherein the second additional therapeutic agent is emtricitabine.

In a particular embodiment, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a first additional therapeutic agent selected from a first additional therapeutic agent selected from dolutegravir, cabotegravir, islatravir, darunavir, bictegravir, elsulfavirine, rilpivirine, and lenacapavir and a second additional therapeutic agent selected from emtricitabine and lamivudine.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 5-30 mg tenofovir alafenamide fumarate, tenofovir alafenamide hemifumarate, or tenofovir alafenamide, and 200 mg emtricitabine. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 5-10, 5-15, 5-20, 5-25, 25-30, 20-30, 15-30, or 10-30 mg tenofovir alafenamide fumarate, tenofovir alafenamide hemifumarate, or tenofovir alafenamide, and 200 mg emtricitabine. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 10 mg tenofovir alafenamide fumarate, tenofovir alafenamide hemifumarate, or tenofovir alafenamide, and 200 mg emtricitabine. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 25 mg tenofovir alafenamide fumarate, tenofovir alafenamide hemifumarate, or tenofovir alafenamide, and 200 mg emtricitabine. As appropriate, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with the agents provided herein in any dosage amount (e.g., from 1 mg to 500 mg of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein) the same as if each combination of dosages were specifically and individually listed.

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 200-400 mg tenofovir disoproxil fumarate, tenofovir disoproxil hemifumarate, or tenofovir disoproxil, and 200 mg emtricitabine. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 200-250, 200-300, 200-350, 250-350, 250-400, 350-400, 300-400, or 250-400 mg tenofovir disoproxil fumarate, tenofovir disoproxil hemifumarate, or tenofovir disoproxil, and 200 mg emtricitabine. In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with 300 mg tenofovir disoproxil fumarate, tenofovir disoproxil hemifumarate, or tenofovir disoproxil, and 200 mg emtricitabine. The IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, can be combined with the agents provided herein in any dosage amount (e.g., from 1 mg to 500 mg of the anti-HIV gp120 V3 glycan directed antibodies or antigen-binding fragments) the same as if each combination of dosages were specifically and individually listed.

Long-Acting HIV Inhibitors

In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a long-acting HIV inhibitor. Examples of drugs that are being developed as long acting HIV inhibitors include without limitation: cabotegravir LA, rilpivirine LA, any integrase LA, VM-1500 LAI, maraviroc (LAI), tenofovir implant, islatravir (MK-8591) implant, long-acting dolutegravir.

Broadly Neutralizing Antibodies (bNAbs)

In some embodiments, the combination therapy entails co-administration of an anti-HIV broadly neutralizing antibody or bNAb (i.e., a neutralizing antibody that neutralizes multiple HIV-1 viral strains). Various bNAbs are known in the art and may be used as a combining therapeutic agent. Illustrative bNAbs of use include, those that comprise VH and VL that bind to or compete with an epitope or region of gp120 selected from the group consisting of: (i) third variable loop (V3) and/or high mannose patch comprising a N332 oligomannose glycan; (ii) second variable loop (V2) and/or Env trimer apex; (iii) CD4 binding site (CD4bs); (iv) gp120/gp41 interface; or (v) silent face of gp120. See, McCoy, *Retrovirology* (2018) 15:70; Sok and Burton, *Nat Immunol.* 2018 19(11):1179-1188; Possas, et al., *Expert Opin Ther Pat.* 2018 July; 28(7):551-560; and Stephenson and Barouch, *Curr HIV/AIDS Rep* (2016) 13:31-37.

In some embodiments, the combination therapy includes an antibody that binds to an epitope or region of gp120 in the third variable loop (V3) and/or high mannose patch comprising a N332 oligomannose glycan and competes with or comprises CDRs and/or VH and VL regions from an antibody selected from the group consisting of GS-9722 (elipovimab), PGT-121, PGT-121.66, PGT-121.414, PGT-122, PGT-123, PGT-124, PGT-125, PGT-126, PGT-128, PGT-130, PGT-133, PGT-134, PGT-135, PGT-136, PGT-137, PGT-138, PGT-139, GS-2872, 10-1074, 10-1074-J, VRC24, 2G12, BG18, 354BG8, 354BG18, 354BG42, 354BG33, 354BG129, 354BG188, 354BG411, 354BG426, DH270.1, DH270.6, PGDM12, VRC41.01, PGDM21, PCDN-33A, BF520.1 and VRC29.03.

In some embodiments, the combination therapy includes an antibody that binds to an epitope or region of gp120 in the second variable loop (V2) and/or Env trimer apex and competes with or comprises CDRs and/or VH and VL regions from an antibody selected from the group consisting of PG9, PG16, PGC14, PGG14, PGT-142, PGT-143, PGT-144, PGT-145, CH01, CH59, PGDM1400, CAP256, CAP256-VRC26.08, CAP256-VRC26.09, CAP256-VRC26.25, PCT64-24E and VRC38.01.

In some embodiments, the combination therapy includes an antibody that binds to an epitope or region of gp120 in the CD4 binding site (CD4bs) and competes with or comprises CDRs and/or VH and VL regions from an antibody selected from the group consisting of b12, F105, VRC01, VRC07, VRC07-523, VRC03, VRC06, VRC06b01 VRC08, VRC0801, NIH45-46, GS-9723, GS-5423, 3BNC117, 3BNC60, VRC-PG04, PGV04; CH103, 44-VRC13.01, 1NC9, 12A12, N6, N6LS (VRC-HIVMAB091-00-AB), N49-P7, NC-Cow1, IOMA, CH235 and CH235.12, N49P6, N49P7, N49P11, N49P9 and N60P25.

In some embodiments, the combination therapy includes an antibody that binds to an epitope or region of gp120 in the gp120/gp41 interface and competes with or comprises CDRs and/or VH and VL regions from an antibody selected from the group consisting of PGT-151, CAP248-2B, 35022, 8ANC195, ACS202, VRC34 and VRC34.01.

In some embodiments, the combination therapy includes an antibody that binds to an epitope or region of the gp120 silent face and competes with or comprises second VH and VL regions from antibody VRC-PG05.

In some embodiments, the combination therapy includes an antibody that binds to an epitope or region of gp41 in the membrane proximal region (MPER) and competes with or comprises second VH and VL regions from an antibody selected from the group consisting of 10E8, 10E8v4, 10E8-5R-100cF, 4E10, DH511.11P, 2F5, 7b2, and LN01. In some embodiments, the combination therapy includes an antibody that binds to an epitope or region of KLIC ("KLIC," SEQ ID NO: 174), an immutable site of the transmembrane protein gp41 and competes with or comprises second VH and VL regions from Clone 3 human monoclonal antibody (Cl3hmAb) (Protheragen). See, e.g., Vanini, et al., AIDS. (1993) 7(2):167-74.

In some embodiments, the combination therapy includes an antibody that binds to and epitope or region of the gp41 fusion peptide and competes with or comprises second VH and VL regions from an antibody selected from the group consisting of VRC34 and ACS202.

In some embodiments, the combination therapy includes a multi-specific, e.g., a bispecific or tri-specific antibody that binds to an HIV antigen. Examples of HIV bispecific and trispecific antibodies include MGD014, B12BiTe, BiIA-SG, TMB-bispecific, SAR-441236, VRC-01/PGDM-1400/10E8v4, 10E8.4/iMab, and 10E8v4/PGT121-VRC01.

Prior to administration, the bNAbs may be improved to have enhanced drug-like-properties, reduced immunogenicity, enhanced ADCC, and suitable pharmacokinetic properties. Such antibodies were shown to bind to the HIV envelope glycoprotein expressed on the surface of virion or infected cells, and mediate both direct neutralization of the virus as well as potent NK, Monocyte and PBMC killing of these cells. This property allows the antibodies to treat HIV infections by neutralizing the virus, and also kill and eliminate latently HIV infected cells in infected individuals, potentially leading to a sterilizing cure for HIV.

In various embodiments, all antibodies administered in a combination anti-HIV antibody therapy can have Fc and/or post-translational modifications that increase serum half-life and/or enhance effector activity, as described above.

In various embodiments, the anti-HIV directed antibody or antigen-binding fragments, and optionally combined bNAbs, can be in vivo delivered, e.g., expressed in vivo from administered mRNA or engineered B-cells. Examples of in vivo delivered bNAbs include AAV8-VRC07; mRNA encoding anti-HIV antibody VRC01; and engineered B-cells encoding 3BNC117 (Hartweger et al, *J. Exp. Med.* 2019, 1301).

Anti-HIV Gene Therapy and Cell Therapy

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-HIV gene or cell therapy regimen. Gene therapy and cell therapy include without limitation the genetic modification to silence a gene; genetic approaches to directly kill the infected cells; the infusion of immune cells designed to replace most of the patient's own immune system to enhance the immune response to infected cells, or activate the patient's own immune system to kill infected cells, or find and kill the infected cells; genetic approaches to modify cellular activity to further alter endogenous immune responsiveness against the infection. Examples of anti-HIV cell therapy include LB-1903, ENOB-HV-01, ENOB-HV-21, ENOB-HV-31, GOVX-B01, HSPCs overexpressing ALDH1 (LV-800, HIV infection), AGT103-T, and SupT1 cell-based therapy. Examples of dendritic cell therapy include AGS-004. CCR5 gene editing agents include SB-728T. CCR5 gene inhibitors include Cal-1, and lentivirus vector CCR5 shRNA/TRIM5alpha/TAR decoy-transduced autologous CD34-positive hematopoietic progenitor cells (HIV infection/HIV-related lymphoma). In some embodiments, C34-CCR5/C34-CXCR4 expressing CD4-positive T-cells are co-administered with one or more multi-specific antigen binding molecules. In some embodiments, the agents described herein are co-administered with AGT-103-transduced autologous T-cell therapy or AAV-eCD4-Ig gene therapy.

Anti-HIV CAR-T-Cell Therapy

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a population of immune effector cells engineered to express a chimeric antigen receptor (CAR), wherein the CAR comprises an HIV antigen binding domain. The HIV antigen includes an HIV envelope protein or a portion thereof, gp120 or a portion thereof, a CD4 binding site on gp120, the CD4-induced binding site on gp120, N glycan on gp120, the V2 of gp120, the membrane proximal region on gp41. The immune effector cell is a T-cell or an NK cell. In some embodiments, the T-cell is a CD4+ T-cell, a CD8+ T-cell, or a combination thereof. Cells can be autologous or allogeneic. Examples of HIV CAR-T include convertible CAR-T, VC-CAR-T, CMV-N6-CART, anti-CD4 CART-cell therapy, CD4 CAR+C34-CXCR4+CCR5 ZFN T-cells, dual anti-CD4 CART-T cell therapy (CD4 CAR+C34-CXCR4 T-cells), anti-CD4 MicAbody antibody+anti-MicAbody CAR T-cell therapy (iNKG2D CAR, HIV infection), GP-120 CAR-T therapy, autologous hematopoietic stem cells genetically engineered to express a CD4 CAR and the C46 peptide.

Anti-HIV TCR-T-Cell Therapy

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a population of TCR-T-cells. TCR-T-cells are engineered to target HIV derived peptides present on the surface of virus-infected cells, for example ImmTAV.

B-Cell Therapy

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a population of B cells genetically modified to express broadly neutralizing antibodies, such as 3BNC117

(Hartweger, et al, *J. Exp. Med.* (2019) 1301, Moffett, et al., *Sci. Immunol.* 4, eaax0644 (2019) 17 May 2019).

10. Methods of Prevention and Treatment—Herpesviruses

Further provided are methods for treating or preventing a herpesvirus, such as a herpes simplex virus (HSV) infection or a related disease or disorder in a subject in need thereof (e.g., a human subject), comprising providing to a subject in need thereof an effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. As appropriate, the polynucleotide may be present in a vector, e.g., a viral vector.

In another aspect, provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in treating or preventing a herpesvirus infection or a related disease or disorder in a subject in need thereof.

In some embodiments, the related disease or disorder is caused by infection with a herpes simplex virus (HSV, including HSV-1 and HSV-2. In certain embodiments, the subject is a virologically suppressed HSV-infected mammal, while in other embodiments, the subject is a treatment-naïve HSV-infected mammal. In certain embodiments, the subject has been diagnosed with an HSV, e.g., HSV-1 or HSV-2, infection or is considered at risk for developing an HSV, e.g., HSV-1 or HSV-2, infection. Subjects at risk for herpesvirus-related diseases or disorders include patients who have come into contact with an infected person or who have been exposed to herpesvirus in some other way. Administration of a prophylactic agent can occur prior to the manifestation of symptoms characteristic of herpesvirus-related disease or disorder, such that a disease or disorder is prevented or, alternatively, delayed in its progression.

Also provided are methods for preventing or inhibiting an increase in herpesvirus virus titer, virus replication, virus proliferation or an amount of a herpesvirus viral DNA, proviral DNA, or viral protein in a subject (e.g., a human subject). In one embodiment, the method comprises providing to the subject in need thereof an amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, effective to prevent an increase in herpesvirus titer, virus replication, or an amount of an herpesvirus protein of one or more herpesvirus strains or isolates in the subject. In certain embodiments, the method further comprises measuring an amount of herpesvirus viral or proviral DNA or protein at one or more time points, e.g., before and after the subject is provided with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. Methods and biomarkers for determining an amount of herpesvirus viral or proviral DNA or herpesvirus protein in a subject are known and available in the art, and described for example, in Arshad, et al., *JMIR Public Health Surveill.* (2019) May 23; 5(2):e14216; Krumbholz, et al., *Med Microbiol Immunol.* (2019) 208(2):197-204; Levin, et al., Microbiol Spetr. 2016 June; 4(3) (PMID: 27337486); Quereda, et al., *J Clin Microbiol.* (2000) August; 38(8):3061-7; Lee, et al., *Ann Lab Med.* (2018) 38(5):440-445; Yip, et al., *Biomed Res Int.* (2019) 2019:5715180; Slinger, et al., *J Clin Virol.* (2019) 113:35-38; Sam, et al., *J Clin Virol.* (2018) 99-100:1-4; Lieveld, et al., *J Virol Methods.* (2017) 248:181-186; Paryan, et al., *Appl Immunohistochem Mol Morphol.* (2017) 25(2):139-143; and Faron, et al., *J Clin Microbiol.* (2016) 54(8):2008-13.

In certain aspect, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be used in, for example, methods of inhibiting certain viruses such as herpesvirus isolates described herein, prophylactic inhibiting or preventing infections of certain viruses such as herpesvirus isolates described herein, detection of certain viruses such as herpesvirus isolates described herein in a sample, inhibiting certain viruses such as herpesvirus isolates described herein, or diagnosis of certain viruses such as herpesvirus isolates described herein.

Further provided are methods for treating an herpesvirus infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. In some embodiments, the present disclosure provides a method for preventing an herpesvirus infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

a. Herpesvirus Combination Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional anti-herpesvirus therapeutic agents.

Herpesvirus Targets

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more agents that target a herpesvirus. Illustrative agents include without limitation complement receptor 2 antagonists; atypical chemokine receptor 1 (Duffy blood group) (ACKR1; NCBI Gene ID: 2532) modulators; envelope glycoprotein GP350 modulators; glucocorticoid receptor agonists; helicase inhibitors; HIV gp160 protein inhibitors; HIV gp41 protein inhibitors; HIV-1 reverse transcriptase inhibitors; HLA class I antigen A-2 alpha modulators; HLA class I antigen A-24 alpha modulators; human cytomegalovirus glycoprotein B inhibitors; human cytomegalovirus glycoprotein H modulators; human cytomegalovirus glycoprotein inhibitors; human cytomegalovirus glycoprotein L modulators; immunoglobulin G agonists; interferon alpha 2 ligands; interferon gamma receptor antagonists; latent membrane protein 1 modulators; latent membrane protein 2 stimulators; progesterone receptor agonists; secreted protein BARF1 modulators; serine threonine protein kinase UL97 modulators; T-cell surface glycoprotein CD8 stimulators; thymidine kinase inhibitors; trans-acting transcription protein ICP4 modulators; transferase inhibitors; unspecified gene inhibitors; adenosylhomocysteinase inhibitors; Basigin inhibitors; CCR5 chemokine modulators; CD4 agonists; CD89 agonists; CMV 65 kDa lower matrix phosphoprotein modulators; CRISPR associated endonuclease Cas9 modulators; cyclin dependent kinase inhibitors; cyclin-dependent kinase-9 inhibitors; DNA polymerase inhibitors; DNA primase inhibitors; endonuclease modulators; Epstein-Barr nuclear antigen 1 inhibitors; Epstein-Barr nuclear antigen 1 stimulators; fatty acid synthase inhibitors; Herpesvirus envelope glycoprotein B stimulators; Herpesvirus envelope glycoprotein D inhibitors; HIV gp120 protein inhibitors; HLA class I antigen A-11 alpha modulators; Hsp 90 inhibitors; hyaluronidase inhibitors; immunoglobulin agonists; interferon alpha 1 ligands; interferon alpha 2 ligands; interferon alpha ligand inhibitors; interferon beta ligands; large terminase protein inhibitors; LAT gene inhibitors; NAD-dependent deacetylase sirtuin modulators; nicotinic acetylcholine receptor antagonists; NKG2D ligand modulators; nucleotidyltransferase inhibitors; protein Jumonji inhibitors; ribonuclease stimulators; serine threonine protein kinase UL97 inhibitors; syntaxin-5 inhibitors; TAT protein modulators; T-cell surface glycoprotein CD8 stimulators; TLR-4 agonists; and viral ribonucleotide reductase inhibitors.

Herpesvirus Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a Herpesviridae (NCBI:txid10292) infection, including a herpes simplex virus (HSV), including HSV-1 (NCBI:txid102980) and HSV-2 (NCBI:txid10310); a cytomegalovirus (CMV; NCBI:txid10358); Varicella-zoster virus (VZV; NCBI: txid10335); Epstein-Barr virus (EBV; NCBI:txid10376). Illustrative anti-herpesvirus agents useful for treating and/or preventing a herpesvirus infection that can be combined or co-administered include interferon alpha 2 ligand modulators such as, interferon alfa-2b, ALPHAREKIN®, recombinant human interferon alfa-2b follow-on biologic, HERPFERON®, ANTERFERON®; DNA polymerase inhibitors such as, brincidofovir; protein Jumonji inhibitors such as, ML-324, dimethyloxaloylglycine; nicotinic acetylcholine receptor antagonists such as, anti-herpesvirus envelope glycoprotein D antibodies such as m27f; progesterone receptor agonists such as levonorgestrel; HIV-1 reverse transcriptase inhibitors such as, tenofovir; Endonuclease modulators such as, meganucleases; interferon alpha ligand/Interferon gamma receptor antagonists such as, ANAFERON®; nicotinic acetylcholine receptor antagonists such as RPI-MN; BOR-15001L7, lidocaine; PC-707; and SQX-770.

Herpes Simplex Virus (HSV) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a herpes simplex virus (HSV; NCBI:txid10294) infection. Illustrative agents useful for treating and/or preventing a HSV infection include DNA primase/helicase inhibitors such as, amenamevir, pritelivir; DNA polymerase inhibitors such as penciclovir, valaciclovir, acyclovir, aciclovir, famciclovir, ganciclovir, idoxuridine, penciclovir, tromantadine, valganciclovir and brivudine (Bromovinyldeoxyuridine), and foscarnet sodium; CCR5 chemokine modulators/human cytomegalovirus glycoprotein inhibitors such as, MB-66; Hsp 90 inhibitors such as, BJ-B11; glucocorticoid receptor agonists such as, hydrocortisone; interferon alpha 1 ligand modulators such as, interferon alpha 1b, recombinant human interferon alpha 1b; interferon alpha 2 ligand modulators such as, recombinant human interferon alpha-2b; interferon beta ligand modulators such as, interferon beta-1a (RebiSmart™); anti-HSV envelope glycoprotein D antibodies, such as UB-621; T-cell surface glycoprotein CD8 stimulators such as, immunogenic peptides, fatty acid synthase inhibitors such as, TVB-2640; anti-HSV envelope glycoprotein D monoclonal antibodies such as, HDIT-101; idoxuridine, hyaluronidase inhibitors such as, astodrimer (SPL-7013); HSV-529; BTL-TML-HSV, docosanol, MAR-8644, MAR-8658, NV-HHV-101, and PRL-01.

Herpes Simplex Virus Type 1 (HSV-1) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a Human alphaherpesvirus 1 (a.k.a., Herpes simplex virus (type 1); HSV-1; NCBI:txid10298) infection. Illustrative agents useful for treating and/or preventing a HSV-1 infection include DNA polymerase inhibitors/thymidine kinase inhibitors such as acyclovir, CRISPR associated endonuclease Cas9 modulators such as, EBT-104; nicotinic acetylcholine receptor antagonists such as, RPI-78M; cyclin-dependent kinase-9 inhibitors such as, FIT-039; and ZEP-3Na.

Herpes Simplex Virus Type 2 (HSV-2) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a Human alphaherpesvirus 2 (a.k.a., Herpes simplex virus (type 2); HSV-2; NCBI:txid10310) infection. Illustrative agents useful for treating and/or preventing a HSV-2 infection include nicotinic acetylcholine receptor antagonists such as, RPI-78M; anti-herpes simplex virus monoclonal antibodies such as, HDIT-101; anti-herpesvirus envelope glycoprotein D antibodies such as, UB-621; EBT-105, ALLOFERON™; HIV gp120/gp160/gp41 protein inhibitors such as, griffithsin; hyaluronidase inhibitors such as, astodrimer (SPL-7013).

Genital Herpes Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a genital herpes infection. Illustrative agents useful for treating and/or preventing a genital herpes infection include DNA polymerase inhibitors such as, famciclovir, penciclovir; interferon alpha 2 ligand modulators such as, YALLAFERON®; anti-Herpesvirus envelope glycoprotein D antibodies such as, UB-621; interferon gamma, ALLOFERON™, ZEP-3Na, SQX-77, and anti-STI antibodies.

Anti-HSV Antibodies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antibody that specifically binds to an HSV protein, e.g., HSV glycoprotein B (gB) and HSV glycoprotein D (gD). Illustrative anti-HSV antibodies that can be combined or co-administered include without limitation HDIT101 and mAb 2c, which bind to HSV glycoprotein B (gB). mAb 2c is described in Krawczyk, et al., *J Virol.* 2011 February; 85(4):1793-803; Krawczyk, et al., *Proc Natl Acad Sci USA.* 2013 Apr. 23; 110(17):6760-5; and U.S. Pat. Nos. 8,889,137 and 9,657,088; antibody UB-621, which binds to HSV glycoprotein D (gD) and is described in Lee, et al., *Acta Crystallogr D Biol Crystallogr.* 2013 October; 69(Pt 10): 1935-45 and U.S. Pat. Nos. 8,431,118 and 8,252,906.

Cytomegalovirus (CMV) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a cytomegalovirus (CMV) infection. Illustrative agents useful for treating and/or preventing a CMV infection include DNA polymerase inhibitors such as, ganciclovir, fomivirsen, fomivirsen sodium, valganciclovir; DNA polymerase inhibitor/serine/threonine protein kinase UL97 modulators such as, filociclovir; large terminase protein inhibitors such as, AIC-387, AIC-476; serine/threonine protein kinase UL97 inhibitors such as, maribavir; viral ribonucleotide reductase inhibitors such as, didox; ribonuclease stimulators such as, ranpirnase; syntaxin-5 inhibitors such as, Retro-94; large terminase protein inhibitors such as, letermovir; artemisinin derivatives, such as NPC-21; anti-CMV antibodies such as, BT-084 (Cytotect® CP); HLA class I antigen A-11 alpha/HLA class I antigen A-2 alpha/HLA class I antigen A-24 alpha modulators such as, allogenic anti-CMV-TCR-T-cell therapy; human cytomegalovirus glycoprotein inhibitors such as, CMV-345 (gB inhibitor), CMV-IVIG; and other drugs for treatment of CMV such as, USC-505, USC-596, CMV pp65 and ppM83 derived peptides, artemifone (BAY-44-9585), PG-36, CMX-16669, HN-0141, ALVR-105, CMV pH4 human immunoglobulin, Cytovir™, anti-viral cytotoxic T-cell therapy, CMV TCR-transduced T-cells, andadimlecleucel.

Varicella Zoster Virus (VZV) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing a Varicella Zoster Virus (VZV) infection. Illustrative agents useful for treating and/or preventing a VZV infection include DNA polymerase inhibitors such as, penciclovir, famciclovir, valaciclovir, acyclovir; DNA primase inhibitor/Helicase inhibitor such as, amenamevir; Interferon alpha 2 ligand modulators such as, interferon alfa-2b, YALLAFERON®, pegylated interferon alpha-1b, INTEFEN®, interferon alpha-2a, ANTERFERON®; Interferon beta ligand modulators such as, REBISMART™; Immunoglobulin agonists such as, VARICELLON®, Zoster Immunoglobulin-VF; anti-Varicella Zoster virus antibodies such as, VariZIG®; and other anti-VZV agents, such as OV-02 and HERPECIDE™.

Epstein-Barr Virus (EBV) Combination Therapies

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent useful for treating and/or preventing an Epstein-Barr Virus (EBV) infection. Illustrative agents useful for treating and/or preventing a EBV infection include NKG2D ligand modulators such as, pamidronic acid; Epstein-Barr nuclear antigen 1 inhibitors such as, VK-2019, anti-Epstein-Barr virus (EBV) peptides; HLA class I antigen A-11 alpha/HLA class I antigen A-2 alpha/HLA class I antigen A-24 alpha modulators such as, allogenic anti-EBV-TCR-T-cells; Epstein-Barr nuclear antigen/Latent membrane protein 1 and protein 2/Secreted protein BARF1 modulators such as, baltaleucel-T (CMD-003); and other agents such as, ALVR-105 and anti-viral cytotoxic T-cell therapy.

11. Methods of Prevention and Treatment—Coronavirus

Further provided are methods for treating, mitigating, ameliorating or preventing a coronavirus infection, e.g., a betacoronavirus (NCBI:txid694002) infection, e.g., a sarbecovirus (NCBI:txid2509511) infection, e.g., a severe acute respiratory syndrome (SARS)-related coronavirus infection (NCBI:txid694009), e.g., a severe acute respiratory syndrome coronavirus 2 (SARS-CoV-2; NCBI:txid2697049) infection (e.g., resulting in COVID-19 symptoms and/or illness), wherein the methods comprise administering to a subject in need thereof an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and a therapeutically effective amount of one or more additional therapeutic agents. Administration of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is most useful during the viral replication phase of infection (e.g., during the initial 1 to 3 weeks after infection, e.g., within the first 10, 9, 8, 7, 6, 5, 4, 3 or 2 days after symptomatic onset) and prior to any symptoms or indication of cytokine storm. As appropriate, the polynucleotide may be present in a vector, e.g., a viral vector.

In another aspect, provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in treating, mitigating, ameliorating or preventing a coronavirus infection, e.g., a betacoronavirus (NCBI:txid694002) infection, e.g., a sarbecovirus (NCBI:txid2509511) infection, e.g., a severe acute respiratory syndrome (SARS)-related coronavirus infection (NCBI:txid694009), e.g., a severe acute respiratory syndrome coronavirus 2 (SARS-CoV-2; NCBI:txid2697049) infection (e.g., resulting in COVID-19 symptoms and/or illness).

In some embodiments, the related disease or disorder is caused by infection with a coronavirus infection, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection. Illustrative related diseases or disorders caused by SARS-related coronavirus infection that can be prevented, mitigated, ameliorated or treated by an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, include COVID-19, SARS, Middle East Respiratory Syndrome (MERS) and feline infectious peritonitis (FIP). In certain embodiments, the subject is a virologically suppressed coronavirus-infected mammal, while in other embodiments, the subject is a treatment-naïve coronavirus-infected mammal. In certain embodiments, the subject has been diagnosed with a coronavirus infection, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection, or is considered at risk for developing a coronavirus infection, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection. Subjects at risk for coronavirus-related diseases or disorders include patients who have come into contact with an infected person or who have been exposed to coronavirus in some other way. A prophylactic agent can be administered to a pre-symptomatic subject, prior to the manifestation of symptoms characteristic of coronavirus-related disease or disorder, such that a disease or disorder is prevented or, alternatively, delayed in its progression. In some embodiments, the subject is asymptomatic.

Also provided are methods for preventing or inhibiting an increase in coronavirus virus titer, virus replication, virus proliferation or an amount of a coronavirus viral DNA or coronavirus viral protein in a subject (e.g., a human subject). In one embodiment, the method comprises providing to the subject in need thereof an amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, effective to prevent an increase in coronavirus titer, virus replication, or an amount of a coronavirus protein of one or more coronavirus strains or isolates in the subject. In certain embodiments, the method further comprises measuring an amount of coronavirus viral or protein at one or more time points, e.g., before and after the subject is provided with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. Methods and biomarkers for determining an amount of coronavirus viral DNA or protein in a subject are known and available in the art, including polynucleotide detection tests (e.g., PCR, Loop mediated isothermal amplification (LAMP) assays) and antigen detection tests, e.g. described for example, in Cheng, et al., *Ann Intern Med.* (2020) 172(11):726-734; Deeks, et al., *Cochrane Database Syst Rev.* (2020) 6(6):CD013652; Mathur and Mathur, *Am J Clin Pathol.* (2020) 154(1):1-3; Touma, *J Mol Med* (*Berl*). (2020) 98(7):947-954; Ji, et al., *Biosens Bioelectron.* (2020) 166:112455; Chan, et al., *J Clin Microbiol.* (2020) 58(5):e00310-20; Udugama, et al., *ACS Nano.* (2020) 14(4):3822-3835; Vashist, *Diagnostics* (Basel). (2020) 10(4):202; Oliveira, et al., *Rev Inst Med Trop Sao Paulo.* (2020) 62:e44; and Kashir and Yaquinuddin, *Med Hypotheses* (2020) doi: 10.1016/j.mehy.2020.109786; PMID: 32361529.

In certain aspect, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be used in, for example, methods of inhibiting certain viruses such as coronavirus isolates described herein, prophylactic inhibiting or preventing infections of certain viruses such as coronavirus isolates described herein, detection of certain viruses such as coronavirus isolates described herein in a sample, inhibiting certain viruses such as coronavirus isolates described herein, or diagnosis of certain viruses such as coronavirus isolates described herein.

Further provided are methods for treating a coronavirus infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. In some embodiments, the present disclosure provides a method for preventing a coronavirus infection, comprising administering to a human subject in need thereof a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

a. Coronavirus Combination Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional therapeutic agents useful in treating coronavirus, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection (e.g., resulting in COVID-19 symptoms and/or illness).

Antivirals

In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antiviral agent that inhibits the replication of a coronavirus, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection (e.g., resulting in COVID-19 symptoms and/or illness). Illustrative antiviral agents for use in treating a coronavirus infection include without limitation 5-substituted 2'-deoxyuridine analogues, nucleoside analogues, pyrophosphate analogues, nucleoside reverse transcriptase inhibitors, non-nucleoside reverse transcriptase inhibitors, protease inhibitors, integrase inhibitors, entry inhibitors, acyclic guanosine analogues, acyclic nucleoside phosphonate analogues, interferons, immunostimulators, oligonucleotides, antimitotic inhibitors, quaternary ammonium compounds such as ammonium chloride, cetylpyridinium and miramistin (see, Baker, et al., *Pharm Res.* 2020 May 25; 37(6):104), and combinations thereof.

In some embodiments, the additional therapeutic agent is a 5-substituted 2'-deoxyuridine analogue. For example, in some embodiments, the additional therapeutic agent is selected from the group consisting of idoxuridine, trifluridine, brivudine [BVDU], and combinations thereof.

In some embodiments, the additional therapeutic agent is a nucleoside analogue. For example, in some embodiments, the additional therapeutic agent is selected from the group consisting of remdesivir (VEKLURY®), vidarabine, entecavir (ETV), telbivudine, lamivudine, adefovir dipivoxil, tenofovir disoproxil fumarate (TDF) and combinations thereof. In some embodiments, the additional therapeutic agent is favipiravir, ribavirin, galidesivir, or a combination thereof. In some embodiments, the additional therapeutic agent is β-D-N4-hydroxycytidine (NHC), EIDD-2801 (Ridgeback Biotherapeutics), EIDD-1931 (Ridgeback Biotherapeutics)), sangivamycin or a combination thereof.

In some embodiments, the additional therapeutic agent is nucleoside reverse transcriptase inhibitor. In some embodiments, the antiviral agent is zidovudine, didanosine, zalcitabine, stavudine, lamivudine, abacavir, emtricitabine, and combinations thereof. In some embodiments, the additional therapeutic agent is, β-d-N4-Hydroxycytidine (NHC), EIDD-2801, EIDD-1931, or a combination thereof.

In some embodiments, the additional therapeutic agent is a non-nucleoside reverse transcriptase inhibitor. In some embodiments, the antiviral agent is selected from the group consisting of nevirapine, delavirdine, efavirenz, etravirine, rilpivirine, and combinations thereof.

In some embodiments, the additional therapeutic agent is selected from ivermectin, allogeneic Natural Killer (NK) cells (e.g., CYNK-001; Celularity), a ribonuclease (e.g., Ranpirnase (ONCONASE®)), a synthetic serine protease inhibitor (e.g., Nafamostat mesylate, a viroporine channel blocker, e.g., a coronavirus viroporin E channel blocker (e.g., Amantadine), a coronavirus spike glycoprotein (S1) inhibitor (e.g., tafoxiparin), and combinations thereof.

Antibodies

In some embodiments, the additional therapeutic agent is an antibody, for example a monoclonal antibody, useful in neutralizing a coronavirus infection, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection (e.g., resulting in COVID-19 symptoms and/or illness). In some embodiments, the antibody binds to a target antigen on a coronavirus, e.g., spike protein S1, spike protein S2. In some embodiments, the antibody binds to an epitope or region of SARS-CoV2 spike protein S1. Illustrative antibodies that binds to an epitope or region of a SARS-CoV2 protein, e.g., the spike protein S1, and can be combined or co-administered with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, include without limitation VIR-7831; VIR-7832 (GSK/Vir Biotechnology); 47D11 (Universiteit Utrecht; Abbvie; Harbour BioMed); JS-016 (Lilly; Beijing Institute for Microbiology; Shanghai Junshi Biosciences); REGN-COV2 (combination of REGN10933 and REGN10987 also known as REGN-COV2 or REGEN-COV™ (casirivimab and imdevimab)) (Regeneron; Hansen, et al., *Science* (2020) 369(6506):1010-1014); bamlanivimab (LY-CoV555; Eli Lilly/Abcellera); JS016 (etesevimab; LY-CoV016) (Junshi Biosciences; Chinese Academy of Sciences; Eli Lilly; Amgen); bamlanivimab (LY-CoV555) and etesevimab (LY-CoV016); BD-368-2 (Peking University); S-309 (Humabs); STI-4920 and STI-1499 (Sorrento Therapeutics); 40591-MM43 and 40592-MM57 (Sino Biological); TY027 (Tychan); BAT2019, BAT2020 (Bio-Thera Solutions); C19-AR (Kleo Pharmaceuticals); CT-P59 (Celltrion); STI-1499 (Sorrento Therapeutics); ACE-MAB; CMAB-020; STI-4920 (Mabpharm; Sorrento Therapeutics); CR3022 (a.k.a., ab273073; abcam); IgY-110 (IGY Immune Technologies & Life Sciences); B38 and H4 (described in Wu, et al., *Science,* 2020 May 13; eabc2241. doi: 10.1126/science.abc2241 (PMID: 32404477); polyclonal antibody preparations, such as convalescent plasma (e.g., Thermogenesis; Kamada; Kedrion Biopharma; CSL; Takeda; Biotest; BPL; LFB; Octapharma; Grifols; Emergent BioSolutions; BARDA; Takeda Pharmaceutical); and combinations thereof.

12. Methods of Prevention and Treatment—Cancer

In various embodiments, the herein described IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides can be used to treat, mitigate, ameliorate, and/or delay the progression of cancer, e.g., where administration of IL-2 has been shown to induce a durable response and antitumor activity. IL-2 has been administered, alone or in combination with additional anticancer agents, to human patients for the treatment of several different types of cancers, including without limitation melanoma (Atkins, et al., *Cancer J Sci Am* 6 Suppl. (2000) 1:S11-4; Davar, et al., *J Immunother Cancer.* (2017) 5:74; Buchbinder, et al., *J Immunother Cancer* (2019) 7:49; and Ahmadzadeh, et al., *Blood.* (2006) 107:2409-2414); renal cancer (Buchbinder, et al., supra; and Ahmadzadeh, et al., supra); leukemia (e.g., NCT00058799); acute myeloid leukemia (AML) (Lim, et al., *Cancer Immunol Immunother* (1992) 34:337-342; Foa, et al., *Br J Haematol* (1991) 77:491-496; Macdonald, et al., *Leukemia Res.* (1990) 14:967-973; Miller, et al., *Blood.* (2005) 105:3051-3057; and Bachanova, et al., *Blood.* (2014) 123:3855-3863); Chronic Lymphocytic Leukemia (CLL) (NCT00458679); lymphoma (Burns, et al., *Bone Marrow Transplant.* (2003) 32:177-186); B-cell Non-Hodgkin Lymphoma (e.g., NCT02151903); multiple myeloma (MM) (Burjanadze, et al., *Br J Haematol.* (2007) 139:206-216); head and neck cancer (e.g., NCT03978689; NCT04166006); ovarian (e.g., NCT01883297); mesothelioma (e.g., NCT02414945); endometrial (e.g., NCT04438564); prostate (e.g., NCT00283829); sarcoma (e.g., NCT04052334); Neuroblastoma (e.g., NCT00003750; NCT01662804); liver (e.g., NCT00004248); lung (e.g., NCT00016237); breast (e.g., NCT00027807); and esophageal, gastric, pancreatic (e.g., NCT00003125) cancers. The use of IL-2 for treating, mitigating ameliorating and/or delaying the progression of cancer, alone or in combination with additional anticancer agents, is reviewed in e.g., Qiao, et al., *Cell Mol Immunol* (2020) Jun. 10 (PMID: 32523115); and Bendickova, et al., *J Leukoc Biol.* (2020) Jun. 1 (PMID: 32480431).

Accordingly, in some embodiments, provided are methods of preventing, reducing and/or inhibiting the recurrence, growth, proliferation, migration and/or metastasis of a cancer cell or population of cancer cells in a subject in need thereof. Further provided are methods of enhancing, improving, and/or increasing the response to an anticancer therapy in a subject in need thereof. In some embodiments, the methods entail administering to the subject an effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein.

In another aspect, provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in preventing, reducing and/or inhibiting the recurrence, growth, proliferation, migration and/or metastasis of a cancer cell or population of cancer cells in a subject in need thereof. Further provided are IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, for use in enhancing, improving, and/or increasing the response to an anticancer therapy in a subject in need thereof.

As used herein, the terms "inhibition of cancer" and "inhibition of cancer cell proliferation" refer to the inhibition of the growth, division, maturation or viability of cancer cells, and/or causing the death of cancer cells, individually or in aggregate with other cancer cells, by cytotoxicity, nutrient depletion, or the induction of apoptosis.

In some embodiments, the subject may be a human who exhibits one or more symptoms associated with cancer or hyperproliferative disease (e.g., a tumor). In some embodiments, the subject may be a human who exhibits one or more symptoms associated with cancer. Any of the methods of cancer treatment provided herein may be used to treat cancer at various stages. By way of example, the cancer stage includes but is not limited to early, advanced, locally advanced, remission, refractory, reoccurred after remission and progressive. In some embodiments, the subject is at an early stage of a cancer. In other embodiments, the subject is at an advanced stage of cancer. In various embodiments, the subject has a stage I, stage II, stage III or stage IV cancer. One or more administrations of the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally with one or more additional therapeutic agents, can promote reduction or retraction of a tumor, decrease or inhibit tumor growth or cancer cell proliferation, and/or induce, increase or promote tumor cell killing. In some embodiments, the subject is in cancer remission. One or more administrations of the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally with one or more additional therapeutic agents, can prevent or delay metastasis or recurrence of cancer.

In some embodiments, the subject may be a human who is at risk, or genetically or otherwise predisposed (e.g., risk factor) to developing cancer or hyperproliferative disease who has or has not been diagnosed. In some embodiments, the subject may be a human who is at risk, or genetically or otherwise predisposed (e.g., risk factor) to a disease, disorder, or symptoms thereof, caused by a viral infection who has or has not been diagnosed.

In addition, the subject may be a human who is undergoing one or more standard therapies, such as chemotherapy, radiotherapy, immunotherapy, surgery, or combination thereof. Accordingly, one or more kinase inhibitors may be administered before, during, or after administration of chemotherapy, radiotherapy, immunotherapy, surgery or combination thereof.

In certain embodiments, the subject may be a human who is (i) substantially refractory to at least one chemotherapy treatment, or (ii) is in relapse after treatment with chemotherapy, or both (i) and (ii). In some of embodiments, the subject is refractory to at least two, at least three, or at least four chemotherapy treatments (including standard or experimental chemotherapies).

In some embodiments, a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally, with one or more additional therapeutic agents, as described herein, can (i) reduce the number of diseased cells; (ii) reduce tumor size; (iii) inhibit, retard, slow to some extent, and preferably stop the diseased cell infiltration into peripheral organs; (iv) inhibit (e.g., slow to some extent and preferably stop) tumor metastasis; (v) inhibit tumor growth; (vi) prevent or delay occurrence and/or recurrence of a tumor, and/or (vii) relieve to some extent one or more of the symptoms associated with cancer or myeloproliferative disease. In some embodiments, a therapeutically effective amount of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, optionally, with one or more additional therapeutic agents, as described herein, can (i) reduce the number of cancer cells; (ii) reduce tumor size; (iii) inhibit, retard, slow to some extent, and preferably stop cancer cell infiltration into peripheral organs; (iv) inhibit (e.g., slow to some extent and preferably stop) tumor metastasis; (v) inhibit tumor growth; (vi) prevent or delay occurrence and/or recurrence of a tumor; and/or (vii) relieve to some extent one or more of the symptoms associated with the cancer. In various embodiments, the amount is sufficient to ameliorate, palliate, lessen, and/or delay one or more of symptoms of cancer.

An "increased" or "enhanced" amount (e.g., with respect to antitumor response, cancer cell metastasis) refers to an increase that is 1.1, 1.2, 1.3, 1.4, 1.5, 1.6, 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 2.1, 2.2, 2.3, 2.4, etc.) an amount or level described herein. It may also include an increase of at least 10%, at least 20%, at least 30%, at least 40%, at least 50%, at least 60%, at least 70%, at least 80%, at least 90%, at least 100%, at least 150%, at least 200%, at least 500%, or at least 1000% of an amount or level described herein.

A "decreased" or "reduced" or "lesser" amount (e.g., with respect to tumor size, cancer cell proliferation or growth) refers to a decrease that is 1.1, 1.2, 1.3, 1.4, 1.5, 1.6 1.7, 1.8, 1.9, 2, 2.5, 3, 3.5, 4, 4.5, 5, 6, 7, 8, 9, 10, 15, 20, 30, 40, or 50 or more times (e.g., 100, 500, 1000 times) (including all integers and decimal points in between and above 1, e.g., 1.5, 1.6, 1.7. 1.8, etc.) an amount or level described herein. It may also include a decrease of at least 10%, at least 20%, at least 30%, at least 40%, at least 50%, at least 60%, at least 70%, at least 80%, or at least 90%, at least 100%, at least 150%, at least 200%, at least 500%, or at least 1000% of an amount or level described herein.

Examples of tissues containing cancerous cells whose proliferation can reduced and/or inhibited by an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and against which the methods described herein are useful include but are not limited to breast, prostate, brain, blood, bone marrow, liver, pancreas, skin, kidney, colon, ovary, lung, testicle, penis, thyroid, parathyroid, pituitary, thymus, retina, uvea, conjunctiva, spleen, head, neck, trachea, gall bladder, rectum, salivary gland, adrenal gland, throat, esophagus, lymph nodes, sweat glands, sebaceous glands, muscle, heart, and stomach.

In some embodiments, the subject has a solid tumor. In various embodiments, the cancer or tumor is malignant and/or a metastatic. In various embodiments, the subject has a cancer selected from the group consisting of an epithelial tumor (e.g., a carcinoma, a squamous cell carcinoma, a basal cell carcinoma, a squamous intraepithelial neoplasia), a glandular tumor (e.g., an adenocarcinoma, an adenoma, an adenomyoma), a mesenchymal or soft tissue tumor (e.g., a sarcoma, a rhabdomyosarcoma, a leiomyosarcoma, a liposarcoma, a fibrosarcoma, a dermatofibrosarcoma, a neurofibrosarcoma, a fibrous histiocytoma, an angiosarcoma, an angiomyxoma, a leiomyoma, a chondroma, a chondrosarcoma, an alveolar soft-part sarcoma, an epithelioid hemangioendothelioma, a Spitz tumor, a synovial sarcoma), and a lymphoma.

In various embodiments, the subject has a solid tumor in or arising from a tissue or organ selected from the group consisting of:

bone (e.g., adamantinoma, aneurysmal bone cysts, angiosarcoma, chondroblastoma, chondroma, chondromyxoid fibroma, chondrosarcoma, chordoma, dedifferentiated chondrosarcoma, enchondroma, epithelioid hemangioendothelioma, fibrous dysplasia of the bone, giant cell tumour of bone, haemangiomas and related lesions, osteoblastoma, osteochondroma, osteosarcoma, osteoid osteoma, osteoma, periosteal chondroma, Desmoid tumor, Ewing sarcoma);

lips and oral cavity (e.g., odontogenic ameloblastoma, oral leukoplakia, oral squamous cell carcinoma, primary oral mucosal melanoma); salivary glands (e.g., pleomorphic salivary gland adenoma, salivary gland adenoid cystic carcinoma, salivary gland mucoepidermoid carcinoma, salivary gland Warthin's tumors);

esophagus (e.g., Barrett's esophagus, dysplasia and adenocarcinoma);

gastrointestinal tract, including stomach (e.g., gastric adenocarcinoma, primary gastric lymphoma, gastrointestinal stromal tumors (GISTs), metastatic deposits, gastric carcinoids, gastric sarcomas, neuroendocrine carcinoma, gastric primary squamous cell carcinoma, gastric adenoacanthomas), intestines and smooth muscle (e.g., intravenous leiomyomatosis), colon (e.g., colorectal adenocarcinoma), rectum, anus;

pancreas (e.g., serous neoplasms, including microcystic or macrocystic serous cystadenoma, solid serous cystadenoma, Von Hippel-Landau (VHL)-associated serous cystic neoplasm, serous cystadenocarcinoma; mucinous cystic neoplasms (MCN), intraductal papillary mucinous neoplasms (IPMN), intraductal oncocytic papillary neoplasms (IOPN), intraductal tubular neoplasms, cystic acinar neoplasms, including acinar cell cystadenoma, acinar cell cystadenocarcinoma, pancreatic adenocarcinoma, invasive pancreatic ductal adenocarcinomas, including tubular adenocarcinoma, adenosquamous carcinoma, colloid carcinoma, medullary carcinoma, hepatoid carcinoma, signet ring cell carcinoma, undifferentiated carcinoma, undifferentiated carcinoma with osteoclast-like giant cells, acinar cell carcinoma, neuroendocrine neoplasms, neuroendocrine microadenoma, neuroendocrine tumors (NET), neuroendocrine carcinoma (NEC), including small cell or large cell NEC, insulinoma, gastrinoma, glucagonoma, serotonin-producing NET, somatostatinoma, VIPoma, solid-pseudopapillary neoplasms (SPN), pancreatoblastoma);

gall bladder (e.g. carcinoma of the gallbladder and extrahepatic bile ducts, intrahepatic cholangiocarcinoma);

neuro-endocrine (e.g., adrenal cortical carcinoma, carcinoid tumors, phaeochromocytoma, pituitary adenomas);

thyroid (e.g., anaplastic (undifferentiated) carcinoma, medullary carcinoma, oncocytic tumors, papillary carcinoma, adenocarcinoma);

liver (e.g., adenoma, combined hepatocellular and cholangiocarcinoma, fibrolamellar carcinoma, hepatoblastoma, hepatocellular carcinoma, mesenchymal, nested stromal epithelial tumor, undifferentiated carcinoma; hepatocellular carcinoma, intrahepatic cholangiocarcinoma, bile duct cystadenocarcinoma, epithelioid hemangioendothelioma, angiosarcoma, embryonal sarcoma, rhabdomyosarcoma, solitary fibrous tumor, teratoma, York sac tumor, carcinosarcoma, rhabdoid tumor);

kidney (e.g., ALK-rearranged renal cell carcinoma, chromophobe renal cell carcinoma, clear cell renal cell carcinoma, clear cell sarcoma, metanephric adenoma, metanephric adenofibroma, mucinous tubular and spindle cell carcinoma, nephroma, nephroblastoma (Wilms tumor), papillary adenoma, papillary renal cell carcinoma, renal oncocytoma, renal cell carcinoma, succinate dehydrogenase-deficient renal cell carcinoma, collecting duct carcinoma);

breast (e.g., invasive ductal carcinoma, including without limitation, acinic cell carcinoma, adenoid cystic carcinoma, apocrine carcinoma, cribriform carcinoma, glycogen-rich/clear cell, inflammatory carcinoma, lipid-rich carcinoma, medullary carcinoma, metaplastic carcinoma, micropapillary carcinoma, mucinous carcinoma, neuroendocrine carcinoma, oncocytic carcinoma, papillary carcinoma, sebaceous carcinoma, secretory breast carcinoma, tubular carcinoma; lobular carcinoma, including without limitation, pleomorphic carcinoma, signet ring cell carcinoma, peritoneum (e.g., mesothelioma; primary peritoneal cancer);

female sex organ tissues, including ovary (e.g., choriocarcinoma, epithelial tumors, germ cell tumors, sex cord-stromal tumors), Fallopian tubes (e.g., serous adenocarcinoma, mucinous adenocarcinoma, endometrioid adenocarcinoma, clear cell adenocarcinoma, transitional cell carcinoma, squamous cell carcinoma, undifferentiated carcinoma, mullerian tumors, adenosarcoma, leiomyosarcoma, teratoma, germ cell tumors, choriocarcinoma, trophoblastic tumors), uterus (e.g., carcinoma of the cervix, endometrial polyps, endometrial hyperplasia, intraepithelial carcinoma (EIC), endometrial carcinoma (e.g., endometrioid carcinoma, serous carcinoma, clear cell carcinoma, mucinous carcinoma, squamous cell carcinoma, transitional carcinoma, small cell carcinoma, undifferentiated carcinoma, mesenchymal neoplasia), leiomyoma (e.g., endometrial stromal nodule, leiomyosarcoma, endometrial stromal sarcoma (ESS), mesenchymal tumors), mixed epithelial and mesenchymal tumors (e.g., adenofibroma, carcinofibroma, adenosarcoma, carcinosarcoma (malignant mixed mesodermal sarcoma—MMMT)), endometrial stromal tumors, endometrial malignant mullerian mixed tumours, gestational trophoblastic tumors (partial hydatiform mole, complete hydatiform mole, invasive hydatiform mole, placental site tumour)), vulva, vagina;

male sex organ tissues, including prostate, testis (e.g., germ cell tumors, spermatocytic seminoma), penis;

bladder (e.g., squamous cell carcinoma, urothelial carcinoma, bladder urothelial carcinoma);

brain, (e.g., gliomas (e.g., astrocytomas, including non-infiltrating, low-grade, anaplastic, glioblastomas; oligodendrogliomas, ependymomas), meningiomas, gangliogliomas, schwannomas (neurilemmomas), craniopharyngiomas, chordomas, Non-Hodgkin lymphomas (NHLs), indolent non-Hodgkin's lymphoma (iNHL), refractory iNHL, pituitary tumors;

eye (e.g., retinoma, retinoblastoma, ocular melanoma, posterior uveal melanoma, iris hamartoma);

head and neck (e.g., nasopharyngeal carcinoma, Endolymphatic Sac Tumor (ELST), epidermoid carcinoma, laryngeal cancers including squamous cell carcinoma (SCC) (e.g., glottic carcinoma, supraglottic carcinoma, subglottic carcinoma, transglottic carcinoma), carcinoma in situ, verrucous, spindle cell and basaloid SCC, undifferentiated carcinoma, laryngeal adenocarcinoma, adenoid cystic carcinoma, neuroendocrine carcinomas, laryngeal sarcoma), head and neck paragangliomas (e.g., carotid body, jugulotympanic, vagal);

thymus (e.g., thymoma);

heart (e.g., cardiac myxoma);

lung (e.g., small cell carcinoma (SCLC), non-small cell lung carcinoma (NSCLC), including squamous cell carcinoma (SCC), adenocarcinoma and large cell carcinoma, carcinoids (typical or atypical), carcinosarcomas, pulmonary blastomas, giant cell carcinomas, spindle cell carcinomas, pleuropulmonary blastoma);

lymph (e.g., lymphomas, including Hodgkin's lymphoma, non-Hodgkin's lymphoma (NHL), indolent non-Hodgkin's lymphoma (iNHL), refractory iNHL, Epstein-Barr virus (EBV)-associated lymphoproliferative diseases, including B cell lymphomas and T cell lymphomas (e.g., Burkitt lymphoma; large B cell lymphoma, diffuse large B-cell lymphoma (DLBCL), mantle cell lymphoma, indolent B-cell lymphoma, low grade B cell lymphoma, fibrin-associated diffuse large cell lymphoma; primary effusion lymphoma; plasmablastic lymphoma; extranodal NK/T cell lymphoma, nasal type; peripheral T cell lymphoma, cutaneous T cell lymphoma, angioimmunoblastic T cell lymphoma; follicular T cell lymphoma; systemic T cell lymphoma), lymphangioleiomyomatosis);

central nervous system (CNS) (e.g., gliomas including astrocytic tumors (e.g., pilocytic astrocytoma, pilomyxoid astrocytoma, subependymal giant cell astrocytoma, pleomorphic xanthoastrocytoma, diffuse astrocytoma, fibrillary astrocytoma, gemistocytic astrocytoma, protoplasmic astrocytoma, anaplastic astrocytoma, glioblastoma (e.g., giant cell glioblastoma, gliosarcoma, glioblastoma multiforme) and gliomatosis cerebri), oligodendroglial tumors (e.g., oligodendroglioma, anaplastic oligodendroglioma), oligoastrocytic tumors (e.g., oligoastrocytoma, anaplastic oligoastrocytoma), ependymal tumors (e.g., subependymom, myxopapillary ependymoma, ependymomas (e.g., cellular, papillary, clear cell, tanycytic), anaplastic ependymoma), optic nerve glioma, and non-gliomas (e.g., choroid plexus tumors, neuronal and mixed neuronal-glial tumors, pineal region tumors, embryonal tumors, medulloblastoma, meningeal tumors, primary CNS lymphomas, germ cell tumors, Pituitary adenomas, cranial and paraspinal nerve tumors, stellar region tumors); neurofibroma, meningioma, peripheral nerve sheath tumors, peripheral neuroblastic tumours (including without limitation neuroblastoma, ganglioneuroblastoma, ganglioneuroma), trisomy 19 ependymoma);

neuroendocrine tissues (e.g., paraganglionic system including adrenal medulla (pheochromocytomas) and extra-adrenal paraganglia ((extra-adrenal) paragangliomas);

skin (e.g., clear cell hidradenoma, cutaneous benign fibrous histiocytomas, cylindroma, hidradenoma, melanoma (including cutaneous melanoma, mucosal melanoma), basal cell carcinoma, pilomatricoma, Spitz tumors); and soft tissues (e.g., aggressive angiomyxoma, alveolar rhabdomyosarcoma, alveolar soft part sarcoma, angiofibroma, angiomatoid fibrous histiocytoma, synovial sarcoma, biphasic synovial sarcoma, clear cell sarcoma, dermatofibrosarcoma protuberans, desmoid-type fibromatosis, small round cell tumor, desmoplastic small round cell tumor, elastofibroma, embryonal rhabdomyosarcoma, Ewing's tumors/primitive neurectodermal tumors (PNET), extraskeletal myxoid chondrosarcoma, extraskeletal osteosarcoma, paraspinal sarcoma, inflammatory myofibroblastic tumor, lipoblastoma, lipoma, chondroid lipoma, liposarcoma/malignant lipomatous tumors, liposarcoma, myxoid liposarcoma, fibromyxoid sarcoma, lymphangioleiomyoma, malignant myoepithelioma, malignant melanoma of soft parts, myoepithelial carcinoma, myoepithelioma, myxoinflammatory fibroblastic sarcoma, undifferentiated sarcoma, pericytoma, rhabdomyosarcoma, non-rhabdomyosarcoma soft tissue sarcoma (NRSTS), soft tissue leiomyosarcoma, undifferentiated sarcoma, well-differentiated liposarcoma.

In some embodiments, the subject has a hematological cancer, e.g., a leukemia (e.g., Acute Myelogenous Leukemia (AML), Acute Lymphoblastic Leukemia (ALL), B-cell ALL, Myelodysplastic Syndrome (MDS), myeloproliferative disease (MPD), Chronic Myelogenous Leukemia (CML), Chronic Lymphocytic Leukemia (CLL), undifferentiated leukemia), a lymphoma (e.g., small lymphocytic lymphoma (SLL), mantle cell lymphoma (MCL), follicular lymphoma (FL), T-cell lymphoma, B-cell lymphoma, diffuse large B-cell lymphoma (DLBCL), marginal zone lymphoma (MZL), Waldenström's macroglobulinemia (WM)) and/or a myeloma (e.g., multiple myeloma (MM)).

b. Anticancer Combination Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one, two, three, four or more additional anticancer therapeutic agents.

Illustrative Anticancer Targets

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: acetyl-CoA carboxylase alpha (ACACA, a.k.a., ACC1; NCBI Gene ID: 31); acetyl-CoA carboxylase beta (ACACB, a.k.a., ACC2; NCBI Gene ID: 32); tyrosine kinase non receptor 2 (TNK2, a.k.a., ACK1; NCBI Gene ID: 10188), adenosine deaminase RNA specific (ADAR, a.k.a., ADAR1; NCBI Gene ID: 103); adenosine deaminase RNA specific B1 (ADARB1, ADAR2; NCBI Gene ID: 104); an adenylate cyclase (e.g., ADCY1, ACDY2, ACDY3, ACDY4, ACDY5, 6, ACDY7, ACDY8, ACDY9, ACDY10; NCBI Gene IDs: 107-115 and 55811, respectively), CD38 (a.k.a., ADP ribosyl cyclase-1 (ADPRC1); NCBI Gene ID: 952); melanocortin 2 receptor (MC2R; a.k.a., adrenocorticotropic hormone receptor (ACTHR); NCBI Gene ID: 4158); an alkaline phosphatase (e.g., intestinal (ALPI), placental (ALPP), placental-like (ALPG), liver/bone/kidney ((ALPL) tissue non-specific)); an alpha adrenoceptor (e.g., adrenoceptor alpha IA (ADRA1A; NCBI Gene ID: 148; adrenoceptor alpha 1B (ADRA1B; NCBI Gene ID: 147; adrenoceptor alpha 1D (ADRA1D; NCBI Gene ID: 146; adrenoceptor alpha 2A (ADRA2A; NCBI Gene ID: 150; adrenoceptor alpha 2B; ADRA2B; NCBI Gene ID: 151; adrenoceptor alpha 2C (ADRA2C; NCBI Gene ID: 152)); a beta adrenoceptor (e.g., adrenoceptor beta 1 (ADRB1; NCBI Gene ID: 153); adrenoceptor beta 2 (ADRB2; NCBI Gene ID: 154); adrenoceptor beta 3 (ADRB3; NCBI Gene ID: 155)); oxoglutarate dehydrogenase (OGDH; a.k.a., alpha-ketoglutarate dehydrogenase (AKGDH); NCBI Gene ID: 4967); alanyl aminopeptidase, membrane (ANPEP, a.k.a., APN, CD13; NCBI Gene ID: 290); endoplasmic reticulum aminopeptidase 1 (ERAP1; NCBI Gene ID: 51752); endoplasmic reticulum aminopeptidase 2 (ERAP2; NCBI Gene ID: 64167); an X-prolyl aminopeptidase (e.g., XPNPEP1, XPNPEP2, XPNPEP3; NCBI Gene IDs:7511, 7512 and 63929, respectively); an AMP activated protein kinase (e.g., PRKAA1, PRKAA2, PRKAB1, PRKAG2; NCBI Gene IDs: 5562, 5563, 5564 and 51422, respectively); ALK receptor tyrosine kinase (ALK, a.k.a., CD246; NCBI Gene ID: 238), activin A receptor like type 1 (ACVRL1, a.k.a., ALK1; NCBI Gene ID: 94); activin A receptor type 1 (ACVR1, a.k.a., ALK2; NCBI Gene ID: 90); androgen receptor (AR; NCBI Gene ID: 367); angiopoietin 1 (ANGPT1; NCBI Gene ID: 284); angiopoietin 2 (ANGPT2; NCBI Gene ID: 285); angiotensinogen (AGT; NCBI Gene ID: 183); an AKT serine/threonine kinase 1 (e.g., AKT1, AKT2, AKT3; NCBI Gene IDs:207, 208 and 10000, respectively); apolipoprotein A1 (APOA1; NCBI Gene ID: 335); TNF superfamily member 10 (TNFSF10; a.k.a., APO2L; CD253; TRAIL; NCBI Gene ID: 8743); TNF receptor superfamily member 10a (TNFRSF10A; a.k.a., DR4; APO2; CD261; TRAILR1); TNF receptor superfamily member 10b (TNFRSF10B, a.k.a., CD262, DR5, TRAILR2; NCBI Gene ID: 8795); TNF receptor superfamily member 10c (TNFRSF10C, a.k.a., CD263, TRAILR3; NCBI Gene ID: 8794); TNF receptor superfamily member 10d (TNFRSF10D, a.k.a., CD264, TRAILR4; NCBI Gene ID: 8793); Fas cell surface death receptor (FAS; a.k.a., CD95, APO-1; NCBI Gene ID: 355); Fas ligand (FASLG, a.k.a., CD178, CD95-L, CD95L, FASL, TNFSF6; NCBI Gene ID: 356); mitogen-activated protein kinase kinase kinase 5 (MAP3K5, a.k.a., ASK1; NCBI Gene ID: 4217); arginase 1 (ARG1; NCBI Gene ID: 383); arginase 2 (ARG2; NCBI Gene ID: 384); a peptidyl arginine deiminase (e.g., PADI1, PADI2, PADI3, PADI4, PADI6; NCBI Gene IDs: 29943, 11240, 51702, 23569 and 353238, respectively); cytochrome P450 family 19 subfamily A member 1 (CYP19A1; NCBI Gene ID: 1588); asteroid homolog 1 (ASTE1; NCBI Gene ID: 28990); ATR serine/threonine kinase (ATR; NCBI Gene ID: 545); an aurora kinase A (e.g., AURKA, AURKB, AURKC; NCBI Gene IDs: 6790, 9212, 6795, respectively); AXL receptor tyrosine kinase (AXL; NCBI Gene ID: 558); TNF receptor superfamily member 9 (TNFRSF9, a.k.a., 4-1BB, CD137, CDw137; NCBI Gene ID: 3604); TNF superfamily member 9 (TNFSF9, a.k.a., 4-1BB-L, CD137L, TNLG5A; NCBI Gene ID: 8744); baculoviral IAP repeat containing 5 (BIRC5; NCBI Gene ID: 332); basigin (Ok blood group) (BSG; NCBI Gene ID: 682); BCL2 apoptosis regulator (BCL2; NCBI Gene ID: 596); BCL2 binding component 3 (BBC3; NCBI Gene ID: 27113); BCL2 like 11 (BCL2L11; NCBI Gene ID: 10018); ABL proto-oncogene 1, non-receptor tyrosine kinase (ABL1, a.k.a., BCR-ABL; NCBI Gene ID: 25); BCR activator of RhoGEF and GTPase (BCR; NCBI Gene ID: 613); catenin beta 1 (CTNNB1; NCBI Gene ID: 1499); CD19 (NCBI Gene ID: 930); membrane spanning 4-domains A1 (MS4A1, a.k.a., CD20; NCBI Gene ID: 931); CD22 (a.k.a., SIGLEC2; NCBI Gene ID: 933); TNF superfamily member 13b (TNFSF13B, a.k.a., BAFF, CD257; NCBI Gene ID: 10673); TNF superfamily member 13 (TNFSF13; a.k.a., APRIL, CD256; NCBI Gene ID: 8741); TNF receptor superfamily member 13B (TNFRSF13B, a.k.a., TACI, CD267; NCBI Gene ID: 23495); TNF receptor superfamily member 17 (TNFRSF17; a.k.a., BCMA, CD269; NCBI Gene ID: 608); TNF superfamily member 13b (TNFSF13B, a.k.a., BAFF, CD257; NCBI Gene ID: 10673); TNF receptor superfamily member 13C (TNFRSF13C, a.k.a., BAFFR; CD268; NCBI Gene ID: 115650); bone morphogenetic protein 10 (BMP10; NCBI Gene ID: 27302); growth differentiation factor 2 (GDF2, a.k.a., BMP9; NCBI Gene ID: 2658); a transforming growth factor receptor (e.g., TGFBR1, a.k.a., ALK-5 (NCBI Gene ID: 7046); TGFBR2 (NCBI Gene ID: 7048); TGFBR3 (NCBI Gene ID: 7049)); a transforming growth factor beta (e.g., TGFB1 (NCBI Gene ID: 7040); TGFB2 (NCBI Gene ID: 7042); TGFB3 (NCBI Gene ID: 7043); T-box transcription factor T (TBXT; NCBI Gene ID: 6862); a bradykinin receptor (e.g., BDKRB1 (NCBI Gene ID: 623); BDKRB2 (NCBI Gene ID: 624)); B-Raf proto-oncogene, serine/threonine kinase (BRAF; NCBI Gene ID: 673); a bromodomain containing protein (e.g., BRD1 (NCBI Gene ID: 23774); BRD2 (NCBI Gene ID: 6046); BRD3 (NCBI Gene ID: 8019); BRD4 (NCBI Gene ID: 23476); bromodomain testis associated (BRDT, a.k.a., BRD6 NCBI Gene ID: 676); BRD7 (NCBI Gene ID: 29117); BRD8 (NCBI Gene ID: 10902); BRD9 (NCBI Gene ID: 65980)); Bruton tyrosine kinase (BTK; NCBI Gene ID: 695); a calmodulin (e.g., CALM1 (NCBI Gene ID: 801); CALM2 (NCBI Gene ID: 805); CALM3 (NCBI Gene ID: 808)); a calcium/calmodulin dependent protein kinase (e.g., CAMK1 (NCBI Gene ID: 8536); CAMK1D (NCBI Gene ID: 57118); CAMK2A (NCBI Gene ID: 815); CAMK2B (NCBI Gene ID: 816); CAMK2D (NCBI Gene ID: 817); CAMK2G (NCBI Gene ID: 818)); a cannabinoid receptor (e.g., CNR1 (NCBI Gene ID: 1268); CNR2 (NCBI Gene ID: 1269)); a carbonic anhydrase (e.g., CA1 (NCBI Gene ID: 759); CA2 (NCBI Gene ID: 760); CA3 (NCBI Gene ID: 761); CA4; (NCBI Gene ID: 762); CA5A (NCBI Gene ID: 763); CA6 (a.k.a., GUSTIN; NCBI Gene ID: 765); CA7 (NCBI Gene ID: 766); CA8 (NCBI Gene ID: 767); CA9 (a.k.a., CAIX; NCBI Gene ID: 768); CA10 (NCBI Gene ID: 56934); CA12 (NCBI Gene ID: 771); CA14 (NCBI Gene ID: 23632)); a casein kinase (e.g., CSNK1A1 (NCBI Gene ID: 1452); CSNK1D (NCBI Gene ID: 1453); CSNK1E (NCBI Gene ID: 1454); CSNK2A1 (NCBI Gene ID: 1457); CSNK2A2 (NCBI Gene ID: 1459); CSNK2B; NCBI Gene ID: 1460)); a caspase (e.g., CASP1 (NCBI Gene ID: 834); CASP2 (NCBI Gene ID: 835); CASP3 (NCBI Gene ID: 836); CASP6 (NCBI Gene ID: 839); CASP7 (NCBI Gene ID: 840); CASP8 (NCBI Gene ID: 841); CASP9 (NCBI Gene ID: 842); CASP10 (NCBI Gene ID: 843); CASP12 (NCBI Gene ID: 100506742)); CASP8 and FADD like apoptosis regulator (CFLAR; NCBI Gene ID: 8837); nucleotide binding oligomerization domain containing 2 (NOD2; a.k.a., CARD15; NCBI Gene ID: 64127); cathepsin G (CTSG; NCBI Gene ID: 1511); a chemokine (C-C motif) receptor (e.g., CCR1 (NCBI Gene ID: 1230); CCR2 (NCBI Gene ID: 729230); CCR3 (NCBI Gene ID: 1232); CCR4 (NCBI Gene ID: 1233); CCR5 (NCBI Gene ID: 1234); CCR6 (NCBI Gene ID: 1235); CCR7 (NCBI Gene ID: 1236); CCR8 (NCBI Gene ID: 1237); CCR9 (NCBI Gene ID: 10803)); a chemokine (C-X-C motif) receptor (e.g., CXCR1 (NCBI Gene ID: 3577); CXCR2 (NCBI Gene ID: 3579); CXCR3 (NCBI Gene ID: 2833); CXCR4 (NCBI Gene ID: 7852); CXCR5 (NCBI Gene ID: 643); CXCR6 (NCBI Gene ID: 10663)); cyclin dependent kinase 7 (CDK7; a.k.a., CAK; NCBI Gene ID: 1022); a checkpoint kinase (e.g., CHEK1 (NCBI Gene ID: 1111); CHEK2 (NCBI Gene ID: 11200); C-C motif chemokine ligand 21 (CCL21; NCBI Gene ID: 6366); a cholecystokinin receptor (e.g., CCKAR (NCBI Gene ID: 886); CCKBR (NCBI Gene ID: 887)); chorionic gonadotropin; KIT proto-oncogene, receptor tyrosine kinase (KIT; a.k.a., c-kit, CD117; NCBI Gene ID: 3815); KIT ligand (KITLG, a.k.a., MGF, stem cell factor (SCF), SF, SHEP7, Steel factor (SLF); NCBI Gene ID: 4254); cytokine inducible SH2 containing protein (CISH, a.k.a., suppressor of cytokine signaling (SOCS); NCBI Gene ID: 1154); a claudin (e.g., CLDN1 (NCBI Gene ID: 9076); CLDN2 (NCBI Gene ID: 9075); CLDN3 (NCBI Gene ID: 1365); CLDN4 (NCBI Gene ID: 1364); CLDN5 (NCBI Gene ID: 7122); CLDN6 (NCBI Gene ID: 9074); CLDN7 (NCBI Gene ID: 1366); CLDN8 (NCBI Gene ID: 9073); CLDN10 (NCBI Gene ID: 9071); CLDN11 (NCBI Gene ID: 5010); CLDN14 (NCBI Gene ID: 23562); CLDN16 (NCBI Gene ID: 10686); CLDN18 (NCBI Gene ID: 51208); CLDN23 (NCBI Gene ID: 137075)); CD4 (NCBI Gene ID: 920); CD27 (a.k.a., TNFRSF7; NCBI Gene ID: 939); integrin subunit beta 1 (ITGB1, a.k.a., CD29; NCBI Gene ID: 3688); TNF receptor superfamily member 8 (TNFRSF8, a.k.a., CD30; NCBI Gene ID: 943); CD33 (a.k.a., SIGLEC3; NCBI Gene ID: 945); CD37 (NCBI Gene ID: 951); CD40 (a.k.a., TNFRSF5; NCBI Gene ID: 958); CD40 ligand (CD40LG; a.k.a., TNFSF5, CD40L, CD154; NCBI Gene ID: 959); CD44 molecule (Indian blood group) (CD44; NCBI Gene ID: 960); protein tyrosine phosphatase receptor type C (PTPRC; a.k.a., B220, CD45; NCBI Gene ID: 5788); CD47 (a.k.a., IAP, MER6, OA3; NCBI Gene ID: 961); integrin subunit alpha 2 (ITGA2, a.k.a., CD49B; NCBI Gene ID: 3673); integrin subunit alpha V (ITGAV, a.k.a., CD51; NCBI Gene ID: 3685); CD52 (NCBI Gene ID: 1043); CD55 molecule (Cromer blood group) (CD55; NCBI Gene ID: 1604); CD58 (NCBI Gene ID: 965); CEA cell adhesion molecule 5 (CEACAM5, a.k.a., CD66e; NCBI Gene ID: 1048); CEA cell adhesion molecule 6 (CEACAM6, a.k.a., CD66c; NCBI Gene ID: 4680), CD70 (a.k.a., TNFSF7, CD27L; NCBI Gene ID: 970); CD74 (a.k.a., HLADG, II, Ia-GAMMA; NCBI Gene ID: 972); CD79A (NCBI Gene ID: 973); CD79B (NCBI Gene ID: 974); CD80 (a.k.a., B7, B7-1, CD28LG; NCBI Gene ID: 941); CD28 (NCBI Gene ID: 940); CD99 molecule (Xg blood group) (CD99, a.k.a., MIC2; NCBI Gene ID: 4267); TNF receptor superfamily member 4 (TNFRSF4, a.k.a., CD134, OX40; NCBI Gene ID: 7293); killer cell immunoglobulin like receptor, two Ig domains and long cytoplasmic tail (e.g., KIR2DL1, a.k.a., CD158A (NCBI Gene ID: 3802); KIR2DL2, a.k.a., CD158B1 (NCBI Gene ID: 3803); KIR2DL3, a.k.a., CD158B2 (NCBI Gene ID: 3804); KIR2DL4, a.k.a., CD158D (NCBI Gene ID: 3805); KIR2DL5A, a.k.a., CD158F (NCBI Gene ID: 57292); KIR2DL5B (NCBI Gene ID: 553128)); killer cell immunoglobulin like receptor, two Ig domains and short cytoplasmic tail (e.g., KIR2DS1, a.k.a., CD158H (NCBI Gene ID: 3806); KIR2DS2, a.k.a., CD158J (NCBI Gene ID: 100132285); KIR2DS3 (NCBI Gene ID: 3808); KIR2DS4, a.k.a., CD158I (NCBI Gene ID: 3809); KIR2DS5, a.k.a., CD158G (NCBI Gene ID: 3810); killer cell immunoglobulin like receptor, three Ig domains and long cytoplasmic tail (e.g., KIR3DL1, a.k.a., CD158E1 (NCBI Gene ID: 3811); KIR3DL2, a.k.a., CD158K (NCBI Gene ID: 3812); KIR3DL3, a.k.a., CD158Z (NCBI Gene ID: 115653)); killer cell immunoglobulin like receptor, three Ig domains and short cytoplasmic tail (e.g., KIR3DS1, a.k.a., CD158E2 (NCBI Gene ID: 3813)); CD276 (a.k.a., B7-H3; NCBI Gene ID: 80381); clusterin (CLU, a.k.a., APO-J; NCBI Gene ID: 1191); MET proto-oncogene, receptor tyrosine kinase (MET, a.k.a., HGFR, c-Met; NCBI Gene ID: 4233); complement C3 (C3; NCBI Gene ID: 718); cellular communication network factor 2 (CCN2, a.k.a., connective tissue growth factor (CTGF); NCBI Gene ID: 1490); COP9 signalosome subunit 5 (COPS5; NCBI Gene ID: 10987); colony stimulating factor 1 (CSF1, a.k.a., MCSF; NCBI Gene ID: 1435); colony stimulating factor 1 receptor (CSF1R, a.k.a., C-FMS, CD115; NCBI Gene ID: 1436); colony stimulating factor 2 (CSF2, a.k.a., GMCSF; NCBI Gene ID: 1437); colony stimulating factor 2 receptor subunit alpha (CSF2RA, a.k.a., CD116, GMCSFR; NCBI Gene ID: 1438); colony stimulating factor 2 receptor subunit beta (CSF2RB, a.k.a., CD131, IL3RB, IL5RB; NCBI Gene ID: 1439); cytotoxic T-lymphocyte associated protein 4 (CTLA4, a.k.a., CD152; NCBI Gene ID: 1493); C-type lectin domain containing 9A (CLEC9A, a.k.a., CD370; NCBI Gene ID: 283420); cyclin D1 (CCND1, a.k.a., BCL1; NCBI Gene ID: 595); cyclin G1 (CCNG1; NCBI Gene ID: 900); a cyclin dependent kinase (e.g., CDK1 (NCBI Gene ID: 983); CDK2 (NCBI Gene ID: 1017); CDK3 (NCBI Gene ID: 1018); CDK4 (NCBI Gene ID: 1019); CDK5 (NCBI Gene ID: 1020); CDK6 (NCBI Gene ID: 1021); CDK7 (NCBI Gene ID: 1022); CDK8 (NCBI Gene ID:

1024); CDK9 (NCBI Gene ID: 1025); CDK10 (NCBI Gene ID: 8558); CDK11A (NCBI Gene ID: 728642); CDK11B (NCBI Gene ID: 984); CDK12 (NCBI Gene ID: 51755); CDK13 (NCBI Gene ID: 8621); CDK14 (NCBI Gene ID: 5218); CDK15 (NCBI Gene ID: 65061); CDK16 (NCBI Gene ID: 5127); CDK17 (NCBI Gene ID: 5128); CDK18 (NCBI Gene ID: 5129); CDK19 (NCBI Gene ID: 23097); CDK20 (NCBI Gene ID: 23552)); cytochrome c oxidase subunit I (COX1; NCBI Gene ID: 4512); cytochrome c oxidase subunit II (COX2; NCBI Gene ID: 4513); porcupine O-acyltransferase (PORCN, a.k.a., PORC, PPN; NCBI Gene ID: 64840); a cytochrome P450 enzyme (e.g., CYP11B2 (NCBI Gene ID: 1585); CYB2B6 (NCBI Gene ID: 1555); CYP17A1 (NCBI Gene ID: 1586); CYP2D6 (NCBI Gene ID: 1565); CYP3A4 (NCBI Gene ID: 1576); cytochrome p450 oxidoreductase (POR, P450R; NCBI Gene ID: 5447); a suppressor of cytokine signaling protein (e.g., SOCS1 (NCBI Gene ID: 8651); SOCS2 (NCBI Gene ID: 8835); SOCS3 (NCBI Gene ID: 9021); SOCS4 (NCBI Gene ID: 122809); SOCS5 (NCBI Gene ID: 9655); SOCS6 (NCBI Gene ID: 9306); SOCS7 (NCBI Gene ID: 30837)); an isocitrate dehydrogenase (NADP(+)) (e.g., IDH1 (NCBI Gene ID: 3417); IDH2 (NCBI Gene ID: 3418)); hypoxia inducible factor 1 subunit alpha (HIF1A; NCBI Gene ID: 3091); cytidine deaminase (CDA; NCBI Gene ID: 978); apolipoprotein B mRNA editing enzyme catalytic subunit 3G (APOBEC3G, a.k.a., A3G; NCBI Gene ID: 60489); DNA methyltransferase 1 (DNMT1, a.k.a., MCMT; NCBI Gene ID: 1786); DNA topoisomerase I (NCBI Gene 7150); DNA topoisomerase II alpha (TOP2A; NCBI Gene ID: 7153); DNA topoisomerase II beta (TOP2B; NCBI Gene ID: 7155); DNA topoisomerase III alpha (TOP3A; NCBI Gene ID: 7156); DNA topoisomerase III beta (TOP3B; NCBI Gene ID: 8940); a DNA polymerase catalytic subunit (e.g., POLA1 (NCBI Gene ID: 5422); POLB (NCBI Gene ID: 5423); POLD1 (NCBI Gene ID: 5424); POLE (NCBI Gene ID: 5426); POLG (NCBI Gene ID; 5428); POLL (NCBI Gene ID: 27343)); discoidin domain receptor tyrosine kinase 1 (DDR1; NCBI Gene ID: 780); discoidin domain receptor tyrosine kinase 2 (DDR2; NCBI Gene ID: 4921); a delta like canonical Notch ligand (e.g., DLL1 (NCBI Gene ID: 28514); DLL3 (NCBI Gene ID: 10683); DLL4 (NCBI Gene ID: 54567)); deoxyribonuclease 1 (DNASE1; NCBI Gene ID: 1773); a dickkopf WNT signaling pathway inhibitor (e.g., DKK1 (NCBI Gene ID: 22943); DKK2 (NCBI Gene ID: 27123); DKK3 (NCBI Gene ID: 27122); DKK4 (NCBI Gene ID: 27121)); dihydrofolate reductase (DHFR; NCBI Gene ID: 1719); dihydropyrimidine dehydrogenase (DPYD; NCBI Gene ID: 1806); dipeptidyl peptidase 4 (DPP4, a.k.a., DPPIV, CD26; NCBI Gene ID: 1803); poly(ADP-ribose) polymerase 1 (PARP1; NCBI Gene ID: 142); tumor protein p53 (TP53; NCBI Gene ID: 7157); BRCA1 DNA repair associated (BRCA1; NCBI Gene ID: 672); a DNA primase (e.g., PRIM1 (NCBI Gene ID: 5557); PRIM2 (NCBI Gene ID: 5558); deoxyuridine triphosphatase (DUT, a.k.a., dUTPase; NCBI Gene ID: 1854); dopachrome tautomerase (DCT; NCBI Gene ID: 1638); an echinoderm microtubule like protein (e.g., EML1 (NCBI Gene ID: 2009); EML2 (NCBI Gene ID: 24139); EML3 (NCBI Gene ID: 256364); EML4 (NCBI ID: 27436); EML5 (NCBI Gene ID: 161436); EML6 (NCBI Gene ID: 400954); epidermal growth factor (EGF; NCBI Gene ID: 1950); epidermal growth factor receptor (EGFR, a.k.a., ERBB1, HER1; NCBI Gene ID: 1956); erb-b2 receptor tyrosine kinase 2 (ERBB2; a.k.a., HER2; HER-2/neu; NCBI Gene ID: 2064); erb-b2 receptor tyrosine kinase 3 (ERBB3, a.k.a., HER3; NCBI Gene ID: 2065); erb-b2 receptor tyrosine kinase 4 (ERBB4, a.k.a., HER4; NCBI Gene ID: 2066); elastase, neutrophil expressed (ELANE; NCBI Gene ID: 1991); a eukaryotic translation elongation factor 1 (e.g., EEF1A1 (NCBI Gene ID: 1915); EEF1A2 (NCBI Gene ID: 1917); EEF1B2 (NCBI Gene ID: 1933)); eukaryotic translation elongation factor 2 (EEF2; NCBI Gene ID: 1938); endoglin (ENG; NCBI Gene ID: 2022); heat shock protein 90 beta family member 1 (HSP90B1, a.k.a., GRP94; NCBI Gene ID: 7184); CD248 (a.k.a., endosialin, CD164L1, TEM1; NCBI Gene ID: 57124); collagen type XVIII alpha 1 chain (COL18A1; NCBI Gene ID: 80781; and endostatin, produced by proteolytic processing); an endothelin (e.g., EDN1, a.k.a., ET1, NCBI Gene ID: 1906; EDN2, a.k.a., ET2, NCBI Gene ID: 1907; EDN3, a.k.a., ET3, NCBI Gene ID: 1908); enhancer of zeste 2 polycomb repressive complex 2 subunit (EZH2; NCBI Gene ID: 2146); an ephrin receptor (e.g., EPHA1 (NCBI Gene ID: 2041); EPHA2 (NCBI Gene ID: 1969); EPHA3 (a.k.a., HEK, HEK4; NCBI Gene ID: 2042); EPHA4 (NCBI Gene ID: 2043); EPHA5 (NCBI Gene ID: 2044); EPHA6 (NCBI Gene ID: 285220); EPHA7 (NCBI Gene ID: 2045); EPHA8 (NCBI Gene ID: 2046); EPHA10 (NCBI Gene ID: 284656); EPHB1 (NCBI Gene ID: 2047); EPHB2 (NCBI Gene ID: 2048); EPHB3 (NCBI Gene ID: 2049); EPHB4 (NCBI Gene ID: 2050)); an ephrin (e.g., EFNA1 (NCBI Gene ID: 1942); EFNA2 (NCBI Gene ID: 1943); EFNA3 (NCBI Gene ID: 1944); EFNA4 (NCBI Gene ID: 1945); EFNA5 (NCBI Gene ID: 1946); EPHA6 (NCBI Gene ID: 285220); EFNB1 (NCBI Gene ID: 1947); EFNB2 (NCBI Gene ID: 1948); EFNB3 (NCBI Gene ID: 1949)); epithelial mitogen (EPGN, a.k.a., EPG; NCBI Gene ID: 255324); epithelial cell adhesion molecule (EPCAM; a.k.a., TROP1, TACSTD1; NCBI Gene ID: 4072); a hydroxysteroid 17-beta dehydrogenase (e.g., HSD17B1 (NCBI Gene ID: 3292); HSD17B2 (NCBI Gene ID: 3294); HSD17B3 (NCBI Gene ID: 3293); HSD17B4 (NCBI Gene ID: 3295); HSD17B5 (NCBI Gene ID: 8644); HSD17B6 (NCBI Gene ID: 8630); HSD17B7 (NCBI Gene ID: 51478); HSD17B8 (NCBI Gene ID: 7923); HSD17B9 (NCBI Gene ID: 5959); HSD17B10 (NCBI Gene ID: 3028); HSD17B11 (NCBI Gene ID: 51170); HSD17B12 (NCBI Gene ID: 51144); HSD17B13 (NCBI Gene ID: 345275); HSD17B14 (NCBI Gene ID: 51171)); an estrogen receptor (e.g., ESR1 (a.k.a., ESRA; NCBI Gene ID: 2099); ESR2 (a.k.a., ESRB; NCBI Gene ID: 2100)); an estrogen related receptor (e.g., ESRRA (NCBI Gene ID: 2101); ESRRB (NCBI Gene ID: 2103); ESRRG (NCBI Gene ID: 2104)); an eukaryotic translation initiation factor 5 (e.g., EIF5 (NCBI Gene ID: 1983); EIF5A (NCBI Gene ID: 1984); EIF5A2 (NCBI Gene ID: 56648); EIF5AL1 (NCBI Gene ID: 143244); an exportin (e.g., XPO1 (NCBI Gene ID: 7514); XPO4 (NCBI Gene ID: 64328); XPO5 (NCBI Gene ID: 57510); XPO6 (NCBI Gene ID: 23214); XPO7 (NCBI Gene ID: 23039)); a mitogen-activated protein kinase (e.g., MAPK1, a.k.a., ERK2, p38 (NCBI Gene ID: 5594); MAPK3, a.k.a., ERK1 (NCBI Gene ID: 5595); MAPK4, a.k.a., ERK4 (NCBI Gene ID: 5596); MAPK6, a.k.a., ERK3 (NCBI Gene ID: 5597); MAPK7, a.k.a., ERK5 (NCBI ID: 5598); MAPK8, a.k.a., JNK1 (NCBI Gene ID: 5599); MAPK9, a.k.a., JNK2 (NCBI Gene ID: 5601); MAPK10, a.k.a., JNK3 (NCBI Gene ID: 5602); MAPK11 (NCBI Gene ID: 5600); MAPK12, a.k.a., ERK6 (NCBI Gene ID: 6300); MAPK13 (NCBI Gene ID: 5603); MAPK14, a.k.a., p38 (NCBI Gene ID: 1432); MAPK15, a.k.a., ERK7, ERK8 (NCBI Gene ID: 225689)); MAPK activated protein kinase 2 (MAPKAPK2, a.k.a., MK2; NCBI Gene ID: 9261); a mitogen-activated protein kinase kinase (e.g., MAP2K1, a.k.a., MEK1 (NCBI Gene ID: 5604); MAP2K2, a.k.a., MEK2 (NCBI Gene ID: 5605);

MAP2K3, a.k.a., MEK3 (NCBI Gene ID: 5606); MAP2K4, a.k.a., MEK4 (NCBI Gene ID: 6416); MAP2K5, a.k.a., MEK5 (NCBI Gene ID: 5607); MAP2K6, a.k.a., MEK6 (NCBI Gene ID: 5608); MAP2K7, a.k.a., MEK7 (NCBI Gene ID: 5609)); mitogen-activated protein kinase kinase kinase kinase 1 (MAP4K1, a.k.a., HPK1; NCBI Gene ID: 11184); nuclear receptor subfamily 1 group H member 4 (NR1H4, a.k.a., FXR; NCBI Gene ID: 9971); fatty acid synthase (FASN; NCBI Gene ID: 2194); ferritin (e.g., ferritin heavy chain (FTH1; NCBI Gene ID: 2495) and/or ferritin light chain (FTL; NCBI Gene ID: 2512)); a fibroblast growth factor (e.g., FGF1 (NCBI Gene ID: 2246); FGF2 (NCBI Gene ID: 2247); FGF4 (NCBI Gene ID: 2249); FGF5 (NCBI Gene ID: 2250); FGF6 (NCBI Gene ID: 2252); FGF7 (NCBI Gene ID: 2252); FGF8 (NCBI Gene ID: 2253); FGF9 (NCBI Gene ID: 2254); FGF10 (NCBI Gene ID: 2255); FGF11 (NCBI Gene ID: 2256); FGF12 (NCBI Gene ID: 2257); FGF13 (NCBI Gene ID: 2258); FGF14 (NCBI Gene ID: 2259); FGF15 (NCBI Gene ID: 2259); FGF16 (NCBI Gene ID: 8823); FGF17 (NCBI Gene ID: 8822); FGF18 (NCBI Gene ID: 8817); FGF19 (NCBI Gene ID: 9965); FGF20 (NCBI Gene ID: 26281); FGF21 (NCBI Gene ID: 26291); FGF22 (NCBI Gene ID: 27006); FGF23 (NCBI Gene ID: 8047)); a fibroblast growth factor receptor (e.g., FGFR1 (NCBI Gene ID: 2260); FGFR2 (NCBI Gene ID: 2263); FGFR3 (NCBI Gene ID: 2261); FGFR4 (NCBI Gene ID: 2264)); fibronectin 1 (FN1; NCBI Gene ID: 2335); a focal adhesion kinase (e.g., protein tyrosine kinase 2 (PTK2; NCBI Gene ID: 5747); protein tyrosine kinase 2 beta (PTK2B; NCBI Gene ID: 2185); a folate receptor (e.g., FOLR1, a.k.a., FRalpha (NCBI Gene ID: 2348); FOLR2, a.k.a., FRbeta (NCBI Gene ID: 2350)); folate; solute carrier family 19 member 1 (SLC19A1, a.k.a., FOLT; NCBI Gene ID: 6573); FYN proto-oncogene, Src family tyrosine kinase (FYN; NCBI Gene ID: 2534); furin, paired basic amino acid cleaving enzyme (FURIN, a.k.a., PCSK3; NCBI Gene ID: 5045); glucuronidase beta (GUSB; NCBI Gene ID: 2990); galectin 3 (LGALS3, a.k.a., GAL3; NCBI Gene ID: 3958); Ganglioside GD2, TNF receptor superfamily member 18 (TNFRSF18, a.k.a., GITR, CD357; NCBI Gene ID: 8784); TNF superfamily member 18 (TNFSF18, a.k.a., GITRL; NCBI Gene ID: 8995); folate hydrolase 1 (FOLH1, a.k.a., GCPII, GCP2, PSMA; NCBI Gene ID: 2346); glutaminase (GLS; NCBI Gene ID: 2744); a glutathione S-transferase (e.g., GSTA1 (NCBI Gene ID: 2938); GSTA2 (NCBI Gene ID: 2939); GSTA4 (NCBI Gene ID: 2941); GSTK1 NCBI Gene ID: 373156); GSTM1 (NCBI Gene ID: 2944); GSTM2 (NCBI Gene ID: 2946); GSTM3 (NCBI Gene ID: 2947); GSTM4 (NCBI Gene ID: 2948); GSTO1 (NCBI Gene ID: 9446); GSTO2 (NCBI Gene ID: 119391); GSTP1 (NCBI Gene ID: 2950); GSTT1 (NCBI Gene ID: 2952); GST2 (NCBI Gene ID: 2953)); a glycogen synthase kinase 3 (e.g., GSK3A (NCBI Gene ID: 2931); GSK3B (NCBI Gene ID: 2932)); glypican 3 (GPC3; NCBI Gene ID: 2719); a gonadotropin releasing hormone (e.g., GNRH1 (NCBI Gene ID: 2796); GNRH2 (NCBI Gene ID: 2797)); colony stimulating factor 2 receptor (e.g., CSF2RA, a.k.a., GMCSFR, GM-CSF-R-alpha; NCBI Gene ID: 1438); CSF2RB, a.k.a., CD131, IL3RB, IL5RB; NCBI Gene ID: 1439)); colony stimulating factor 2 (CSF2, a.k.a., GMCSF; NCBI Gene ID: 1437); growth factor receptor bound protein 2 (GRB2; NCBI Gene ID: 2885); a heat shock protein (e.g., HSPA1A (NCBI Gene ID: 3303); HSPA4 (NCBI Gene ID: 3308); HSPA5, a.k.a., GRP78 (NCBI Gene ID: 3309); HSPA8 (NCBI Gene ID: 3312); HSPB1, a.k.a., HSP27; NCBI Gene ID: 3315); HSPB2 (NCBI Gene ID: 3316); HSP90AA1, a.k.a., HSP90A; NCBI Gene ID: 3320); HSP90AB1, a.k.a., HSP90B; NCBI Gene ID: 3326)); heme oxygenase 1 (HMOX1, a.k.a., HO-1; NCBI Gene ID: 3162); heme oxygenase 2 (HMOX2, a.k.a., HO-2; NCBI Gene ID: 3163); sonic hedgehog signaling molecule (SHH, a.k.a., HHG1; NCBI Gene ID: 6469); Indian hedgehog signaling molecule (IHH, a.k.a., HHG2; NCBI Gene ID: 3549); hedgehog interacting protein (HHIP; NCBI Gene ID: 64399); heparinase (HPSE; NCBI Gene ID: 10855); hepatocyte growth factor (HGF; NCBI Gene ID: 3082); a HERV-H LTR-associating protein (e.g., HHLA1 (NCBI Gene ID: 10086); HHLA2 (NCBI Gene ID: 11148); HHLA3 (NCBI Gene ID: 11147)); glucokinase (GCK, a.k.a., hexokinase; HK4, HKIV, HXKP; NCBI Gene ID: 2645); histamine receptor H2 (HRH2; NCBI Gene ID: 3274); DOT1 like histone lysine methyltransferase (DOT1L; NCBI Gene ID: 84444); a histone deacetylase (e.g., HDAC1 (NCBI Gene ID: 3065); HDAC2 (NCBI Gene ID: 3066); HDAC3 (NCBI Gene ID: 8841); HDAC4 (NCBI Gene ID: 9759); HDAC5 (NCBI Gene ID: 10014); HDAC6 (NCBI Gene ID: 10013); HDAC7 (NCBI Gene ID: 51564); HDAC8 (NCBI Gene ID: 55869); HDAC9 (NCBI Gene ID: 9734)); HDAC10 (NCBI Gene ID: 83933); HDAC11 (NCBI Gene ID: 79885)); H1.0 linker histone (H1-0; NCBI Gene ID: 3005); H1.3 linker histone, cluster member (H1-3; NCBI Gene ID: 3007); H1.8 linker histone (H1-8; NCBI Gene ID: 132243); major histocompatibility complex, class I, E (HLA-E; NCBI Gene ID: 3133); major histocompatibility complex, class I, G (HLA-G; NCBI Gene ID: 3135); major histocompatibility complex, class I, H (HLA-H; NCBI Gene ID: 3136); Nanog homeobox (NANOG; NCBI Gene ID: 79923); human papillomavirus (HPV) E6; HPV E7; hyaluronic acid; a hyaluronidase (e.g., HYAL1 (NCBI Gene ID: 3373); HYAL2 (NCBI Gene ID: 8692)); hypoxia inducible factor 1 subunit alpha (HIF1A; NCBI Gene ID: 3091); endothelial PAS domain protein 1 (EPAS1, a.k.a., HIF2A; NCBI Gene ID: 2034); hypoxia inducible factor 3 subunit alpha (HIF3A; NCBI Gene ID: 64344); H19 imprinted maternally expressed transcript (H19; NCBI Gene ID: 283120); mitogen-activated protein kinase kinase kinase kinase 1 (MAP4K1, a.k.a., HPK1; NCBI Gene ID: 11184); HCK proto-oncogene, Src family tyrosine kinase (HCK; NCBI Gene ID: 3055); an inhibitor of nuclear factor kappa B kinase subunit (e.g., IKBKB (NCBI Gene ID: 3551); IKBKE (NCBI Gene ID: 9641); IKBKG (NCBI Gene ID: 8517)); interleukin 1 alpha (ILIA; NCBI Gene ID: 3552); interleukin 1 beta (IL1B; NCBI Gene ID: 3553); interleukin 12A (IL12A; NCBI Gene ID: 3592); interleukin 12B (IL12B; NCBI Gene ID: 3593); interleukin 15 (I15; NCBI Gene ID: 3600); interleukin 17A (IL17A; NCBI Gene ID: 3605); interleukin 21 (IL-21; NCBI Gene ID: 59067); interleukin 2 receptor subunit beta (IL-2RB, a.k.a., CD122, IL15RB; NCBI Gene ID: 3560); interleukin 3 receptor subunit alpha (IL3RA, a.k.a., CD123; NCBI Gene ID: 3563); interleukin 4 (IL4; NCBI Gene ID: 3565); interleukin 6 (IL6; NCBI Gene ID: 3569); interleukin 7 (IL7; NCBI Gene ID: 3574); C-X-C motif chemokine ligand 8 (CXCL8, a.k.a., IL8; NCBI Gene ID: 3576); interleukin 13 (IL13; NCBI Gene ID: 3596); interleukin 13 receptor subunit alpha 1 (IL13RA, a.k.a., CD213A1; NCBI Gene ID: 3597); a Fc fragment of IgG receptor (e.g., FCGR1A, a.k.a., CD64, FCRI (NCBI Gene ID: 2209); FCGR2A, a.k.a., CD32A (NCBI Gene ID: 2212); FCGR2B, a.k.a., CD32B, FcRII-c (NCBI Gene ID: 2213); FCGR3A, a.k.a., CD16A, FCRIIIA (NCBI Gene ID: 2214); FCGR3B, a.k.a., CD16B, FCRIIIb (NCBI Gene ID: 2215); indoleamine 2,3-dioxygenase 1 (IDO1; NCBI Gene ID: 3620); indoleamine 2,3-dioxygenase 2 (IDO2; NCBI Gene ID: 169355); insulin receptor (INSR, a.k.a., CD220; NCBI Gene ID: 3643); insulin like growth factor 1 receptor (IGF1R; NCBI Gene ID: 3480); insulin like growth factor 2 receptor (IGF2R; NCBI Gene ID: 3482); insulin like growth factor 1 (IGF1; NCBI Gene ID: 3479); insulin like growth factor 2 (IGF2; NCBI Gene ID: 3481); integrin subunit alpha 4 (ITGA4; NCBI Gene ID: 3676); integrin subunit alpha 5 (ITGA5; NCBI Gene ID: 3678); integrin subunit beta 1 (ITGB1; NCBI Gene ID: 3688); integrin subunit beta 5 (ITGB5; NCBI Gene ID: 3693); integrin subunit beta 6 (ITGB6; NCBI Gene ID: 3694); integrin subunit beta 7 (ITGB7; NCBI Gene ID: 3695) (e.g., integrin α4β1, α4β7, 501, α5β3, α5β5, α5β6); intercellular adhesion molecule 1 (ICAM1; NCBI Gene ID: 3383); an interferon (e.g., interferon alpha 1 (IFNA1; NCBI Gene ID: 3439); interferon alpha 2 (IFNA2; NCBI Gene ID: 3440); interferon beta 1 (IFNB1; NCBI Gene ID: 3456); interferon gamma (IFNG; NCBI Gene ID: 3458); interferon lambda 1 (IFNL1, a.k.a., IL-29; NCBI Gene ID: 282618); an interferon receptor (e.g., interferon alpha and beta receptor subunit 1 (IFNAR1; NCBI Gene ID: 3454); interferon alpha and beta receptor subunit 2 (IFNAR2 (NCBI Gene ID: 3455); interferon gamma receptor 1 (IFNGR1; NCBI Gene ID: 3459); interferon gamma receptor 2 (IFNGR2; NCBI Gene ID: 3460); an interferon induced transmembrane protein (e.g., IFITM1 (NCBI Gene ID: 8519); IFITM2 (NCBI Gene ID: 10581); IFITM3 (NCBI Gene ID: 10410); IFITM5 (NCBI Gene ID: 387733)); interferon gamma inducible protein 16 (IFI16; NCBI Gene ID: 3428); absent in melanoma 2 (AIM2; NCBI Gene ID: 9447); interleukin 1 receptor associated kinase 4 (IRAK4; NCBI Gene ID: 51135); a Janus kinase (e.g., JAK1 (NCBI Gene ID: 3716); JAK2 (NCBI Gene ID: 3717); JAK3 (NCBI Gene ID: 3718)); Jun proto-oncogene, AP-1 transcription factor subunit (JUN, a.k.a., c-Jun, API; NCBI Gene ID: 3725); kallikrein related peptidase 3 (KLK3; NCBI Gene ID: 354); a killer cell immunoglobulin like receptor (e.g., KIR2DL1 (NCBI Gene ID: 3802); KIR2DL2 (NCBI Gene ID: 3803); KIR2DL3 (NCBI Gene ID: 3804); KIR2DL4 (NCBI Gene ID: 3805); KIR2DL5A (NCBI Gene ID: 57292); KIR2DL5B (NCBI Gene ID: 553128); KIR2DS1 (NCBI Gene ID: 3806); KIR2DS2 (NCBI Gene ID: 100132285); KIR2DS3 (NCBI Gene ID: 3808); KIR2DS4 (NCBI Gene ID: 3809); KIR2DS5 (NCBI Gene ID: 3810); KIR3DL1 (NCBI Gene ID: 3811); KIR3DL2 (NCBI Gene ID: 3812); KIR3DL3 (NCBI Gene ID: 115653); KIR3DS1 (NCBI Gene ID: 3813)); a vascular endothelial growth factor (VEGF) (e.g., VEGFA (NCBI Gene ID: 7422); VEGFB (NCBI Gene ID: 7423) VEGFC (NCBI Gene ID: 7424) VEGFD (NCBI Gene ID: 2277)); a VEGF receptor (e.g., fms related receptor tyrosine kinase 1 (FLT1, a.k.a., VEFGR1; NCBI Gene ID: 2321); kinase insert domain receptor (KDR, a.k.a., CD309, FLK1, VEGFR2; NCBI Gene ID: 3791); fms related receptor tyrosine kinase 4 (FLT4, a.k.a., VEGFR3; NCBI Gene ID: 2324)); kinesin family member 11 (KIF11; NCBI Gene ID: 3832); KRAS proto-oncogene, GTPase (KRAS; NCBI Gene ID: 3845); NRAS proto-oncogene, GTPase (NRAS; NCBI Gene ID: 4893); KiSS-1 metastasis suppressor (KISS1, a.k.a., kisspeptin, metastin; NCBI Gene ID: 3814); lactotransferrin (LTF, a.k.a., lactoferrin (LF); NCBI Gene ID: 4057); cytochrome P450 family 51 subfamily A member 1 (CYP51A1, a.k.a., lanosterol-14 demethylase, LDM, P450-14DM; NCBI Gene ID: 1595); LDL receptor related protein 1 (LRP1, a.k.a., APOER, CD91; NCBI ID: 4035); a leukocyte immunoglobulin like receptor B (e.g., LILRB1, a.k.a., ILT2, CD85J (NCBI Gene ID: 10859); LILRB2, a.k.a., ILT4, CD85D (NCBI Gene ID: 10288); LILRB4, a.k.a., ILT3, CD85K (NCBI Gene ID: 11006)); leukotriene A4 hydrolase (LTA4H; NCBI Gene ID: 4048); luteinizing hormone/choriogonadotropin receptor (LHCGR; NCBI Gene ID: 3973); lymphocyte activating 3 (LAG3, a.k.a., CD223; NCBI Gene ID: 3902); lymphocyte antigen 75 (LY75, a.k.a., CD205; NCBI Gene ID: 4065); LCK proto-oncogene, Src family tyrosine kinase (LCK; NCBI Gene ID: 3932); YES proto-oncogene 1, Src family tyrosine kinase (YES1; NCBI Gene ID: 7525); X-C motif chemokine ligand 1 (XCL1, a.k.a., lymphotactin (LPTN, LTN); NCBI Gene ID: 6375); argininosuccinate lyase (ASL; NCBI Gene ID: 435); a lysine demethylase (e.g., KDM1A (NCBI Gene ID: 23028); KDM1B (NCBI Gene ID: 221656); KDM2A (NCBI Gene ID: 22992); KDM2B (NCBI Gene ID: 84678); KDM3A (NCBI Gene ID: 55818); KDM3B (NCBI Gene ID: 51780); KDM4A (NCBI Gene ID: 9682); KDM4B (NCBI Gene ID: 23030); KDM4C (NCBI Gene ID: 23081); KDM4D (NCBI Gene ID: 55693); KDM4E (NCBI Gene ID: 390245); KDM4F (NCBI Gene ID: 100129053); KDM5A (NCBI Gene ID: 5927); KDM5B (NCBI Gene ID: 10765); KDM5C (NCBI Gene ID: 8242); KDM6A (NCBI Gene ID: 7403); KDM6B (NCBI Gene ID: 23135); KDM7A (NCBI Gene ID: 80853); KDM8 (NCBI Gene ID: 79831)); lysophosphatidic acid receptor 1 (LPAR1; NCBI Gene ID: 1902); a lysosomal associated membrane protein (e.g., LAMP1 (NCBI Gene ID: 3916); LAMP2 (NCBI Gene ID: 3920); LAMP3 (NCBI Gene ID: 27074); CD68, a.k.a., LAMP4 (NCBI Gene ID: 968); LAMP5 (NCBI Gene ID: 24141)); lysyl oxidase (LOX; NCBI Gene ID: 4015); a lysyl oxidase like (LOXL) protein (e.g., LOXL1 (NCBI Gene ID: 4016); LOXL2 (NCBI Gene ID: 4017); LOXL3 (NCBI Gene ID: 84695); LOXL4 (NCBI Gene ID: 84171)); arachidonate 5-lipoxygenase (ALOX5, a.k.a., 5-LOX; NCBI Gene ID: 240); MET proto-oncogene, receptor tyrosine kinase (MET, a.k.a., HGFR; NCBI Gene ID: 4233); macrophage migration inhibitory factor (MIF; NCBI Gene ID: 4282); a MAGE family member (e.g., MAGEA1 (NCBI Gene ID: 4100); MAGEA2 (NCBI Gene ID: 4101); MAGEA3 (NCBI Gene ID: 4102); MAGEA4 (NCBI Gene ID: 4103); MAGEA5 (NCBI Gene ID: 4104); MAGEA6 (NCBI Gene ID: 4105); MAGEA8 (NCBI Gene ID: 4107); MAGEA9 (NCBI Gene ID: 4108); MAGEA9B (NCBI Gene ID: 728269); MAGEA10 (NCBI Gene ID: 4109); MAGEA11 (NCBI Gene ID: 4110); MAGEA12 (NCBI Gene ID: 4111); MAGEB1 (NCBI Gene ID: 4112); MAGEB2 (NCBI Gene ID: 4113); MAGEB3 (NCBI Gene ID: 4114); MAGEB4 (NCBI Gene ID: 4115); MAGEB5 (NCBI Gene ID: 347541); MAGEB6 (NCBI Gene ID: 158809); MAGEC1 (NCBI Gene ID: 9947); MAGEC2 (NCBI Gene ID: 51438); MAGEC3 (NCBI Gene ID: 139081); MAGED1 (NCBI Gene ID: 9500); MAGED2 (NCBI Gene ID: 10916); trophinin (TRO, a.k.a., MAGED3; NCBI Gene ID: 7216); MAGED4 (NCBI Gene ID: 728239); MAGED4B (NCBI Gene ID: 81557)); major vault protein (MVP; NCBI Gene ID: 9961); MAS1 proto-oncogene, G protein-coupled receptor (MAS1, a.k.a., MAS; (NCBI Gene ID: 4142); a matrix metalloprotease (e.g., MMP1 (NCBI Gene ID: 4312); MMP2 (NCBI Gene ID: 4313); MMP3 (NCBI Gene ID: 4314); MMP7 (NCBI Gene ID: 4316); MMP8 (NCBI Gene ID: 4317); MMP9 (NCBI Gene ID: 4318); MMP10 (NCBI Gene ID: 4319); MMP11 (NCBI Gene ID: 4320); MMP12 (NCBI Gene ID: 4321); MMP13 (NCBI Gene ID: 4322); MMP14 (NCBI Gene ID: 4323); MMP15 (NCBI ID: 4324); MMP16 (NCBI Gene ID: 4325); MMP17 (NCBI Gene ID: 4326); MMP19 (NCBI Gene ID: 4327); MMP20 (NCBI Gene ID: 9313); MMP21 (NCBI Gene ID: 118856); MMP23B (NCBI Gene ID: 8510); MMP24 (NCBI Gene ID: 10893); MMP25 (NCBI Gene ID: 64386); MMP26 (NCBI Gene ID: 56547); MMP27; NCBI Gene ID: 64066); MMP28 (NCBI Gene ID: 79148)); MCL1 apoptosis regulator, BCL2 family member (MCL1; NCBI Gene ID: 4170); MDM2 proto-oncogene (MDM2; NCBI Gene ID: 4193); MDM4 regulator of p53 (MDM4; NCBI Gene ID: 4194); melan-A (MLANA, a.k.a., MART-1; NCBI Gene ID: 2315); premelanosome protein (PMEL, a.k.a., PMEL17; NCBI Gene ID: 6490); proopiomelanocortin (POMC, a.k.a., MSH; NCBI Gene ID: 5443); melanocortin 1 receptor (MC1R, a.k.a., MSH-R; NCBI Gene ID: 4157); PReferentially expressed Antigen in Melanoma (PRAME) nuclear receptor transcriptional regulator (PRAME; NCBI Gene ID: 23532); a copper containing amine oxidase (e.g., AOC1 (NCBI Gene ID: 26); AOC2 (NCBI Gene ID: 314); AOC3 (NCBI Gene ID: 8639)); mesothelin (MSLN; NCBI Gene ID: 10232); a glutamate metabotropic receptor (e.g., GRM1 (NCBI Gene ID: 2911); GRM2 (NCBI Gene ID: 2912); GRM3 (NCBI Gene ID: 2913); GRM4 (NCBI Gene ID: 2914); GRM5 (NCBI Gene ID: 2915); GRM6 (NCBI Gene ID: 2916); GRM7 (NCBI Gene ID: 2917); GRM8 (NCBI Gene ID: 2918)); STEAP family member 1 (STEAP1; NCBI Gene ID: 26872); methionyl aminopeptidase 2 (METAP2; NCBI Gene ID: 10988); mechanistic target of rapamycin kinase (MTOR; NCBI Gene ID: 2475); regulatory associated protein of MTOR complex 1 (RPTOR; NCBI Gene ID: 57521); RPTOR independent companion of MTOR complex 2 (RICTOR; NCBI Gene ID: 253260); MYC proto-oncogene, bHLH transcription factor (MYC; NCBI Gene ID: 4609); myristoylated alanine rich protein kinase C substrate (MARCKS; NCBI Gene ID: 4082); nudix hydrolase 1 (NUDT1, a.k.a., Mut T homolog 1 (MTH1; NCBI Gene ID: 4521); a cell surface associated mucin (e.g., MUC1 (NCBI Gene ID: 4582); MUC4 (NCBI Gene ID: 4585); MUC13 (NCBI Gene ID: 56667); MUC15 (NCBI Gene ID: 143662); MUC16 (NCBI Gene ID: 94025); MUC17 (NCBI Gene ID: 140453); MUC20 (NCBI Gene ID: 200958); MUC21 (NCBI Gene ID: 394263)); mucin 5AC, oligomeric mucus/gel-forming (MUC5AC; NCBI Gene ID: 4586); a poly (ADP-ribose) polymerase (e.g., PARP1 (NCBI Gene ID: 142); PARP2 (NCBI Gene ID: 10038); PARP3 (NCBI Gene ID: 10039); PARP4 (NCBI Gene ID: 143); PARP6 (NCBI Gene ID: 56965); PARP7 (NCBI Gene ID: 25976); PARP8 (NCBI Gene ID: 79668); PARP9 (NCBI Gene ID: 83666); PARP10 (NCBI Gene ID: 84875); PARP11 (NCBI Gene ID: 57097); PARP12 (NCBI Gene ID: 64761); PARP14 (NCBI Gene ID: 54625)); PARP15 (NCBI Gene ID: 165631); PARP16 (NCBI Gene ID: 54956)); natriuretic peptide C (NPPC; NCBI Gene ID: 4880); neural cell adhesion molecule 1 (NCAM1; NCBI Gene ID: 4684); a tachykinin receptor, a.k.a., neurokinin receptor (e.g., TACR1, a.k.a., NK1R (NCBI Gene ID: 6869); TACR2, a.k.a., NK2R (NCBI Gene ID: 6865); TACR3, a.k.a., NK3R (NCBI Gene ID: 6870)); neuropilin 2 (NRP2; NCBI Gene ID: 8828); nuclear factor kappa B subunit (e.g., NFKB1 (NCBI Gene ID: 4790); NFKB2 (NCBI Gene ID: 4791)); an NF-kappB activating protein (e.g., TRAF family member associated NFKB activator (TANK; NCBI Gene ID: 10010); TANK binding kinase 1 (TBK1; NCBI Gene ID: 29110); TNF receptor associated factor 2 (TRAF2; NCBI Gene ID: 7186); a TNF receptor associated factor (e.g., TRAF (NCBI Gene ID: 7185); TRAF2 (NCBI Gene ID: 7186); TRAF3 (NCBI Gene ID: 7187); TRAF4 (NCBI Gene ID: 9618); TRAF5 (NCBI Gene ID: 7188); TRAF6 (NCBI Gene ID: 7189); TRAF7 (NCBI Gene ID: 84231)); TRAF3 interacting protein 2 (TRAF3IP2; NCBI Gene ID: 10758)); NEDD8 ubiquitin like modifier (NEDD8; NCBI Gene ID: 4738); NIMA related kinase 9 (NEK9; NCBI Gene ID: 91754); a nitric oxide synthase (e.g., NOS1 (NCBI Gene ID: 4842); NOS2 (NCBI Gene ID: 4843); NOS3 (NCBI Gene ID: 4846)); a killer cell lectin like receptor (e.g., KLRB1 (a.k.a., CD161; NCBI Gene ID: 3820); KLRC1 (NCBI Gene ID: 3821); KLRC2 (NCBI Gene ID: 3822); KLRC3 (NCBI Gene ID: 3823); KLRC4 (NCBI Gene ID: 8302); KLRD1 (NCBI Gene ID: 3824); KLRF1 (NCBI Gene ID: 51348); KLRF2 (NCBI Gene ID: 100431172); KLRG1 (NCBI Gene ID: 10219); KLRG2 (NCBI Gene ID: 346689); KLRK1 (NCBI Gene ID: 22914)); NLR family pyrin domain containing 3 (NLRP3; NCBI Gene ID: 114548); solute carrier family 6 member 2 (SLC6A2, a.k.a., NAT1, NET1; NCBI Gene ID: 6530); a notch receptor (e.g., NOTCH1 (NCBI Gene ID: 4851); NOTCH2 (NCBI Gene ID: 4853); NOTCH3 (NCBI Gene ID: 4854); NOTCH4 (NCBI Gene ID: 4855)); a nuclear factor, erythroid 2 like (e.g., NFE2L1 (NCBI Gene ID: 4779); NFE2L2 (NCBI Gene ID: 4780); NFE2L3 (NCBI Gene ID: 9603)); nucleolin (NCL; NCBI Gene ID: 4691); nucleophosmin 1 (NPM1; NCBI Gene ID: 4869); oncogenic tyrosine kinase nucleophosmin-anaplastic lymphoma kinase (NPM-ALK); oxoglutarate dehydrogenase (OGDH; NCBI Gene ID: 4967); an 2'-5'-oligoadenylate synthetase (e.g., OAS1 (NCBI Gene ID: 4938); OAS2 (NCBI Gene ID: 4939)); O-6-methylguanine-DNA methyltransferase (MGMT; NCBI Gene ID: 4255); ornithine decarboxylase 1 (ODC1; NCBI Gene ID: 4953); uridine monophosphate synthetase (UMPS, a.k.a., orotate phosphoribosyltransferase (OPRT); NCBI Gene ID: 7372); nuclear receptor subfamily 4 group A member 1 (NR4A1; NCBI Gene ID: 3164); bone gamma-carboxyglutamate protein (BGLAP, a.k.a., osteocalcin (OC, OCN); NCBI Gene ID: 632); TNF superfamily member 11 (TNFSF11, a.k.a., CD254, osteoclast differentiation factor (ODF), RANKL; NCBI Gene ID: 8600); secreted phosphoprotein 1 (SPP1, a.k.a., osteopontin (OPN); NCBI Gene ID: 6696); solute carrier family 10 member 3 (SLC10A3, a.k.a., P3; NCBI Gene ID: 8273); tumor protein p53 (TP53; NCBI Gene ID: 7157); parathyroid hormone (PTH; NCBI Gene ID: 5741); parathyroid hormone 1 receptor (PTH1R; NCBI Gene ID: 5745); a peroxisome proliferator activated receptor (e.g., PPARA (NCBI Gene ID: 5465); PPARD (NCBI Gene ID: 5467); PPARG (NCBI Gene ID: 5468)); an ATP binding cassette subfamily B member (e.g., ABCB1, a.k.a., P-glycoprotein (P-GP, PGY1) (NCBI Gene ID: 5243); ABCB4, a.k.a., PGY3 (NCBI Gene ID: 5244); ABCB11, a.k.a., PGY4 (NCBI Gene ID: 8647); ATP binding cassette subfamily G member 2 (Junior blood group) (ABCG2, a.k.a., ABC15, CD338; NCBI Gene ID: 9429)); phosphatase and tensin homolog (PTEN; NCBI Gene ID: 5728); phosphatidylinositol-4,5-bisphosphate 3-kinase catalytic subunit (e.g., PIK3CA (alpha) (NCBI Gene ID: 5290); PIK3CB (beta) (NCBI Gene ID: 5291); PIK3CG (gamma) (NCBI Gene ID: 5294); PIK3CD (delta) (NCBI Gene ID: 5293)); a phosphorylase kinase regulatory subunit (e.g., PHKA1 (NCBI Gene ID: 5255); PHKA2 (NCBI Gene ID: 5256); PHKB (NCBI Gene ID: 5257); PHKG1 (NCBI Gene ID: 5260); PHKG2 (NCBI Gene ID: 5261)); a calmodulin (e.g., CALM1 (NCBI Gene ID: 801); CALM2 (NCBI Gene ID: 805); CALM3 (NCBI Gene ID: 808)); protein kinase N3 (PKN3; NCBI Gene ID: 29941); placental growth factor (PGF, a.k.a., PIGF, PLGF; NCBI Gene ID: 5228); a platelet derived growth factor subunit (e.g., PDGFA (NCBI Gene ID: 5154); PDGFB (NCBI Gene ID: 5155)); a platelet derived growth factor receptor (e.g., PDGFRA (NCBI Gene ID: 5156); PDGFRB (NCBI Gene ID: 5159)); a plexin (e.g., PLXNA1 (NCBI Gene ID: 5361); PLXNA2 (NCBI Gene ID: 5362); PLXNA3 (NCBI Gene ID: 55558); PLXNA4 (NCBI Gene ID: 91584); PLXNB1 (NCBI Gene ID: 5364); PLXNB2 (NCBI Gene ID: 23654); PLXNB3 (NCBI Gene ID: 5365); PLXNC1 (NCBI Gene ID: 10154); PLXND1 (NCBI Gene ID: 23129)); polo like kinase 1 (PLK1; NCBI Gene ID: 5347); PML nuclear body scaffold (PML; NCBI Gene ID: 5371); progesterone receptor (PGR; NCBI Gene ID: 5241); programmed cell death 1 (PDCD1, a.k.a., CD279, PD-1, PD1; NCBI Gene ID: 5133); CD274 molecule (CD274, a.k.a., B7-H, PD-L1, PDL1; NCBI Gene ID: 29126); prosaposin (PSAP; NCBI Gene ID: 5660); prostaglandin E receptor 4 (PTGER4, a.k.a., EP4, EP4R; NCBI Gene ID: 5734); prostaglandin-endoperoxide synthase 1 (PTGS1, a.k.a., COX1; NCBI Gene ID: 5742); prostaglandin-endoperoxide synthase 2 (PTGS2, a.k.a., COX2; NCBI Gene ID: 5743); epoxide hydrolase 2 (EPHX2, a.k.a., SEH; NCBI Gene ID: 2053); kallikrein related peptidase 3 (KLK3, a.k.a., prostate specific antigen (PSA); NCBI Gene ID: 354); acid phosphatase 3 (ACP3, a.k.a., prostatic acid phosphatase (PAP); NCBI Gene ID: 55); a proteasome 20S subunit beta (e.g., PSMB1 (NCBI Gene ID: 5689); PSMB2 (NCBI Gene ID: 5690); PSMB3 (NCBI Gene ID: 5691); PSMB4 (NCBI Gene ID: 5692); PSMB5 (NCBI Gene ID: 5693); PSMB6 (NCBI Gene ID: 5694); PSMB7 (NCBI Gene ID: 5695); PSMB8 (NCBI Gene ID: 5696); PSMB9 (NCBI Gene ID: 5698); PSMB10 (NCBI Gene ID: 5699)); farnesyl-diphosphate farnesyltransferase 1 (FDFT1; NCBI Gene ID: 2222); a farnesyltransferase, CAAX box (e.g., FNTA (NCBI Gene ID: 2339); FNTB (NCBI Gene ID: 2342)); a phosphatidylinositol-4,5-bisphosphate 3-kinase (PI3K) catalytic subunit (e.g., PIK3CA (NCBI Gene ID: 5290); PIK3CB (NCBI Gene ID: 5291); PIK3CG (NCBI Gene ID: 5294); PIK3CD (NCBI Gene ID: 5293); PIK3C3 (NCBI Gene ID: 5289); PIK3C2B (NCBI Gene ID: 5287)); protein tyrosine phosphatase receptor type B (PTPRB; NCBI Gene ID: 5787); a proto-oncogene, serine/threonine kinase (PIM) (e.g., PIM1 (NCBI Gene ID: 5292); PIM2 (NCBI Gene ID: 11040); PIM3 (NCBI Gene ID: 415116)); selectin E (SELE, a.k.a., CD62E, ELAM; NCBI Gene ID: 6401); selectin L (SELL, a.k.a., CD62L; NCBI Gene ID: 6402); selectin P (SELP, a.k.a., CD62; LECAM3, NCBI Gene ID: 6403); purine nucleoside phosphorylase (PNP; NCBI Gene ID: 4860); a purinergic receptor P2X (e.g., P2RX1 (NCBI Gene ID: 5023); P2RX2 (NCBI Gene ID: 22953); P2RX3 (NCBI Gene ID: 5024); P2RX4 (NCBI Gene ID: 5025); P2RX5 (NCBI Gene ID: 5026); P2RX6 (NCBI Gene ID: 9127); P2RX7 (NCBI Gene ID: 5027)); a pyruvate dehydrogenase E1 subunit alpha (e.g., PDHA1 (NCBI Gene ID: 5160); PDHA2 (NCBI Gene ID: 5161)); a pyruvate dehydrogenase kinase (e.g., PDK1 (NCBI Gene ID: 5163); PDK2 (NCBI Gene ID: 5164); PDK3 (NCBI Gene ID: 5165); PDK4 (NCBI Gene ID: 5166)); a pyruvate kinase (e.g., PKM (NCBI Gene ID: 5315); PKLR (NCBI Gene ID: 5313)); a steroid 5 alpha-reductase (SRD5A1 (NCBI Gene ID: 6715); SRD5A2 (NCBI Gene ID: 6716); SRD5A3 (NCBI Gene ID: 79644)); B-Raf proto-oncogene, serine/threonine kinase (BRAF; NCBI Gene ID: 673); Raf-1 proto-oncogene, serine/threonine kinase (RAFI; NCBI Gene ID: 5894); ret proto-oncogene (RET; NCBI Gene ID: 5979); glial cell derived neurotrophic factor (GDNF; NCBI Gene ID: 2668); RB transcriptional corepressor 1 (RB1; NCBI Gene ID: 5925); a RB transcriptional corepressor like (e.g., RBL1 (NCBI Gene ID: 5933); RBL2 (NCBI Gene ID: 5934)); E2F transcription factor 1 (E2F1; NCBI Gene ID: 1869); a retinoic acid receptor (e.g., RARA or alpha (NCBI Gene ID: 5914); RARB or beta (NCBI Gene ID: 5915); RARG or gamma (NCBI Gene ID: 5916)); a retinoid X receptor (e.g., RXRA or alpha (NCBI Gene ID: 6256); RXRB or beta (NCBI Gene ID: 6257); RXRG or gamma (NCBI Gene ID: 6258); Ras homolog, mTORC1 binding (RHEB; NCBI Gene ID: 6009); a ras homolog family member (e.g., RHOA (NCBI Gene ID: 387); RHOB (NCBI Gene ID: 388); RHOC (NCBI Gene ID: 389); RHOD (NCBI Gene ID: 29984)); a Rho associated coiled-coil containing protein kinase (e.g., ROCK1 (NCBI Gene ID: 6093); ROCK2 (NCBI Gene ID: 9475)); ribonucleotide reductase regulatory subunit M2 (RRM2; NCBI Gene ID: 6241); ribonucleotide reductase regulatory TP53 inducible subunit M2B (RRM2B; NCBI Gene ID: 50484); a ribosomal protein S6 kinase (e.g., RPS6KA1 (NCBI Gene ID: 6195); RPS6KA2 (NCBI Gene ID: 6196); RPS6KA3 (NCBI Gene ID: 6197); RPS6KA4 (NCBI Gene ID: 8986); RPS6KA5 (NCBI Gene ID: 9252); RPS6KA6 (NCBI Gene ID: 27330); RPS6KB1 (NCBI Gene ID: 6198); RPS6KB2 (NCBI Gene ID: 6199); RPS6KC1 (NCBI Gene ID: 26750)); an RNA polymerase I subunit (e.g., POLR1A (NCBI Gene ID: 25885); POLR1B (NCBI Gene ID: 84172); POLR1C (NCBI Gene ID: 9533); POLR1D (NCBI Gene ID: 51082); POLR1E (NCBI Gene ID: 64425); POLR1F (NCBI Gene ID: 221830); POLR1G (NCBI Gene ID: 10849); POLR1H (NCBI Gene ID: 30834)); an RNA polymerase II subunit (e.g., POLR2A (NCBI Gene ID: 5430); POLR2B (NCBI Gene ID: 5431); POLR2C (NCBI Gene ID: 5432); POLR2D (NCBI Gene ID: 5433); POLR2E (NCBI Gene ID: 5434); POLR2F (NCBI Gene ID: 5435); POLR2G (NCBI Gene ID: 5436); POLR2H (NCBI Gene ID: 5437); POLR2I (NCBI Gene ID: 5438); POLR2J (NCBI Gene ID: 5439); POLR2K (NCBI Gene ID: 5440); POLR2L (NCBI Gene ID: 5441); POLR2M (NCBI Gene ID: 81488)); TATA-box binding protein associated factor, RNA polymerase I subunit B (TAF1B; NCBI Gene ID: 9014); macrophage stimulating 1 receptor (MST1R, a.k.a., CD136, Recepteur d'Origine Nantais (RON); NCBI Gene ID: 4486); ROS proto-oncogene 1, receptor tyrosine kinase (ROS1; NCBI Gene ID: 6098); a RUNX family transcription factor (e.g., RUNX1 (NCBI Gene ID: 861); RUNX2 (NCBI Gene ID: 860); RUNX3 (NCBI Gene ID: 864)); a gamma-secretase subunit (e.g., presenilin enhancer, gamma-secretase subunit (PSENEN; NCBI Gene ID: 55851); aph-1 homolog A, gamma-secretase subunit (APH1A; NCBI Gene ID: 51107); aph-1 homolog B, gamma-secretase subunit (APH1B; NCBI Gene ID: 83464)); S100 calcium binding protein A9 (S100A9; NCBI Gene ID: 6280); a sarcoplasmic/endoplasmic reticulum Ca2+ transporting ATPase (e.g., ATP2A1 (NCBI Gene ID: 487); ATP2A2 (NCBI Gene ID: 488); ATP2A3 (NCBI Gene ID: 489)); diablo IAP-binding mitochondrial protein (DIABLO, a.k.a., second mitochondria-derived activator of caspases (SMAC); NCBI Gene ID: 56616); a secreted frizzled related protein (e.g., SFRP1 (NCBI Gene ID: 6422); SFRP2 (NCBI Gene ID: 6423)); phospholipase A2 group IVA (PLA2G4A; NCBI Gene ID: 5321); semaphorin 4D (SEMA4D; NCBI Gene ID: 10507); a transmembrane serine protease (e.g., TMPRSS2 (NCBI Gene ID: 7113); TMPRSS3 (NCBI Gene ID: 64699); TMPRSS4 (NCBI Gene ID: 56649); TMPRSS5 (NCBI Gene ID: 80975); TMPRSS6 (NCBI Gene ID: 164656); TMPRSS9 (NCBI Gene ID: 360200); TMPRSS11A (NCBI Gene ID: 339967); TMPRSS11B (NCBI Gene ID: 132724); TMPRSS11D (NCBI Gene ID: 9407); TMPRSS11E (NCBI Gene ID: 28983); TMPRSS15 (NCBI Gene ID: 5651)); a signal transducer and activator of transcription (e.g., STAT1 (NCBI Gene ID: 6772); STAT2 (NCBI Gene ID: 6773); STAT3 (NCBI Gene ID: 6774)); STAT4 (NCBI Gene ID: 6775); STAT5A (NCBI Gene ID: 6776); STAT5B (NCBI Gene ID: 6777); STAT6 (NCBI Gene ID: 6778)); a signaling lymphocytic activation molecule family member (e.g., SLAMF1 (NCBI Gene ID: 6504); CD48, a.k.a., SLAMF2 (NCBI Gene ID: 962); LY9, a.k.a., CD229, SLAMF3 (NCBI Gene ID: 4063); CD244, a.k.a., SLAMF4 (NCBI Gene ID: 51744); CD84, a.k.a., SLAMF5 (NCBI Gene ID: 8832); SLAMF6 (NCBI Gene ID: 114836); SLAMF7 (NCBI Gene ID: 57823); SLAMF8 (NCBI Gene ID: 56833); SLAMF9 (NCBI Gene ID: 89888)); a six-transmembrane epithelial antigen of the prostate (STEAP) metalloreductase family member (e.g., STEAP1 (NCBI Gene ID: 26872); STEAP1B (NCBI Gene ID: 256227); STEAP2 (NCBI Gene ID: 261729); STEAP3 (NCBI Gene ID: 55240); STEAP4 (NCBI Gene ID: 79689)); smoothened, frizzled class receptor (SMO; NCBI Gene ID: 6608); solute carrier family 5 member 5 (SLC5A5, a.k.a., sodium iodide symporter (NIS) NCBI Gene ID: 6528); solute carrier family 34 member 2 (SLC34A2, a.k.a., pH-sensitive sodium-dependent phosphate transporter (NPTIIb; NAPI-3B; NAPI-IIb); NCBI Gene ID: 10568); a somatostatin receptor (e.g., SSTR1 (NCBI Gene ID: 6751); SSTR2 (NCBI Gene ID: 6752); SSTR3 (NCBI Gene ID: 6753); SSTR4 (NCBI Gene ID: 6754); SSTR5 (NCBI Gene ID: 6755)); sonic hedgehog signaling molecule (SHH; NCBI Gene ID: 6469); a son of sevenless (SOS) Ras/Rac guanine nucleotide exchange factor (e.g., SOS1 (NCBI Gene ID: 6654); SOS2 (NCBI Gene ID: 6655)); Sp1 transcription facto (SP1; NCBI Gene ID: 6667); a sphingomyelin synthase (e.g., SGMS1 (NCBI Gene ID: 259230); SGMS2 (NCBI Gene ID: 166929)); a sphingosine kinase (e.g., SPHK1 (NCBI Gene ID: 8877); SPHK2 (NCBI Gene ID: 56848)); sphingosine-1-phosphate receptor (e.g., S1PR1 (NCBI Gene ID: 1901); S1PR2 (NCBI Gene ID: 9294); S1PR3 (NCBI Gene ID: 1903)); S1PR4 (NCBI Gene ID: 8698); S1PR5 (NCBI Gene ID: 53637)); spleen associated tyrosine kinase (SYK; NCBI Gene ID: 6850); SRC proto-oncogene, non-receptor tyrosine kinase (SRC; NCBI Gene ID: 6714); steroid sulfatase (STS; NCBI Gene ID: 412); stimulator of interferon response cGAMP interactor 1 (STING1; NCBI Gene ID: 340061); C-X-C motif chemokine ligand 12 (CXCL12, a.k.a., stromal cell-derived factor-1 (SDF1); NCBI Gene ID: 6387); a small ubiquitin like modifier (e.g., SUMO1 (NCBI Gene ID: 7341); SUMO2 (NCBI Gene ID: 6613); SUMO3 (NCBI Gene ID: 6612); SUMO4 (NCBI Gene ID: 387082)); a superoxide dismutase (e.g., SOD1 (NCBI Gene ID: 6647); SOD2 (NCBI Gene ID: 6648); SOD3 (NCBI Gene ID: 6649)); baculoviral IAP repeat containing 5 (BIRC5, a.k.a., survivin; NCBI Gene ID: 332); a synapsin (e.g., SYN1 (NCBI Gene ID: 6853); SYN2 (NCBI Gene ID: 6854); SYN3 (NCBI Gene ID: 8224)); a syndecan (e.g., SDC1 (NCBI Gene ID: 6382); SDC2 (NCBI Gene ID: 6383); SDC3 (NCBI Gene ID: 9672); SDC4 (NCBI Gene ID: 6385)); a synuclein (e.g., SNCA (alpha; NCBI Gene ID: 6622); SNCB (beta; NCBI Gene ID: 6620); SNCG (gamma; NCBI Gene ID: 6623)); a tankyrase (e.g., TNKS (NCBI Gene ID: 8658); TNKS2 (NCBI Gene ID: 80351)); TANK binding kinase 1 (TBK1; NCBI Gene ID: 29110); CD247 (a.k.a., CD3-ZETA; NCBI Gene ID: 919); CD6 (NCBI Gene ID: 923); hepatitis A virus cellular receptor 2 (HAVCR2, a.k.a., CD366, TIM3, Tim-3; NCBI Gene ID: 84868); CD8A (a.k.a., CD8; NCBI Gene ID: 925); tec protein tyrosine kinase (TEC; NCBI Gene ID: 7006); TEK receptor tyrosine kinase (TEK, a.k.a., TIE2, CD202B; NCBI Gene ID: 7010); tyrosine kinase with immunoglobulin like and EGF like domains 1 (TIE1; NCBI Gene ID: 7075); telomerase reverse transcriptase (TERT; NCBI Gene ID: 7015); telomerase RNA component (TERC; NCBI Gene ID: 7012); a tenascin (e.g., TNC (NCBI Gene ID: 3371); TNR (NCBI Gene ID: 7143); TNXB (NCBI Gene ID: 7148)); MPL proto-oncogene, thrombopoietin receptor (MPL; NCBI Gene ID: 4352); a thymidine kinase (e.g., TK1 (NCBI Gene ID: 7083); TK2 (NCBI Gene ID: 7084)); thymidine phosphorylase (TYMP (NCBI Gene ID: 1890); thymidylate synthetase (TYMS; NCBI Gene ID: 7298); prothymosin alpha (PTMA, a.k.a., thymosin $\alpha$ (TMSA); NCBI Gene ID: 5757); a $\beta$-thymosin (e.g., TMSB4X (NCBI Gene ID: 7114); TMSB4Y (NCBI Gene ID: 9087); TMSB10 (NCBI Gene ID: 9168); TMSB15A (NBCI Gene ID: 11013); TMSB15B (NCBI Gene ID: 286527)); a thyroid hormone receptor (e.g., THRA (NCBI Gene ID: 7067); THRB (NCBI Gene ID: 7068)); thyroid stimulating hormone receptor (TSHR; NCBI Gene ID: 7253); coagulation factor III, tissue factor (F3; NCBI Gene ID: 2152); a toll like receptor (e.g., TLR1 (NCBI Gene ID: 7096); TLR2 (NCBI Gene ID: 7097); TLR3 (NCBI Gene ID: 7098); TLR4 (NCBI Gene ID: 7099); TLR5 (NCBI Gene ID: 7100); TLR6 (NCBI Gene ID: 10333); TLR7 (NCBI Gene ID: 51284); TLR8 (NCBI Gene ID: 51311); TLR9 (NCBI Gene ID: 54106); TLR10 (NCBI Gene ID: 81793)); transferrin (TF; NCBI Gene ID: 7018); a transglutaminase (e.g., TGM1 (NCBI Gene ID: 7051); TGM2 (NCBI Gene ID: 7052); TGM3 (NCBI Gene ID: 7053); TGM4 (NCBI Gene ID: 7047); TGM5 (NCBI Gene ID: 9333); TGM6 (NCBI Gene ID: 343641); TGM7 (NCBI Gene ID: 116179)); glycoprotein nmb (GPNMB, a.k.a., NMB; NCBI Gene ID: 10457); triggering receptor expressed on myeloid cells 1 (TREM1; NCBI Gene ID: 54210); triggering receptor expressed on myeloid cells 2 (TREM2; NCBI Gene ID: 54209); epithelial cell adhesion molecule (EPCAM, a.k.a., tumor associated calcium signal transducer 2 (TACSTD2), TROP1; NCBI Gene ID: 4072); tumor associated calcium signal transducer 2 (TACSTD2, a.k.a., TROP2; NCBI Gene ID: 4070); trophoblast glycoprotein (TPBG; NCBI Gene ID: 7162); a neurotrophic receptor tyrosine kinase (e.g., NTRK1, a.k.a., TRKA (NCBI Gene ID: 4914); NTRK2, a.k.a., TRKB (NCBI Gene ID: 4915); NTRK3, a.k.a., TRKC (NCBI Gene ID: 4916)); a tryptophan hydroxylase (TPH1 (NCBI Gene ID: 7166); TPH2 (NCBI Gene ID: 121278)); a tubulin (e.g., TUBA1A (NCBI Gene ID: 7846); TUBA4A (NCBI Gene ID: 7277); TUBA1B (NCBI Gene ID: 10376); TUBB (NCBI Gene ID: 203068); TUBB1 (NCBI Gene ID: 81027); TUBB2A (NCBI Gene ID: 7280); TUBB3 (NCBI Gene ID: 10381); TUBB4A (NCBI Gene ID: 10382); TUBB4B (NCBI Gene ID: 10383); TUBG1 (NCBI Gene ID: 7283)); tumor necrosis factor (TNF, a.k.a., TNF-alpha, TNFA; NCBI Gene ID: 7124); lymphotoxin alpha (LTA, a.k.a., TNFB; NCBI Gene ID: 4049); mitogen-activated protein kinase kinase kinase 8 (MAP3K8, a.k.a., TPL2; NCBI Gene ID: 1326); tumor protein p53 (TP53; NCBI Gene ID: 7157); tumor suppressor candidate 1 (TUSC1; NCBI Gene ID: 286319); tumor suppressor 2, mitochondrial calcium regulator (TUSC2; NCBI Gene ID: 11334); tyrosinase (TYR; NCBI Gene ID: 7299); tyrosine hydroxylase (TH; NCBI Gene ID: 7054); a ubiquitin (e.g., UBB (NCBI Gene ID: 7314); UBC (NCBI Gene ID: 7316); UBD (NCBI Gene ID: 10537)); ubiquitin C-terminal hydrolase L5 (UCHL5; NCBI Gene ID: 51377); ubiquitin conjugating enzyme E2 I (UBE2I, a.k.a., UBC9; NCBI Gene ID: 7329); an OTU deubiquitinase (e.g., OTUB1 (NCBI Gene ID: 55611); OTUB2 (NCBI Gene ID: 78990; YOD1 (NCBI Gene ID: 55432)); plasminogen activator, urokinase (PLAU; NCBI Gene ID: 5328); plasminogen activator, urokinase receptor (PLAUR; NCBI Gene ID: 5329); a secretoglobin family member (e.g., SCGB1A1, a.k.a., uteroglobin (NCBI Gene ID: 7356); SCGB1C1 (NCBI Gene ID: 147199); SCGB1C2 (NCBI Gene ID:

653486); SCGB1D1 (NCBI Gene ID: 10648); SCGB1D2 (NCBI Gene ID: 10647); SCGB1D4 (NCBI Gene ID: 404552); SCGB2A1 (NCBI Gene ID: 4246); SCGB2A2 (NCBI Gene ID: 4250); SCGB2B2 (NCBI Gene ID: 284402); SCGB3A1 (NCBI Gene ID: 92304); SCGB3A2 (NCBI Gene ID: 117156)); transient receptor potential cation channel subfamily V member 1 (TRPV1, a.k.a., vanilloid receptor 1 (VR1); NCBI Gene ID: 7442); vascular cell adhesion molecule 1 (VCAM1; NCBI Gene ID: 7412); V-set immunoregulatory receptor (VSIR, a.k.a., B7-H5, VISTA; NCBI Gene ID: 64115); vimentin (VIM; NCBI Gene ID: 7431); vitamin D receptor (VDR; NCBI Gene ID: 7421); MER proto-oncogene, tyrosine kinase (MERTK, a.k.a., MER, c-mer, NCBI Gene ID: 10461); Yes1 associated transcriptional regulator (YAP1; NCBI Gene ID: 10413); WEE1 G2 checkpoint kinase (WEE1; NCBI Gene ID: 7465); WT1 transcription factor (WT1; NCBI Gene ID: 7490); tafazzin (TAZ; NCBI Gene ID: 6901); WW domain containing transcription regulator 1 (WWTR1; NCBI Gene ID: 25937); and X-linked inhibitor of apoptosis (XIAP; NCBI Gene ID: 331).

In some embodiments, the one or more additional therapeutic agents include, without limitation, an inhibitor, agonist, antagonist, ligand, modulator, stimulator, blocker, activator or suppressor of a target (e.g., polypeptide or polynucleotide) including without limitation: 5'-nucleotidase ecto (NT5E or CD73; NCBI Gene ID: 4907); adenosine A2A receptor (ADORA2A; NCBI Gene ID: 135); adenosine A2B receptor (ADORA2B; NCBI Gene ID: 136); C-C motif chemokine receptor 8 (CCR8, CDw198; NCBI Gene ID: 1237); cytokine inducible SH2 containing protein (CISH; NCBI Gene ID: 1154); diacylglycerol kinase alpha (DGKA, DAGK, DAGK1 or DGK-alpha; NCBI Gene ID: 1606); fms like tyrosine kinase 3 (FLT3, CD135; NCBI Gene ID: 2322); integrin associated protein (IAP, CD47; NCBI Gene ID: 961); interleukin-2 (IL2; NCBI Gene ID: 3558); interleukin 2 receptor (IL2RA, IL2RB, IL2RG; NCBI Gene IDs: 3559, 3560, 3561); Kirsten rat sarcoma virus (KRAS; NCBI Gene ID: 3845; including mutations, such as KRAS G12C or G12D); mitogen-activated protein kinase kinase kinase kinase 1 (MAP4K1) (also called Hematopoietic Progenitor Kinase 1 (HPK1), NCBI Gene ID: 11184); myeloid cell leukemia sequence 1 apoptosis regulator (MCL1; NCBI Gene ID: 4170); phosphatidylinositol-4,5-bisphosphate 3-kinase, catalytic subunit delta (PIK3CD; NCBI Gene ID: 5293); programmed death-ligand 1 (PD-L1, CD274; NCBI Gene ID 29126); programmed cell death protein 1 (PD-1, CD279; NCBI Gene ID: 5133); proto-oncogen c-KIT (KIT, CD117; NCBI Gene ID: 3815); signal-regulatory protein alpha (SIRPA, CD172A; NCBI Gene ID: 140885); TCDD inducible poly(ADP-ribose) polymerase (TIPARP, PARP7; NCBI Gene ID: 25976); T cell immunoreceptor with Ig and ITIM domains (TIGIT; NCBI Gene ID: 201633); triggering receptor expressed on myeloid cells 1 (TREM1; NCBI Gene ID: 54210); triggering receptor expressed on myeloid cells 2 (TREM2; NCBI Gene ID: 54209); tumor-associated calcium signal transducer 2 (TACSTD2, TROP2, EGP1; NCBI Gene ID: 4070); tumor necrosis factor receptor superfamily, member 4 (TNFRSF4, CD134, OX40; NCBI Gene ID: 7293); tumor necrosis factor receptor superfamily, member 9 (TNFRSF9, 4-1BB, CD137; NCBI Gene ID: 3604); tumor necrosis factor receptor superfamily, member 18 (TNFRSF18, CD357, GITR; NCBI Gene ID: 8784); WRN RecQ like helicase (WRN; NCBI Gene ID: 7486); zinc finger protein Helios (IKZF2; NCBI Gene ID: 22807).

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more therapeutic agents categorized by their mechanism of action, e.g., into the following groups:

- agents targeting adenosine deaminase, such as pentostatin or cladribine;
- agents targeting ATM, such as AZD1390;
- agents targeting MET, such as savolitinib, capmatinib, tepotinib, ABT-700, AG213, JNJ-38877618 (OMO-1), merestinib, HQP-8361, BMS-817378, or TAS-115;
- agents targeting mitogen-activated protein kinase, such as antroquinonol, binimetinib, cobimetinib, selumetinib, trametinib, uprosertib, mirdametinib (PD-0325901), pimasertib, refametinib, or compounds disclosed in WO2011008709, WO2013112741, WO2006124944, WO2006124692, WO2014064215, WO2018005435, Zhou, et al., Cancer Lett. 2017 Nov. 1, 408:130-137, Teli, et al., J Enzyme Inhib Med Chem. (2012) 27(4): 558-70; Gangwall, et al., Curr Top Med Chem. (2013) 13(9):1015-35; Wu, et al., Bioorg Med Chem Lett. (2009) 19(13):3485-8; Kaila, et al., Bioorg Med Chem. (2007) 15(19):6425-42, or Hu, et al., Bioorg Med Chem Lett. (2011) 21(16):4758-61;
- agents targeting thymidine kinase, such as aglatimagene besadenovec (ProstAtak, PancAtak, GliAtak, GMCI, or AdV-tk);
- agents targeting an interleukin pathway, such as pegilodecakin (AM-0010) (pegylated IL10), CA-4948 (IRAK4 inhibitor);
- agents targeting cytochrome P450 family members, such as letrozole, anastrozole, aminoglutethimide, megestrol acetate (MEGACE®), exemestane, formestane, fadrozole, vorozole (RIVISOR®), letrozole (FEMARA®), or anastrozole (ARIMIDEX®);
- agents targeting CD73, such as a CD73 inhibitor (e.g., quemliclustat (AB680)) or an anti-CD73 antibody (e.g., oleclumab);
- agents targeting DKK3, such as MTG-201;
- agents targeting EEF1A2, such as plitidepsin;
- agents targeting EIF4A1, such as rohinitib;
- agents targeting endoglin, such as TRC105 (carotuximab);
- agents targeting exportin-1, such as eltanexor,
- agents targeting fatty acid amide hydrolase, such as compounds disclosed in WO2017160861;
- agents targeting heat shock protein 90 beta family member 1, such as anlotinib;
- agents targeting lactotransferrin, such as ruxotemitide (LTX-315);
- agents targeting lysyl oxidase, such as compounds disclosed in U.S. Pat. Nos. 4,965,288, 4,997,854, 4,943,593, 5,021,456, 5,059,714, 5,120,764, 5,182,297, 5,252,608, or US20040248871;
- agents targeting MAGE family members, such as KITE-718, MAGE-A10C796T, or MAGE-A10 TCR;
- agents targeting MDM2, such as ALRN-6924, CMG-097, milademetan monotosylate monohydrate (DS-3032b), or AMG-232;
- agents targeting MDM4, such as ALRN-6924;
- agents targeting melan-A, such as MART-1 F5 TCR engineered PBMCs;
- agents targeting mesothelin, such as CSG-MESO or TC-210;
- agents targeting METAP2, such as M8891 or APL-1202;
- agents targeting NLRP3, such as BMS-986299;
- agents targeting oxoglutarate dehydrogenase, such as devimistat (CPI-613);

agents targeting placenta growth factor, such as aflibercept;

agents targeting SLC10A3, such as compounds disclosed in WO2015148954, WO2012082647, or WO2017160861;

agents targeting transforming growth factor alpha (TGFα), such as compounds disclosed in WO2019103203;

agents targeting tumor protein p53, such as kevetrin (stimulator);

agents targeting vascular endothelial growth factor A, such as aflibercept;

agents targeting vascular endothelial growth factor receptor, such as fruquintinib or MP0250;

agents targeting VISTA, such as CA-170, or HMBD-002;

agents targeting WEE1, such as adavosertib (AZD-1775);

small molecule inhibitors targeting ABL1, such as imatinib, rebastinib, asciminib, or ponatinib (ICLUSIG®);

small molecule antagonists targeting adenosine receptor, such as CPI-444, AZD-4635, preladenant, etrumadenant (AB928), or PBF-509;

small molecule inhibitors targeting arachidonate 5-lipoxygenase, such as meclofenamate sodium or zileuton;

small molecule inhibitors targeting ATR serine/threonine kinase, such as BAY-937, ceralasertib (AZD6738), AZD6783, VX-803, or VX-970 (berzosertib);

small molecule inhibitors targeting AXL receptor tyrosine kinase, such as bemcentinib (BGB-324), SLC-0211, or gilteritinib (Ax1/Flt3);

small molecule inhibitors targeting Bruton's tyrosine kinase (BTK), such as (S)-6-amino-9-(1-(but-2-ynoyl)pyrrolidin-3-yl)-7-(4-phenoxyphenyl)-7H-purin-8 (9H)-one, acalabrutinib (ACP-196), zanubrutinib (BGB-3111), CB988, poseltinib (HM71224), ibrutinib (Imbruvica), M-2951 (evobrutinib), tirabrutinib (ONO-4059), rilzabrutinib (PRN-1008), spebrutinib (CC-292), vecabrutinib, ARQ-531 (MK-1026), SHR-1459, DTRMWXHS-12, or TAS-5315;

small molecule inhibitors targeting neurotrophic receptor tyrosine kinase such as larotrectinib, entrectinib, or selitrectinib (LOXO-195);

small molecule inhibitors targeting ROS proto-oncogene 1, receptor tyrosine kinase, such as entrectinib, repotrectinib (TPX-0005), or lorlatinib;

small molecule inhibitors targeting SRC proto-oncogene, non-receptor tyrosine kinase, such as VAL-201, tirbanibulin (KX2-391), or ilginatinib maleate (NS-018);

small molecule inhibitors targeting B-cell lymphoma 2, such as navitoclax (ABT-263), venetoclax (ABT-199, RG-7601), or AT-101 (gossypol);

small molecule inhibitors targeting bromodomain and external domain (BET) bromodomain containing protein, such as ABBV-744, INCB-054329, INCB057643, AZD-5153, ABT-767, BMS-986158, CC-90010, NHWD-870, ODM-207, ZBC246, ZEN3694, CC-95775 (FT-1101), mivebresib, BI-894999, PLX-2853, PLX-51107, CPI-0610, or GS-5829;

small molecule inhibitors targeting carbohydrate sulfotransferase 15, such as STNM-01;

small molecule inhibitors targeting carbonic anhydrase, such as polmacoxib, acetazolamide, or methazolamide;

small molecule inhibitors targeting catenin beta 1, such as CWP-291, or PRI-724;

small molecule antagonists targeting a C-C motif chemokine receptor, such as CCX-872, BMS-813160 (CCR2/CCR5) or MK-7690 (vicriviroc);

small molecule antagonists targeting a C-X-C motif chemokine receptor (e.g., CXCR4), blixafortide;

small molecule inhibitors targeting cereblon, such as avadomide (CC-122), CC-92480, CC-90009, or iberdomide;

small molecule inhibitors targeting checkpoint kinase 1, such as SRA737;

small molecule inhibitors targeting a complement component, such as Imprime PGG (Biothera Pharmaceuticals);

small molecule inhibitor targeting a C-X-C motif chemokine ligand (e.g., CXCL12), such as olaptesed pegol (NOX-A12);

small molecule inhibitors targeting cytochrome P450 family, such as ODM-209, LAE-201, seviteronel (VT-464), CFG920, abiraterone, or abiraterone acetate;

small molecule inhibitors targeting DEAD-box helicase 5, such as supinoxin (RX-5902);

small molecule inhibitors targeting DGKα, e.g., such as described in WO2021130638;

small molecule inhibitors targeting diablo IAP-binding mitochondrial protein, such as BI-891065;

small molecule inhibitors targeting dihydrofolate reductase, such as pralatrexate or pemetrexed disodium;

small molecule inhibitors targeting DNA dependent protein kinase, such as MSC2490484A (nedisertib), VX-984, AsiDNA (DT-01), LXS-196, or sotrastaurin;

small molecule inhibitors targeting MARCKS, such as BIO-11006;

small molecule inhibitors targeting RIPK1, such as GSK-3145094;

small molecule inhibitors targeting Rho associated coiled-coil containing protein kinase, such as AT13148 or KD025;

small molecule inhibitors targeting DNA topoisomerase, such as irinotecan, firtecan pegol, or amrubicin;

small molecule inhibitors targeting dopamine receptor D2, such as ONC-201;

small molecule inhibitors targeting DOT1 like histone lysine methyltransferase, such as pinometostat (EPZ-5676);

small molecule inhibitors targeting EZH2, such as tazemetostat, CPI-1205, or PF-06821497;

small molecule inhibitors targeting fatty acid synthase, such as TVB-2640 (Sagimet Biosciences);

small molecule inhibitors targeting fibroblast growth factor receptor 2 (FGFR2), such as bemarituzumab (FPA144);

small molecule inhibitors targeting focal adhesion kinase (FAK, PTK2), such as VS-4718, defactinib, or GSK2256098;

small molecule inhibitors targeting folate receptor 1, such as pralatrexate;

small molecule inhibitors targeting FOXM1, such as thiostrepton;

small molecule inhibitors targeting galectin 3, such as belapectin (GR-MD-02);

small molecule antagonists targeting glucocorticoid receptor, such as relacorilant (CORT-125134);

small molecule inhibitors targeting glutaminase include without limitation CB-839 (telaglenastat), or bis-2-(5-phenylacetamido-1,3,4-thiadiazol-2-yl)ethyl sulfide (BPTES);

small molecule inhibitors targeting GNRHR, such as elagolix, relugolix, or degarelix;

small molecule inhibitors targeting EPAS1, such as belzutifan (PT-2977 (Merck & Co.));

small molecule inhibitors targeting isocitrate dehydrogenase (NADP(+)), such as limitation ivosidenib (AG-120), vorasidenib (AG-881) (IDH1 and IDH2), IDH-305, or enasidenib (AG-221);

small molecule inhibitors targeting lysine demethylase IA, such as CC-90011;

small molecule inhibitors targeting MAPK interacting serine/threonine kinase, such as tomivosertib (eFT-508);

small molecule inhibitors targeting notch receptor, such as AL-101 (BMS-906024);

small molecule inhibitors targeting polo like kinase 1 (PLK1), such as volasertib or onvansertib;

small molecule inhibitors targeting poly(ADP-ribose) polymerase (PARP), such as olaparib (MK7339), rucaparib, veliparib, talazoparib, ABT-767, pamiparib (BGB-290), fluazolepali (SHR-3162), niraparib (JNJ-64091742), stenoparib (2X-121 (e-7499)), simmiparib, IMP-4297, SC-10914, IDX-1197, HWH-340, CEP 9722, CEP-8983, E7016, 3-aminobenzamide, or CK-102;

small molecule inhibitors targeting polycomb protein EED, such as MAK683;

small molecule inhibitors targeting porcupine O-acyltransferase, such as WNT-974;

small molecule inhibitors targeting prostaglandin-endoperoxide synthase, such as HP-5000, lornoxicam, ketorolac tromethamine, bromfenac sodium, otenaproxesul (ATB-346), mofezolac, GLY-230, TRK-700, diclofenac, meloxicam, parecoxib, etoricoxib, celecoxib, AXS-06, diclofenac potassium, reformulated celecoxib (DRGT-46), AAT-076, meisuoshuli, lumiracoxib, meloxicam, valdecoxib, zaltoprofen, nimesulide, anitrazafen, apricoxib, cimicoxib, deracoxib, flumizole, firocoxib, mavacoxib, pamicogrel, parecoxib, robenacoxib, rofecoxib, rutecarpine, tilmacoxib, zaltoprofen, or imrecoxib;

small molecule inhibitors targeting protein arginine N methyltransferase, such as MS203, PF-06939999, GSK3368715, or GSK3326595;

small molecule inhibitors targeting PTPN11, such as TNO155 (SHP-099), RMC-4550, JAB-3068, RMC-4630 (SAR442720), or compounds disclosed in WO2018172984 or WO2017211303;

small molecule antagonist targeting retinoic acid receptor, such as tamibarotene (SY-1425);

small molecule inhibitors targeting ribosomal protein S6 kinase B1, such as MSC2363318A;

small molecule inhibitors targeting S100 calcium binding protein A9, such as tasquinimod;

small molecule inhibitors targeting selectin E, such as uproleselan sodium (GMI-1271);

small molecule inhibitors targeting SF3B1, such as H3B-8800;

small molecule inhibitors targeting Sirtuin-3, such as YC8-02;

small molecule inhibitors targeting SMO, such as sonidegib (Odomzo®, formerly LDE-225), vismodegib (GDC-0449), glasdegib (PF-04449913), itraconazole, or patidegib, taladegib;

small molecule antagonists targeting somatostatin receptor, such as OPS-201;

small molecule inhibitors targeting sphingosine kinase 2, such as opaganib (Yeliva®, ABC294640);

small molecule inhibitors targeting STAT3, such as napabucasin (BBI-608);

small molecule inhibitors targeting tankyrase, such as G007-LK or stenoparib (2X-121 (e-7499));

small molecule inhibitors targeting TFGBR1, such as galunisertib, PF-06952229;

small molecule inhibitors targeting thymidylate synthase, such as idetrexed (ONX-0801);

small molecule inhibitors targeting tumor protein p53, such as CMG-097;

small molecule inhibitors targeting valosin-containing protein, such as CB-5083;

small molecule inhibitors targeting WT1, such as ombipepimut-S (DSP-7888);

small molecule agonists targeting adenosine receptor, such as namodenoson (CF102);

small molecule agonist(s) targeting asparaginase, such as crisantaspase (Erwinase®), GRASPA (ERY-001, ERY-ASP), calaspargase pegol, or pegaspargase;

small molecule agonists targeting CCAAT enhancer binding protein alpha, such as MTL-501;

small molecule agonists targeting cytochrome P450 family, such as mitotane;

small molecule agonists targeting DExD/H-box helicase 58, such as RGT-100;

small molecule agonists targeting GNRHR, such as leuprorelin acetate, leuprorelin acetate sustained release depot (ATRIGEL), triptorelin pamoate, or goserelin acetate;

small molecule agonists targeting GRB2, such as prexigebersen (BP1001);

small molecule agonists targeting NFE2L2, such as omaveloxolone (RTA-408);

small molecule agonists targeting NOD2, such as mifamurtide (liposomal);

small molecule agonists targeting RAR-related orphan receptor gamma, such as cintirorgon (LYC-55716);

small molecule agonists targeting retinoic acid receptor (RAR), such as tretinoin;

small molecule agonists targeting STING1, such as ADU-S100 (MIW-815), SB-11285, MK-1454, SR-8291, AdVCA0848, GSK-532, SYN-STING, MSA-1, SR-8291, cyclic-GAMP (cGAMP), or cyclic-di-AMP;

small molecule agonists targeting thyroid hormone receptor beta, such as levothyroxine sodium;

small molecule agonists targeting tumor necrosis factor, such as tasonermin;

antisense agents targeting baculoviral IAP repeat containing 5, such as EZN-3042;

antisense agents targeting GRB2, such as prexigebersen;

antisense agents targeting heat shock protein 27, such as apatorsen;

antisense agents targeting STAT3, such as danvatirsen (IONIS-STAT3-2.5Rx);

gene therapies targeting a C-C motif chemokine receptor, such as SB-728-T;

gene therapies targeting an interleukin, such as EGENE-001, tavokinogene telseplasmid, nogapendekin alfa (ALT-803), NKTR-255, NIZ-985 (hetIL-15), SAR441000, or
MDNA-55;

antibodies targeting claudin 18, such as claudiximab;

antibodies targeting clusterin, such as AB-16B5;

antibodies targeting a complement component, such as ravulizumab (ALXN-1210);

antibodies targeting a C-X-C motif chemokine ligand, such as BMS-986253 (HuMax-Inflam);

- antibodies targeting delta like canonical Notch ligand 4 (DLL4), such as demcizumab, navicixizumab (DLL4/VEGF);
- antibodies targeting EPH receptor A3, such as fibatuzumab (KB-004);
- antibodies targeting epithelial cell adhesion molecule, such as oportuzumab monatox (VB4-845);
- antibodies targeting fibroblast growth factor, such as GAL-F2, B-701 (vofatamab);
- antibodies targeting hepatocyte growth factor, such as MP-0250;
- antibodies targeting an interleukin, such as canakinumab (ACZ885), gevokizumab (VPM087), CJM-112, guselkumab, talacotuzumab (JNJ-56022473), siltuximab, or tocilizumab;
- antibodies targeting LRRC15, such as ABBV-085 or cusatuzumab (ARGX-110);
- antibodies targeting mesothelin, such as BMS-986148, SEL-403, or anti-MSLN-MMAE;
- antibodies targeting myostatin, such as landogrozumab;
- antibodies targeting notch receptor, such as tarextumab;
- antibodies targeting TGFB1 (TGFβ1), such as SAR439459, ABBV-151, NIS793, SRK-181, XOMA089, or compounds disclosed in WO2019103203;
- vaccines targeting fms related receptor tyrosine kinase, such as HLA-A2402/HLA-A0201 restricted epitope peptide vaccine;
- vaccines targeting heat shock protein 27, such as PSV-AML (PhosphoSynVax);
- vaccines targeting PD-L1, such as IO-120+IO-103 (PD-L1/PD-L2 vaccines) or IO-103;
- vaccines targeting tumor protein p53, such as MVA-p53;
- vaccines targeting WT1, such as WT-1 analog peptide vaccine (WT1-CTL);
- cell therapies targeting baculoviral IAP repeat containing 5, such as tumor lysate/MUC1/survivin PepTivator-loaded dendritic cell vaccine;
- cell therapies targeting carbonic anhydrase, such as DC-Ad-GMCAIX;
- cell therapies targeting C-C motif chemokine receptor, such as CCR5-SBC-728-HSPC;
- cell therapies targeting folate hydrolase 1, such as CIK-CAR.PSMA or CART-PSMA-TGFβRDN;
- cell therapies targeting GSTP1, such as CPG3-CAR (GLYCAR);
- cell therapies targeting HLA-A, such as FH-MCVA2TCR or NeoTCR-P1;
- cell therapies targeting an interleukin, such as CST-101;
- cell therapies targeting KRAS, such as anti-KRAS G12D mTCR PBL;
- cell therapies targeting MET, such as anti-cMet RNA CAR T;
- cell therapies targeting MUC16, such as JCAR-020;
- cell therapies targeting PD-1, such as PD-1 knockout T cell therapy (esophageal cancer/NSCLC);
- cell therapies targeting PRAME, such as BPX-701;
- cell therapies targeting transforming protein E7, such as KITE-439;
- cell therapies targeting WT1, such as WT1-CTL, ASP-7517, or JTCR-016.

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more therapeutic agents selected from a PI3K inhibitor, a Trop-2 binding agent, CD47 antagonist, a SIRPα antagonist, a FLT3R agonist, a PD-1 antagonist, a PD-L1 antagonist, an MCL1 inhibitor, a CCR8 binding agent, an HPK1 antagonist, a DGKα inhibitor, a CISH inhibitor, a PARP-7 inhibitor, a Cbl-b inhibitor, a KRAS inhibitor (e.g., a KRAS G12C or G12D inhibitor), a KRAS degrader, a beta-catenin degrader, a helios degrader, a CD73 inhibitor, an adenosine receptor antagonist, a TIGIT antagonist, a TREM1 binding agent, a TREM2 binding agent, a CD137 agonist, a GITR binding agent, an OX40 binding agent, and a CAR-T cell therapy.

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more therapeutic agents selected from a PI3Kδ inhibitor (e.g., idealisib), an anti-Trop-2 antibody drug conjugate (e.g., sacituzumab govitecan, datopotamab deruxtecan (DS-1062)), an anti-CD47 antibody or a CD47-blocking agent (e.g., magrolimab, DSP-107, AO-176, ALX-148, letaplimab (IBI-188), lemzoparlimab, TTI-621, TTI-622), an anti-SIRPα antibody (e.g., GS-0189), a FLT3L-Fc fusion protein (e.g., GS-3583), an anti-PD-1 antibody (pembrolizumab, nivolumab, zimberelimab), a small molecule PD-L1 inhibitor (e.g., GS-4224), an anti-PD-L1 antibody (e.g., atezolizumab, avelumab), a small molecule MCL1 inhibitor (e.g., GS-9716), a small molecule HPK1 inhibitor (e.g., GS-6451), a HPK1 degrader (PROTAC; e.g., ARV-766), a small molecule DGKα inhibitor, a small molecule CD73 inhibitor (e.g., quemliclustat (AB680)), an anti-CD73 antibody (e.g., oleclumab), a dual A2a/A2b adenosine receptor antagonist (e.g., etrumadenant (AB928)), an anti-TIGIT antibody (e.g., tiragolumab, vibostolimab, domvanalimab, AB308), an anti-TREM1 antibody (e.g., PY159), an anti-TREM2 antibody (e.g., PY314), a CD137 agonist (e.g., AGEN-2373), a GITR/OX40 binding agent (e.g., AGEN-1223) and a CAR-T cell therapy (e.g., axicabtagene ciloleucel, brexucabtagene autoleucel, tisagenlecleucel).

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with one or more therapeutic agents selected from idealisib, sacituzumab govitecan, magrolimab, GS-0189, GS-3583, zimberelimab, GS-4224, GS-9716, GS-6451, quemliclustat (AB680), etrumadenant (AB928), domvanalimab, AB308, PY159, PY314, AGEN-1223, AGEN-2373, axicabtagene ciloleucel and brexucabtagene autoleucel.

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with an immunotherapy comprising one or more antibodies, T-cell receptors (TCRs) or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins directed against one or more targets or tumor associated antigens (TAAs) selected from the group consisting of: CD19; membrane spanning 4-domains A1 (MS4A1; CD20); CD22 (SIGLEC2); CD27 (TNFRSF7); TNFRSF8 (CD30); CD33 (SIGLEC3); CD37; CD38; CD40 (TNFRSF5), CD44; CD47; CD48 (SLAMF2); CD52; CD70 (TNFSF7; CD27L); 5'-nucleotidase ecto (NT5E; CD73), ectonucleoside triphosphate diphosphohydrolase 1 (CD39), CD74; CD79B; CD80; CD86; interleukin 3 receptor subunit alpha (IL3RA), prominin 1 (PROM1; CD133); TNFRSF9 (CD137); syndecan 1

(SDC1; CD138); CD200 molecule (CD200); alpha fetoprotein (AFP), BAG cochaperone 6 (BAG6); MET proto-oncogene, receptor tyrosine kinase (MET); KIT proto-oncogene, receptor tyrosine kinase (Kin; C-type lectin domain family 12 member A (CLEC12A; CD371); C-type lectin domain containing 9A (CLEC9A; CD370); cadherin 3 (CDH3); carbonic anhydrase 6 (CA6); carbonic anhydrase 9 (CA9); carcinoembryonic antigen related cell adhesion molecule 3 (CEACAM3); carcinoembryonic antigen related cell adhesion molecule 5 (CEACAM5); carcinoembryonic antigen related cell adhesion molecule 6 (CEACAM6); chorionic somatomammotropin hormone 1 (CSH1); coagulation factor III, tissue factor (F3); collectin subfamily member 10 (COLEC10; CLL1); delta like canonical Notch ligand 3 (DLL3); ectonucleotide pyrophosphatase/phosphodiesterase 3 (ENPP3); ephrin A1 (EFNA1); epidermal growth factor receptor (EGFR; ERBB; HER1); EGFR variant III (EGFRvIII); EPH receptor A2 (EPHA2); epithelial cell adhesion molecule (EPCAM); erb-b2 receptor tyrosine kinase 2 (ERBB2; HER-2/neu); fibroblast activation protein alpha (FAP); fibroblast growth factor receptor 2 (FGFR2); fibroblast growth factor receptor 3 (FGFR3); folate hydrolase 1 (FOLH1); folate receptor 1 (FOLR1); GD2 ganglioside; glycoprotein NMB (GPNMB; osteoactivin); guanylate cyclase 2C (GUCY2C); human papillomavirus (HPV) E6; HPV E7; major histocompatibility complex (MHC) class I-presented neoantigens, major histocompatibility complex (MHC) class II-presented neoantigens, major histocompatibility complex, class I, E (HLA-E); major histocompatibility complex, class I, F (HLA-F); major histocompatibility complex, class I, G (HLA-G); MHC class I polypeptide-related sequence A (MICA); MHC class I polypeptide-related sequence B (MICB); integrin subunit beta 7 (ITGB7); leukocyte immunoglobulin like receptor B1 (LILRB1; ILT2); leukocyte immunoglobulin like receptor B2 (LILRB2; ILT4); LY6/PLAUR domain containing 3 (LYPD3); glypican 3 (GPC3); KRAS proto-oncogene, GTPase (KRAS); MAGE family member A1 (MAGEA1); MAGE family member A3 (MAGEA3); MAGE family member A4 (MAGEA4); MAGE family member A11 (MAGEA11); MAGE family member C1 (MAGEC1); MAGE family member C2 (MAGEC2); MAGE family member C3 (MAGEC3); MAGE family member D1 (MAGED1); MAGE family member D2 (MAGED2); mesothelin (MSLN); mucin 1 (MUC1) and splice variants thereof (e.g., including MUC1/A, C, D, X, Y, Z and REP); mucin 16 (MUC16; CA125); natural killer cell cytotoxicity receptor 3 ligand 1 (NCR3LG1; B7-H6); necdin, MAGE family member (NDN); nectin cell adhesion molecule 2 (NECTIN2); nectin cell adhesion molecule 4 (NECTIN4); SLIT and NTRK like family member 6 (SLITRK6); promyelocytic leukemia (PML); protein tyrosine kinase 7 (inactive) (PTK7); Poliovirus receptor (PVR) cell adhesion molecule (PVR); SLAM family member 6 (SLAMF6); SLAM family member 7 (SLAMF7); sialic acid binding Ig like lectin 7 (SIGLEC7); sialic acid binding Ig like lectin 9 (SIGLEC9); sialic acid binding Ig like lectin 10 (SIGLEC10); signal regulatory protein alpha (SIRPA) solute carrier family 34 (sodium phosphate), member 2 (SLC34A2); solute carrier family 39 member 6 (SLC39A6); STEAP family member 1 (STEAP1); suppression of tumorigenicity 2 (ST2); TNF receptor superfamily member 4 (TNFRSF4; OX40); TNF superfamily member 9 (TNFSF9; 4-1BB-L, CD137L); TNFRSF10A (DR4, TRAILR1); TNFRSF10B (DR5, TRAILR2); TNFRSF13B (BAFF); TNFRSF17 (BCMA); TNFRSF18 (GITR); transferrin (TF); transforming growth factor beta 1 (TGFB1) and isoforms thereof; triggering receptor expressed on myeloid cells 1 (TREM1); triggering receptor expressed on myeloid cells 2 (TREM2); trophoblast glycoprotein (TPBG); trophinin (TRO); tumor associated calcium signal transducer 2 (TACSTD2); Fucosyl GM1; sialyl Lewis adhesion molecule (sLe); and Lewis Y antigen.

In some embodiments, the IL-2v, the Fc-IL-2v fusion protein, the homodimer, the heterodimer, the conjugate, the polynucleotide, the vector, the lipoplex (e.g., LNP) and/or the pharmaceutical composition is co-administered with an immunotherapy comprising one or more antibodies, T-cell receptors (TCRs) or antigen-binding antibody fragments thereof, or antibody-drug conjugates thereof, CD3-targeting multi-specific molecules, NK cell-activating receptor-targeting multi-specific molecules, or non-immunoglobulin antigen-binding domains or antibody mimetic proteins that bind to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen IA (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member CI (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PI-WIL-2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPSIL1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., *Trends Cancer* 2018 October; 4(10):701-712 and the CT database website at cta.lncc.br/index.php. Illustrative TCRs and TCR-like antibodies that bind to an epitope of NY-ESO-1 presented in an MHC include GSK01 (NY-ESO-1) and those described, e.g., in Stewart-Jones, et al., *Proc Natl Acad Sci USA.* 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC include IMC-F106C (PRAME) and those described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Illustrative Mechanisms of Action

In various embodiments, the one or more additional therapeutic agents may be categorized by their mechanism of action into, for example, the following groups:

- anti-metabolites/anti-cancer agents, such as pyrimidine analogs floxuridine, capecitabine, cytarabine, CPX-351 (liposomal cytarabine, daunorubicin), and TAS-118;
- purine analogs, folate antagonists (such as pralatrexate), cladribine, pentostatin, fludarabine and related inhibitors;
- antiproliferative/antimitotic agents including natural products, such as vinca alkaloids (vinblastine, vincristine) and microtubule disruptors such as taxane (paclitaxel, docetaxel), vinblastin, nocodazole, epothilones, vinorelbine (NAVELBINE®), PM-184, BAL-101553 (lisavanbulin), OXI-4503, fluorapacin (AC-0001), plinabulin and vinflunine;
- anti-neoplastic or chemotherapeutic agents such as a nucleoside analog (e.g., 5-fluorouracil, gemcitabine, fluorocyclopentenylcytosine (RX-3117), cytarabine, cladribine, pentostatin, fludarabine, DFP-10917), a taxane (e.g., paclitaxel, nab-paclitaxel, docetaxel, cabazitaxel), a platinum coordination complex (cisplatin, carboplatin, oxaliplatin, nedaplatin, triplatin tetranitrate, phenanthriplatin, picoplatin, satraplatin, dicycloplatin, eptaplatin, lobaplatin, miriplatin), a dihydrofolate reductase (DHFR) inhibitor (e.g., methotrexate, trimetrexate, pemetrexed), a topoisomerase inhibitor (e.g., doxorubicin, daunorubicin, dactinomycin, DaunoXome, Caelyx, eniposide, epirubicin, etoposide, idarubicin, irinotecan, mitoxantrone, pixantrone, sobuzoxane, topotecan, irinotecan, MM-398 (liposomal irinotecan), vosaroxin and GPX-150, aldoxorubicin, AR-67, mavelertinib, AST-2818, avitinib (ACEA-0010), irofulven (MGI-114)), an alkylating agent (e.g., TEMODAR® (temozolomide; CCRG-81045), a nitrogen mustard (e.g., cyclophosphamide, chlormethine, uramustine or uracil mustard, melphalan, chlorambucil, ifosfamide, bendamustine, temozolomide, carmustine), a nitrosourea (e.g., carmustine, lomustine, streptozocin), an alkyl sulfonate (e.g., busulfan)), DNA repair inhibitor (e.g., KRX-0402), and mixtures thereof;
- DNA methyltransferase (e.g., DNMT1 (NCBI Gene ID: 1786); DNMT3A (NCBI Gene ID: 1788)) inhibitors, such RRx-001 (dinitroazetidine derivative);
- DNA topoisomerase II (e.g., TOP2A (NCBI Gene ID: 7153); TOP2B (NCBI Gene ID: 7155)) inhibitors, such as pixantrone (PIXUVRI®), sobuzoxane (MST-16) and epipodophyllotoxins (etoposide, teniposide);
- DNA topoisimerase I (TOP1; NCBI Gene ID: 7150) inhibitors, such as amrubicin (SM-5887), irinotecan hydrochloride, Onivyde;
- DNA topoisomerase I (TOP1)/hypoxia inducible factor 1 subunit alpha (HIF1A; NCBI Gene ID: 3091) dual inhibitors, such as PEG-SN38 (firtecan pegol);
- hypoxia inducible factor 1 subunit alpha (HIF1A) inhibitors, such as PT-2977, PT-2385;

DNA damaging agents, such as actinomycin, amsacrine, busulfan, carboplatin, chlorambucil, cisplatin, cyclophosphamide (CYTOXAN®), dactinomycin, daunorubicin, doxorubicin, DEBDOX, epirubicin, iphosphamide, melphalan, merchlorethamine, mitomycin C, mitoxantrone, nitrosourea, procarbazine, taxol, Taxotere, teniposide, etoposide, and triethylenethiophosphoramide;

DNA hypomethylating agents, such as guadecitabine (SGI-110), decitabine, azacytidine (CC-486), ASTX727;

DNAi oligonucleotides targeting Bcl-2, such as PNT2258; agents that activate or reactivate latent human immunodeficiency virus (HIV), such as panobinostat and romidepsin;

DNA polymerase inhibitors, such as sapacitabine;

DNA polymerase/Ribonucleotide reductase inhibitors, such as clofarabine;

DNA interference oligonucleotides, such as PNT2258, AZD-9150;

phosphorylated RNA polymerase II degraders, such has ZEPZELCA™ (lurbinectedin; PM-1183);

rRNA synthesis inhibitor (inhibits RNA polymerase I-driven transcription of rRNA), such as CX-5461;

elongation factor 1 alpha 2 (EEF1A2; NCBI Gene ID: 1915) inhibitors, such as plitidepsin (APLIDIN®);

antiproliferative/antimitotic alkylating agents, such as nitrogen mustard cyclophosphamide and analogs (e.g., melphalan, chlorambucil, hexamethylmelamine, thiotepa), alkyl nitrosoureas (e.g., carmustine) and analogs, streptozocin, and triazenes (e.g., dacarbazine);

antiproliferative/antimitotic antimetabolites, such as folic acid analogs (methotrexate);

cell cycle/Microtubule inhibitors, such as eribulin mesylate;

platinum coordination complexes (e.g., cisplatin, oxiloplatinim, and carboplatin), procarbazine, hydroxyurea, mitotane, and aminoglutethimide;

antibiotics such as dactinomycin, daunorubicin, doxorubicin, idarubicin, anthracyclines, mitoxantrone, bleomycins, plicamycin (mithramycin);

hormones, hormone analogs (e.g., estrogen, tamoxifen, goserelin, bicalutamide, and nilutamide), and aromatase inhibitors (e.g., letrozole and anastrozole);

estrogen receptor 1 (ESR1, a.k.a., ER; NCBI Gene ID: 2099) modulators, such as bazedoxifene (e.g., stimulates estrogen receptors in bone and has antagonistic effects in the breast and uterus);

selective estrogen receptor degrader (SERD), such as fulvestrant (Faslodex®), RG6046, RG6047, RG6171, elacestrant (RAD-1901), SAR439859 and AZD9496, AZD9833;

selective estrogen receptor covalent antagonists (SERCAs), such as H3B-6545;

selective androgen receptor modulator (SARM), such as GTX-024, darolutamide;

Estrogen receptor agonists/Progesterone receptor antagonists, such as TRI-CYCLEN LO (norethindrone+ethinyl estradiol);

Progesterone receptor (PGR; NCBI Gene ID: 5241) agonists, such as levonorgestrel;

antiplatelet agents; anticoagulants such as heparin, synthetic heparin salts, and other inhibitors of thrombin;

fibrinolytic agents such as tissue plasminogen activator, streptokinase, urokinase, aspirin, dipyridamole, ticlopidine, and clopidogrel;

antimigratory agents; antisecretory agents (e.g., breveldin);

immunosuppressives, such as tacrolimus, sirolimus, azathioprine, and mycophenolate;

growth factor inhibitors, and vascular endothelial growth factor inhibitors;

alpha adrenoceptor (e.g., adrenoceptor alpha IA (ADRA1A; NCBI Gene ID: 148; adrenoceptor alpha 1B (ADRA1B; NCBI Gene ID: 147; adrenoceptor alpha 1D (ADRA1D; NCBI Gene ID: 146; adrenoceptor alpha 2A (ADRA2A; NCBI Gene ID: 150; adrenoceptor alpha 2B; ADRA2B; NCBI Gene ID: 151; adrenoceptor alpha 2C (ADRA2C; NCBI Gene ID: 152) antagonists, such as phenoxybenzamine hydrochloride (injectable, pheochromocytoma);

androgen receptor (AR; NCBI Gene ID: 367) antagonists, such as nilutamide;

anti-cadherin 6 (CDH6; NCBI Gene ID: 1004) antibodies, such as HKT-288;

anti-leucine-rich repeat containing 15 (LRRC15; NCBI Gene ID: 131578) antibodies, such as ABBV-085. ARGX-110;

angiotensin receptor blockers, nitric oxide donors;

antisense oligonucleotides, such as AEG35156, IONIS-KRAS-2.5Rx, EZN-3042, RX-0201, IONIS-AR-2.5Rx, BP-100 (prexigebersen), IONIS-STAT3-2.5Rx;

anti-angiopoietin 2 (ANGPT2; NCBI Gene ID: 285) antibodies, such as MEDI3617, and LY3127804;

anti-angiopoietin 1 (ANGPT1; NCBI Gene ID: 284)/ANGPT2 antibodies, such as AMG-780;

anti-colony stimulating factor 1 receptor (CSF1R; NCBI Gene ID: 1436) antibodies, such as emactuzumab, LY3022855, AMG-820, FPA-008 (cabiralizumab);

anti-endoglin (ENG; NCBI Gene ID: 2022) antibodies, such as TRC105 (carotuximab);

an anti-major histocompatibility complex, class II, DR (e.g., HLA-DRA (NCBI Gene ID: 3122); HLA-DRB1 (NCBI Gene ID: 3123; HLA-DRB3 (NCBI Gene ID: 3125) antibody, such as IMMU-114;

an anti-major histocompatibility complex, class I, G (HLA-G; NCBI Gene ID: 3135) antibody, such as TTX-080;

an anti-leukocyte immunoglobulin like receptor B2 (LILRB2, a.k.a., CD85D, ILT4; NCBI Gene ID: 10288) antibody, such as JTX-8064, MK-4830, IO-108;

an anti-leukocyte immunoglobulin like receptor B1 (LILRB1, a.k.a., CD85J, ILT-2, ILT2, LIR-1, LIR1, MIR-7, MIR7, PIR-B, PIRB (NCBI Gene ID: 10859) antibody, such as BND-22, 12D12, 30A10, 11D9.A4, c138 dimer, NGM-707, IMC138, HuB1-176-N297A;

HLA antigen modulator, such as FIT-001, NeoTCR-P1;

EPH receptor A2 (EPHA2; NCBI Gene ID: 1969) inhibitors, such as MM-310;

anti-EPH receptor A3 (NCBI Gene ID: 2042) antibodies, such as fibatuzumab (KB-004);

anti-CD37 (NCBI Gene ID: 951) antibodies, such as otlertuzumab (TRU-016);

fibroblast growth factor receptor (e.g., FGFR1 (NCBI Gene ID: 2260), FGFR2 (NCBI Gene ID: 2263), FGFR3 (NCBI Gene ID: 2261)) inhibitors, such as LY3076226, B-701, AZD4547, GAL-F2, hFR2-14, FGF-401, INCB-054828, BAY-1163877, JNJ-42756493, LY2874455, Debio-1347;

anti-complement C5 (C5; NCBI Gene ID: 727) antibodies, such as ULTOMIRIS® (ravulizumab; ALXN-1210); eculizumab;

anti-epithelial cell adhesion molecule (EPCAM; NCBI Gene ID: 4072) antibodies, such as edrecolomab, catumaxomab, adecatumumab, VB4-845, 17-1A and IGN101;

anti-CEA cell adhesion molecule (e.g., CEACAM3; (NCBI Gene ID: 1084); CEACAM5 (NCBI Gene ID: 1048); CEACAM6; a.k.a., CD66c; NCBI Gene ID: 4680)) antibodies, such as labetuzumab, cergutuzumab amunaleukin (RG7813);

anti-CEACAM6 antibodies, such as BAY-1834942, NEO-201 (CEACAM 5/6);

anti-disialoganglioside GD2 antibodies, such as APN-301; ch14.18/CHO (dinutuximab beta);

anti-carbonic anhydrase 9 (CA9, CAIX; NCBI Gene ID: 768) antibodies, such as TX-250, cG250;

anti-mucin 1, cell surface associated (MUC1; NCBI Gene ID: 4582) antibodies, such as gatipotuzumab, Mab-AR-20.5;

MUC1 inhibitors, such as pentumomab, oregovomab, cantuzumab and GO-203-2C;

anti-CD33 (NCBI Gene ID: 945; a.k.a., SIGLEC3) antibodies, such as gemtuzumab ozogamicin (Mylotarg), IMGN-779;

Anti-C-type lectin domain family 12 member A (CLEC12A, a.k.a., CD371, CLL-1, CLL1; NCBI Gene ID: 160364) antibodies, (see, e.g., WO 2017/173384);

anti-immunoglobulin kappa (IGK; NCBI Gene ID: 50802) antibodies, such as MDX-1097 (IST-1097 or KappaMab);

anti-CD55 molecule (Cromer blood group) (CD55; NCBI Gene ID: 1604) antibodies, such as PAT-SC1;

anti-folate hydrolase 1 (FOLH1; a.k.a., PSMA; NCBI Gene ID: 2346 antibodies, such as ATL-101, ADC and J591;

anti-semaphorin 4D (SEMA4D; a.k.a., CD100; NCBI Gene ID: 10507) antibodies, such as VX-15;

anti-fucosyl-GM1 antibodies, such as BMS-986012;

anti-myostatin (MSTN, a.k.a., GDF8; NCBI Gene ID: 2660) antibodies, such as landogrozumab (LY2495655);

anti-delta like canonical Notch ligand 3 (DLL3; NCBI Gene ID: 10683) antibodies, such as rovalpituzumab tesirine (Rova-T);

anti-delta like canonical Notch ligand 4 (DLL4; NCBI Gene ID: 54567) antibodies, such as demcizumab;

anti-clusterin (CLU; NCBI Gene ID: 1191) antibodies, such as AB-16B5;

anti-ephrin A4 (EFNA4; NCBI Gene ID: 1945) antibodies, such as PF-06647263;

anti-mesothelin (MSLN; NCBI Gene ID: 10232) antibodies, such as BMS-986148, Anti-MSLN-MMAE, SEL-403;

anti-solute carrier family 34 member 2 (SLC34A2; a.k.a., NaPi2b, PULAM; NPTIIb; NAPI-3B; NAPI-IIb; NCBI Gene ID: 10568) antibodies, such as lifastuzumab vedotin (RG7599);

H+K+ ATPase inhibitors, such as omeprazole, esomeprazole;

anti-transforming growth factor beta 1 (TGFB1, a.k.a., TGF-beta1, TGFB, TGFbeta; NCBI Gene ID: 7040) antibodies, such as SAR439459, XOMA 089, NIS793;

anti-leucine rich repeat containing 32 (LRRC32, a.k.a., GARP; NCBI Gene ID: 2615)/anti-TGFB1 antibodies, such as ABBV-151;

anti-transforming growth factor beta receptor 2 (TGFBR2; NCBI Gene ID: 7048) antibodies, such as LY3022859;

ROS proto-oncogene 1, receptor tyrosine kinase (ROS1; NCBI Gene ID: 6098) and ALK receptor tyrosine kinase (ALK; NCBI Gene ID: 238) inhibitors, such as lorlatinib;

pan-neurotrophic receptor tyrosine kinase 1 (NTRK1; a.k.a., TRK, TRKA; NCBI Gene ID: 4914), ROS proto-oncogene 1, receptor tyrosine kinase (ROS1; NCBI Gene ID: 6098) and ALK receptor tyrosine kinase (ALK; NCBI Gene ID: 238) inhibitors, such as ROZLYTREK® (entrectinib), Repotrectinib (TPX-0005);

a neurotrophic receptor tyrosine kinase (e.g., NTRK1 (NCBI Gene ID: 4914); NTRK2 (a.k.a., TRKB; NCBI Gene ID: 4915); NTRK3 (a.k.a., TRKC; NCBI Gene ID: 4916)) inhibitor, such as selitrectinib (BAY 2731954, LOXO-195), ONO-7579, larotrectinib sulfate (VITRAKVI®);

anaplastic lymphoma kinase (ALK) inhibitors, such as alectinib, ceritinib, alecensa (RG7853), ALUNBRIG® (brigatinib);

an AMP activated protein kinase (AMPK) (e.g., PRKAA1; NCBI Gene ID: 5562; PRKAA2; NCBI Gene ID: 5563) stimulator, such as metformin hydrochloride;

anti-CD38 (CD38, a.k.a., ADP ribosyl cyclase 1 (ADPRC1); NCBI Gene ID: 952) antibodies, such as daratumumab (DARZALEX®), isatuximab, MOR-202, TAK-079;

anti-CD38-attenukine, such as TAK573;

nucleotide binding oligomerization domain containing 2 (NOD2, a.k.a., caspase recruitment domain protein-15 (CARD15); NCBI Gene ID: 64127) stimulators, such as mifamurtide (liposomal), inarigivir soproxil (SB-9200), IR-103 cell division cycle 7 (CDC7; NCBI Gene ID: 8317) protein kinase inhibitors, such as TAK-931;

cytochrome P450 family 11 subfamily A member 1 (CYP11A1; NCBI Gene ID: 1583) inhibitors, such as ODM-208 and ODM-209;

dihydropyrimidine dehydrogenase (DPYD; NCBI Gene ID: 1806)/uridine monophosphate synthetase (UMPS; a.k.a., orotate phosphoribosyltransferase (OPRT); NCBI Gene ID: 7372) dual inhibitors, such as Cefesone (tegafur+gimeracil+oteracil potassium);

colony stimulating factor 3 (CSF3, a.k.a., GSCF; NCBI Gene ID: 1440), such as NEULASTA® (pegfilgrastim), PF-06881894;

gonadotropin releasing hormone receptor (GNRHR; NCBI Gene ID: 2798) agonists, such as leuprorelin acetate, leuprorelin acetate sustained release depot (ATRIGEL), triptorelin pamoate, goserelin acetate;

GNRHR antagonists, such as elagolix, relugolix, degarelix;

intercellular adhesion molecule 1 (ICAM1; NCBI Gene ID: 3383)/CD55 molecule (Cromer blood group) (CD55; NCBI Gene ID: 1604) dual inhibitors, such as CAVATAK® (V937);

lysine demethylase 1A (KDM1A, a.k.a., LSD1; NCBI Gene ID: 23028) inhibitors, such as CC-90011, ORY-1001, IMG-7289, INCB-59872, GSK-2879552;

lysine methyltransferase 2A (KMT2A, a.k.a., MLL; NCBI Gene ID: 4297) inhibitors such as KO-539;

cereblon (CRBN; NCBI Gene ID: 51185) E3 ubiquitin ligase modulating agent (CELMoD), such as CC-92480, CC-90009;

CRBN modulator/IKAROS family zinc finger 1 (IKZF1; NCBI Gene ID: 10320) inhibitor/IKAROS family zinc finger 3 (IKZF3, a.k.a., AIOLOS; NCBI Gene ID: 22806) inhibitor, such as iberdomide (CC-220);

a retinoid X receptor (e.g., RXRA (NCBI Gene ID: 6256); RXRB (NCBI Gene ID: 6257); RXRG (NCBI Gene ID: 6258)) activator or agonist, such as alitretinoin, bexarotene (oral formulation), IRX4204;

retinoic acid receptor (e.g., retinoic acid receptor alpha (RARA; NCBI Gene ID: 5914); retinoic acid receptor beta (RARB NCBI Gene ID: 5915); retinoic acid receptor gamma (RARG; NCBI Gene ID: 5916) agonists, such as tretinoin;

retinoic acid receptor alpha (RARA) inhibitors, such as SY-1425;

RAR related orphan receptor C (RORC, a.k.a., RORG, RZR-GAMMA, RZRG; NCBI Gene ID: 6097) agonists, such as cintirorgon (LYC-55716);

receptor interacting serine/threonine kinase 1 (RIPK1; NCBI Gene ID: 8737) inhibitors, such as GSK-3145095;

SUMOylation enzymatic cascade inhibitors, such as TAK-981. TAK-981 targets and covalently binds to a small ubiquitin-like modifier (e.g., SUMO1 (NCBI Gene ID: 7341); SUMO2 (NCBI Gene ID: 6613); SUMO3 (NCBI Gene ID: 6612); SUMO4 (NCBI Gene ID: 387082)) protein, forming an adduct with a SUMO protein (TAK-981-SUMO adduct). This prevents the transfer of SUMO from the SUMO-activating enzyme (SAE) to SUMO-conjugating enzyme UBC9. This prevents SUMO conjugation to lysine residues on target proteins and abrogates many SUMOylated protein-mediated cellular processes;

MPL proto-oncogene, thrombopoietin receptor (MPL, a.k.a., TPOR; NCBI Gene ID: 4352) agonists, such as PROMACTA® (eltrombopag);

a thyroid hormone receptor (e.g., thyroid hormone receptor alpha (THRA; NCBE Gene ID: 7067); thyroid hormone receptor beta (THRB; NCBI Gene ID: 7068) agonist, such as levothyroxine sodium (SYNTHROID®);

signal regulatory protein alpha (SIRPA; NCBI Gene ID: 140885) inhibitors, such as AL-008, RRx-001, CTX-5861, FSI-189 (GS-0189), ES-004, BI765063, ADU1805, CC-95251 and SIRPα-targeting agents described in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752;

embryonic ectoderm development (EED; NCBI Gene ID: 8726) inhibitors, such as MAK683;

dihydrofolate reductase DHFR (NCBI Gene ID: 1719) inhibitor/folate analog metabolic inhibitor, such as pralatrexate;

folate antagonists, such as arfolitixorin;

DHFR/phosphoribosylglycinamide formyltransferase, phosphoribosylglycinamide synthetase, phosphoribosylaminoimidazole synthetase (GART; NCBI Gene ID: 2618)/thymidylate synthase (TYMS; NCBI Gene ID: 7298) inhibitors, such as pemetrexed disodium;

TYMS inhibitors, such as ONX-0801;

HSV thymidine kinase gene therapy, such as aglatimagene besadenovec, a.k.a., AdV-tk;

a p38 MAP kinase (e.g., MAPK1 (NCBI Gene ID: 5594); MAPK14 (NCBI Gene ID: 1432); MAPK11 (NCBI Gene ID: 5600); MAPK12 (NCBI Gene ID: 6300) MAPK13 (NCBI Gene ID: 5603)) inhibitor, such as ralimetinib (LY2228820);

a protein arginine methyltransferase (PRMT) (e.g., PRMT1 (NCBI Gene ID: 3276); PRMT3 (NCBI Gene ID: 10196); PRMT5 (NCBI Gene ID: 10419); PRMT6 (NCBI Gene ID: 55170)) inhibitor, such as MS203, PF-06939999, GSK3368715, GSK3326595;

methionyl aminopeptidase 2 (METAP2; NCBI Gene ID: 10988) inhibitors, such as M8891, APL-1202;

protein arginine methyltransferase 5 (PRMT5; NCBI Gene ID: 10419) inhibitors, such as GSK-3326595;

PEGylated arginine deiminase (e.g., PADI1 (NCBI Gene ID: 29943); PADI2 (NCBI Gene ID: 11240); PADI3 (NCBI Gene ID 51702); PADI4 (NCBI Gene ID: 23569); PADI6 (NCBI Gene ID: 353238)), such as pegargiminase (ADI-PEG-20);

asparaginase (ASPG; NCBI Gene ID: 374569) stimulators, including recombinant L-asparaginase, crisantaspase (Erwinase®), GRASPA (ERY-001, ERY-ASP), calaspargase pegol, pegaspargase;

glutaminase (GLS; NCBI Gene ID: 2744) inhibitors, such as CB-839 (telaglenastat), bis-2-(5-phenylacetamido-1,3,4-thiadiazol-2-yl)ethyl sulfide (BPTES);

Sphingosine kinase 2 (SPHK2; NCBI Gene ID: 56848) inhibitors, such as opaganib;

nuclear factor, erythroid 2 like 2 (NFE2L2; NCBI Gene ID: 4780) stimulators, such as omaveloxolone (RTA-408);

myristoylated alanine rich protein kinase C substrate (MARCKS; NCBI Gene ID: 4082) protein inhibitors, such as BIO-11006;

galectin-3 (LGALS3; NCBI Gene ID: 3958) inhibitors, such as GR-MD-02;

phosphorylated DEAD-box helicase 5 (DDX5, a.k.a., p68; NCBI Gene ID: 1655) inhibitors, such as RX-5902 (supinoxin);

Fas cell surface death receptor (FAS, a.k.a., CD95; NCBI Gene ID: 355) inhibitors, such as APG-101, APO-010, asunercept;

vascular endothelial growth factor A (VEGFA; NCBI Gene ID: 7422)/hepatocyte growth factor (HGF; NCBI Gene ID: 3082) antagonists, such as MP-0250;

antibodies that disrupt binding of VEGFA to its cognate receptors fms related receptor tyrosine kinase 1 (FLT1, a.k.a., VEGFR1; NCBI Gene ID: 2321) and/or kinase insert domain receptor (KDR, a.k.a., VEGFR2; NCBI Gene ID: 3791), such as bevacizumab and biosimilars thereof (targeting VEGFA), ramucirumab (CYRAMZA™) (targeting VEGFR2), IM-2C6 and CDP791;

VEGFR1/VEGFR2/fms related receptor tyrosine kinase 4 (FLT4, a.k.a., VEGFR3; NCBI Gene ID: 2324) antagonists; such as fruquintinib;

HLA-A2402/HLA-A0201 restricted VEGFR1/VEGFR2 epitope peptides (see, e.g., Rahat, *Front Immunol.* (2019) 10:1924; Yoshimura, et al., *Br J Cancer.* (2013) 108(6):1260-1266);

soluble decoy receptor that binds VEGFA, vascular endothelial growth factor B (VEGFB; NCBI Gene ID: 7423) and placental growth factor (PGF, a.k.a., PIGF; NCBI Gene ID: 5228), such as aflibercept;

VEGFR (e.g., VEGFR1, VEGFR2, VEGFR3)/platelet derived growth factor receptor (PDGFR) (e.g., PDGFRA (NCBI Gene ID: 5156); PDGFRB (NCBI Gene ID: 5159) inhibitors, such as vorolanib;

anti-epidermal growth factor receptor (EGFR; a.k.a., ERBB, ERBB1, HER1; NCBI Gene ID: 1956) antibodies, such as CDX-3379, HLX-02, seribantumab, cetuximab, panitumumab, nimotuzumab and 806;

erb-b2 receptor tyrosine kinase 2 (ERBB2; a.k.a., HER2; HER-2/neu; NCBI Gene ID: 2064) inhibitors, such as neratinib, tucatinib (ONT-380) and targeting antibodies, such as HERCEPTIN® (trastuzumab), trastuzumab biosimilar, margetuximab, MEDI4276, BAT-8001, Pertuzumab (Perjeta), RG6264, ZW25 (a bispecific HER2-directed antibody targeting the extracellular domains 2 and 4; Cancer Discov. 2019 January; 9(1):8; PMID: 30504239);

EGFR/ERBB2 inhibitors, such as TAK-788, varlitinib, DZD9008, osimertinib (AZD-9291), cetuximab;

EGFR/ERBB2/kinase insert domain receptor (KDR, a.k.a., VEGFR; NCBI Gene ID: 3791)/EPH receptor B4 (EPHB4; NCBI Gene ID: 2050) inhibitors, such as tesevatinib;

Mutant selective EGFR inhibitors, such as PF-06747775, EGF816 (nazartinib), ASP8273, ACEA-0010, BI-1482694;

ERBB2 inhibitor/hyaluronan (HA) (a non-sulfated glycosaminoglycan) degrader, such as Herceptin HYLECTA™ (trastuzumab- and hyaluronidase-oysk);

hyaluronan (HA) degraders, such as PEGPH-20 (PEGylated recombinant PH20 hyaluronidase);

CD44 molecule (NCBI Gene ID: 960; a receptor for HA) binders, such as A6 (a capped eight 1-amino acid peptide (Ac-KPSSPPEE-$NH_2$; SEQ ID NO: 247) derived from amino acid residues 136-143 of the connecting peptide domain of human urokinase plasminogen activator (uPA));

anti-erb-b2 receptor tyrosine kinase 3 (ERBB3, a.k.a., HER3; NCBI Gene ID: 2065) antibodies, such as LJM716, GSK2849330;

VEGFR (e.g., VEGFR1, VEGFR2, VEGFR3)/EGFR/ret proto-oncogene (RET; NCBI Gene ID: 5979) inhibitors, such as CAPRELSA® (vandetanib);

kinase insert domain receptor (KDR, a.k.a., VEGFR2, CD309; NCBI Gene ID: 3791) and/or fms related receptor tyrosine kinase 4 (FLT4; aka, VEGFR3; NCBI Gene ID: 2324) inhibitors, such as anlotinib hydrochloride (AL3818);

platelet derived growth factor receptor alpha (PDGFRA)/KIT proto-oncogene, receptor tyrosine kinase (KIT; NCBI Gene ID: 3815) mutant-specific dual antagonists/inhibitors such as BLU-285, DCC-2618;

anti-MET proto-oncogene, receptor tyrosine kinase (MET; a.k.a., c-Met, hepatocyte growth factor receptor (HGFR); NCBI Gene ID: 4233) antibodies, such as ABBV-399, AMG 102, METMAB and SCH900105;

MET small molecule inhibitors, such as AMG-337, savolitinib, tivantinib (ARQ-197), capmatinib, and tepotinib, ABT-700, AG213, AMG-208, JNJ-38877618 (OMO-1), merestinib, HQP-8361;

MET/VEGFR inhibitors, such as BMS-817378, TAS-115;

MET/macrophage stimulating 1 receptor (MST1R, a.k.a., RON, CD136; NCBI Gene ID: 4486) inhibitors, such as BMS-777607;

AXL receptor tyrosine kinase (AXL; NCBI Gene ID: 558) inhibitors, such as BGB-324 (bemcentinib), SLC-0211;

AXL/fms related receptor tyrosine kinase 3 (FLT3; NCBI Gene ID: 2322) dual inhibitors, such as gilteritinib;

KIT proto-oncogene, receptor tyrosine kinase (KIT, a.k.a., CD117; NCBI Gene ID: 3815) inhibitors, such as PLX-9486, imatinib mesylate, JSP-191, BLU-263, CD117-ADC, AZD3229 (KIT/PDGFR inhibitor), telatinib (KIT/PDGF/VEGF2 inhibitor), quizartinib dihydrochloride (VANFLYTA®) (FLT3/KIT), pexidartinib hydrochloride (PLX3397) (CSF1R/FLT3/KIT), avapritinib (PDGFR/KIT inhibitor), vorolanib (multikinase VEGF/PDGFR/KIT inhibitor), and ripretinib (KIT/PDGFRα inhibitor). Examples of c-kit multi-kinase inhibitors, such as dasatinib, imatinib, nilotinib, sorafenib, lenvatinib mesylate, cabozantinib malate, AL-8326, ZLJ-33, KBP-7018, sunitinib malate, pazopanib derivatives, AGX-73, rebastinib, NMS-088, lucitanib hydrochloride, midostaurin, cediranib, dovitinib, sitravatinib, tivozanib, masitinib, regorafenib, HQP-1351, cabozantinib, ponatinib, and famitinib L-malate;

class III receptor tyrosine kinase inhibitors, e.g., FMS-related tyrosine kinase 3 (FLT3/STK1), colony-stimulating factor 1 receptor (CSFIR/FMS), stem cell factor receptor (SCFR/KIT), and platelet derived growth factor receptors (PDGFRs), such as quizartinib dihydrochloride;

pan-Pim proto-oncogene, serine/threonine kinase (e.g., PIM1 (NCBI Gene ID: 5292); PIM2 (NCBI Gene ID: 11040); PIM3 (NCBI Gene ID: 415116)) inhibitors, such as INCB-053914;

a heat shock protein HSP90 (e.g., HSP90AA1 (NCBI Gene ID: 3320); HSP90AB1 (NCBI Gene ID: 3326)) inhibitors, such as TAS-116, PEN-866, AUY922, onalespib (AT13387), SNX-2112, SNX5422;

spleen associated tyrosine kinase (SYK; NCBI Gene ID: 6850)/janus kinase (e.g., JAK1 (NCBI Gene ID: 3716); JAK2 (NCBI Gene ID: 3717); JAK3 (NCBI Gene ID: 3718)) dual inhibitors, such as gusacitinib (ASN002);

NLR family pyrin domain containing 3 (NLRP3; NCBI Gene ID: 114548) agonists, such as BMS-986299;

DExD/H-box helicase 58 (DDX58, a.k.a., RIG-I; NCBI Gene ID: 23586) agonists, such as RGT-100;

an ATP binding cassette subfamily B member 1 (ABCB1, a.k.a., P-GP, PGY1, MDR1, CD243; NCBI ID: 5243) inhibitor, such as encequidar (HM30181; HM30181A);

colony stimulating factor 1 (CSF1; NCBI Gene ID: 1435) antagonists, such as ARRY-382, BLZ-945;

polo like kinase 1 (PLK1; NCBI Gene ID: 5347) inhibitors, such as PCM-075, onvansertib;

NEDD8 activating enzyme E1 subunit 1 (NAE1; NCBI Gene ID: 8883) inhibitors, such as pevonedistat (TAK-924/MLN4924), TAS-4464; Pleiotropic pathway modulators, such as avadomide (CC-122);

forkhead box M1 (FOXM1; NCBI Gene ID: 2305) inhibitors, such as thiostrepton;

ubiquitin like modifier activating enzyme 1 (UBA 1; Gene ID: 7317) inhibitors, such as TAK-243 (MLN7243);

SRC proto-oncogene, non-receptor tyrosine kinase (SRC; NCBI ID: 6714) inhibitors, such as VAL-201;

a voltage-dependent anion channel (e.g., VDAC1 (NCBI Gene ID: 7416); VDAC2 (NCBI Gene ID: 7417); VDAC3 (NCBI Gene ID: 7419))/hexokinase 2 (HK2; NCBI Gene ID: 3099) inhibitors, such as VDA-1102;

heat shock transcription factor 1 (HSF1; NCBI Gene ID: 3297) inhibitors, such as rohinitib;

a eukaryotic translation initiation factor 4A (e.g., EIF4A1 (NCBI Gene ID: 1973); EIF4A2 (NCBI Gene ID: 1974); EIF4A3 (NCBI Gene ID: 9775)) inhibitor, such as eFT226;

tumor protein p53 (TP53; NCBI Gene ID: 7157 gene stimulators, such as Ad-p53 (gendicine); TP53 tumor protein stimulators, such as kevetrin;

acute promyelocytic leukemia (APML, APL) cell differentiation inducers and proliferation inhibitors, such as tretinoin;

sirtuin 3 (SIRT3; NCBI Gene ID: 23410) inhibitors, such as YC8-02;

arginase 1 (ARG1; NCBI Gene ID: 383) enzyme replacement therapy, such as pegzilarginase;

triggering receptor expressed on myeloid cells 1 (TREM1; NCBI Gene ID: 54210) targeting antibodies, such as PY159;

triggering receptor expressed on myeloid cells 2 (TREM2; NCBI Gene ID: 54209) targeting antibodies, such as PY314;

tumor associated calcium signal transducer 2 (TACSTD2) (NCBI Gene ID: 4070; EGP-1, EGP1, GA733-1, GA7331, GP50, M1S1, TROP-2, TROP2) targeting antibodies, such as sacituzumab (e.g., sacituzumab govitecan), TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Kus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech);

MDM2 proto-oncogene (MDM2; NCBI Gene ID: 4193) inhibitors, such as siremadlin (NVP-HDM201), idasanutlin (RG7388), DS-3032b, RG7775, AMG-232, NVP-CMG-097 (CMG-097);

MDM2/MDM4 regulator of p53 (MDM4, a.k.a., MDMX; NCBI Gene ID: 4194) dual inhibitors, such as ALRN-6924;

kinesin spindle protein (KIF11, a.k.a., HKSP; NCBI Gene ID: 3832) inhibitors, such as filanesib (ARRY-520);

CD80 (NCBI Gene ID: 941)-Fc fusion protein, such as FPT-155;

nuclear receptor subfamily 1 group H member 2 (NR1H2, a.k.a., liver X receptor beta (LXRB); NCBI Gene ID: 7376) agonists, such as RGX-104;

interleukin 1 receptor associated kinase 4 (IRAK4; NCBI Gene ID: 51135) inhibitors, such as CA-4948;

calmodulin 1 (CALM1; NCBI Gene ID: 801)-binding peptide, such as CBP-501;

nuclear receptor subfamily 3 group C member 1 (NR3C1, a.k.a., glucocorticoid receptor (GR); NCBI Gene ID: 2908) antagonists, such as relacorilant (CORT-125134);

diablo IAP-binding mitochondrial protein (DIABLO, a.k.a., second mitochondria-derived activator of caspases (SMAC); NCBI Gene ID: 56616) mimetics, such as ciapavir, BI-891065, TL32711, LCL161, GDC-0917, HGS1029, AT-406;

cationic antimicrobial oncolytic peptide derived from the pepsin-mediated hydrolysis of the iron-binding bovine glycoprotein lactotransferrin (LTF, a.k.a., lactoferrin (Lf); NCBI Gene ID: 280846), such as LTX-315 (Ruxotemitide);

Exportin 1 (XPO1; NCBI Gene ID: 7514) inhibitors, such as eltanexor, selinexor (KPT-330);

carbohydrate sulfotransferase 15 (CHST15; NCBI Gene ID: 51363) gene inhibitors, such as STNM-01;

somatostatin receptor 2 (SSTR2; NCBI Gene ID: 6752) antagonists, such as OPS-201;

CCAAT enhancer binding protein alpha (CEBPA; NCBI Gene ID: 1050) gene stimulators, such as MTL-501;

dickkopf WNT signaling pathway inhibitor 3 (DKK3; NCBI Gene ID: 27122) gene modulators, such as MTG-201;

ribosomal protein S6 kinase B1 (RPS6KB1, a.k.a., p70-S6K; NCBI Gene ID: 6198) inhibitors, such as MSC2363318A;

transferrin receptor (TFRC, a.k.a., CD71, TFR1; NCBI Gene ID: 7037)-targeted probody-drug conjugate (PDC), such as CX-2029 (ABBV-2029);

ATM serine/threonine kinase (ATM, a.k.a., ataxia telangiectasia mutated; NCBI Gene ID: 472) inhibitors, such as AZD0156, AZD1390;

checkpoint kinase 1 (CHEK1, a.k.a., CHK1; NCBI Gene ID: 1111) inhibitors, such as GDC-0575, LY2606368 (prexasertib), SRA737, RG7741 (CHK1/2);

enhancer of zeste 2 polycomb repressive complex 2 subunit (EZH2; NCBI Gene ID: 2146) inhibitors, such as tazemetostat, CPI-1205, GSK2816126, PF06821497;

anti-colony stimulating factor 2 receptor subunit alpha (CSF2RA, a.k.a., GM-CSF; NCBI Gene ID: 1438) antibodies, such as lenzilumab;

protein kinase, DNA-activated, catalytic subunit (PRKDC, a.k.a., DNA-PKC, DNAPK, DNPK1; NCBI Gene ID: 5591) inhibitors, such as MSC2490484A (nedisertib), VX-984, AsiDNA (DT-01);

protein kinase C (PKC) (e.g., PRKCA (NCBI Gene ID: 5578); PRKCB (NCBI Gene ID: 5579); PRKCQ (NCBI Gene ID: 5588); PRKCE (NCBI Gene ID: 5581); PRKCI (NCBI Gene ID: 5584); PRKCZ (NCBI Gene ID: 5590); PRKCD (NCBI Gene ID: 5580); PRKCH (NCBI Gene ID: 5583); PRKCG (NCBI Gene ID: 5582)) inhibitors, such as LXS-196, sotrastaurin (AEB071);

transforming growth factor beta receptor 1 (TGFBR1, a.k.a. ALK5; NCBI Gene ID: 7046) inhibitors, such as galunisertib (LY2157299 monohydrate), LY3200882, PF-06952229, and those described in WO 2019/103203;

oxoglutarate dehydrogenase (OGDH, a.k.a., alpha-ketoglutarate dehydrogenase (AKGDH); NCBI Gene ID: 4967) inhibitors, such as CPI-613;

isocitrate dehydrogenase (NADP(+)) 2 (IDH2; NCBI Gene ID: 3418) inhibitors, such as enasidenib (AG-221);

isocitrate dehydrogenase (NADP(+)) 1 (IDH1; NCBI Gene ID: 3417) inhibitors, such as AG-120, IDH-305, BAY-1436032 and AG-881 (IDH1/IDH2 dual inhibitor);

IDH1 gene inhibitors, such as ivosidenib;

claudin 18 (CLDN18; NCBI Gene ID: 51208) inhibitors, such as claudiximab;

catenin beta 1 (CTNNB1; NCBI Gene ID: 1499) inhibitors, such as CWP232291 (CWP291);

Wnt signalling pathway inhibitors, such as SM-04755, PRI-724 (specific inhibitor of CREB binding protein (CBP)/β-Catenin (CTNNB1) complex), WNT-974 (binds to and inhibits porcupine O-acyltransferase (PORCN; NCBI Gene ID: 64840) in the endoplasmic reticulum (ER));

poly(ADP-ribose) polymerase 1 (PARP1, a.k.a., PARP; NCBI Gene ID: 142)/poly(ADP-ribose) polymerase 2 (PARP2; NCBI Gene ID: 10038) inhibitors, such as LYNPARZA® (olaparib; MK7339), rucaparib, veliparib (ABT-888), TALZENNA® (talazoparib), ABT-767, BGB-290, fluzolepali (SHR-3162), niraparib (JNJ-64091742), bendamustine hydrochloride, senaparib (IMP-4297), SC-10914, IDX-1197, HWH-340, CK-102, simmiparib;

PARP/tankyrase (TNKS; NCBI Gene ID: 8658) inhibitors such as 2X-121 (e-7499);

TNKS inhibitors, such as G007-LK;

Pim-1 proto-oncogene, serine/threonine kinase (PIM1; NCBI Gene ID: 5292) inhibitors, such as PIM447 (LGH447);

sphingosine kinase 2 (SPHK2, a.k.a., SK-2; NCBI Gene ID: 56848) inhibitors, such as Yeliva® (ABC294640);

ABL proto-oncogene 1, non-receptor tyrosine kinase (ABL1, a.k.a., ABL, BCR-ABL; NCBI Gene ID: 25) inhibitors, such as rebastinib (DCC-2036), asciminib (ABL001), ponatinib (ICLUSIG®);

MAPK interacting serine/threonine kinase 1 (MKNK1; NCBI Gene ID: 8569)/MAPK interacting serine/threonine kinase 2 (MKNK2; NCBI Gene ID: 2872) dual inhibitors, such as tomivosertib (eFT508);

AKT serine/threonine kinase 1 (AKT1, a.k.a., AKT, RAC; NCBI Gene ID: 207) inhibitors, such as capivasertib (AZD-5363), afuresertib (ASB-183; GSK-2110183), ipatasertib dihydrochloride (GDC-0068), miransertib (ARQ-092), uprosertib (GSK-2141795), uprosertib/trametinib dimethyl sulfoxide, selumetinib sulfate (MK-2206), triciribine phosphate (VQD-002), honokiol (HU-002), CLR-124, CLR-131, CMX-2043, RX-0301, TIC-10, TAS-117, LAE-201;

cytochrome P450 family member (e.g., CYP11A1, a.k.a., P450SCC (NCBI Gene ID: 1583) CYP11B1; a.k.a., P450C11 (NCBI Gene ID: 1584) CYP11B2, a.k.a., P450C18, ALDOS (NCBI Gene ID: 1585)) and hydroxysteroid dehydrogenase (e.g., HSD3B1 (NCBI Gene ID: 3283), HSD3B2 (NCBI Gene ID: 3284) inhibitors, such as mitotane (LYSODREN);

corticosteroids, such as cortisone, dexamethasone, hydrocortisone, methylprednisolone, prednisone, prednisolone;

selectin E (SELE, a.k.a., CD62E, ELAM, ELAM1, ESEL, LECAM2; NCBI Gene ID: 6401) antagonists, such as GMI-1271;

Inhibitors of bromodomain and extra-terminal motif (BET) proteins, including BRD2 (NCBI Gene ID: 6046), BRD3 (NCBI Gene ID: 8019), BRD4 (NCBI Gene ID: 23476), and bromodomain testis-specific protein (BRDT; NCBI Gene ID: 676), such as ABBV-744, INCB-054329, INCB057643, TEN-010, AZD-5153, ABT-767, BMS-986158, CC-90010, GSK525762 (molibresib), NHWD-870, ODM-207, GSK-2820151, GSK-1210151A, ZBC246, ZBC260, ZEN3694, FT-1101, RG-6146, CC-90010, CC-95775, mivebresib, BI-894999, PLX-2853, PLX-51107, CPI-0610, GS-5829;

Proteasome inhibitors, such as ixazomib (NINLARO®), KYPROLIS® (carfilzomib), marizomib, bortezomib;

mitochondrial complex I inhibitors, such as metformin, phenformin;

signal transducer and activator of transcription 3 (STAT3; NCBI Gene ID: 6774) inhibitors, such as napabucasin (BBI-608);

valosin containing protein (VCP, a.k.a., p97; NCBI Gene ID: 7415) inhibitors, such as CB-5083;

smoothened, frizzled class receptor (SMO; NCBI Gene ID: 6608)/hedgehog (e.g., IHH, HHG2 (NCBI Gene ID: 3549), SHH, HHG1 (NCBI Gene ID: 6469)) signaling pathway inhibitors, such as ODOMZO® (sonidegib, formerly LDE-225), saridegib (IPI-926), LEQ506, vismodegib (GDC-0449), BMS-833923, glasdegib (PF-04449913), taladegib (LY2940680), and itraconazole;

hedgehog (e.g., IHH, HHG2 (NCBI Gene ID: 3549), SHH, HHG1 (NCBI Gene ID: 6469)) signaling pathway inhibitors, such as patidegib;

telomerase reverse transcriptase (TERT; NCBI Gene ID: 7015) inhibitors, such as, tertomotide (GV-1001, HR-2802, RIAVAX™) and imetelstat (GRN-163, JNJ-63935937);

Bcl-2 family protein (e.g., BCL2 apoptosis regulator (BCL2; NCBI Gene ID: 596); BCL2 associated agonist of cell death (BAD; NCBI Gene ID: 5720); BCL2 associated X, apoptosis regulator (BAX; NCBI Gene ID: 581); BCL2 like 1 (BCL2L1; NCBI Gene ID: 598)) inhibitors, such as navitoclax (ABT-263), venetoclax (GDC-0199, ABT-199, RG-7601), ABT-737, obatoclax mesylate (GX15-070), RG7601, BGB-11417 and AT-101;

notch receptor (e.g., NOTCH1 (NCBI Gene ID: 4851); NOTCH2 (NCBI Gene ID: 4853); NOTCH3 (NCBI Gene ID: 4854); NOTCH4 (NCBI Gene ID: 4855)) inhibitors, such as crenigacestat (LY3039478), tarextumab (anti-Notch2/3), BMS-906024;

presenilin enhancer, gamma-secretase subunit (PSENEN; NCBI Gene ID: 55851) inhibitors, such as Nirogacestat (PF-03084014, PF-3084014), MK-0752, RO-4929097;

growth factor receptor bound protein 2 (GRB2; NCBI Gene ID: 2885) inhibitors, such as BP1001;

dopamine receptor D2 (DRD2; NCBI Gene ID: 1813) antagonists, such as ONC201;

protein tyrosine kinase 2 (PTK2, a.k.a., focal adhesion kinase (FAK); NCBI Gene ID: 5747) inhibitors, such as VS-4718, defactinib (VS-6063, PF-04554878), GSK2256098;

aurora kinase (e.g., AURKA (NCBI Gene ID: 6790), AURKB (NCBI Gene ID: 9212)) inhibitors, such as alisertib (MLN-8237), and AZD-2811, AMG-900, barasertib, ENMD-2076;

antisense oligonucleotide targeting heat shock protein 27 (Hsp27), such as apatorsen (OGX 427);

ATR serine/threonine kinase (ATR; NCBI Gene ID: 545) inhibitors, such as BAY-937, AZD6738, AZD6783, VX-803, VX-970 (berzosertib);

fatty acid synthase (FASN; NCBI Gene ID: 2194) inhibitors, such as TVB-2640;

protein phosphatase 2 phosphatase activator (PTPA, a.k.a., PP2A; NCBI Gene ID: 5524) inhibitors, such as LB-100;

cytochrome P450 family 17 subfamily A member 1 (CYP17A1; NCBI Gene ID: 1586) inhibitors, such as seviteronel (VT-464), ASN-001, ODM-204, CFG920, abiraterone acetate;

C-type lectin domain containing 7A (CLEC7A, a.k.a., DECTIN1; NCBI Gene ID: 64581) agonists, such as Imprime PGG;

DOT1 like histone lysine methyltransferase (DOT1L; NCBI Gene ID: 84444) inhibitors, such as pinometostat (EPZ-5676);

a double-stranded bacterial DNA plasmid construct containing the diphtheria toxin A chain engineered to be expressed under the control of regulatory sequences from the H19 imprinted maternally expressed transcript (H19; NCBI Gene ID: 283120) gene, such as BC-819 (inodiftagene vixteplasmid);

polo like kinase (e.g., PLK1 (NCBI Gene ID: 5347); PLK2 (NCBI Gene ID: 10769); PLK3 (NCBI Gene ID: 1263); PLK4 (NCBI Gene ID: 10733); PLK5 (NCBI Gene ID: 126520)) inhibitors, such as volasertib (PLK1);

WEE1 G2 checkpoint kinase (WEE1; NCBI Gene ID: 7465) inhibitors, such as AZD-1775 (adavosertib); Rho kinase (ROCK) inhibitors, such as AT13148, KD025;

X-linked inhibitor of apoptosis (XIAP; NCBI Gene ID: 331)/baculoviral IAP repeat containing 2 (BIRC2; NCBI Gene ID: 329) single or dual inhibitors, such as ASTX660, debio-1143, birinapant, APG-1387, LCL-161;

WT1 transcription factor (WT1; NCBI Gene ID: 7490) inhibitors, such as DSP-7888;

splicing factor 3B subunit 1 (SF3B1; NCBI Gene ID: 23451) inhibitors, such as H3B-8800;

microbiome modulators, such as SER-401 (a donor-derived microbiome therapeutic candidate that incorporates the bacterial signature found in melanoma patients who have a robust response to immunotherapy), EDP-1503 (oral monoclonal microbial candidate, derived from *Bifidobacterium animalis* ssp. *lactis* strain), MRx-0518 (live *Enterococcus gallinarum*, a commensal bacterial strain isolated from a healthy human gut).

anti-protein tyrosine phosphatase receptor type C (PTPRC, a.k.a., B220, CD45; NCBI Gene ID: 5788) antibodies, such as 131I-BC8 (lomab-B);

anti-CD52 (NCBI Gene ID: 1043) antibodies, such as alemtuzumab;

anti-CD19 molecule (NCBI Gene ID: 930) antibodies, such as tafasitamab (MOR208, formerly Xmab®5574), inebilizumab (MEDI-551), AFM-11 CD19/CD3-directed tandem diabody (TandAb®));

CLDN18 isoform 2 (CLDN18.2; NCBI Gene ID: 51208; NP_001002026.1)-targeted antibodies, such as zolbetuximab;

intercellular adhesion molecule 1 (ICAM1, a.k.a., CD54; NCBI Gene ID: 3383) inhibitors, such as tyroserleutide, alicaforsen sodium, enlimomab, bersanlimab, GI-270384X, ICM-3, AIC-100, DZ-13, tICAM-1-453, BAY-Z-9700;

In some embodiments, a compound as described herein, is co-administered with one or more additional therapeutic agents comprising an inhibitor or antagonist of: protein tyrosine phosphatase, non-receptor type 11 (PTPN11, a.k.a., SHP2; NCBI Gene ID: 5781), myeloid cell leukemia sequence 1 (MCL1) apoptosis regulator (NCBI Gene ID: 4170); mitogen-activated protein kinase 1 (MAP4K1) (also called Hematopoietic Progenitor Kinase 1 (HPK1), NCBI Gene ID: 11184); phosphatidylinositol-4,5-bisphosphate 3-kinase, including catalytic subunit alpha (PIK3CA; NCBI Gene ID: 5290), catalytic subunit beta (PIK3CB; NCBI Gene ID: 5291), catalytic subunit gamma (PIK3CG; NCBI Gene ID: 5294) and catalytic subunit delta (PIK3CD), diacylglycerol kinase alpha (DGKA, DAGK, DAGK1 or DGK-alpha; NCBI Gene ID: 1606); 5'-nucleotidase ecto (NT5E or CD73; NCBI Gene ID: 4907); ectonucleoside triphosphate diphosphohydrolase 1 (ENTPD1 or CD39; NCBI Gene ID: 593); transforming growth factor beta 1 (TGFB1 or TGFβ; NCBI Gene ID: 7040); heme oxygenase 1 (HMOX1, HO-1 or HO1; NCBI Gene ID: 3162); heme oxygenase 2 (HMOX2, HO-2 or HO2; NCBI Gene ID: 3163); vascular endothelial growth factor A (VEGFA or VEGF; NCBI Gene ID: 7422); erb-b2 receptor tyrosine kinase 2 (ERBB2, HER2, HER2/neu or CD340; NCBI Gene ID: 2064), epidermal growth factor receptor (EGFR, ERBB, ERBB1 or HER1; NCBI Gene ID: 1956); ALK receptor tyrosine kinase (ALK, CD246; NCBI Gene ID: 238); poly (ADP-ribose) polymerase 1 (PARP1; NCBI Gene ID: 142); poly(ADP-ribose) polymerase 2 (PARP2; NCBI Gene ID: 10038); TCDD inducible poly(ADP-ribose) polymerase (TIPARP, PARP7; NCBI Gene ID: 25976); cyclin dependent kinase 4 (CDK4; NCBI Gene ID: 1019); cyclin dependent kinase 6 (CDK6; NCBI Gene ID: 1021); TNF receptor superfamily member 14 (TNFRSF14, HVEM, CD270; NCBI Gene ID: 8764); T cell immunoreceptor with Ig and ITIM domains (TIGIT; NCBI Gene ID: 201633); X-linked inhibitor of apoptosis (XIAP, BIRC4, IAP-3; NCBI Gene ID: 331); baculoviral IAP repeat containing 2 (BIRC2, cIAP1; NCBI Gene ID: 329); baculoviral IAP repeat containing 3 (BIRC3, cIAP2; NCBI Gene ID: 330); baculoviral IAP repeat containing 5 (BIRC5, surviving; NCBI Gene ID: 332); C-C motif chemokine receptor 2 (CCR2, CD192; NCBI Gene ID: 729230); C-C motif chemokine receptor 5 (CCR5, CD195; NCBI Gene ID: 1234); C-C motif chemokine receptor 8 (CCR8, CDw198; NCBI Gene ID: 1237); C-X-C motif chemokine receptor 2 (CXCR2, CD182; NCBI Gene ID: 3579); C-X-C motif chemokine receptor 3 (CXCR3, CD182, CD183; NCBI Gene ID: 2833); C-X-C motif chemokine receptor 4 (CXCR4, CD184; NCBI Gene ID: 7852); cytokine inducible SH2 containing protein (CISH; NCBI Gene ID: 1154); arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240) and/or soluble epoxide hydrolase 2 (EPHX2, SEH; NCBI Gene ID: 2053); a secreted phospholipase A2 (e.g., PLA2G1B (NCBI Gene ID: 5319); PLA2G7 (NCBI Gene ID: 7941), PLA2G3 (NCBI Gene ID: 50487), PLA2G2A (NCBI Gene ID: 5320); PLA2G4A (NCBI Gene ID: 5321); PLA2G12A (NCBI Gene ID: 81579); PLA2G12B (NCBI Gene ID: 84647); PLA2G10 (NCBI Gene ID: 8399); PLA2G5 (NCBI Gene ID: 5322); PLA2G2D (NCBI Gene ID: 26279); PLA2G15 (NCBI Gene ID: 23659)); indoleamine 2,3-dioxygenase 1 (IDO1; NCBI Gene ID: 3620); indoleamine 2,3-dioxygenase 2 (IDO2; NCBI Gene ID:

169355); hypoxia inducible factor 1 subunit alpha (HIF1A; NCBI Gene ID: 3091); angiopoietin 1 (ANGPT1; NCBI Gene ID: 284); Endothelial TEK tyrosine kinase (TIE-2, TEK, CD202B; NCBI Gene ID: 7010); Janus kinase 1 (JAK1; NCBI Gene ID: 3716); catenin beta 1 (CTNNB1; NCBI Gene ID: 1499); histone deacetylase 9 (HDAC9; NCBI Gene ID: 9734), 5'-3' exoribonuclease 1 (XRN1; NCBI Gene ID: 54464) and/or WRN RecQ like helicase (WRN; NCBI Gene ID: 7486).

Adenosine Signaling Pathway Targets

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of the adenosine signaling pathway. Illustrative targets include an adenosine receptor, CD39 and CD73. In some embodiments that combination agent is an agonist of ADORA3 or an antagonist or inhibitor of adenosine A1 receptor (ADORA1; NCBI Gene ID: 134), ADORA2A, ADORA2B, CD73, CD39, dipeptidyl peptidase 4 (DPP4, a.k.a., CD26; NCBI Gene ID: 1803) and adenosine deaminase (ADA). Examples of adenosine A3 receptor (ADORA3, a.k.a., A3AR; NCBI Gene ID: 140) agonists include namodenoson (CF102). Examples of adenosine A2a receptor (ADORA2A, a.k.a., A2aR; NCBI Gene ID: 135)/adenosine A2b receptor (ADORA2B; NCBI Gene ID: 136) antagonists include AB928. Examples of ADORA2A antagonists, such as CPI-444, AZD-4635, preladenant, PBF-509. Examples of 5'-nucleotidase ecto (NT5E, a.k.a., CD73; NCBI Gene ID: 4907) inhibitors include AB-680, PSB-12379, PSB-12441, PSB-12425, CB-708; and those described in Int Patent Publication No. WO19173692. Examples of anti-CD73 antibodies include GS-1423, MEDI-9447 (oleclumab), CPX-006, IPH-53, BMS-986179, NZV-930, CPI-006. Examples of anti-ectonucleoside triphosphate diphosphohydrolase 1 (ENTPD1, a.k.a., CD39; NCBI Gene ID: 953) antibodies include TTX-030. Examples of CD39/CD73 inhibitors include PBF-1662. Examples of adenosine deaminase (ADA; NCBI Gene ID: 100) inhibitors include pentostatin, cladribine.

MCL1 Apoptosis Regulator, BCL2 Family Member (MCL1) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of MCL1 apoptosis regulator, BCL2 family member (MCL1, TM; EAT; MCL1L; MCL1S; Mcl-1; BCL2L3; MCL1-ES; bcl2-L-3; mcl1/EAT; NCBI Gene ID: 4170). Examples of MCL1 inhibitors include GS-9716, tapotoclax (AMG-176), AMG-397, S-64315, and AZD-5991, 483-LM, A-1210477, UMI-77, JKY-5-037, PRT-1419, and those described in WO2018183418, WO2016033486, and WO2017147410.

Cytokine Inducible SH2 Containing Protein (CISH) Inhibitors

In various embodiments, a compound as described herein, is combined with an inhibitor of cytokine inducible SH2 containing protein (CISH; CIS; G18; SOCS; CIS-1; BACTS2; NCBI Gene ID: 1154). Examples of CISH inhibitors include those described in WO2017100861, WO2018075664 and WO2019213610.

Protein Tyrosine Phosphatase Non-Receptor Type 11 (PTPN11; SHP2) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of protein tyrosine phosphatase non-receptor type 11 (PTPN11; BPTP3, CFC, JMML, METCDS, NS1, PTP-1D, PTP2C, SH-PTP2, SH-PTP3, SHP2; NCBI Gene ID: 5781). Examples of SHP2 inhibitors include TNO155 (SHP-099), RMC-4550, JAB-3068, RMC-4630, SAR442720 and those described in WO2018172984 and WO2017211303.

Mitogen-Activated Protein Kinase 7 (MAP2K7; MEK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of mitogen-activated protein kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, CK-127, cobimetinib (GDC-0973, XL-518), MT-144, selumetinib (AZD6244), sorafenib, trametinib (GSK1120212), uprosertib+trametinib, PD-0325901, pimasertib, LT7462, AS703988, CC-90003, refametinib, TAK-733, CI-1040, RG7421.

Hematopoietic Progenitor Kinase 1 (HPK1) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of mitogen-activated protein kinase kinase kinase kinase 1 (MAP4K1, HPK1; NCBI Gene ID: 11184). Examples of Hematopoietic Progenitor Kinase 1 (HPK1) inhibitors include without limitation BGB-15025, and those described in WO2018183956, WO2018183964, WO2018167147, WO2018183964, WO2016205942, WO2018049214, WO2018049200, WO2018049191, WO2018102366, WO2018049152, WO2020092528, WO2020092621 and WO-2016090300.

Apoptosis Signal-Regulating Kinase (ASK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of an ASK inhibitor, e.g., mitogen-activated protein kinase kinase kinase 5 (MAP3K5; ASK1, MAPKKK5, MEKK5; NCBI Gene ID: 4217). Examples of ASK1 inhibitors include without limitation, those described in WO 2011/008709 (Gilead Sciences) and WO 2013/112741 (Gilead Sciences).

Cyclin-Dependent Kinase (CDK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9, include without limitation abemaciclib, alvocidib (HMR-1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, trilaciclib, and TG-02.

Discoidin Domain Receptor (DDR) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of discoidin domain receptor tyrosine kinase 1 (DDR1, CAK, CD167, DDR, EDDR1, HGK2, MCK10, NEP, NTRK4, PTK3, PTK3A, RTK6, TRKE; NCBI Gene ID: 780); and/or discoidin domain receptor tyrosine kinase 2 (DDR2, MIG20a, NTRKR3, TKT, TYRO10, WRCN; NCBI Gene ID: 4921). Examples of DDR inhibitors include without limitation, dasatinib and those disclosed in WO2014/047624 (Gilead Sciences), US 2009-0142345 (Takeda Pharmaceutical), US 2011-0287011 (Oncomed Pharmaceuticals), WO 2013/027802 (Chugai Pharmaceutical), and WO2013/034933 (Imperial Innovations).

Targeted E3 Ligase Ligand Conjugates

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a targeted E3 ligase ligand conjugate. Such conjugates have a target protein binding moiety and an E3 ligase binding moiety (e.g., an inhibitor of apoptosis protein (IAP) (e.g., XIAP, c-IAP1, c-IAP2, NIL-IAP, Bruce, and surviving) E3 ubiquitin ligase binding moiety, Von Hippel-Lindau E3 ubiquitin ligase (VHL) binding moiety, a cereblon E3 ubiquitin ligase binding moiety, mouse double minute 2 homolog (MDM2) E3 ubiquitin ligase binding moiety), and can be used to promote or increase the degradation of targeted proteins, e.g., via the ubiquitin pathway. In one embodiment, the targeted E3 ligase ligand conjugates comprise a targeting or binding moiety that targets or binds a target protein identified in herein, and an E3 ligase ligand or binding moiety. In one embodiment, the targeted E3 ligase ligand conjugates comprise a targeting or binding moiety that targets or binds a protein selected from Cbl proto-oncogene B (CBLB; Cbl-b, Nbla00127, RNF56; NCBI Gene ID: 868) and hypoxia inducible factor 1 subunit alpha (HIF1A; NCBI Gene ID: 3091). In one embodiment, the targeted E3 ligase ligand conjugates comprise a kinase inhibitor (e.g., a small molecule kinase inhibitor, e.g., of BTK and an E3 ligase ligand or binding moiety. See, e.g., WO2018098280. In another embodiment, the targeted E3 ligase ligand conjugates comprise a binding moiety targeting or binding to Interleukin-1 (IL-1) Receptor-Associated Kinase-4 (IRAK-4); Rapidly Accelerated Fibrosarcoma (RAF, such as c-RAF, A-RAF and/or B-RAF), c-Met/p38, or a BRD protein; and an E3 ligase ligand or binding moiety. See, e.g., WO2019099926, WO2018226542, WO2018119448, WO2018223909, WO2019079701. Additional targeted E3 ligase ligand conjugates that can be co-administered are described, e.g., in WO2018237026, WO2019084026, WO2019084030, WO2019067733, WO2019043217, WO2019043208 and WO2018144649.

Indoleamine-Pyrrole-2,3-Dioxygenase (IDO1) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of indoleamine 2,3-dioxygenase 1 (IDO1; NCBI Gene ID: 3620). Examples of IDO1 inhibitors include without limitation, BLV-0801, epacadostat, linrodostat (F-001287, BMS-986205), GBV-1012, GBV-1028, GDC-0919, indoximod, NKTR-218, NLG-919-based vaccine, PF-06840003, pyranonaphthoquinone derivatives (SN-35837), resminostat, SBLK-200802, BMS-986205, and shIDO-ST, EOS-200271, KHK-2455, LY-3381916.

Janus Kinase (JAK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of Janus kinase 1 (JAK1, JAK1A, JAK1B, JTK3; NCBI Gene ID: 3716); Janus kinase 2 (JAK2, JTK10, THCYT3; NCBI Gene ID: 3717); and/or Janus kinase 3 (JAK3, JAK-3, JAK3_HUMAN, JAKL, L-JAK, UAK; NCBI Gene ID: 3718). Examples of JAK inhibitors include without limitation, AT9283, AZD1480, baricitinib, BMS-911543, fedratinib, filgotinib (GLPG0634), gandotinib (LY2784544), INCB039110 (itacitinib), lestaurtinib, momelotinib (CYT0387), ilginatinib maleate (NS-018), pacritinib (SB1518), peficitinib (ASP015K), ruxolitinib, tofacitinib (formerly tasocitinib), INCB052793, and XL019.

Lysyl Oxidase-Like Protein (LOXL) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of a LOXL protein, e.g., LOXL1 (NCBI Gene ID: 4016), LOXL2 (NCBI Gene ID: 4017), LOXL3 (NCBI Gene ID: 84695), LOXL4 (NCBI Gene ID: 84171), and/or LOX (NCBI Gene ID: 4015). Examples of LOXL inhibitors include without limitation, the antibodies described in WO 2009/017833 (Arresto Biosciences). Examples of LOXL2 inhibitors include without limitation, simtuzumab (GS-6624) and the antibodies described in WO 2009/017833 (Arresto Biosciences), WO 2009/035791 (Arresto Biosciences), and WO 2011/097513 (Gilead Biologics).

Matrix Metalloprotease (MMP) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined with an inhibitor of a matrix metallopeptidase (MMP), e.g., an inhibitor of MMP1 (NCBI Gene ID: 4312), MMP2 (NCBI Gene ID: 4313), MMP3 (NCBI Gene ID: 4314), MMP7 (NCBI Gene ID: 4316), MMP8 (NCBI Gene ID: 4317), MMP9 (NCBI Gene ID: 4318); MMP10 (NCBI Gene ID: 4319); MMP11 (NCBI Gene ID: 4320); MMP12 (NCBI Gene ID: 4321), MMP13 (NCBI Gene ID: 4322), MMP14 (NCBI Gene ID: 4323), MMP15 (NCBI Gene ID: 4324), MMP16 (NCBI Gene ID: 4325), MMP17 (NCBI Gene ID: 4326), MMP19 (NCBI Gene ID: 4327), MMP20 (NCBI Gene ID: 9313), MMP21 (NCBI Gene ID: 118856), MMP24 (NCBI Gene ID: 10893), MMP25 (NCBI Gene ID: 64386), MMP26 (NCBI Gene ID: 56547), MMP27 (NCBI Gene ID: 64066) and/or MMP28 (NCBI Gene ID: 79148). Examples of MMP9 inhibitors include without limitation, marimastat (BB-2516), cipemastat (Ro 32-3555), GS-5745 (andecaliximab) and those described in WO 2012/027721 (Gilead Biologics).

RAS and RAS Pathway Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of KRAS proto-oncogene, GTPase (KRAS; a.k.a., NS; NS3; CFC2; RALD; K-Ras; KRAS1; KRAS2; RASK2; KI-RAS; C—K-RAS; K-RAS2A; K-RAS2B; K-RAS4A; K-RAS4B; c-Ki-ras2; NCBI Gene ID: 3845); NRAS proto-oncogene, GTPase (NRAS; a.k.a., NS6; CMNS; NCMS; ALPS4; N-ras; NRAS1; NCBI Gene ID: 4893); HRas proto-oncogene, GTPase (HRAS; a.k.a., CTLO; KRAS; HAMSV; HRAS1; KRAS2; RASH1; RASK2; Ki-Ras; p21ras; C-H-RAS; c-K-ras; H-RASIDX; c-Ki-ras; C-BAS/HAS; C-HA-RAS1; NCBI Gene ID: 3265). The Ras inhibitors can inhibit Ras at either the polynucleotide (e.g., transcriptional inhibitor) or polypeptide (e.g., GTPase enzyme inhibitor) level. In some embodiments, the inhibitors target one or more proteins in the Ras pathway, e.g., inhibit one or more of EGFR, Ras, Raf (A-Raf, B-Raf, C-Raf), MEK (MEK1, MEK2), ERK, PI3K, AKT and mTOR. Illustrative K-Ras inhibitors that can be co-administered include ARS-1620 (G12C), SML-8-73-1 (G12C), Compound 3144 (G12D), Kobe0065/2602 (Ras GTP), RT11, MRTX-849 (G12C) and K-Ras(G12D)-selective inhibitory peptides, including KRpep-2 (Ac-RRCPLYISYDPVCRR-$NH_2$) (SEQ ID NO: 248) and KRpep-2d (Ac-RRRRCPLYISYDPVCRRRR-$NH_2$) (SEQ ID NO: 249). Illustrative KRAS mRNA inhibitors include anti-KRAS U1 adaptor, AZD-4785, siG12D-LODER™, and siG12D exosomes. Illustrative MEK inhibitors that can be co-administered include binimetinib, cobimetinib, PD-0325901, pimasertib, RG-7304, selumetinib, trametinib, and those described below and herein. Illustrative Raf dimer inhibitors that can be co-administered BGB-283, HM-95573, LXH-254, LY-3009120, RG7304 and TAK-580. Illustrative ERK inhibitors that can be co-administered include LT7-462, LY-3214996, MK-8353, ravoxertinib and ulixertinib. Illustrative Ras GTPase inhibitors that can be co-administered include rigosertib. Illustrative PI3K inhibitors that can be co-administered include idelalisib (Zydelig®), alpelisib, buparlisib, pictilisib, inavolisib (RG6114), ASN-003, and those described below and herein. Illustrative PI3K/mTOR inhibitors that can be co-administered include dactolisib, omipalisib, voxtalisib, gedatolisib, GSK2141795, GSK-2126458, inavolisib (RG6114), sapanisertib, ME-344, sirolimus (oral nano-amorphous formulation, cancer), racemetyrosine (TYME-88 (mTOR/cytochrome P450 3A4)), temsirolimus (TORISEL®, CCI-779), CC-115, onatasertib (CC-223), SF-1126, and PQR-309 (bimiralisib). Illustrative AKT inhibitors that can be co-administered include capivasertib and GSK2141795. In certain embodiments, Ras-driven cancers (e.g., NSCLC) having CDKN2A mutations can be inhibited by co-administration of the MEK inhibitor selumetinib and the CDK4/6 inhibitor palbociclib. See, e.g., Zhou, et al., *Cancer Lett.* 2017 Nov. 1; 408:130-137. Also, K-RAS and mutant N-RAS can be reduced by the irreversible ERBB1/2/4 inhibitor neratinib. See, e.g., Booth, et al., *Cancer Biol Ther.* 2018 Feb. 1; 19(2):132-137.

Mitogen-Activated Protein Kinase (MEK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of mitogen-activated protein kinase kinase 7 (MAP2K7, JNKK2, MAPKK7, MEK, MEK 7, MKK7, PRKMK7, SAPKK-4, SAPKK4; NCBI Gene ID: 5609). Examples of MEK inhibitors include antroquinonol, binimetinib, cobimetinib (GDC-0973, XL-518), MT-144, selumetinib (AZD6244), sorafenib, trametinib (GSK1120212), uprosertib+trametinib, PD-0325901, pimasertib, LT7462, AS703988, CC-9000 and refametinib.

Spleen Tyrosine Kinase (SYK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of spleen associated tyrosine kinase (SYK, p72-Syk, Gene ID: 6850). Examples of SYK inhibitors include without limitation, 6-(1H-indazol-6-yl)-N-(4-morpholinophenyl)imidazo[1,2-a]pyrazin-8-amine, BAY-61-3606, cerdulatinib (PRT-062607), entospletinib, fostamatinib (R788), HMPL-523, NVP-QAB 205 AA, R112, R343, tamatinib (R406), gusacitinib (ASN-002), and those described in U.S. Pat. No. 8,450,321 (Gilead Connecticut) and those described in U.S. 2015/0175616.

Tyrosine-Kinase Inhibitors (TKIs)

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a tyrosine kinase inhibitor (TKI). TKIs may target epidermal growth factor receptors (EGFRs) and receptors for fibroblast growth factor (FGF), platelet-derived growth factor (PDGF), and vascular endothelial growth factor (VEGF). Examples of TKIs include without limitation, afatinib, ARQ-087 (derazantinib), asp5878, AZD3759, AZD4547, bosutinib, brigatinib, cabozantinib, cediranib, crenolanib, dacomitinib, dasatinib, dovitinib, E-6201, erdafitinib, erlotinib, gefitinib, gilteritinib (ASP-2215), FP-1039, HM61713, icotinib, imatinib, KX2-391 (Src), lapatinib, lestaurtinib, lenvatinib, midostaurin, nintedanib, ODM-203, osimertinib (AZD-9291), ponatinib, poziotinib, quizartinib, radotinib, rociletinib, sulfatinib (HMPL-012), sunitinib, famitinib L-malate, (MAC-4), tivoanib, TH-4000, and MEDI-575 (anti-PDGFR antibody). Exemplary EGFR targeting agents include neratinib, tucatinib (ONT-380), tesevatinib, mobocertinib (TAK-788), DZD-9008, varlitinib, abivertinib (ACEA-0010), EGF816 (nazartinib), olmutinib (BI-1482694), osimertinib (AZD-9291), AMG-596 (EGFRvIII/CD3), lifirafenib (BGB-283), vectibix, lazertinib (LECLAZA®), and compounds disclosed in Booth, et al., *Cancer Biol Ther.* 2018 Feb. 1; 19(2):132-137. Antibodies targeting EGFR include without limitation modotuximab, cetuximab sarotalocan (RM-1929), seribantumab, necitumumab, depatuxizumab mafodotin (ABT-414), tomuzotuximab, depatuxizumab (ABT-806), and cetuximab.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antibody targeting tumor-associated calcium signal transducer 2 (TROP-2; TACSTD2; EGP-1; NCBI Gene ID: 4070). Illustrative anti-TROP-2 antibodies include without limitation TROP2-XPAT (Amunix), BAT-8003 (Bio-Thera Solutions), TROP-2-IR700 (Chiome Bioscience), datopotamab deruxtecan (Daiichi Sankyo, AstraZeneca), GQ-1003 (Genequantum Healthcare, Samsung BioLogics), DAC-002 (Hangzhou DAC Biotech, Shanghai Junshi Biosciences), sacituzumab govitecan (Gilead Sciences), E1-3s (Immunomedics/Gilead, IBC Pharmaceuticals), TROP2-TRACTr (Janux Therapeutics), LIV-2008 (LivTech/Chiome, Yakult Honsha, Shanghai Henlius BioTech), LIV-2008b (LivTech/Chiome), anti-TROP-2a (Oncoxx), anti-TROP-2b (Oncoxx), OXG-64 (Oncoxx), OXS-55 (Oncoxx), humanized anti-Trop2-SN38 antibody conjugate (Shanghai Escugen Biotechnology, TOT Biopharma), anti-Trop2 antibody-CLB-SN-38 conjugate (Shanghai Fudan-Zhangjiang Bio-Pharmaceutical), SKB-264 (Sichuan Kelun Pharmaceutical/Kus Pharma), TROP2-Ab8 (Abmart), Trop2-IgG (Nanjing Medical University (NMU)), 90Y-DTPA-AF650 (Peking University First Hospital), hRS7-CM (SynAffix), 89Zr-DFO-AF650 (University of Wisconsin-Madison), anti-Trop2 antibody (Mediterranea Theranostic, LegoChem Biosciences), KD-065 (Nanjing KAEDI Biotech), and those described in WO2020016662 (Abmart), WO2020249063 (Bio-Thera Solutions), US20190048095 (Bio-Thera Solutions), WO2013077458 (LivTech/Chiome), EP20110783675 (Chiome), WO2015098099 (Daiichi Sankyo), WO2017002776 (Daiichi Sankyo), WO2020130125 (Daiichi Sankyo), WO2020240467 (Daiichi Sankyo), US2021093730 (Daiichi Sankyo), U.S. Pat. No. 9,850,312 (Daiichi Sankyo), CN112321715 (Biosion), US2006193865 (Immunomedics/Gilead), WO2011068845 (Immunomedics/Gilead), US2016296633 (Immunomedics/Gilead), US2017021017 (Immunomedics/Gilead), US2017209594 (Immunomedics/Gilead), US2017274093 (Immunomedics/Gilead), US2018110772 (Immunomedics/Gilead), US2018185351 (Immunomedics/Gilead), US2018271992 (Immunomedics/Gilead), WO2018217227 (Immunomedics/Gilead), US2019248917 (Immunomedics/Gilead), CN111534585 (Immunomedics/Gilead), US2021093730 (Immunomedics/Gilead), US2021069343 (Immunomedics/Gilead), U.S. Pat. No. 8,435,539 (Immunomedics/Gilead), U.S. Pat. No. 8,435,529 (Immunomedics/Gilead), U.S. Pat. No. 9,492,566 (Immunomedics/Gilead), WO2003074566 (Gilead), WO2020257648 (Gilead), US2013039861 (Gilead), WO2014163684 (Gilead), U.S. Pat. No. 9,427,464 (LivTech/Chiome), U.S. Pat. No. 10,501,555 (Abruzzo Theranostic/Oncoxx), WO2018036428 (Sichuan Kelun Pharma), WO2013068946 (Pfizer), WO2007095749 (Roche), and WO2020094670 (SynAffix). In some embodiments, the anti-Trop-2 antibody is selected from hRS7, Trop-2-XPAT, and BAT-8003. In some embodiments, the anti-Trop-2 antibody is hRS7. In some embodiments, hRS7 is as disclosed in U.S. Pat. Nos. 7,238,785; 7,517,964 and 8,084,583, which are incorporated herein by reference. In some embodiments, the antibody-drug conjugate comprises an anti-Trop-2 antibody and an anticancer agent linked by a linker. In some embodiments, the linker includes the linkers disclosed in U.S. Pat. No. 7,999,083. In some embodiments, the linker is CL2A. In some embodiments, the drug moiety of antibody-drug conjugate is a chemotherapeutic agent. In some embodiments, the chemotherapeutic agent is selected from doxorubcin (DOX), epirubicin, morpholinodoxorubicin (morpholino-DOX), cyanomorpholino-doxorubicin (cyanomorpholino-DOX), 2-pyrrolino-doxorubicin (2-PDOX), CPT, 10-hydroxy camptothecin, SN-38, topotecan, lurtotecan, 9-aminocamptothecin, 9-nitrocamptothecin, taxanes, geldanamycin, ansamycins, and epothilones. In some embodiments, the chemotherapeutic moiety is SN-38. In some embodiments, sacituzumab govitecan is co-administered.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antibody targeting carcinoembryonic antigen-related cell adhesion molecule 1 (CEACAM1; CD66a; NCBI Gene ID: 634). In some embodiments the CEACAM1 antibody is hMN-14 (e.g., as described in WO1996011013). In some embodiments the CEACAM1-ADC is as described in WO2010093395 (anti-CEACAM-1-CL2A-SN38). In some embodiments the antibody and/or fusion protein provided herein is administered with the CEACAM1-ADC IMMU-130.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antibody targeting MHC class II cell surface receptor encoded by the human leukocyte antigen complex (HLA-DR). In some embodiments the HLA-DR antibody is hL243 (e.g., as described in WO2006094192). In some embodiments the HLA-DR-ADC is as described in WO2010093395 (anti-HLA-DR-CL2A-SN38). In some embodiments the antibody and/or fusion protein provided herein is administered with the HLA-DR-ADC IMMU-140.

Chemotherapeutic Agents (Standard of Care)

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a chemotherapeutic agent or anti-neoplastic agent.

As used herein, the term "chemotherapeutic agent" or "chemotherapeutic" (or "chemotherapy" in the case of treatment with a chemotherapeutic agent) is meant to encompass any non-proteinaceous (e.g., non-peptidic) chemical compound useful in the treatment of cancer. Examples of chemotherapeutic agents include but not limited to: alkylating agents such as thiotepa and cyclophosphamide (CYTOXAN®); alkyl sulfonates such as busulfan, improsulfan, and piposulfan; aziridines such as benzodepa, carboquone, meturedepa, and uredepa; ethylenimines and methylamelamines including altretamine, triethylenemelamine, triethylenephosphoramide, triethylenethiophosphoramide, and trimemylolomelamine; acetogenins, e.g., bullatacin and bullatacinone; a camptothecin, including synthetic analog topotecan; bryostatin, callystatin; CC-1065, including its adozelesin, carzelesin, and bizelesin synthetic analogs; cryptophycins, particularly cryptophycin 1 and cryptophycin 8; dolastatin; duocarmycin, including the synthetic analogs KW-2189 and CBI-TMI; eleutherobin; 5-azacytidine; pancratistatin; a sarcodictyin; spongistatin; nitrogen mustards such as chlorambucil, chlornaphazine, cyclophosphamide, glufosfamide, evofosfamide, bendamustine, estramustine, ifosfamide, mechlorethamine, mechlorethamine oxide hydrochloride, melphalan, novembichin, phenesterine, prednimustine, trofosfamide, and uracil mustard; nitrosoureas such as carmustine, chlorozotocin, foremustine, lomustine, nimustine, and ranimustine; antibiotics such as the enediyne antibiotics (e.g., calicheamicin, especially calicheamicin gammaII and calicheamicin phiI1), dynemicin including dynemicin A, bisphosphonates such as clodronate, an esperamicin, neocarzinostatin chromophore and related chromoprotein enediyne antibiotic chromomophores, aclacinomycins, actinomycin, authramycin, azaserine, bleomycins, cactinomycin, carabicin, carminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin, and deoxydoxorubicin), epirubicin, esorubicin, idarubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, and zorubicin; anti-metabolites such as methotrexate and 5-fluorouracil (5-FU); folic acid analogs such as demopterin, methotrexate, pteropterin, and trimetrexate; purine analogs such as cladribine, pentostatin, fludarabine, 6-mercaptopurine, thiamiprine, and thioguanine; pyrimidine analogs such as ancitabine, azacitidine, 6-azauridine, carmofur, cytarabine, dideoxyuridine, doxifluridine, enocitabine, and floxuridine; androgens such as calusterone, dromostanolone propionate, epitiostanol, mepitiostane, and testolactone; anti-adrenals such as aminoglutethimide, mitotane, and trilostane; folic acid replinishers such as frolinic acid; radiotherapeutic agents such as Radium-223; trichothecenes, especially T-2 toxin, verracurin A, roridin A, and anguidine; taxoids such as paclitaxel (TAXOL®), abraxane, docetaxel (TAXOTERE®), cabazitaxel, BIND-014, tesetaxel; sabizabulin (Veru-111); platinum analogs such as cisplatin and carboplatin, NC-6004 nanoplatin; aceglatone; aldophosphamide glycoside; aminolevulinic acid; eniluracil; amsacrine; hestrabucil; bisantrene; edatraxate; defofamine; demecolcine; diaziquone; elformthine; elliptinium acetate; an epothilone; etoglucid; gallium nitrate; hydroxyurea; lentinan; leucovorin; lonidamine; maytansinoids such as maytansine and ansamitocins; mitoguazone; mitoxantrone; mopidamol; nitracrine; pentostatin; phenamet; pirarubicin; losoxantrone; fluoropyrimidine; folinic acid; podophyllinic acid; 2-ethylhydrazide; procarbazine; polysaccharide-K (PSK); razoxane; rhizoxin; sizofiran; spirogermanium; tenuazonic acid; trabectedin, triaziquone; 2,2',2"-trichlorotriemylamine; urethane; vindesine; dacarbazine; mannomustine; mitobronitol; mitolactol; pipobroman; gacytosine; arabinoside ("Ara-C"); cyclophosphamide; thiopeta; chlorambucil; gemcitabine (GEMZAR®); 6-thioguanine; mercaptopurine; methotrexate; vinblastine; platinum; etoposide (VP-16); ifosfamide; mitroxantrone; vancristine; vinorelbine (NAVELBINE®); novantrone; teniposide; edatrexate; daunomycin; aminopterin; xeoloda; ibandronate; CPT-11; topoisomerase inhibitor RFS 2000; difluoromethylornithine (DFMO); retinoids such as retinoic acid; capecitabine; NUC-1031; FOLFOX (folinic acid, 5-fluorouracil, oxaliplatin); FOLFIRI (folinic acid, 5-fluorouracil, irinotecan); FOLFOXIRI (folinic acid, 5-fluorouracil, oxaliplatin, irinotecan), FOLFIRINOX (folinic acid, 5-fluorouracil, irinotecan, oxaliplatin), and pharmaceutically acceptable salts, acids, or derivatives of any of the above. Such agents can be conjugated onto an antibody or any targeting agent described herein to create an antibody-drug conjugate (ADC) or targeted drug conjugate.

Anti-Hormonal Agents

Also included in the definition of "chemotherapeutic agent" are anti-hormonal agents such as anti-estrogens and selective estrogen receptor modulators (SERMs), inhibitors of the enzyme aromatase, anti-androgens, and pharmaceutically acceptable salts, acids or derivatives of any of the above that act to regulate or inhibit hormone action on tumors.

Examples of anti-estrogens and SERMs include, for example, tamoxifen (including NOLVADEX™), raloxifene, droloxifene, 4-hydroxytamoxifen, trioxifene, keoxifene, LY117018, onapristone, and toremifene (FARESTON®).

Inhibitors of the enzyme aromatase regulate estrogen production in the adrenal glands. Examples include 4(5)-imidazoles, aminoglutethimide, megestrol acetate (MEGACE®), exemestane, formestane, fadrozole, vorozole (RIVISOR®), letrozole (FEMARA®), and anastrozole (ARIMIDEX®).

Examples of anti-androgens include apalutamide, abiraterone, enzalutamide, flutamide, galeterone, nilutamide, bicalutamide, leuprolide, goserelin, ODM-201, APC-100, ODM-204.

An example progesterone receptor antagonist includes onapristone.

Anti-Angiogenic Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-angiogenic agent. Anti-angiogenic agents that can be co-administered include, but are not limited to, retinoid acid and derivatives thereof, 2-methoxyestradiol, ANGIOSTATIN®, ENDOSTATIN®, regorafenib, necuparanib, suramin, squalamine, tissue inhibitor of metalloproteinase-1, tissue inhibitor of metalloproteinase-2, plasminogen activator inhibitor-1, plasminogen activator inhibitor-2, cartilage-derived inhibitor, paclitaxel (nab-paclitaxel), platelet factor 4, protamine sulphate (clupeine), sulphated chitin derivatives (prepared from queen crab shells), sulphated polysaccharide peptidoglycan complex (sp-pg), staurosporine, modulators of matrix metabolism including proline analogs such as 1-azetidine-2-carboxylic acid (LACA), cishydroxyproline, d,I-3,4-dehydroproline, thiaproline, $\alpha,\alpha'$-dipyridyl, beta-aminopropionitrile fumarate, 4-propyl-5-(4-pyridinyl)-2(3h)-oxazolone, methotrexate, mitoxantrone, heparin, interferons, 2 macroglobulin-serum, chicken inhibitor of metalloproteinase-3 (ChIMP-3), chymostatin, beta-cyclodextrin tetradecasulfate, eponemycin, fumagillin, gold sodium thiomalate, d-penicillamine, beta-1-anticollagenase-serum, alpha-2-antiplasmin, bisantrene, lobenzarit disodium, n-2-carboxyphenyl-4-chloroanthronilic acid disodium or "CCA", thalidomide, angiostatic steroid, carboxy aminoimidazole, metalloproteinase inhibitors such as BB-94, inhibitors of S100A9 such as tasquinimod. Other anti-angiogenesis agents include antibodies, preferably monoclonal antibodies against these angiogenic growth factors: beta-FGF, alpha-FGF, FGF-5, VEGF isoforms, VEGF-C, HGF/SF, and Ang-1/Ang-2.

Anti-Fibrotic Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-fibrotic agent. Anti-fibrotic agents that can be co-administered include, but are not limited to, the compounds such as beta-aminoproprionitrile (BAPN), as well as the compounds disclosed in U.S. Pat. No. 4,965,288 relating to inhibitors of lysyl oxidase and their use in the treatment of diseases and conditions associated with the abnormal deposition of collagen and U.S. Pat. No. 4,997,854 relating to compounds which inhibit LOX for the treatment of various pathological fibrotic states, which are herein incorporated by reference. Further exemplary inhibitors are described in U.S. Pat. No. 4,943,593 relating to compounds such as 2-isobutyl-3-fluoro-, chloro-, or bromo-allylamine, U.S. Pat. Nos. 5,021,456, 5,059,714, 5,120,764, 5,182,297, 5,252,608 relating to 2-(1-naphthyloxymemyl)-3-fluoroallylamine, and US 2004-0248871, which are herein incorporated by reference.

Exemplary anti-fibrotic agents also include the primary amines reacting with the carbonyl group of the active site of the lysyl oxidases, and more particularly those which produce, after binding with the carbonyl, a product stabilized by resonance, such as the following primary amines: emylenemamine, hydrazine, phenylhydrazine, and their derivatives; semicarbazide and urea derivatives; aminonitriles such as BAPN or 2-nitroethylamine; unsaturated or saturated haloamines such as 2-bromo-ethylamine, 2-chloroethylamine, 2-trifluoroethylamine, 3-bromopropylamine, and p-halobenzylamines; and selenohomocysteine lactone.

Other anti-fibrotic agents are copper chelating agents penetrating or not penetrating the cells. Exemplary compounds include indirect inhibitors which block the aldehyde derivatives originating from the oxidative deamination of the lysyl and hydroxylysyl residues by the lysyl oxidases. Examples include the thiolamines, particularly D-penicillamine, and its analogs such as 2-amino-5-mercapto-5-methylhexanoic acid, D-2-amino-3-methyl-3-((2-acetamidoethyl)dithio)butanoic acid, p-2-amino-3-methyl-3-((2-aminoethyl)dithio)butanoic acid, sodium-4-((p-1-dimethyl-2-amino-2-carboxyethyl)dithio)butane sulphurate, 2-acetamidoethyl-2-acetamidoethanethiol sulphanate, and sodium-4-mercaptobutanesulphinate trihydrate.

Anti-Inflammatory Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-inflammatory agent. Example anti-inflammatory agents include without limitation inhibitors of one or more of arginase (ARG1 (NCBI Gene ID: 383), ARG2 (NCBI Gene ID: 384)), carbonic anhydrase (CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)), prostaglandin-endoperoxide synthase 1 (PTGS1, COX-1; NCBI Gene ID: 5742), prostaglandin-endoperoxide synthase 2 (PTGS2, COX-2; NCBI Gene ID: 5743), secreted phospholipase A2, prostaglandin E synthase (PTGES, PGES; Gene ID: 9536), arachidonate 5-lipoxygenase (ALOX5, 5-LOX; NCBI Gene ID: 240), soluble epoxide hydrolase 2 (EPHX2, SEH; NCBI Gene ID: 2053) and/or mitogen-activated protein kinase kinase kinase 8 (MAP3K8, TPL2; NCBI Gene ID: 1326). In some embodiments, the inhibitor is a dual inhibitor, e.g., a dual inhibitor of COX-2/COX-1, COX-2/SEH, COX-2/CA, COX-2/5-LOX.

Examples of inhibitors of prostaglandin-endoperoxide synthase 1 (PTGS1, COX-1; NCBI Gene ID: 5742) that can be co-administered include without limitation mofezolac, GLY-230, and TRK-700.

Examples of inhibitors of prostaglandin-endoperoxide synthase 2 (PTGS2, COX-2; NCBI Gene ID: 5743) that can be co-administered include without limitation diclofenac, meloxicam, parecoxib, etoricoxib, AP-101, celecoxib, AXS-06, diclofenac potassium, DRGT-46, AAT-076, meisuoshuli, lumiracoxib, meloxicam, valdecoxib, zaltoprofen, nimesulide, Anitrazafen, Apricoxib, Cimicoxib, Deracoxib, Flumizole, Firocoxib, Mavacoxib, NS-398, Pamicogrel, Parecoxib, Robenacoxib, Rofecoxib, Rutecarpine, Tilmacoxib, and Zaltoprofen. Examples of dual COX1/COX2 inhibitors that can be co-administered include without limitation, HP-5000, lornoxicam, ketorolac tromethamine, bromfenac sodium, ATB-346, HP-5000. Examples of dual COX-2/carbonic anhydrase (CA) inhibitors that can be co-administered include without limitation polmacoxib and imrecoxib.

Examples of inhibitors of secreted phospholipase A2, prostaglandin E synthase (PTGES, PGES; Gene ID: 9536) that can be co-administered include without limitation LY3023703, GRC 27864, and compounds described in WO2015158204, WO2013024898, WO2006063466, WO2007059610, WO2007124589, WO2010100249, WO2010034796, WO2010034797, WO2012022793, WO2012076673, WO2012076672, WO2010034798, WO2010034799, WO2012022792, WO2009103778, WO2011048004, WO2012087771, WO2012161965, WO2013118071, WO2013072825, WO2014167444, WO2009138376, WO2011023812, WO2012110860, WO2013153535, WO2009130242, WO2009146696, WO2013186692, WO2015059618, WO2016069376, WO2016069374, WO2009117985, WO2009064250, WO2009064251, WO2009082347, WO2009117987, and WO2008071173. Metformin has further been found to repress the COX2/PGE2/STAT3 axis, and can be co-administered. See, e.g., Tong, et al., *Cancer Lett.* (2017) 389:23-32; and Liu, et al., *Oncotarget.* (2016) 7(19):28235-46.

Examples of inhibitors of carbonic anhydrase (e.g., one or more of CA1 (NCBI Gene ID: 759), CA2 (NCBI Gene ID: 760), CA3 (NCBI Gene ID: 761), CA4 (NCBI Gene ID: 762), CA5A (NCBI Gene ID: 763), CA5B (NCBI Gene ID: 11238), CA6 (NCBI Gene ID: 765), CA7 (NCBI Gene ID: 766), CA8 (NCBI Gene ID: 767), CA9 (NCBI Gene ID: 768), CA10 (NCBI Gene ID: 56934), CA11 (NCBI Gene ID: 770), CA12 (NCBI Gene ID: 771), CA13 (NCBI Gene ID: 377677), CA14 (NCBI Gene ID: 23632)) that can be co-administered include without limitation acetazolamide, methazolamide, dorzolamide, zonisamide, brinzolamide and dichlorphenamide. A dual COX-2/CA1/CA2 inhibitor that can be co-administered includes CG100649.

Examples of inhibitors of arachidonate 5-lipoxygenase (ALOX5, 5-LOX; NCBI Gene ID: 240) that can be co-administered include without limitation meclofenamate sodium, zileuton.

Examples of inhibitors of soluble epoxide hydrolase 2 (EPHX2, SEH; NCBI Gene ID: 2053) that can be co-administered include without limitation compounds described in WO2015148954. Dual inhibitors of COX-2/SEH that can be co-administered include compounds described in WO2012082647. Dual inhibitors of SEH and fatty acid amide hydrolase (FAAH; NCBI Gene ID: 2166) that can be co-administered include compounds described in WO2017160861.

Examples of inhibitors of mitogen-activated protein kinase kinase kinase 8 (MAP3K8, tumor progression loci-2, TPL2; NCBI Gene ID: 1326) that can be co-administered include without limitation GS-4875, GS-5290, BHM-078 and those described, e.g., in WO2006124944, WO2006124692, WO2014064215, WO2018005435, Teli, et al., *J Enzyme Inhib Med Chem.* (2012) 27(4):558-70; Gangwall, et al., *Curr Top Med Chem.* (2013) 13(9):1015-35; Wu, et al., *Bioorg Med Chem Lett.* (2009) 19(13):3485-8; Kaila, et al., *Bioorg Med Chem.* (2007) 15(19):6425-42; and Hu, et al., *Bioorg Med Chem Lett.* (2011) 21(16):4758-61.

Tumor Oxygenation Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent that promotes or increases tumor oxygenation or reoxygenation, or prevents or reduces tumor hypoxia. Illustrative agents that can be co-administered include, e.g., Hypoxia inducible factor-1 alpha (HIF-1α) inhibitors, such as PT-2977, PT-2385; VEGF inhibitors, such as bevasizumab, IMC-3C5, GNR-011, tanibirumab, LYN-00101, ABT-165; and/or an oxygen carrier protein (e.g., a heme nitric oxide and/or oxygen binding protein (HNOX)), such as OMX-302 and HNOX proteins described in WO 2007/137767, WO 2007/139791, WO 2014/107171, and WO 2016/149562.

Immunotherapeutic Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an immunotherapeutic agent. Example immunotherapeutic agents that can be co-administered include without limitation abagovomab, ABP-980, adecatumumab, afutuzumab, alemtuzumab, altumomab, amatuximab, anatumomab, arcitumomab, bavituximab, bectumomab, bevacizumab, bivatuzumab, blinatumomab, brentuximab, cantuzumab, catumaxomab, CC49, cetuximab, citatuzumab, cixutumumab, clivatuzumab, conatumumab, dacetuzumab, dalotuzumab, daratumumab, detumomab, dinutuximab, domvanalimab, drozitumab, duligotumab, dusigitumab, ecromeximab, elotuzumab, emibetuzumab, ensituximab, ertumaxomab, etaracizumab, farletuzumab, ficlatuzumab, figitumumab, flanvotumab, futuximab, ganitumab, gemtuzumab, girentuximab, glembatumumab, ibritumomab, igovomab, imgatuzumab, indatuximab, inotuzumab, intetumumab, ipilimumab (YERVOY®, MDX-010, BMS-734016, and MDX-101), iratumumab, labetuzumab, lexatumumab, lintuzumab, lorvotuzumab, lucatumumab, mapatumumab, matuzumab, milatuzumab, minretumomab, mitumomab, mogamulizumab, moxetumomab, naptumomab, narnatumab, necitumumab, nimotuzumab, nofetumomab, OBI-833, obinutuzumab, ocaratuzumab, ofatumumab, olaratumab, onartuzumab, oportuzumab, oregovomab, panitumumab, parsatuzumab, pasudotox, patritumab, pemtumomab, pertuzumab, pintumomab, pritumumab, racotumomab, radretumab, ramucirumab (Cyramza®), rilotumumab, rituximab, robatumumab, sacituzumab, samalizumab, satumomab, sibrotuzumab, siltuximab, solitomab, simtuzumab, tacatuzumab, taplitumomab, tenatumomab, teprotumumab, tigatuzumab, tositumomab, trastuzumab, tucotuzumab, ubilituximab, veltuzumab, vorsetuzumab, votumumab, zalutumumab, zimberelimab and 3F8. Rituximab can be used for treating indolent B-cell cancers, including marginal-zone lymphoma, WM, CLL and small lymphocytic lymphoma. A combination of Rituximab and chemotherapy agents is especially effective.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a bispecific antibody. Illustrative bi-specific antibodies that can be combined or co-administered include without limitation ABT-165 (DLL4NEGF), MM-141 (IGF-1/ErbB3), MM-Ill (Erb2/Erb3), JNJ-64052781 (CD19/CD3), PRS-343 (CD-137/HER2), AFM26 (BCMA/CD16A), JNJ-61186372 (EGFR/cMET), AMG-211 (CEA/CD3), RG7802 (CEA/CD3), ERY-974 (CD3/GPC3) vancizumab (angiopoietinsNEGF), PF-06671008 (Cadherins/CD3), AFM-13 (CD16/CD30), APV0436 (CD123/CD3), flotetuzumab (CD123/CD3), REGN-1979 (CD20/CD3), MCLA-117 (CD3/CLEC12A), MCLA-128 (HER2/HER3), JNJ-0819, JNJ-7564 (CD3/heme), AMG-757 (DLL3-CD3), MGD-013 (PD-1/LAG-3), FS-118 (LAG-3/PD-L1) MGD-019 (PD-1/CTLA-4), KN-046 (PD-1/CTLA-4), MEDI-5752 (CTLA-4/PD-1), RO-7121661 (PD-1/TIM-3), XmAb-20717 (PD-1/CTLA-4), AK-104 (CTLA-4/PD-1), AMG-330 (CD33/CD3), AMG-420 (BCMA/CD3), BI-836880 (VEFG/ANG2), JNJ-63709178 (CD123/CD3), MGD-007 (CD3/gpA33), MGD-009 (CD3/B7H3), AGEN1223, IMCgp100 (CD3/gp100), AGEN-1423, ATOR-1015 (CTLA-4/OX40), LY-3415244 (TIM-3/PDL1), INHIBRX-105 (4-1BB/PDL1), faricimab (VEGF-A/ANG-2), FAP-4-IBBL (4-1BB/FAP), XmAb-13676 (CD3/CD20), TAK-252 (PD-1/OX40L), TG-1801 (CD19/CD47), XmAb-18087 (SSTR2/CD3), catumaxomab (CD3/EpCAM), SAR-156597 (IL4/IL13), EMB-01 (EGFR/cMET), REGN-4018 (MUC16/CD3), REGN-1979 (CD20/CD3), RG-7828 (CD20/CD3), CC-93269 (CD3/BCMA), REGN-5458 (CD3/BCMA), navicixizumab (DLL4NEGF), GRB-1302 (CD3/Erbb2), vanucizumab (VEGF-A/ANG-2), GRB-1342 (CD38/CD3), GEM-333 (CD3/CD33), IMM-0306 (CD47/CD20), RG6076, MEDI5752 (PD-1/CTLA-4), and LY3164530 (MET/EGFR).

The exemplified therapeutic antibodies may be further labeled or combined with a radioisotope particle such as indium-111, yttrium-90 (90Y-clivatuzumab), or iodine-131.

In some embodiments, the immunotherapeutic agent is an antibody-drug conjugate (ADC). Illustrative therapeutic agents (e.g., anticancer or antineoplastic agents) that can be conjugated to the drug-conjugated antibodies, fragments thereof, or antibody mimetics include without limitation monomethyl auristatin E (MMAE), monomethyl auristatin F (MMAF), a calicheamicin, ansamitocin, maytansine or an analog thereof (e.g., mertansine/emtansine (DM1), ravtansine/soravtansine (DM4)), an anthracyline (e.g., doxorubicin, daunorubicin, epirubicin, idarubicin), pyrrolobenzodiazepine (PBD) DNA cross-linking agent SC-DR002 (D6.5), duocarmycin, a microtubule inhibitors (MTI) (e.g., a taxane, a vinca alkaloid, an epothilone), a pyrrolobenzodiazepine (PBD) or dimer thereof, a duocarmycin (A, B1, B2, C1, C2, D, SA, CC-1065), cholera toxin, ricin, *Pseudomonas* exotoxin, *Bordetella pertussis* adenylate cyclase toxin, diphtheria toxin, caspase activators, and other anticancer or anti-neoplastic agents described herein. In some embodiments, the therapeutic agent conjugated to the drug-conjugated antibody is a topoisomerase I inhibitor (e.g., a camptothecin analog, such as irinotecan or its active metabolite SN38).

Illustrative ADCs that can be co-administered include without limitation drug-conjugated antibodies, fragments thereof, or antibody mimetics targeting the proteins or antigens listed above and herein. Example ADCs that can be co-administered include without limitation gemtuzumab, brentuximab, belantamab (e.g., belantamab mafodotin), camidanlumab (e.g., camidaniumab tesirine), trastuzumab (e.g., trastuzumab deruxtecan; trasuzumab emtansine), inotuzumab, glembatumumab, anetumab, mirvetuximab (e.g., mirvetuximab soravtansine), depatuxizumab, vadastuximab, labetuzumab, ladiratuzumab (e.g., ladiratuzumab vedotin), loncastuximab (e.g., loncastuximab tesirine), sacituzumab (e.g., sacituzumab govitecan), datopotamab (e.g., datopotamab deruxtecan; DS-1062; Dato-DXd), patritumab (e.g., patritumab deruxtecan), lifastuzumab, indusatumab, polatuzumab (e.g., polatuzumab vedotin), pinatuzumab, coltuximab, upifitamab (e.g., upifitamab rilsomotin), indatuximab, milatuzumab, rovalpituzumab (e.g., rovalpituzumab tesirine), enfortumab (e.g., enfortumab vedotin), tisotumab (e.g., tisotumab vedotin), tusamitamab (e.g., tusamitamab ravtansine), disitamab (e.g., disitamab vedotin), telisotuzumab vedotin (ABBV-399), AGS-16C3F, ASG-22ME, AGS67E, AMG172, AMG575, BAY 1129980, BAY 1187982, BAY94-9343, GSK2857916, Humax-TF-ADC, IMGN289, IMGN529, IMGN853, LOP628, PCA062, MDX-1203 (BMS936561), MEDI-547, PF-06263507, PF-06647020, PF-06647263, PF-06664178, RG7450, RG7458, RG7598, SAR566658, SGN-CD19A, SGN-CD33A, SGN-CD70A, SGN-LIV1A and SYD985. ADCs that can be co-administered are described, e.g., in Lambert, et al., *Adv Ther* (2017) 34:1015-1035 and in de Goeij, *Current Opinion in Immunology* (2016) 40:14-23.

Cancer Gene Therapy and Cell Therapy

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a cancer gene therapy and cell therapy. Cancer gene therapies and cell therapies include the insertion of a normal gene into cancer cells to replace a mutated or altered gene; genetic modification to silence a mutated gene; genetic approaches to directly kill the cancer cells; including the infusion of immune cells designed to replace most of the patient's own immune system to enhance the immune response to cancer cells, or activate the patient's own immune system (T cells or Natural Killer cells) to kill cancer cells, or find and kill the cancer cells; genetic approaches to modify cellular activity to further alter endogenous immune responsiveness against cancer.

Cellular Therapies

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more cellular therapies. Illustrative cellular therapies include without limitation co-administration of one or more of a population of immune cells. In some embodiments, the immune cells are natural killer (NK) cells, NK-T cells, T cells, gamma delta T cells, B-cells, cytokine-induced killer (CIK) cells, macrophage (MAC) cells, tumor infiltrating lymphocytes (TILs) a granulocyte, an innate lymphoid cell, a megakaryocyte, a monocyte, a macrophage, a platelet, a thymocyte, a myeloid cell, and/or dendritic cells (DCs). In some embodiments, the cellular therapy entails a T cell therapy, e.g., co-administering a population of alpha/beta TCR T cells, gamma/delta TCR T cells, regulatory T (Treg) cells and/or TRuC™ T cells. In some embodiments, the cellular therapy entails a NK cell therapy, e.g., co-administering NK-92 cells. As appropriate, a cellular therapy can entail the co-administration of cells that are autologous, syngeneic or allogeneic to the subject.

In some embodiments, the cellular therapy entails co-administering immune cells engineered to express chimeric antigen receptors (CARs) or T cell receptors (TCRs) TCRs. In particular embodiments, a population of immune cells is engineered to express a CAR, wherein the CAR comprises a tumor antigen-binding domain. In other embodiments, a population of immune cells is engineered to express T cell receptors (TCRs) engineered to target tumor derived peptides presented on the surface of tumor cells. In one embodiment, the immune cell engineered to express chimeric antigen receptors (CARs) or T cell receptors (TCRs) TCRs is a T cell. In another embodiment, the immune cell engineered to express chimeric antigen receptors (CARs) or T cell receptors (TCRs) TCRs is an NK cell.

With respect to the structure of a CAR, in some embodiments, the CAR comprises an antigen binding domain, a transmembrane domain, and an intracellular signaling domain. In some embodiments, the intracellular domain comprises a primary signaling domain, a costimulatory domain, or both of a primary signaling domain and a costimulatory domain. In some embodiments, the primary signaling domain comprises a functional signaling domain of one or more proteins selected from the group consisting of CD3 zeta, CD3 gamma, CD3 delta, CD3 epsilon, common FcR gamma (FCERIG), FcR beta (Fc Epsilon Rlb), CD79a, CD79b, Fcgamma RIIa, DAP10, and DAP12, 4.1BB/CD137, activating NK cell receptors, an Immunoglobulin protein, B7-H3, BAFFR, BLAME (SLAMF8), BTLA, CD100 (SEMA4D), CD103, CD160 (NK1, NK28, BY55), CD161, CD18, CD19, CD19a, CD2, CD247, CD27, CD276 (B7-H3), CD28, CD29, CD3 delta, CD3 epsilon, CD3 gamma, CD30, CD4, CD40, CD49a, CD49D, CD49f, CD69, CD7, CD84, CD8alpha, CD8beta, CD96 (Tactile), CD11a, CD11b, CD11c, CD11d, CDS, CEACAM1, CRT AM, cytokine receptor, DAP-10, DNAM1 (CD226), Fc gamma receptor, GADS, GITR, HVEM (LIGHTR), IA4, ICAM-1, ICAM-1, Ig alpha (CD79a), IL-2R beta, IL-2R gamma, IL-7R alpha, inducible T cell costimulator (ICOS), integrins, ITGA4, ITGA4, ITGA6, ITGAD, ITGAE, ITGAL, ITGAM, ITGAX, ITGB2, ITGB7, ITGB1, KIRDS2, LAT, LFA-1, LFA-1, ligand that binds with CD83, LIGHT, LIGHT, LTBR, Ly9 (CD229), Ly108), lymphocyte function-associated antigen-1 (LFA-1; CD1-1a/CD18), MHC class 1 molecule, NKG2C, NKG2D, NKp30, NKp44, NKp46, NKp80 (KLRF1), OX-40, PAG/Cbp, programmed death-1 (PD-1), PSGL1, SELPLG (CD162), Signaling Lymphocytic Activation Molecules (SLAM proteins), SLAM (SLAMF1; CD150; IPO-3), SLAMF4 (CD244; 2B4), SLAMF6 (NTB-A, SLAMF7, SLP-76, TNF receptor proteins, TNFR2, TNFSF14, a Toll ligand receptor, TRANCE/RANKL, VLA1, or VLA-6, or a fragment, truncation, or a combination thereof.

In some embodiments, the costimulatory domain comprises a functional domain of one or more proteins selected from the group consisting of CD27, CD28, 4-IBB(CD137), OX40, CD30, CD40, PD-1, ICOS, CD2, CD7, LIGHT, NKG2C, lymphocyte function-associated antigen-1 (LFA-1), MYD88, B7-H3, a ligand that specifically binds with CD83, CDS, ICAM-1, GITR, BAFFR, HVEM (LIGHTR), SLAMF7, NKp80 (KLRFI), CD19, CD4, CD8alpha, CD8beta, IL-2R beta, IL-2R gamma, IL7R alpha, ITGA4, VLA1, CD49a, ITGA4, IA4, CD49D, ITGA6, VLA-6, CD49f, ITGAD, ITGAE, CD103, ITGAL, CD1A (NCBI Gene ID: 909), CD1B (NCBI Gene ID: 910), CD1C (NCBI Gene ID: 911), CD1D (NCBI Gene ID: 912), CD1E (NCBI Gene ID: 913), ITGAM, ITGAX, ITGB1, CD29, ITGB2 (CD18, LFA-1), ITGB7, TNFR2, TRANCE/RANKL, DNAM1 (CD226), SLAMF4 (CD244, 2B4), CD84, CD96 (Tactile), CEACAM1, CRTAM, Ly9 (CD229), CD160 (NK1, NK28, BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, NKp44, NKp30, NKp46, and NKG2D.

In some embodiments, the transmembrane domain comprises a transmembrane domain derived from a protein selected from the group consisting of the alpha, beta or zeta chain of the T-cell receptor, CD28, CD3 epsilon, CD3 delta, CD3 gamma, CD45, CD4, CD5, CD7, CD8 alpha, CD8 beta, CD9, CD11a, CD11b, CD11c, CD11d, CD16, CD18, CD22, CD33, CD37, CD64, CD80, CD86, CD134, CD137, CD154, KIRDS2, OX40, CD2, CD27, ICOS (CD278), 4-1BB(CD137), GITR, CD40, BAFFR, HVEM (LIGHTR), SLAMF7, NKp80 (KLRF1), CD19, CD19a, IL-2R beta, IL-2R gamma, IL7R alpha, ITGA1, VLA1, CD49a, ITGA4, IA4, CD49D, ITGA6, VLA-6, CD49f, ITGAD, CD1A, CD1B, CD1C, CD1D, CD1E, ITGAE, CD103, ITGAL, ITGAM, ITGAX, ITGB1, ITGB2, ITGB7, CD29, ITGB2 (LFA-1, CD18), ITGB7, TNFR2, DNAM1 (CD226), SLAMF4 (CD244, 2B4), CD84, CD96 (TACTILE), CEACAM1, CRTAM, Ly9 (CD229), CD160 (NK1, NK28, BY55), PSGL1, CD100 (SEMA4D), SLAMF6 (NTB-A, Ly108), SLAM (SLAMF1, CD150, IPO-3), BLAME (SLAMF8), SELPLG (CD162), LTBR, PAG/Cbp, NKp44, NKp30, NKp46, NKG2D, and NKG2C activating NK cell receptors, an Immunoglobulin protein, BTLA, CD247, CD276 (B7-H3), CD30, CD84, CDS, cytokine receptor, Fc gamma receptor, GADS, ICAM-1, Ig alpha (CD79a), integrins, LAT, a ligand that binds with CD83, LIGHT, MHC class 1 molecule, PAG/Cbp, TNFSF14, a Toll ligand receptor, TRANCE/RANKL, or a fragment, truncation, or a combination thereof.

In some embodiments, the CAR comprises a hinge domain. A hinge domain may be derived from a protein selected from the group consisting of the CD2, CD3 delta, CD3 epsilon, CD3 gamma, CD4, CD7, CD8.alpha., CD8.beta., CD11a (ITGAL), CD11b (ITGAM), CD11c (ITGAX), CD1 id (ITGAD), CD18 (ITGB2), CD19 (B4), CD27 (TNFRSF7), CD28, CD28T, CD29 (ITGB1), CD30 (TNFRSF8), CD40 (TNFRSF5), CD48 (SLAMF2), CD49a (ITGA1), CD49d (ITGA4), CD49f (ITGA6), CD66a (CEACAM1), CD66b (CEACAM8), CD66c (CEACAM6), CD66d (CEACAM3), CD66e (CEACAM5), CD69 (CLEC2), CD79A (B-cell antigen receptor complex-associated alpha chain), CD79B (B-cell antigen receptor complex-associated beta chain), CD84 (SLAMF5), CD96 (Tactile), CD100 (SEMA4D), CD103 (ITGAE), CD134 (OX40), CD137 (4-1BB), CD150 (SLAMF1), CD158A (KIR2DL1), CD158B1 (KIR2DL2), CD158B2 (KIR2DL3), CD158C (KIR3DP1), CD158D (KIRDL4), CD158F1 (KIR2DL5A), CD158F2 (KIR2DL5B), CD158K (KIR3DL2), CD160 (NK1, NK28, BY55), CD162 (SELPLG), CD226 (DNAM1), CD229 (SLAMF3), CD244 (SLAMF4), CD247 (CD3-zeta), CD258 (LIGHT), CD268 (BAFFR), CD270 (TNFSF14), CD272 (BTLA), CD276 (B7-H3), CD279 (PD-1), CD314 (NKG2D), CD319 (SLAMF7), CD335 (NK-p46), CD336 (NK-p44), CD337 (NK-p30), CD352 (SLAMF6), CD353 (SLAMF8), CD355 (CRTAM), CD357 (TNFRSF18), inducible T cell co-stimulator (ICOS), LFA-1 (CD11a/CD18), NKG2C, DAP-10, ICAM-1, NKp80 (KLRF1), IL-2R beta, IL-2R gamma, IL-7R alpha, LFA-1, SLAMF9, LAT, GADS (GrpL), SLP-76 (LCP2), PAG1/CBP, a CD83 ligand, Fc gamma receptor, MHC class 1 molecule, MHC class 2 molecule, a TNF receptor protein, an immunoglobulin protein, a cytokine receptor, an integrin, activating NK cell receptors, or Toll ligand receptor, IgG1, IgG2, IgG3, IgG4, IgA, IgD, IgE, IgM or fragment or combination thereof.

In some embodiments, the TCR or CAR antigen binding domain or the immunotherapeutic agent described herein (e.g., monospecific or multi-specific antibody or antigen-binding fragment thereof or antibody mimetic) binds a tumor-associated antigen (TAA). In some embodiments, the tumor-associated antigen is selected from the group consisting of: CD19; CD123; CD22; CD30; CD171; CS-1 (also referred to as CD2 subset 1, CRACC, SLAMF7, CD319, and 19A24); C-type lectin-like molecule-1 (CLL-1 or CLECLI); CD33; epidermal growth factor receptor variant III (EGFRvlll); ganglioside G2 (GD2); ganglioside GD3 (αNeuSAc(2-8)αNeuSAc(2-3)βDGaip(1-4)bDGIcp(1-1) Cer); ganglioside GM3 (αNeuSAc(2-3)βDGalp(1-4) βDGlcp(1-1)Cer); GM-CSF receptor, TNF receptor superfamily member 17 (TNFRSF17, BCMA); B-lymphocyte cell adhesion molecule; Tn antigen ((Tn Ag) or (GaINAcu-Ser/Thr)); prostate-specific membrane antigen (PSMA); Receptor tyrosine kinase-like orphan receptor 1 (RORI); Tumor-associated glycoprotein 72 (TAG72); CD38; CD44v6; Carcinoembryonic antigen (CEA); Epithelial cell adhesion molecule (EPCAM); B7H3 (CD276); KIT (CD117); Interleukin-13 receptor subunit alpha-2 (IL-13Ra2 or CD213A2); Mesothelin; Interleukin 11 receptor alpha (IL-11Ra); prostate stem cell antigen (PSCA); Protease Serine 21 (Testisin or PRSS21); vascular endothelial growth factor receptor 2 (VEGFR2); HLA class I antigen A-2 alpha; HLA antigen; Lewis(Y) antigen; CD24; Platelet-derived growth factor receptor beta (PDGFR-beta); Stage-specific embryonic antigen-4 (SSEA-4); CD20; delta like 3 (DLL3); Folate receptor alpha; Folate receptor beta, GDNF alpha 4 receptor, Receptor tyrosine-protein kinase, ERBB2 (Her2/neu); Mucin 1, cell surface associated (MUC1); APRIL receptor, ADP ribosyl cyclase-1; Ephb4 tyrosine kinase receptor, DCAMKL1 serine threonine kinase, Aspartate beta-hydroxylase, epidermal growth factor receptor (EGFR); neural cell adhesion molecule (NCAM); Prostase; prostatic acid phosphatase (PAP); elongation factor 2 mutated (ELF2M); Ephrin B2; fibroblast activation protein alpha (FAP); insulin-like growth factor 1 receptor (IGF-I receptor), carbonic anhydrase IX (CAIX); Proteasome (Prosome, Macropain) Subunit, Beta Type, 9 (LMP2); glycoprotein 100 (gp100); oncogene fusion protein consisting of breakpoint cluster region (BCR) and Abelson murine leukemia viral oncogene homolog 1 (Abl) (bcr-abl); tyrosinase; ephrin type-A receptor 2 (EphA2); ephrin type-A receptor 3 (EphA3), Fucosyl GM1; sialyl Lewis adhesion molecule (sLe); transglutaminase 5 (TGS5); high molecular weight-melanomaassociatedantigen (HMWMAA); o-acetyl-GD2 ganglioside (OAcGD2); Folate receptor beta; tumor endothelial marker 1 (TEM1/CD248); tumor endothelial marker 7-related (TEM7R); six transmembrane epithelial antigen of the prostate I (STEAP1); claudin 6 (CLDN6); thyroid stimulating hormone receptor (TSHR); G protein-coupled receptor class C group 5, member D (GPRCSD); IL-15 receptor (IL-15); chromosome X open reading frame 61 (CXORF61); CD97; CD179a; anaplastic lymphoma kinase (ALK); Polysialic acid; placenta-specific 1 (PLAC1); hexasaccharide portion of globoH glycoceramide (GloboH); mammary gland differentiation antigen (NY-BR-1); uroplakin 2 (UPK2); Hepatitis A virus cellular receptor 1 (HAVCR1); adrenoceptor beta 3 (ADRB3); pannexin 3 (PANX3); G protein-coupled receptor 20 (GPR20); lymphocyte antigen 6 complex, locus K 9 (LY6K); Olfactory receptor 51E2 (ORS IE2); TCR Gamma Alternate Reading Frame Protein (TARP); Wilms tumor protein (WT1); Cancer/testis antigen 1 (NY-ESO-1); Cancer/testis antigen 2 (LAGE-la); Melanoma associated antigen 1 (MAGE-A1); Melanoma associated antigen 3 (MAGE-A3); Melanoma associated antigen 4 (MAGE-A4); T cell receptor beta 2 chain C; ETS translocation-variant gene 6, located on chromosome 12p (ETV6-AML); sperm protein 17 (SPA17); X Antigen Family, Member 1A (XAGE1); angiopoietin-binding cell surface receptor 2 (Tie 2); melanoma cancer testis antigen-1 (MADCT-1); melanoma cancer testis antigen-2 (MAD-CT-2); Fos-related antigen 1; tumor protein p53, (p53); p53 mutant; prostein; survivin; telomerase; prostate carcinoma tumor antigen-1 (PCTA-1 or Galectin 8), melanoma antigen recognized by T cells 1 (MelanA or MARTI); Rat sarcoma (Ras) mutant; human Telomerase reverse transcriptase (hTERT); sarcoma translocation breakpoints; melanoma inhibitor of apoptosis (ML-IAP); ERG (transmembrane protease, serine 2 (TMPRSS2) ETS fusion gene); N-Acetyl glucosaminyl-transferase V (NA17); paired box protein Pax-3 (PAX3); Androgen receptor, Cyclin-A1; Cyclin B1; v-myc avian myelocytomatosis viral oncogene neuroblastoma derived homolog (MYCN); Ras Homolog Family Member C (RhoC); Tyrosinase-related protein 2 (TRP-2); Cytochrome P450 1B1(CYP IBI); CCCTC-Binding Factor (Zinc Finger Protein)-Like (BORIS or Brother of the Regulator of Imprinted Sites), Squamous Cell Carcinoma Antigen Recognized By T Cells 3 (SART3); Paired box protein Pax-5 (PAX5); proacrosin binding protein sp32 (OY-TES I); lymphocyte-specific protein tyrosine kinase (LCK); A kinase anchor protein 4 (AKAP-4); Peptidoglycan recognition protein, synovial sarcoma, X breakpoint 2 (SSX2); Receptor for Advanced Glycation Endproducts (RAGE-I); renal ubiquitous 1 (RUI); renal ubiquitous 2 (RU2); legumain; human papilloma virus E6 (HPV E6); human papilloma virus E7 (HPV E7); intestinal carboxyl esterase; heat shock protein 70-2 mutated (mut hsp70-2); CD79a; CD79b; CD72; Leukocyte-associated immunoglobulin-like receptor 1 (LAIRI); Fc fragment of IgA receptor (FCAR or CD89); Leukocyte immunoglobulin-like receptor subfamily A member 2 (LILRA2); CD300 molecule-like family member f (CD300LF); C-type lectin domain family 12 member A (CLEC12A); bone marrow stromal cell antigen 2 (BST2); EGF-like module containing mucin-like hormone receptor-like 2 (EMR2); lymphocyte antigen 75 (LY75); Glypican-2 (GPC2); Glypican-3 (GPC3); Fc receptor-like 5 (FCRL5); and immunoglobulin lambda-like polypeptide 1 (IGLL1). In some embodiments, the target is an epitope of the tumor associated antigen presented in an MHC.

In some embodiments, the tumor antigen is selected from CD150, 5T4, ActRIIA, B7, TNF receptor superfamily member 17 (TNFRSF17, BCMA), CA-125, CCNA1, CD123, CD126, CD138, CD14, CD148, CD15, CD19, CD20, CD200, CD21, CD22, CD23, CD24, CD25, CD26, CD261, CD262, CD30, CD33, CD362, CD37, CD38, CD4, CD40, CD40L, CD44, CD46, CD5, CD52, CD53, CD54, CD56, CD66a-d, CD74, CD8, CD80, CD92, CE7, CS-1, CSPG4, ED-B fibronectin, EGFR, EGFRvIII, EGP-2, EGP-4, EPHa2, ErbB2, ErbB3, ErbB4, FBP, HER1-HER2 in combination, HER2-HER3 in combination, HERV-K, HIV-1 envelope glycoprotein gp120, HIV-1 envelope glycoprotein gp41, HLA-DR, HLA class I antigen alpha G, HM1.24, K-Ras GTPase, HMW-MAA, Her2, Her2/neu, IGF-1R, IL-IIRalpha, IL-13R-alpha2, IL-2, IL-22R-alpha, IL-6, IL-6R, Ia, Ii, L1-CAM, L1-cell adhesion molecule, Lewis Y, L1-CAM, MAGE A3, MAGE-A1, MART-1, MUC1, NKG2C ligands, NKG2D Ligands, NYESO-1, OEPHa2, PIGF, PSCA, PSMA, ROR1, T101, TAC, TAG72, TIM-3, TRAIL-R1, TRAIL-R1 (DR4), TRAIL-R2 (DR5), VEGF, VEGFR2, WT-I, a G-protein coupled receptor, alphafetoprotein (AFP), an angiogenesis factor, an exogenous cognate binding molecule (ExoCBM), oncogene product, anti-folate receptor, c-Met, carcinoembryonic antigen (CEA), cyclin (D 1), ephrinB2, epithelial tumor antigen, estrogen receptor, fetal acetylcholine e receptor, folate binding protein, gp100, hepatitis B surface antigen, Epstein-Barr nuclear antigen 1, Latent membrane protein 1, Secreted protein BARFI, P2X7 purinoceptor, Syndecan-1, kappa chain, kappa light chain, kdr, lambda chain, livin, melanoma-associated antigen, mesothelin, mouse double minute 2 homolog (MDM2), mucin 16 (MUC16), mutated p53, mutated ras, necrosis antigens, oncofetal antigen, ROR2, progesterone receptor, prostate specific antigen, tEGFR, tenascin, P2-Microgiobuiin, Fc Receptor-like 5 (FcRL5).

In some embodiments, the antigen binding domain binds to an epitope of a target or tumor associated antigen (TAA) presented in a major histocompatibility complex (MHC) molecule. In some embodiments, the TAA is a cancer testis antigen. In some embodiments, the cancer testis antigen is selected from the group consisting of acrosin binding protein (ACRBP; CT23, OY-TES-1, SP32; NCBI Gene ID: 84519), alpha fetoprotein (AFP; AFPD, FETA, HPAFP; NCBI Gene ID: 174); A-kinase anchoring protein 4 (AKAP4; AKAP 82, AKAP-4, AKAP82, CT99, FSC1, HI, PRKA4, hAKAP82, p82; NCBI Gene ID: 8852), ATPase family AAA domain containing 2 (ATAD2; ANCCA, CT137, PRO2000; NCBI Gene ID: 29028), kinetochore scaffold 1 (KNL1; AF15Q14, CASC5, CT29, D40, MCPH4, PPP1R55, Spc7, hKNL-1, hSpc105; NCBI Gene ID: 57082), centrosomal protein 55 (CEP55; C10orf3, CT111, MARCH, URCC6; NCBI Gene ID: 55165), cancer/testis antigen IA (CTAG1A; ESO1; CT6.1; LAGE-2; LAGE2A; NY-ESO-1; NCBI Gene ID: 246100), cancer/testis antigen 1B (CTAG1B; CT6.1, CTAG, CTAG1, ESO1, LAGE-2, LAGE2B, NY-ESO-1; NCBI Gene ID: 1485), cancer/testis antigen 2 (CTAG2; CAMEL, CT2, CT6.2, CT6.2a, CT6.2b, ESO2, LAGE-1, LAGE2B; NCBI Gene ID: 30848), CCCTC-binding factor like (CTCFL; BORIS, CT27, CTCF-T, HMGB1L1, dJ579F20.2; NCBI Gene ID: 140690), catenin alpha 2 (CTNNA2; CAP-R, CAPR, CDCBM9, CT114, CTNR; NCBI Gene ID: 1496), cancer/testis antigen 83 (CT83; CXorf61, KK-LC-1, KKLC1; NCBI Gene ID: 203413), cyclin A1 (CCNA1; CT146; NCBI Gene ID: 8900), DEAD-box helicase 43 (DDX43; CT13, HAGE; NCBI Gene ID: 55510), developmental pluripotency associated 2 (DPPA2; CT100, ECAT15-2, PESCRG1; NCBI Gene ID: 151871), fetal and adult testis expressed 1 (FATE1; CT43, FATE; NCBI Gene ID: 89885), FMR1 neighbor (FMR1NB; CT37, NY-SAR-35, NYSAR35; NCBI Gene ID: 158521), HORMA domain containing 1 (HORMAD1; CT46, NOHMA; NCBI Gene ID: 84072), insulin like growth factor 2 mRNA binding protein 3 (IGF2BP3; CT98, IMP-3, IMP3, KOC, KOC1, VICKZ3; NCBI Gene ID: 10643), leucine zipper protein 4 (LUZP4; CT-28, CT-8, CT28, HOM-TES-85; NCBI Gene ID: 51213), lymphocyte antigen 6 family member K (LY6K; CT97, HSJ001348, URLC10, ly-6K; NCBI Gene ID: 54742), maelstrom spermatogenic transposon silencer (MAEL; CT128, SPATA35; NCBI Gene ID: 84944), MAGE family member A1 (MAGEA1; CT1.1, MAGE1; NCBI Gene ID: 4100); MAGE family member A3 (MAGEA3; CT1.3, HIP8, HYPD, MAGE3, MAGEA6; NCBI Gene ID: 4102); MAGE family member A4 (MAGEA4; CT1.4, MAGE-41, MAGE-X2, MAGE4, MAGE4A, MAGE4B; NCBI Gene ID: 4103); MAGE family member A11 (MAGEA11; CT1.11, MAGE-11, MAGE11, MAGEA-11; NCBI Gene ID: 4110); MAGE family member C1 (MAGEC1; CT7, CT7.1; NCBI Gene ID: 9947); MAGE family member C2 (MAGEC2; CT10, HCA587, MAGEE1; NCBI Gene ID: 51438); MAGE family member D1 (MAGED1; DLXIN-1, NRAGE; NCBI Gene ID: 9500); MAGE family member D2 (MAGED2; 11B6, BARTS5, BCG-1, BCG1, HCA10, MAGE-D2; NCBI Gene ID: 10916), kinesin family member 20B (KIF20B; CT90, KRMP1, MPHOSPH1, MPP-1, MPP1; NCBI Gene ID: 9585), NUF2 component of NDC80 kinetochore complex (NUF2; CDCA1, CT106, NUF2R; NCBI Gene ID: 83540), nuclear RNA export factor 2 (NXF2; CT39, TAPL-2, TCP11X2; NCBI Gene ID: 56001), PAS domain containing repressor 1 (PASD1; CT63, CT64, OXTES1; NCBI Gene ID: 139135), PDZ binding kinase (PBK; CT84, HEL164, Nori-3, SPK, TOPK; NCBI Gene ID: 55872), piwi like RNA-mediated gene silencing 2 (PIWIL2; CT80, HILI, PIWIL1L, mili; NCBI Gene ID: 55124), preferentially expressed antigen in melanoma (PRAME; CT130, MAPE, OIP-4, OIP4; NCBI Gene ID: 23532), sperm associated antigen 9 (SPAG9; CT89, HLC-6, HLC4, HLC6, JIP-4, JIP4, JLP, PHET, PIG6; NCBI Gene ID: 9043), sperm protein associated with the nucleus, X-linked, family member A1 (SPANXA1; CT11.1, CT11.3, NAP-X, SPAN-X, SPAN-Xa, SPAN-Xb, SPANX, SPANX-A; NCBI Gene ID: 30014), SPANX family member A2 (SPANXA2; CT11.1, CT11.3, SPANX, SPANX-A, SPANX-C, SPANXA, SPANXC; NCBI Gene ID: 728712), SPANX family member C (SPANXC; CT11.3, CTp11, SPANX-C, SPANX-E, SPANXE; NCBI Gene ID: 64663), SPANX family member D (SPANXD; CT11.3, CT11.4, SPANX-C, SPANX-D, SPANX-E, SPANXC, SPANXE, dJ171K16.1; NCBI Gene ID: 64648), SSX family member 1 (SSX1; CT5.1, SSRC; NCBI Gene ID: 6756), SSX family member 2 (SSX2; CT5.2, CT5.2A, HD21, HOM-MEL-40, SSX; NCBI Gene ID: 6757), synaptonemal complex protein 3 (SYCP3; COR1, RPRGL4, SCP3, SPGF4; NCBI Gene ID: 50511), testis expressed 14, intercellular bridge forming factor (TEX14; CT113, SPGF23; NCBI Gene ID: 56155), transcription factor Dp family member 3 (TFDP3; CT30, DP4, HCA661; NCBI Gene ID: 51270), serine protease 50 (PRSS50; CT20, TSP50; NCBI Gene ID: 29122), TTK protein kinase (TTK; CT96, ESK, MPH1, MPS1, MPS1L1, PYT; NCBI Gene ID: 7272) and zinc finger protein 165 (ZNF165; CT53, LD65, ZSCAN7; NCBI Gene ID: 7718). T cell receptors (TCRs) and TCR-like antibodies that bind to an epitope of a cancer testis antigen presented in a major histocompatibility complex (MHC) molecule are known in the art and can be used in the herein described heterodimers. Cancer testis antigens associated with neoplasia are summarized, e.g., in Gibbs, et al., Trends Cancer 2018 October; 4(10):701-712 and the CT database website at cta.lncc.br/index.php. Illustrative TCRs and TCR-like antibodies that bind to an epitope of NY-ESO-1 presented in an MHC are described, e.g., in Stewart-Jones, et al., Proc Natl Acad Sci USA. 2009 Apr. 7; 106(14):5784-8; WO2005113595, WO2006031221, WO2010106431, WO2016177339, WO2016210365, WO2017044661, WO2017076308, WO2017109496, WO2018132739, WO2019084538, WO2019162043, WO2020086158 and WO2020086647. Illustrative TCRs and TCR-like antibodies that bind to an epitope of PRAME presented in an MHC are described, e.g., in WO2011062634, WO2016142783, WO2016191246, WO2018172533, WO2018234319 and WO2019109821. Illustrative TCRs and TCR-like antibodies that bind to an epitope of a MAGE variant presented in an MHC are described, e.g., in WO2007032255, WO2012054825, WO2013039889, WO2013041865, WO2014118236, WO2016055785, WO2017174822, WO2017174823, WO2017174824, WO2017175006, WO2018097951, WO2018170338, WO2018225732 and WO2019204683. Illustrative TCRs and TCR-like antibodies that bind to an epitope of alpha fetoprotein (AFP) presented in an MHC are described, e.g., in WO2015011450. Illustrative TCRs and TCR-like antibodies that bind to an epitope of SSX2 presented in an MHC are described, e.g., in WO2020063488. Illustrative TCRs and TCR-like antibodies that bind to an epitope of KK-LC-1 (CT83) presented in an MHC are described, e.g., in WO2017189254.

Examples of cell therapies that can be combined or co-administered include without limitation: axicabtagene ciloleucel (YESCARTA®), brexucabtagene autoleucel (TECARTUS™), AMG-119, Algenpantucel-L, ALOFISEL®, Sipuleucel-T, (BPX-501) rivogenlecleucel U.S. Pat. No. 9,089,520, WO2016100236, AU-105, ACTR-087, activated allogeneic natural killer cells CNDO-109-AANK, MG-4101, AU-101, BPX-601, FATE-NK100, LFU-835 hematopoietic stem cells, Imilecleucel-T, baltaleucel-T, PNK-007, UCARTCS1, ET-1504, ET-1501, ET-1502, ET-190, CD19-ARTEMIS, ProHema, FT-1050-treated bone marrow stem cell therapy, CD4CARNK-92 cells, SNK-01, NEXI-001, CryoStim, AlloStim, lentiviral transduced huCART-meso cells, CART-22 cells, EGFRt/19-28z/4-1BBL CAR T cells, autologous 4H11-28z/fIL-12/EFGRt T cell, CCR5-SBC-728-HSPC, CAR4-1BBZ, CH-296, dnTGFbRII-NY-ESOc259T, Ad-RTS-IL-12, IMA-101, IMA-201, CARMA-0508, TT-18, CMD-501, CMD-503, CMD-504, CMD-502, CMD-601, CMD-602, CSG-005, LAAP T-cell therapy, PD-1 knockout T cell therapy (esophageal cancer/NSCLC), anti-MUC1 CAR T-cell therapy (esophageal cancer/NSCLC), anti-MUC1 CAR T-cell therapy+PD-1 knockout T cell therapy (esophageal cancer/NSCLC), anti-KRAS G12D mTCR PBL, anti-CD123 CAR T-cell therapy, anti-mutated neoantigen TCR T-cell therapy, tumor lysate/MUC1/survivin PepTivator-loaded dendritic cell vaccine, autologous dendritic cell vaccine (metastatic malignant melanoma, intradermal/intravenous), anti-LeYscFv-CD28-zeta CAR T-cells, PRGN-3005, iC9-GD2-CAR-IL-15 T-cells, HSC-100, ATL-DC-101, MIDRIX4-LUNG, MIDRIXNEO, FCR-001, PLX stem cell therapy, MDR-101, GeniusVac-Mel4, ilixadencel, allogeneic mesenchymal stem cell therapy, romyelocel L, CYNK-001, ProTrans, ECT-100, MSCTRAIL, dilanubicel, FT-516, AST-VAC-2, E-CEL UVEC, CK-0801, allogenic alpha/beta CD3+ T cell and CD19+ B cell depleted stem cells (hematologic diseases, TBX-1400, HLCN-061, umbilical cord derived Hu-PHEC cells (hematological malignancies/aplastic anemia), AP-011, apceth-201, apceth-301, SENTI-101, stem cell therapy (pancreatic cancer), ICOVIRi5-cBiTE, CD33HSC/CD33 CAR-T, PLX-Immune, SUBCUVAX, CRISPR allogeneic gamma-delta T-cell-based gene therapy (cancer), ex vivo CRISPR allogeneic healthy donor NK-cell-based gene therapy (cancer), ex-vivo allogeneic induced pluripotent stem cell-derived NK-cell-based gene therapy (solid tumor), and anti-CD20 CAR T-cell therapy (non-Hodgkin's lymphoma).

Illustrative Cellular Therapies

Further examples of cellular therapies that can combined or co-administered with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are provided below.

- autologous human T lymphocytes transduced with a gene encoding T-cell receptor (TCR) specific for the human melanoma antigen A4 (MAGEA4; NCBI Gene ID: 4103), such as IMC-C103C (MAGE-A4), and the CD8alpha co-receptor, such as ADP-A2M4CD8 (autologous genetically-modified MAGE-A4 C1032 CD8alpha T cells);
- CEA cell adhesion molecule 5 (CEACAM5; NCBI Gene ID: 1048)-targeted CAR-T cells, such as MG7-CART;
- colony stimulating factor 2 (CSF2, a.k.a., GMCSF; NCBI Gene ID: 1437)/CA9-transduced dendritic cells, such as DC-Ad-GMCAIX;
- MUC1-targeted CAR-T cells, such as ICTCAR-052, Tn MUC-1 CAR-T, ICTCAR-053;
- mucin 16, cell surface associated (MUC16, a.k.a., CA125; NCBI Gene ID: 94025)-targeted CAR-T cells, such as 4H11-28z/fIL-12/EGFRt-expressing autologous T lymphocytes (i.e., T-lymphocytes transduced with a gene encoding a chimeric antigen receptor (CAR) targeting MUC16 and encoding interleukin-12 (IL-12), fused to the signaling domain of the zeta chain of the TCR/CD3 complex (28z), and a truncated form of the human epidermal growth factor receptor (EGFRt));
- CD33 (a.k.a., SIGLEC3; NCBI Gene ID: 945)-targeted CAR-T cells such as CIK-CAR.CD33, CD33CART;
- CD33/CLEC12A (CLL1)-dual targeted CAR-T cells, such as LB-1910;
- MSLN-targeted CAR-T cells, such as CSG-MESO, TC-210;
- CD38 targeted CAR-T cells, such as T-007, UCART-38;
- Merkel cell polyomavirus (MCPyV, MCV) viral oncoprotein-specific (KLLEIAPNC (SEQ ID NO: 263) epitope (KLL epitope) HLA-A02-restricted TCR-transduced CD8+ and CD4+ T cells, such as FH-MCVA2TCR;
- melan-A (MLANA, a.k.a., MART-1; NCBI Gene ID: 2315)-specific, HLA-A02-restricted TCR-transduced CD8+ and CD4+ T cells and/or peripheral blood lymphocytes (PBLs), such as MART-1 F5;
- ERBB2-targeted CAR-T cells, such as anti-HER2-CAR-4-1BB-CD3zeta-CD19t+-expressing Tcm-enriched T lymphocytes (genetically modified autologous central memory (Tcm) enriched T cells transduced with gene encoding a chimeric antigen receptor (CAR) having an anti-human epidermal growth factor 2 (HER2) single chain variable fragment (scFv) derived from trastuzumab, with a 4-1BB (CD137) costimulatory domain that is linked to the signaling domain of the T-cell antigen receptor complex zeta chain (CD3-zeta) (BBz), and truncated CD19 (CD19t));
- MET-targeted CAR-T cells, such as autologous mRNA-modified anti-cMET CAR-T cells (autologous, genetically-engineered T lymphocytes transduced with an mRNA encoding a chimeric antigen receptor (CAR) comprising an anti-MET single chain variable fragment (scFv));
- alpha fetoprotein (AFP; NCBI Gene ID: 174)-targeted CAR-T cells, such as ET-1402 and engineered cytotoxic T lymphocytes with AFP-specific TCR gene, such as AFP-TCR;
- ANTXR cell adhesion molecule 1 (ANTXR1, a.k.a., TEM8, docking protein or receptor for *Bacillus anthracis* toxin; NCBI Gene ID: 84168)-targeted CAR-T cells, such as anti-TEM8 CAR T-cell therapy;
- natural killer cell cytotoxicity receptor 3 ligand 1 (NCR3LG1, a.k.a., B7-H6, B7H6; NCBI Gene ID: 374383)-targeted engineered CAR T cells, such as CAR-NKp30 and CAR-B7H6 (e.g., having NKp30 extracellular domains to target B7H6-expressing tumor cells);
- CD19-targeted CAR-T cells, such as TBI-1501, CTL-119 huCART-19 T cells, lisocabtagene maraleucel (liso-cel; JCAR017), JCAR-015 U.S. Pat. No. 7,446,190, JCAR-014, JCAR-017, (WO2016196388, WO2016033570, WO2015157386), axicabtagene ciloleucel (KTE-C19, Yescarta®), KTE-X19, U.S. Pat. Nos. 7,741,465, 6,319,494, UCART-19, EBV-CTL, T tisagenlecleucel-T (CTL019), WO2012079000, WO2017049166, CD19CAR-CD28-CD3zeta-EGFRt-expressing T cells, CD19/4-1BBL armored CAR T cell therapy, C-CAR-011, CIK-CAR.CD19, CD19CAR-28-zeta T cells, PCAR-019, MatchCART, DSCAR-01, IM19 CAR-T, TC-110; anti-CD19 CAR T-cell therapy (B-cell acute lymphoblastic leukemia, Universiti Kebangsaan Malaysia); anti-CD19 CAR T-cell therapy (acute lymphoblastic leukemia/Non-Hodgkin's lymphoma, University Hospital Heidelberg), anti-CD19 CAR T-cell therapy (silenced IL-6 expression, cancer, Shanghai Unicar-Therapy Bio-medicine Technology), MB-CART2019.1 (CD19/CD20), GC-197 (CD19/CD7), CLIC-1901, ET-019003, anti-CD19-STAR-T cells, AVA-001, BCMA-CD19 cCAR (CD19/APRIL), ICG-134, ICG-132 (CD19/CD20), CTA-101, WZTL-002, dual anti-CD19/anti-CD20 CAR T-cells (chronic lymphocytic leukemia/B-cell lymphomas), HY-001, ET-019002, YTB-323, GC-012 (CD19/APRIL), GC-022 (CD19/CD22), CD19CAR-CD28-CD3zeta-EGFRt-expressing Tn/mem; UCAR-011, ICTCAR-014, GC-007F, PTG-01, CC-97540 and GC-007G;
- CD19/CD22 (a.k.a., SIGLEC2; NCBI Gene ID: 933) dual targeted TRuC™-T cells, such as TC-310;
- CD22-targeted CAR-T cells, such as anti-CD22 CART, UCART-22, JCAR-018, WO2016090190;
- CD19/CD7 (NCBI Gene ID: 924)-dual targeted CAR-T cells, such as GC-197;

CD7-targeted CAR-T cells, such as anti-CD7 CAR T-cell therapy (CD7-positive hematological malignancies);

membrane spanning 4-domains A1 (MS4A1, a.k.a., CD20; NCBI Gene ID: 931)-targeted CAR-T cells, such as ACTR707 ATTCK-20, PBCAR-20A, LB-1905;

individualized cell immunotherapy co-culturing autologous dendritic cells derived from peripheral blood mononuclear cells (PBMNCs) (Autologous Dendritic Cell/Tumor Antigen (ADCTA)), such as ADCTA-SSI-G;

cancer/testis antigen 1 (CTAG1A (NCBI Gene ID: 246100), CTAG1B (NCBI Gene ID: 1485), a.k.a., NY-ESO-1)-targeted TCRs, such as GSK01 (NY-ESO-1), GSK-3377794 (TCR-transduced polyclonal T cells), TBI-1301 (TCR-transduced lymphocytes), GSK-3537142 (monoclonal TCR);

interleukin 3 receptor subunit alpha (IL3RA, a.k.a., CD123; NCBI Gene ID: 3563)-targeted CAR-T cells, such as MB-102, IM-23, JEZ-567, UCART-123, UniCAR02-T-CD123;

CD4 (NCBI Gene ID: 920)-targeted CAR-T cells, such as ICG-122;

CD5 (NCBI Gene ID: 921)-targeted CAR-T cells, such as CD5.28z CART cells;

allogeneic NCAM1 (a.k.a., CD56; NCBI Gene ID: 4684)-positive CD3-negative natural killer cells (useful against myeloid malignancies);

CD276 (NCBI Gene ID: 80381)-targeted CAR-T cells, such as anti-CD276 CART;

CLDN18 isoform 2 (CLDN18.2)-targeted CAR-T cells, such as LB-1904, CT041;

Chlorotoxin (CLTX; a 36-amino acid C1-channel blocker from *Leiurus quinquestriatus* scorpion venom)-targeted CAR-T cells, such as CLTX-CART;

Epstein-Barr virus (EBV)-positive cancer-targeted T cells, such as CMD-003 (baltaleucel-T), rovaleucel (TT10 EBVSTs);

EBV-specific, DNR (Dominant Negative Receptor; i.e., resistant to TGFbeta) cytotoxic T cells, such as DNR.NPC T-cells, e.g., for use in treating nasopharyngeal carcinoma (NPC);

Ganglioside (GD2)-targeted CAR-T cells, such as 4SCAR-GD2;

gamma-delta T cells, such as ICS-100 (targeting leukemia and lymphoma) and ICS-200 (targeting glioblastoma);

folate hydrolase 1 (FOLH1, a.k.a., glutamate carboxypeptidase II, PSMA; NCBI Gene ID: 2346)-targeted CAR-T cells, such as CIK-CAR.PSMA, CART-PSMA-TGFβRDN, P-PSMA-101;

glypican 3 (GPC3; NCBI Gene ID: 2719)-targeted CAR-T cells, such as TT-16, GLYCAR;

CAR-T cells directed against the human papillomavirus (HPV) type 16 E7 oncoprotein, such as KITE-439 (see, for example, PCT/US2015/033129);

HPV-targeted T cells, such as TT-12 (human papillomavirus specific T cell therapy (HPVST));

autologous T lymphocytes transduced with gene encoding an antibody-coupled T cell receptor (ATCR) containing the extracellular Fc receptor CD16 (FCGR3A (NCBI Gene ID: 2214); FCGR3B (NCBI Gene ID: 2215)); domain, e.g., coupled to TNFRSF9 (a.k.a., CD137, 4-BB; NCBI Gene ID: 3604) signaling domain, linked to the intracellular CD3 zeta domain (CD247, CD3z; NCBI Gene ID: 919)), such as anti-ACTR/4-1BB/CD3zeta-viral vector-transduced autologous T lymphocytes (ACTR087);

autologous peripheral blood lymphocytes (PBLs) transduced with an HLA class I histocompatibility antigen A*11:01 (HLA-A1101)-restricted murine T-cell receptor (mTCR) that recognizes the glycine to valine point mutation at position 12 (G12V) variant of KRAS proto-oncogene, GTPase (KRAS; NCBI Gene ID: 38450) in HLA-A*11:01, such as anti-KRAS G12V mTCR cell therapy;

L1 cell adhesion molecule (L1CAM, a.k.a., CD171, NCAM-L1; NCBI Gene ID: 3897)-targeted CAR-T cells, such as JCAR-023;

autologous dendritic cells (DCs) transduced with the replication-deficient adenoviral vector Ad5F53 encoding the Epstein-Barr virus (EBV) transmembrane latent membrane protein LMP-1 (LMP-1; NCBI Gene ID: 3783750)/membrane protein LMP-2A (LMP-2A; NCBI Gene ID: 3783751)/membrane protein LMP-2B (LMP-2B; NCBI Gene ID: 3783760), such as Ad5F35-LMP1/LMP2-transduced autologous dendritic cells;

adoptive transfer of melan-A (MLANA, a.k.a., MART-1 (NCBI Gene ID: 2315)) F5 TCR engineered peripheral blood mononuclear cells (PBMC), with administration of MART-126.35-pulsed dendritic cells and interleukin-2 (such as the IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein), e.g., in patients with advanced melanoma;

autologous T lymphocytes transduced with a retroviral vector encoding a high-affinity T-cell receptor (TCR) specific for human leukocyte antigen (HLA)-A2-restricted, human melanoma-associated antigen A10 (MAGE-A10; NCBI Gene ID: 4109), clone 796 (c796), such as autologous MAGE-A10-specific HLA-A2-restricted TCR c796 gene-engineered T lymphocytes (MAGE-A10C796T MAGE-A10 TCR);

autologous T lymphocytes genetically modified to express a T-cell receptor (TCR) that specifically targets MAGE family member A3 (MAGEA3, a.k.a., MAGEA6; NCBI Gene ID: 4102) and MAGE family member A6 (MAGEA6, a.k.a., MAGE3B; NCBI Gene ID: 4105), such as autologous MAGE-A3/A6-specific TCR gene-engineered lymphocytes KITE-718 (see, for example, WO 2014/043441);

NKG2D-based CAR T-cell comprising a single short hairpin RNA (shRNA) targeting the conserved regions of MHC class I polypeptide-related sequence A (MICA; NCBI Gene ID: 100507436) and MHC class I polypeptide-related sequence B (MICB; NCBI Gene ID: 4277), such as CYAD-02 (see, Fontaine, et al., *Blood* (2019) 134(Suppl. 1): 3931);

autologous T cells genetically modified to express a chimeric antigen receptor (CAR) comprising a fusion of the natural killer group 2D (NKG2D) receptor, e.g., with the CD3z signalling domain, which associates with the adaptor molecule DNAX-activating protein of 10 kDa (DAP10) to provide co-stimulatory signal upon ligand binding, such as NKR-2;

receptor tyrosine kinase like orphan receptor 1 (ROR1, a.k.a., NTRKR1; NCBI Gene ID: 4919)-targeted CAR-T-lymphocytes, such as JCAR-024;

allogeneic T lymphocytes transduced with a retroviral vector encoding a high-affinity T-cell receptor (TCR) specific for human leukocyte antigen (HLA)-A2-01-restricted, PRAME nuclear receptor transcriptional regulator (PRAME; NCBI Gene ID: 23532)-targeted T-cell receptor, such as IMC-F106C (PRAME), optionally containing the chemical induction of dimerization (CID) suicide/safety switch, composed of a drug binding domain coupled to the signaling domain of the suicide enzyme caspase-9, such as PRAME-targeting T-cell receptor/Inducible caspase 9 (BPX-701);

prostate stem cell antigen (PSCA; NCBI Gene ID: 8000)-targeted CAR-T cells, such as MB-105;

roundabout guidance receptor 1 (ROBO1; NCBI Gene ID: 6091)-targeted allogeneic CAR-NK cells, such as ATCG-427;

autologous tumor cells transfected with the peptidoglycan recognition protein 1 (PGLYRP1, a.k.a., TAG7, PGRP-S; NCBI Gene ID: 8993) gene, such as ag-7 gene modified inactivated tumor cells (see, NCT04180774; Moiseyenko, et al., *Ann Oncol.* 2005 January; 16(1): 162-8; Maples, et al., IMMUNITY AND TOLERANCE TO TRANSGENES AND VECTORS (2008) 16 (Suppl. 1) S91);

SLAM family member 7 (SLAMF7, a.k.a., CD319; NCBI Gene ID: 57823)-targeted CAR-T cells, such as IC9-Luc90-CD828Z (see, WO 2020/009868);

tumor-derived T-lymphocytes composed of tumor infiltrating lymphocytes (TILs), such as Lifileucel (LN-144), LN-145 and autologous clonal neoantigen T cells (ATL001);

thyroid stimulating hormone receptor (TSHR; NCBI Gene ID: 7253)-targeted CAR-T cells, such as ICT-CAR-TC (TSHR);

CD8+ T Cells that have been transduced to express WT1 transcription factor (WT1, a.k.a., Wilms tumor protein; NCBI Gene ID: 7490)-targeted T-cell receptors (TCRs), such as JTCR-016, WT1-CTL, ASP-7517;

Exemplified Anticancer Combination Therapies

Lymphoma or Leukemia Combination Therapy

Some chemotherapy agents are suitable for treating lymphoma or leukemia. These agents include aldesleukin (which can be replaced by an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein), alvocidib, amifostine trihydrate, aminocamptothecin, antineoplaston A10, antineoplaston AS2-1, anti-thymocyte globulin, arsenic trioxide, Bcl-2 family protein inhibitor ABT-263, beta alethine, BMS-345541bortezomib (VELCADE®, PS-341), bryostatin 1, bulsulfan, campath-1H, carboplatin, carfilzomib (Kyprolis®), carmustine, caspofungin acetate, CC-5103, chlorambucil, CHOP (cyclophosphamide, doxorubicin, vincristine, and prednisone), cisplatin, cladribine, clofarabine, curcumin, CVP (cyclophosphamide, vincristine, and prednisone), cyclophosphamide, cyclosporine, cytarabine, denileukin diftitox, dexamethasone, docetaxel, dolastatin 10, doxorubicin, doxorubicin hydrochloride, DT-PACE (dexamethasone, thalidomide, cisplatin, doxorubicin, cyclophosphamide, and etoposide), enzastaurin, epoetin alfa, etoposide, everolimus (RAD001), FCM (fludarabine, cyclophosphamide, and mitoxantrone), FCR (fludarabine, cyclophosphamide, and rituximab), fenretinide, filgrastim, flavopiridol, fludarabine, FR (fludarabine and rituximab), geldanamycin (17 AAG), hyperCVAD (hyperfractionated cyclophosphamide, vincristine, doxorubicin, dexamethasone, methotrexate, and cytarabine), ICE (iphosphamide, carboplatin, and etoposide), ifosfamide, irinotecan hydrochloride, interferon alpha-2b, ixabepilone, lenalidomide (REVLIMID®, CC-5013), pomalidomide (POMALYST®/IMNOVID®), lymphokine-activated killer cells, MCP (mitoxantrone, chlorambucil, and prednisolone), melphalan, mesna, methotrexate, mitoxantrone hydrochloride, motexafin gadolinium, mycophenolate mofetil, nelarabine, obatoclax (GX15-070), oblimersen, octreotide acetate, omega-3 fatty acids, Omr-IgG-am (WNIG, Omrix), oxaliplatin, paclitaxel, palbociclib (PD0332991), pegfilgrastim, PEGylated liposomal doxorubicin hydrochloride, perifosin, prednisolone, prednisone, recombinant flt3 ligand, recombinant human thrombopoietin, recombinant interferon alfa, recombinant interleukin-11, recombinant interleukin-12, rituximab, R-CHOP (rituximab and CHOP), R-CVP (rituximab and CVP), R-FCM (rituximab and FCM), R-ICE (rituximab and ICE), and R MCP (rituximab and MCP), R-roscovitine (seliciclib, CYC202), sargramostim, sildenafil citrate, simvastatin, sirolimus, styryl sulphones, tacrolimus, tanespimycin, temsirolimus (CCl-779), thalidomide, therapeutic allogeneic lymphocytes, thiotepa, tipifarnib, vincristine, vincristine sulfate, vinorelbine ditartrate, SAHA (suberanilohydroxamic acid, or suberoyl, anilide, and hydroxamic acid), vemurafenib (Zelboraf®), venetoclax (ABT-199).

One modified approach is radioimmunotherapy, wherein a monoclonal antibody is combined with a radioisotope particle, such as indium-111, yttrium-90, and iodine-131. Examples of combination therapies include, but are not limited to, iodine-131 tositumomab (BEXXAR®), yttrium-90 ibritumomab tiuxetan (ZEVALIN®), and BEXXAR® with CHOP.

The above-mentioned therapies can be supplemented or combined with stem cell transplantation or treatment. Therapeutic procedures include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme technique, low-LET cobalt-60 gamma ray therapy, bleomycin, conventional surgery, radiation therapy, and nonmyeloablative allogeneic hematopoietic stem cell transplantation.

Non-Hodgkin's Lymphomas Combination Therapy

Treatment of non-Hodgkin's lymphomas (NHL), especially those of B cell origin, includes using monoclonal antibodies, standard chemotherapy approaches (e.g., CHOP (cyclophosphamide, doxorubicin, vincristine, and prednisone), CVP (cyclophosphamide, vincristine, and prednisone), FCM (fludarabine, cyclophosphamide, and mitoxantrone), MCP (Mitoxantrone, Chlorambucil, Prednisolone), all optionally including rituximab (R) and the like), radioimmunotherapy, and combinations thereof, especially integration of an antibody therapy with chemotherapy.

Examples of unconjugated monoclonal antibodies for the treatment of NHL/B-cell cancers include rituximab, alemtuzumab, human or humanized anti-CD20 antibodies, lumiliximab, anti-TNF-related apoptosis-inducing ligand (anti-TRAIL), bevacizumab, galiximab, epratuzumab, SGN-40, and anti-CD74.

Examples of experimental antibody agents used in treatment of NHL/B-cell cancers include ofatumumab, ha20, PRO131921, alemtuzumab, galiximab, SGN-40, CHIR-12.12, epratuzumab, lumiliximab, apolizumab, milatuzumab, and bevacizumab.

Examples of standard regimens of chemotherapy for NHL/B-cell cancers include CHOP, FCM, CVP, MCP, R-CHOP (rituximab, cyclophosphamide, doxorubicin, vincristine, and prednisone), R-FCM, R-CVP, and R MCP.

Examples of radioimmunotherapy for NHL/B-cell cancers include yttrium-90 ibritumomab tiuxetan (ZEVALIN®) and iodine-131 tositumomab (BEXXAR®).

Mantle Cell Lymphoma Combination Therapy

Therapeutic treatments for mantle cell lymphoma (MCL) include combination chemotherapies such as CHOP, hyperCVAD, and FCM. These regimens can also be supplemented with the monoclonal antibody rituximab to form combination therapies R-CHOP, hyperCVAD-R, and R-FCM. Any of the abovementioned therapies may be combined with stem cell transplantation or ICE in order to treat MCL.

An alternative approach to treating MCL is immunotherapy. One immunotherapy uses monoclonal antibodies like rituximab. Another uses cancer vaccines, such as GTOP-99, which are based on the genetic makeup of an individual patient's tumor.

A modified approach to treat MCL is radioimmunotherapy, wherein a monoclonal antibody is combined with a radioisotope particle, such as iodine-131 tositumomab (BEXXAR®) and yttrium-90 ibritumomab tiuxetan (ZEVALIN®). In another example, BEXXAR® is used in sequential treatment with CHOP (cyclophosphamide, doxorubicin hydrochloride (hydroxydaunorubicin), vincristine sulfate (Oncovin), and prednisone).

Other approaches to treating MCL include autologous stem cell transplantation coupled with high-dose chemotherapy, administering proteasome inhibitors such as bortezomib (VELCADE® or PS-341), or administering antiangiogenesis agents such as thalidomide, especially in combination with rituximab.

Another treatment approach is administering drugs that lead to the degradation of Bcl-2 protein and increase cancer cell sensitivity to chemotherapy, such as oblimersen, in combination with other chemotherapeutic agents.

A further treatment approach includes administering mTOR inhibitors, which can lead to inhibition of cell growth and even cell death. Non-limiting examples are sirolimus, temsirolimus (TORISEL®, CCI-779), CC-115, CC-223, SF-1126, PQR-309 (bimiralisib), voxtalisib, GSK-2126458, and temsirolimus in combination with RITUXAN®, VELCADE®, or other chemotherapeutic agents.

Other recent therapies for MCL have been disclosed. Such examples include flavopiridol, palbociclib (PD0332991), R-roscovitine (selicicilib, CYC202), styryl sulphones, obatoclax (GX15-070), TRAIL, Anti-TRAIL death receptors DR4 and DR5 antibodies, temsirolimus (TORISEL®, CCl-779), everolimus (RAD001), BMS-345541, curcumin, SAHA, thalidomide, lenalidomide (REVLIMID®, CC-5013), and geldanamycin (17 AAG).

Waldenström's Macroglobulinemia Combination Therapy

Therapeutic agents used to treat Waldenström's Macroglobulinemia (WM) include aldesleukin (which can be replaced by an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein), alemtuzumab, alvocidib, amifostine trihydrate, aminocamptothecin, antineoplaston A10, antineoplaston AS2-1, antithymocyte globulin, arsenic trioxide, autologous human tumor-derived HSPPC-96, Bcl-2 family protein inhibitor ABT-263, beta alethine, bortezomib (VELCADE®), bryostatin 1, busulfan, campath-1H, carboplatin, carmustine, caspofungin acetate, CC-5103, cisplatin, clofarabine, cyclophosphamide, cyclosporine, cytarabine, denileukin diftitox, dexamethasone, docetaxel, dolastatin 10, doxorubicin hydrochloride, DT-PACE, enzastaurin, epoetin alfa, epratuzumab (hLL2-anti-CD22 humanized antibody), etoposide, everolimus, fenretinide, filgrastim, fludarabine, ibrutinib, ifosfamide, indium-111 monoclonal antibody MN-14, iodine-131 tositumomab, irinotecan hydrochloride, ixabepilone, lymphokine-activated killer cells, melphalan, mesna, methotrexate, mitoxantrone hydrochloride, monoclonal antibody CD19 (such as tisagenlecleucel-T, CART-19, CTL-019), monoclonal antibody CD20, motexafin gadolinium, mycophenolate mofetil, nelarabine, oblimersen, octreotide acetate, omega-3 fatty acids, oxaliplatin, paclitaxel, pegfilgrastim, PEGylated liposomal doxorubicin hydrochloride, pentostatin, perifosine, prednisone, recombinant flt3 ligand, recombinant human thrombopoietin, recombinant interferon alfa, recombinant interleukin-11, recombinant interleukin-12, rituximab, sargramostim, sildenafil citrate (VIAGRA®), simvastatin, sirolimus, tacrolimus, tanespimycin, thalidomide, therapeutic allogeneic lymphocytes, thiotepa, tipifarnib, tositumomab, ulocuplumab, veltuzumab, vincristine sulfate, vinorelbine ditartrate, vorinostat, WT1 126-134 peptide vaccine, WT-1 analog peptide vaccine, yttrium-90 ibritumomab tiuxetan, yttrium-90 humanized epratuzumab, and any combination thereof.

Examples of therapeutic procedures used to treat WM include peripheral blood stem cell transplantation, autologous hematopoietic stem cell transplantation, autologous bone marrow transplantation, antibody therapy, biological therapy, enzyme inhibitor therapy, total body irradiation, infusion of stem cells, bone marrow ablation with stem cell support, in vitro-treated peripheral blood stem cell transplantation, umbilical cord blood transplantation, immunoenzyme techniques, low-LET cobalt-60 gamma ray therapy, bleomycin, conventional surgery, radiation therapy, and nonmyeloablative allogeneic hematopoietic stem cell transplantation.

Diffuse Large B-Cell Lymphoma Combination Therapy

Therapeutic agents used to treat diffuse large B-cell lymphoma (DLBCL) include cyclophosphamide, doxorubicin, vincristine, prednisone, anti-CD20 monoclonal antibodies, etoposide, bleomycin, many of the agents listed for WM, and any combination thereof, such as ICE and RICE. In some embodiments therapeutic agents used to treat DLBCL include rituximab (Rituxan®), cyclophosphamide, doxorubicin hydrochloride (hydroxydaunorubicin), vincristine sulfate (Oncovin®), prednisone, bendamustine, ifosfamide, carboplatin, etoposide, ibrutinib, polatuzumab vedotin piiq, bendamustine, copanlisib, lenalidomide (Revlimid®), dexamethasone, cytarabine, cisplatin, Yescarta®, Kymriah®, Polivy® (polatuzumab vedotin), BR (bendamustine (Treanda®), gemcitabine, oxiplatin, oxaliplatin, tafasitamab, polatuzumab, cyclophosphamide, or combinations thereof. In some embodiments therapeutic agents used to treat DLBCL include R-CHOP (rituximab+cyclophosphamide+doxorubicin hydrochloride (hydroxydaunorubicin)+vincristine sulfate (Oncovin®), +prednisone), rituximab+bendamustine, R-ICE (Rituximab+Ifosfamide+Carboplatin+Etoposide), rituximab+lenalomide, R-DHAP (rituximab+dexamethasone+high-dose cytarabine (Ara C)+cisplatin), Polivy® (polatuzumab vedotin)+BR (bendamustine (Treanda®) and rituximab (Rituxan®), R-GemOx (Gemcitabine+oxaliplatin+rituximab), Tafa-Len (tafasitamab+lenalidomide), Tafasitamab+Revlimid®, polatuzumab+bendamustine, Gemcitabine+oxaliplatin, R-EPOCH (rituximab+etoposide phosphate+prednisone+vincristine sulfate (Oncovin®)+cyclophosphamide+doxorubicin hydrochloride (hydroxydaunorubicin)), or CHOP (cyclophosphamide+doxorubicin hydrochloride (hydroxydaunorubicin)+vincristine sulfate (Oncovin®)+prednisone). In some embodiments therapeutic agents used to treat DLBCL include tafasitamab, glofitamab, epcoritamab, Lonca-T (loncastuximab tesirine), Debio-1562, polatuzumab, Yescarta, JCAR017, loncastuximab tesirine (ADCT-402), brentuximab vedotin, MT-3724, odronextamab, Auto-03, Allo-501A, or TAK-007.

Chronic Lymphocytic Leukemia Combination Therapy

Examples of therapeutic agents used to treat chronic lymphocytic leukemia (CLL) include chlorambucil, cyclophosphamide, fludarabine, pentostatin, cladribine, doxorubicin, vincristine, prednisone, prednisolone, alemtuzumab, many of the agents listed for WM, and combination chemotherapy and chemoimmunotherapy, including the following common combination regimens: CVP, R-CVP, ICE, R-ICE, FCR, and FR.

Myelofibrosis Combination Therapy

Myelofibrosis inhibiting agents include, but are not limited to, hedgehog inhibitors, histone deacetylase (HDAC) inhibitors, and tyrosine kinase inhibitors. Non-limiting examples of hedgehog inhibitors are saridegib and vismodegib. Examples of HDAC inhibitors include, but are not limited to, pracinostat and panobinostat. Non-limiting examples of tyrosine kinase inhibitors are lestaurtinib, bosutinib, imatinib, radotinib, and cabozantinib.

Hyperproliferative Disorder Combination Therapy

Gemcitabine, nab-paclitaxel, and gemcitabine/nab-paclitaxel may be used with a JAK inhibitor and/or PI3K8 inhibitor to treat hyperproliferative disorders.

High Risk Myelodysplastic Syndrome (HR MDS) Combination Therapy

Therapeutic agents used to treat HR MDS include azacitidine (Vidaza®), decitabine (Dacogen®), lenalidomide (Revlimid®), cytarabine, idarubicin, daunorubicin, and combinations thereof. In some embodiments, combinations include cytarabine+daunorubicin and cytarabine+idarubicin. In some embodiments therapeutic agents used to treat HR MDS include magrolimab, pevonedistat, venetoclax, sabatolimab, guadecitabine, rigosertib, ivosidenib, enasidenib, selinexor, BGB324, DSP-7888, or SNS-301.

Low Risk Myelodysplastic Syndrome (LR MDS) Combination Therapy

Therapeutic agents used to treat LR MDS include lenalidomide, azacytidine, and combinations thereof. In some embodiments therapeutic agents used to treat LR MDS include magrolimab, roxadustat, luspatercept, imetelstat, LB-100, or rigosertib.

Acute Myeloid Leukemia (AML) Combination Therapy

Therapeutic agents used to treat AML include cytarabine, idarubicin, daunorubicin, midostaurin (Rydapt®), venetoclax, azacitidine, ivasidenib, gilteritinib, enasidenib, low-dose cytarabine (LoDAC), mitoxantrone, fludarabine, granulocyte-colony stimulating factor, idarubicin, gilteritinib (Xospata®), enasidenib (Idhifa®), ivosidenib (Tibsovo®), decitabine (Dacogen®), mitoxantrone, etoposide, Gemtuzumab ozogamicin (Mylotarg®), glasdegib (Daurismo®), and combinations thereof. In some embodiments therapeutic agents used to treat AML include FLAG-Ida (fludarabine, cytarabine (Ara-C), granulocyte-colony stimulating factor (G-CSF) and idarubicin), cytarabine+idarubicin, cytarabine+daunorubicin+midostaurin, venetoclax+azacitidine, cytarabine+daunorubicin, or MEC (mitoxantrone, etoposide, and cytarabine). In some embodiments, therapeutic agents used to treat AML include magrolimab, pevonedistat, venetoclax, sabatolimab, eprenetapopt, or lemzoparlimab.

Multiple Myeloma (MM) Combination Therapy

Therapeutic agents used to treat MM include lenalidomide, bortezomib, dexamethasone, daratumumab (Darzalex®), pomalidomide, Cyclophosphamide, Carfilzomib (Kyprolis®), Elotuzumab (Empliciti), and combinations thereof. In some embodiments therapeutic agents used to treat MM include RVS (lenalidomide+bortezomib+dexamethasone), RevDex (lenalidomide plus dexamethasone), CYBORD (Cyclophosphamide+Bortezomib+Dexamethasone), Vel/Dex (bortezomib plus dexamethasone), or PomDex (Pomalidomide+low-dose dexamethasone). In some embodiments therapeutic agents used to treat MM include JCARH125, TAK-573, belantamab-m, ide-cel (CAR-T).

Breast Cancer Combination Therapy

Therapeutic agents used to treat breast cancer include albumin-bound paclitaxel, anastrozole, capecitabine, carboplatin, cisplatin, cyclophosphamide, docetaxel, doxorubicin, epirubicin, everolimus, exemestane, fluorouracil, fulvestrant, gemcitabine, Ixabepilone, lapatinib, Letrozole, methotrexate, mitoxantrone, paclitaxel, pegylated liposomal doxorubicin, pertuzumab, tamoxifen, toremifene, trastuzumab, vinorelbine, and any combinations thereof. In some embodiments therapeutic agents used to treat breast cancer (e.g., HR+/−/HER2+/−) include trastuzumab (Herceptin®), pertuzumab (Perjeta®), docetaxel, carboplatin, palbociclib (Ibrance®), letrozole, trastuzumab emtansine (Kadcyla), fulvestrant (Faslodex®), olaparib (Lynparza), eribulin, tucatinib, capecitabine, lapatinib, everolimus (Afinitor®), exemestane, eribulin mesylate (Halaven®), and combinations thereof. In some embodiments therapeutic agents used to treat breast cancer include trastuzumab+pertuzumab+docetaxel, trastuzumab+pertuzumab+docetaxel+carboplatin, palbociclib+letrozole, tucatinib+capecitabine, lapatinib+capecitabine, palbociclib+fulvestrant, or everolimus+exemestane. In some embodiments therapeutic agents used to treat breast cancer include trastuzumab deruxtecan (Enhertu®), datopotamab deruxtecan (DS-1062), enfortumab vedotin (Padcev®), balixafortide, elacestrant, or a combination thereof. In some embodiments therapeutic agents used to treat breast cancer include balixafortide+eribulin.

Triple Negative Breast Cancer Combination Therapy

Therapeutic agents used to treat triple negative breast cancer include cyclophosphamide, docetaxel, doxorubicin, epirubicin, fluorouracil, paclitaxel, and combinations thereof. In some embodiments therapeutic agents used to treat TNBC include olaparib (Lynparza®), atezolizumab (Tecentriq®), paclitaxel (Abraxane®), eribulin, bevacizumab (Avastin®), carboplatin, gemcitabine, eribulin mesylate (Halaven®), sacituzumab govitecan (Trodelvy®), pembrolizumab (Keytruda®), cisplatin, doxorubicin, epirubicin, or a combination thereof. In some embodiments therapeutic agents to treat TNBC include atezolizumab+paclitaxel, bevacizumab+paclitaxel, carboplatin+paclitaxel, carboplatin+gemcitabine, or paclitaxel+gemcitabine. In some embodiments therapeutic agents used to treat TNBC include eryaspase, capivasertib, alpelisib, rucaparib+nivolumab, atezolumab+paclitaxel+gemcitabine+capecitabine+carboplatin, ipatasertib+paclitaxel, ladiratuzumab vedotin+pembrolimab, durvalumab+DS-8201a, trilaciclib+gemcitabine+carboplatin. In some embodiments therapeutic agents used to treat TNBC include trastuzumab deruxtecan (Enhertu®), datopotamab deruxtecan (DS-1062), enfortumab vedotin (Padcev®), balixafortide, adagloxad simolenin, nelipepimut-s (NeuVax®), nivolumab (Opdivo®), rucaparib, toripalimab (Tuoyi®), camrelizumab, capivasertib, durvalumab (Imfinzi®), and combinations thereof. In some embodiments therapeutic agents use to treat TNBC include nivolumab+rucaparib, bevacizumab (Avastin)+chemotherapy, toripalimab+paclitaxel, toripalimab+albumin-bound paclitaxel, camrelizumab+chemotherapy, pembrolizumab+chemotherapy, balixafortide+eribulin, durvalumab+trastuzumab deruxtecan, durvalumab+paclitaxel, or capivasertib+paclitaxel.

Bladder Cancer Combination Therapy

Therapeutic agents used to treat bladder cancer include atezolizumab, carboplatin, cisplatin, docetaxel, doxorubicin, fluorouracil (5-FU), gemcitabine, idosfamide, Interferon alfa-2b, methotrexate, mitomycin, nab-paclitaxel, paclitaxel, pemetrexed, thiotepa, vinblastine, and any combination thereof. In some embodiments therapeutic agents used to treat bladder cancer include eganelisib+nivolumab, pembrolizumab (Keytruda®)+enfortumab vedotin (Padcev®), nivolumab+ipilimumab, duravalumab+tremelimumab, lenvatinib+pembrolizumab, enfortumab vedotin (Padcev)+pembrolizumab, and bempegaldesleukin+nivolumab.

Colorectal Cancer Combination Therapy

Therapeutic agents used to treat colorectal cancer include bevacizumab, capecitabine, cetuximab, fluorouracil, irinotecan, leucovorin, oxaliplatin, panitumumab, ziv-aflibercept, and any combinations thereof. In some embodiments therapeutic agents used to treat CRC include bevacizumab (Avastin®), leucovorin, 5-FU, oxaliplatin (FOLFOX), pembrolizumab (Keytruda®), FOLFIRI, regorafenib (Stivarga®), aflibercept (Zaltrap®), cetuximab (Erbitux®), Lonsurf (Orcantas®), XELOX, FOLFOXIRI, or a combination thereof. In some embodiments therapeutic agents used to treat CRC include bevacizumab+leucovorin+5-FU+oxaliplatin (FOLFOX), bevacizumab+FOLFIRI, bevacizumab+FOLFOX, aflibercept+FOLFIRI, cetuximab+FOLFIRI, bevacizumab+XELOX, and bevacizumab+FOLFOXIRI. In some embodiments therapeutic agents used to treat CRC include binimetinib+encorafenib+cetuximab, trametinib+dabrafenib+panitumumab, trastuzumab+pertuzumab, napabucasin+FOLFIRI+bevacizumab, nivolumab+ipilimumab.

Castration-Resistant Prostate Cancer Combination Therapy

Therapeutic agents used to treat castration-resistant prostate cancer include abiraterone, cabazitaxel, docetaxel, enzalutamide, prednisone, sipuleucel-T, an Aeromonas protoxin proaerolysin (PA), bearing a prostate-specific protease cleavage site, such as PRX302 (topsalysin); and any combinations thereof.

Esophageal and Esophagogastric Junction Cancer Combination Therapy

Therapeutic agents used to treat esophageal and esophagogastric junction cancer include capecitabine, carboplatin, cisplatin, docetaxel, epirubicin, fluoropyrimidine, fluorouracil, irinotecan, leucovorin, oxaliplatin, paclitaxel, ramucirumab, trastuzumab, and any combinations thereof. In some embodiments therapeutic agents used to treat gastroesophageal junction cancer (GEJ) include herceptin, cisplatin, 5-FU, ramicurimab, or paclitaxel. In some embodiments therapeutic agents used to treat GEJ cancer include magrolimab, ALX-148, AO-176, or IBI-188.

Gastric Cancer Combination Therapy

Therapeutic agents used to treat gastric cancer include capecitabine, carboplatin, cisplatin, docetaxel, epirubicin, fluoropyrimidine, fluorouracil, Irinotecan, leucovorin, mitomycin, oxaliplatin, paclitaxel, ramucirumab, trastuzumab, and any combinations thereof.

Head and Neck Cancer Combination Therapy

Therapeutic agents used to treat head and neck cancer include afatinib, bleomycin, capecitabine, carboplatin, cetuximab, cisplatin, docetaxel, fluorouracil, gemcitabine, hydroxyurea, methotrexate, nivolumab, paclitaxel, zimberelimab (AB122), pembrolizumab, vinorelbine, and any combinations thereof.

Therapeutic agents used to treat head and neck squamous cell carcinoma (HNSCC) include pembrolizumab, carboplatin, 5-FU, docetaxel, cetuximab (Erbitux®), cisplatin, nivolumab (Opdivo®), and combinations thereof. In some embodiments therapeutic agents used to treat HNSCC include pembrolizumab+carboplatin+5-FU, cetuximab+cisplatin+5-FU, cetuximab+carboplatin+5-FU, cisplatin+5-FU, and carboplatin+5-FU. In some embodiments therapeutic agents used to treat HNSCC include durvalumab, durvalumab+tremelimumab, nivolumab+ipilimumab, rovaluecel, pembrolizumab, pembrolizumab+epacadostat, GSK3359609+pembrolizumab, lenvatinib+pembrolizumab, retifanlimab, retifanlimab+enobituzumab, ADU-S100+pembrolizumab, epacadostat+nivolumab+ipilimumab/lirilumab.

Hepatobiliary Cancer Combination Therapy

Therapeutic agents used to treat hepatobiliary cancer include capecitabine, cisplatin, fluoropyrimidine, 5-fluorourcil, gemecitabine, oxaliplatin, sorafenib, and any combinations thereof.

Hepatocellular Carcinoma Combination Therapy

Therapeutic agents used to treat hepatocellular carcinoma include capecitabine, doxorubicin, gemcitabine, sorafenib, and any combinations thereof.

Non-Small Cell Lung Cancer Combination Therapy

Therapeutic agents used to treat non-small cell lung cancer (NSCLC) include afatinib, albumin-bound paclitaxel, alectinib, bevacizumab, bevacizumab biosimilar, cabozantinib, carboplatin, cisplatin, crizotinib, dabrafenib, docetaxel, erlotinib, etoposide, gemcitabine, nivolumab, paclitaxel, zimberelimab (AB122), pembrolizumab, pemetrexed, ramucirumab, trametinib, trastuzumab, vandetanib, vemurafenib, vinblastine, vinorelbine, and any combinations thereof. In some embodiments therapeutic agents used to treat NSCLC include alectinib (Alecensa®), dabrafenib (Tafinlar®), trametinib (Mekinist®), osimertinib (Tagrisso®), entrectinib (Tarceva®), crizotinib (Xalkori®), pembrolizumab (Keytruda®), carboplatin, pemetrexed (Alimta®), nab-paclitaxel (Abraxane®), ramucirumab (Cyramza®), docetaxel, bevacizumab (Avastin®), brigatinib, gemcitabine, cisplatin, afatinib (Gilotrif®), nivolumab (Opdivo®), gefitinib (Iressa®), and combinations thereof. In some embodiments therapeutic agents used to treat NSCLC include dabrafenib+trametinib, pembrolizumab+carboplatin+pemetrexed, pembrolizumab+carboplatin+nab-paclitaxel, ramucirumab+docetaxel, bevacizumab+carboplatin+pemetrexed, pembrolizumab+pemetrexed+carboplatin, cisplatin+pemetrexed, bevacizumab+carboplatin+nab-paclitaxel, cisplatin+gemcitabine, nivolumab+docetaxel, carboplatin+pemetrexed, carboplatin+nab-paclitaxel, or pemetrexed+cisplatin+carboplatin. In some embodiments therapeutic agents used to NSCLC include datopotamab deruxtecan (DS-1062), trastuzumab deruxtecan (Enhertu®), enfortumab vedotin (Padcev®), durvalumab, canakinumab, cemiplimab, nogapendekin alfa, avelumab, tiragolumab, domvanalimab, vibostolimab, ociperlimab, or a combination thereof. In some embodiments therapeutic agents used to treat NSCLC include datopotamab deruxtecan+pembrolizumab, datopotamab deruxtecan+durvalumab, durvalumab+tremelimumab, pembrolizumab+lenvatinib+pemetrexed, pembrolizumab+olaparib, nogapendekin alfa (N-803)+pembrolizumab, tiragolumab+atezolizumab, vibostolimab+pembrolizumab, or ociperlimab+tislelizumab.

Small Cell Lung Cancer Combination Therapy

Therapeutic agents used to treat small cell lung cancer (SCLC) include bendamustime, carboplatin, cisplatin, cyclophosphamide, docetaxel, doxorubicin, etoposide, gemcitabine, ipillimumab, irinotecan, nivolumab, paclitaxel, temozolomide, topotecan, vincristine, vinorelbine, and any combinations thereof. In some embodiments therapeutic agents used to treat SCLC include atezolizumab, carboplatin, cisplatin, etoposide, paclitaxel, topotecan, nivolumab, durvalumab, trilaciclib, or combinations thereof. In some embodiments therapeutic agents used to treat SCLC include atezolizumab+carboplatin+etoposide, atezolizumab+carboplatin, atezolizumab+etoposide, or carboplatin+paclitaxel.

Melanoma Combination Therapy

Therapeutic agents used to treat melanoma cancer include albumin bound paclitaxel, carboplatin, cisplatin, cobiemtinib, dabrafenib, dacrabazine, IL-2, imatinib, interferon alfa-2b, ipilimumab, nitrosourea, nivolumab, paclitaxel, zimberelimab (AB122), pembrolizumab, pilimumab, temozolomide, trametinib, vemurafenib, vinblastine, and any combinations thereof.

Ovarian Cancer Combination Therapy

Therapeutic agents used to treat ovarian cancer include 5-flourouracil, albumin bound paclitaxel, altretamine, anastrozole, bevacizumab, capecitabine, carboplatin, cisplatin, cyclophosphamide, docetaxel, doxorubicin, etoposide, exemestane, gemcitabine, ifosfamide, irinotecan, letrozole, leuprolide acetate, liposomal doxorubicin, megestrol acetate, melphalan, olaparib, oxaliplatin, paclitaxel, Pazopanib, pemetrexed, tamoxifen, topotecan, vinorelbine, and any combinations thereof.

Prostate Cancer Combination Therapies

Therapeutic agents used to treat prostate cancer include enzalutamide (Xtandi®), leuprolide, trifluridine, tipiracil (Lonsurf), cabazitaxel, prednisone, abiraterone (Zytiga®), docetaxel, mitoxantrone, bicalutamide, LHRH, flutamide, ADT, sabizabulin (Veru-111), and combinations thereof. In some embodiments therapeutic agents used to treat prostate cancer include enzalutamide+leuprolide, trifluridine+tipiracil (Lonsurf), cabazitaxel+prednisone, abiraterone+prednisone, docetaxel+prednisone, mitoxantrone+prednisone, bicalutamide+LHRH, flutamide+LHRH, leuprolide+flutamide, and abiraterone+prednisone+ADT.

Pancreatic Cancer Combination Therapy

Therapeutic agents used to treat pancreatic cancer include 5-fluorourcil, albumin-bound paclitaxel, capecitabine, cisplatin, docetaxel, erlotinib, fluoropyrimidine, gemcitabine, irinotecan, leucovorin, oxaliplatin, paclitaxel, and any combinations thereof. In some embodiments therapeutic agents used to treat pancreatic cancer include 5-FU+leucovorin+oxaliplatin+irinotecan, 5-FU+nanoliposomal irinotecan, leucovorin+nanoliposomal irinotecan, and gemcitabine+nab-paclitaxel.

Renal Cell Carcinoma Combination Therapy

Therapeutic agents used to treat renal cell carcinoma include axitinib, bevacizumab, cabozantinib, erlotinib, everolimus, levantinib, nivolumab, pazopanib, sorafenib, sunitinib, temsirolimus, and any combinations thereof.

13. Combination Therapies—Antiviral and Anticancer

CD47 Targeting Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agent that disrupts the binding of CD47 to SIRPα, e.g., an agent that targets or binds to CD47 or an agent that targets SIRPα. In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of CD47 (IAP, MER6, OA3; NCBI Gene ID: 961). Examples of CD47 inhibitors include without limitation anti-CD47 mAbs (Vx-1000, Vx-1004), anti-human CD47 mAbs (CNTO-7108), CC-90002, CC-90002-ST-001, humanized anti-CD47 antibody (Hu5F9-G4; magrolimab), lemzoparlimab (TJC-4), letaplimab (IBI-188), NI-1701, NI-1801, RCT-1938, STI-6643, GenSci-059 and TTI-621. In some embodiments, the CD47 inhibitor, e.g., anti-human CD47 antibody, is magrolimab. In some embodiments, the CD47 inhibitor is a bispecific antibodies targeting CD47, such as IBI-322 (CD47/PD-L1), IMM-0306 (CD47/CD20), TJ-L1C4 (CD47/PD-L1), HX-009 (CD47/PD-1), PMC-122 (CD47/PD-L1), PT-217, (CD47/DLL3), IMM-26011 (CD47/FLT3), IMM-0207 (CD47/VEGF), IMM-2902 (CD47/HER2), BH29xx (CD47/PD-L1), IMM-03 (CD47/CD20), IMM-2502 (CD47/PD-L1), HMBD-004B (CD47/BCMA), HMBD-004A (CD47/CD33), TG-1801 (NI-1701), or NI-1801. In some embodiments, the CD47 inhibitor is magrolimab. In some embodiments, the CD47 targeting agent is a CAR-T cell, such as KD 045.

SIRPα Targeting Agents

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a SIRPα targeting agent (NCBI Gene ID: 140885; UniProt P78324). Examples of SIRPα targeting or binding agents include without limitation SIRPα inhibitors, such as AL-008, RRx-001, and CTX-5861, and anti-SIRPα antibodies, such as FSI-189 (GS-0189), ES-004, BI-765063, ADU1805, CC-95251 and Q-1801 (SIRPα/PD-L1). Additional SIRPα-targeting agents of use are described, for example, in WO200140307, WO2002092784, WO2007133811, WO2009046541, WO2010083253, WO2011076781, WO2013056352, WO2015138600, WO2016179399, WO2016205042, WO2017178653, WO2018026600, WO2018057669, WO2018107058, WO2018190719, WO2018210793, WO2019023347, WO2019042470, WO2019175218, WO2019183266, WO2020013170 and WO2020068752.

FLT3 Agonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agonist of FLT3 (NCBI Gene ID: 2322; a.k.a., CD135, FLK-2, FLK2, STK1). In some embodiments, the antibody and/or fusion protein provided herein is administered with a FLT3 ligand. In some embodiments, the antibody and/or fusion protein provided herein is administered with a FLT3L-Fc fusion protein, e.g., as described in WO2020263830. In some embodiments the antibody and/or fusion protein provided herein is administered with GS-3583 or CDX-301. an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with GS-3583.

Phosphatidylinositol 3-Kinase (PI3K) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of a phosphatidylinositol-4,5-bisphosphate 3-kinase catalytic subunit, e.g., phosphatidylinositol-4,5-bisphosphate 3-kinase catalytic subunit alpha (PIK3CA, CLAPO, CLOVE, CWS5, MCAP, MCM, MCMTC, PI3K, PI3K-alpha, p110-alpha; NCBI Gene ID: 5290); phosphatidylinositol-4,5-bisphosphate 3-kinase catalytic subunit beta (PIK3CB, P110BETA, PI3K, PI3KBETA, PIK3C1; NCBI Gene ID: 5291); phosphatidylinositol-4,5-bisphosphate 3-kinase catalytic subunit gamma (PIK3CG, PI3CG, PI3K, PI3Kgamma, PIK3, p110gamma, p120-PI3K; Gene ID: 5494); and/or phosphatidylinositol-4,5-bisphosphate 3-kinase catalytic subunit delta (PIK3CD, APDS, IMD14, P110DELTA, PI3K, p110D, NCBI Gene ID: 5293). In some embodiments, the PI3K inhibitor is a pan-PI3K inhibitor. Examples of PI3K inhibitors include without limitation, ACP-319, AEZA-129, AMG-319, AS252424, AZD8186, BAY 1082439, BEZ235, bimiralisib (PQR309), buparlisib (BKM120), BYL719 (alpelisib), carboxyamidotriazole orotate (CTO), CH5132799, CLR-457, CLR-1401, copanlisib (BAY 80-6946), DS-7423, dactolisib, duvelisib (IPI-145), fimepinostat (CUDC-907), gedatolisib (PF-05212384), GDC-0032, GDC-0084 (RG7666), GDC-0077, pictilisib (GDC-0941), GDC-0980, GSK2636771, GSK2269577, GSK2141795, idelalisib (Zydelig®), INCB040093, INCB50465, IPI-443, IPI-549, KAR4141, LY294002, LY3023414, NERLYNX® (neratinib), nemiralisib (GSK2269557), omipalisib (GSK2126458, GSK458), OXY 1I A, panulisib (P7170, AK151761), PA799, perifosine (KRX-0401), Pilaralisib (SAR245408; XL147), puquitinib mesylate (XC-302), SAR260301, seletalisib (UCB-5857), serabelisib (INK-1117, MLN-1117, TAK-117), SF1126, sonolisib (PX-866), RG6114, RG7604, rigosertib sodium (ON-01910 sodium), RP5090, tenalisib (RP6530), RV-1729, SRX3177, taselisib, TG100115, umbralisib (TGR-1202), TGX221, voxtalisib (SAR245409), VS-5584, WX-037, X-339, X-414, XL499, XL756, wortmannin, ZSTK474, and the compounds described in WO 2005/113556 (ICOS), WO 2013/052699 (Gilead Calistoga), WO 2013/116562 (Gilead Calistoga), WO 2014/100765 (Gilead Calistoga), WO 2014/100767 (Gilead Calistoga), and WO 2014/201409 (Gilead Sciences).

Bruton Tyrosine Kinase (BTK) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of Bruton tyrosine kinase (BTK, AGMX1, AT, ATK, BPK, IGHD3, IMD1, PSCTK1, XLA; NCBI Gene ID: 695). Examples of BTK inhibitors include without limitation, tirabrutinib (GS-4059), (S)-6-amino-9-(1-(but-2-ynoyl)pyrrolidin-3-yl)-7-(4-phenoxyphenyl)-7H-purin-8(9H)-one, ABBV-105, acalabrutinib (ACP-196), AC-058, AC-0025, ARQ-531, BMS-986142, dasatinib, ibrutinib (PCI-32765, CRA-032765), GDC-0853, PRN-1008, SNS-062, zanubrutinib (BGB-3111), CB988, HM71224, KBP-7536, M-2951 (evobrutinib), M7583, tirabrutinib (ONO-4059), ML-319, MSC-2364447, PRN-1008, RDX-022, RG-7845, spebrutinib (CC-292), TAK-020, TAS-5315, TP-0158, TP-4207, vecabrutinib (SNS-062), ARQ-531, SHR-1459, DTRMWXHS-12, and the compounds disclosed in US20140330015 (Ono Pharmaceutical), US20130079327 (Ono Pharmaceutical), and US20130217880 (Ono Pharmaceutical).

Alpha-4/Beta-7 Antagonists

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an alpha-4/beta-7 antagonist. Examples of Integrin alpha-4/beta-7 antagonists include PTG-100, TRK-170, abrilumab, etrolizumab, carotegrast methyl, and vedolizumab.

Histone Deacetylase (HDAC) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of a histone deacetylase, e.g., histone deacetylase 1 (HDAC1; NCBI Gene ID: 3065), histone deacetylase 2 (HDAC2; NCBI Gene ID: 3066), histone deacetylase 3 (HDAC3; NCBI Gene ID: 8841), histone deacetylase 4 (HDAC4; NCBI Gene ID: 9759), histone deacetylase 5 (HDAC5; NCBI Gene ID: 10014), histone deacetylase 6 (HDAC6; NCBI Gene ID: 10013), histone deacetylase 7 (HDAC7; NCBI Gene ID: 51564), histone deacetylase 8 (HDAC8; NCBI Gene ID: 55869), histone deacetylase 9 (HDAC9; NCBI Gene ID: 9734), histone deacetylase 11 (HDAC11; NCBI Gene ID: 79885). Examples of HDAC inhibitors that can be combined with the one or more multi-specific antigen binding molecules, described herein, include without limitation, abexinostat, ACY-241, AR-42, BEBT-908, belinostat, CKD-581, CS-055 (HBI-8000), CT-101, CUDC-907 (fimepinostat), entinostat, givinostat, mocetinostat, panobinostat, pracinostat, quisinostat (JNJ-26481585), resminostat, ricolinostat, romidepsin, SHP-141, TMB-ADC, valproic acid (VAL-001), vorinostat, tinostamustine, remetinostat, romidepsin, tucidinostat.

Cyclin-Dependent Kinase (CDK) Inhibitors or Antagonists

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with inhibitor of cyclin dependent kinase 1 (CDK1, CDC2; CDC28A; P34CDC2; NCBI Gene ID: 983); cyclin dependent kinase 2 (CDK2, CDKN2; p33(CDK2); NCBI Gene ID: 1017); cyclin dependent kinase 3 (CDK3; NCBI Gene ID: 1018); cyclin dependent kinase 4 (CDK4, CMM3; PSK-J3; NCBI Gene ID: 1019); cyclin dependent kinase 6 (CDK6, MCPH12; PLSTIRE; NCBI Gene ID: 1021); cyclin dependent kinase 7 (CDK7, CAK; CAK1; HCAK; MO15; STK1; CDKN7; p39MO15; NCBI Gene ID: 1022); cyclin dependent kinase 9 (CDK9, TAK; C-2k; CTK1; CDC2L4; PITALRE; NCBI Gene ID: 1025). Inhibitors of CDK 1, 2, 3, 4, 6, 7 and/or 9 that can be combined or co-administered include without limitation abemaciclib, alvocidib (HMR- 1275, flavopiridol), AT-7519, dinaciclib, ibrance, FLX-925, LEE001, palbociclib, ribociclib, rigosertib, selinexor, UCN-01, SY1365, CT-7001, SY-1365, G1T38, milciclib, simurosertib hydrate (TAK931), trilaciclib, PF-06873600, AZD4573, and TG-02. In some embodiments, the CDK4/CDK6/CDK9 inhibitor or antagonist is selected from the group consisting of VS2-370.

Histone Deacetylase (HDAC) Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of a histone deacetylase, e.g., histone deacetylase 9 (HDAC9, HD7, HD7b, HD9, HDAC, HDAC7, HDAC7B, HDAC9B, HDAC9FL, HDRP, MITR; Gene ID: 9734). Examples of HDAC inhibitors include abexinostat, ACY-241, AR-42, BEBT-908, belinostat, CKD-581, CS-055 (HBI-8000), CUDC-907 (fimepinostat), entinostat, givinostat, mocetinostat, panobinostat, pracinostat, quisinostat (JNJ-26481585), resminostat, ricolinostat, SHP-141, valproic acid (VAL-001), vorinostat, tinostamustine, remetinostat, and entinostat.

14. Combination Therapies—Immune Response Enhancement

In the context of antiviral and anticancer therapies, in various embodiments an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an immunostimulatory therapy. Illustrative immunostimulatory therapies include without limitation blockers or inhibitors of inhibitory immune checkpoint proteins or receptors, stimulators, activators or agonists of stimulatory immune checkpoint proteins or receptors, toll-like receptor (TLR) agonists, cytokine or chemokine receptor agonists. T-cell engagers and Natural Killer (NK) cell engagers.

Immune Checkpoint Receptor Proteins

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more blockers or inhibitors of inhibitory immune checkpoint proteins or receptors and/or with one or more stimulators, activators or agonists of stimulatory immune checkpoint proteins or receptors. Blockade or inhibition of inhibitory immune checkpoints can positively regulate T-cell or NK cell activation and prevent immune escape of infected cells. Activation or stimulation of stimulatory immune check points can augment the effect of immune checkpoint inhibitors in infective therapeutics. In various embodiments, the immune checkpoint proteins or receptors regulate T cell responses (e.g., reviewed in Xu, et al., *J Exp Clin Cancer Res.* (2018) 37:110; and Wykes, et al., *Nat Rev Immunol.* (2018) 18(2):91-104). In various embodiments, the immune checkpoint proteins or receptors regulate NK cell responses (e.g., reviewed in Davis, et al., *Semin Immunol.* (2017) 31:64-75 and Chiossone, et al., *Nat Rev Immunol.* (2018) 18(11):671-688).

Examples of immune checkpoint proteins or receptors that can be combined with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, include without limitation CD27, CD70; CD40, CD40LG; CD47, CD48 (SLAMF2), transmembrane and immunoglobulin domain containing 2 (TMIGD2, CD28H), CD84 (LY9B, SLAMF5), CD96, CD160 (NK1, NK28, BY55), MS4A1 (CD20), CD244 (SLAMF4); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); natural killer cell cytotoxicity receptor 3 ligand 1 (NCR3LG1, B7H6); HERV-H LTR-associating 2 (HHLA2, B7H7); inducible T cell co-stimulator (ICOS, CD278); inducible T cell co-stimulator ligand (ICOSLG, B7H2); TNF receptor superfamily member 4 (TNFRSF4, OX40); TNF superfamily member 4 (TNFSF4, OX40L); TNFRSF8 (CD30), TNFSF8 (CD30L); TNFRSF10A (CD261, DR4, TRAILR1), TNFRSF9 (CD137), TNFSF9 (CD137L); TNFRSF10B (CD262, DR5, TRAILR2), TNFRSF10 (TRAIL); TNFRSF14 (HVEM, CD270), TNFSF14 (HVEML); CD272 (B and T lymphocyte associated (BTLA)); TNFRSF17 (BCMA, CD269), TNFSF13B (BAFF); TNFRSF18 (GITR), TNFSF18 (GITRL); MHC class I polypeptide-related sequence A (MICA); MHC class I polypeptide-related sequence B (MICB); CD274 (CD274, PDL1, PD-L1); programmed cell death 1 (PDCD1, PD1, PD-1); cytotoxic T-lymphocyte associated protein 4 (CTLA4, CD152); CD80 (B7-1), CD28; nectin cell adhesion molecule 2 (NECTIN2, CD112); CD226 (DNAM-1); Poliovirus receptor (PVR) cell adhesion molecule (PVR, CD155); PVR related immunoglobulin domain containing (PVRIG, CD112R); T cell immunoreceptor with Ig and ITIM domains (TIGIT); T cell immunoglobulin and mucin domain containing 4 (TIMD4; TIM4); hepatitis A virus cellular receptor 2 (HAVCR2, TIMD3, TIM3); galectin 9 (LGALS9); lymphocyte activating 3 (LAG3, CD223); signaling lymphocytic activation molecule family member 1 (SLAMF1, SLAM, CD150); lymphocyte antigen 9 (LY9, CD229, SLAMF3); SLAM family member 6 (SLAMF6, CD352); SLAM family member 7 (SLAMF7, CD319); sialic acid binding Ig like lectin 7 (SIGLEC7); sialic acid binding Ig like lectin 9 (SIGLEC9); UL16 binding protein 1 (ULBP1); UL16 binding protein 2 (ULBP2); UL16 binding protein 3 (ULBP3); retinoic acid early transcript 1E (RAET1E; ULBP4); retinoic acid early transcript 1G (RAET1G; ULBP5); retinoic acid early transcript 1L (RAET1L; ULBP6); killer cell immunoglobulin like receptor, three Ig domains and long cytoplasmic tail 1 (KIR, CD158E1); killer cell lectin like receptor C1 (KLRC1, NKG2A, CD159A); killer cell lectin like receptor K1 (KLRK1, NKG2D, CD314); killer cell lectin like receptor C2 (KLRC2, CD159c, NKG2C); killer cell lectin like receptor C3 (KLRC3, NKG2E); killer cell lectin like receptor C4 (KLRC4, NKG2F); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); killer cell lectin like receptor D1 (KLRD1); killer cell lectin like receptor G1 (KLRG1; CLEC15A, MAFA, 2F1) and Hematopoietic Progenitor Kinase 1 (HPK1, MAP4K1).

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more blockers or inhibitors of one or more T-cell inhibitory immune checkpoint proteins or receptors. Illustrative T-cell inhibitory immune checkpoint proteins or receptors include without limitation CD274 (CD274, PDL1, PD-L1); programmed cell death 1 ligand 2 (PDCD1LG2, PD-L2, CD273); programmed cell death 1 (PDCD1, PD1, PD-1); cytotoxic T-lymphocyte associated protein 4 (CTLA4, CD152); CD276 (B7H3); V-set domain containing T cell activation inhibitor 1 (VTCN1, B7H4); V-set immunoregulatory receptor (VSIR, B7H5, VISTA); immunoglobulin superfamily member 11 (IGSF11, VSIG3); TNFRSF14 (HVEM, CD270), TNFSF14 (HVEML); CD272 (B and T lymphocyte associated (BTLA)); PVR related immunoglobulin domain containing (PVRIG, CD112R); T cell immunoreceptor with Ig and ITIM domains (TIGIT); lymphocyte activating 3 (LAG3, CD223); hepatitis A virus cellular receptor 2 (HAVCR2, TIMD3, TIM3); galectin 9 (LGALS9); killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); and killer cell immunoglobulin like receptor, three Ig domains and long cytoplasmic tail 1 (KIR3DL1). In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more agonist or activators of one or more T-cell stimulatory immune checkpoint proteins or receptors. Illustrative T-cell stimulatory immune checkpoint proteins or receptors include without limitation CD27, CD70; CD40, CD40LG; inducible T cell costimulator (ICOS, CD278); inducible T cell costimulator ligand (ICOSLG, B7H2); TNF receptor superfamily member 4 (TNFRSF4, OX40); TNF superfamily member 4 (TNFSF4, OX40L); TNFRSF9 (CD137), TNFSF9 (CD137L); TNFRSF18 (GITR), TNFSF18 (GITRL); CD80 (B7-1), CD28; nectin cell adhesion molecule 2 (NECTIN2, CD112); CD226 (DNAM-1); CD244 (2B4, SLAMF4), Poliovirus receptor (PVR) cell adhesion molecule (PVR, CD155). See, e.g., Xu, et al., J Exp Clin Cancer Res. (2018) 37:110.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more blockers or inhibitors of one or more NK-cell inhibitory immune checkpoint proteins or receptors. Illustrative NK-cell inhibitory immune checkpoint proteins or receptors include without limitation killer cell immunoglobulin like receptor, three Ig domains and long cytoplasmic tail 1 (KIR, CD158E1); killer cell immunoglobulin like receptor, two Ig domains and long cytoplasmic tail 1 (KIR2DL1); killer cell immunoglobulin like receptor, two Ig domains and long cytoplasmic tail 2 (KIR2DL2); killer cell immunoglobulin like receptor, two Ig domains and long cytoplasmic tail 3 (KIR2DL3); killer cell immunoglobulin like receptor, three Ig domains and long cytoplasmic tail 1 (KIR3DL1); CD160 (a.k.a., BY55, NK1, NK28; NCBI Gene ID: 11126); killer cell lectin like receptor BI (KLRB1, a.k.a., CD161, CLEC5B; NCBI Gene ID: 3820); killer cell lectin like receptor C1 (KLRC1, NKG2A, CD159A); and killer cell lectin like receptor D1 (KLRD1, CD94). In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more agonist or activators of one or more NK-cell stimulatory immune checkpoint proteins or receptors. Illustrative NK-cell stimulatory immune checkpoint proteins or receptors include without limitation CD16, CD226 (DNAM-1); CD244 (2B4, SLAMF4); killer cell lectin like receptor K1 (KLRK1, NKG2D, CD314); SLAM family member 7 (SLAMF7). See, e.g., Davis, et al., Semin Immunol. (2017) 31:64-75; Fang, et al., Semin Immunol. (2017) 31:37-54; and Chiossone, et al., Nat Rev Immunol. (2018) 18(11):671-688.

In some embodiments, the one or more immune checkpoint inhibitors comprises a proteinaceous (e.g., antibody or fragment thereof, or antibody mimetic) inhibitor of PD-L1 (CD274), PD-1 (PDCD1) or CTLA4. In some embodiments, the one or more immune checkpoint inhibitors comprises a small organic molecule inhibitor of PD-L1 (CD274), PD-1 (PDCD1) or CTLA4.

Examples of inhibitors of CTLA4 that can be combined or co-administered include without limitation ipilimumab, tremelimumab, BMS-986218, AGEN1181, AGEN1884 (zalifrelimab), BMS-986249, MK-1308, REGN-4659, ADU-1604, CS-1002 (ipilimumab biosimilar), BCD-145, APL-509, JS-007, BA-3071, ONC-392, AGEN2041, JHL-1155, KN-044, CG-0161, ATOR-1144, PBI-5D3H5, BPI-002, as well as multi-specific inhibitors FPT-155 (CTLA4/PD-L1/CD28), PF-06936308 (PD-1/CTLA4), MGD-019 (PD-1/CTLA4), KN-046 (PD-1/CTLA4), MEDI-5752 (CTLA4/PD-1), XmAb-20717 (PD-1/CTLA4), and AK-104 (CTLA4/PD-1).

Examples of inhibitors of programmed cell death 1 (PDCD1; NCBI Gene ID: 5133; CD279, PD-1, PD1) that can be combined or co-administered include without limitation zimberelimab (AB122, GLS-010, WBP-3055), pembrolizumab (KEYTRUDA®, MK-3475, SCH900475), nivolumab (OPDIVO®, BMS-936558, MDX-1106), cemiplimab (LIBTAYO®; cemiplimab-rwlc, REGN-2810), pidilizumab (CT-011), AMG-404, MEDI0680 (AMP-514), spartalizumab (PDR001), tislelizumab (BGB-A317), toripalimab (JS-001), genolimzumab (CBT-501, APL-501, GB 226), SHR-1201, camrelizumab (SHR-1210), sintilimab (TYVYT®; IBI-308), dostarlimab (TSR-042, WBP-285), lambrolizumab (MK-3475); sasanlimab (PF-06801591), cetrelimab (JNJ-63723283), serplulimab (HLX-10), retifanlimab (MGA-012), balstilimab (AGEN2034), prolgolimab (BCD 100), budigalimab (ABBV-181), vopratelimab (JTX-4014), AK-103 (HX-008), AK-105, CS-1003, BI-754091, LZM-009, Sym-021, BAT-1306, PD1-PIK, tebotelimab (MGD013; PD-1/LAG-3), RO-7247669 (PD-1/LAG-3), FS-118 (LAG-3/PD-L1), RO-7121661 (PD-1/TIM-3), RG7769 (PD-1/TIM-3), PF-06936308 (PD-1/CTLA4), MGD-019 (PD-1/CTLA4), KN-046 (PD-1/CTLA4), XmAb-20717 (PD-1/CTLA4), AK-104 (CTLA4/PD-1) and MEDI-5752 (CTLA4/PD-1). In some embodiments, the first and/or second antigen binding domain comprises the extracellular domain of the human programmed cell death 1 ligand 2 (PD-L2) and binds to PD1 (e.g., AMP-224).

Examples of inhibitors of CD274 molecule (NCBI Gene ID: Gene ID: 29126; B7-H, B7H1, PD-L1) that can be combined or co-administered include without limitation atezolizumab (TECENTRIQ®), avelumab (BAVENCIO®; MSB0010718C), envafolimab (ASC22), durvalumab (IMFINZI®; MEDI-4736), BMS-936559 (MDX1105), cosibelimab (CK-301), lodapolimab (LY 3300054), garivulimab (BGB A333), envafolimab (KN035), opucolimab (HLX 20), manelimab (BCD 135), CX-072, CBT-502 (TQB2450), MSB-2311, SHR-1316, sugemalimab (CS-1001; WBP3155), A167 (KL-A167, HBM 9167), STI-A1015 (IMC-001), FAZ-053, BMS-936559 (MDX1105), INCB086550, GEN-1046 (PD-L1/4-1BB), FPT-155 (CTLA4/PD-L1/CD28), M7824 (PD-L1/TGFβ-EC domain), CA-170 (PD-L1/VISTA), CDX-527 (CD27/PD-L1), LY-3415244 (TIM-3/PDL1), INBRX-105 (4-1BB/PDL1) and GNS-1480 (PD-L1/EGFR), and further includes human-derived, allogeneic, natural killer cells engineered to express a chimeric antigen receptor (CAR) targeting PD-L1, such as PD-L1 t-haNK.

In some embodiments, a small molecule inhibitor of CD274 or PDCD1 is combined or co-administered, e.g., such as those selected from the group consisting of GS-4224, GS-4416, INCB086550 and MAX10181. Additional examples of small molecule PD-L1 inhibitors that can be combined or co-administered include those disclosed in U.S. Publication No. US2018305315 (Gilead Sciences), US2020017471 (Gilead Sciences) and US2019270727 (Gilead Sciences). In some embodiments, the small molecule inhibitor of CTLA4 comprises BPI-002.

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-TIGIT antibody, such as etigilimab, BMS-986207, tiragolumab (a.k.a., MTIG-7192A; RG-6058; RO 7092284), vibostolimab (MK-7684), AGEN1307, AGEN1327, AGEN1777, COM-902, IBI-939, AB154, SGN-TGT, MG1131, BGB-A1217 and EOS884448 (EOS-448).

Regulatory T-Cell Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of regulatory T cells. Inhibition of regulatory T-cell (Treg) activity or Treg depletion can mitigate, overcome or reverse the suppression of antiviral or antitumor immune responses and have antiviral or anticancer effects. See, e.g., Plitas and Rudensky, *Annu. Rev. Cancer Biol.* (2020) 4:459-77; Tanaka and Sakaguchi, *Eur. J. Immunol.* (2019) 49:1140-1146. In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more inhibitors of Treg activity or a Treg depleting agent. Treg inhibition or depletion can augment the effect of immune checkpoint inhibitors in antiviral and anticancer therapeutics.

In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more Treg inhibitors. In some embodiments, the Treg inhibitor can suppress the migration of Tregs into the tumor microenvironment. In some embodiments, Treg inhibitor can reduce the immunosuppressive function of Tregs. In some embodiments, the Treg inhibitor can modulate the cellular phenotype and induce production of proinflammatory cytokines. Exemplary Treg inhibitors include without limitation, CCR4 (NCBI Gene ID: 1233) antagonists and degraders of Ikaros zinc-finger proteins (e.g., Ikaros (IKZF1; NCBI Gene ID: 10320), Helios (IKZF2; NCBI Gene ID: 22807), Aiolos (IKZF3; NCBI Gene ID: 22806), and Eos (IKZF4; NCBI Gene ID: 64375).

Examples of Helios degraders that can be co-administered include without limitation I-57 (Novartis) and compounds disclosed in WO2019038717, WO2020012334, WO20200117759, and WO2021101919.

In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more Treg depleting agents. In some embodiments the Treg depleting agent is an antibody. In some embodiments the Treg depleting antibody has antibody-dependent cytotoxic (ADCC) activity. In some embodiments, the Treg depleting antibody is Fc-engineered to possess an enhanced ADCC activity. In some embodiments the Treg depleting antibody is an antibody-drug conjugate (ADC). Illustrative targets for Treg depleting agents include without limitation CD25 (IL2RA; NCBI Gene ID: 3559), CTLA4 (CD152; NCBI Gene ID: 1493); GITR (TNFRSF18; NCBI Gene ID: 8784); 4-1BB (CD137; NCBI Gene ID: 3604), OX-40 (CD134; NCBI Gene ID: 7293), LAG3 (CD223; NCBI Gene ID: 3902), TIGIT (NCBI Gene ID: 201633), CCR4 (NCBI Gene ID: 1233), and CCR8 (NCBI Gene ID: 1237).

In some embodiments the Treg inhibitor or Treg depleting agent that can be co-administered comprises an antibody or antigen-binding fragment thereof that selectively binds to a cell surface receptor selected from the group consisting of C-C motif chemokine receptor 4 (CCR4), C-C motif chemokine receptor 7 (CCR7), C-C motif chemokine receptor 8 (CCR8), C-X-C motif chemokine receptor 4 (CXCR4; CD184), TNFRSF4 (OX40), TNFRSF18 (GITR, CD357), TNFRSF9 (4-1BB, CD137), cytotoxic T-lymphocyte associated protein 4 (CTLA4, CD152), programmed cell death 1 (PDCD1, PD-1), Sialyl Lewis x (CD15s), CD27, ectonucleoside triphosphate diphosphohydrolase 1 (ENTPD1; CD39), protein tyrosine phosphatase receptor type C (PTPRC; CD45), neural cell adhesion molecule 1 (NCAM1; CD56), selectin L (SELL; CD62L), integrin subunit alpha E (ITGAE; CD103), interleukin 7 receptor (IL7R; CD127), CD40 ligand (CD40LG; CD154), folate receptor alpha (FOLR1), folate receptor beta (FOLR2), leucine rich repeat containing 32 (LRRC32; GARP), IKAROS family zinc finger 2 (IKZF2; HELIOS), inducible T cell costimulatory (ICOS; CD278), lymphocyte activating 3 (LAG3; CD223), transforming growth factor beta 1 (TGFB1), hepatitis A virus cellular receptor 2 (HAVCR2; CD366; TIM3), T cell immunoreceptor with Ig and ITIM domains (TIGIT), TNF receptor superfamily member 1B (CD120b; TNFR2), IL2RA (CD25) or a combination thereof.

Examples of Treg depleting anti-CCR8 antibodies that can be administered include without limitation JTX-1811 (GS-1811) (Jounce Therapeutics, Gilead Sciences), BMS-986340 (Bristol Meyers Squibb), S-531011 (Shionogi), FPA157 (Five Prime Therapeutics), SRF-114 (Surface Oncology), HBM1022 (Harbor BioMed), IO-1 (Oncurious), and antibodies disclosed in WO2021163064, WO2020138489, and WO2021152186.

Examples of Treg depleting anti-CCR4 antibodies that can be administered include mogamulizumab.

Inhibiting, depleting, or reprogramming of non-stimulatory myeloid cells in the tumor microenvironment can enhance antiviral or anticancer immune responses (see, e.g., Binnewies, et al., *Nat. Med.* (2018) 24(5): 541-550; WO2016049641). Illustrative targets for depleting or reprogramming non-stimmulatory myeloid cells include triggering receptors expressed on myeloid cells, TREM-1 (CD354, NCBI Gene ID: 54210) and TREM-2 (NCBI Gene ID: 54209). In some embodiments an antibody and/or fusion protein provided herein is administered with one or more myeloid cell depleting or reprogramming agents, such as an anti-TREM-1 antibody (e.g. PY159; antibodies disclosed in WO2019032624) or an anti-TREM-2 antibody (e.g., PY314; antibodies disclosed in WO2019118513).

Hematopoietic Progenitor Kinase 1 (HPK1) Inhibitors

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an inhibitor of mitogen-activated protein kinase kinase kinase kinase 1 (MAP4K1, a.k.a., Hematopoietic Progenitor Kinase 1 (HPK1); NCBI Gene ID: 11184). Examples of HPK1 inhibitors that can be combined or co-administered include, without limitation, ZYF-0272 and ZYF-0057.

TNF Superfamily (TNFSF) Member and TNF Receptor Superfamily (TNFRSF) Member Agonists or Activators In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agonist of one or more TNF receptor superfamily (TNFRSF) members, e.g., an agonist of one or more of TNFRSF1A (NCBI Gene ID: 7132), TNFRSF1B (NCBI Gene ID: 7133), TNFRSF4 (OX40, CD134; NCBI Gene ID: 7293), TNFRSF5 (CD40; NCBI Gene ID: 958), TNFRSF6 (FAS, NCBI Gene ID: 355), TNFRSF7 (CD27, NCBI Gene ID: 939), TNFRSF8 (CD30, NCBI Gene ID: 943), TNFRSF9 (4-1BB, CD137, NCBI Gene ID: 3604), TNFRSF10A (CD261, DR4, TRAILR1, NCBI Gene ID: 8797), TNFRSF10B (CD262, DR5, TRAILR2, NCBI Gene ID: 8795), TNFRSF10C (CD263, TRAILR3, NCBI Gene ID: 8794), TNFRSF10D (CD264, TRAILR4, NCBI Gene ID: 8793), TNFSF11 (CD254, RANKL; NCBI Gene ID: 8600), TNFRSF11A (CD265, RANK, NCBI Gene ID: 8792), TNFRSF11B (NCBI Gene ID: 4982), TNFRSF12A (CD266, NCBI Gene ID: 51330), TNFSF13 (APRIL, CD256; NCBI Gene ID: 8741), TNFRSF13B (CD267, NCBI Gene ID: 23495), TNFRSF13C (CD268, NCBI Gene ID: 115650), TNFRSF16 (NGFR, CD271, NCBI Gene ID: 4804), TNFRSF17 (BCMA, CD269, NCBI Gene ID: 608), TNFRSF18 (GITR, CD357, NCBI Gene ID: 8784), TNFRSF19 (NCBI Gene ID: 55504), TNFRSF21 (CD358, DR6, NCBI Gene ID: 27242), and TNFRSF25 (DR3, NCBI Gene ID: 8718).

Example tumor necrosis factor (TNF) receptor (e.g., TNFRSF1A (NCBI Gene ID: 7132); TNFRSF1B (NCBI Gene ID: 7133)) agonists that can be combined or co-administered includes tasonermin (recombinant human tumor necrosis factor alpha-1a (TNFα)). Further, an anti-angiogenic gene therapy fusion protein comprising the extracellular and intramembrane domains of the human TNFRSF1A and the intracellular domain of the Fas cell surface death receptor (FAS, a.k.a., CD95; NCBI Gene ID: 355), such as ofranergene obadenovec (VB-111) can be combined or co-administered;

Example anti-TNFRSF4 (OX40) antibodies that can be combined or co-administered include without limitation, MEDI6469, MEDI6383, MEDI0562 (tavolixizumab), MOXR0916, PF-04518600, RG-7888, GSK-3174998, INCAGN1949, BMS-986178, GBR-8383, ABBV-368, and those described in WO2016179517, WO2017096179, WO2017096182, WO2017096281, and WO2018089628.

Example TNFRSF5 (CD40) agonists (e.g., including agonist antibodies) that can be combined or co-administered include without limitation lucatumumab, RG7876, SEA-CD40, APX-005M, ABBV-428 and MEDI5083 (CD40L-Fc fusion protein).

CD40 ligand (CD40LG, a.k.a., CD154, TNFSF5; NCBI Gene ID: 959)-targeted CAR-DC cells, such as BPX-201 (autologous dendritic cells that are genetically modified to express an inducible co-stimulatory CD40 receptor), Example anti-TNFRSF7 (CD27) antibodies that can be combined or co-administered include without limitation varlilumab (CDX-1127).

Example TNFRSF8 (CD30)-targeted CAR-T cells that can be combined or co-administered include without limitation TT-11;

Example anti-TNFRSF9 (4-1BB, CD137) antibodies/agonists that can be combined or co-administered include without limitation urelumab, utomilumab (PF-05082566), AGEN2373, ADG-106, BT-7480, QL1806.

Example TNFRSF10A (CD261, DR4, TRAILR1, NCBI Gene ID: 8797) agonists that can be combined or co-administered include mapatumumab (HGS-ETR1), ABBV-621 and (TNF superfamily member 10 (TNFSF10, a.k.a., TRAIL; NCBI Gene ID: 8743)-trimer fusion protein, such as SCB-313.

An Example anti-fibroblast activation protein alpha (FAP; NCBI Gene ID: 2191)/anti-TNF receptor superfamily member 10b (TNFRSF10B, a.k.a., CD262, DR5, TRAILR2; NCBI Gene ID: 8795) antibody that can be combined or co-administered includes RG7386.

Example TNFSF11 (CD254, RANKL) antibodies that can be combined or co-administered include without limitation denosumab.

Example TNFSF13 (APRIL, CD256; NCBI Gene ID: 8741)-targeted therapies that can be combined or co-administered include antibodies, such as BION-1301, and engineered CAR T-cells, such as AUTO-2 (APRIL-CAR).

Example TNFRSF17 (BCMA, CD269, NCBI Gene ID: 608) targeted engineered CAR T-cells that can be combined or co-administered include bb-2121 (ide-cel), bb-21217, JCARH125, UCART-BCMA, ET-140, MCM-998, LCAR-B38M, CART-BCMA, SEA-BCMA, BB212, ET-140, P-BCMA-101, JNJ-68284528, CART-ddBCMA, BCMA-CS1 cCAR and Descartes-011.

Example anti-TNFRSF18 (GITR) antibodies that can be combined or co-administered include without limitation, MEDI1873, FPA-154, INCAGN-1876, TRX-518, BMS-986156, MK-1248, MK-4166, GWN-323, and those described in WO2017096179, WO2017096276, WO2017096189, and WO2018089628. In some embodiments, an antibody, or fragment thereof, co-targeting TNFRSF4 (OX40) and TNFRSF18 (GITR) is co-administered. Such antibodies are described, e.g., in WO 2017/096179, WO 2017/096276, WO 2017/096189; and WO 2018/089628.

Bi-specific antibodies targeting TNFRSF family members that can be co-administered include PRS-343 (CD-137/HER2), AFM26 (BCMA/CD16A), AFM-13 (CD16/CD30), odronextamab (REGN-1979; CD20/CD3), AMG-420 (BCMA/CD3), INHIBRX-105 (4-1BB/PDL1), FAP-4-IBBL (4-1BB/FAP), plamotamab (XmAb-13676; CD3/CD20), RG-7828 (CD20/CD3), CC-93269 (CD3/BCMA), REGN-5458 (CD3/BCMA), and IMM-0306 (CD47/CD20).

Toll-Like Receptor (TLR) Agonists

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agonist of a toll-like receptor (TLR), e.g., an agonist of TLR1 (NCBI Gene ID: 7096), TLR2 (NCBI Gene ID: 7097), TLR3 (NCBI Gene ID: 7098), TLR4 (NCBI Gene ID: 7099), TLR5 (NCBI Gene ID: 7100), TLR6 (NCBI Gene ID: 10333), TLR7 (NCBI Gene ID: 51284), TLR8 (NCBI Gene ID: 51311), TLR9 (NCBI Gene ID: 54106), and/or TLR10 (NCBI Gene ID: 81793).

Illustrative anti-toll like receptor 2 (TLR2; NCBI Gene ID: 7097) antibodies that can be combined or co-administered include OPN-305.

Illustrative toll like receptor 3 (TLR3; NCBI Gene ID: 7098) agonist/interferon inducers that can be combined or co-administered include poly-ICLC (NSC-301463), rintatolimod, RIBOXXON®, Apoxxim, RIBOXXIM®, IPH-33, MCT-465, MCT-475, and ND-1.1.

Illustrative toll like receptor (TLR4; NCBI Gene ID: 7099) agonists that can be combined or co-administered include G-100, GSK-179509 and PEPA-10.

Example toll like receptor 7 (TLR7; NCBI Gene ID: 51284) agonists that can be combined or co-administered with the one or more multi-specific antigen binding molecules, described herein, include without limitation AL-034, DSP-0509, GS-9620 (vesatolimod), vesatolimod analogs, LHC-165, TMX-101 (imiquimod), GSK-2245035, resiquimod, DSR-6434, DSP-3025, IMO-4200, MCT-465, telratolimod (MEDI-9197), 3M-051, SB-9922, 3M-052, Limtop, TMX-30X, TMX-202, RG-7863, RG-7854, RG-7795, RO-7011785 and corresponding prodrug RO-702053, and the compounds disclosed in US20100143301 (Gilead Sciences), US20110098248 (Gilead Sciences), and US20090047249 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Illustrative toll like receptor 8 (TLR8; NCBI Gene ID: 51311) agonists that can be co-administered or combined with the one or more multi-specific antigen binding molecules, described herein, include without limitation E-6887, IMO-4200, IMO-8400, IMO-9200, MCT-465, telratolimod (MEDI-9197), motolimod, resiquimod, selgantolimod (GS-9688), HRS-9950, SBT-8230, VTX-1463, VTX-763, 3M-051, 3M-052, SBT6050, and the compounds disclosed in US2016289229 (Gilead Sciences), US20140045849 (Janssen), US20140073642 (Janssen), WO2014/056953 (Janssen), WO2014/076221 (Janssen), WO2014/128189 (Janssen), US20140350031 (Janssen), WO2014/023813 (Janssen), US20080234251 (Array Biopharma), US20080306050 (Array Biopharma), US20100029585 (Ventirx Pharma), US20110092485 (Ventirx Pharma), US20110118235 (Ventirx Pharma), US20120082658 (Ventirx Pharma), US20120219615 (Ventirx Pharma), US20140066432 (Ventirx Pharma), US20140088085 (Ventirx Pharma), US20140275167 (Novira Therapeutics), and US20130251673 (Novira Therapeutics).

Illustrative TLR7/TLR8 dual agonists that can be combined or co-administered include NKTR-262, telratolimod, BDB-001 and CV8102.

Illustrative TLR9 agonists that can be combined or co-administered include without limitation AST-008 (cavrotolimod), cobitolimod, CMP-001, IMO-2055, IMO-2125, S-540956, litenimod, MGN-1601, BB-001, BB-006, IMO-3100, IMO-8400, IR-103, IMO-9200, agatolimod, DIMS-9054, DV-1079, DV-1179, AZD-1419, lefitolimod (MGN-1703), CYT-003, CYT-003-QbG10, tilsotolimod and PUL-042.

Cytokine or Chemokine Receptor Agonists

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more cytokine or chemokine receptor agonists. Illustrative cytokine or chemokine receptor agonists that can be co-administered include without limitation IL-10, IL-12, IL-18, gamma chain-dependent cytokines (e.g., IL-4, IL-7, IL-9, IL-15 and IL-21), fms related tyrosine kinase 3 (FLT3) ligand (FLT3LG), interferon (IFN)-α, IFN-β, a PEGylated interferon (e.g., PEG-IFN-α2a and/or PEG-IFN-α2b), IFN-γ, CXCL9/Mig (monokine induced by interferon-γ), CXCL10/IP10 (interferon-γ-inducible 10 kDa protein) and CXCL11/I-TAC (interferon-inducible T cell α-chemoattractant), CXCL4/PF4 (platelet factor 4), monocyte chemoattractant protein 2 (MCP-2), macrophage inflammatory protein 1 alpha (MIP-1α), macrophage inflammatory protein 1 beta (MIP-1β) and regulated on activation normal T expressed and secreted protein (RANTES). Examples of IL-15 receptor agonists include without limitation ALT-803, NKTR-255, and hetIL-15, interleukin-15/Fc fusion protein, AM-0015, NIZ-985, SO-C101, IL-15 Synthorin (pegylated IL-15), P-22339, and the IL-15-PD-1 fusion protein N-809. An illustrative IL-7 receptor agonist that can be co-administered includes CYT-107. Illustrative fms related tyrosine kinase 3 (FLT3; NCBI Gene ID: 2322; CD135, FLK-2, FLK2, STK1) agonists that can be co-administered include GS-3583 and CDX-301.

anti-interleukin 1 beta (IL1B; NCBI Gene ID: 3553) antibodies, such as canakinumab (ACZ885), VPM087;

anti-interleukin 3 (IL3; NCBI Gene ID: 3562) antibodies, such as JNJ-56022473;

JAK3/JAK1/TANK binding kinase 1 (TBK1; NCBI Gene ID: 29110) inhibitors, such as CS-12912; interleukin-3 receptor (IL-3R) modulators, such as SL-401;

interleukin 4 receptor (IL4R; NCBI Gene ID: 3566) receptor targeted immunotherapy, such as MDNA-55;

interleukin 6 receptor (IL6R; NCBI Gene ID: 3570) inhibitors, such as tocilizumab, atlizumab, AS-101 (CB-06-02, IVX-Q-101);

IL-10 receptor (e.g., IL10RA (NCBI Gene ID: 3587); IL10RB (NCBI Gene ID: 3588)) agonists, such as pegilodecakin (AM-0010);

interleukin 6 receptor IL6R (NCBI Gene ID: 3570)/MCL1 apoptosis regulator, BCL2 family member (MCL1; NCBI Gene ID: 4170)/heat shock protein family A (Hsp70) member (e.g., HSPA1A (NCBI Gene ID: 3303); HSPA1B (NCBI Gene ID: 3304); HSPA2 (NCBI Gene ID: 3306); HSPA4 (NCBI Gene ID: 3308); HSPA5 (NCBI Gene ID: 3309); HSPA6 (NCBI Gene ID: 3310); HSPA8 (NCBI Gene ID: 3312); HSPA9 (NCBI Gene ID: 3313)) inhibitors, such as SYLVANT® (siltuximab);

IL-12A (NCBI Gene ID: 3592)+IL-12B (NCBI Gene ID: 3593) mRNAs, such as MEDI1191;

IL-12 gene stimulators, such as EGEN-001, tavokinogene telseplasmid;

dendritic cells transduced to express IL-12, such as DC-RTS-IL-12;

autologous T-Cells genetically engineered to secrete IL-12 and to target the mucin 16, cell surface associated (MUC16, a.k.a., CA125; NCBI Gene ID: 94025), such as JCAR-020;

interleukin 13 receptor subunit alpha 2 (IL13RA2; NCBI Gene ID: 3598)-targeted CAR-T cells, such as MB-101;

mRNA encoding the cytokines interleukin-12 single chain (IL-12sc), interleukin-15+IL15RA sushi domain (IL-15sushi), interferon alpha (IFNα) and granulocyte-macrophage colony-stimulating factor (GM-CSF), such as SAR441000 (BNT131);

IL-15 receptor agonist, such as PRGN-3006, ALT-803; interleukin-15/Fc fusion protein (e.g., XmAb24306); recombinant interleukin-15 (e.g., AM0015, NIZ-985); pegylated IL-15 (e.g., NKTR-255), and hetIL-15;

anti-interleukin 17A (IL17A; NCBI Gene ID: 3605) antibodies, such as CJM-112;

interleukin 23A subunit alpha (IL-23A; NCBI Gene ID: 51561) inhibitors, such as guselkumab;

IL-24 receptor (e.g., IL-20RA (NCBI Gene ID: 53832), IL-20RB (NCBI Gene ID: 53833) and IL-22RA1 (NCBI Gene ID: 58985)) agonists, such as an adenovirus vector expressing IL-24 (Ad-IL-24/INGN241);

C-C motif chemokine receptor 2 (CCR2; NCBI Gene ID: 729230) inhibitors, such as PF-04136309, CCX-872, BMS-813160 (CCR2/C-C motif chemokine receptor 5 (CCR5; NCBI Gene ID: 1234) dual inhibitor);

C-C motif chemokine receptor 4 (CCR4; NCBI Gene ID: 1233) inhibitors, such as POTELIGEO® (mogamulizumab);

C-C motif chemokine receptor 5 (CCR5, CD195; NCBI Gene ID: 1234) antagonists, such as MK-7690 (vicriviroc);

zinc finger nuclease-mediated, CCR5-modified autologous CD4 T-cells, such as SB-728;

CCR5 gene inhibitor/TAT gene/TRIM5 gene stimulator, such as lentivirus vector CCR5 shRNA/TRIM5alpha/TAR decoy-transduced autologous CD34-positive hematopoietic progenitor cells;

C-C motif chemokine receptor 8 (CCR8; NCBI Gene ID: 1237) inhibitors, such as JTX-1811, I-309, SB-649701, HG-1013, RAP-310;

C-X-C motif chemokine receptor 1 (CXCR1; NCBI Gene ID: 3577)/C-X-C motif chemokine receptor 2 (CXCR2; NCBI Gene ID: 3579) dual inhibitors, such as SX-682;

CXCR2 antagonists, such as AZD-5069;

C-X-C motif chemokine receptor 4 (CXCR4; NCBI Gene ID: 7852) antagonists, such as BL-8040, LY2510924, burixafor (TG-0054), X4P-002, X4P-001-IO, Plerixafor, anti-C-X-C motif chemokine ligand 8 (CXCL8, a.k.a., IL8; NCBI Gene ID: 3576) antibodies, such as HuMax-Inflam;

C-X-C motif chemokine ligand 12 (CXCL12, a.k.a., SDF1; NCBI Gene ID ID: 6387) inhibitors, such as olaptesed pegol (NOX-A12);

Bi-Specific T-Cell Engagers

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a bi-specific T-cell engager (e.g., not having an Fc) or an anti-CD3 bi-specific antibody (e.g., having an Fc). Illustrative anti-CD3 bi-specific antibodies or BiTEs that can be co-administered include duvortuxizumab (JNJ-64052781; CD19/CD3), blinatumomab (CD19/CD3), AMG-211 (CEA/CD3), RG7802 (CEA/CD3), ERY-974 (CD3/GPC3), PF-06671008 (Cadherins/CD3), APV0436 (CD123/CD3), flotetuzumab (CD123/CD3), odronextamab (REGN-1979; CD20/CD3), MCLA-117 (CD3/CLEC12A), JNJ-0819, JNJ-7564 (CD3/heme), AMG-757 (DLL3-CD3), AMG-330 (CD33/CD3), AMG-420 (BCMA/CD3), JNJ-63709178 (CD123/CD3), MGD-007 (CD3/gpA33), MGD-009 (CD3/B7H3), IMCgp100 (CD3/gp100), XmAb-14045 (CD123/CD3), XmAb-13676 (CD3/CD20), tidutamab (XmAb-18087; SSTR2/CD3), catumaxomab (CD3/EpCAM), REGN-4018 (MUC16/CD3), mosunetuzumab (RG-7828; CD20/CD3), CC-93269 (CD3/BCMA), REGN-5458 (CD3/BCMA), GRB-1302 (CD3/Erbb2), GRB-1342 (CD38/CD3), GEM-333 (CD3/CD33). As appropriate, the anti-CD3 binding bi-specific molecules may or may not have an Fc. Illustrative bi-specific T-cell engagers that can be co-administered target CD3 and a tumor-associated antigen as described herein, including, e.g., CD19 (e.g., blinatumomab); CD33 (e.g., AMG330); CEA (e.g., MEDI-565); receptor tyrosine kinase-like orphan receptor 1 (ROR1) (Gohil, et al., *Oncoimmunology.* (2017) May 17; 6(7):e1326437); PD-L1 (Horn, et al., *Oncotarget.* 2017 Aug. 3; 8(35):57964-57980); and EGFRvIII (Yang, et al., *Cancer Lett.* 2017 Sep. 10; 403:224-230).

Bi- and Tri-Specific Natural Killer (NK)-Cell Engagers

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with a bi-specific NK-cell engager (BiKE) or a tri-specific NK-cell engager (TriKE) (e.g., not having an Fc) or bi-specific antibody (e.g., having an Fc) against an NK cell activating receptor, e.g., CD16A, C-type lectin receptors (CD94/NKG2C, NKG2D, NKG2E/H and NKG2F), natural cytotoxicity receptors (NKp30, NKp44 and NKp46), killer cell C-type lectin-like receptor (NKp65, NKp80), Fc receptor FcγR (which mediates antibody-dependent cell cytotoxicity), SLAM family receptors (e.g., 2B4, SLAMF6 and SLAMF7), killer cell immunoglobulin-like receptors (KIR) (KIR-2DS and KIR-3DS), DNAM-1 and CD137 (41BB). Illustrative anti-CD16 bi-specific antibodies, BiKEs or TriKEs that can be co-administered include AFM26 (BCMA/CD16A) and AFM-13 (CD16/CD30). As appropriate, the anti-CD16 binding bi-specific molecules may or may not have an Fc. Illustrative bi-specific NK-cell engagers that can be co-administered target CD16 and one or more tumor-associated antigens as described herein, including, e.g., CD19, CD20, CD22, CD30, CD33, CD123, EGFR, EpCAM, ganglioside GD2, HER2/neu, HLA Class II and FOLR1. BiKEs and TriKEs are described, e.g., in Felices, et al., *Methods Mol Biol.* (2016) 1441:333-346; Fang, et al., *Semin Immunol.* (2017) 31:37-54. Examples of a trispecific NK cell engager (TRiKE) that can be co-administered include OXS-3550, HIV-TriKE, and CD16-IL-15-B7H3 TriKe.

Innate Immune System Stimulation

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more stimulators or agonists of the innate immune system. Illustrative stimulators or agonists of the innate immune system include without limitation interferon receptor ligands, stimulator of interferon genes (STING) agonists, RIG-I agonists, as well as inhibitors of LAG-3 and/or TIM-3.

Interferon Receptor Ligands

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with one or more interferon receptor (e.g., interferon alpha and beta receptor subunit 1 (IFNAR1; NCBI Gene ID: 3454); interferon alpha and beta receptor subunit 2 (IFNAR2; NCBI Gene ID: 3455); interferon gamma receptor 1 (IFNGR1; NCBI Gene ID: 3459); interferon gamma receptor 2 (IFNGR2; NCBI Gene ID: 3460) ligands, which can be recombinant, PEGylated, fusion proteins and/or conjugates. Examples of interferon receptor ligands that can be combined or co-administered include an interferon alpha-1b, an interferon alpha-2a, an interferon alpha-2b, an interferon beta-1a, and an interferon gamma. Illustrative interferon alpha-1b that can be combined or co-administered include without limitation, recombinant human interferon alpha-1b, interferon alpha 1b, PEGylated interferon alpha-1b, interferon alpha 1b (HAPGEN®). Illustrative interferon alpha-2a that can be combined or co-administered include without limitation, recombinant human interferon alpha-2a, interferon alfa 2a, PEG-IFN-alpha, pegylated interferon alpha-2a (PEGASYS®), YPEG-interferon alfa-2a (YPEG-rhIFNalpha-2a), interferon alpha-2a biosimilar (Biogenomics), rHSA-IFN alpha-2a (recombinant human serum albumin interferon alpha 2a fusion protein), interferon alfa-2a follow-on biologic (Biosidus)(Inmutag, Inter 2A). Illustrative interferon alpha-2b that can be combined or co-administered include without limitation, recombinant human interferon alpha-2b, alpha-2b (INTRON A®), interferon alfa-2b (from numerous sources, including, e.g., Amega, Axxo, IFN, Laboratorios Bioprofarma, Virchow, Zydus-Cadila, BioGeneric Pharma, Changchun Institute of Biological Products), ropeginterferon alfa-2b (AOP-2014, P-1101, PEG IFN alpha-2b), peginterferon alfa-2b (Amega), Ypeginterferon alfa-2b (YPEG-rhIFNalpha-2b), peginterferon alfa-2b (PEG-INTRON®), rHSA-IFN alpha 2b (recombinant human serum albumin interferon alpha 2b fusion protein), veltuzumab-IFN alpha 2b conjugate, interferon alfa-2b follow-on biologic (Biosidus-Bioferon, Citopheron, Ganapar, Beijing Kawin Technology—Kaferon). Additional illustrative interferon alpha and beta receptor ligands that can be combined or co-administered include without limitation Veldona, Infradure, Roferon-A, Algeron, Alfarona, Ingaron (interferon gamma), rSIFN-co (recombinant super compound interferon), MOR-22, Bioferon, Novaferon, Inmutag (Inferon), MULTIFERON® (Alfanative, Viragen), interferon alfa-n1 (HUMOFERON®, SM-10500, Sumiferon), Shaferon, Alfaferone, interferon-alpha 2 (CJ), Laferonum, VIPEG, BLAUFERON-A, BLAUFERON-B, Dynavax (SD-101), Intermax Alpha, Realdiron, Lanstion, Pegaferon, PDferon-B, Pegnano, Feronsure, PegiHep, Optipeg A, Realfa 2B, Reliferon, Reaferon-EC, Roferon-A (Canferon, Ro-25-3036), Proquiferon, Uniferon, Urifron, Anterferon, Shanferon, Layfferon, Shang Sheng Lei Tai, INTEFEN, SINOGEN, Fukangtai, Pegstat, SFR-9216, Interapo (Interapa), GEPON®, NORMFERON™. Illustrative interferon beta-1a that can be combined or co-administered include without limitation, interferon beta-1a (AVONEX®). Illustrative interferon gamma receptor ligands that can be combined or co-administered include without limitation, interferon gamma (OH-6000, Ogamma 100) and RPI-MN (modified cobratoxin).

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an autologous tumor cell vaccine+systemic CpG-B+IFN-alpha. See, e.g., Koster, et al., *Cancer Immunol Immunother.* (2019) 68(6): 1025-1035.

Stimulator of Interferon Genes (STING) Agonists

In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agonist of stimulator of interferon response cGAMP interactor 1 (STING1; NCBI Gene ID: 340061). In some embodiments, the STING receptor agonist or activator is selected from the group consisting of ADU-S100 (MIW-815), SB-11285, MK-1454, SR-8291, AdVCA0848, GSK-532, SYN-STING, MSA-1, SR-8291, GSK3745417, 5,6-dimethylxanthenone-4-acetic acid (DMXAA), cyclic-GAMP (cGAMP) and cyclic-di-AMP.

RIG-I Agonists

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an agonist of DExD/H-box helicase 58 (DDX58; a.k.a., RIG-I, RIG1, RIGI, RLR-1, SGMRT2; NCBI Gene ID: 23586). In some embodiments, the agents described herein are combined with a RIG-I modulator such as RGT-100, or NOD2 modulator, such as SB-9200 (a.k.a., GS 9992; inarigivir soproxil), and IR-103. An illustrative RIG-I agonist is KIN 1148, described by Hemann, et al., J Immunol May 1, 2016, 196 (1 Supplement) 76.1. Additional RIG-I agonists are described, e.g., in Elion, et al., Cancer Res. (2018) 78(21):6183-6195; and Liu, et al., J Virol. (2016) 90(20): 9406-19. RIG-I agonists are commercially available, e.g., from Invivogen (invivogen.com).

LAG-3 and TIM-3 Inhibitors

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-TIM-3 (a.k.a., hepatitis A virus cellular receptor 2 antibody (HAVCR2; NCBI Gene ID: 84868), antibody, such as cobolimab (TSR-022), LY-3321367, sabatolimab (MBG-453), INCAGN-2390, BMS-986258, BGB-A425, SHR-1702 and Sym-023. In some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-lymphocyte activating 3 (LAG3, a.k.a., CD223; NCBI Gene ID: 3902) antibody, such as relatlimab (ONO-4482), leramilimab (LAG-525), MK-4280, REGN-3767, INCAGN2385.

15. Combination Therapies—Vaccine Response Enhancement

Further provided are methods of enhancing, improving, and/or increasing the response to a vaccine therapy in a subject in need thereof, comprising co-administering to the subject an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and an effective amount of a vaccine. In various embodiments, the vaccine is selected from the group consisting of an antiviral vaccine, an antibacterial vaccine and an anti-cancer vaccine. Illustrative vaccines that can be co-administered with an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, include without limitation a DNA vaccine, an RNA vaccine, a live-attenuated vaccine, a protein-based vaccine, and combinations thereof. The vaccine may be therapeutic or prophylactic.

With respect to antiviral vaccines that can be combined or co-administered, in some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antiviral vaccine against a virus selected from the group consisting of hepatitis A virus (HAV), hepatitis B virus (HBV), human immunodeficiency virus (HIV), cytomegalovirus (CMV), a herpes simplex virus (HSV), Epstein-Barr virus (EBV), human orthopneumovirus or human respiratory syncytial virus (RSV), human papillomavirus (HPV), varicella-zoster virus (VZV), measles virus, mumps virus, poliovirus vaccine, influenza virus, paramyxovirus, rotavirus, Zika virus, Dengue virus, Ebola virus and coronavirus (e.g., betacoronavirus, e.g., severe acute respiratory syndrome-related coronavirus, e.g., SARS-CoV2).

With respect to antibacterial vaccines that can be combined or co-administered, in some embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an antibacterial vaccine against a bacterium selected from the group consisting of *Mycobacterium tuberculosis*, pertussis, tetanus, diphtheria, meningococcus, pneumococcus, *Haemophilus* influenza, cholera, typhoid, and anthrax.

In various embodiments, the methods comprise a prime-boost regimen. In some embodiments, the prime-boost regimen entails administering a priming composition at a first time point and administering one or more boosting compositions at one or more subsequent time points. In various embodiments, the administrations of the priming composition and the one or more boosting compositions are spaced at least 1 week and up to at least 2 weeks, 3 weeks, 1 month, 2 months, 3 months, 4 months, 5 months or 6 months apart. As appropriate, the dosage or dosing frequency of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, can be in the priming composition and/or the boosting composition. The priming composition and the boosting composition can be the same or different. As appropriate, the dosage or dosing frequency of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, may be adjusted over the course of the treatment, based on the judgment of the administering physician.

HBV Vaccines

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more anti-HBV vaccines. HBV vaccines that can be combined or co-administered (e.g., in a prime-boost prevention regimen) include both prophylactic and therapeutic vaccines.

Examples of HBV prophylactic vaccines include Vaxelis, Hexaxim, Heplisav, Mosquirix, DTwP-HBV vaccine, Bio-Hep-B, D/T/P/HBV/M (LBVP-0101; LBVW-0101), DTwP-Hepb-Hib-IPV vaccine, Heberpenta L, DTwP-HepB-Hib, V-419, CVI-HBV-001, Tetrabhay, hepatitis B prophylactic vaccine (Advax Super D), Hepatrol-07, GSK-223192A, ENGERIX B®, PEDIARIX, HEPLISAV-B, AND RECOMBIVAX HB, recombinant hepatitis B vaccine (intramuscular, Kangtai Biological Products), recombinant hepatitis B vaccine (Hansenual polymorpha yeast, intramuscular, Hualan Biological Engineering), recombinant hepatitis B surface antigen vaccine, Bimmugen, CARG-101, Euforavac, Eutravac, anrix-DTaP-IPV-Hep B, HBAI-20, Infanrix-DTaP-IPV-Hep B-Hib, Pentabio Vaksin DTP-HB-Hib, Comvac 4, Twinrix, Euvax-B, Tritanrix HB, Infanrix Hep B, Comvax, DTP-Hib-HBV vaccine, DTP-HBV vaccine, Yi Tai, Heberbiovac HB, Trivac HB, GerVax, DTwP-Hep B-Hib vaccine, Bilive, Hepavax-Gene, SUPERVAX, Comvac5, Shanvac-B, Hebsulin, Recombivax HB, Revac B mcf, Revac B+, Fendrix, DTwP-HepB-Hib, DNA-001, Shan5, Shan6, rhHBsAG vaccine, HBI pentavalent vaccine, LBVD, Infanrix HeXa, YS-HBV-001, TVAX-008 and DTaP-rHB-Hib vaccine.

Examples of HBV therapeutic vaccines that can be combined or co-administered (e.g., in a prime-boost treatment regimen) include HBsAG-HBIG complex, ARB-1598, Bio-Hep-B, abi-HB (intravenous), ABX-203 (NASVAC), CP-BNPs, Tetrabhay, GX-110E, GS-4774, peptide vaccine (epsilonPA-44), Hepatrol-07, NASVAC (NASTERAP), IMP-321, BEVAC, Revac B mcf, Revac B+, MGN-1333, KW-2, CVI-HBV-002, AltraHepB, VGX-6200, FP-02, FP-02.2 (HepTcell), NU-500, HBVax, imvTriGrid/antigen vaccine, Mega-CD40L-adjuvanted vaccine, HepB-v, RG7944 (INO-1800), recombinant VLP-based therapeutic vaccine (HBV infection, VLP Biotech), AdTG-17909, AdTG-17910 AdTG-18202, ChronVac-B, TG-1050, VVX-001, GSK-3528869A (ChAd155-hli-HBV+MVA-HBV+Hbc-HBs/AS01B-4), VBI-2601, VTP-300 (ChAdOx1-SIi-HBV-CPmut-TPA-Ssh prime and MVA-SIi-HBV-CPmut-TPA-Ssh boost), Lm HBV and BM32 (Tulaeva, et al., EBioMedicine (2020) 102953). Illustrative HBV Arenavirus vaccines that can be combined or co-administered are described, e.g., in WO2017076988 and WO2017198726. Additional HBV viral vector vaccines that can be combined or co-administered are described, e.g., in WO 2018/189522 and WO 2019/115816.

HIV Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-HIV vaccine. HIV vaccines that can be combined or co-administered (e.g., in a prime-boost prevention regimen) include both prophylactic and therapeutic vaccines.

Examples of HIV vaccines include peptide vaccines, recombinant subunit protein vaccines, live vector vaccines, DNA vaccines, HIV MAG DNA vaccines, CD4-derived peptide vaccines, vaccine combinations, adenoviral vector vaccines (e.g., Ad5, Ad26 or Ad35), simian adenovirus (chimpanzee, gorilla, rhesus i.e., rhAd), adeno-associated virus vector vaccines, chimpanzee adenoviral vaccines (e.g., ChAdOX1, ChAd68, ChAd3, ChAd63, ChAd83, ChAd155, ChAd157, Pan5, Pan6, Pan7, Pan9), Coxsackieviruses based vaccines, enteric virus based vaccines, Gorilla adenovirus vaccines, lentiviral vector based vaccine, bi-segmented or tri-segmented arenavirus based vaccines (e.g., LCMV, Pichinde), trimer-based HIV-1 vaccine, measles virus based vaccine, flavivirus vector based vaccines, tobacco mosaic virus vector based vaccine, Varicella-zoster virus based vaccine, Human parainfluenza virus 3 (PIV3) based vaccines, poxvirus based vaccine (modified vaccinia virus Ankara (MVA), orthopoxvirus-derived NYVAC, and avipoxvirus-derived ALVAC (canarypox virus) strains); fowlpox virus based vaccine, rhabdovirus-based vaccines, such as Vesicular stomatitis virus (VSV) and marabavirus; recombinant human CMV (rhCMV) based vaccine, alphavirus-based vaccines, such as Semliki forest virus, Venezuelan equine encephalitis virus and sindbis virus (see, e.g., Lauer, et al., *Clin Vaccine Immunol.* (2017) 24(1): e00298-16); LNP formulated mRNA based therapeutic vaccines; and LNP-formulated self-replicating RNA/self-amplifying RNA vaccines.

Examples of HIV vaccines include without limitation AAVLP-HIV vaccine, anti-CD40.Env-gp140 vaccine, Ad4-EnvC150, BG505 SOSIP.664 gp140 adjuvanted vaccine, BG505 SOSIP.GT1.1 gp140 adjuvanted vaccine, ChAdOx1.tHIVconsv1 vaccine, CMV-MVA triplex vaccine, ChAdOx1.HTI, Chimigen HIV vaccine, ConM SOSIP.v7 gp140, rgp120 (AIDSVAX), ALVAC HIV (vCP1521)/AIDSVAX B/E (gp120) (RV144), monomeric gp120 HIV-1 subtype C vaccine, MPER-656 liposome subunit vaccine, Remune, ITV-1, Contre Vir, Ad5-ENVA-48, DCVax-001 (CDX-2401), Vacc-4x, Vacc-C5, VAC-3S, multiclade DNA recombinant adenovirus-5 (rAd5), rAd5 gag-pol env A/B/C vaccine, Pennvax-G, Pennvax-GP, Pennvax-G/MVA-CMDR, HIV-TriMix-mRNA vaccine, HIV-LAMP-vax, Ad35, Ad35-GRIN, NAcGM3/VSSP ISA-51, poly-ICLC adjuvanted vaccines, TatImmune, GTU-multiHIV (FIT-06), ChAdV63.HIVconsv, gp140[delta]V2.TV1+MF-59, rVSVIN HIV-1 gag vaccine, SeV-EnvF, SeV-Gag vaccine, AT-20, DNK-4, ad35-Grin/ENV, TBC-M4, HIVAX, HIVAX-2, N123-VRC-34.01 inducing epitope-based HIV vaccine, NYVAC-HIV-PT1, NYVAC-HIV-PT4, DNA-HIV-PT123, rAAV1-PG9DP, GOVX-B11, GOVX-B21, GOVX-C55, TVI-HIV-1, Ad-4 (Ad4-env Clade C+Ad4-mGag), Paxvax, EN41-UGR7C, EN41-FPA2, ENOB-HV-11, PreVaxTat, AE-H, MYM-V101, CombiHIVvac, ADVAX, MYM-V201, MVA-CMDR, MagaVax, DNA-Ad5 gag/pol/nef/nev (HVTN505), MVATG-17401, ETV-01, CDX-1401, DNA and Sev vectors vaccine expressing SCaVII, rcAD26.MOS1.HIV-Env, Ad26.Mod.HIV vaccine, Ad26.Mod.HIV+MVA mosaic vaccine+gp140, AGS-004, AVX-101, AVX-201, PEP-6409, SAV-001, ThV-01, TL-01, TUTI-16, VGX-3300, VIR-1111, IHV-001, and virus-like particle vaccines such as pseudovirion vaccine, CombiVICHvac, LFn-p24 B/C fusion vaccine, GTU-based DNA vaccine, HIV gag/pol/nef/env DNA vaccine, anti-TAT HIV vaccine, conjugate polypeptides vaccine, dendritic-cell vaccines (such as DermaVir), gag-based DNA vaccine, GI-2010, gp41 HIV-1 vaccine, HIV vaccine (PIKA adjuvant), i-key/MHC class II epitope hybrid peptide vaccines, ITV-2, ITV-3, ITV-4, LIPO-5, multiclade Env vaccine, MVA vaccine, Pennvax-GP, pp71-deficient HCMV vector HIV gag vaccine, rgp160 HIV vaccine, RNActive HIV vaccine, SCB-703, Tat Oyi vaccine, TBC-M4, UBI HIV gp120, Vacc-4x+romidepsin, variant gp120 polypeptide vaccine, rAd5 gag-pol env A/B/C vaccine, DNA.HTI and MVA.HTI, VRC-HIVDNA016-00-VP+VRC-HIVADV014-00-VP, INO-6145, JNJ-9220, gp145 C.6980; eOD-GT8 60mer based vaccine, PD-201401, env (A, B, C, A/E)/gag (C) DNA Vaccine, gp120 (A,B,C,A/E) protein vaccine, PDPHV-201401, Ad4-EnvCN54, EnvSeq-1 Envs HIV-1 vaccine (GLA-SE adjuvanted), HIV p24gag prime-boost plasmid DNA vaccine, HIV-1 iglb12 neutralizing VRC-01 antibody-stimulating anti-CD4 vaccine, arenavirus vector-based vaccines (VaxWave®, TheraT®). MVA-BN HIV-1 vaccine regimen, UBI HIV gp120, mRNA based prophylactic vaccines, VPI-211, TBL-1203HI, CH505 TF chTrimer, CD40.HIVRI.Env vaccine, Drep-HIV-PT-1, mRNA-1644, and mRNA-1574.

Herpesvirus Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-herpesvirus vaccine. Herpesvirus vaccines that can be combined or co-administered (e.g., in a prime-boost prevention regimen) include both prophylactic and therapeutic vaccines.

Illustrative herpesvirus vaccines that can be combined or co-administered include live-attenuated vaccines (e.g., HSV vaccine with deletions in UL20 and UL53 such as, VC2; HSV vaccine mutated in R2 coding region of UL37 such as, R2; AuroVax; EXD-12; delta-gD2 based viral vaccines); inactivated vaccines (e.g., live-inactivated Theravax-HSV-2 vaccine; formalin-inactivated herpesvirus (FI-HSV2) vaccine; VITAHERPAVAC®); HSV-2 subunit trivalent vaccine (containing gC2, gD2, gE2) such as, HSV-2 trivalent vaccine; HSV-2 replication-defective vaccine with UL5 and UL29 deleted such as, HSV-529; TLR-4 agonists such as, IDC-G103 vaccines; RBT-26 T-cell-based subunit vaccine; DNA vaccines such as, pDNA/rVSV vector vaccine; CD4 agonist/T-cell surface glycoprotein CD8 vaccine such as GENO-2; TAT protein modulators such as HerpesVaxTat® vaccines; CD89 agonist/Duffy antigen chemokine receptor modulator/Immunoglobulin G agonist such as, glycoprotein D+liposome encapsulated glycoprotein D boost vaccine; Profavax-HSV-2 vaccine; HSV-2 mRNA vaccine; glycoprotein D DNA vaccine; NE-gD2 intranasal nanoemulsion NE-based adjuvanted HSV-2 vaccine; NE-gD2 intranasal nanoemulsion NE-based adjuvanted vaccine; and a CD4 modulator peptide vaccine such as, CEL-1000.

Cytomegalovirus (CMV) Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-CMV vaccine. CMV vaccines that can be combined or co-administered (e.g., in a prime-boost prevention regimen) include both prophylactic and therapeutic vaccines. Illustrative cytomegovirus (CMV) vaccines that can be combined or co-administered include Human cytomegalovirus glycoprotein B and glycoprotein H modulator vaccines such as mRNA-1647; CMV 65 kDa lower matrix phosphoprotein vaccines such as, IRB-12022; mRNA-based vaccines; BD-03 plasmid DNA vaccine; V-212 heat-treated varicella zoster virus vaccine; protein subunit vaccines such as, VBI-1501A; CMV-MVA pentamer vaccine (RhUL128C-MVA); CMV-MVA Triplex vaccine; herpesvirus envelope glycoprotein B stimulator vaccine such as, HB-101; CMV 65 kDa lower matrix phosphoprotein modulator vaccine such as, AVX-601; peptide vaccines, such as CMVpp65 peptide vaccine; V-160.

Varicella Zoster Virus (VZV) Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-VZV vaccine. VZV vaccines that can be combined or co-administered (e.g., in a prime-boost prevention regimen) include both prophylactic and therapeutic vaccines. Illustrative anti-VZV vaccines that can be combined or co-administered include varicella vaccine, live attenuated viral vaccines such as, NBP-608, Suduvax® II, VZV-7D; triple live-attenuated vaccines such as, M-M-RvaxPRO®; MMRV vaccine; herpes zoster vaccine; recombinant varicella-zoster virus vaccine; zoster recombinant adjuvanted vaccine; ProQuad®; Priorix-Tetra® (MeMuRu-OKA); protein subunit TLR-4 agonist vaccines such as, CRV-101; VZV ORF29 mutant-based vaccine; chickenpox vaccine Sinovac; VARILRIX® vaccine (VZV-OKA-strain); attenuated recombinant subunit vaccine containing gE such as, GSK-137173A; protein subunit vaccines such as, SP-0204; pneumococcal conjugate vaccines such as, SP-0202; adenovirus-vectored vaccine such as, VTP-400; and EG-HZ.

Epstein-Barr Virus (EBV) Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-EBV vaccine. EBV vaccines that can be combined or co-administered (e.g., in a prime-boost prevention regimen) include both prophylactic and therapeutic vaccines.

Examples of EBV vaccines include without limitation Basigin modulators such as, EBV gH/gUgp42 vaccine; basigin modulator/Envelope glycoprotein GP350 modulator/Human cytomegalovirus glycoprotein B modulator/Human cytomegalovirus glycoprotein H modulator/Human cytomegalovirus glycoprotein L modulator such as, mRNA-1189 vaccine; EBV gH/gL vaccine; P-989; mRNA vaccine; EBV cancer vaccine (mRNA, LPP nanoparticle); Epstein-Barr nuclear antigen 1/Latent membrane protein 2 stimulators such as MVA-based vaccines; and EBV-VLP vaccine.

HPV Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anti-HPV vaccine. HPV vaccines that can be combined or co-administered (e.g., in a prime-boost prevention regimen) include both prophylactic and therapeutic vaccines.

Examples of HPV vaccines include without limitation cervarix, gardasil 9, Gardasil and KITE-439 (HPV16 E7).

Coronavirus Vaccines

In various embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, are combined or co-administered with one or more vaccines useful to induce an immune response against a coronavirus infection, e.g., a betacoronavirus infection, e.g., a sarbecovirus infection, e.g., a severe acute respiratory syndrome (SARS)-related coronavirus infection, e.g., a severe acute respiratory syndrome coronavirus 2 (SARS-CoV-2) infection (e.g., resulting in COVID-19 symptoms and/or illness). Vaccines useful to induce an immune response against a coronavirus infection that can be combined or co-administered (e.g., in a prime-boost prevention regimen) include both prophylactic and therapeutic vaccines.

In some embodiments, the vaccine against a coronavirus is a genetic vaccine, e.g., an mRNA vaccine or a DNA vaccine. Illustrative mRNA vaccines against a coronavirus infection include mRNA-1273 (Moderna; National Institutes of Health (NIH)); BNT162b2 (COMIRNATY®; BioNTech; Pfizer, Fosun Pharma); SARS-CoV-2 Vaccine CVnCoV (CureVac); A006 (eTheRNA immunotherapies;

EpiVax); Exosome-SARS-CoV-2 mRNA vaccine (Capricor Therapeutics; Johns Hopkins University); LUNAR-COV19 (ARCT-021) (Arcturus Therapeutics; Duke-NUS Medical School; Catalent); mRNA-1730 (RNAimmune); ARCoV (Suzhou Abogen Biosciences); LNP-nCoVsaRNA (Imperial College London); and ZIP-1642 (Ziphius Therapeutics). Illustrative DNA vaccines against a coronavirus infection include GX-19 (Genexine; GeneNBio); INO-4700 or INO-4800 (Inovio Pharmaceuticals; Beijing Advaccine Biotechnology; Ology Bioservices; International Vaccine Institute (IVI); Richter-Helm BioLogics); bacTRL-Spike (Symvivo Corporation); CORVax12 (OncoSec); bacTRL-Spike (Symvivo Corporation); COVID-eVax (Takis; Rottapharm); COVIDITY (Scancell); Covigenix (Entos Pharmaceuticals; EpiVax; PrecisionNanoSystems; Cytiva); ZyCoV-D (Zydus Cadila); AG0301-COVID19 (AnGes; Osaka University; Takara Bio; Brickell Biotechand); LinearDNA vaccine against COVID-19 (LineaRx; Takis Biotech).

In some embodiments, the vaccine against a coronavirus employs a protein immunogen. Illustrative protein-based vaccines include NVX-CoV2373 (Novavax; Emergent BioSolutions; AGC Biologics; PolyPeptide Group); SCB-2019 (COVID-19 S-Trimer) (Sichuan Clover Biopharmaceuticals; Dynavax); RBD219-N1 (Baylor College of Medicine; University of Texas Medical Branch; New York Blood Center; Fudan University); Chimigan SARS-CoV-2 (Akshaya; Cytovance (Shenzhen Hepalink)); Corona Subunit Vaccine (MIGAL Galilee Research Institute; MigiVax); Coronavirus VLP (Mitsubishi Tanabe (Medicago); Laval University); CoVepiT (OSE Immunotherapeutics); DPX-COVID-19 (IMV); EPV-CoV19 (EpiVax); Exosome-SARS-CoV-2 Display vaccine (Capricor Therapeutics; Johns Hopkins University); ExpreS2-CoV (ExpreS2ion Biotech Holding; AdaptVac; Bavarian Nordic; University of Tubingen; Leiden University Medical Center; University of Copenhagen; Wageningen University); FlowVax COVID-19 (Flow Pharma); IBIO-200 (iBio; Texas A&M University; Infectious Disease Research Institute); IBIO-201 (iBio); Ii-Key-SARS-2 (Generex Biotechnology; EpiVax); KBP-COVID-19 (British American Tobacco (Kentucky BioProcessing)); MF59 adjuvanted SARS-CoV-2 Sclamp vaccine (University of Queensland; Seqiris; CSL; CEPI); MVC-COV1901 (Medigen; NIH; Dynavax); PDS0203 (PDS Biotechnology); PDS0204 (PDS Biotechnology; Farmacore Biotechnology); PittCoVacc (University of Pittsburgh); PolyPEPI-SCoV-2 (Treos Bio (PepTC Vaccines)); RBD SARS-CoV-2 HBsAg VLP Vaccine (SpyBiotech; Serum Institute of India); SCB-2019 (COVID-19 S-Trimer) (Sichuan Clover Biopharmaceuticals; Dynavax; GlaxoSmithKline; CEPI); TaliCoVax19 (InnoMedica); SARS-CoV-2 vaccine (Sanofi; GSK; BARDA); VBI-2901 Pan-Coronavirus Vaccine (VBI Vaccines); VF-COVID-19 (Farmacore Biotecnologia); and VXL-301, VXL-302 and/or VXL-303 (Vaxil Bio).

In some embodiments, the vaccine against a coronavirus is a viral vector vaccine, e.g., AZD1222 (ChAdOx1 nCoV-19; Covishield; Vaxzevria; University of Oxford; AstraZeneca; Serum Institute of India); Ad5-nCoV (CanSino Biologics); Gam-Covid-Vac Lyo (Gamaleya Research Institute); AAVCOVID (Massachusetts Eye and Ear; Massachusetts General Hospital); Ad26.COV2.S (Johnson & Johnson; Beth Israel Deaconess Medical Center; BARDA; Catalent; Emergent BioSolutions); Ad5 2nd Generation Adenovirus (ImmunityBio; NantKwest); AdCOVID (Altimmune; University of Alabama); NasoVAX (Altimmune); AVIDIO COVID-19 vaccine (CaroGen); CoroFlu (FluGen; Bharat Biotech; University of Wisconsin); OraPro-COVID-19 (Stabilitech); PeptiCRAd COVID-19 vaccine (Valo Therapeutics); Sputnik V (Gam-COVID-Vac) (Gamaleya Institute; Binnopharm; Dr. Reddy's Laboratories); Gam-COVID-Vac Lyo (Gamaleya Institute; Sechenov University); GRAd-COV2 (ReiThera; Leukocare; Univercells).

In some embodiments, the vaccine against a coronavirus is an inactivated coronavirus, e.g., COVID-19 vaccine (China National Biotech Group (Sinopharm)); CoronaVac (PiCoVacc) (Sinovac Biotech); Inactivated SARS-CoV-2 Vaccine (Chinese Academy of Medical Sciences); BBIBP-CorV (Beijing Biological Products Institute (Sinopharm)); V-SARS (Immunitor); CORAVAX (Thomas Jefferson University); Covaxin (BBV152) Bharat Biotech; Indian Council of Medical Research (ICMR)); and VLA2001 (Valneva; Dynavax).

In some embodiments, the vaccine useful to induce an immune response against a coronavirus infection is a live attenuated vaccine, e.g., a live attenuated bacteria or live attenuated virus. Illustrative live attenuated bacterial vaccines useful to induce an immune response against a coronavirus infection include without limitation tuberculosis vaccines, e.g., a Bacille Calmette-Guérin (BCG) Vaccine and VPM1002 (Vakzine Projekt Management; Serum Institute of India). Illustrative live attenuated viral vaccines useful to induce an immune response against a coronavirus infection include without limitation, a Measles, mumps, rubella (MMR) vaccine, a live-attenuated oral poliovirus vaccine (OPV or Sabin vaccine), and engineered live attenuated vaccines, e.g., TMV-083 (Merck & Co.; Institut Pasteur; CEPI); CDX-005 (CDX-CoV) (Codagenix; Serum Institute of India); Live Attenuated SARS-CoV-2 vaccine (Griffith University; Indian Immunologicals); rVSVAG-SARS-CoV-2 (Merck; IAVI); and TNX-1800, TNX-1810, TNX-1820 and/or TNX-1830, (Tonix Pharmaceuticals).

In some embodiments, the vaccine against a coronavirus is a cellular (e.g., dendritic cell (DC)) vaccine, e.g., AV-COVID-19 (Aivita); Chimeric COVID-19 epitope DC vaccine (Shenzhen Third People's Hospital); LV-SMENP-DC+ antigen-specific CTLs (Shenzhen Genoimmune Medical Institute); Pathogen-specific aAPC (Shenzhen Genoimmune Medical Institute); and STI-6991 (Sorrento Therapeutics).

Other Antiviral Vaccines

In some embodiments, the additional therapeutic agent is live-attenuated RSV vaccine MEDI-559, human monoclonal antibody REGN2222 against RSV, palivizumab, respiratory syncytial virus immune globulin, intravenous [RSV-IGIV], and combinations thereof. In some embodiments, the additional therapeutic agent is a VZV vaccine, for example zostavax and varivax. In some embodiments, the additional therapeutic agent is an influenza virus vaccine. For example, a (i) monovalent vaccine for influenza A (e.g. influenza A [H5N1] virus monovalent vaccine and influenza A [HIN1] 2009 virus monovalent vaccines), (ii) trivalent vaccine for influenza A and B viruses (e.g. Afluria, Agriflu, Fluad, Fluarix, Flublok, Flucelvax, FluLaval, Fluvirin, and Fluzone), and (iii) quadrivalent vaccine for influenza A and B viruses (FluMist, Fluarix, Fluzone, and FluLaval). In some embodiments, the additional therapeutic agent is a human adenovirus vaccine (e.g. Adenovirus Type 4 and Type 7 Vaccine, Live, Oral). In some embodiments, the additional therapeutic agent is a rotavirus vaccine (e.g. Rotarix for rotavirus serotype G1, G3, G4, or G9 and RotaTeq for rotavirus serotype G1, G2, G3, or G4). In some embodiments, the additional therapeutic agent is a hepatitis A virus vaccine (e.g. Havrix and Vaqta). In some embodiments, the additional therapeutic agent is poliovirus vaccines (e.g. Kinrix, Quadracel, and Ipol). In some embodiments, the additional therapeutic agent is a yellow fever virus vaccine (e.g. YF-Vax). In some embodiments, the additional therapeutic agent is a Japanese encephalitis virus vaccine (e.g. Ixiaro and JE-Vax). In some embodiments, the additional therapeutic agent is a measles vaccine (e.g. M-M-R II and ProQuad). In some embodiments, the additional therapeutic agent is a mumps vaccine (e.g. M-M-R II and ProQuad). In some embodiments, the additional therapeutic agent is a rubella vaccine (e.g. M-M-R II and ProQuad). In some embodiments, the additional therapeutic agent is a varicella vaccine (e.g. ProQuad). In some embodiments, the additional therapeutic agent is a rabies vaccine (e.g. Imovax and RabAvert). In some embodiments, the additional therapeutic agent is a variola virus (smallpox) vaccine (ACAM2000). In some embodiments, the additional therapeutic agent is a and hepatitis E virus (HEV) vaccine (e.g. HEV239).

Anticancer Vaccines

In certain embodiments, an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, is combined or co-administered with an anticancer vaccine. Anticancer vaccines that can be combined or co-administered (e.g., in a prime-boost prevention regimen) include both prophylactic and therapeutic vaccines.

Illustrative anticancer vaccines that can be combined or co-administered include without limitation, peptide vaccine TG-01 (RAS), GALE-301, GALE-302, nelipepimut-s, SurVaxM, DSP-7888, TPIV-200, PVX-410, VXL-100, DPX-E7, ISA-101, 6MHP, OSE-2101, galinpepimut-S, SVN53-67/M57-KLH, IMU-131, peptide subunit vaccine (acute lymphoblastic leukemia, University Children's Hospital Tubingen); bacterial vector vaccines such as CRS-207/GVAX, axalimogene filolisbac (ADXS11-001); adenovirus vector vaccines such as nadofaragene firadenovec; autologous Gp96 vaccine; dendritic cells vaccines, such as CVactm, tapuldencel-T, eltrapuldencel-T, SL-701, BSK01TM, rocapuldencel-T (AGS-003), DCVAC, CVactm, stapuldencel-T, eltrapuldencel-T, SL-701, BSK01TM, ADXS31-142, autologous dendritic cell vaccine (metastatic malignant melanoma, intradermal/intravenous, Universitatsklinikum Erlangen); oncolytic vaccines such as, talimogene laherparepvec, pexastimogene devacirepvec, GL-ONC1, MG1-MA3, parvovirus H-1, ProstAtak, enadenotucirev, MG1MA3, ASN-002 (TG-1042); therapeutic vaccines, such as CVAC-301, CMP-001, CreaVax-BC, PF-06753512, VBI-1901, TG-4010, ProscaVax™; tumor cell vaccines, such as Vigil® (IND-14205), Oncoquest-L vaccine; live attenuated, recombinant, serotype 1 poliovirus vaccine, such as PVS-RIPO; Adagloxad simolenin; MEDI-0457; DPV-001 a tumor-derived, autophagosome enriched cancer vaccine; RNA vaccines such as, CV-9209, LV-305; DNA vaccines, such as MEDI-0457, MVI-816, INO-5401; modified vaccinia virus Ankara vaccine expressing p53, such as MVA-p53; DPX-Survivac; BriaVax™; GI-6301; GI-6207; GI-4000; IO-103; Neoantigen peptide vaccines, such as AGEN-2017, GEN-010, NeoVax, RG-6180, GEN-009, PGV-001 (TLR-3 agonist), GRANITE-001, NEO-PV-01; Peptide vaccines that target heat shock proteins, such as PhosphoSynVax™; Vitespen (HSPPC-96-C), NANT Colorectal Cancer Vaccine containing aldoxorubicin, autologous tumor cell vaccine+systemic CpG-B+IFN-alpha (cancer), IO-120+IO-103 (PD-L1/PD-L2 vaccines), HB-201, HB-202, HB-301, TheraT®*-based vaccines.

16. Kits

Further provided are kits comprising one or more containers comprising one or more unitary doses of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. In some embodiments, the kits comprise two or more unitary doses of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, in two or more containers. In some embodiments, the kit comprises one or more unitary doses of an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, and one or more (e.g., one, two, three, one or two, or one to three) additional therapeutic agents in separate containers. The one or more additional therapeutic agents (e.g., for vaccination against and/or for treating cancer or a viral infection) are as described above and herein. In some embodiments, the kits comprise two or more unitary doses wherein the unitary doses are the same. In some embodiments, the kits comprise two or more unitary doses, wherein the unitary doses are different.

In one embodiment, the kit comprises one or more pharmaceutical packs comprising one or more containers (e.g., vials, ampules, pre-loaded syringes) containing one or more of the ingredients of the pharmaceutical compositions described herein, such as an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein. In some instances, the kits contain a pharmaceutical composition described herein. In some embodiments, the kit comprises one or more containers comprising an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, in an aqueous solution. In some embodiments, the aqueous solution comprises an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, at a concentration in the range of 0.05 mg/ml to 50 mg/ml, e.g., from 0.05 mg/ml to 20 mg/ml, e.g., from 0.1 mg/ml to 40 mg/ml, e.g., from 1.0 mg/ml to 30 mg/ml, e.g., from 0.05 mg/ml to 0.06 mg/ml, 0.07 mg/ml, 0.08 mg/ml, 0.09 mg/ml, 0.1 mg/ml, 0.2 mg/ml, 0.3 mg/ml, 0.4 mg/ml, 0.5 mg/ml, 0.6 mg/ml, 0.7 mg/ml, 0.8 mg/ml, 0.9 mg/ml, 1.0 mg/ml, 1.5 mg/ml, 2.0 mg/ml, 2.5 mg/ml, 3.0 mg/ml, 3.5 mg/ml, 4.0 mg/ml, 4.5 mg/ml, 5.0 mg/ml, 6 mg/ml, 7 mg/ml, 8 mg/ml, 9 mg/ml, 10 mg/ml, 11 mg/ml, 12 mg/ml, 13 mg/ml, 14 mg/ml, 15 mg/ml, 16 mg/ml, 17 mg/ml, 18 mg/ml, 19 mg/ml, 20 mg/ml, 25 mg/ml, 30 mg/ml, 35 mg/ml, 40 mg/ml, 45 mg/ml or 50 mg/ml. In some embodiments, each unitary dose is in the range of 0.5 μg/kg to 1000 μg/kg, e.g., in the range of from 1 μg/kg to 500 μg/kg, e.g., in the range of from 10 μg/kg to 300 μg/kg, e.g., in the range of from 30 μg/kg to 600 μg/kg, e.g., at least 0.5

μg/kg per dose and up to 0.2 μg/kg, 0.3 μg/kg, 0.4 μg/kg, 0.5 μg/kg, 0.6 μg/kg, 0.7 μg/kg, 0.8 μg/kg, 0.9 μg/kg, 1 μg/kg, 1.5 μg/kg, 2 μg/kg, 2.5 μg/kg, 3 μg/kg, 3.5 μg/kg, 4 μg/kg, 4.5 μg/kg, 5 μg/kg, 6 μg/kg, 7 μg/kg, 8 μg/kg, 9 μg/kg, 10 μg/kg, 15 μg/kg, 20 μg/kg, 25 μg/kg, 30 μg/kg, 40 μg/kg, 50 μg/kg, 60 μg/kg, 70 μg/kg, 80 μg/kg, 90 μg/kg, 100 μg/kg, 110 μg/kg, 120 μg/kg, 130 μg/kg, 140 μg/kg, 150 μg/kg, 200 μg/kg, 250 μg/kg, 300 μg/kg, 400 μg/kg, 500 μg/kg, 600 μg/kg, 700 μg/kg, 800 μg/kg, 900 μg/kg, 1000 μg/kg per dose. In some embodiments, each unitary dose is in the range of 0.02 mg to 100 mg, e.g., 0.04 mg to 80 mg, e.g., at least 0.02 mg per dose and up to 0.03 mg, 0.04 mg, 0.05 mg, 0.1 mg, 0.5 mg, 1 mg, 2 mg, 3 mg, 4 mg, 5 mg, 10 mg, 12 mg, 15 mg, 20 mg, 40 mg, 50 mg, 60 mg, 70 mg, 80 mg or 100 mg per dose. In some embodiments, the kit comprises one or more containers comprising an IL-2v, serum half-life extended IL-2v, e.g., Fc-IL-2v fusion proteins, and homodimers and heterodimers thereof, polynucleotides encoding such polypeptides, vectors, a lipoplex (e.g., LNP), and compositions comprising such polypeptides or polynucleotides, as described herein, in lyophilized form.

EXAMPLES

The following examples are offered to illustrate, but not to limit the claimed invention.

Example 1

In-Silico Identification of IL-2 Amino Acid Residues Mediating Binding to IL-2Rα

In this example we performed in-silico analyses of the x-ray crystallography structure of the high-affinity IL-2 receptor complex (IL-2Rα (NCBI Gene ID: 3559; CD25), IL-2Rβ (NCBI Gene ID: 3560; CD122), IL-2Rγ (NCBI Gene ID: 3561; CD132)) bound to the IL-2 cytokine. Through this analysis we selected amino acids on IL-2 that interact with IL-2Rα, which upon mutation could lead to the destabilization of the IL-2-IL-2Rα interaction.

Methods

The quaternary complex x-ray crystallography structure of the IL-2 high-affinity receptor, comprising the IL-2R α, β and γ subunits with its ligand (IL-2) bound, solved at a resolution of 2.3 Å was downloaded from the Protein Data Bank (PDB code: 2B5I, rcsb.org; Wang, et al., *Science* (2005) 310(5751):1159-63; The Protein Data Bank (PDB; Berman, Westbrook et al. (2000), *Nucleic Acids Res.* 28, 235-242; pdb.org). The structure was prepared using the protein preparation tool in Maestro (Schrödinger, LLC, New York, NY, 2020), which involved assignment of correct atom type, bond order, protonation states and constrained minimization. The protein-protein interaction interface between IL-2 and IL-2Rα, which has a buried surface area of >1500 $Å^2$, was analyzed for residues with inter unit interactions which when mutated could reduce the affinity between IL-2 and IL-2Rα (see, Stanton and Jurs, *Anal. Chem.* (1990) 62(21):2323-2329).

Results

Based on in-silico analyses a set of ten IL-2 residues were selected for evaluation as IL-2 variant Fc fusion proteins. The mutations selected were either glycine or alanine. Glycine or alanine residues that have small, uncharged side chains were chosen as the amino acids for substitution to avoid introducing changes that might otherwise result in large but very different side chains to the wild-type residue as this might have resulted in a higher possibility of variants being immunogenic in humans. IL-2 residues which were located within an alpha helix (Glu61, Glu62, Glu68) were selected to be mutated to alanine. Residues located in a non-structured region (Leu72, Gln74) were selected to be mutated to glycine, while those in a semi structured region (Arg38, Thr41, Phe42, Tyr45, Tyr107) were selected to be mutated to both alanine and glycine. The key inter and intra unit interactions observed for these IL-2 residues with the IL-2 receptor complex are shown in Table 1 and depicted in FIG. 1.

TABLE 1

IL-2 Amino Acids Selected at the IL-2/IL-2Rα Binding Interface to Evaluate Based on In Silico Analyses

| IL-2 Amino Acid | IL-2Rα Amino Acid Interactions Observed |
|---|---|
| Arg 38 | Cys3 and Asp4 backbone carbonyl H-bond, Asp6 sidechain polar interaction, His120 sidechain cation-π interaction |
| Thr 41 | Asn27 sidechain polar interaction |
| Phe 42 | Leu42 hydrophobic, Tyr43, His120 π-π interaction |
| Tyr 45 | Arg35 cation-π interaction, Arg36 π interaction |
| Glu 61 | Lys38 salt-bridge, Ser39 backbone H-bond |
| Glu 62 | Arg36 salt-bridge |
| Glu 68 | Ser41 sidechain and Leu42 backbone H-bond |
| Leu 72 | Tyr43 and IL-2 Phe42 sidechain hydrophobic interaction |
| Gln 74 | Glu1 sidechain H-bond |
| Tyr 107 | Arg35 sidechain cation-π interaction |

Example 2

Design of IL-2 Variant Fc Fusion Proteins

Figure 2:
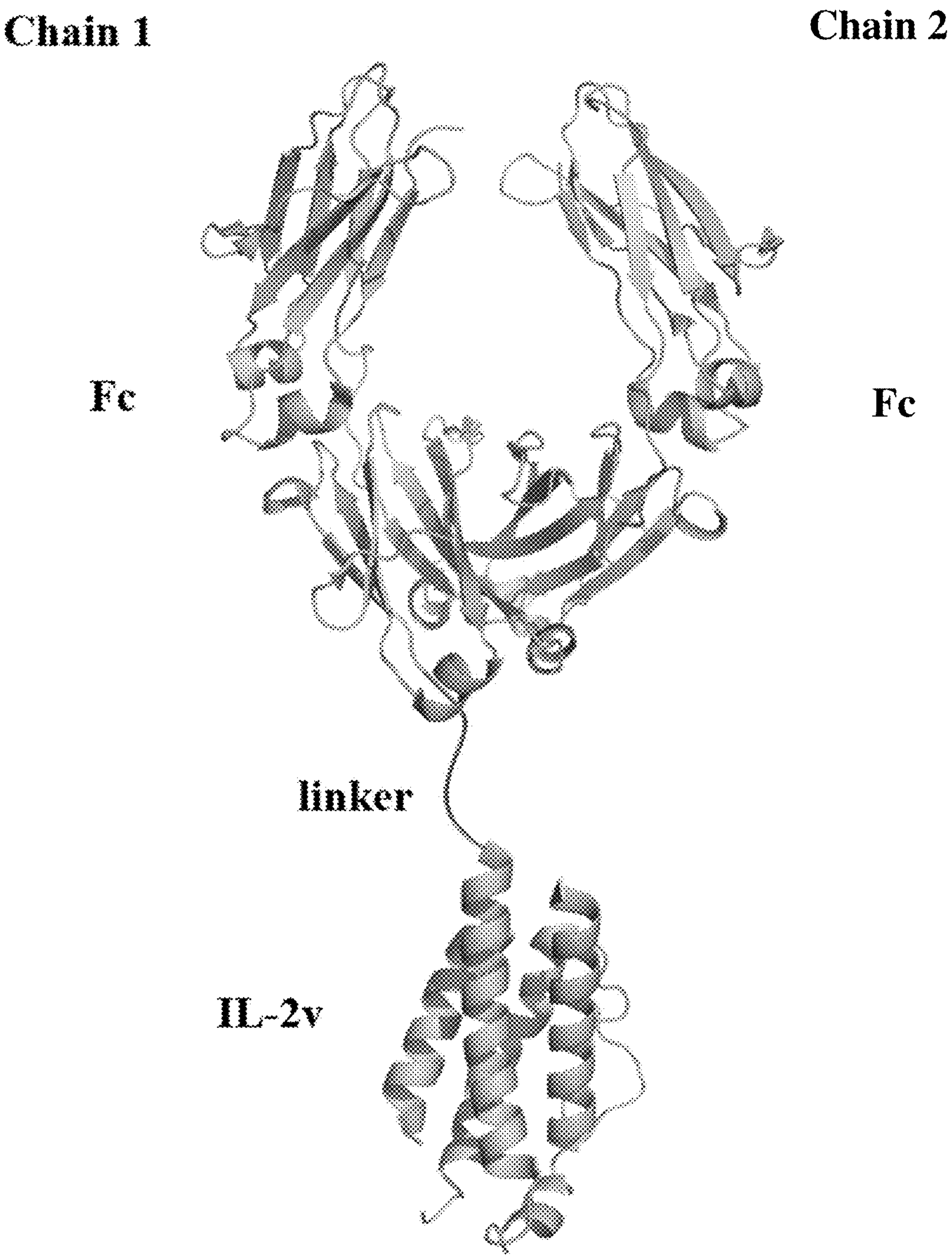
FIG. 2 illustrates a ribbon diagram of the designed heterodimeric Fc-IL-2v fusion proteins, described herein. Chain 1 is a variant IgG4 Fc subunit fused to IL-2v via a flexible polypeptide linker. Chain 2 is a complementary variant IgG4 Fc subunit that preferentially heterodimerizes with chain 1.

In addition to mutations that disrupt binding of IL-2 to IL-2Rα, other desired characteristics for an IL-2 variant biotherapeutic are enhanced pharmacokinetic properties that would enable infrequent human dosing relative to Proleukin, and favorable manufacturing properties. To that end, a fusion construct was designed in which the IL-2 variant molecule was fused to the C-terminus of one chain of a heterodimeric Fc variant of human IgG4. The use of a "knob-in-hole" heterodimeric Fc enabled fusion of a single copy of the IL-2v to dimeric Fc. This fusion design therefore mimics the monovalent nature of native IL-2 and avoids the potential for avidity-driven binding to IL-2Rα, despite mutations to disrupt this interaction. In addition to knob-in-hole modifications of the Fc region to promote heterodimerization, other changes relative to wild type IgG4 were made to prevent half-chain exchange with other IgG4 molecules, minimize the possibility of interactions with Fc gamma receptors and to disrupt protein A binding on the hole-containing Fc subunit to avoid co-purification of any hole-hole homodimer contaminant. The use of an Fc variant derived from human IgG4 is preferable to IgG1 due to its lower potential for Fc gamma receptor binding. For instance, substitution of Fc residues 234 and 235 (EU numbering) with alanine is well known to significantly reduce Fc gamma receptor binding in either an IgG1 or IgG4 background, but residual receptor binding is lower in the case of IgG4 (Xu et. al. *Cellular Immunology* (2000) 200, 16-26). Additionally, IgG4 naturally lacks the ability to activate the complement receptor, unlike human IgG1 (Diebolder et. al., *Science*, (2014) Mar. 14; 343(6176):1260-3). These Fc modifications were combined with changes in the IL-2v to enhance manufacturability, namely, substitution of Cys125 with Ser to prevent unwanted aggregation or modification that might otherwise occur at this unpaired Cys residue, and deletion of the first five residues of the mature native IL-2 sequence to eliminate a potential O-glycosylation site at Thr3 (Robb, et. al., *Proc Natl Acad Sci USA*, (1984) 81(20):6486-90). Deletion of the first five residues of mature native IL-2 sequence is a novel approach for an IL-2 variant biotherapeutic as it does not require mutation of the Thr3 position to eliminate O-glycosylation thereby minimizing the potential for immunogenicity that might otherwise be introduced due to such mutation. Finally, a flexible linker containing 4 repeats of the Gly-Gly-Gly-Gly-Ser motif tethered the IL-2v to its Fc fusion partner. A summary of substitutions present in the designed heterodimeric Fc-IL-2v fusion proteins are shown in Table 2 and the molecule is depicted in FIG. 2. Illustrative Fc-IL-2v fusion protein heterodimers described herein are summarized in Table 3. Heterodimers are named according to the SEQ ID NO. of the Fc-IL-2v fusion protein and the SEQ ID NO. of the heterodimerizing empty (untargeted, unfused) Fc domain. Amino acid sequences of the Fc-IL-2v fusion proteins described herein are provided in Table D. The amino acid sequence of SEQ ID NO: 46 is provided in Table E.

TABLE 2

List of Modifications Present in Template Design of Fc-IL-2v Fusion Protein

| Modification* | Region of molecule | Purpose | Chain number§ |
|---|---|---|---|
| S228P | Fc | Prevent half-chain exchange | 1 and 2 |
| F234A | Fc | Minimize Fc gamma receptor binding | 1 and 2 |
| L235A | Fc | Minimize Fc gamma receptor binding | 1 and 2 |
| T366W | Fc | Promote Fc heterodimerization | 1 |
| T366S | Fc | Promote Fc heterodimerization | 2 |
| L368A | Fc | Promote Fc heterodimerization | 2 |
| Y407V | Fc | Promote Fc heterodimerization | 2 |
| H435R | Fc | Disrupt protein A binding | 2 |
| Y436F | Fc | Disrupt protein A binding | 2 |
| Deletion K447 | Fc | Remove terminal Fc residue to mimic natural processing in IgGs | 1 |
| 4 × (GGGGS) (SEQ ID NO: 246) | linker | Flexible linkage between Fc and IL-2v | 1 |
| C125S | IL-2v | Prevent unwanted aggregation/modification | 1 |
| Deletion of mature IL-2 residues 1-5 (APTSS; SEQ ID NO: 163); IL-2v Δ1-5) | IL-2v | Eliminate potential O-glycosylation site | 1 |

*Fc region numbering according to EU scheme; IL-2 numbering according to sequence of mature human IL-2 (i.e., lacking signal peptide).

§Chain 1 is a variant IgG4 Fc subunit fused to IL-2v via a flexible polypeptide linker. Chain 2 is a complementary variant IgG4 Fc subunit that preferentially heterodimerizes with chain 1.

TABLE 3

Illustrative Human Fc-IL-2 Variant Fusion Protein Heterodimers

| Heterodimer name | Features |
|---|---|
| 81.46 | hIL-2v_Δ1-5_R38G_C125S |
| 82.46 | hIL-2v_Δ1-5_R38A_C125S |
| 83.46 | hIL-2v_Δ1-5_T41G_C125S |
| 84.46 | hIL-2v_Δ1-5_T41A_C125S |
| 85.46 | hIL-2v_Δ1-5_F42G_C125S |
| 86.46 | hIL-2v_Δ1-5_F42A_C125S |
| 87.46 | hIL-2v_Δ1-5_Y45G_C125S |
| 88.46 | hIL-2v_Δ1-5_Y45A_C125S |
| 89.46 | hIL-2v_Δ1-5_E61A_C125S |
| 90.46 | hIL-2v_Δ1-5_E62A_C125S |
| 91.46 | hIL-2v_Δ1-5_E68A_C125S |
| 92.46 | hIL-2v_Δ1-5_L72G_C125S |
| 93.46 | hIL-2v_Δ1-5_Q74G_C125S |
| 94.46 | hIL-2v_Δ1-5_Y107G_C125S |
| 95.46 | hIL-2v_Δ1-5_Y107A_C125S |
| 96.46 | hIL-2v_Δ1-5_Y45G_E61A_C125S |
| 97.46 | hIL-2v_Δ1-5_Y45G_E62A_C125S |
| 98.46 | hIL-2v_Δ1-5_R38G_Y45G_C125S |
| 99.46 | hIL-2v_Δ1-5_R38G_E61A_C125S |
| 100.46 | hIL-2v_Δ1-5_F42A_E61A_C125S |
| 101.46 | hIL-2v_Δ1-5_F42A_Y45G_C125S |
| 102.46 | hIL-2v_Δ1-5_Y45G_E61A_E62A_C125S |
| 103.46 | hIL-2v_Δ1-5_E61A_E62A_C125S |
| 104.46 | hIL-2v_Δ1-5_R38G_F42A_C125S |
| 105.46 | hIL-2v_Δ1-5_F42A_Y45A_L72G_C125S |
| 106.46 | hIL-2v_Δ1-5_R38G_F42A_Y45G_C125S |
| 107.46 | hIL-2v_Δ1-5_F42A_E62A_C125S |
| 108.46 | hIL-2v_Δ1-5_F42A_Y45G_E62A_C125S |
| 109.46 | hIL-2v_Δ1-5_F42A_Y45G_E61A_C125S |
| 110.46 | hIL-2v_Δ1-5_R38G_Y45G_E61A_C125S |
| 111.46 | hIL-2v_Δ1-5_R38G_F42A_E61A_C125S |
| 112.46 | hIL-2v_Δ1-5_R38G_Y45G_E62A_C125S |
| 113.46 | hIL-2v_Δ1-5_R38G_E62A_C125S |
| 114.46 | hIL-2v_Δ1-5_R38G_F42A_E62A_C125S |
| 115.46 | hIL-2v_Δ1-5_F42A_E61A_E62A_C125S |
| 116.46 | hIL-2v_Δ1-5_R38G_E61A_E62A_C125S |
| 117.46 | hIL-2v_Δ1-5_C125S |
| 118.46* | hIL-2v_T3A_C125S |

*All Fc-IL-2v fusions followed the design described in Example 2 except for 118.46 which did not have deletion of IL-2 residues 1-5, and contained a T3A mutation within this region.

Example 3

Expression and Purification of IL-2 Variants with Single Amino Acid Substitutions in IL-2 at the IL-2Rα Binding Interface as Fc Fusion Proteins In this example, we evaluated the expression and purification yields of 17 human Fc-IL-2 fusion protein variants. Fc-IL-2 variant fusion proteins were expressed transiently in Expi293™ cells and purified using protein A and anion exchange chromatography.

Methods

Fc-IL-2 variant fusion proteins were transiently produced by expression in Expi293™ cells using the Expifectamine293 system following the manufacturer's protocol (ThermoFisher Scientific). One microgram total DNA was used per ml of Expi293™ cells transfected. DNA was codon-biased for *Homo sapiens* expression and cloned into pcDNA3.1 vector. Expression vector 1 encodes Fc-IL-2 fusion sequence while expression vector 2 encodes Fc only sequence. Polynucleotide sequences encoding the Fc-IL-2 fusion proteins and heterodimerizing Fc domain are described herein are provided in Tables F and G, respectively. The two vectors were mixed at a ratio of 3:2 (w:w), respectively, and diluted in OptiMEM medium (ThermoFisher Scientific) before adding to diluted Expifectamine293 reagent to allow complex formation. After 20 minutes incubation at room temperature, the reagent DNA complex was added to cells seeded at 3 million cells/mL. Cultures were incubated at 37° C. in 8% $CO_2$ with shaking for four days. Cell free culture supernatant was harvested and filtered through a 0.2 μm filter for purification.

Cell free culture supernatants were purified on a Bio-Rad NGC chromatography system by injecting onto a MabSelect SuRe column (Cytiva). After affinity capture of the protein, the resin was washed with 25 mM Tris-HCl, 25 mM NaCl, pH 7.5 prior to elution with 100 mM NaAcetate pH 3.7. The eluted pools were neutralized to pH 8.0 with Tris Base and injected onto a Q-HP anion-exchange column (Cytiva) to remove additional impurities. The captured protein was washed with 10 mM NaPhosphate, pH 8.0 and eluted with an increasing NaCl gradient up to 200 mM. All proteins were formulated into 1×PBS, pH 7.4 by dialysis, sterile filtered, and stored at 4° C. The concentration of the formulated protein was determined by application of the Beer Lambert law following measurement of sample absorbance at 280 nm and computation of the molar extinction coefficient for this wavelength based on the amino acid sequence. Purity was determined by analytical size-exclusion chromatography and expressed as the percentage of the total area residing under the monodisperse product peak.

Results

A total of 17 human Fc-IL-2 variant fusion proteins were expressed and purified, with 15 of these containing a single mutation within the IL-2Rα binding interface, heterodimerized with the Fc domain of SEQ ID NO:46, and two control fusion proteins that retained the wild type binding interface (Table 4). Two Fc-IL-2 fusion protein variants containing Y107G (heterodimer 94.46) and Y107A (heterodimer 95.46) substitutions in IL-2 exhibited poor expression and were prone to aggregation after protein A purification, so these were not further purified. The fully purified yields for the remaining Fc-IL-2 variant fusion proteins ranged from 2-238 mg per liter of expression culture, with final purity levels of 95% or higher. Purified yields for most variants were in the range of 70 to 180 mg/L, but those containing the F42G (heterodimer 85.46) or L72G (heterodimer 92.46) mutations gave a particularly poor yield. Along with the Y107A and Y107G variants, these four low yielding variants appeared to suffer from poor expression and/or propensity to aggregate.

TABLE 4

Yields and Purity for Human Fc-IL-2 Variant Fusion Protein Heterodimers

| Heterodimer name | IL-2Rα Interface Mutation | Purified yield (mg/L) | Purity (%) |
|---|---|---|---|
| 81.46 | R38G | 68 | 98 |
| 82.46 | R38A | 129 | 99 |
| 83.46 | T41G | 178 | 98 |
| 84.46 | T41A | 183 | 99 |
| 85.46 | F42G | 3 | 95 |
| 86.46 | F42A | 92 | 98 |
| 87.46 | Y45G | 162 | 98 |
| 88.46 | Y45A | 126 | 98 |
| 89.46 | E61A | 70 | 96 |
| 90.46 | E62A | 117 | 98 |
| 91.46 | E68A | 150 | 95 |
| 92.46 | L72G | 2 | 99 |
| 93.46 | Q74G | 147 | 98 |
| 94.46 | Y107G | N/A* | N/A |
| 95.46 | Y107A | N/A | N/A |
| 117.46 | none | 178 | 98 |
| 118.46§ | none | 238 | 98 |

*N/A: not applicable

§All Fc-IL-2v fusions followed the design described in Example 2 except for heterodimer 118.46 which did not have deletion of IL-2 residues 1-5, and contained a T3A mutation with this region.

Example 4

In Vitro Binding of Fc-IL-2 Variant Fusion Proteins with Single Amino Acid Substitutions in IL-2 at the IL-2/IL-2Rα Binding Interface to IL-2Rα, IL-2Rβ, and IL-2Rβγ

In this example, we determined the in vitro binding affinity of Fc-IL-2 variant fusion proteins with single amino acid substitutions in the IL-2Rα binding interface, heterodimerized with the Fc domain of SEQ ID NO:46, to recombinant IL-2 receptor α, IL-2 receptor β, and IL-2 receptor βγ heterodimer. To do this, we performed surface plasmon resonance (SPR) assays.

Methods

Data for binding of Fc-IL-2 variant fusion proteins to IL-2Rα, IL-2Rβ and IL-2Rβγ heterodimer were collected on a Biacore platform using either C1 or CM5 chips. Neutravidin was immobilized using standard amine coupling methods and used to capture biotinylated receptors. Commercially sourced IL-2Rα (R&D Systems Cat #: 223-2A/CF) and IL-2Rβ receptors (R&D Systems Cat #: 224-2B-025/CF) were biotinylated using sulfo-NHS-LC-LC-Biotin, desalted, and then captured on the neutravidin surfaces. In the case of the IL-2Rβγ heterodimer, a custom biotinylated Fc fusion protein reagent was produced in-house through co-expression of the extracellular regions of human IL-2Rβ (amino acids 27-240) and IL-2Rγ (amino acids 23-262) fused to respective knob and hole subunits of an IgG1 Fc heterodimer (SEQ ID NOs: 255 and 256). Distinct purification tags were appended to the C-terminus of each chain. A FLAG epitope tag (DYKDDDDK; SEQ ID NO: 257) was added at the C-terminus of IL-2Rβ subunit, followed by C-terminal $His_8$ tag (HHHHHHHH; SEQ ID NO: 258). An AviTag™ (GLNDIFEAQKIEWHE; SEQ ID NO: 259) motif on the IL-2Rγ subunit allowed for site-specific biotinylation of the heterodimer.

human IL-2Rβ (amino acids 27-240)-Fc-FLAG (SAV+RF; hole):

(SEQ ID NO: 255)

```
AVNGTSQFTCFYNSRANISCVWSQDGALQDTSCQVHAWPDRRRWNQTCEL

LPVSQASWACNLILGAPDSQKLTTVDIVTLRVLCREGVRWRVMAIQDFKP

FENLRLMAPISLQVVHVETHRCNISWEISQASHYFERHLEFEARTLSPGH

TWEEAPLLTLKQKQEWICLETLTPDTQYEFQVRVKPLQGEFTTWSPWSQP

LAFRTKPAALGKDTGAQDKTHTCPPCPAPELLGGPSVFLFPPKPKDTLMI

SRTPEVTCVVVDVSHEDPEVKFNWYVDGVEVHNAKTKPREEQYNSTYRVV

SVLTVLHQDWLNGKEYKCKVSNKALPAPIEKTISKAKGQPREPQVYTLPP

SRDELTKNQVSLSCAVKGFYPSDIAVEWESNGQPENNYKTTPPVLDSDGS

FFLVSKLTVDKSRWQQGNVFSCSVMHEALHNRFTQKSLSLSPGKGSGSDY

KDDDDK
```

human IL-2Rγ (amino acids 23-262)-Fc-AviHis (W; knob):

(SEQ ID NO: 256)

```
LNTTILTPNGNEDTTADFFLTTMPTDSLSVSTLPLPEVQCFVFNVEYMNC

TWNSSSEPQPTNLTLHYWYKNSDNDKVQKCSHYLFSEEITSGCQLQKKEI

HLYQTFVVQLQDPREPRRQATQMLKLQNLVIPWAPENLTLHKLSESQLEL

NWNNRFLNHCLEHLVQYRTDWDHSWTEQSVDYRHKFSLPSVDGQKRYTFR
```

-continued

```
VRSRFNPLCGSAQHWSEWSHPIHWGSNTSKENPFLFALEAGAQDKTHTCP
PCPAPELLGGPSVFLFPPKPKDTLMISRTPEVTCVVVDVSHEDPEVKFNW
YVDGVEVHNAKTKPREEQYNSTYRVVSVLTVLHQDWLNGKEYKCKVSNKA
LPAPIEKTISKAKGQPREPQVYTLPPSRDELTKNQVSLWCLVKGFYPSDI
AVEWESNGQPENNYKTTPPVLDSDGSFFLYSKLTVDKSRWQQGNVFSCSV
MHEALHNHYTQKSLSLSPGKGSGSGLNDIFEAQKIEWHEHHHHHHHH
```

Proleukin was used as a comparator and an Fc heterodimer without a fused IL-2 moiety (SEQ ID NOs: 260 and 261; heterodimer name: 260:261) was used as a negative control.

Fc Heterodimer without a Fused IL-2 Moiety Fusion:

```
Fc1 (hG4_FALA):
                                    (SEQ ID NO: 260)
ESKYGPPCPPCPAPEAAGGPSVFLFPPKPKDTLMISRTPEVTCVVVDV
SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLWCLVKGFYPSDIAVEWESNGQPENNYKTTPPVLDSDGSFFLYSRL
TVDKSRWQEGNVFSCSVMHEALHNHYTQKSLSLSLGK

Fc2 (hG4 FALA_RF KiH):
                                    (SEQ ID NO: 261)
ESKYGPPCPPCPAPEAAGGPSVFLFPPKPKDTLMISRTPEVTCVVVDV
SQEDPEVQFNWYVDGVEVHNAKTKPREEQFNSTYRVVSVLTVLHQDWL
NGKEYKCKVSNKGLPSSIEKTISKAKGQPREPQVYTLPPSQEEMTKNQ
VSLSCAVKGFYPSDIAVEWESNGQPENNYKTTPPVLDSDGSFFLVSRL
TVDKSRWQEGNVFSCSVMHEALHNRFTQKSLSLSLGK
```

Fc IL 2 fusion protein variants, Fc protein, and Proleukin were injected at various concentrations over these surfaces. Kinetic data obtained from these injections was used to extract $k_{on}$ and $k_{off}$ to calculate KD (KD=$k_{off}/k_{on}$). Experiments were run at 25° C. in HBS-EP+ running buffer (10 mM HEPES, 150 mM NaCl, 3 mM EDTA, 0.05% Tween-20, pH 7.4 with 0.1 mg/ml BSA). Data shown in Table 5 for Fc IL-2 fusion protein variants binding to the indicated IL-2R surfaces were derived from the global fitting of data obtained from 2-5 independent surfaces.

Results

The data demonstrated a range of affinities for human Fc-IL-2 fusion protein variants of SEQ ID NOs: 81-93, heterodimerized with the Fc domain of SEQ ID NO:46, binding to IL-2Rα with KD values of 21 to 4,900 nM. Ten of these human Fc-IL-2 variant fusion proteins of SEQ ID NOs: 81-82, 84-90 and 92 had a measurable decrease in IL-2Rα affinity compared to an Fc-IL-2 fusion protein with a native IL-2Rα binding interface (SEQ ID NO: 117). Surprisingly, substitution R38G (heterodimer 81.46; KD=685 nM) had a 6-fold larger effect on reducing IL-2Rα affinity as compared to a variant containing R38A (heterodimer 82.46; KD=108 nM). All Fc-IL-2 fusion protein variants with single IL-2 substitutions in the IL-2Rα binding interface (SEQ ID NOs: 81-93) demonstrated similar binding affinity to IL-2Rβ as compared to an Fc-IL-2 fusion protein without any IL-2Rα binding interface mutation (SEQ ID NO: 117) with $K_D$ values from 5.9 to 8.8 μM. Six Fc-IL-2 fusion protein variants (SEQ ID NOs: 81, 83, 86, 87, 89 and 90) were also evaluated for binding to IL-2Rβγ heterodimer and demonstrated similar binding affinity as compared to an Fc-IL-2 fusion protein with a native IL-2Rα binding interface (SEQ ID NO: 117) with KD values of 16 to 152 pM. A control Fc protein with no IL-2 fusion (SEQ ID NOs: 260 and 261) demonstrated no detectable binding to IL-2Rα, IL-2Rβ or IL-2Rβγ. These results are summarized in Table 5.

TABLE 5

Affinity of Fc-IL-2v Fusion Proteins with Single IL-2 Amino Acid Substitutions Binding to IL-2Rα, IL-2Rβ, or IL-2Rβγ

| Heterodimer name | IL-2Rα $K_D$ (nM) | IL-2Rβ $K_D$ (μM) | IL-2Rβγ $K_D$ (pM) |
|---|---|---|---|
| 81.46 | 685 | 7.0 | 71 |
| 82.46 | 108 | 8.2 | ND* |
| 83.46 | 29 | 7.3 | 150 |
| 84.46 | 119 | 7.0 | ND |
| 85.46 | 4,900 | 7.5 | ND |
| 86.46 | 2,000 | 7.1 | 94 |
| 87.46 | 269 | 7.0 | 16 |
| 88.46 | 120 | 8.0 | ND |
| 89.46 | 419 | 8.8 | 65 |
| 90.46 | 2,400 | 8.1 | 152 |
| 91.46 | 32 | 5.9 | ND |
| 92.46 | 503 | 8.0 | ND |
| 93.46 | 21 | 8.2 | ND |
| 117.46 | 15 | 7.0 | 142 |
| 260:261 | NBD§ | NBD | NBD |
| Proleukin | 15 | 2.3 | ND* |

*ND, not determined;

§NBD, no binding detected

Example 5

In Vitro Potency of Fc-IL-2 Variant Fusion Proteins with Single IL-2 Amino Acid Substitutions In this example, we compared the potency of 13 Fc-IL-2 fusion protein variants with single amino acid substitutions in IL-2 at the IL-2/IL-2Rα binding interface heterodimerized with the Fc domain of SEQ ID NO:46. For this comparison, we tested the in vitro potency using a CTLL-2 STAT5 reporter cell line. CTLL-2 cells are a T cell lymphoblast line that expresses the high affinity IL 2Rαβγ(Gillis and Smith, *Nature*. (1977) 268(5616):154-6). IL 2 signaling through the IL-2Rαβγ is evaluated by measuring luciferase signal through a STAT5 luciferase reporter gene engineered into the CTLL-2 cell line. STAT5 activation is a method to quantify IL-2 signaling as activation of STAT5 through the Janus kinase (JAK)/STAT5 signal transduction pathway occurs downstream of the IL-2R (Gilmour, et al., *Proc Natl Acad Sci USA* (1995) 92(23):10772-6; Gaffen, *Cytokine* (2001) 14(2):63-77).

Methods

Figure 3:
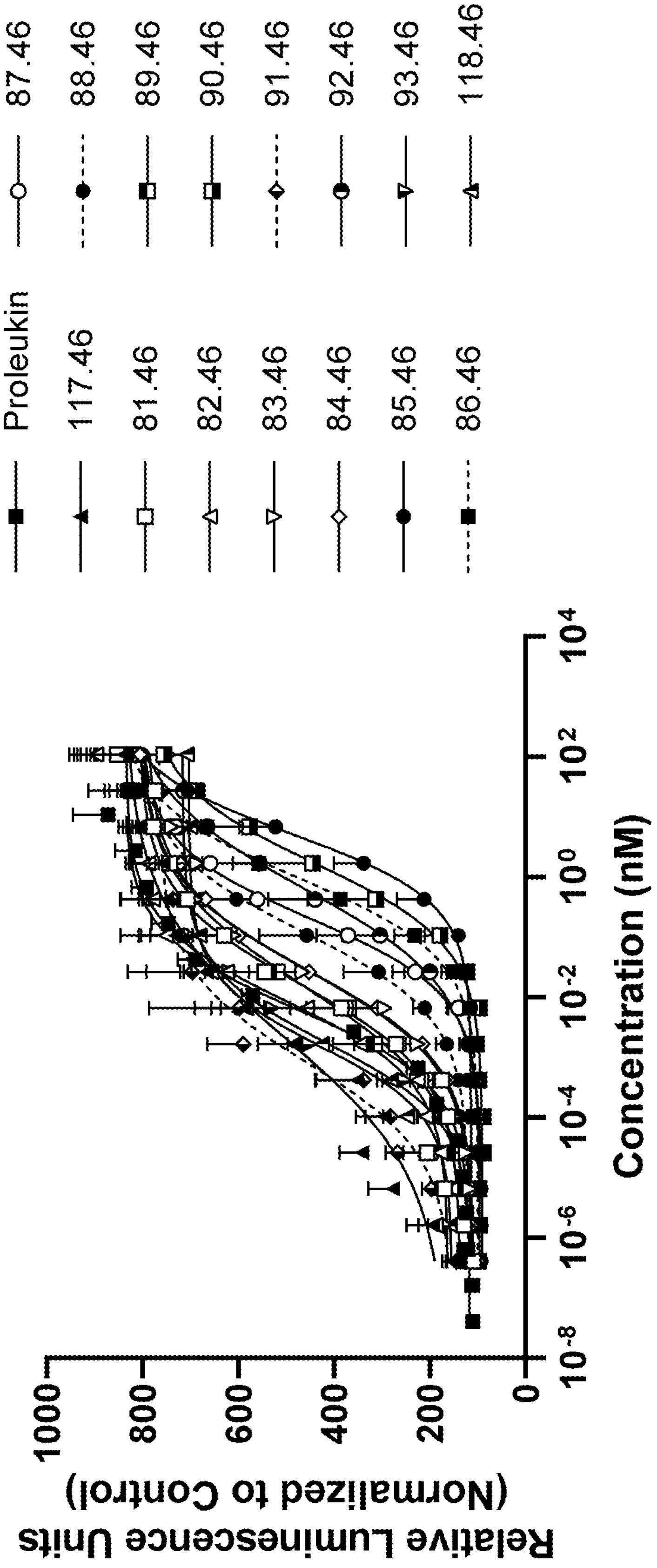
FIG. 3 illustrates in vitro potency of Fc-IL-2 variant fusion proteins with single substitutions in IL-2 at IL-2Rα binding interface on CTLL-2 cells.

CTLL-2 STAT5 Reporter Assay: CTLL-2 cells engineered with a STAT5 luciferase reporter gene (Promega) were cultured in tissue culture medium (IMDM, 10% FBS, 1×NEAA, 1× L-glutamine, 1× sodium pyruvate, Hygromycin B) supplemented with IL-2 necessary for growth. To assess Fc-IL-2 variant potency, CTLL-2 cells were washed twice in IL-2 free medium and seeded in a white 96 well tissue culture treated plate (Corning #3917) at a density of 40,000 cells per well in complete medium without IL-2 for 16 hours at 37° C. The next day, CTLL-2 cells were treated with serially diluted Fc-IL-2 variants or with Proleukin as a control and incubated for 4 hours at 37° C. Following manufacturer's instructions, the plate was then equilibrated to ambient temperature for 15 minutes prior to the addition of Bio-Glo luciferase reagent (Promega #G7940). After 15 minutes of incubation, luminescence was measure using SpectorMax reader (Molecular Devices). Data in Table 6 represent mean values of two replicates and data in FIG. 3 represent mean values of two replicates ±standard deviation.

Results

The data demonstrated a range of potencies for 13 human Fc-IL-2 variant fusion proteins with single amino acid substitutions in IL-2 at the IL-2/IL-2Rα binding interface (SEQ ID NOs: 81-93), heterodimerized with the Fc domain of SEQ ID NO:46, for STAT5 activation in CTLL-2 cells expressing the trimeric murine IL-2 receptor (IL-2Rα, IL-2Rβ, and IL-2Rγ) with EC50 values from 0.001 to 5.5 nM. Eleven of the human Fc-IL-2 variants (SEQ ID NOs: 81-90 and 92) with single IL-2 substitutions demonstrated 3-fold to 1833-fold decreases in STAT5 activation of CTLL-2 cells compared to Fc-IL-2 fusion proteins with a native IL-2Rα binding interface (SEQ ID NOs: 117, 118). Four of the five least potent molecules in the CTLL-2 assay were a subset of the five Fc-IL-2 variant fusion proteins with the most significantly impacted IL-2Rα binding affinity as shown in Table 5 (SEQ ID NOs: 85, 86, 90 and 92). This demonstrated a strong correlation between binding to human IL-2Rα and bioactivity on CTLL-2 cells. Two Fc-IL-2 fusion protein variants (SEQ ID NOs: 91,93; EC50=0.001 and 0.002 nM, respectively) with single IL-2 substitutions demonstrated similar potency to Fc-IL-2 fusion proteins with a native IL-2Rα binding interface (SEQ ID NOs: 117, 118; EC50=0.003, 0.002 nM, respectively). Additionally, these data demonstrated that deletion of the first five amino acids of the N terminus of IL-2 in the Fc-IL-2 fusion protein (SEQ ID NO: 117, EC50=0.003 nM) resulted in no change in potency as compared to an Fc-IL-2 fusion protein with an intact N-terminus (SEQ ID NO: 118; EC50=0.002 nM). The results are summarized in Table 6 and depicted in FIG. 3.

TABLE 6

EC50 Values for STAT5 Activation of CTLL-2 Cells by Fc-IL-2 Variants with Single Substitutions in IL-2

| Heterodimer name | EC50 (nM) |
|---|---|
| 81.46 | 0.02 |
| 82.46 | 0.01 |
| 83.46 | 0.04 |
| 84.46 | 0.03 |
| 85.46 | 5.5 |
| 86.46 | 1.0 |
| 87.46 | 0.2 |
| 88.46 | 0.1 |
| 89.46 | 0.02 |
| 90.46 | 2.0 |
| 91.46 | 0.001 |
| 92.46 | 0.7 |
| 93.46 | 0.002 |
| 117.46 | 0.003 |
| 118.46 | 0.002 |
| Proleukin | 0.006 |

Example 6

In Vitro Potency of Fc-IL-2 Fusion Proteins with Single Amino Acid Substitutions in IL-2 at IL-2/IL-2Rα Binding Interface in Primary CD8+ T Cells and Treg Cells In this example, we compared the potency of Fc-IL-2 variant fusion proteins with single amino acid substitutions in IL-2 at the IL-2/IL-2Rα binding interface, heterodimerized with the Fc domain of SEQ ID NO:46. For this comparison, we evaluated the in vitro potency using a human peripheral blood mononuclear cell (PBMC) STAT5 activation assay. The PBMC STAT5 activation assays allows for immune cell activation after IL-2 treatment of PBMCs to be evaluated by measuring the phosphorylation of signal transducer and activator of transcription 5 (STAT5) by flow cytometry. STAT5 phosphorylation is a method to quantify IL-2 signaling since activation of STAT5 through the Janus kinase (JAK)/STAT5 signal transduction pathway occurs downstream of the IL-2R (Gilmour, et al., *Proc Natl Acad Sci USA* (1995) 92(23):10772-6; Gaffen, *Cytokine* (2001) 14(2):63-77; Varker, et al., *Clin Cancer Res* (2006) 12(19): 5850-8).

Methods

PBMC STAT5 Assay: Cryopreserved human peripheral blood mononuclear cells (PBMC) isolated from multiple donors (Cellular Technology Limited) were thawed and washed twice with culture medium (RPMI-1640, 10% HI FBS, 1× PS, 1×HEPES) to remove DMSO. Following a resting period of 20 minutes at 37° C. in culture medium, the PBMCs were plated in a 96 well round bottom plate (Corning #9018) at a density of 250,000 cells per well and treated with serially diluted Fc-IL-2 fusion protein variants or with Proleukin as control for 20 minutes. After incubation, cells were fixed with pre-warmed Phosflow Fix Buffer (Becton Dickinson #557870) for 20 minutes at room temperature. Cells were washed twice and permeabilized with pre-chilled Phosflow Perm Buffer III (Becton Dickinson #558050) for 30 minutes on ice followed by FACS staining composed of a panel of antibodies against CD3, CD4, CD8, CD25, FoxP3, and phosphorylated STAT5 to define CD8+ T cells (CD3+, CD8+) and Treg cells (CD3+, CD4+, CD25hi, FoxP3+). After 60 minutes, the cells were washed twice and analyzed using an LSRFortessa X-20 (BD Biosciences) for phosphorylation of STAT5 in various lymphocyte subpopulation. Data in Table 7 represent mean values of two to six replicates.

Results

The data demonstrated a range of potencies for human Fc-IL-2 variant fusion proteins (SEQ ID NOs: 117, 118, 81-93), heterodimerized with the Fc domain of SEQ ID NO:46, for STAT5 activation of Treg cells (EC50 values from <0.001 to 0.3 nM) and CD8+ T cells (EC50 values from 7.9 to 165.1 nM). Six of the human Fc-IL-2 variant fusion proteins (SEQ ID NOs: 81, 85, 86, 87, 89 and 90) with single substitutions in the IL-2/IL-2Rα binding interface demonstrated approximately 30-fold to 300-fold decreases in STAT5 activation of Treg cells compared to Fc-IL-2 fusion proteins with a native IL-2Rα binding interface (SEQ ID NOs: 117, 118). Seven Fc-IL-2 variant fusion proteins (SEQ ID NOs: 82, 83, 84, 88, 91, 92 and 93) with single substitutions in the IL-2/IL-2Rα binding interface had Treg EC50 values <0.001 nM which was of similar potency to Fc-IL-2 fusion proteins with a native IL-2Rα interface (SEQ ID NOs: 117 and 118; EC50=<0.001 nM). Four of the five molecules with the greatest decreases in STAT5 activation of Treg cells were a subset of the five Fc-IL-2 variant fusion proteins with the most significantly impacted IL-2Rα binding affinity as shown in Table 5 (heterodimers 81.46, 85.46, 86.46 and 90.46). This demonstrated a strong correlation between binding to human IL-2Rα and potency of STAT5 activation in Treg cells. Surprisingly, heterodimer 92.46 which contains the L72G mutation in the IL 2Rα binding interface, did not exhibit a measurable decrease in STAT5 activation of Treg cells relative to the 117.46 heterodimer control despite it showing measurable decreases in IL-2Rα binding affinity (Table 5) and CTLL-2 bioactivity (Table 6). Additionally, it was surprising that the substitution of R38G (heterodimer 81.46) was more potent at reducing STAT5 activation of Treg cells (0.07 nM) than substitution to R38A (<0.001 nM, heterodimer 82.46). Twelve of the Fc-IL-2 variant fusion proteins with single substitutions in the IL-2/IL-2Rα binding interface (SEQ ID NOs: 81-92) had STAT5 activation of CD8+ T cells (EC50 values 9.0-33.7 nM) of similar potency to Fc-IL-2 fusion proteins with a native IL-2Rα interface (SEQ ID NOs: 117, 118; EC50=15.5 nM and 7.9 nM, respectively). Only the Fc-IL-2 variant fusion protein of SEQ ID NO: 93 demonstrated reduced potency on CD8+ T cells with an EC50 value of 165.1 nM. Additionally, these data demonstrated that deletion of the first five amino acids of the N-terminus of IL-2 in the Fc-IL-2 fusion protein (SEQ ID NO: 117; EC50=15.5 nM) resulted in minimal change to CD8+ T cell or Treg cell activation as compared to an Fc-IL-2 fusion protein with an intact N-terminus (SEQ ID NO: 118; EC50=7.9 nM). The results are summarized in Table 7.

TABLE 7

EC50 Values for STAT5 Activation of Treg cells and CD8+ T cells by Fc-IL-2 Variants with Single Substitutions in IL-2/IL-2Rα Binding Interface

| Heterodimer name | Treg EC50 (nM) | CD8+ T cell EC50 (nM) |
|---|---|---|
| 81.46 | 0.07 | 17.9 |
| 82.46 | <0.001 | 33.7 |
| 83.46 | <0.001 | 9.0 |
| 84.46 | <0.001 | 15.1 |
| 85.46 | 0.06 | 19.1 |
| 86.46 | 0.3 | 12.6 |
| 87.46 | 0.03 | 11.5 |
| 88.46 | <0.001 | 13.2 |
| 89.46 | 0.04 | 11.8 |
| 90.46 | 0.08 | 21.6 |
| 91.46 | <0.001 | 16.9 |
| 92.46 | <0.001 | 17.0 |
| 93.46 | <0.001 | 165.1 |
| 117.46 | <0.001 | 15.5 |
| 118.46 | <0.001 | 7.9 |
| Proleukin | <0.001 | 4.2 |

Example 7

Design, Expression and Purification of IL-2 Variants with Two or Three Amino Acid Substitutions in IL-2 at IL-2/IL-2Rα Binding Interface as Fc Fusion Proteins In an effort to further improve the activity profile of an Fc-IL-2 variant protein, individual point mutations in the IL-2Rα binding interface were considered for potential combination. Based on the biochemical and cellular profiling of variant proteins containing a single substitution in the IL-2Rα binding interface, preferred mutations were identified as R38G, F42A, F42G, Y45G, E61A and E62A. However, the much lower production yield for the F42G-containing variant (heterodimer 88.46) and the L72G-containing variant (heterodimer 92.46), compared to other candidates in this set, and the negative impact this could have on manufacturability of a biotherapeutic, led to their exclusion from further consideration. Additionally, it was previously observed in the context of an IL-2 fusion protein that proteoloytic cleavage occurred at position T37, that is, between residues T37 and R38 (Schneider, et al., *Biotechnol Bioeng*. (2019) 116(10):2503-2513). Thus, mutation at position R38 could also improve manufacturing by reducing the potential for proteolysis at this site. Accordingly, a set of 20 Fc-IL-2 variant fusion proteins containing a combination of two or three mutations selected from R38G, F42A, Y45G, E61A and E62A were designed, with other attributes of the design following that described in Example 2 (the Fc-IL-2v fusion proteins of SEQ ID NOs: 96-115 heterodimerized with the Fc domain of SEQ ID NO:46). One additional variant was added having F42A/Y45A/L72G three IL-2Rα binding interface mutations (heterodimer 105.46). Expression and purification of these human Fc-IL-2 variant fusion proteins followed the same procedures described above in Example 3.

Results

The set of 21 human Fc-IL-2 variant fusion proteins containing two or three mutations within the IL-2Rα binding interface were expressed and purified, and a summary of these data are presented in Table 8. The fully purified yields for Fc-IL-2 variant proteins containing multiple mutations in the IL-2Rα binding interface ranged from 24 to 172 mg/L, with final purity at or above 97% for all samples.

TABLE 8

Expression Yields and Purity for Human Fc-IL-2 Variant Fusion Protein Heterodimers Containing Two or Three Amino Acid Substitutions in the IL-2Rα Binding Interface

| Heterodimer name | IL-2Rα binding interface mutations | Purified yield (mg/L) | Purity (%) |
|---|---|---|---|
| 104.46 | R38G/F42A | 92 | 99.7 |
| 98.46 | R38G/Y45G | 76 | 99.9 |
| 99.46 | R38G/E61A | 29 | 98.6 |
| 113.46 | R38G/E62A | 52 | 99.3 |
| 101.46 | F42A/Y45G | 60 | 98.7 |
| 100.46 | F42A/E61A | 43 | 99.5 |
| 107.46 | F42A/E62A | 74 | 99.6 |
| 96.46 | Y45G/E61A | 172 | 98.3 |
| 97.46 | Y45G/E62A | 154 | 99.7 |
| 103.46 | E61A/E62A | 73 | 99.1 |
| 106.46 | R38G/F42A/Y45G | 139 | 98.7 |
| 111.46 | R38G/F42A/E61A | 24 | 99.8 |
| 114.46 | R38G/F42A/E62A | 94 | 99.6 |
| 110.46 | R38G/Y45G/E61A | 77 | 99.6 |
| 112.46 | R38G/Y45G/E62A | 77 | 99.7 |
| 116.46 | R38G/E61A/E62A | 35 | 98.6 |
| 109.46 | F42A/Y45G/E61A | 125 | 99.8 |
| 108.46 | F42A/Y45G/E62A | 108 | 99.7 |
| 115.46 | F42A/E61A/E62A | 65 | 99.5 |
| 102.46 | Y45G/E61A/E62A | 71 | 99.6 |
| 105.46 | F42A/Y45A/L72G | 129 | 97.0 |

Example 8

In Vitro Binding of Fc-IL-2 Variant Fusion Proteins with Two or Three Amino Acid Substitutions in IL-2 at the IL-2/IL-2Rα Binding Interface to IL-2Rα and IL-2Rβγ

In this example, we determined the in vitro binding affinity of 21 Fc-IL-2 variant fusion proteins with two or three amino acid substitutions in IL-2 at the IL-2/IL-2Rα binding interface to recombinant IL-2 receptor a and IL-2 receptor βγ heterodimer, heterodimerized with the Fc domain of SEQ ID NO:46. To do this, we performed surface plasmon resonance (SPR) assays.

Methods

Fc-IL-2 variant binding data was collected on a Biacore platform using a CM4 chip. Neutravidin was immobilized using standard amine coupling methods and used to capture biotinylated receptors. The source, preparation and immobilization of biotinylated IL-2Rα and IL-2Rβγ heterodimer was as described in Example 4. Proleukin was used as a comparator. Fc-IL-2 variants and Proleukin were injected at various concentrations over these surfaces. Kinetic data obtained from these injections was used to extract $k_{on}$ and $k_{off}$ to calculate $K_D$ ($K_D$=$k_{off}$/$k_{on}$). Experiments were run at 25° C. in HBS-EP+ running buffer (10 mM HEPES, 150 mM NaCl, 3 mM EDTA, 0.05% Tween-20, pH 7.4 with 0.1 mg/ml BSA. $K_D$ values reported in Table 9 resulted from the global fitting of data obtained from 3-5 independent surfaces.

Results

Figure 4A:
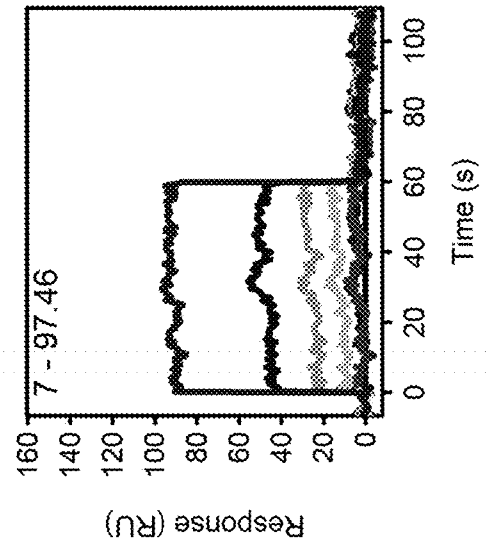
FIGS. 4A-4R illustrate Biacore binding responses obtained following injection of different concentrations of Fc-IL-2 variant fusion proteins over an IL-2Rα surface. Binding was tested at concentrations up to 20.0 μM in a two-fold concentration series for all samples (97.46 (FIG. 4A), 100.46 (FIG. 4B), 101.46 (FIG. 4C), 102.46 (FIG. 4D), 103.46 (FIG. 4E), 105.46 (FIG. 4G), 106.46 (FIG. 4H), 107.46 (FIG. 4I), 108.46 (FIG. 4J), 109.46 (FIG. 4K), 110.46 (FIG. 4L), 112.46 (FIG. 4N), 114.46 (FIG. 4P), 115.46 (FIG. 4Q), 116.46 (FIG. 4R) except 104.46 (FIG. 4F), 111.46 (FIG. 4M) and 113.46 (FIG. 4O) which were studied up to 12.3 μM, 14.8 μM and 16.1 μM, respectively.
Figure 4B:
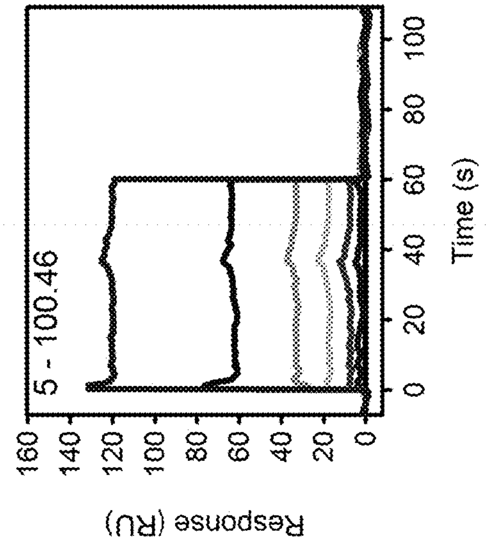
Figure 4C:
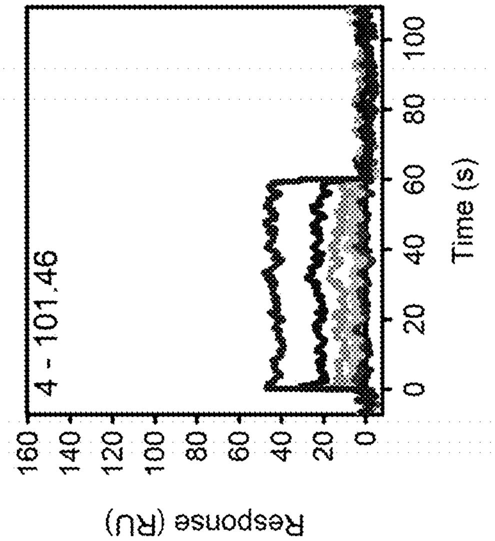
Figure 4F:
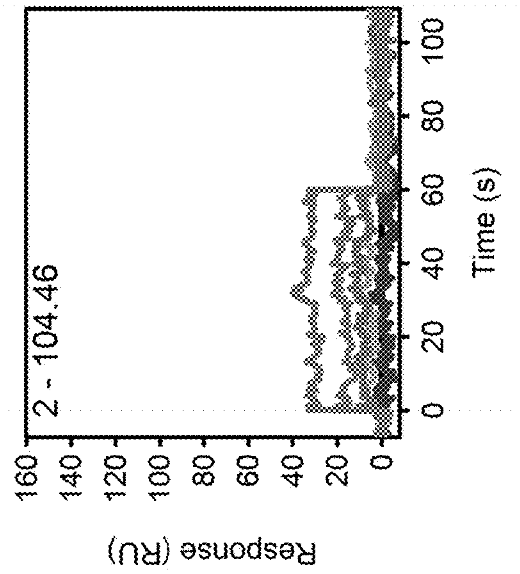
Figure 4E:
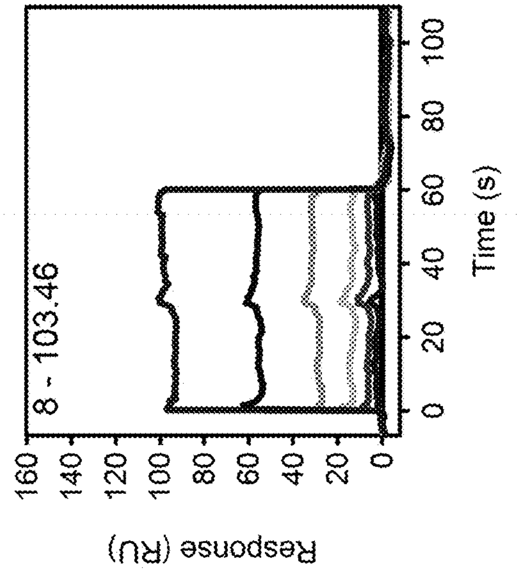
Figure 4D:
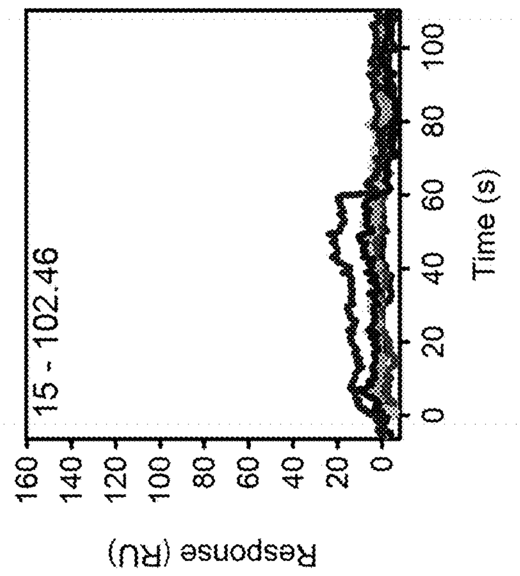
Figure 4I:
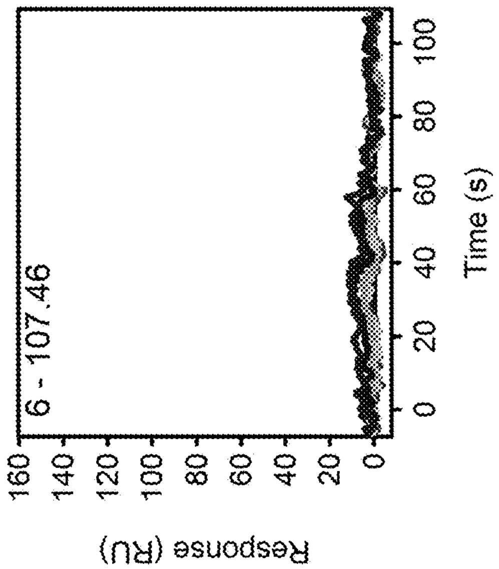
Figure 4H:
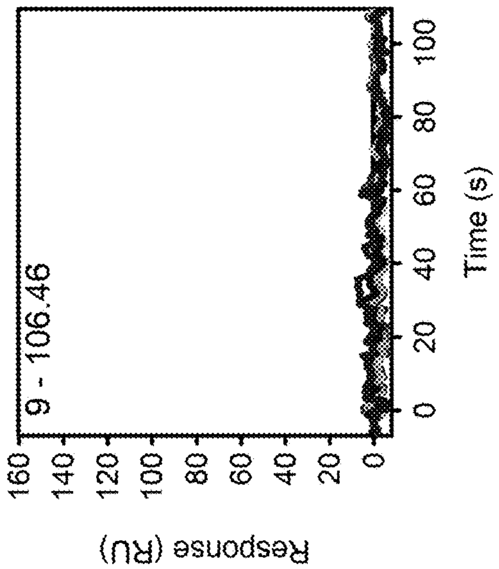
Figure 4G:
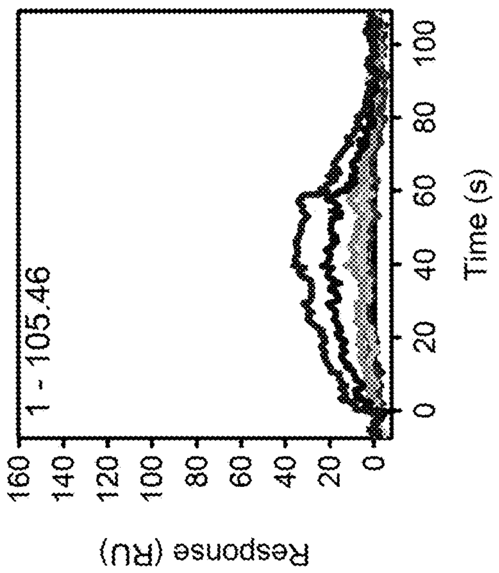
Figure 4L:
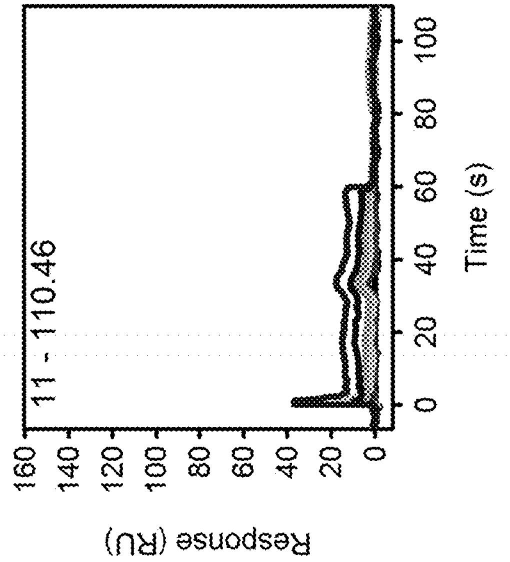
Figure 4K:
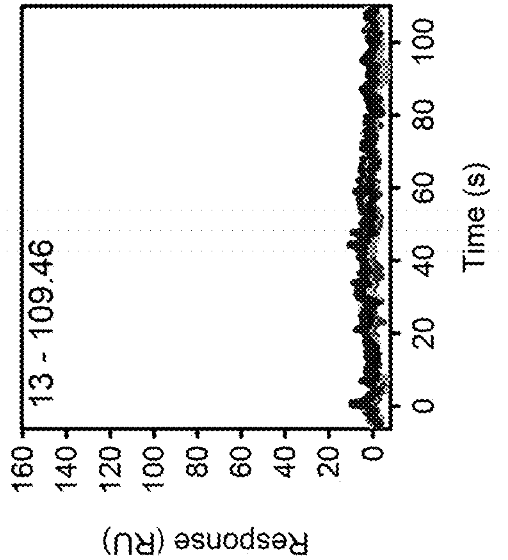
Figure 4J:
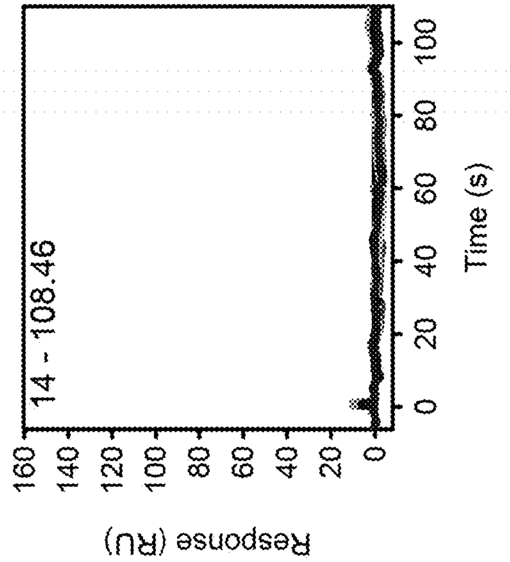
Figure 4M:
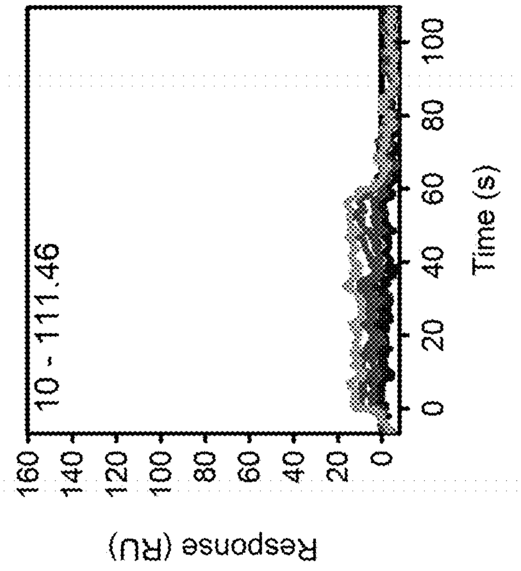
Figure 4N:
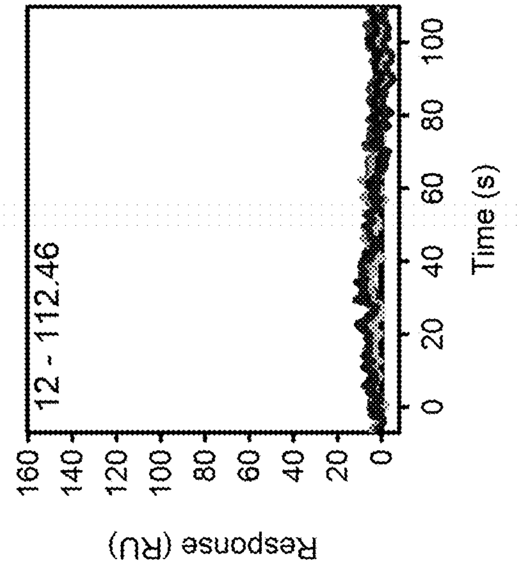
Figure 4O:
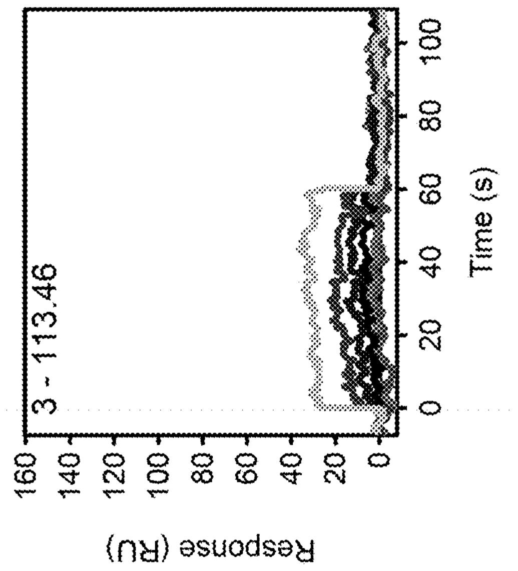
Figure 4P:
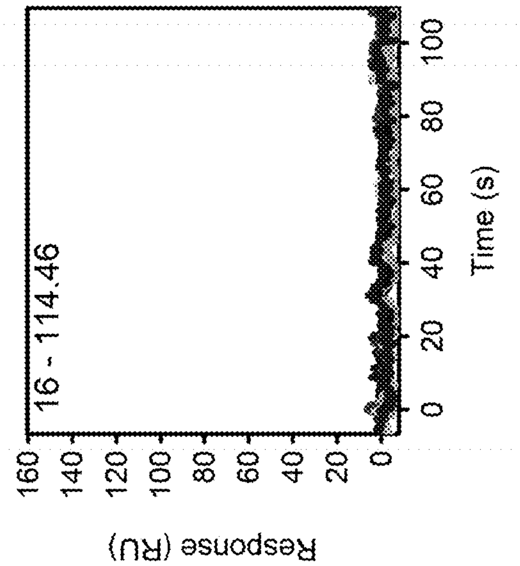
Figure 4Q:
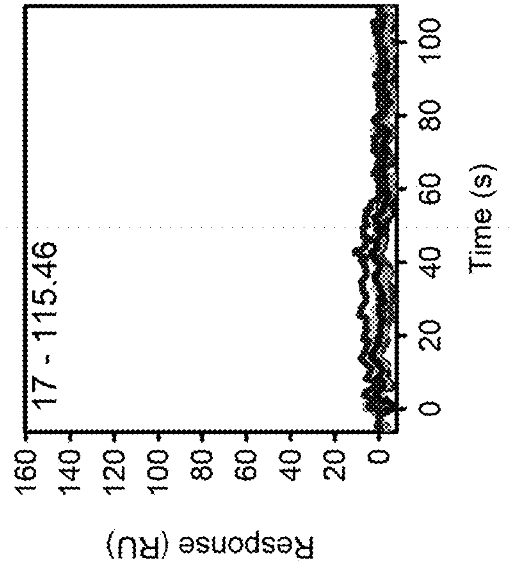
Figure 4R:
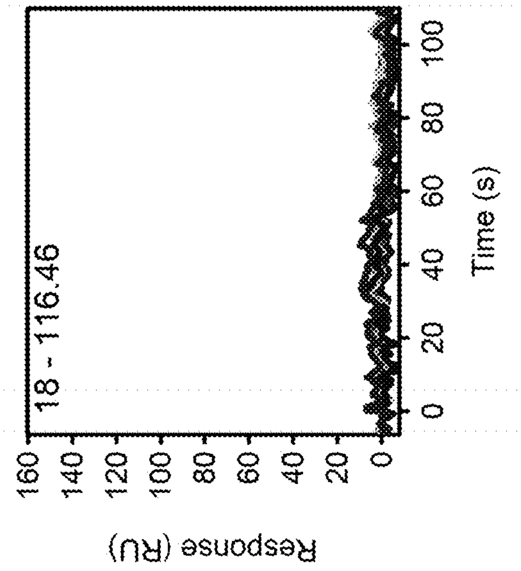

Fc-IL-2 variant binding data is summarized in Table 9. These data demonstrated reduced IL-2Rα binding affinity for all human Fc-IL-2 variant fusion proteins with two to three amino acid substitutions in IL-2 (SEQ ID NOs: 96-115), heterodimerized with the Fc domain of SEQ ID NO:46, with $K_D$ values ranging from 39 μM to greater than 60 μM. This is in comparison to IL-2Rα affinity measurements for an Fc-IL-2 fusion protein with a native IL-2Rα binding interface (SEQ ID NO: 117; KD=0.06 μM) and Proleukin ($K_D$=0.08 μM). In comparison to human Fc-IL-2 variant fusion proteins containing a single substitution in the IL-2Rα binding interface (Table 5), additive effects in decreasing IL-2Rα binding were seen with variants that combined with two to three of these substitutions. For many of the combination variants, residual binding to IL-2Rα was extremely weak or essentially undetectable at the highest tested concentration, which varied from 12 to 20 μM depending on the sample. Accordingly, the data for many of these combination variants did not allow for calculation of IL-2Rα binding constants, although small responses in the binding isotherm data was suggestive of affinity differences among some members of the subset of variants for which $K_D$ values could not be calculated, as shown in FIGS. 4A-4R. For example, the R38G/F42A/E62A-containing variant (heterodimer 114.46) and F42A/E62A-containing variant (heterodimer 107.46) show no measurable responses in binding isotherm data for IL-2Rα as compared to observed residual binding isotherm data for the F42A/Y45A/L72G-containing variant (heterodimer 105.46) as shown in FIGS. 4G, 4I, and 4P. In contrast to IL-2Rα binding, all Fc-IL-2 variant fusion proteins with two or three substitutions in IL-2 at the IL-2/IL-2Rα binding interface (SEQ ID NOs: 96-115) demonstrated similar binding affinity to IL-2Rβγ heterodimer as compared to an Fc-IL-2 fusion protein with a native IL-2Rα binding interface (SEQ ID NO: 117) and Proleukin with $K_D$ values ranging from 52 to 115 pM.

TABLE 9

In vitro Binding Data of Fc-IL-2 Fusion Proteins with Two or Three Amino Acid Substitutions to IL-2Rα and IL-2Rβγ

| Heterodimer name | IL-2Rα $K_D$ (μM) | IL-2Rβγ $K_D$ (pM) |
|---|---|---|
| 96.46 | 56 | 64 |
| 97.46 | >60 | 65 |
| 98.46 | 59 | 56 |
| 99.46 | 39 | 65 |
| 100.46 | >60 | 61 |
| 101.46 | >60 | 54 |
| 102.46 | >60 | 73 |
| 103.46 | >60 | 96 |
| 104.46 | >60 | 61 |
| 105.46 | >60 | 63 |
| 106.46 | >60 | 60 |
| 107.46 | >60 | 69 |
| 108.46 | >60 | 62 |
| 109.46 | >60 | 56 |
| 110.46 | >60 | 59 |
| 111.46 | >60 | 69 |
| 112.46 | >60 | 66 |
| 113.46 | >60 | 72 |
| 114.46 | >60 | 76 |
| 115.46 | >60 | 93 |
| 116.46 | >60 | 115 |
| 117.46 | 0.06 | 56 |
| Proleukin | 0.08 | 52 |

Example 9

In Vitro Potency of Fc-IL-2 Fusion Proteins with Two or Three Amino Acid Substitutions in IL-2 at IL-2/IL-2Rα Binding Interface In this example, we compared the potencies of Fc-IL-2 variant fusion proteins with two or three amino acid substitutions in IL-2 at the IL-2/IL-2Rα binding interface, heterodimerized with the Fc domain of SEQ ID NO:46. For this comparison, we evaluated in vitro potencies using a CTLL-2 STAT5 reporter cell line. Methods are described in Example 4.

Results

Figure 5:
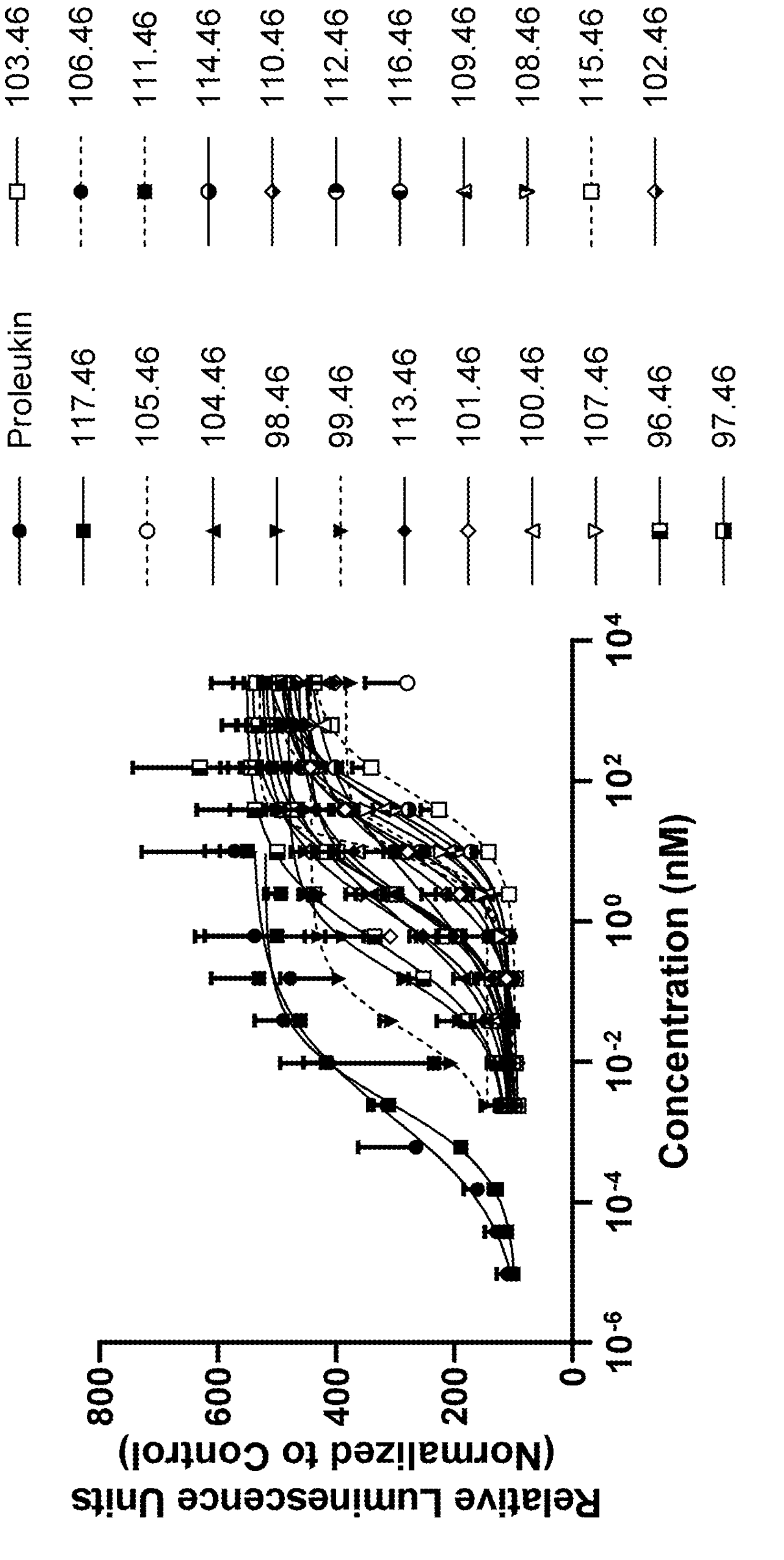
FIG. 5 illustrates in vitro potency of Fc-IL-2 variant fusion proteins with two or three amino acid substitutions in IL-2 at IL-2Rα binding interface on CTLL-2 cells.

The data demonstrated a range of potencies for human Fc-IL-2 variant fusion proteins (SEQ ID NOs: 96-115), heterodimerized with the Fc domain of SEQ ID NO:46, for STAT5 activation in CTLL-2 cells expressing the trimeric murine IL-2 receptor (IL-2Rα, IL-2Rβ, and IL-2Rγ) with EC50 values from 0.03 to 67.1 nM. This range in EC50 potency in STAT5 activation for Fc-IL-2 variant proteins was decreased by approximately 15-fold to 33,550-fold compared to Fc-IL-2 fusion proteins with a native IL-2Rα binding interface (SEQ ID NO: 117). Proleukin and the Fc-IL-2 fusion protein of SEQ ID NO: 117 demonstrated similar EC50 values in this assay (EC50=0.002 nM). Heterodimers 107.46, 108.46, 109.46, 114.46 and 115.46 demonstrated the weakest overall potencies in this assay (EC50=25.5 to 67.1 nM) and had weaker potencies as compared to heterodimer 105.46 (F42A, Y45G, L72G; EC50=7.7 nM). Surface plasmon resonance (SPR) data indicated that the R38G/F42A/E62A-containing variant (heterodimer 114.46) and the F42A/E62A-containing variant (heterodimer 107.46) had no residual binding to IL-2Rα (Example 8), but surprisingly in this cell based assay, the R38G/F42A/E62A-containing variant (heterodimer 114.46) had weaker overall potency compared to the F42A/E62A-containing variant (heterodimer 107.46) for IL-2Rαβγ-mediated pSTAT5 activation. Thus the CTLL-2 pSTAT5 assay, where cells express very high levels of IL-2Rα, is a more sensitive assay for measuring residual IL-2Rα binding and indicates that some of our IL-2 variants, including the F42A/E62A-containing variant (heterodimer 107.46), maintain residual IL-2Rα binding. The results are summarized in Table 10 and represent average values of two to three replicates. The results are depicted in FIG. 5 where data represents average values of two to three replicates ±standard deviation.

TABLE 10

In vitro Potency of Fc-IL-2 Variant Fusion Proteins with Two or Three Amino Acid Substitutions on CTLL-2 Cells

| Heterodimer name | STAT5 EC50 (nM) |
|---|---|
| 96.46 | 0.4 |
| 97.46 | 3.4 |
| 98.46 | 0.2 |
| 99.46 | 0.03 |
| 100.46 | 1.6 |
| 101.46 | 7.7 |
| 102.46 | 6.1 |
| 103.46 | 2.7 |
| 104.46 | 1.4 |
| 105.46 | 7.7 |
| 106.46 | 19.6 |
| 107.46 | 25.5 |
| 108.46 | 41.4 |
| 109.46 | 36.2 |
| 110.46 | 1.5 |
| 111.46 | 11.0 |
| 112.46 | 13.1 |
| 113.46 | 3.1 |
| 114.46 | 61.2 |
| 115.46 | 67.1 |
| 116.46 | 16.3 |
| 117.46 | 0.002 |
| Proleukin | 0.002 |

Example 10

In Vitro Potency of Fc-IL-2 Variant Fusion Proteins with Two or Three Amino Acid Substitutions in IL-2 at IL-2/IL-2Rα Binding Interface on CD8+ T Cells and Treg Cells In this Example, we Compared the Potency of 21 Fc-IL-2 Variant Fusion proteins with double or triple amino acid substitutions in IL-2 at the IL-2/IL-2Rα binding interface, heterodimerized with the Fc domain of SEQ ID NO:46. For this comparison, we evaluated the in vitro potency using a human peripheral blood mononuclear cell (PBMC) STAT5 activation assay. Methods are described in Example 5.

Results

Figure 6A:
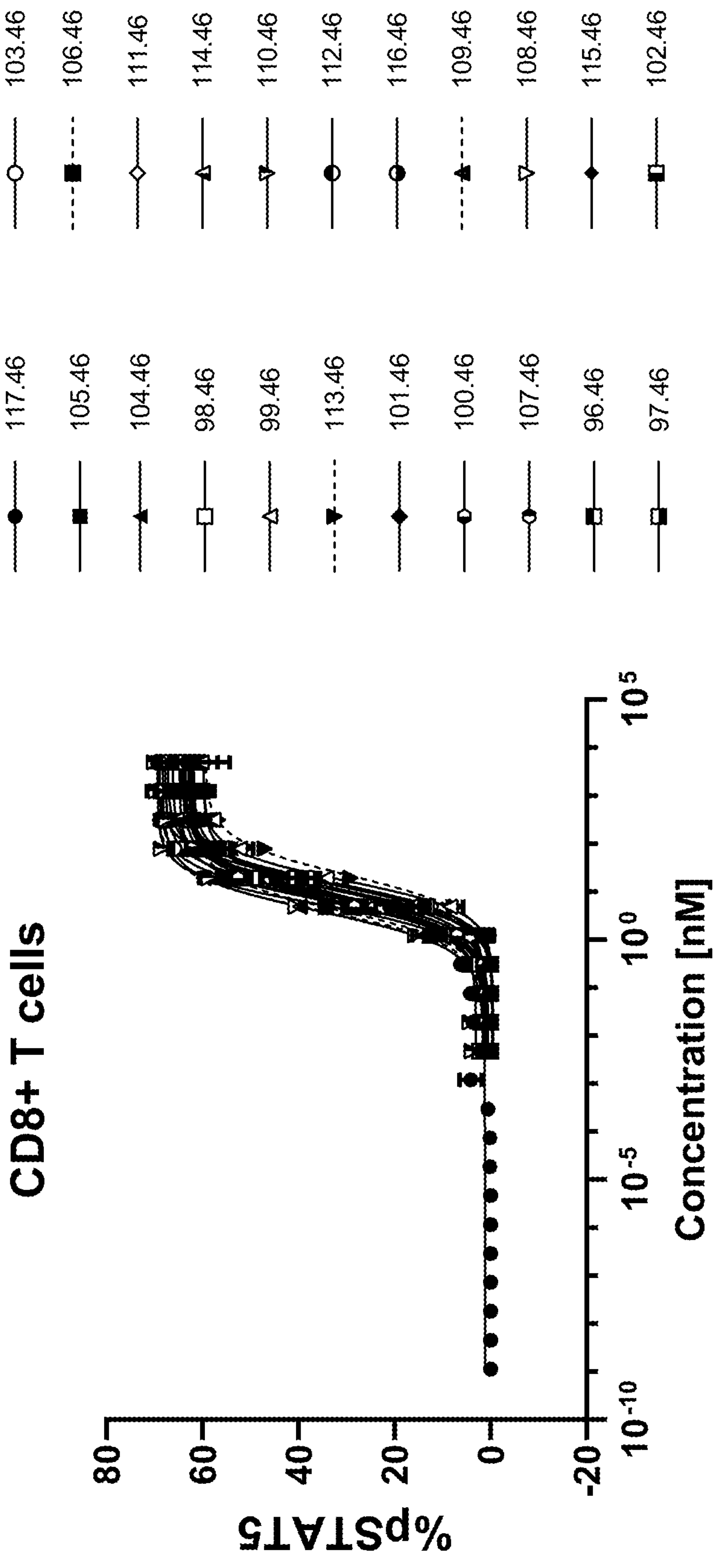
FIGS. 6A-6B illustrate in vitro potency of Fc-IL-2 variant fusion proteins with two or three amino acid substitutions in IL-2 at IL-2Rα binding interface on CD8+ T cell (FIG. 6A) and Treg (FIG. 6B) cell STAT5 activation.
Figure 6B:
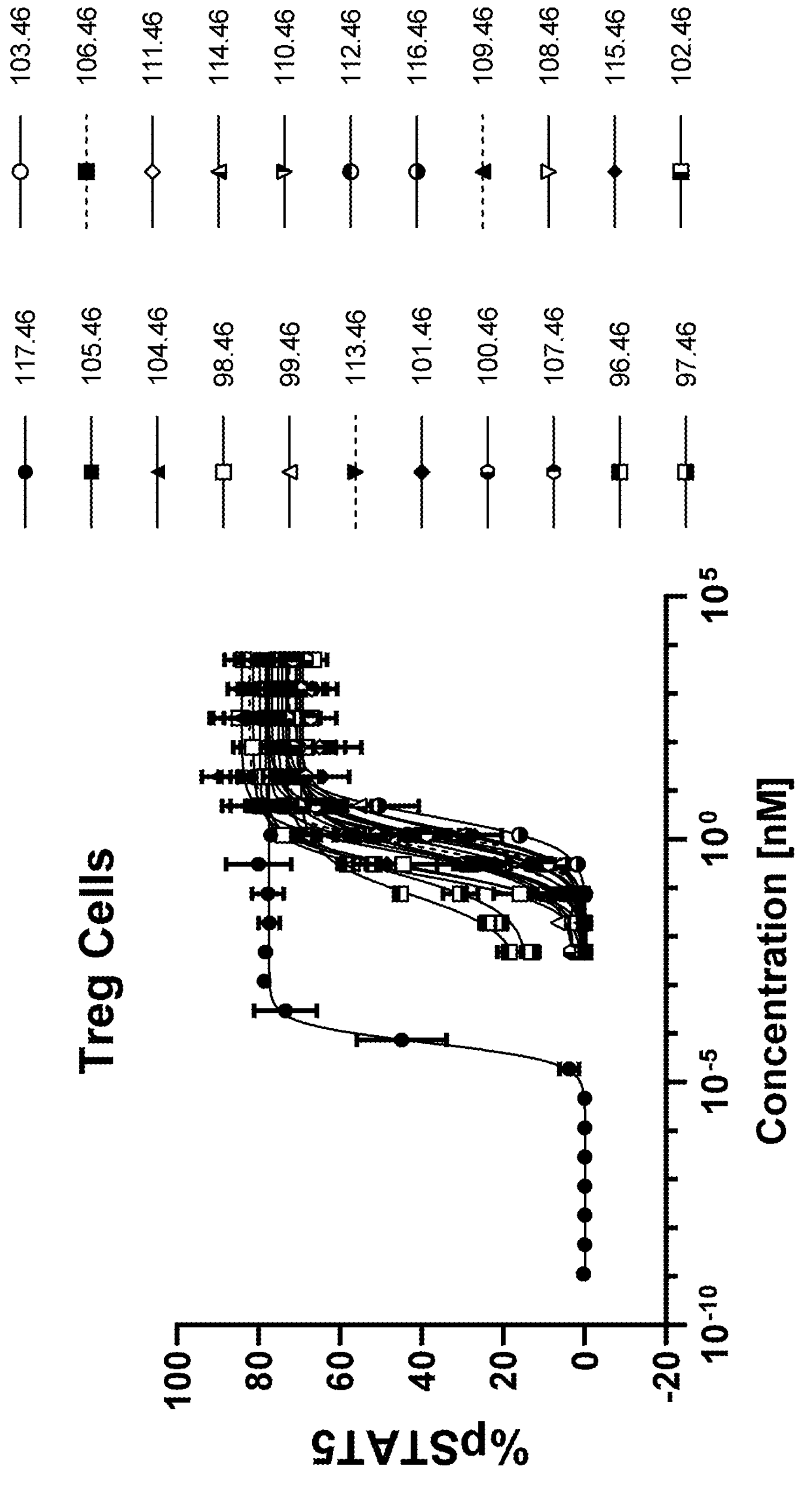

The data demonstrated a range of potencies for human Fc-IL-2 variant fusion proteins (SEQ ID NOs: 96-115), heterodimerized with the Fc domain of SEQ ID NO:46, for STAT5 activation of Treg cells with EC50 values from 0.090 to 4.2 nM. This is an approximately 90-fold to 4,200-fold decrease in STAT5 activation of Treg cells for all 21 Fc-IL-2 variant proteins with two or three substitutions as compared to an Fc-IL-2 fusion protein with a native IL-2Rα binding interface (SEQ ID NO: 117; EC50<0.001). Heterodimers 107.46, 108.46, 113.46, 114.46, 115.46 and 116.46 demonstrated the weakest overall potencies in this assay (EC50=1.6 to 4.2 nM). All 21 Fc-IL-2 variant fusion proteins demonstrated similar STAT5 activation of CD8+ T cells (EC50 values 4.7 to 20 nM) to an Fc-IL-2 fusion protein with a native IL-2Rα binding interface (SEQ ID NO: 117; EC50=8.0 nM). The mean values of two to ten biological replicates (n=2 to 10 human donor PBMCs) are summarized in Table 11 and FIG. 6 depicts mean data ±standard deviation of technical replicates from a representative human donor.

TABLE 11

EC50 Values for STAT5 Activation of Treg cells and CD8+ T cells by Fc-IL-2 Variants with Two or Three Amino Acid Substitutions in IL-2 at IL-2/IL-2Rα Binding Interface

| Heterodimer name | Treg EC50 (nM) | CD8$^+$ T cell EC50 (nM) |
|---|---|---|
| 96.46 | 0.09 | 6.2 |
| 97.46 | 0.2 | 6.2 |
| 98.46 | 0.2 | 7.9 |
| 99.46 | 0.3 | 10.6 |
| 100.46 | 0.4 | 6.7 |
| 101.46 | 0.5 | 7.2 |
| 102.46 | 0.8 | 7.9 |
| 103.46 | 0.6 | 15.5 |
| 104.46 | 0.7 | 7.4 |
| 105.46 | 1.2 | 9.8 |
| 106.46 | 0.9 | 4.7 |
| 107.46 | 1.6 | 10.8 |
| 108.46 | 2.6 | 8.0 |
| 109.46 | 1.0 | 6.6 |
| 110.46 | 1.1 | 5.7 |
| 111.46 | 1.1 | 7.9 |
| 112.46 | 1.1 | 6.8 |
| 113.46 | 4.2 | 16.4 |
| 114.46 | 3.0 | 10.7 |
| 115.46 | 1.8 | 12.7 |
| 116.46 | 3.2 | 20.0 |
| 117.46 | <0.001 | 8.0 |
| Proleukin | <0.001 | 0.71 |

Example 11

In Vitro Potency of Fc-IL-2 Variant Fusion Proteins with Two or Three Amino Acid Substitutions in IL-2 at IL-2/IL-2Rα Binding Interface on KHYG-1 NK Cells In this example, we evaluated the potencies of four Fc-IL-2 variant fusion proteins with two or three amino acid substitutions in IL-2 at the IL-2/IL-2Rα binding interface, heterodimerized with the Fc domain of SEQ ID NO:46. For this comparison, we evaluated in vitro potency by measuring proliferation of KHYG-1 NK cells. KHYG-1 is a natural killer (NK) leukemia cell line that expresses IL-2Rαβγ and is dependent on extracellular IL-2 for proliferation (Yagita, et al., *Leukemia* (2000) 14(5):922-30). Thus, IL-2 activity via signaling through the IL-2Rαβγreceptor can be assessed in KHYG-1 cells by measuring their IL-2-mediated proliferation.

Methods

Figure 7:
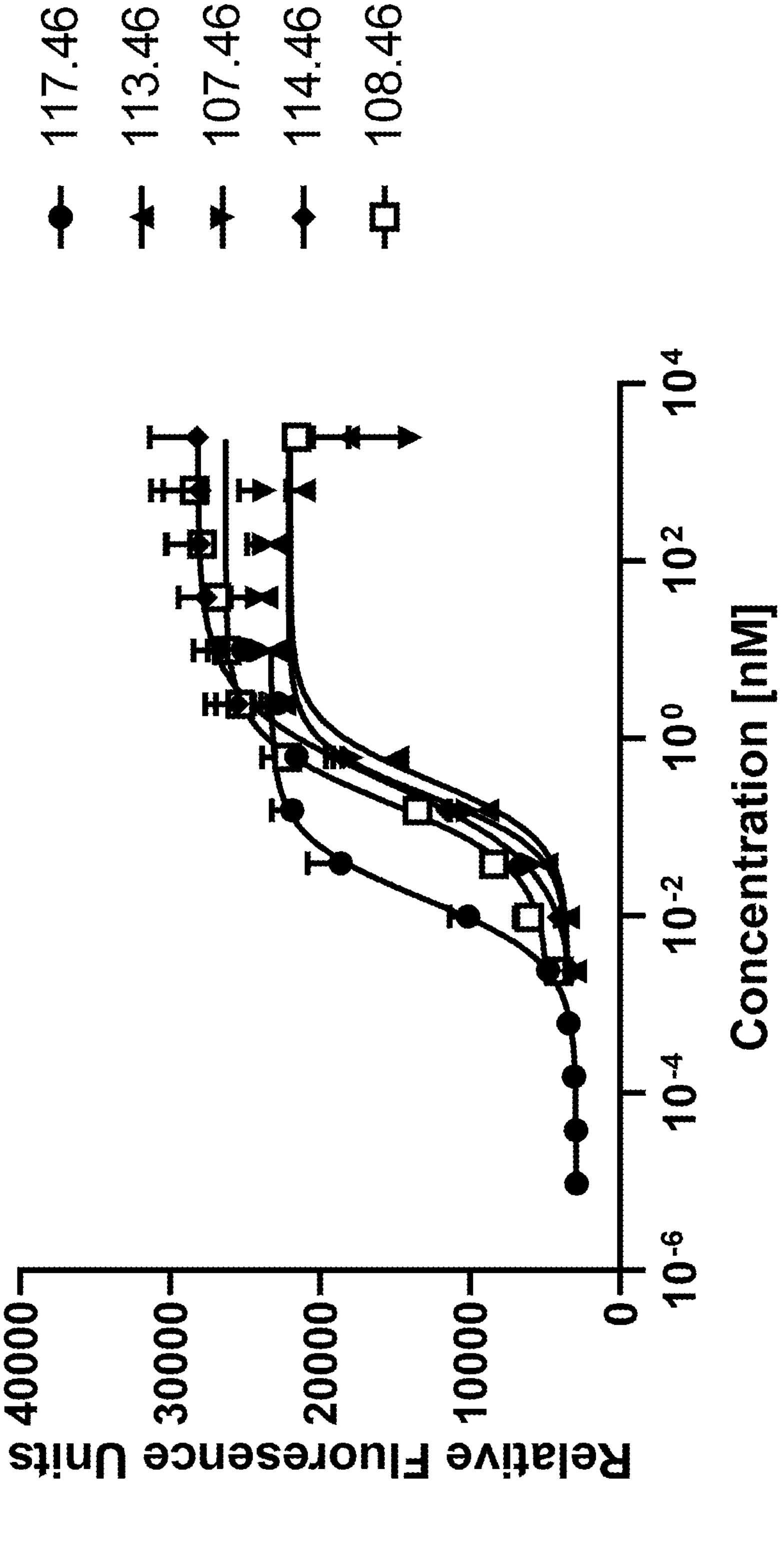
FIG. 7 illustrates in vitro potency of Fc-IL-2 variant fusion proteins with two or three amino acid substitutions in IL-2 at IL-2Rα binding interface on KHYG-1 NK cells.

The human NK leukemia cell line (KHYG-1) that expresses IL-2Rα, β, and γ was cultured in tissue culture medium (RPMI-1640, 10% FBS) supplemented with IL-2 necessary for growth. To assess Fc-IL-2 variant potency, KHYG-1 cells were washed twice in IL-2 free medium and seeded in a black 96 well tissue culture treated plate (Corning #3603) at a density of 15,000 cells per well in complete medium without IL-2. KHYG-1 cells were treated with Fc-IL-2 fusion protein variants for 48 hours at 37° C. To measure proliferation, alamarBlue was added to the cells at a 10% final concentration and incubated for 3 hours at 37° C. After incubation, fluorescence was measure using a SpectroMax reader (Molecular Devices). Data in Table 12 represent mean values of two replicates and data in FIG. 7 represent mean values of two replicates ±standard deviation.

Results

The data demonstrated a similar range of potency for human Fc-IL-2 variant fusion proteins (SEQ ID NOs: 107, 108, 113 and 114), heterodimerized with the Fc domain of SEQ ID NO:46, for KHYG-1 proliferation with EC50 values from 0.191 to 0.344 nM. This is an approximately 12-fold to 22-fold decrease in proliferation compared to an Fc-IL-2 fusion protein with a native IL-2Rα interface (SEQ ID NO: 117; EC50=0.016 nM). The results are summarized in Table 12 and depicted in FIG. 7.

TABLE 12

EC50 Values for Proliferation of KHYG-1 NK Cells by Fc-IL-2 Variants with Two or Three Amino Acid Substitutions in IL-2 at IL-2/IL-2Rα Binding Interface

| Heterodimer name | EC50 (nM) |
|---|---|
| 107.46 | 0.235 |
| 108.46 | 0.191 |
| 113.46 | 0.344 |
| 114.46 | 0.336 |
| 117.46 | 0.016 |

Example 12

In Vitro Potency of Fc-IL-2 Variant Fusion Proteins with Two or Three Amino Acid Substitutions in IL-2 at IL-2/IL-2Rα Binding Interface on CD8+ T Cell and NK Cell Proliferation In this example, we evaluated the potencies of five Fc-IL-2 variant fusion proteins with double or triple amino acid substitutions in IL-2 at the IL-2/IL-2Rα binding interface, heterodimerized with the Fc domain of SEQ ID NO:46. For this comparison, we evaluated the in vitro potency using a human peripheral blood mononuclear cell (PBMC) proliferation assay.

Methods

Cryopreserved human peripheral blood mononuclear cells (PBMC) isolated from multiple donors (Cellular Technology Limited) were thawed and washed twice with culture medium (RPMI-1640, 10% heat-inactivated FBS, 1× Pen/Strep, 1×HEPES) to remove DMSO. After resting the cells overnight at 37° C. in culture medium, the PBMCs were plated in a 96 well round bottom plate (Corning #9018) at a density of 250,000 cells per well and treated with increasing concentrations of Fc-IL-2 variant proteins for 5 days. On the fifth day, the cells were washed twice with PBS and incubated with viability dye (Molecular Probes #L34966) for 30 minutes. The cells were then washed with FACS buffer (1% FBS in PBS) and stained with a panel of flow cytometry antibodies against CD3, CD8, CD16, and CD56 for 40 minutes at room temperature to define CD8+ T cells as CD3+ CD8+ and NK cells as CD3−, CD16+, CD56+. After surface staining, the cells were fixed (BD #554722) for 20 minutes followed by intracellular staining with Ki67 antibody for 1 hour in the presence of permeabilization buffer (BD #554723). The cells were washed twice in FACS buffer and analyzed using an LSR Fortessa X-20 (BD Biosciences) for Ki67 proliferation staining in various lymphocyte subpopulations.

Results

Figure 8A:
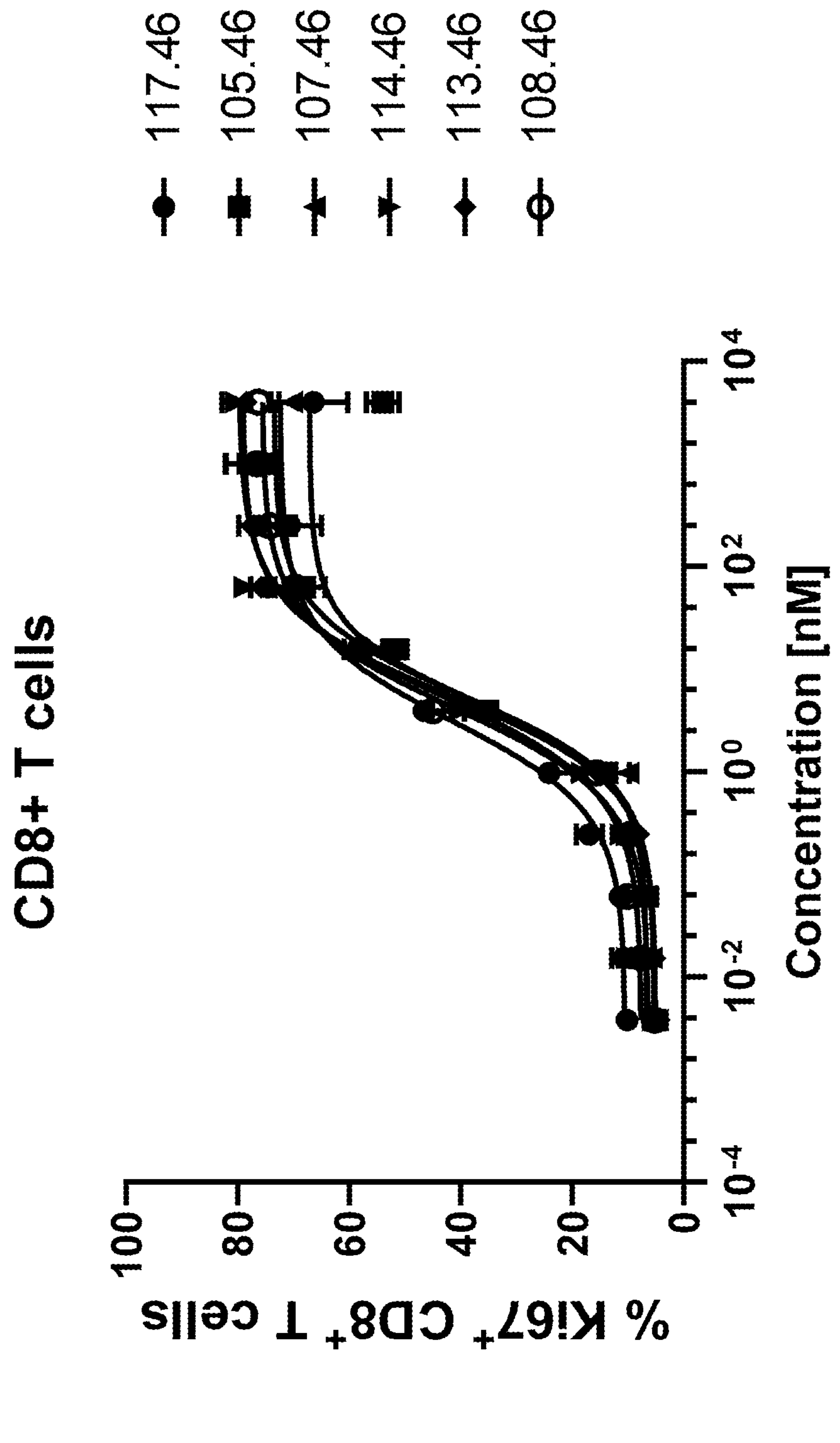
FIGS. 8A-8B illustrate in vitro potency of Fc-IL-2 variant fusion proteins with two or three amino acid substitutions in IL-2 at IL-2Rα binding interface on CD8+ T cell (FIG. 8A) and NK cell (FIG. 8B) proliferation.
Figure 8B:
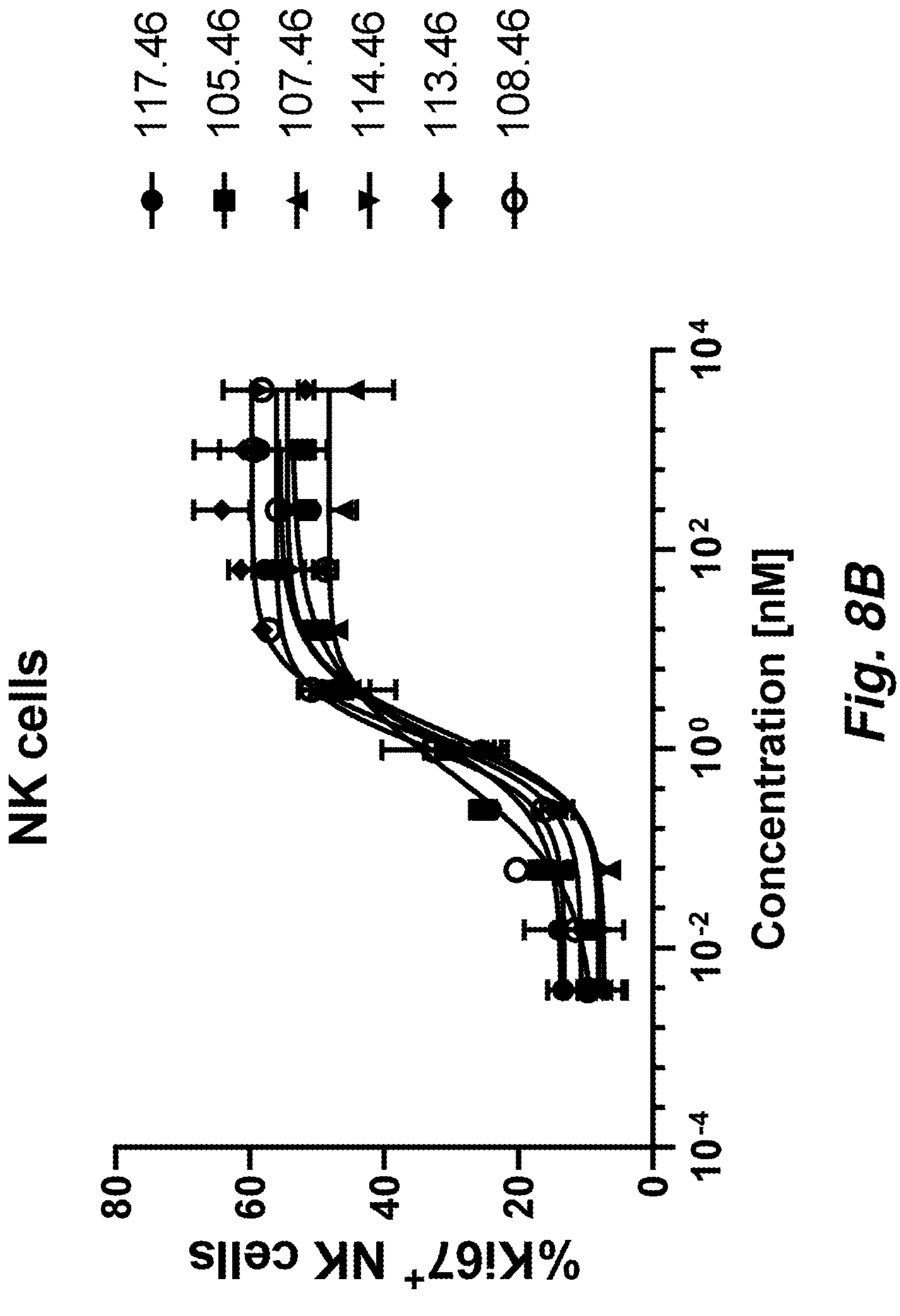

The data demonstrated that Fc-IL-2 variant fusion proteins with two or three amino acid substitutions in IL-2 (SEQ ID NOs: 105, 107, 108 and 114), heterodimerized with the Fc domain of SEQ ID NO:46, result in similar proliferation of CD8+ T cells (EC50 values 7.2 to 10.5 nM) and NK cells (EC50 values 0.9 to 1.8 nM) as compared to an Fc-IL-2 fusion protein with a native IL-2Rα binding interface (SEQ ID NO: 117; CD8+ EC50=9.5 nM; NK cell EC50=0.9 nM). The mean value of seven to nine biological replicates (n=7 to 9 human donor PBMCs) are summarized in Table 13 and FIG. 8 depicts mean data ±standard deviation of technical replicates from a representative donor.

TABLE 13

EC50 Values for Proliferation of CD8+ T cells and NK cells by Fc-IL-2 Variants with Two or Three Amino Acid Substitutions in IL-2 at IL-2/IL-2Rα Binding Interface

| Heterodimer name | $CD8^+$ T cell EC50 (nM) | NK cell EC50 (nM) |
|---|---|---|
| 105.46 | 9.7 | 0.9 |
| 107.46 | 9.5 | 1.0 |
| 108.46 | 7.2 | 1.8 |
| 113.46 | 10.5 | 1.1 |
| 114.46 | 10.4 | 1.5 |
| 117.46 | 9.5 | 0.9 |

Example 13

In Vitro Potency of Fc-IL-2 Variant Fusion Proteins on Cynomolgus Macaque CD8+ T Cells and Treg Cells In this example, we determined the in vitro potencies of four Fc-IL-2 variant fusion proteins, heterodimerized with the Fc domain of SEQ ID NO:46, on cynomolgus macaque cells. For this comparison, we evaluated STAT5 activation of cynomolgus macaque peripheral blood mononuclear cells (PBMC).

Methods

Figure 9A:
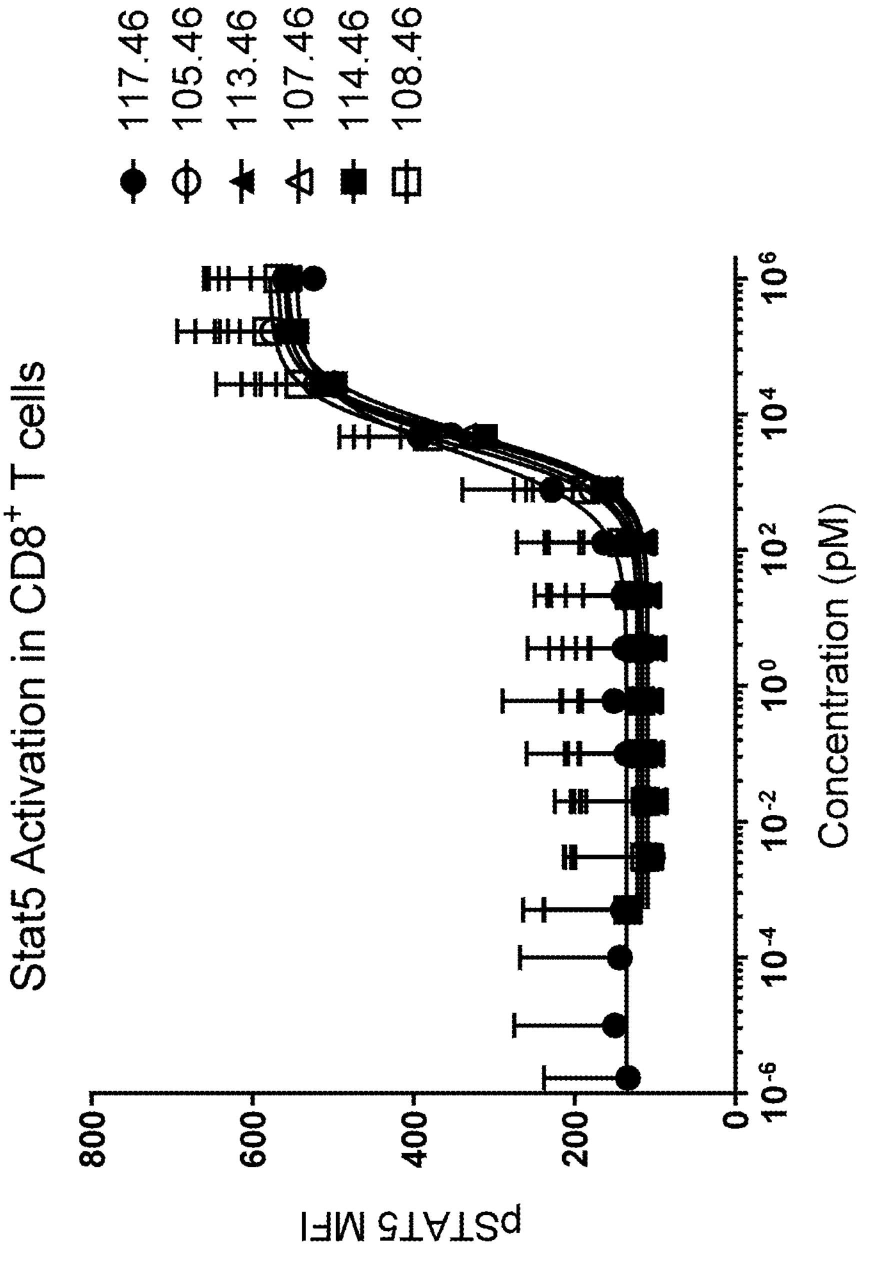
FIGS. 9A-9B illustrate in vitro potency of Fc-IL-2 variant fusion proteins on cynomolgus macaque CD8+ T cell (FIG. 9A) and Treg cell (FIG. 9B) STAT5 activation.
Figure 9B:
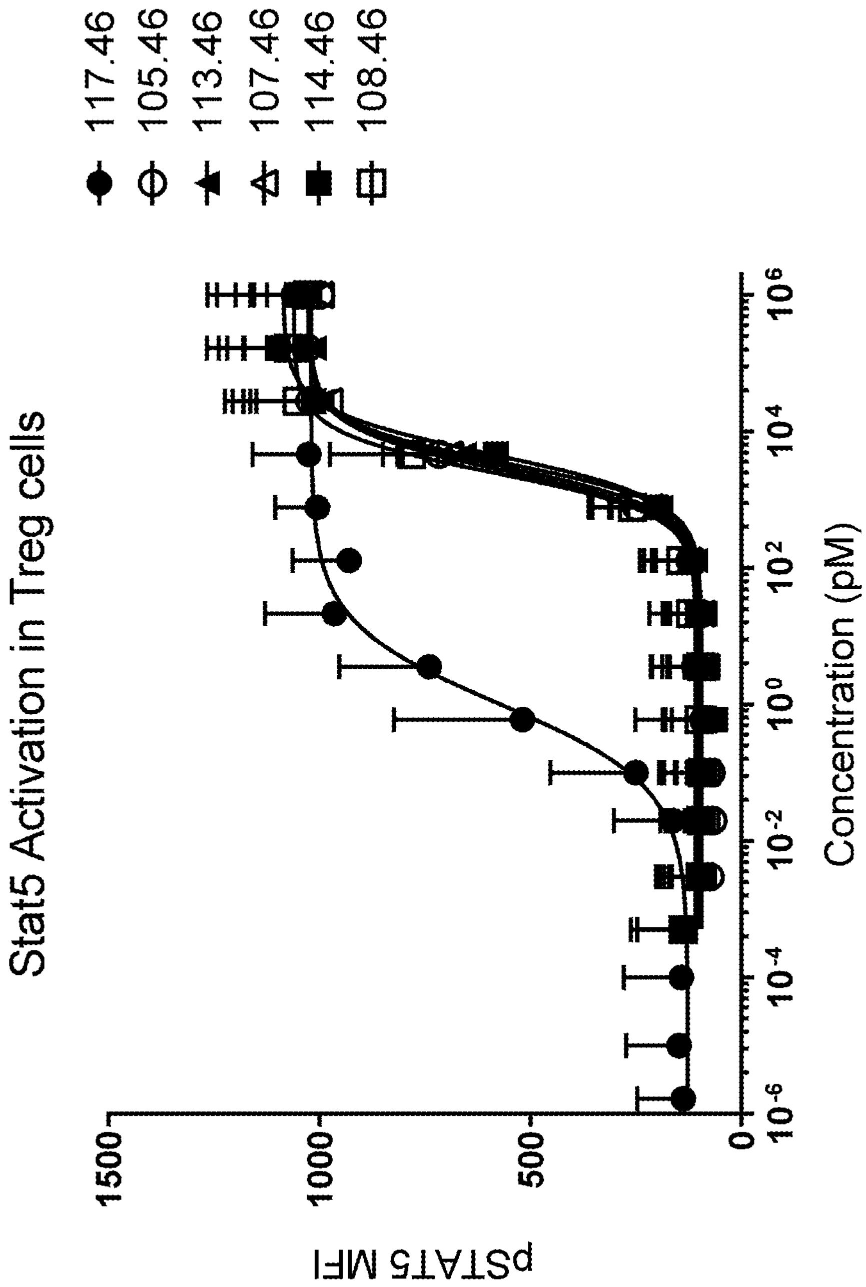

PBMC STAT5 Assay: Cryopreserved cynomolgus macaque PBMCs isolated from multiple animals (BioIVT) were thawed and washed twice with culture medium (RPMI-1640, 10% HI FBS, 1×PS, 1×NEAA, 25 mM HEPES) to remove DMSO. PBMCs were plated in a 96 well round bottom plate (Corning #9018) at a density of 250,000 cells in culture medium per well. Following a resting period of 30 minutes at 37° C., the PBMCs were treated with serially diluted Fc-IL-2 variant fusion proteins for 30 minutes. After incubation, cells were fixed with pre-warmed Phosflow Fix Buffer I (Becton Dickinson #557870) for 20 minutes at room temperature. Cells were washed twice and permeabilized with pre-chilled Phosflow Perm Buffer III (Becton Dickinson #558050) for 30 minutes on ice followed by incubation with a panel of antibodies against CD3, CD4, CD8, CD25, FoxP3, and phosphorylated STAT5 (pSTAT5) for 60 minutes to define CD8+ T cells as CD3+, CD8+ and Teg cells as CD3+, CD4+, CD25hi, FoxP3+. The cells were then washed twice in FACS buffer and analyzed using an LSR Fortessa X-20 (BD Biosciences) for STAT5 activation (i.e., phosphorylation of STAT5) in PBMC subpopulations. Geometric mean fluorescence intensity (MFI) of pSTAT5 was used to determine the EC50 values of Fc-IL-2 fusion variants. Data in Table 14 and FIG. 9 represent mean EC50 values from seven cynomolgus macaques. Error bars in FIG. 9 represent mean standard error.

Results

The data demonstrated similar potencies of human Fc-IL-2 variant fusion proteins (SEQ ID NOs: 107, 108, 113 and 114), heterodimerized with the Fc domain of SEQ ID NO:46, for STAT5 activation of cynomolgus monkey Treg cells with EC50 values ranging from 2.7 to 4.8 nM. This is a 1350-fold to 2400-fold decrease in STAT5 activation of Treg cells for all four Fc-IL-2 variant proteins as compared to an Fc-IL-2 fusion proteins with a native IL-2Rα binding interface (SEQ ID NO: 117; EC50=0.002 nM). All four Fc-IL-2 variant fusion proteins demonstrated comparable STAT5 activation of CD8+ T cells (EC50 values: 3.9 nM to 5.9 nM) to an Fc-IL-2 fusion protein with a native IL-2Rα binding interface (SEQ ID NO: 117; EC50=2.9 nM). The results are summarized in Table 14 and depicted in FIG. 9.

TABLE 14

EC50 Values for STAT5 Activation of Cynomolgus Macaque Treg cells and CD8+ T cells by Fc-IL-2 Variant Proteins

| Heterodimer name | Treg EC50 (nM) | CD8+ T cell EC50 (nM) |
|---|---|---|
| 107.46 | 4.3 | 4.9 |
| 108.46 | 4.8 | 5.9 |
| 113.46 | 3.7 | 5.4 |
| 114.46 | 2.8 | 3.9 |
| 117.46 | 0.002 | 2.9 |

Example 14

Design, Expression and Purification of Mouse Surrogate IL-2 Variants as Fc Fusion Proteins To facilitate the in vivo study of Fc-IL-2 variant fusion proteins in mice, a series of surrogate molecules were designed with the same architecture as described in Example 2, but where the component IL-2 and Fc sequences were of mouse rather than human origin. Accordingly, all surrogate Fc-IL-2 variant fusion proteins contained a modified “knob-in-hole” murine IgG2a Fc heterodimer with F234A/L235A/P329G substitutions (EU numbering) in both chains to eliminate effector function as previously described (Lo et. al., J. Biol. Chem., 292, 3900-3908, 2017), and murine IL-2 variants fused to the “knob” containing Fc arm. These Fc modifications were combined with changes in the IL-2 region to enhance manufacturability, namely, substitution of Cys140 with Ser to prevent unwanted aggregation or modification that might otherwise occur at this unpaired Cys residue, and deletion of the first 23 residues of the mature native IL-2 sequence to eliminate an unstructured, polyGln-containing N-terminal insertion that exists in murine IL-2. As with the human sequence molecules, a flexible linker containing 4 repeats of the Gly-Gly-Gly-Gly-Ser motif tethered the IL-2 to its Fc fusion partner. Surrogate molecules were designed with one or more substitutions in the IL-2Rα binding interface corresponding to R38G, F42A, Y45G, E62A and L72G in human IL-2, which mapped to R52G, F56A, Y59G, E76A and L86G in the murine IL-2 sequence. Illustrative mouse surrogate Fc-IL-2v heterodimers are provided as Fc-IL-2v fusion proteins of one of SEQ ID NOs: 165-171 heterodimerized with an Fc domain of SEQ ID NO:250 (summarized in Table 15).

TABLE 15

Illustrative Mouse Surrogate Fc-IL-2 Variant Fusion Protein Heterodimers

| Heterodimer name | Features |
|---|---|
| 165.250 | IL2v_C140A |
| 166.250 | IL2v_F56A_Y59A_L86G_C140A |
| 167.250 | IL2v_F56A_C140A |
| 168.250 | IL2v_F56A_E76A_C140A |
| 169.250 | IL2v_F56A_Y59G_E76A_C140A |
| 170.250 | IL2v_R52G_E76A_C140A |
| 171.250 | IL2v_R52G_F56A_E76A_C140A |

Expression and Purification Methods

Recombinant expression of surrogate molecules followed the same procedure described previously in Example 3 for human sequence molecules. Purification and final quantitation of surrogate molecules also followed the same procedures previously described for human sequence molecules, except that elution from the Q-HP anion-exchange column required a gradient rising to 300 mM NaCl, and a final preparative size exclusion chromatography (SEC) step was added to remove remaining aggregation and homodimer contaminants present in the anion exchange pool. This polishing step was conducted by injection of the anion exchange pool material onto a Superdex 200 Prep Grade 16/600 preparative SEC column (Cytiva) pre-equilibrated with a 20 mM HEPES, 150 mM NaCl, pH 7.5 mobile phase. Since the mobile phase was the same as the final formulation buffer, no dialysis was necessary.

Results

A total of seven mouse Fc-IL-2 variant fusion proteins containing modifications to the mouse IL-2 sequence were expressed and purified (Table 16). The fully purified yields for the seven mouse Fc-IL-2 variant proteins ranged from 6 to 28 mg per liter of expression culture, with final purity levels at or above 97%.

TABLE 16

Yields and Purity for Murine Surrogate Fc-IL-2 Variant Fusion Protein Heterodimers

| Heterodimer name | IL-2Rα Interface Mutations | Purified yield (mg/L) | Purity (%) |
|---|---|---|---|
| 165.250 | none | 9 | 99 |
| 166.250 | F56A/Y59A/L86G | 6 | 97 |
| 167.250 | F56A | 28 | 98 |
| 168.250 | F56A/E76A | 8 | 98 |
| 169.250 | F56A/Y59G/E76A | 6 | 98 |
| 170.250 | R52G/E76A | 9 | 100 |
| 171.250 | R52G/F56A/E76A | 8 | 97 |

Example 15

In Vitro Potency of Murine Surrogate Fc-IL-2 Variant Fusion Proteins on CTLL-2 Cells In this example, we evaluated the potencies of six mouse surrogate Fc-IL-2 fusion protein variants with different amino acid substitutions in IL-2 at the IL-2/IL-2Rα binding interface, heterodimerized with the Fc domain of SEQ ID NO:250. For this comparison, we tested the in vitro potency using a CTLL-2 STAT5 reporter cell line. Methods are as described in Example 4.

Results

Figure 10:
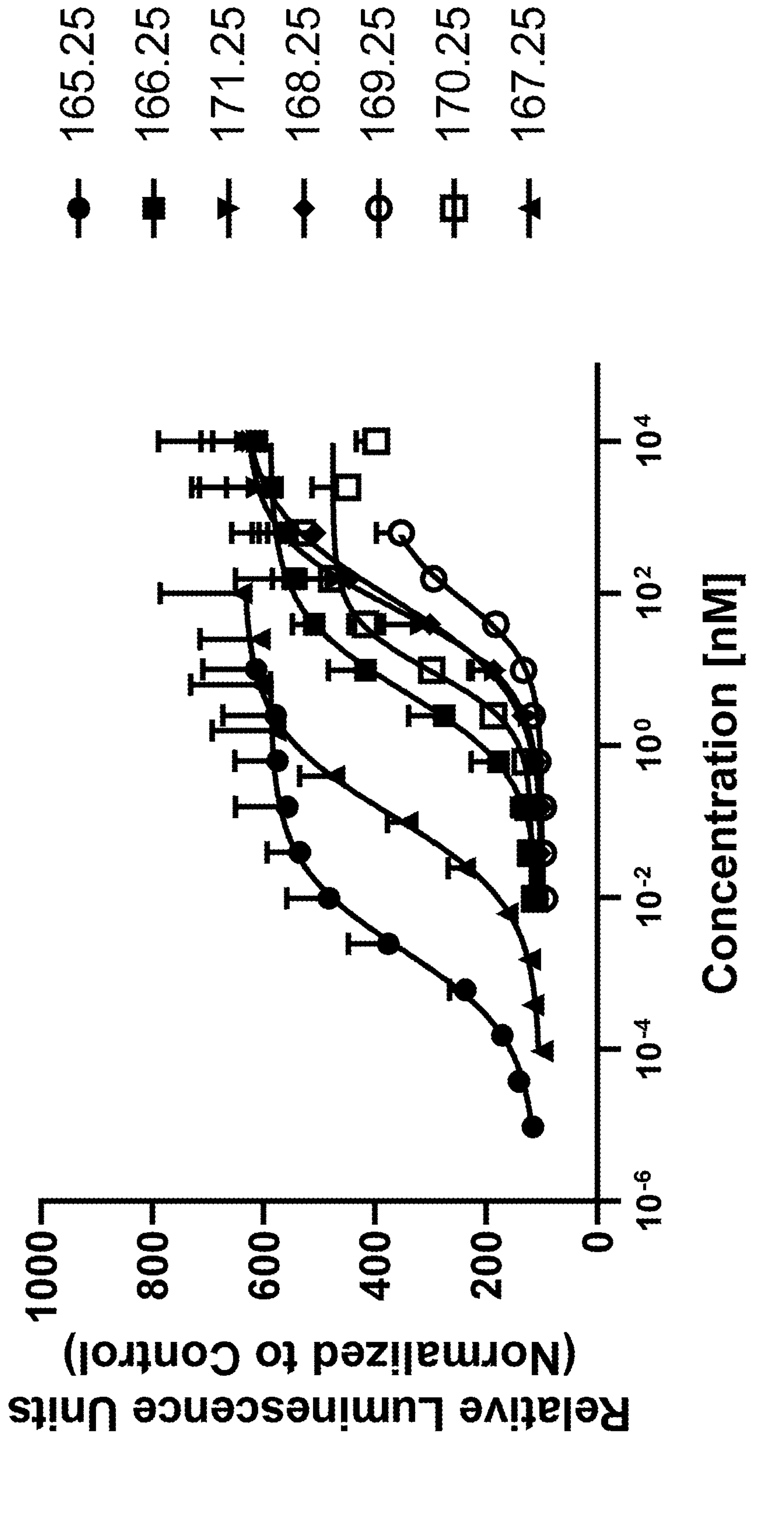
FIG. 10 illustrates in vitro potency of mouse surrogate Fc-IL-2 variant fusion proteins on CTLL-2 cells.

The data demonstrated a range of potencies for mouse surrogate Fc-IL-2 variant fusion proteins (SEQ ID NOs: 166-171), heterodimerized with the Fc domain of SEQ ID NO:250, for STAT5 activation in CTLL-2 cells expressing the trimeric IL-2 receptor (IL-2Rα, IL-2Rβ, and IL-2Rγ) with EC50 values from 0.12 to 88.7 nM. Mouse surrogate proteins demonstrated approximately 60-fold to 44,000-fold decreases in STAT5 activation of CTLL-2 cells compared to Fc-IL-2 fusion proteins with a native IL-2Rα binding interface (SEQ ID NO: 165; EC50=0.002). The results are summarized in Table 17 and represent average values of two to four replicates. The results are depicted in FIG. 10 where data represents average values of two to four replicates f standard deviation.

TABLE 17

EC50 Values for STAT5 Activation of CTLL-2 Cells by Mouse Surrogate Fc-IL-2 Variants

| Heterodimer name | pSTAT5 EC50 (nM) |
|---|---|
| 165.250 | 0.002 |
| 166.250 | 5.4 |
| 167.250 | 0.120 |
| 168.250 | 63.1 |
| 169.250 | 51.4 |
| 170.250 | 9.6 |
| 171.250 | 88.7 |

Example 16

In Vitro Potency of Murine Surrogate Fc-IL-2 Variant Fusion Proteins on Ba/F3 Cells Expressing IL-2Rβ/γ

In this example, we evaluated the potencies of four mouse surrogate Fc-IL-2 variant fusion proteins with amino acid substitutions in IL-2 at the IL-2/IL-2Rα binding interface, heterodimerized with the Fc domain of SEQ ID NO:250. For this comparison, we tested the in vitro potency by evaluating proliferation of Ba/F3 cells.

Methods

Figure 11:
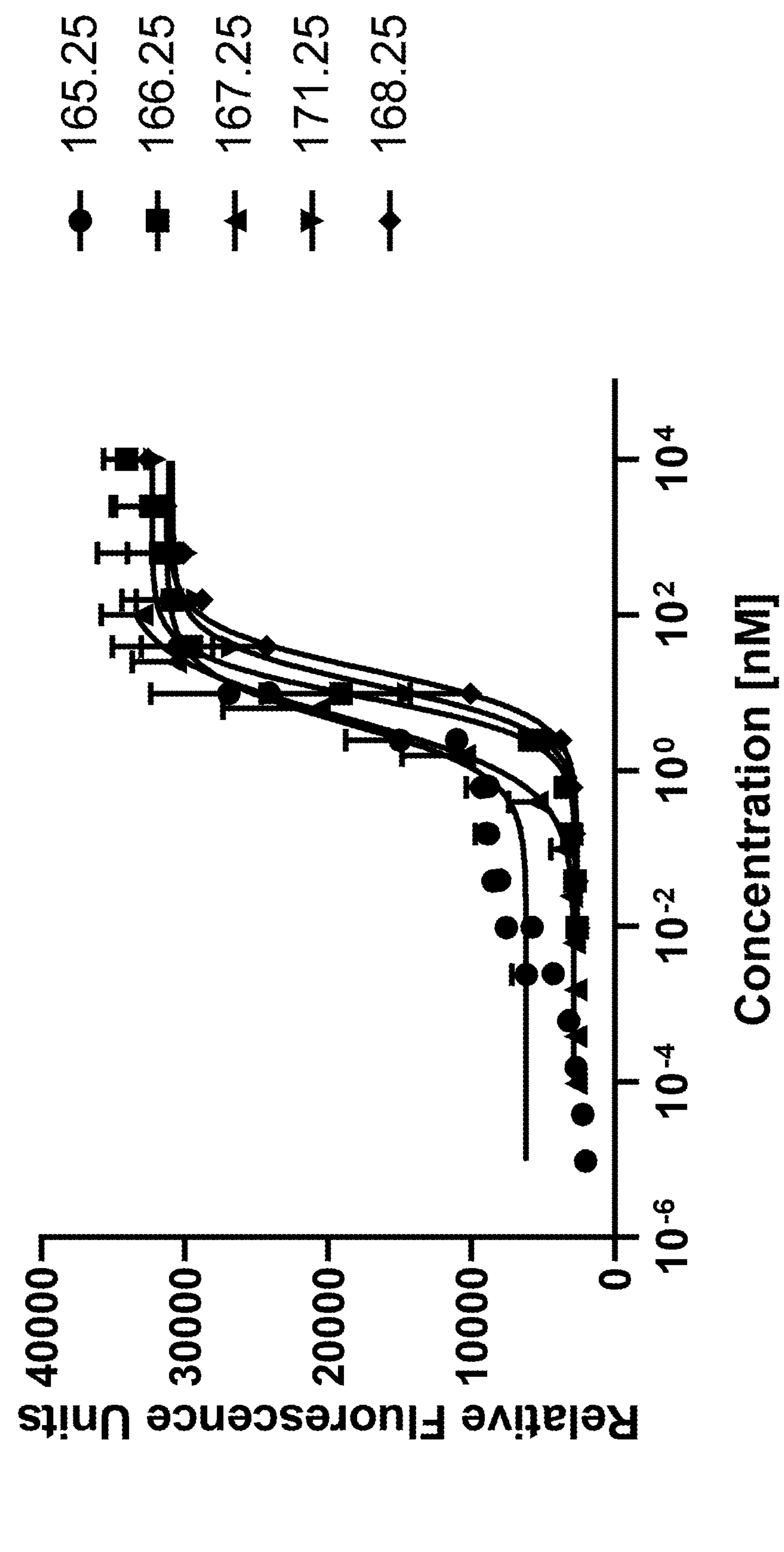
FIG. 11 illustrates in vitro potency of mouse surrogate Fc-IL-2 variant fusion proteins on Ba/F3 cells.

Ba/F3 cells were engineered to express murine IL-2Rβ and cultured in tissue culture medium (RPMI-1640, 10% heat-inactivated FBS, and 1 μg/ml puromycin, 10 ng/mL IL-3). To assess Fc IL-2 variant fusion protein potency, Ba/F3 cells were washed twice in IL-3 free medium and seeded in a black 96 well tissue culture treated plate (Corning #3603) at a density of 15,000 cells per well in complete medium without IL-3. Ba/F3 cells were treated with increasing concentrations of Fc-IL-2 variant fusion proteins for 48 hours at 37° C. To measure proliferation, alamarBlue was added to the cells at 10% final concentration and incubated for 3 hours at 37° C. After incubation, fluorescence was measure using SpectroMax reader (Molecular Devices). The results are summarized in Table 18 and represent average values of three replicates and depicted in FIG. 11 where data represents average values of three replicates ±standard deviation.

Results

Mouse surrogate Fc-IL-2 variant fusion proteins (SEQ ID NOs: 166, 167, 168 and 171), heterodimerized with the Fc domain of SEQ ID NO:250, demonstrated similar potencies in Ba/F3 cells expressing IL-2Rβ and IL-2Rγ with EC50 values for cell proliferation of 5.2 to 20.6 nM. These values were similar to proliferation by a mouse Fc-IL-2 fusion protein with a native IL-2 sequence at the IL-2Rα binding interface (SEQ ID NO: 165; EC50=4.1 nM). The results are summarized in Table 18 and depicted in FIG. 11.

TABLE 18

EC50 Values for Proliferation of Ba/F3 Cells by Mouse Surrogate Fc-IL-2 Variants

| Heterodimer name | Proliferation EC50 (nM) |
|---|---|
| 165.250 | 4.1 |
| 166.250 | 9.5 |
| 167.250 | 5.2 |
| 168.250 | 20.6 |
| 171.250 | 13.0 |

Example 17

Single Dose Pharmacokinetics of Fc-IL-2 Variants after IV Administration in Cynomolgus Monkeys In this example, we compared the single dose pharmacokinetics (PK) of four different human Fc-IL-2 variant fusion proteins in cynomolgus macaques.

Methods

Four Fc-IL-2 variant heterodimers (107.46, 108.46, 113.46 and 114.46) were administered to cynomolgus macaques n=3/group (Covance, WI) at 0.1 mg/kg via a single intravenous (IV) bolus infusion to characterize their basic PK profiles. Serial plasma samples collected from monkeys were analyzed using a selective bioanalytical method of sufficient sensitivity to determine serum concentration-time profiles and mean serum PK parameters by non-compartmental analysis (NCA). The bioanalytical method utilized an anti-human IL-2 antibody (R&D, MN) as a capture reagent and biotin conjugated goat anti-human IgG antibody (Southern Biotech, AL) as a secondary reagent, with SULFO-TAG™ labeled Streptavidin (MesoScale Discovery, MD) for electrochemiluminescence (ECL) detection on a Mesoscale Discovery Quickplex SQ 120 plate reader. The calibration curve used the respective individual Fc-IL-2 variant fusion proteins as reference standards in spiked macaque matrix fit to a 4-parameter logistic model with 1/Y2 weighting. Analyte concentrations were determined from the ECL signals back-fitted to the calibration curve. Plasma concentration-time profiles were used to calculate the mean±standard deviation serum PK parameters by NCA.

Results

Figure 12:
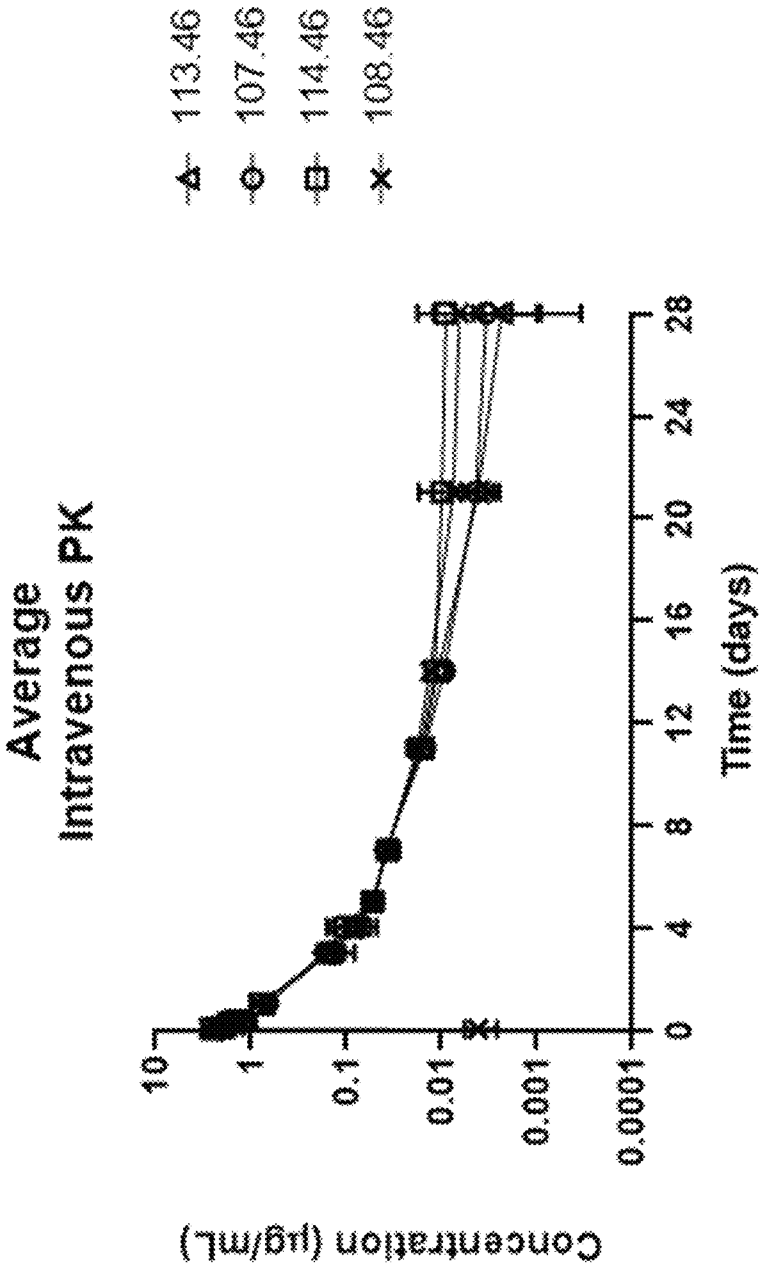
FIG. 12 illustrates single dose pharmacokinetic (PK) curves for Fc-IL-2v heterodimers 107.46 (circle), 108.46 (X), 113.46 (triangle) and 114.46 (square) in cynomolgus macaques.

PK analysis demonstrated that all four Fc-IL-2 variant fusion proteins had IgG-like PK with clearance (Cl) values ranging from 31.16 to 41.17 mL/d/kg following IV administration in cynomolgus macaques. Fc-IL-2v heterodimers 114.46 and 108.46 containing the R38G/F42A/E62A and F42A/Y45G/E62A modifications, respectively, had reduced Cl relative to Fc-IL-2v heterodimers 113.46 and 107.46, that have R38G/E62A or F42A/E62A, modifications respectively. Thus, Fc-IL-2v heterodimers containing three mutations at the IL-2/IL-2Rα interface had improved Cl compared to Fc-IL-2v heterodimers containing two mutations at the IL-2/IL-2Rα interface. The results are summarized in Table 19 and depicted in FIG. 12.

TABLE 19

Single Dose PK Values for Fc-IL-2v Heterodimers in Cynomolgus Macaques

| Heterodimer name | $AUC_{0\text{-}last}$ (µg*d/mL) | Cl (mL/d/kg) |
|---|---|---|
| 113.46 | 2.86 ± 0.22 | 34.04 ± 3.14 |
| 107.46 | 2.48 ± 15.6 | 41.17 ± 7.76 |
| 114.46 | 2.82 ± 0.42 | 32.89 ± 4.76 |
| 108.46 | 3.03 ± 0.67 | 31.16 ± 8.00 |

AUC0-last = Area under the curve from time zero to time at last measurable concentration

Example 18

Repeat Dose Pharmacokinetics of Fc-IL-2 Variants after Subcutaneous Administration in Cynomolgus Monkeys In this example, we compared the repeat dose PK of two recombinant human Fc-IL-2 variant fusion proteins in cynomolgus macaques.

Methods

Recombinant human Fc-IL-2v heterodimers 107.46 and 114.46) were administered to cynomolgus macaques n=4/group (Covance, WI) at 30, 100 and 300 µg/kg via three repeat subcutaneous administration to characterize the basic PK profiles. Serial plasma samples collected from macaques were analyzed using a bioanalytical method which utilized anti-human IL-2 antibody (R&D, MN) as a capture reagent and biotin conjugated goat anti-human IgG antibody (Southern Biotech, AL) as a secondary reagent, with SULFO-TAG™ labeled Streptavidin (MesoScale Discovery, MD) for electrochemical detection on a Mesoscale Discovery Quickplex SQ 120 plate reader. The calibration curve used the respective individual Fc-IL-2 variant fusion proteins as reference standards in spiked macaque matrix fit to a 4-parameter logistic model with 1/Y2 weighting. Analyte concentrations were determined from the ECL signals back-fitted to the calibration curve. Analyte concentrations were determined from the ECL signals back-fitted to the calibration curve. Plasma concentration-time profiles were used to calculate the mean±standard deviation plasma PK parameters by NCA.

Results

Figure 13A:
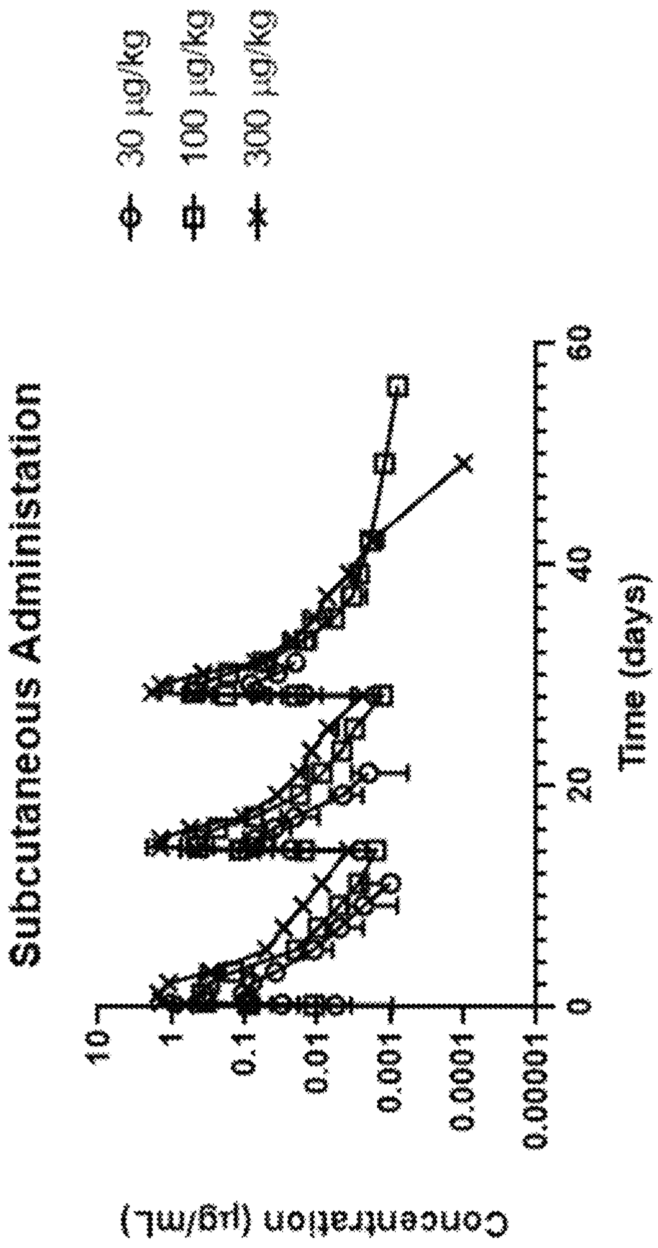
FIGS. 13A-13B illustrate repeat dose PK Values for Fc-IL-2v heterodimers 107.46 (FIG. 13A) and 114.46 (FIG. 13B) following repeat subcutaneous administrations to cynomolgus macaques.
Figure 13B:
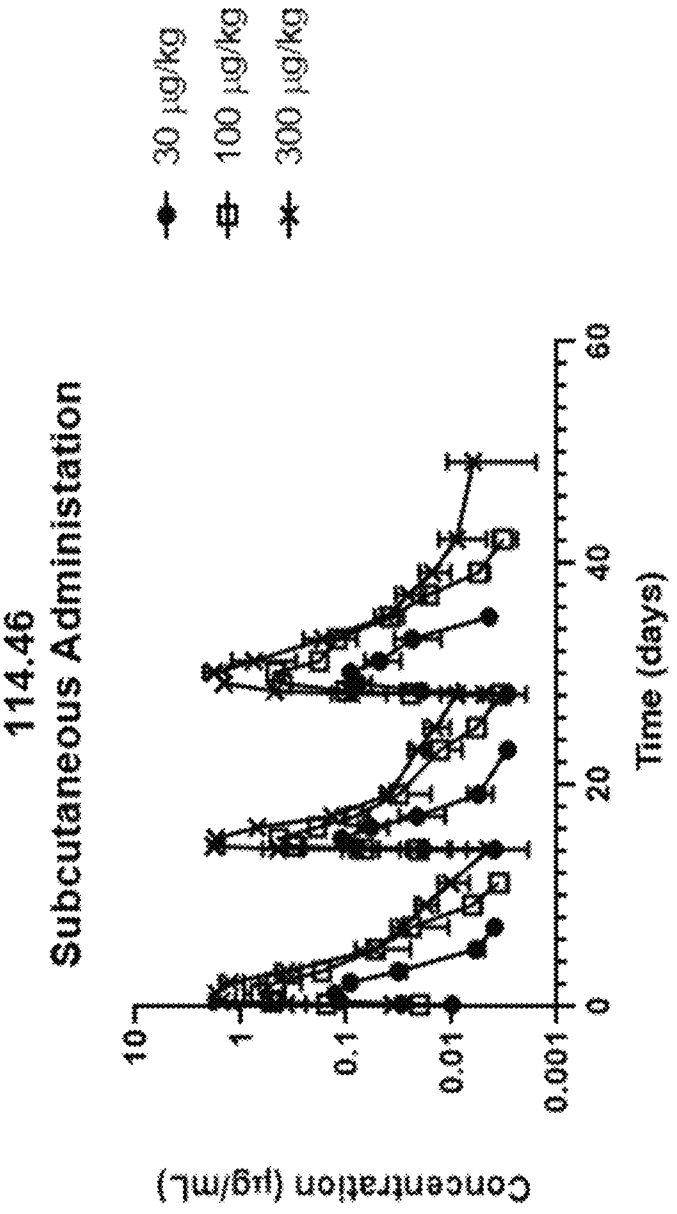

PK analysis following repeat subcutaneous administration in cynomolgus macaques demonstrated that the Fc-IL-2 variant fusion proteins (SEQ ID NO: 107.46 and 114.46) showed nearly dose proportional PK at Cmax with evidence of target mediated drug disposition at the terminal phase. The Fc-IL-2 variant containing R38G/F42A/E62A mutations (heterodimer 114.46) had improved AUC and Cmax values compared to the Fc-IL-2 variant containing F42A/E62A mutations (heterodimer 107.46). The smaller difference in the AUC at dose 3 and the reduced accumulation ratio (AR) is consistent with greater IL-2 receptor mediated Cl. There was also evidence of anti-drug antibodies (ADA) due to the human IL-2 and Fc sequences, which may have contributed to the reduced exposure following dose 2. The repeat dose PK results are summarized in Table 20 and depicted in FIG. 13.

TABLE 20

Repeat Dose PK Values for Fc-IL-2v Heterodimers Following Repeat Subcutaneous Administrations to Cynomolgus Macaques

| Heterodimer name | Dose (µg/kg) | $Cmax_{0\text{-}14\ d}$ (µg/mL) | $AUC_{0\text{-}14\ d}$ (µg*day/mL) | $AUC_{28\text{-}42\ d}$ (µg*day/mL) | Mean AR | ADA |
|---|---|---|---|---|---|---|
| 107.46 | 30 | 0.11 ± 0.03 | 0.31 ± 0.03 | 0.05* | 0.16 | 3/3 |
| | 100 | 0.41 ± 0.01 | 1.11 ± 0.18 | 0.92 ± 0.025 | 0.83 | 0/3 |
| | 300 | 1.61 ± 0.18 | 3.78 ± 0.30 | 2.69 ± 0.07 | 0.71 | 1/3 |
| 114.46 | 30 | 0.12 ± 0.02 | 0.26 ± 0.03 | 0.16 ± 0.01 | 0.60 | 3/3 |
| | 100 | 0.68 ± 0.03 | 1.64 ± 0.60 | 0.94 ± 0.06 | 0.57 | 1/3 |
| | 300 | 1.81 ± 0.19 | 4.27 ± 0.29 | 3.57 ± 1.12 | 0.83 | 1/3 |

SD = Standard Deviation;

AR = Accumulation Ratio;

*Single animal data due to ADA positive based on an aberrant decline in PK and confirmed by ADA bridging assay

Example 19

Expansion of Cynomolgus Macaque CD8+ T Cells and Regulatory T Cells after Repeat Dose Subcutaneous Administration of Human Fc-IL-2 Variant Fusion Proteins In this example, we evaluated the in vivo pharmacodynamics of human Fc-IL-2 variant fusion proteins. For this evaluation, we monitored numbers of peripheral blood CD8+ T cells and Treg cells using flow cytometry.

Methods

Figure 14A:
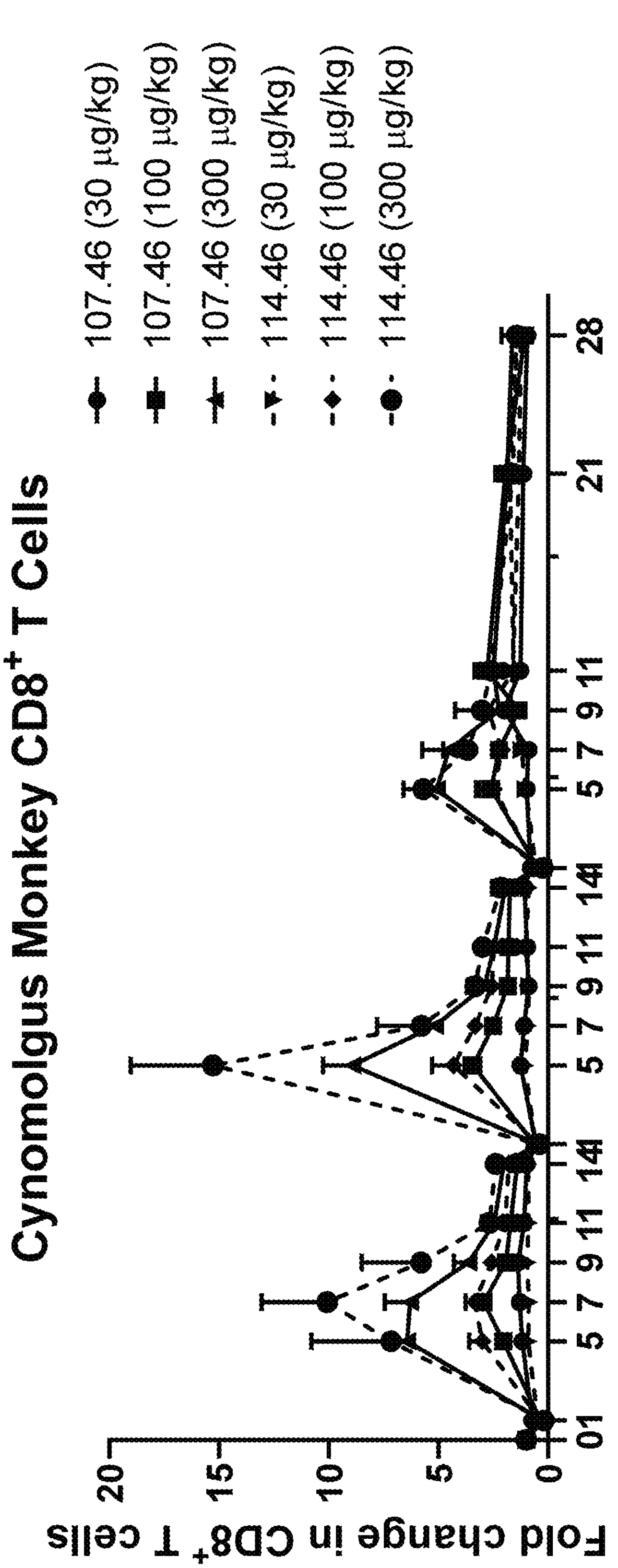
FIGS. 14A-14B illustrate the effect of repeat dose subcutaneous administration of Fc-IL-2v heterodimers 107.46 and 114.46 on number of cynomolgus macaque CD8+ T cells (FIG. 14A) and Treg cells (FIG. 14B).
Figure 14B:
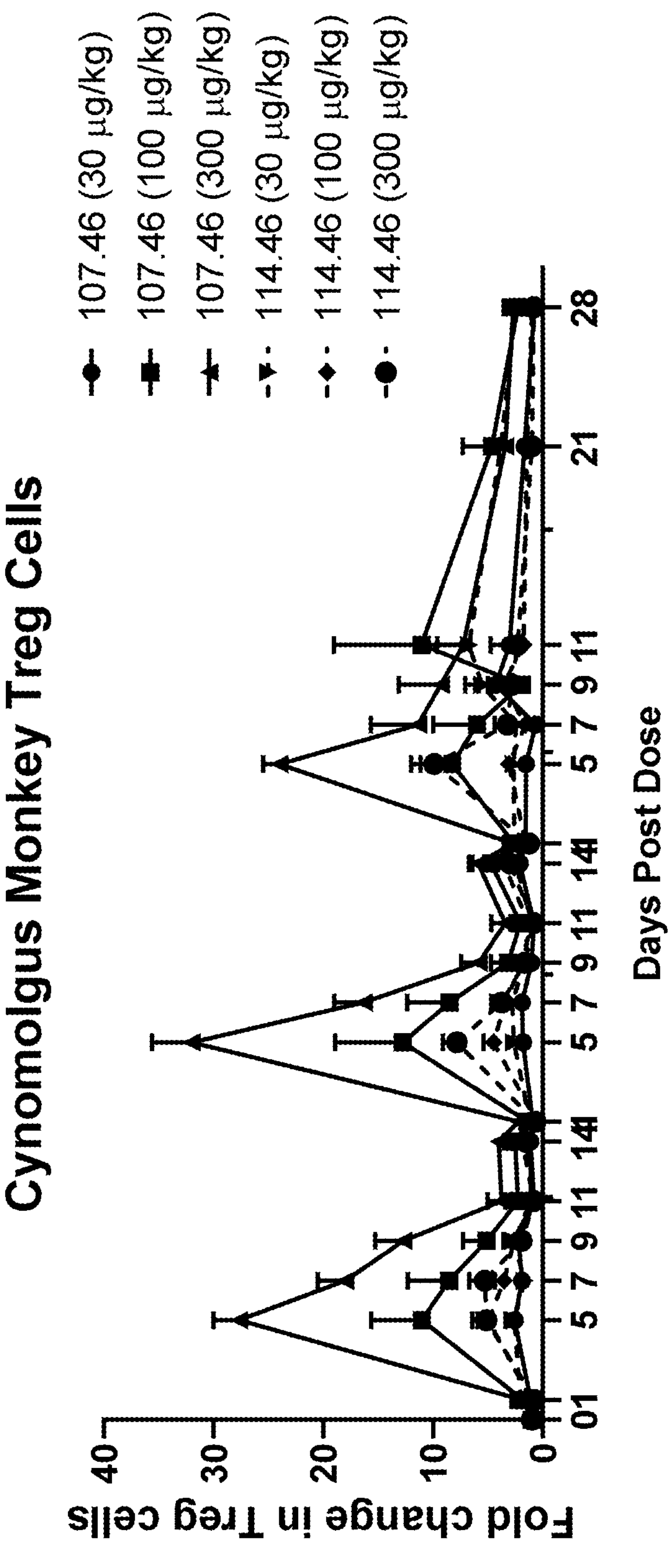

Recombinant human Fc-IL-2v heterodimers 107.46 and 114.46 were administered to cynomolgus macaques n=4/group (Covance, WI) at 30, 100 and 300 µg/kg via three repeat subcutaneous administrations to characterize pharmacodynamics. Peripheral blood samples were collected for immune phenotyping by flow cytometry. Each whole blood sample was incubated in Trucount tubes (BD Biosciences #340334) for 30 min with a panel of antibodies including CD45, CD3, CD4, CD8, CD25 for identifying CD8+ T cells and Treg cells. Intracellular staining was performed with antibodies for FoxP3 after incubating the cells with FoxP3/Transcription buffer (Invitrogen #0-5523-00). The absolute cell number per microliter of blood was determined using Trucount beads. Samples were run on a BD™ LSR II flow cytometer (BD Biosciences, San Jose, CA) and analyzed using FlowJo (ver 10.3, FlowJo LLC, Ashland, OR). Fold changes of cell numbers at various timepoints were calculated based on pretreatment cell counts. FIG. 14 depicts mean fold changes ±standard error of indicated cell-types.

Results

Subcutaneous administration of Fc-IL-2v heterodimers 107.46 and 114.46 resulted in dose dependent increases in the expansion of CD8+ T cells and Treg cells, with peak expansion around Day 5 after each dose. Heterodimer 114.46 (R38G/F42A/E62A-containing variant) elicited more than 4-fold lower or less expansion of Treg cells compared to heterodimer 107.46 (F42A/E62A-containing variant). There was a 6.4-fold expansion of Tregs by 114.46 versus 27.3-fold expansion of Tregs by 107.46 at 300 μg/kg dose. Fold increases in absolute cell numbers per μl of blood over pre-treatment cell counts are depicted in FIG. 14 and shown in Tables 21 and 22, respectively.

TABLE 21

CD8⁺ T cell Fold Change on Day 5 after Repeat Subcutaneous Administration of Fc-IL-2v Heterodimers 107.46 and 114.46 to Cynomolgus Macaques

| Heterodimer name | Dose (μg/kg) | Dose 1 | Dose 2 | Dose 3 |
|---|---|---|---|---|
| 107.46 | 30 | 1.2 ± 0.2 | 1.4 ± 0.2 | 1.0 ± 0.1 |
| | 100 | 1.8 ± 0.1 | 3.4 ± 0.8 | 2.5 ± 1.1 |
| | 300 | 5.3 ± 1.1 | 9.2 ± 2.2 | 4.9 ± 1.4 |
| 114.46 | 30 | 0.9 ± 0.2 | 1.1 ± 0.3 | 1.0 ± 0.2 |
| | 100 | 2.6 ± 1.0 | 4.3 ± 1.7 | 2.4 ± 1.1 |
| | 300 | 5.8 ± 2.6 | 14.9 ± 6.1 | 5.3 ± 0.9 |

Fold change calculated relative to pre-dose levels.
Mean ± standard deviation shown

TABLE 22

Treg Fold Change on Day 5 after Repeat Subcutaneous Administration of Fc-IL-2v Heterodimers 107.46 and 114.46 to Cynomolgus Macaques

| Heterodimer name | Dose (μg/kg) | Dose 1 | Dose 2 | Dose 3 |
|---|---|---|---|---|
| 107.46 | 30 | 2.6 ± 1.3 | 1.7 ± 0.8 | 1.4 ± 0.1 |
| | 100 | 11.0 ± 8 | 12.3 ± 11.1 | 8.7 ± 5.5 |
| | 300 | 27.3 ± 4.2 | 29.3 ± 6.4 | 24.7 ± 2.3 |
| 114.46 | 30 | 2.6 ± 0.8 | 2.4 ± 1.4 | 2.7 ± 1.5 |
| | 100 | 4.9 ± 1.7 | 3.9 ± 1.1 | 3.3 ± 0.3 |
| | 300 | 6.4 ± 2.3 | 8.3 ± 1.1 | 10.8 ± 3.1 |

Fold change calculated relative to pre-dose levels.
Mean ± standard deviation shown

Example 20

Activation of CD8+ T Cells from Chronic HBV Subjects by Fc-IL-2 Variant Protein In this example, we evaluated the in vitro effect of a human Fc-IL-2 fusion protein variant on the HBV antigen-specific CD8+ T cell response. For this evaluation, we utilized an antigen recall response assay with peripheral blood mononuclear cells (PBMC) from chronic HBV (CHB) subjects.

Methods

Cryopreserved peripheral blood mononuclear cells (PBMC) isolated from CHB subjects (n=8 donors; BioIVT) were thawed and washed twice with culture medium (RPMI-1640, 10% HI FBS, 1×PS, 1×NEAA, 25 mM HEPES) to remove DMSO. PBMCs were plated in a 96 well round bottom plate (Corning #9018) at a density of 250,000 cells in culture medium per well and stimulated for 6 days with HBV core peptides (15-mer overlapping peptide pool covering the entire sequence of HBV core antigen) or Actin control peptides (JPT Peptide Technologies #PM-ACTS) at 100 ng/ml in the presence or absence of Fc-IL-2v heterodimer 114.46 at 8 nM. On Day 6, PBMCs were re-stimulated overnight with peptides, followed by staining with a panel of flow cytometry antibodies against CD3, CD4 and CD8 for 45 minutes at room temperature. After surface staining, the cells were fixed with fixation buffer (Invitrogen #00-8222-49), permeabilized with 1× permeabilization buffer (Invitrogen #00-8333) and stained with antibodies against intracellular markers IFN-γ and Ki67. The cells were then washed and analyzed using an LSR Fortessa X-20 (BD). Frequencies of CD8+ T cells (mean±standard deviation) positive for IFN-γ and Ki67 were used to compare the treatment groups. Statistical significance was determined using one-way ANOVA with Tukey's post hoc test.

Results

Figure 15A:
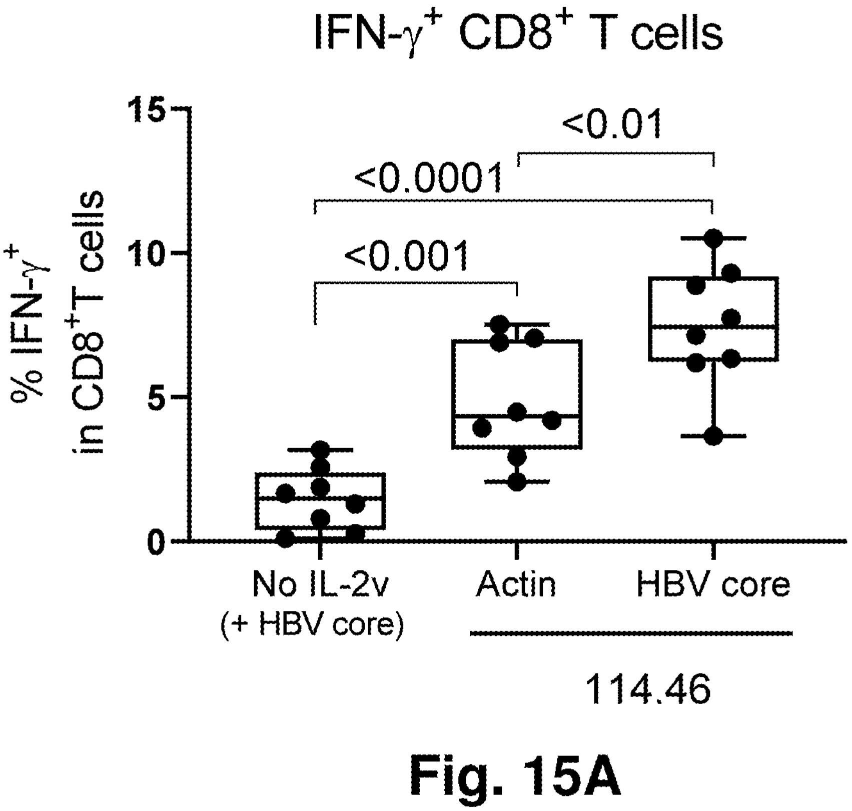
FIGS. 15A-15B illustrate in vitro effect of an Fc-IL-2v heterodimer 114.46 on HBV-specific IFN-γ+ CD8+ T cells (FIG. 15A) and Ki67+ CD8+ T cells (FIG. 15B).
Figure 15B:
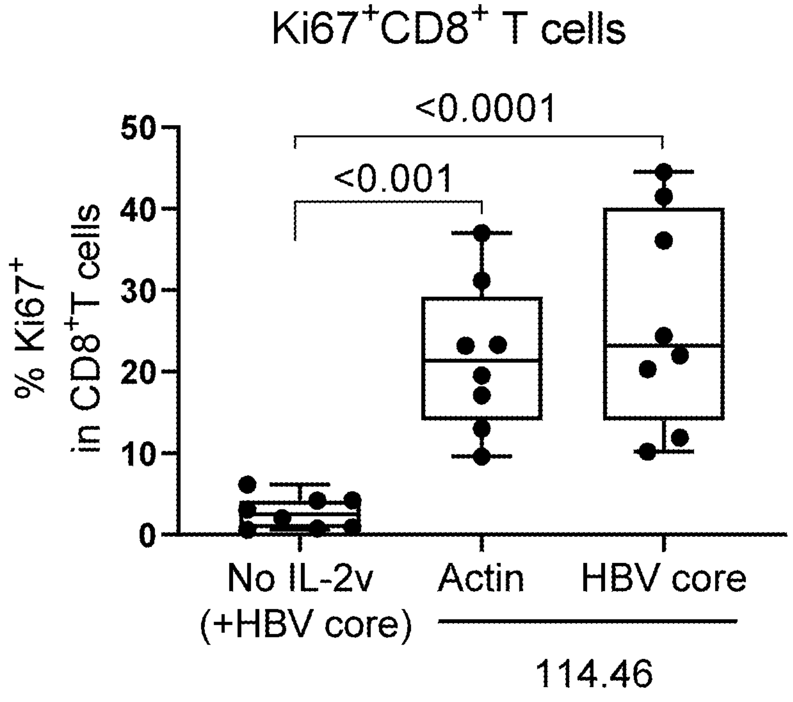

The data demonstrated that stimulation of PBMCs from chronic HBV subjects with Fc-IL-2v heterodimer 114.46 resulted in an increase in the percentage of IFN-γ and Ki67 expression in CD8+ T cells in response to HBV peptides. Compared to the no Fc-IL-2 variant treatment group (+HBV core peptide), treatment with the Fc-IL-2 variant increased the frequency of IFN-γ+ CD8+ T cells by an average of 3.3-fold in the control actin peptide treated cells and 5.1-fold in the HBV core peptide treated cells. Fc-IL-2 variant treatment also increased the frequency of Ki67+ CD8+ T cells by 7.9-fold in actin treated cells and 9.6-fold in HBV core peptide treated cells. The results are depicted in FIG. 15.

In summary, the evaluations of Examples 1 to 20, including biophysical data, in vitro cell assay data, in vivo pharmacodynamics and pharmacokinetics data from non-human primates, demonstrated several advantages of an Fc-IL-2v molecule containing the three R38G, F42A, E62A mutations in IL-2 (heterodimer 114.46), in comparison to the other IL-2v tested. With respect to biophysical data, heterodimer 114.46 displayed no measurable binding affinity or detectable isotherm binding to IL-2Rα as assessed by SPR analysis (Example 8, $K_D$>60 μM) and abrogated IL-2Rα binding affinity important for reducing Treg potency through the trimeric IL-2Rαβγ constitutively expressed on Tregs. Additionally, molecule 114.46 maintained its binding to Fc-IL-2Rβγ as measured by SPR analysis (Example 8, $K_D$=76 pM), which is important for effector cell activation (e.g., CD8⁺ T cells). With respect to in vitro cell assays, heterodimer 114.46 had greatly reduced potency compared to Proleukin on CTLL-2 cells (greater than 30,000-fold), which express high levels of IL-2Rα as part of the trimeric IL-2 receptor (IL-2Rα, IL-2Rβ, and IL-2Rγ), and thus serve as a sensitive assay for activation through trimeric IL-2Rαβγ. Additionally, primary cell PBMC assays showed that Treg activation by heterodimer 114.46 was reduced by about 3000-fold compared to Proleukin while CD8⁺ T cell and NK cell activation and proliferation were unaffected (Examples 10 and 12). With respect pharmacokinetics (PK) data from non-human primate models, heterodimer 114.46 had improved area under curve (AUC) and clearance (Cl) PK properties (Examples 17 and 18), in comparison to other Fc-IL-2v molecules tested, such as those that only contained two mutations at the IL-2/IL-2Rα interface (e.g., heterodimers 113.46 (R38G, E62A) and 107.46 (F42A, E62A)). Additionally, in vivo Treg expansion by heterodimer 114.46 was reduced more than 4-fold compared to heterodimer 107.46 that only contained two mutations at the IL-2/IL-2Rα interface (Example 19).

Example 21

Antiviral and Immune Effects of Murine Surrogate Fc-IL-2 Heterodimers in an HBV Transgenic Mouse Model In this example, we further confirm the in vivo antiviral efficacy as well as immunological activity of a murine Fc-IL-2 variant fusion protein. For this evaluation, we utilize an HBV transgenic mouse model and measure peripheral levels of HBV DNA as well as the number and function of leukocytes, including liver HBV-specific $CD8^+$ T cells after treatment.

Methods

Mice for use in this study are HBV-replication competent transgenic mice (lineage 1.3.32 on a C57BL/6 background; described in Guidotti, et al., *J. Virol.* (1995) 69(10):6158-69). All mice receive $2\times10^4$-$5\times10^6$ HBV core-specific naïve $CD8^+$ T cells (Cor93 TCR) at Day 0 as described in Benechet, et al. *Nature*, (2019) 574(7777):200-205. Mice are either untreated (negative control) or treated by administration of 0.05 to 0.5 mg/kg of mouse surrogate Fc-IL-2 molecules (e.g., having SEQ ID NOs: 167.250 or 165.250) 24 hours after Cor93 TCR transfer. Whole blood is collected per time point (Days −21, 1, 3, 5) and serum isolated from whole blood samples are analyzed for HBV DNA. Three to five days after Cor93 TCR transfer, mice are sacrificed and leukocytes are isolated from the liver and spleen. The number and function of leukocytes, including HBV-specific T cells, are evaluated as described in Guidotti, et al., Cell (2015) 161(3):486-500. Liver histology (H&E staining and anti-HBcAg immunofluorescence or immunohistochemistry) are carried out on fixed samples.

Example 22

Anti-Tumor Activity of Murine Surrogate Fc-IL-2v Heterodimer

In this example, we evaluated the anti-tumor activity of a murine surrogate Fc-IL-2v heterodimer 168.250 in a mouse tumor model.

Methods

Female C57BL6 mice (The Jackson Laboratory) were inoculated subcutaneously with $2\times10^5$ B16-F10 cells. On Day 0 mice were randomized when mean tumor volume reached 94.8 $mm^3$ (variability of 1.8%) into 10 animals/treatment group. Murine surrogate Fc-IL-2v heterodimer 168.250 or mouse IgG2a Fc control proteins were administered intraperitoneally once weekly at 0.5 mg/kg starting on Day 4. Tumor dimensions were measured three times weekly for all animals using the equation: tumor volume $(mm^3)=(length\times width^2\times\pi)/6$. Statistical significance of survival between groups was determined by log-rank Mantel-Cox test. Animals were assessed for clinical condition daily as well as body weight loss and tumor burden in accordance with ethical guidelines. Tumor burden exceeding 2000 $mm^3$, or severe tumor ulceration, cavitation, or bleeding over several days were considered as criteria for euthanasia.

Results

Figure 16:
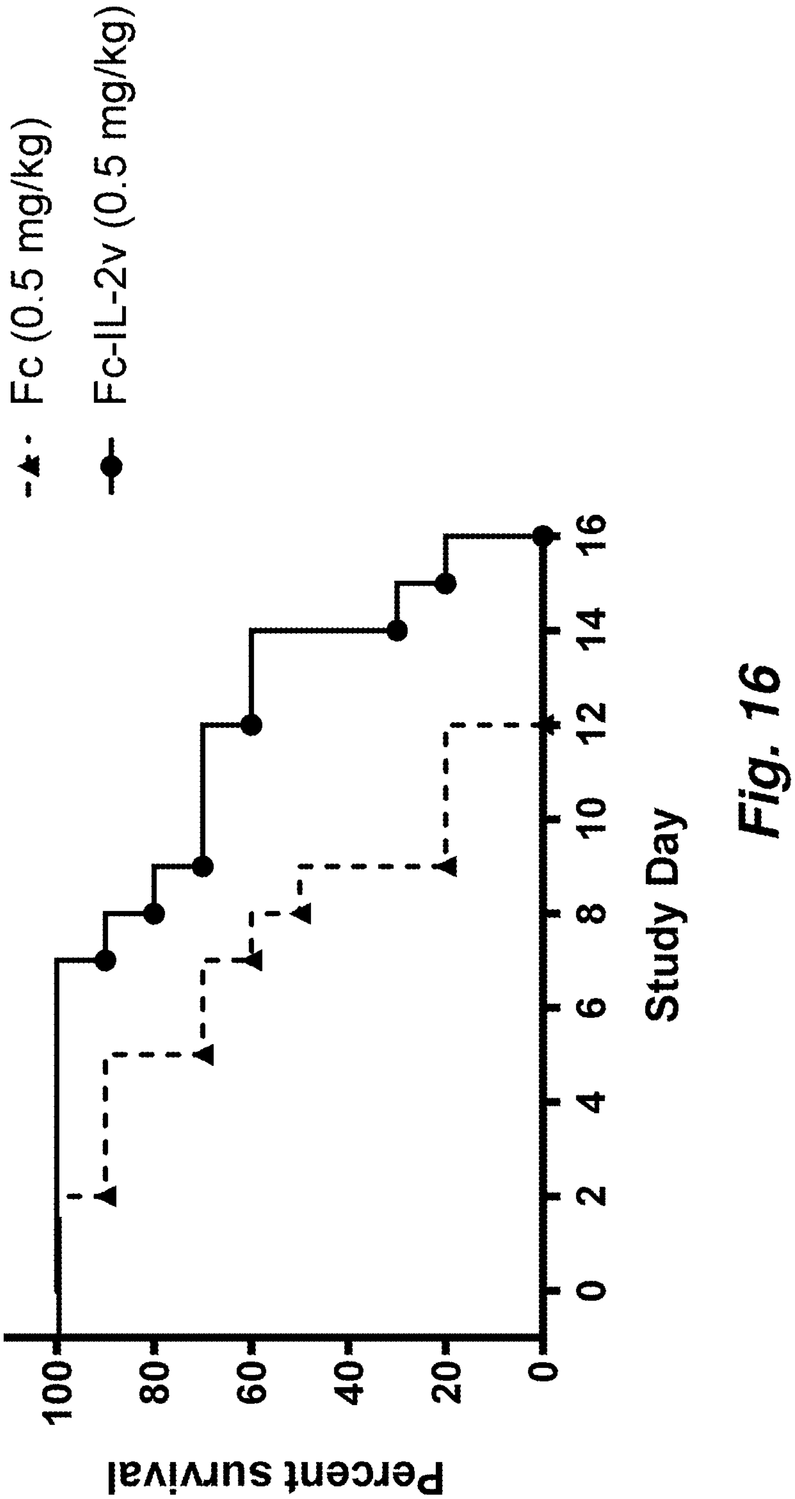
FIG. 16 illustrates survival of mice with B16-F10 tumors treated with murine surrogate Fc-IL-2v heterodimer 168.250.
Figure 17:
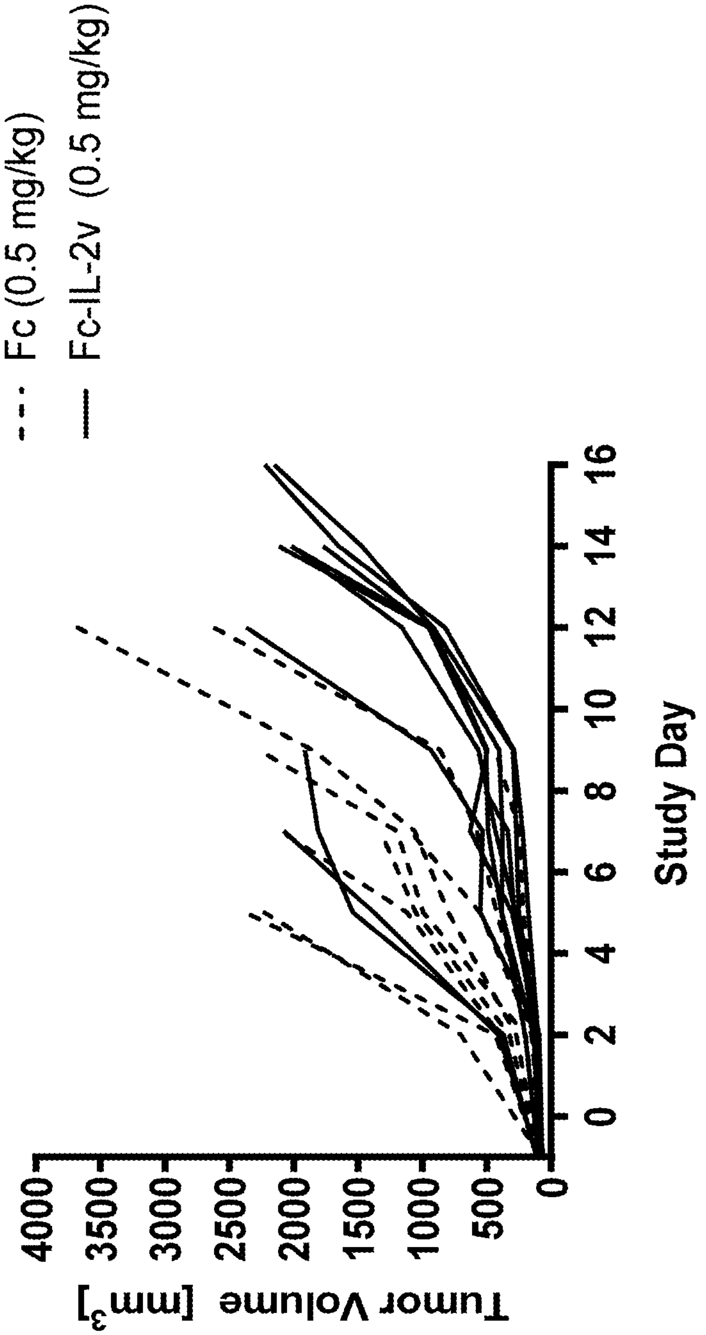
FIG. 17 illustrates individual B16-F10 tumor volumes in mice treated with murine surrogate Fc-IL-2v heterodimer 168.250.

The data demonstrated that treatment with murine surrogate Fc-IL-2v heterodimer 168.250 significantly increased the survival (median survival: 14 days; $p\leq0.05$) compared with Fc protein control treatment (median survival: 8.5 days) of mice with B16-F10 tumors. Tumor growth inhibition was also evaluated and demonstrated the murine surrogate Fc-IL-2 variant resulted in moderate inhibition of tumor growth by Day 7 compared with Fc protein control treatment (mean tumor growth inhibition=33.90% and 36.95%). By Day 12 post-treatment, tumor volume of surviving animals in Fc-IL-2 variant group was reduced compared to the few surviving animals in the Fc protein control treatment group. The results are depicted in FIGS. 16 and 17.

Example 23

Anti-Tumor Activity of Murine Surrogate Fc-IL-2v Heterodimer Alone and in Combination with Anti-PD-1 Antibody in CT26 Tumor Model In this example, we evaluated the anti-tumor activity of a murine surrogate Fc-IL-2v heterodimer 171.250 alone and in combination with anti-mouse PD-1 antibody in the syngeneic CT26 colon adenocarcinoma mouse tumor model. Tumor burden as well as survival of animals was monitored.

Female C57BL/6 mice (Taconic Biosciences) were inoculated subcutaneously with $0.8\times10^6$ CT26 cells. On Day 0 mice were randomized when the tumor volume reached an average of 80-100 $mm^3$ into 10 animals/treatment group. Murine surrogate Fc-IL-2v heterodimer 171.250 or mouse IgG2a Fc control proteins were administered intraperitoneally once weekly at 0.50 mg/kg or 0.25 mg/kg starting on Day 0. Anti-PD-1 (BioXcell; clone RMP1-14) or rat IgG2a isotype control were administered intraperitoneally twice a week at 10 mg/kg starting on Day 0. Tumor dimensions were measured three times weekly for all animals using the equation: tumor volume $(mm^3)=0.5\times length\times width^2$. Statistical comparisons of tumor volume data were performed using measurements made on Study Day 15, when there were 10 animals remaining in all groups. Pairwise group comparisons were based on t-tests with Bonferroni adjustment. A p-value of $\leq0.05$ was considered significant. Statistical significance of survival between groups was determined by log-rank Mantel-Cox test. Animals were assessed for clinical condition, body weight loss and tumor burden in accordance with ethical guidelines. Tumor burden exceeding 2000 $mm^3$, or severe tumor ulceration, cavitation, or bleeding over several days were considered as criteria for euthanasia. Mean tumor volumes were calculated ±SEM.

Results

Figure 18:
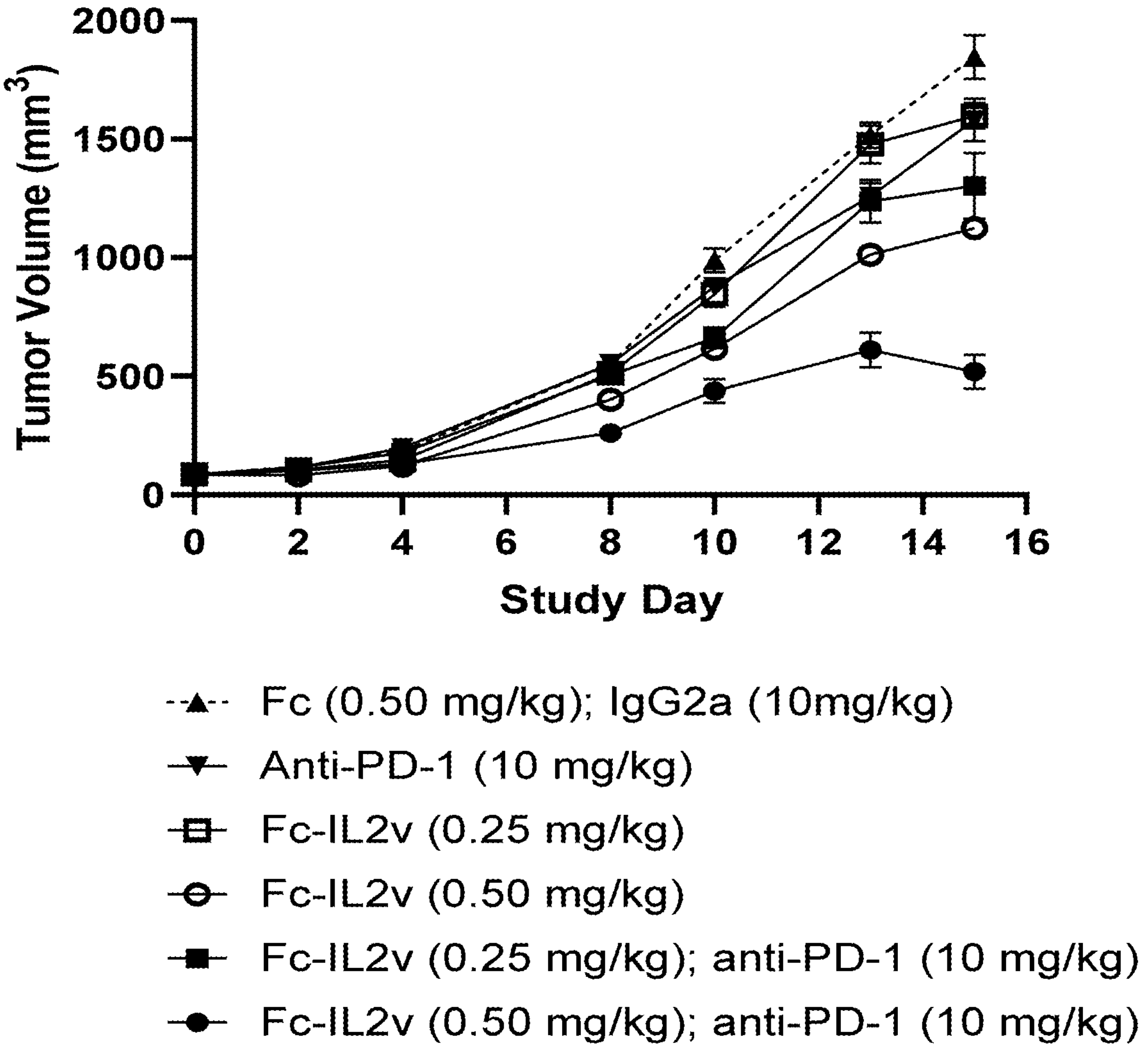
FIG. 18 illustrates mean CT26 tumor volumes in mice treated with murine surrogate Fc-IL-2v heterodimer 171.250 alone and in combination with anti-PD-1 antibody.
Figure 19:
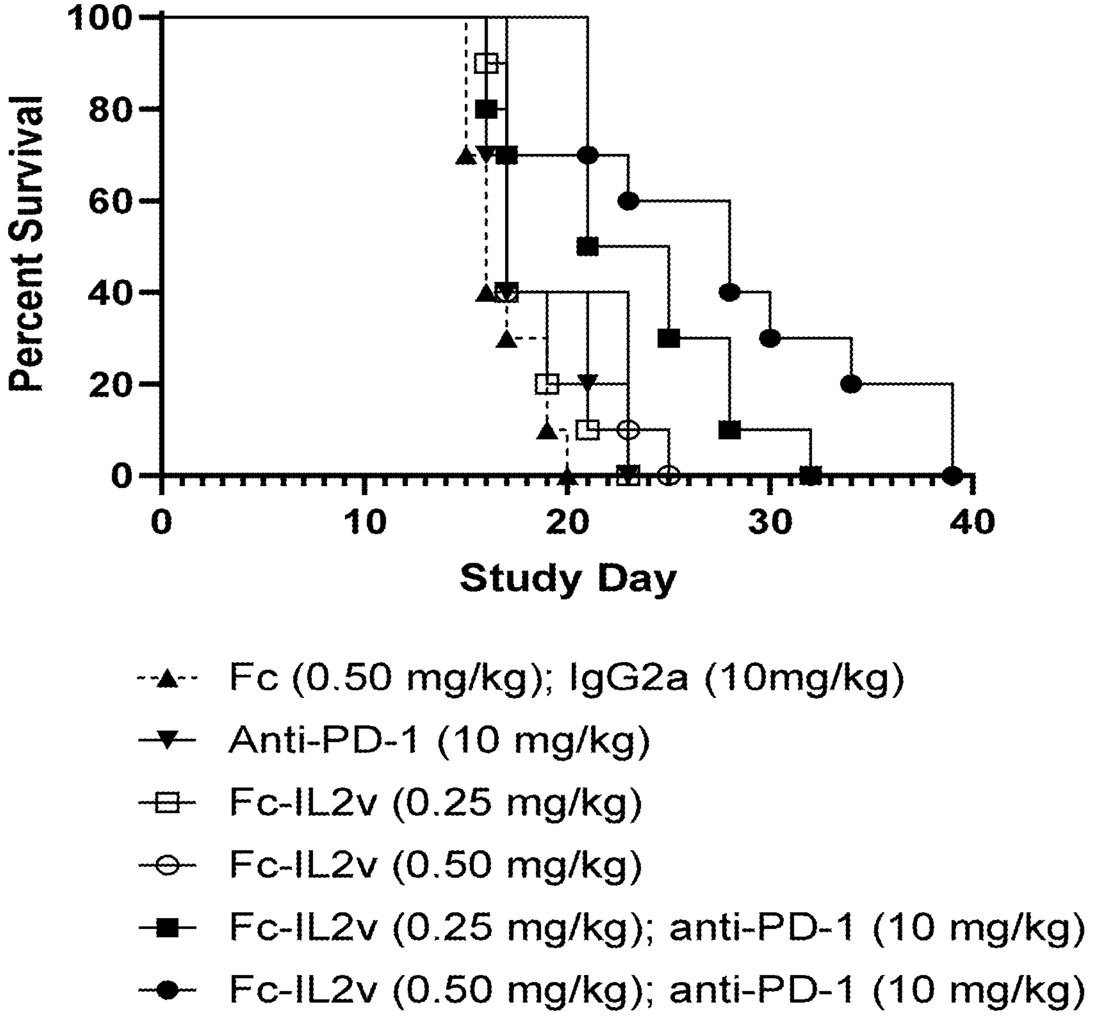
FIG. 19 illustrates survival of mice with CT26 tumors treated with murine surrogate Fc-IL-2v heterodimer 171.250 alone and in combination with anti-PD-1 antibody.

The data demonstrated that treatment of murine surrogate Fc-IL-2v heterodimer 171.250 as a single agent or in combination with anti-PD-1 significantly inhibited CT26 tumor growth (Day 15 t-test; $p\leq0.05$). Additionally, treatment with Fc-IL-2v heterodimer 171.250 at 0.50 mg/kg or in combination with anti-PD-1 at 0.25 and 0.50 mg/kg significantly increased survival (Log-rank Mantel-Cox test; $p=<0.0001$) expanding median survival up to 28 days (171.250 at 0.50 mg/kg+anti-PD-1) compared with Fc protein control treatment (median survival: 16 days). The results are depicted in FIGS. 18 and 19.

Example 24

Antiviral Effect of Murine Surrogate Fc-IL-2v Heterodimer and Anti-PD-L1 in a Mouse Model of Chronic LCMV Infection In this example, we evaluated the in vivo antiviral efficacy of a murine Fc-IL-2 variant fusion protein alone and in combination with an anti-PD-L1 antibody. For this evaluation, we utilized a mouse model of chronic lymphocytic choriomeningitis virus (LCMV) infection, and measured serum viral titer as well as liver viral titer and CD8+ T cell numbers after treatment.

Methods

C57BL/6 mice were infected with LCMV clone 13 at $2.0\times10^6$ plaque-forming units (pfu) by tail vein injection. At Day 16 and 23 post-infection, mice (n=5-7 mice/group) were treated with 0.4 mg/kg of Fc only control (mIgG2a_LALA_PG Fc KiH; SEQ ID NOs: 172 and 173), 0.4 mg/kg of murine Fc-IL-2v heterodimer 171.250, 10 mg/kg of a murine anti-PD-L1 antibody, or a combination of 0.4 mg/kg of murine Fc-IL-2v heterodimer 171.250 and 10 mg/kg of murine anti-PD L1 antibody to assess liver viral titers. To evaluate serum viral titer, mice (n=6-8 mice/group) were treated with 0.4 mg/kg Fc only control, 0.4 mg/kg of murine Fc-IL-2v heterodimer 171.50, 10 mg/kg of a murine anti-PD-L1 antibody, or a combination of 0.4 mg/kg of murine Fc-IL-2v heterodimer 171.250 and 10 mg/kg of murine anti-PD L1 antibody at Days 21, 27 and 37 post-infection.

```
                                         (SEQ ID NO: 172)
GPTIKPCPPCKCPAPNAAGGPSVFIFPPKIKDVLMISLSPIVTCVVVD

VSEDDPDVQISWFVNNVEVHTAQTQTHREDYNSTLRVVSALPIQHQDW

MSGKEFKCKVNNKDLGAPIERTISKPKGSVRAPQVYVLPPPEEEMTKK

QVTLWCMVTDFMPEDIYVEWTNNGKTELNYKNTEPVLDSDGSYFMYSK

LRVEKKNWVERNSYSCSVVHEGLHNHHTTKSFSRTPGK

                                         (SEQ ID NO: 173)
GPTIKPCPPCKCPAPNAAGGPSVFIFPPKIKDVLMISLSPIVTCVVVD

VSEDDPDVQISWFVNNVEVHTAQTQTHREDYNSTLRVVSALPIQHQDW

MSGKEFKCKVNNKDLGAPIERTISKPKGSVRAPQVYVLPPPEEEMTKK

QVTLSCAVTDFMPEDIYVEWTNNGKTELNYKNTEPVLDSDGSYFMVSK

LRVEKKNWVERNSYSCSVVHEGLHNHHTTKSFSRTPGK
```

Figures 20A, 20B, 20C:
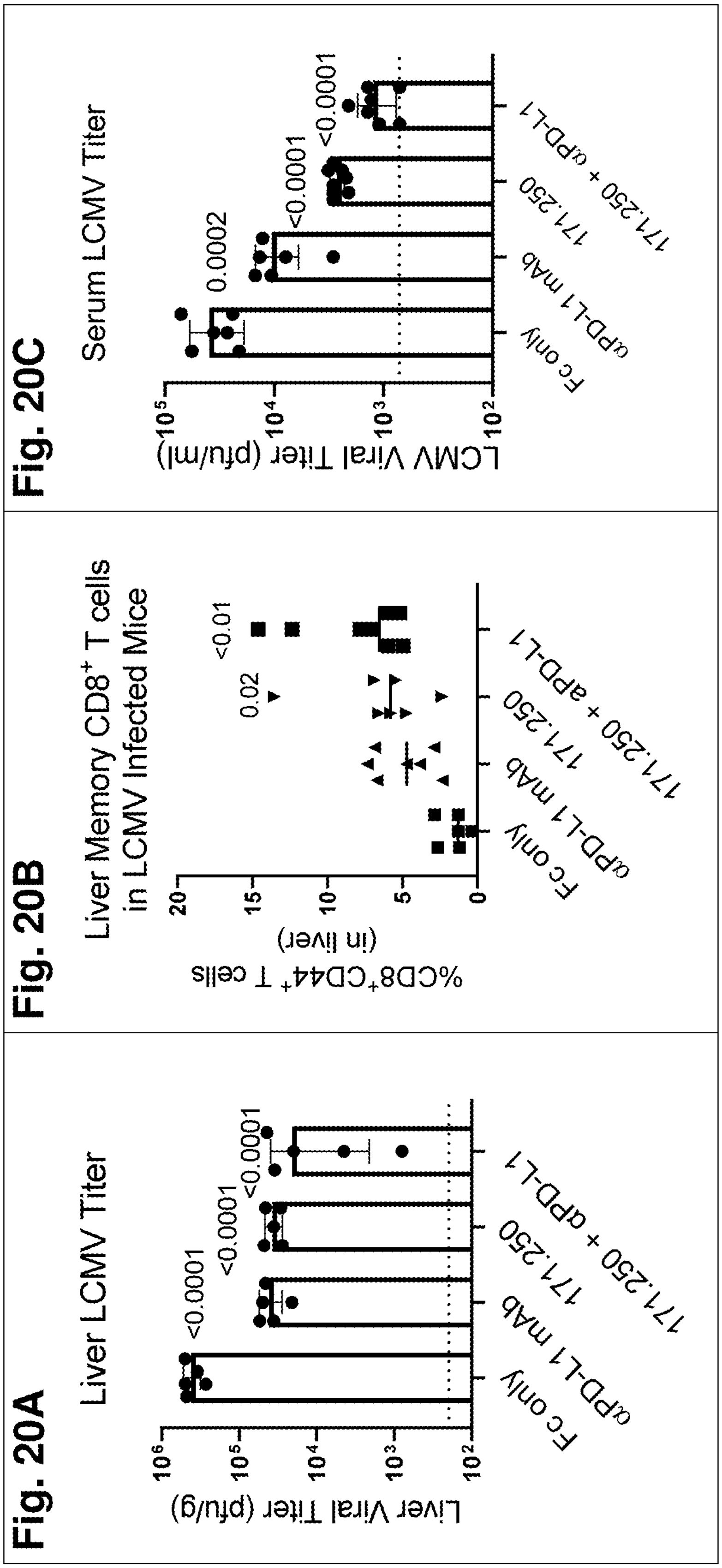
FIGS. 20A-20C illustrate in vivo antiviral effect of murine surrogate Fc-IL-2v heterodimer 171.250 alone and in combination with αPD-L1 in mice infected with LCMV. Liver LCMV titer (FIG. 20A). Liver memory $CD8^+$ T cells in LCMV mice (FIG. 20B). Serum LCMV titer (FIG. 20C).

Mice were sacrificed at Day 28 post-infection and viral titer in homogenized liver tissues was determined using a plaque forming assay. Mice were sacrificed at Day 40 post-infection and viral titer in serum was determined using a plaque forming assay. For immune phenotyping by flow cytometry, a portion of liver tissue samples were processed using a Liver Dissociation Kit (Miltenyi Biotec #130-105-807) and single cell suspension was obtained using a gentleMACS tissue homogenizer (Miltenyi Biotec). Cells were stained with a panel of antibodies including TCRβ, CD4, CD8 and CD44. Absolute count of CD8+ T cells was calculated based on volume of sample acquired on MACSQuant Analyzer 10 Flow Cytometer. Samples were analyzed using FlowJo (ver 10.3, FlowJo LLC, Ashland, OR). Data is represented as mean±standard error. Statistical significance was determined using one-way ANOVA with Tukey's post hoc test Results Compared to treatment with the Fc only control (mIgG2a_LALA_PG Fc KiH; SEQ ID NOs: 172 and 173), single agent treatment with Fc-IL-2v heterodimer 171.250 or αPD-L1 antibody reduced liver LCMV titer by approximately 9-fold in each group at Day 28. Fc-IL-2v heterodimer treatment in combination with αPD-L1 reduced liver LCMV titers by 20-fold. Compared to treatment with the Fc only control (mIgG2a_LALA_PG Fc KiH; SEQ ID NOs: 172 and 173) serum viral titer was also reduced by single agent treatment with Fc-IL-2v heterodimer 171.250 or αPD-L1 antibody by approximately 15-fold and 4-fold, respectively, at Day 40. Fc-IL-2v heterodimer treatment in combination with αPD-L1 reduced serum LCMV titers by approximately 32-fold at Day 40. Reduction of the LCMV titer in the liver, as compared to the Fc only treatment group, was accompanied by an increase in the frequency of memory CD44+ CD8+ T cells by 3-fold in the Fc-IL-2 fusion variant group, 4-fold in the αPD L1 group, and 5-fold in the combination group. The results are depicted in FIG. 20.

Example 25

Antiviral Effect of Murine Fc-IL-2 Variant Fusion Protein and Anti-PD-L1 in Mouse Model of AAV-HBV Infection In this example, we evaluated the in vivo antiviral efficacy of a murine surrogate Fc-IL-2 variant fusion protein alone, heterodimerized with the Fc domain of SEQ ID NO:250 and in combination with anti-PD-L1 antibody treatment using the mouse model of persistent AAV-HBV infection.

Methods

Figure 21A:
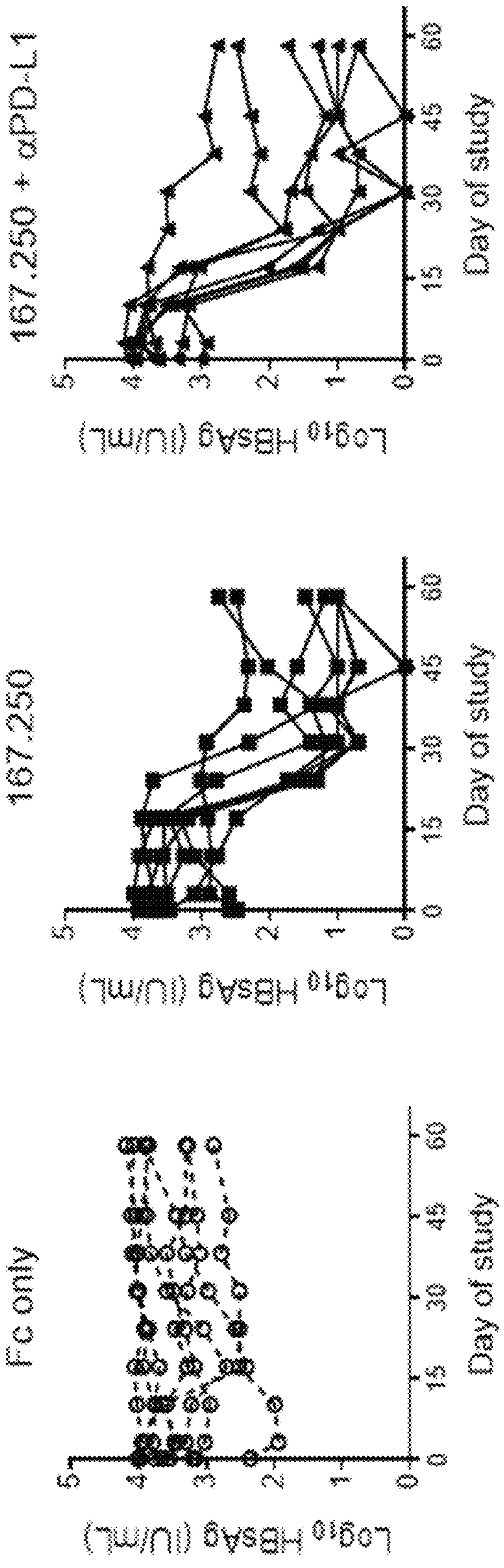
FIGS. 21A-21C illustrate HBsAg (FIG. 21A), HBeAg (FIG. 21B) and HBV DNA (FIG. 21C) levels after treatment of AAV-HBV infected mice with murine Fc-IL-2v heterodimer 167.250 and anti-PD-L1 antibody.
Figure 21B:
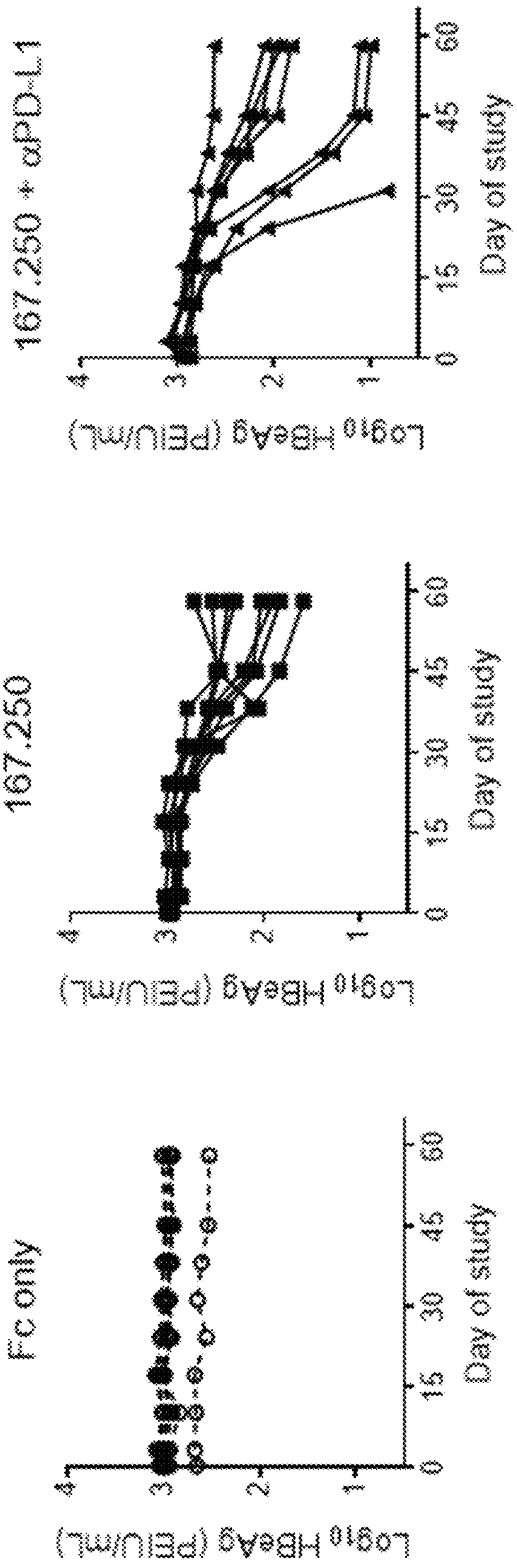
Figure 21C:
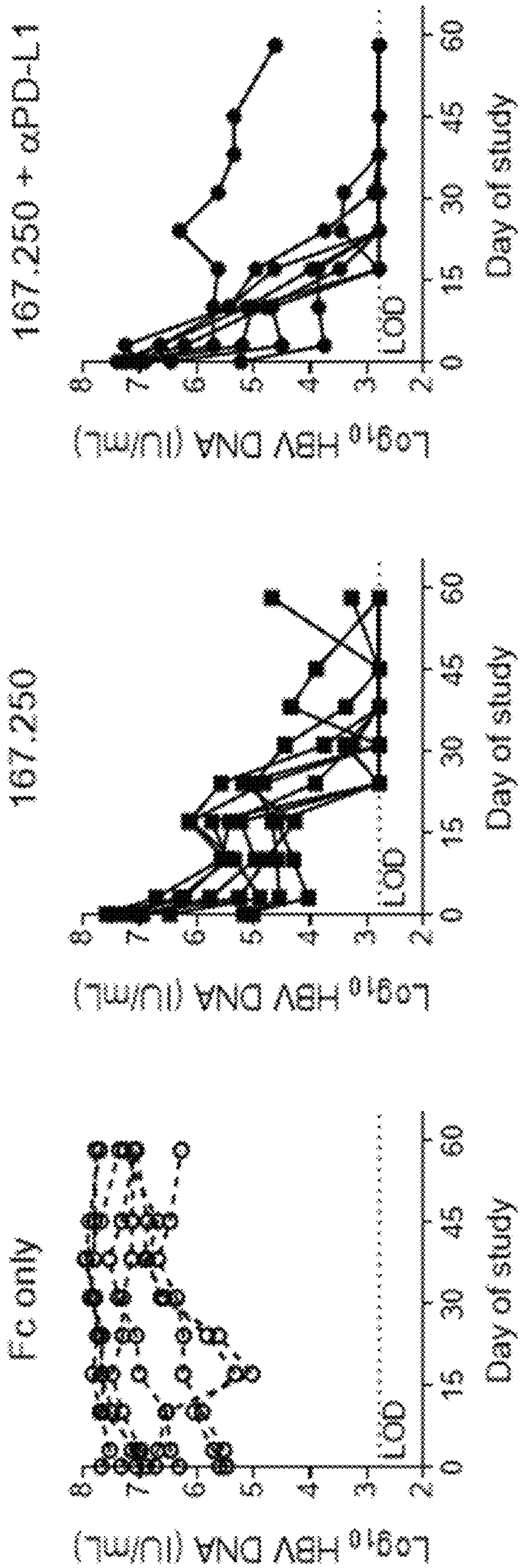

C57BL/6 mice were infected with recombinant adeno associated virus (AAV) carrying the HBV genome rAAV8-1.3HBVayw at $4.0\times10^{10}$ viral genome copies per mouse by intravenous injection. Starting at five weeks post infection, mice (n=8/group) were treated weekly with 0.5 mg/kg of Fc protein only (mIgG2a_LALA_PG Fc KiH; SEQ ID NOs: 172 and 173), 0.5 mg/kg of murine Fc-IL-2 variant fusion protein (SEQ ID NO: 167), 10 mg/kg of murine anti-PD-L1 monoclonal antibody, or a combination of 0.5 mg/kg of murine Fc-IL-2 variant (SEQ ID NO: 167) and 10 mg/kg of murine anti-PD-L1 antibody via intraperitoneal injection until Day 45. Three days post each dose, plasma samples were collected and HBsAg, HBeAg, and HBV DNA levels were measured. Plasma HBsAg and HBeAg were determined by ARCHITECT i2000 (Abbott Laboratories, Lake Bluff, IL, USA). Plasma HBV-DNA was analyzed by ABI7500 Real-Time PCR System (Applied Biosystems, Foster City, CA, USA) and detection kit (Sansure Biotech Inc., Changsha, Hunan, China). Plasma levels of HBsAg and HBV DNA are depicted in FIGS. 21A and 21C as international unit (IU) per mL and HBeAg in FIG. 21B as Paul Ehrlich Institute Unit (PEIU) per mL.

At Day 56, all mice were euthanized, and spleen samples were processed to obtain single cell suspension by mechanical disruption and red blood cell lysis (using ACK lysis buffer, Invitrogen #A1049201). IFN-γ producing T cells in mouse splenocytes were quantified after overnight stimulation of $2\times10^5$ cells with medium alone or 2 μg/ml of HBsAg or HBV core antigen (HBcAg) peptide pools (15-mer peptides covering the entire sequence of HBsAg or HBcAg) by using a mouse IFN-γ ELISpotPLUS kit (Mabtec #3321-4APW-10). IFN-γ spot forming units (SFU) were revealed using streptavidin-ALP and BCIP/NBT chromogen substrate included in the kit. The SFUs were counted using AID iSpot ELISpot reader (Autoimmun Diagnostika GmbH, Strasburg, Germany). Responses were considered positive if the mean of antigen wells was greater than 15 SFU/$10^6$ splenocytes and exceeded by 3-fold the background value of medium alone (plus DMSO) wells. The background SFU values obtained in medium alone conditions were subtracted from the peptide treated conditions, and data represented as mean SFU ±standard error. Statistical significance among the Fc-IL-2 variant treatment groups was determined using Kruskal-Wallis test with Dunn's comparison.

Results

As compared to pre-treatment levels of HBsAg, HBeAg, and HBV DNA, treatment with murine surrogate Fc-IL-2 variant alone or in combination with αPD-L1 antibody reduced HBsAg, HBeAg, and HBV DNA levels by 0.5 to 4.5 log in all mice (n=8 in each group). For the Fc-IL-2 variant and αPD-L1 combination arm, HBsAg, HBeAg, and HBV DNA levels demonstrated a trend toward faster kinetics of decline compared to Fc-IL-2 variant treatment alone. This was most evident for HBeAg levels in the combination group which were 5.4% to 16.7% lower than the Fc-IL-2 variant treatment group at all time points after Day 17. At Day 56 HBeAg levels were 2.16 log PEIU/mL in Fc-IL-2 variant group and 1.80 log PEIU/mL in combination group. Data are depicted in FIG. 21.

Figure 22:
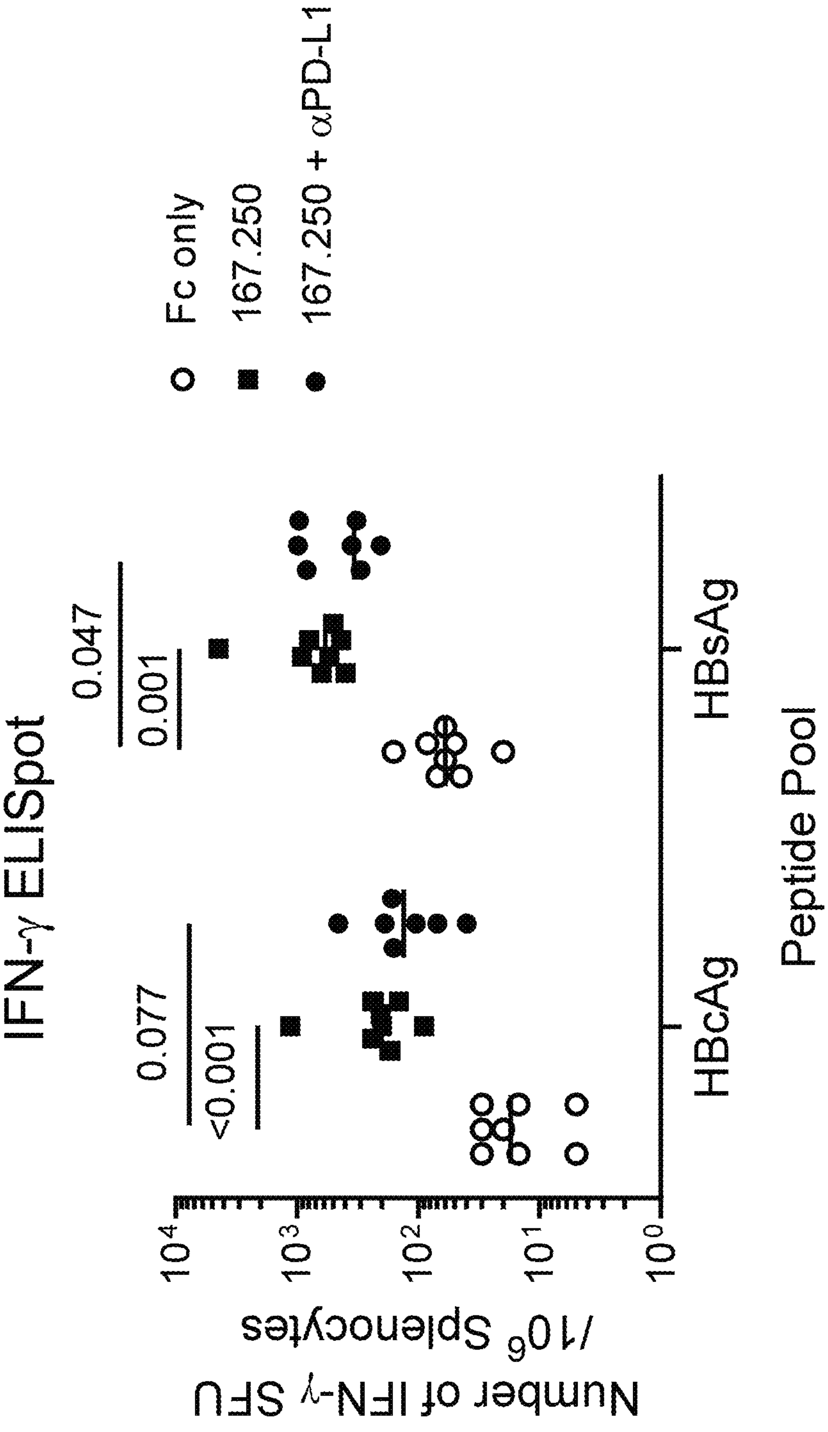
FIG. 22 illustrates number of HBcAg-specific and HBsAg-specific IFN-γ+HBV-specific T cells in AAV-HBV infected mice after treatment with murine Fc-IL-2v heterodimer 167.250 and anti-PD-L1 antibody.

HBV-specific T cell responses were measured at Day 56 post treatment initiation in AAV-HBV infected mice by IFN-γ ELISpot assay. As compared to the control group of mice treated with Fc only (19 SFU/$10^6$ splenocytes), Fc-IL-2 variant single arm treatment and Fc-IL-2 variant and PD-L1 combination treatment groups had enhanced production of IFN-γ by T cells (average 303 and 143 SFU per $10^6$ splenocytes, respectively) after stimulation with an HBcAg peptide pool. Similarly, after stimulation with an HBsAg peptide pool, Fc-IL-2 variant and Fc-IL-2 variant and PD-L1 combination treatment groups showed higher IFN-γ response (1084 and 496 SFU per $10^6$ splenocytes, respectively), as compared with the Fc only group (69 SFU per $10^6$ splenocytes). Results are depicted in FIG. 22.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A heterodimer comprising a human IgG4 Fc-IL-2v fusion protein comprising (i) a first amino acid sequence of SEQ ID NO: 114 comprising a first Fc domain; and (ii) a second Fc domain comprising an amino acid sequence of SEQ ID NO: 46.

2. The heterodimer of claim 1, wherein the fusion protein comprising the first Fc domain comprises a first N-terminal signal peptide or leader sequence and the second Fc domain comprises a second N-terminal signal peptide or leader sequence.

3. The heterodimer of claim 1, wherein the heterodimer does not specifically bind any antigen other than an Fc receptor or a complex of interleukin 2 receptor subunit beta (IL-2RB; CD122) and interleukin 2 receptor subunit gamma (IL-2RG; CD132).

4. The heterodimer of claim 1, wherein the second Fc domain is not fused to an antigen binding domain.

5. The heterodimer of claim 1, wherein neither the first Fc domain nor the second Fc domain is fused to an antigen binding domain.

6. The heterodimer of claim 1, wherein the heterodimer comprises a serum half-life in a human of at least 6, 9, 12, 15, 18, 21, 24 hours, at least 1, 2, 3, 4, 5, 6, 7, 8, 9, 10, 11, 12, 13, 14 days, or longer.

7. A polynucleotide or multiple polynucleotides encoding the Fc-IL-2v fusion protein and the second Fc domain of the heterodimer of claim 1.

8. An expression cassette or multiple expression cassettes comprising one or more regulatory sequences operably linked to the polynucleotide or polynucleotides of claim 7.

9. A vector comprising the polynucleotide or polynucleotides of claim 7.

10. A cell or population of cells comprising the polynucleotide or polynucleotides of claim 7.

11. A method of producing an Fc-IL-2 fusion protein heterodimer, the method comprising:

a) culturing a cell or population of cells transformed with the polynucleotide or polynucleotides of claim 7, in a cell culture under conditions sufficient to express the Fc-IL-2 fusion protein heterodimer molecules; and b) isolating or purifying the Fc-IL-2 fusion protein heterodimer molecules from the cell culture.

12. A pharmaceutical composition comprising the heterodimer of claim 1, and a pharmaceutically acceptable carrier.

13. A method of preventing, reducing and/or inhibiting the recurrence, growth, proliferation, migration and/or metastasis of a cancer cell or population of cancer cells in a subject in need thereof, comprising administering to the subject an effective amount of the heterodimer of claim 1, wherein the cancer cell or population of cancer cells are selected from melanoma and colon cancer.

14. A kit comprising one or more unitary doses of the the heterodimer of claim 1.

* * * * *

UNITED STATES PATENT AND TRADEMARK OFFICE

CERTIFICATE OF CORRECTION

PATENT NO. : 11,896,648 B2
APPLICATION NO. : 17/506483
DATED : February 13, 2024
INVENTOR(S) : Manuel Baca et al.

It is certified that error appears in the above-identified patent and that said Letters Patent is hereby corrected as shown below:

In the Claims

Column 733, Line 13, Claim 14, delete "the the" and insert -- the --.

Signed and Sealed this
Twelfth Day of March, 2024

Katherine Kelly Vidal

Katherine Kelly Vidal
*Director of the United States Patent and Trademark Office*